US011926617B2

(12) United States Patent
Wiles et al.

(10) Patent No.: US 11,926,617 B2
(45) Date of Patent: *Mar. 12, 2024

(54) ARYL, HETEROARYL, AND HETEROCYCLIC COMPOUNDS FOR TREATMENT OF IMMUNE AND INFLAMMATORY DISORDERS

(71) Applicant: Achillion Pharmaceuticals, Inc., Boston, MA (US)

(72) Inventors: Jason Allan Wiles, Madison, CT (US); Avinash S. Phadke, Branford, CT (US); Milind Deshpande, Madison, CT (US); Atul Agarwal, Hamden, CT (US); Dawei Chen, Guilford, CT (US); Venkat Rao Gadhachanda, Hamden, CT (US); Akihiro Hashimoto, Branford, CT (US); Godwin Pais, Hamden, CT (US); Qiuping Wang, Bethany, CT (US); Xiangzhu Wang, Branford, CT (US); William Greenlee, Teaneck, NJ (US)

(73) Assignee: Achillion Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/835,098

(22) Filed: Jun. 8, 2022

(65) Prior Publication Data

US 2022/0315562 A1 Oct. 6, 2022

Related U.S. Application Data

(63) Continuation of application No. 16/867,475, filed on May 5, 2020, now Pat. No. 11,407,738, which is a continuation of application No. 15/905,524, filed on Feb. 26, 2018, now Pat. No. 10,662,175, which is a continuation of application No. PCT/US2016/048788, filed on Aug. 25, 2016.

(60) Provisional application No. 62/210,116, filed on Aug. 26, 2015.

(51) Int. Cl.
| | | |
|---|---|---|
| C07D 405/14 | (2006.01) |
| C07D 401/14 | (2006.01) |
| C07D 403/04 | (2006.01) |
| C07D 403/14 | (2006.01) |
| C07D 471/04 | (2006.01) |
| C07D 413/14 | (2006.01) |
| C07F 9/6558 | (2006.01) |
| C07D 417/14 | (2006.01) |
| C07D 487/04 | (2006.01) |
| C07D 519/00 | (2006.01) |
| C07D 403/12 | (2006.01) |
| C07D 407/14 | (2006.01) |
| C07D 409/14 | (2006.01) |
| C07D 403/10 | (2006.01) |
| C07D 513/04 | (2006.01) |
| C07D 487/22 | (2006.01) |
| A61P 37/00 | (2006.01) |
| A61P 1/16 | (2006.01) |
| A61P 29/00 | (2006.01) |
| C07D 493/04 | (2006.01) |

(52) U.S. Cl.
CPC .............. *C07D 403/04* (2013.01); *A61P 1/16* (2018.01); *A61P 29/00* (2018.01); *A61P 37/00* (2018.01); *C07D 401/14* (2013.01); *C07D 403/10* (2013.01); *C07D 403/12* (2013.01); *C07D 403/14* (2013.01); *C07D 405/14* (2013.01); *C07D 407/14* (2013.01); *C07D 409/14* (2013.01); *C07D 413/14* (2013.01); *C07D 417/14* (2013.01); *C07D 471/04* (2013.01); *C07D 487/04* (2013.01); *C07D 487/22* (2013.01); *C07D 493/04* (2013.01); *C07D 513/04* (2013.01); *C07D 519/00* (2013.01); *C07F 9/65583* (2013.01)

(58) Field of Classification Search
CPC ... C07D 405/14; C07D 401/14; C07D 403/04
See application file for complete search history.

(56) References Cited

U.S. PATENT DOCUMENTS

| | | |
|---|---|---|
| 6,489,476 B1 | 12/2002 | Dang et al. |
| 6,653,340 B1 | 11/2003 | Babu et al. |
| 7,629,340 B2 | 12/2009 | Schmitz et al. |

(Continued)

FOREIGN PATENT DOCUMENTS

| | | |
|---|---|---|
| CN | 103402996 A | 11/2013 |
| EA | 201890594 A1 | 8/2018 |

(Continued)

OTHER PUBLICATIONS

"Are There Any Treatments for ALS?" WebMD, <https://www.webmd.com/brain/understanding-als-treatment#1>, retrieved on May 3, 2019 (8 pages).
"Arteriosclerosis/atherosclerosis," Mayo Clinic, <https://www.mayoclinic.org/diseases-conditions/arteriosclerosis-atherosclerosis/diagnosis-treatment/drc-20350575>, retrieved on Apr. 24, 2018 (10 pages).

(Continued)

*Primary Examiner* — Shawquia Jackson
(74) *Attorney, Agent, or Firm* — Clark & Elbing LLP

(57) ABSTRACT

Compounds, methods of use, and processes for making inhibitors of complement Factor D are provided comprising Formula I, I" and I'" or a pharmaceutically acceptable salt or composition thereof. The inhibitors described herein target Factor D and inhibit or regulate the complement cascade. The inhibitors of Factor D described herein reduces the excessive activation of complement.

20 Claims, 105 Drawing Sheets

(56) References Cited

U.S. PATENT DOCUMENTS

| | | | |
|---|---|---|---|
| 8,524,716 B2 * | 9/2013 | Raboisson | C07D 487/06 514/254.01 |
| 9,085,555 B2 | 7/2015 | Altmann et al. | |
| 9,421,240 B2 | 8/2016 | Francois et al. | |
| 9,598,446 B2 | 3/2017 | Gadhachanda et al. | |
| 9,643,986 B2 | 5/2017 | Wiles et al. | |
| 9,663,543 B2 | 5/2017 | Wiles et al. | |
| 9,695,205 B2 | 7/2017 | Wiles et al. | |
| 9,732,103 B2 | 8/2017 | Wiles et al. | |
| 9,732,104 B2 | 8/2017 | Gadhachanda et al. | |
| 9,758,537 B2 | 9/2017 | Wiles et al. | |
| 9,796,741 B2 | 10/2017 | Gadhachanda et al. | |
| 9,828,396 B2 | 11/2017 | Wiles et al. | |
| 10,000,516 B2 | 6/2018 | Wiles et al. | |
| 10,005,802 B2 | 6/2018 | Wiles et al. | |
| 10,011,612 B2 | 7/2018 | Wiles et al. | |
| 10,081,645 B2 | 9/2018 | Wiles et al. | |
| 10,087,203 B2 | 10/2018 | Wiles et al. | |
| 10,092,547 B2 | 10/2018 | Wiles et al. | |
| 10,092,584 B2 | 10/2018 | Wiles et al. | |
| 10,100,072 B2 | 10/2018 | Wiles et al. | |
| 10,106,563 B2 | 10/2018 | Wiles et al. | |
| 10,138,225 B2 | 11/2018 | Wiles et al. | |
| 10,189,869 B2 | 1/2019 | Gadhachanda et al. | |
| 10,253,053 B2 | 4/2019 | Wiles et al. | |
| 10,287,301 B2 | 5/2019 | Wiles et al. | |
| 10,301,336 B2 | 5/2019 | Wiles et al. | |
| 10,370,394 B2 | 8/2019 | Wiles et al. | |
| 10,385,097 B2 | 8/2019 | Wiles et al. | |
| 10,428,094 B2 | 10/2019 | Wiles et al. | |
| 10,428,095 B2 | 10/2019 | Wiles et al. | |
| 10,464,956 B2 | 11/2019 | Wiles et al. | |
| 10,550,140 B2 | 2/2020 | Wiles et al. | |
| 10,660,876 B2 | 5/2020 | Wiles et al. | |
| 10,662,175 B2 | 5/2020 | Wiles et al. | |
| 10,689,409 B2 | 6/2020 | Gadhachanda et al. | |
| 10,807,952 B2 | 10/2020 | Wiles et al. | |
| 10,822,352 B2 | 11/2020 | Wiles et al. | |
| 10,906,887 B2 | 2/2021 | Wiles et al. | |
| 10,919,884 B2 | 2/2021 | Wiles et al. | |
| 11,001,600 B2 | 5/2021 | Wiles et al. | |
| 11,053,253 B2 | 7/2021 | Wiles et al. | |
| 11,084,800 B2 | 8/2021 | Wiles et al. | |
| 11,407,738 B2 | 8/2022 | Wiles et al. | |
| 11,447,465 B2 | 9/2022 | Wiles et al. | |
| 2002/0133004 A1 | 9/2002 | Sekiyama et al. | |
| 2005/0228000 A1 | 10/2005 | Smallheer et al. | |
| 2005/0267108 A1 | 12/2005 | Hsieh et al. | |
| 2007/0155712 A1 | 7/2007 | Zahn et al. | |
| 2008/0075720 A1 | 3/2008 | Holers et al. | |
| 2008/0075728 A1 | 3/2008 | Newman | |
| 2008/0108691 A1 | 5/2008 | Hamann et al. | |
| 2010/0041628 A1 | 2/2010 | Enomoto et al. | |
| 2011/0280808 A1 | 11/2011 | Kroth et al. | |
| 2012/0231471 A1 | 9/2012 | Sato et al. | |
| 2012/0295884 A1 | 11/2012 | Altmann et al. | |
| 2013/0296377 A1 | 11/2013 | Adams et al. | |
| 2013/0344073 A1 | 12/2013 | Schwaeble et al. | |
| 2014/0371133 A1 | 12/2014 | Francois et al. | |
| 2015/0141455 A1 | 5/2015 | Altmann et al. | |
| 2015/0148374 A1 | 5/2015 | Hommel et al. | |
| 2015/0191462 A1 | 7/2015 | Hommel et al. | |
| 2015/0239837 A1 | 8/2015 | Wiles et al. | |
| 2015/0239838 A1 | 8/2015 | Phadke et al. | |
| 2015/0239868 A1 | 8/2015 | Pais et al. | |
| 2015/0239893 A1 | 8/2015 | Wang et al. | |
| 2015/0239894 A1 | 8/2015 | Gadhachanda et al. | |
| 2015/0239895 A1 | 8/2015 | Gadhachanda et al. | |
| 2015/0239919 A1 | 8/2015 | Gadhachanda et al. | |
| 2015/0239920 A1 | 8/2015 | Gadhachanda et al. | |
| 2015/0239921 A1 | 8/2015 | Wiles et al. | |
| 2015/0322060 A1 | 11/2015 | Flohr et al. | |
| 2015/0368271 A1 | 12/2015 | Su et al. | |
| 2016/0015810 A1 | 1/2016 | Deschatelets et al. | |
| 2016/0024079 A1 | 1/2016 | Adams et al. | |
| 2016/0361329 A1 | 12/2016 | Wiles et al. | |
| 2016/0362398 A1 | 12/2016 | Wiles et al. | |
| 2016/0362399 A1 | 12/2016 | Wiles et al. | |
| 2016/0362432 A1 | 12/2016 | Wiles et al. | |
| 2016/0362433 A1 | 12/2016 | Wiles et al. | |
| 2017/0056428 A1 | 3/2017 | Wiles et al. | |
| 2017/0057950 A1 | 3/2017 | Wiles et al. | |
| 2017/0057983 A1 | 3/2017 | Wiles et al. | |
| 2017/0057993 A1 | 3/2017 | Wiles et al. | |
| 2017/0066783 A1 | 3/2017 | Wiles et al. | |
| 2017/0189410 A1 | 7/2017 | Gadhachanda et al. | |
| 2017/0226142 A1 | 8/2017 | Wiles et al. | |
| 2017/0260219 A1 | 9/2017 | Wiles et al. | |
| 2017/0298084 A1 | 10/2017 | Wiles et al. | |
| 2017/0298085 A1 | 10/2017 | Wiles et al. | |
| 2018/0022766 A1 | 1/2018 | Wiles et al. | |
| 2018/0022767 A1 | 1/2018 | Wiles et al. | |
| 2018/0030075 A1 | 2/2018 | Wiles et al. | |
| 2018/0072762 A1 | 3/2018 | Wiles et al. | |
| 2018/0177761 A1 | 6/2018 | Wiles et al. | |
| 2018/0179185 A1 | 6/2018 | Wiles et al. | |
| 2018/0179186 A1 | 6/2018 | Wiles et al. | |
| 2018/0179236 A1 | 6/2018 | Wiles et al. | |
| 2018/0186782 A1 | 7/2018 | Wiles et al. | |
| 2018/0201580 A1 | 7/2018 | Wiles et al. | |
| 2018/0291046 A1 | 10/2018 | Wiles et al. | |
| 2018/0291047 A1 | 10/2018 | Wiles et al. | |
| 2018/0305375 A1 | 10/2018 | Wiles et al. | |
| 2019/0023729 A1 | 1/2019 | Wiles et al. | |
| 2019/0031692 A1 | 1/2019 | Wiles et al. | |
| 2019/0038623 A1 | 2/2019 | Huang et al. | |
| 2019/0048033 A1 | 2/2019 | Wiles et al. | |
| 2019/0085005 A1 | 3/2019 | Wiles et al. | |
| 2019/0144473 A1 | 5/2019 | Gadhachanda et al. | |
| 2019/0211033 A1 | 7/2019 | Wiles et al. | |
| 2019/0382376 A1 | 12/2019 | Wiles et al. | |
| 2020/0002347 A1 | 1/2020 | Wiles et al. | |
| 2020/0062790 A1 | 2/2020 | Wiles et al. | |
| 2020/0071301 A1 | 3/2020 | Wiles et al. | |
| 2020/0101071 A1 | 4/2020 | Huang et al. | |
| 2020/0262818 A1 | 8/2020 | Wiles et al. | |
| 2021/0332026 A1 | 10/2021 | Phadke et al. | |

FOREIGN PATENT DOCUMENTS

| | | |
|---|---|---|
| JP | 2014-506877 A | 3/2014 |
| JP | 2015-522005 A | 8/2015 |
| JP | 2015-522006 A | 8/2015 |
| JP | 2015-522007 A | 8/2015 |
| JP | 2015-522008 A | 8/2015 |
| JP | 2015-522062 A | 8/2015 |
| JP | 2017-511815 A | 4/2017 |
| JP | 6400738 B2 | 10/2018 |
| JP | 2018-199714 A | 12/2018 |
| JP | 6537532 B2 | 7/2019 |
| JP | 6688352 B2 | 4/2020 |
| KR | 2014-0027090 A | 3/2014 |
| WO | WO-93/20099 A2 | 10/1993 |
| WO | WO-95/29697 A1 | 11/1995 |
| WO | WO-99/48492 A1 | 9/1999 |
| WO | WO-2004/007501 A1 | 1/2004 |
| WO | WO-2004/045518 A2 | 6/2004 |
| WO | WO-2004/111041 A1 | 12/2004 |
| WO | WO-2008/047831 A1 | 4/2008 |
| WO | WO-2009/091826 A2 | 7/2009 |
| WO | WO-2011/057158 A1 | 5/2011 |
| WO | WO-2012/093101 A1 | 7/2012 |
| WO | WO-2012/177782 A1 | 12/2012 |
| WO | WO-2013/166436 A1 | 11/2013 |
| WO | WO-2013/192345 A1 | 12/2013 |
| WO | WO-2014/002051 A2 | 1/2014 |
| WO | WO-2014/002052 A1 | 1/2014 |
| WO | WO-2014/002053 A1 | 1/2014 |
| WO | WO-2014/002054 A1 | 1/2014 |
| WO | WO-2014/002057 A1 | 1/2014 |
| WO | WO-2014/002058 A2 | 1/2014 |
| WO | WO-2014/002059 A1 | 1/2014 |
| WO | WO-2014/005150 A1 | 1/2014 |
| WO | WO-2014/009833 A2 | 1/2014 |

(56) References Cited

FOREIGN PATENT DOCUMENTS

| | | |
|---|---|---|
| WO | WO-2014/037480 A1 | 3/2014 |
| WO | WO-2014/116880 A1 | 7/2014 |
| WO | WO-2015/008861 A1 | 1/2015 |
| WO | WO-2015/130784 A1 | 9/2015 |
| WO | WO-2015/130795 A1 | 9/2015 |
| WO | WO-2015/130806 A1 | 9/2015 |
| WO | WO-2015/130830 A1 | 9/2015 |
| WO | WO-2015/130838 A1 | 9/2015 |
| WO | WO-2015/130842 A2 | 9/2015 |
| WO | WO-2015/130845 A1 | 9/2015 |
| WO | WO-2015/130854 A1 | 9/2015 |
| WO | WO-2017/035348 A1 | 3/2017 |
| WO | WO-2017/035349 A1 | 3/2017 |
| WO | WO-2017/035351 A1 | 3/2017 |
| WO | WO-2017/035352 A1 | 3/2017 |
| WO | WO-2017/035353 A1 | 3/2017 |
| WO | WO-2017/035355 A1 | 3/2017 |
| WO | WO-2017/035357 A1 | 3/2017 |
| WO | WO-2017/035360 A1 | 3/2017 |
| WO | WO-2017/035361 A1 | 3/2017 |
| WO | WO-2017/035362 A1 | 3/2017 |
| WO | WO-2017/035401 A1 | 3/2017 |
| WO | WO-2017/035405 A1 | 3/2017 |
| WO | WO-2017/035408 A1 | 3/2017 |
| WO | WO-2017/035409 A1 | 3/2017 |
| WO | WO-2017/035411 A1 | 3/2017 |
| WO | WO-2017/035413 A2 | 3/2017 |
| WO | WO-2017/035415 A1 | 3/2017 |
| WO | WO-2017/035417 A1 | 3/2017 |
| WO | WO-2017/035418 A1 | 3/2017 |
| WO | WO-2017/098328 A2 | 6/2017 |
| WO | WO-2017/136395 A1 | 8/2017 |
| WO | WO-2018/005552 A1 | 1/2018 |
| WO | WO-2018/160889 A1 | 9/2018 |
| WO | WO-2018/160891 A1 | 9/2018 |
| WO | WO-2018/160892 A1 | 9/2018 |
| WO | WO-2019/028284 A1 | 2/2019 |
| WO | WO-2019/070714 A1 | 4/2019 |
| WO | WO-2020/069024 A1 | 4/2020 |
| WO | WO-2020/109343 A1 | 6/2020 |
| WO | WO-2021/021909 A1 | 2/2021 |

OTHER PUBLICATIONS

"Cancer," MedLine Plus, <http://www.nlm.nih.gov/medlineplus/cancer.html>, retrieved Jul. 6, 2007 (10 pages).
"Dermatomyositis," Mayo Clinic, <https://www.mayoclinic.org/diseases-conditions/dermatomyositis/diagnosis-treatment/drc-20353192>, retrieved on Aug. 1, 2017 (7 pages).
"History of Changes for Study: NCT03053102—A Treatment Study of ACH-0144471 in Patients With Paroxysmal Nocturnal Hemoglobinuria (PNH)," U.S. National Library of Medicine, available at: <https://clinicaltrials.gov/ct2/history/NCT03053102?V_4=View#StudyPageTop>, submitted Jun. 6, 2017, retrieved Mar. 9, 2021 (3 pages).
"NCT03472885—A Treatment Study of ACH-0144471 in Patients With Paroxysmal Nocturnal Hemoglobinuria (PNH) With Inadequate Response to Eculizumab (PNH)," U.S. National Library of Medicine, available at: <https://clinicaltrials.gov/ct2/show/NCT03472885>, first posted Mar. 21, 2018, last update posted Dec. 3, 2019, retrieved Mar. 27, 2020 (7 pages).
"Reperfusion injury," Wikipedia, <https://en.wikipedia.org/wiki/Reperfusion_injury>, retrieved Apr. 30, 2020 (8 pages).
"Treatment for Multiple Sclerosis," WebMD, <https://www.webmd.com/multiple-sclerosis/ms-treatment#1>, retrieved on May 3, 2019 (24 pages).
"What Are the Treatments for Cirrhosis?," WebMD, <https://www.webmd.com/digestive-disorders/understanding-cirrhosis-treatment#1>, retrieved May 3, 2019 (15 pages).
"What is Cardiovascular Disease?" American Heart Association, <https://www.heart.org/en/health-topics/consumer-healthcare/what-is-cardiovascular-disease>, dated May 31, 2017 (4 pages).

Airey et al., "A Convenient Preparation of Thieno[3,2-c]pyrazole," Synthesis. 46: 96-100 (2014).
Armand, "Fatty liver disease: What it is and what to do about it," Harvard Health Publishing, <https://www.health.harvard.edu/blog/fatty-liver-disease-what-it-is-and-what-to-do-about-it-2019011015746>, dated Jan. 10, 2019, retrieved May 2, 2019 (3 pages).
Barraclough et al., "Synthesis of (2S,3R)-and (2S,3S)-[3-$^2$H$_1$]-proline via highly selective hydrolysis of a silyl enol ether," Tetrahedron Letters. 46(1): 4653-4655 (2005).
Barraclough et al., "Two separate and distinct syntheses of stereospecifically deuteriated samples of (2S)-proline," Org Biomol Chem. 4(8):1483-1491 (2006).
Carter, "Complement Activation: An Emerging Player in the Pathogenesis of Cardiovascular Disease," Scientifica. 2012(1):1-14 (2012) (14 pages).
CAS RN 1236228-05-9, dated Aug. 16, 2010 (1 page).
CAS RN 1236251-51-6, dated Aug. 17, 2010 (2 pages).
CAS RN 1270608-88-2, dated 2019 (1 page).
CAS RN 1277041-86-7, dated Apr. 8, 2011 (2 pages).
Cole et al. "Structure of 3,4-Dichloroisocoumarin-Inhibited Factor D," Acta Crystallogr D Biol Crystallogr. 54(Pt 5): 711-717 (1998).
Compound Summary for CID 1129904, PubChem. <https://pubchem.ncbi.nlm.nih.gov/compound/1129904> retrieved Jul. 14, 2020, entered Jul. 10, 2005 (10 pages).
Compound Summary for CID 118324207, PubChem, <https://pubchem.ncbi.nlm.nih.gov/compound/118324207>, created Feb. 23, 2016, retrieved on Jul. 14, 2020 (8 pages).
Compound Summary for CID 123543544, PubChem, <https://pubchem.ncbi.nlm.nih.gov/compound/123543544>, created on Jan. 25, 2017, retrieved on Jul. 13, 2020 (8 pages).
Compound Summary for CID 134222466, PubChem, <https://pubchem.ncbi.nlm.nih.gov/compound/134222466>, created on Jun. 23, 2018, retrieved on Jul. 14, 2020 (11 pages).
Compound Summary for CID 59912842, PubChem, <https://pubchem.ncbi.nlm.nih.gov/compound/59912842>, entered Aug. 20, 2012, retrieved Jul. 14, 2020 (9 pages).
Database Registry Chemical Abstracts Service, Columbus, Ohio, Accession No. RN1236248-20-6, Entered STN: Aug. 16, 2010 (1 page).
Database Registry Chemical Abstracts Service, Columbus, Ohio, Accession No. RN1380849-41-1, Entered STN: Jul. 3, 2012 (2 pages).
De Luca et al., "HIV-1 integrase strand-transfer inhibitors: Design, synthesis and molecular modeling investigation," Eur J Med Chem. 46(2): 756-764 (2011).
Dezern et al., "Paroxysmal nocturnal hemoglobinuria: a complement-mediated hemolytic anemia," available in PMC Dec. 30, 2015, published in final edited form as: Hematol Oncol Clin North Am. 29(3):479-94 (Jun. 2015) (18 pages).
Donthiri et al., "Copper-Catalyzed C—H Functionalization of Pyridines and Isoquinolines with Vinyl Azides: Synthesis of Imidazo Heterocycles," J Org Chem. 79(22): 11277-11284 (2014).
Dormoy et al., "Synthesis of N-t-Butoxycarbonyl-4,4-dideuterio-L-proline," Synthesis. 1: 81-82 (1986).
Ellis-Pegler et al., "An Orally Administered Small Molecule Factor D Inhibitor (ACH-4471) For Treatment of PNH and Complement Diseases: Preliminary Phase 1 Results In Healthy Volunteers," European Hematology Association. Abstract LB2250, available <https://library.ehaweb.org/eha/2016/21st/135361/roderick.b.ellis-pegler.an.orally.administered.small.molecule.factor.d.html>, dated May 19, 2016 (2 pages).
Ellis-Pegler et al., "An Orally Administered Small Molecule Factor D Inhibitor (ACH-4471) For Treatment of Pnh, C3G and Complement—Mediated Diseases: Interim Phase 1 Results In Healthy Volunteers," European Hematology Association, Copenhagen 21st Congress, June 9-12, Abstract ID: EHA-4145 (Jun. 2016) (1 page).
Extended European Search Report for European Application No. 19897806.6, dated Jul. 18, 2022 (12 pages).
Gadhachanda et al., CAplus Database Summary Sheet for Document No. 164:507515, Accession No. 2016:627420, CAplus on STN. (Feb. 2018) (6 pages).

(56) References Cited

OTHER PUBLICATIONS

Gavriilaki et al., "275 Small Molecule Factor D Inhibitors Block Complement Activation in Paroxysmal Nocturnal Hemoglobinuria and Atypical Hemolytic Uremic Syndrome," ASH 57th Annual Meeting & Exposition, Session: 101. Dec. 6, 2015 (2 pages).
Golub et al., "Molecular classification of cancer: class discovery and class prediction by gene expression monitoring," Science. 286(5439):531-7 (1999) (8 pages).
Haddrill, "Stargardt's Disease (Fundus Flavimaculatus)," All About Vision, <https://www.allaboutvision.com/conditions/stargardts.htm#article-section-2>, retrieved May 3, 2019 (5 pages).
Harris et al., "Developments in anti-complement therapy; from disease to clinical trial," Mol Immunol. 102:89-119 (Oct. 2018).
Hecker et al., "Liver-Targeted Prodrugs of 2'-C-Methyladenosine for Therapy of Hepatitis C Virus Infection," J Med Chem. 50(16): 3891-3896 (2007).
Hruby et al., "$^{13}$C Nuclear Magnetic Resonance Studies of the Peptide Hormones Oxytocin, Arginine Vasopressin, Isotocin, Mesotocin, Glumitocin, Aspartocin, Related Analogues, and Diastereoisomers. Use of Specifically Deuterated Hormone Derivatives for Assignments and Effects of Structural Changes on $^{13}$C NMR Chemical Shifts in Peptides," J Am Chem Soc. 101(1): 202-212 (1979).
Latropoulos et al., "Cluster Analysis Identifies Distinct Pathogenetic Patterns in C3 Glomerulopathies/Immune Complex-Mediated Membranoproliferative GN," J Am Soc Nephrol. 29(1):283-94 (with supplemental material) (Jan. 2018) (36 pages).
International Preliminary Report on Patentability for International Application No. PCT/US2021/018871, dated Sep. 1, 2022 (6 pages).
International Search Report and Written Opinion for International Application No. PCT/US2015/017523, dated May 14, 2015 (7 pages).
International Search Report and Written Opinion for International Application No. PCT/US2015/017538, dated May 14, 2015 (8 pages).
International Search Report and Written Opinion for International Application No. PCT/US2015/017554, dated May 14, 2015 (7 pages).
International Search Report and Written Opinion for International Application No. PCT/US2015/017583, dated May 27, 2015 (12 pages).
International Search Report and Written Opinion for International Application No. PCT/US2015/017593, dated Jun. 16, 2015 (6 pages).
International Search Report and Written Opinion for International Application No. PCT/US2015/017597, dated Jan. 29, 2016 (10 pages).
International Search Report and Written Opinion for International Application No. PCT/US2015/017600, dated May 27, 2015 (12 pages).
International Search Report and Written Opinion for International Application No. PCT/US2015/017609, dated May 29, 2015 (6 pages).
International Search Report and Written Opinion for International Application No. PCT/US2016/048688, dated Dec. 28, 2016 (11 pages).
International Search Report and Written Opinion for International Application No. PCT/US2016/048690, dated Dec. 28, 2016 (11 pages).
International Search Report and Written Opinion for International Application No. PCT/US2016/048693, dated Jan. 13, 2017 (11 pages).
International Search Report and Written Opinion for International Application No. PCT/US2016/048695, dated Dec. 30, 2016 (10 pages).
International Search Report and Written Opinion for International Application No. PCT/US2016/048696, dated Jan. 5, 2017 (10 pages).
International Search Report and Written Opinion for International Application No. PCT/US2016/048701, dated Jan. 10, 2017 (10 pages).
International Search Report and Written Opinion for International Application No. PCT/US2016/048704, dated Dec. 27, 2016 (7 pages).
International Search Report and Written Opinion for International Application No. PCT/US2016/048707, dated Jan. 5, 2017 (10 pages).
International Search Report and Written Opinion for International Application No. PCT/US2016/048709, dated Jan. 17, 2017 (9 pages).
International Search Report and Written Opinion for International Application No. PCT/US2016/048710, dated Jan. 5, 2017 (8 pages).
International Search Report and Written Opinion for International Application No. PCT/US2016/048779, dated Dec. 27, 2016 (8 pages).
International Search Report and Written Opinion for International Application No. PCT/US2016/048783, dated Feb. 3, 2017 (8 pages).
International Search Report and Written Opinion for International Application No. PCT/US2016/048787, dated Jan. 5, 2017 (13 pages).
International Search Report and Written Opinion for International Application No. PCT/US2016/048788, dated Jan. 5, 2017 (12 pages).
International Search Report and Written Opinion for International Application No. PCT/US2016/048793, dated Dec. 28, 2016 (8 pages).
International Search Report and Written Opinion for International Application No. PCT/US2016/048795, dated Feb. 17, 2017 (12 pages).
International Search Report and Written Opinion for International Application No. PCT/US2016/048797, dated Jan. 5, 2017 (12 pages).
International Search Report and Written Opinion for International Application No. PCT/US2016/048799, dated Nov. 15, 2016 (7 pages).
International Search Report and Written Opinion for International Application No. PCT/US2016/048800, dated Jan. 5, 2017 (12 pages).
International Search Report for International Application No. PCT/US18/20530, dated Jun. 25, 2018 (3 pages).
International Search Report for International Application No. PCT/US18/20531, dated May 15, 2018 (3 pages).
International Search Report for International Application No. PCT/US2018/020528, dated Apr. 24, 2018 (3 pages).
International Search Report for International Application No. PCT/US2019/034210, dated Sep. 13, 2019 (4 pages).
International Search Report for International Application No. PCT/US2019/047252, dated Dec. 17, 2019 (4 pages).
International Search Report for International Application No. PCT/US2019/050065, dated Feb. 25, 2020 (4 pages).
International Search Report for International Application No. PCT/US2019/053012, dated Jan. 28, 2020 (4 pages).
International Search Report for International Application No. PCT/US2019/066999, dated Feb. 12, 2020 (3 pages).
Józsi, "Anti-Complement Autoantibodies in Membranoproliferative Glomerulonephritis and Dense Deposit Disease", *An Update on Glomerulopathies—Etiology and Pathogenesis*. Prof. Sharma Prabhakar, 31-46 (2011) (18 pages).
Kathuria, "Membranoproliferative Glomerulonephritis Medication," Medscape, <https://emedicine.medscape.com/article/240056-medication>, dated Jun. 23, 2016, retrieved May 3, 2019 (1 page).
Kinman, "COPD Drugs: A List of Medications to Help Relieve Your Symptoms," Healthline, <https://www.healthline.com/health/copd/drugs>, retrieved on May 3, 2019 (12 pages).
Komiya et al., CAplus Database Summary Sheet for Document No. 162:229476, Accession No. 2015:126147, CAplus on STN. (Jul. 2017) (2 pages).
Kuang et al., "Synthesis of (Z)-1-bromo-1-alkenes and terminal alkynes from anti-2,3-dibromoalkanoic acids by microwave-induced reaction," Tetrahedron. 61(16):4043-4052 (2005).
Lala et al., "Role of nitric oxide in tumor progression: lessons from experimental tumors," Cancer Metastasis Rev. 17(1):91-106 (1998).

(56) References Cited

OTHER PUBLICATIONS

Lassmann, "What drives disease in multiple sclerosis: Inflammation or neurodegeneration?" Clinical and Experimental Neuroimmunology. 1:2-11 (2010).
MacKay et al., "Rapid Synthesis of the N-Methylwelwitindolinone Skeleton," Org Lett. 7(16):3421-4 (2005).
Marinozzi et al., "C5 nephritic factors drive the biological phenotype of C3 glomerulopathies," Kidney Int. 92(5):1232-41 (Nov. 2017).
Michels et al., "Long-term follow-up including extensive complement analysis of a pediatric C3 glomerulopathy cohort," Pediatr Nephrol. 37(3):601-12 (Mar. 2022).
Noris et al., "Overview of Complement Activation and Regulation," Semin Nephrol. 33(6):479-92 (2013).
Office Action issued for Eurasian Patent Application No. 201992005, dated Oct. 23, 2020 (6 pages).
Okutani et al., "Conversion of Bromoalkenes into Alkynes by Wet Tetra-n-butylammonium Fluoride," J Org Chem. 74(1):442-444 (2009).
Oseini et al., "Therapies in Non-Alcoholic Steatohepatitis (NASH)," available in PMC Jan. 1, 2018, published in final edited form as: Liver Int. 37(Suppl 1):97-103 (Jan. 2017) (15 pages).
Pandya et al., "Complement System in Lung Disease," Am J Respir Cell Mol Biol. 51(4):467-473 (2014).
Partial Supplementary European Search Report for European Application No. 18761960.6, dated Nov. 27, 2020 (12 pages).
Patel et al., "In Vitro Combination Studies of ACH-4471 with Eculizumab to Assess a Potential 'Switch' Treatment Approach for Paroxysmal Nocturnal Hemoglobinuria," 59th American Society of Hematology Annual Meeting and Exposition, Dec. 9-12, Atlanta, Georgia. Poster Abstract 2198 (Dec. 2017) (1 page).
Peifer et al., "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors," J Med Chem. 51(13):3814-3824 (2008).
Pugsley et al., "Inhibitors of the complement system currently in development for cardiovascular disease," Cardiovasc Toxicol. 3(1):43-69 (2003).
Qu et al., "Recent Developments in Low Molecular Weight Complement Inhibitors," available in PMC, Dec. 1, 2010, published in final edited form as: Mol Immunol. 47(2-3):185-195 (2009) (25 pages).
Quesada et al., "One-pot conversion of activated alcohols into terminal alkynes using manganese dioxide in combination with the Bestmann—Ohira reagent," Tetrahedron Letters. 46:6473-6476 (2005).
Ricklin et al., "Complement in immune and inflammatory disorders: pathophysiological mechanisms," J Immunol. 190(8):3831-3838 (2013) (9 pages).
Rohrer et al., "Eliminating complement factor D reduces photoreceptor susceptibility to light-induced damage," Invest Ophthalmol Vis Sci. 48(11):5282-9 (2007).
Roth et al., "Further Improvements of the Synthesis of Alkynes from Aldehydes," Synthesis. 1:59-62 (2004).
Ruiz-Gómez et al., "Structure—Activity Relationships for Substrate-Based Inhibitors of Human Complement Factor B," J Med Chem. 52(19):6042-6052 (2009).
Salifu, "Chronic Glomerulonephritis Medication," Medscape, <https://emedicine.medscape.com/article/239392-medication>, dated Feb. 1, 2017, retrieved on May 2, 2019 (1 page).
Segers et al., "Complement Alternative Pathway Activation in Human Nonalcoholic Steatohepatitis," Plos One. 9(10):e110053 (2014) (9 pages).
Stanton et al., "Complement Factor D in Age-Related Macular Degeneration," Invest Ophthalmol Vis Sci. 52(12):8828-8834 (2011) (15 pages).
Strobel et al., "Anti-factor B autoantibody in dense deposit disease," Mol Immunol. 47:1476-1483 (2010).
Tandon et al., "Substrate specificity of human prolyl-4-hydroxylase," Bioorg Med Chem Lett. 8(10):1139-1144 (1998).
Tang et al., "Palladium-Catalyzed Carbonylative Sonogashira Coupling of Aryl Bromides via tert-Butyl Isocyanide Insertion," J Org Chem. 78(7):3170-3175 (2013).
Written Opinion for International Application No. PCT/US18/20528, dated Apr. 24, 2018 (6 pages).
Written Opinion for International Application No. PCT/US18/20530, dated Jun. 25, 2018 (6 pages).
Written Opinion for International Application No. PCT/US18/20531, dated May 15, 2018 (7 pages).
Written Opinion for International Application No. PCT/US19/47252, dated Dec. 17, 2019 (6 pages).
Written Opinion for International Application No. PCT/US19/50065, dated Feb. 25, 2020 (7 pages).
Written Opinion for International Application No. PCT/US19/53012, dated Jan. 28, 2020 (5 pages).
Written Opinion for International Application No. PCT/US19/66999, dated Feb. 12, 2020 (7 pages).
Yonemoto-Kobayashi et al., "Carboxylation of alkynylsilanes with carbon dioxide mediated by cesium fluoride in DMSO," Org Biomol Chem. 11(23):3773-5 (2013).
Yuan et al., "Small-molecule Factor D Inhibitors Selectively Block the Alternative Pathway of Complement in Paroxysmal Nocturnal Hemoglobinuria and Atypical Hemolytic Uremic Syndrome," Haematologica. 102(3):466-75 (Mar. 2017).
Zhang et al., "Defining the complement biomarker profile of C3 glomerulopathy," Clin J Am Soc Nephrol. 9(11):1876-82 (supplemental materials) (Nov. 7, 2014) (10 pages).

\* cited by examiner

ARYL, HETEROARYL, AND HETEROCYCLIC COMPOUNDS FOR TREATMENT OF IMMUNE AND INFLAMMATORY DISORDERS

CROSS-REFERENCE TO RELATED APPLICATIONS

This application is a continuation of U.S. patent application Ser. No. 16/867,475, filed May 5, 2020, which is a continuation of U.S. patent application Ser. No. 15/905,524, now U.S. Pat. No. 10,662,175, filed Feb. 26, 2018, which is a continuation of International Patent Application No. PCT/US16/48788, filed Aug. 25, 2016, which claims the benefit of provisional U.S. Application No. 62/210,116, filed Aug. 26, 2015. The entirety of this application is hereby incorporated by reference for all purposes.

BACKGROUND

An immune disorder occurs when the immune system is not performing in a normal manner. Inflammation is a protective response that involves immune cells, the immune system generally, blood vessels, and molecular mediators. A wide variety of medical disorders are caused by detrimental immune or inflammatory responses, or the inability of a cell to respond to a normal immune or inflammatory process.

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phaogytosis of antigens), chemotaxis (attracting macrophages and neutrophils), cell lysis (rupturing membranes of foreign cells) and agglutination (clustering and binding of pathogens together).

The complement system has three pathways: classical, alternative and lectin. Complement Factor D plays an early and central role in activation of the alternative pathway of the complement cascade. Activation of the alternative complement pathway is initiated by spontaneous hydrolysis of a thioester bond within C3 to produce $C3(H_2O)$, which associates with Factor B to form the $C3(H_2O)B$ complex. Complement Factor D acts to cleave Factor B within the $C3(H_2O)B$ complex to form Ba and Bb. The Bb fragment remains associated with $C3(H_2O)$ to form the alternative pathway C3 convertase $C3(H_2O)Bb$. Additionally, C3b generated by any of the C3 convertases also associates with Factor B to form C3bB, which Factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway. Some examples of disorders mediated by the complement pathway include age-related macular degeneration (AMD), paroxysmal nocturnal hemoglobinuria (PNH), multiple sclerosis, and rheumatoid arthritis.

Age-related macular degeneration (AMD) is a leading cause of vision loss in industrialized countries. Based on a number of genetic studies, there is evidence of the link between the complement cascade and macular degeneration. Individuals with mutations in the gene encoding complement Factor H have a fivefold increased risk of macular degeneration and individuals with mutations in other complement factor genes also have an increased risk of AMID. Individuals with mutant Factor H also have increased levels of C-reactive protein, a marker of inflammation. Without adequate functioning Factor H, the alternative pathway of the complement cascade is overly activated leading to cellular damage. Inhibition of the alternative pathway is thus desired.

Paroxysmal nocturnal hemoglobinuria (PNH) is a non-malignant, hematological disorder characterized by the expansion of hematopoietic stem cells and progeny mature blood cells which are deficient in some surface proteins. PNH erythrocytes are not capable of modulating their surface complement activation, which leads to the typical hallmark of PNH—the chronic activation of complement mediated intravascular anemia. Currently, only one product, the anti-C5 monoclonal antibody eculizumab, has been approved in the U.S. for treatment of PNH. However, many of the patients treated with eculizumab remain anemic, and many patients continue to require blood transfusions. In addition, treatment with eculizumab requires life-long intravenous injections. Thus, there is an unmet need to develop novel inhibitors of the complement pathway.

Other disorders that have been linked to the complement cascade include atypical hemolytic uremic syndrome (aHUS), hemolytic uremic syndrome (HUS), abdominal aortic aneurysm, hemodialysis complications, hemolytic anemia, or hemodialysis, neuromyelitis (NMO), myasthenia gravis (MG), fatty liver, nonalcoholic steatohepatitis (NASH), liver inflammation, cirrhosis, liver failure, dermatomyocitis, and amyotrophic lateral sclerosis.

Factor D is an attractive target for inhibition or regulation of the complement cascade due to its early and essential role in the alternative complement pathway, and its potential role in signal amplification within the classical and lectin complement pathways. Inhibition of Factor D effectively interrupts the pathway and attenuates the formation of the membrane attack complex.

While initial attempts have been made to develop inhibitors of Factor D, there are currently no small molecule Factor D inhibitors in clinical trials. Examples of Factor D inhibitors or prolyl compounds are described in the following disclosures.

Biocryst Pharmaceuticals U.S. Pat. No. 6,653,340 titled "Compounds useful in the complement, coagulat and kallikrein pathways and method for their preparation" describes fused bicyclic ring compounds that are potent inhibitors of Factor D. Development of the Factor D inhibitor BCX1470 was discontinued due to lack of specificity and short half-life of the compound.

Novartis PCT patent publication WO2012/093101 titled "Indole compounds or analogues thereof useful for the treatment of age-related macular degeneration" describes certain Factor D inhibitors. Additional Factor D inhibitors are described in Novartis PCT patent publications WO2014/002051, WO2014/002052, WO2014/002053, WO2014/002054, WO2014/002057, WO2014/002058, WO2014/002059, WO2014/005150, and WO2014/009833.

Bristol-Myers Squibb PCT patent publication WO2004/045518 titled "Open chain prolyl urea-related modulators of androgen receptor function" describes open chain prolyl urea and thiourea related compounds for the treatment of androgen receptor-associated conditions, such as age-related diseases, for example, sarcopenia.

Japan Tobacco Inc. PCT patent publication WO1999/048492 titled "Amide derivatives and nociceptin antagonists" describes compounds with a proline-like core and aromatic substituents connected to the proline core through amide linkages useful for the treatment of pain.

Ferring B. V. and Yamanouchi Pharmaceutical Co. lTD. PCT patent publication WO1993/020099 titled "CCK and/or gastrin receptor ligands" describes compounds with a proline-like core and heterocyclic substituents connected to the proline core through amide linkages for the treatment of, for example, gastric disorders or pain.

Alexion Pharmaceuticals PCT patent publication WO1995/029697 titled "Methods and compositions for the treatment of glomerulonephritis and other inflammatory diseases" discloses antibodies directed to C5 of the complement pathway for the treatment of glomerulonephritis and inflammatory conditions involving pathologic activation of the complement system. Alexion Pharmaceutical's anti-C5 antibody eculizumab (Soliris®) is currently the only complement-specific antibody on the market, and is the first and only approved treatment for paroxysmal nocturnal hemoglobinuria (PNH).

On Feb. 25, 2015, Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders" and U.S. patent application Ser. No. 14/630,959 titled "Factor D Inhibitors Useful for Treating Infectious Disorders."

Given the wide variety of medical disorders that are caused by detrimental immune or inflammatory responses, new uses and compounds are needed for medical treatment. In one aspect, new uses and compounds are needed to mediate the complement pathway, and for example, which act as Factor D inhibitors for treatment of disorders in a host, including a human, associated with misregulation of the complement cascade, or with undesired result of the complement cascade performing its normal function.

SUMMARY

This invention includes an active compound of Formula I, Formula I' or Formula I" or a pharmaceutically acceptable salt or composition thereof, wherein at least one of $R^{12}$ or $R^{13}$ on the A group is an aryl, heteroaryl or heterocycle substituent, for example $R^{32}$. In one embodiment, an active compound or its salt or composition, as described herein is used to treat a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

These compounds can be used to treat such condition in a host in need thereof, typically a human. The active compound may act as an inhibitor of the complement factor D cascade. In one embodiment, a method for the treatment of such a disorder is provided that includes the administration of an effective amount of a compound of Formula I, Formula I' or Formula I" or a pharmaceutically acceptable salt thereof, optionally in a pharmaceutically acceptable carrier, as described in more detail below.

In one embodiment, the disorder is associated with the alternative complement cascade pathway. In yet another embodiment, the disorder is associated with the complement classical pathway. In a further embodiment, the disorder is associated with the complement lectin pathway. Alternatively, the active compound or its salt or prodrug may act through a different mechanism of action than the complement cascade, or in particular as a complement factor D inhibitor, to treat the disorder described herein.

In one embodiment, a method for the treatment of paroxysmal nocturnal hemoglobinuria (PNH) is provided that includes the administration of an effective amount of a compound to a host of Formula I, Formula I' or Formula I" or a pharmaceutically acceptable salt thereof, optionally in a pharmaceutically acceptable carrier. In another embodiment, a method for the treatment of wet or dry age-related macular degeneration (AMD) in a host is provided that includes the administration of an effective amount of a compound of Formula I, Formula I' or Formula I" or a pharmaceutically acceptable salt thereof, optionally in a pharmaceutically acceptable carrier. In another embodiment, a method for the treatment of rheumatoid arthritis in a host is provided that includes the administration of an effective amount of a compound of Formula I, Formula I' or Formula I" or a pharmaceutically acceptable salt thereof, optionally in a pharmaceutically acceptable carrier. In another embodiment, a method for the treatment of multiple sclerosis in a host is provided that includes the administration of an effective amount of a compound of Formula I, Formula I' or Formula I" or a pharmaceutically acceptable salt thereof, optionally in a pharmaceutically acceptable carrier.

In other embodiments, an active compound or its salt or prodrug as described herein can be used to treat fatty liver and conditions stemming from fatty liver, nonalcoholic steatohepatitis (NASH), liver inflammation, cirrhosis, and liver failure, dermatomyocitis, or amyotrophic lateral sclerosis.

The active compound or its pharmaceutically acceptable salt, prodrug or a pharmaceutical composition thereof as disclosed herein is also useful for administration in combination or alternation with a second pharmaceutical agent for use in ameliorating or reducing a side effect of the second pharmaceutical agent. For example, in one embodiment, the active compound may be used in combination with an adoptive cell transfer therapy to reduce an inflammatory response associated with such therapy, for example, a cytokine mediated response such as cytokine response syndrome. In one embodiment, the adoptive cell transfer therapy is a chimeric antigen receptor T-Cell (CAR T) or a dendritic cell used to treat a hematologic or solid tumor, for example, a B-cell related hematologic cancer. In one embodiment, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19. In one embodiment, the associated inflammatory response is a cytokine mediated response.

Another embodiment is provided that includes the administration of an effective amount of an active compound or a pharmaceutically acceptable salt thereof, optionally in a pharmaceutically acceptable carrier to a host to treat an ocular, pulmonary, gastrointestinal, or other disorder that can benefit from topical or local delivery.

Any of the compounds described herein (Formula I, Formula I' or Formula I") can be administered to the eye in any desired form of administration, including via intravitreal, intrastromal, intracameral, sub-tenon, sub-retinal, retro-bulbar, peribulbar, suprachorodial, choroidal, subchoroidal, conjunctival, subconjunctival, episcleral, posterior juxtascleralscleral, circumcorneal, and tear duct injections, or through a mucus, mucin, or a mucosal barrier, in an immediate or controlled release fashion.

In other embodiments of the invention, an active compound provided herein can be used to treat or prevent a disorder in a host mediated by complement factor D, or by an excessive or detrimental amount of the complement-C3 amplification loop of the complement pathway. As examples, the invention includes methods to treat or prevent complement associated disorders that are induced by antibody-antigen interactions, a component of an immune or autoimmune disorder or by ischemic injury. The invention also provides methods to decrease inflammation or an immune response, including an autoimmune response, where mediated or affected by factor D.

In another embodiment, a method is provided for treating a host, typically a human, with a disorder mediated by the complement system, that includes administration of a prophylactic antibiotic or vaccine to reduce the possibility of a bacterial infection during the treatment using one of the compounds described herein. In certain embodiments, the host, typically a human, is given a prophylactic vaccine prior to, during or after treatment with one of the compounds described herein. In certain embodiments, the host, typically a human, is given a prophylactic antibiotic prior to, during or after treatment with one of the compounds described herein. In some embodiment, the infection is a meningococcal infection (e.g., septicemia and/or meningitis), an *Aspergillus* infection, or an infection due to an encapsulated organism, for example, *Streptococcus pneumoniae* or *Haemophilus* influenza type b (Hib), especially in children. In other embodiments, the vaccine or antibiotic is administered to the patient after contracting an infection due to, or concommitent with inhibition of the complement system.

The disclosure provides a compound of Formula I.

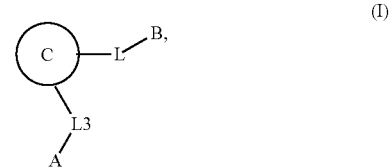

or a pharmaceutically acceptable composition, salt, isotopic analog, or prodrug thereof.

A is selected from A1, A1' and A2.
B is selected from B1, B1', B2, B3, and B4.
C is selected from C1, C1', C2, C3, and C4.
L is selected from L1, L1', L2, and L2'.
L3 is selected from L4 and L5.
At least one of A, B, C, L, or L3 is selected from A2, B3, C3, L2, L2', or L5.
Or at least one of A, B, C, L, or L3 is selected from A2, B3, C4, L2, L2', or L5
If C is C1, C1' or C2, then Formula I includes at least one of A2, B3, L2, L2' or L5.
If C is C3, then Formula I can be any of A, B, L or L3.
C1 is

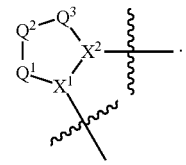

$Q^1$ is $N(R^1)$ or $C(R^1R^{1'})$.
$Q^2$ is $C(R^2R^{2'})$, $C(R^2R^{2'})$—$C(R^2R^{2'})$, S, O, $N(R^2)$ or $C(R^2R^{2'})O$.
$Q^3$ is $N(R^3)$, S, or $C(R^3R^{3'})$.
$X^1$ and $X^2$ are independently N, CH, or CZ, or $X^1$ and $X^2$ together are C=C.
$Q^1$, $Q^2$, $Q^3$, $X^1$, and $X^2$ are selected such that a stable compound results.
Z is F, Cl, $NH_2$, $CH_3$, $CH_2D$, $CHD_2$, or $CD_3$.
$R^1$, $R^{1'}$, $R^2$, $R^{2'}$, $R^3$, and $R^{3'}$ are independently replaced at each occurrence, as appropriate, and only where a stable compound results, from hydrogen, halogen, hydroxyl, nitro, cyano, amino, $C_1$-$C_6$alkyl, $C_2$-$C_6$alkenyl, $C_2$-$C_6$alkynyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkyl$NR^9R^{10}$, —$C(O)OR^9$, —$OC(O)R^9$, —$NR^9C(O)R^{10}$, —$C(O)NR^9R^{10}$, —$OC(O)NR^9R^{10}$, —$NR^9C(O)OR^{10}$, $C_1$-$C_2$haloalkyl, and $C_1$-$C_2$haloalkoxy.

$R^9$ and $R^{10}$ are independently replaced at each occurrence from hydrogen, $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl).

In alternative embodiments, $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently replaced from N, O, or S; $R^2$ and $R^{2'}$ may be taken together to form a 3- to 6-membered carbocyclic spiro ring; or $R^2$ and $R^{2'}$ may be taken together to form a 3- to 6-membered heterocyclic spiro ring; each of which spiro ring each of which ring may be unsubstituted or substituted with 1 or more substituents independently replaced from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^2$ may be taken together to form a 3-membered carbocyclic ring; $R^1$ and $R^2$ may be taken together to form a 4- to 6-membered carbocyclic or aryl ring or a 4- to 6-membered heterocyclic or heteroaryl ring containing 1 or 2 heteroatoms independently replaced from N, O, and S; or $R^2$ and $R^3$, if bound to adjacent carbon atoms, may be taken together to form a 3- to 6-membered carbocyclic or aryl ring or a 3- to 6-membered heterocyclic or heteroaryl ring; each of which ring may be unsubstituted or substituted with 1 or more substituents independently replaced from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^{1'}$, $R^2$ and $R^{2'}$, or $R^3$ and $R^{3'}$ can be taken together to form a carbonyl group. In alternative embodiments, $R^1$ and $R^2$ or $R^{2'}$ and $R^3$ can be taken together to form a carbon-carbon double bond.

Any of the structures illustrated herein, e.g., A1, A1', A2, B1, B1', B2, B3, B4, C1, C1', C2, C3, C4, L1, L1', L2, L2', L4 or L5 can be optionally substituted with 0, 1, 2, 3, or 4, as appropriate, and independently, of an $R^{48}$ substituent.

Non-limiting examples of C1 include the structures of FIG. 1, wherein R and R' (see FIG. 5) are independently replaced from H, alkyl, cycloalkyl, cycloalkylalkyl, heterocycle, heterocycloalkyl, aryl, arylalkyl, heteroaryl, heteroarylalkyl wherein each group can be optionally substituted or any other substituent group herein that provides the desired properties. In some embodiments, the ring includes one or more chiral carbon atoms. The invention includes embodiments in which the chiral carbon can be provided as an enantiomer, or mixtures of enantiomers, including a racemic mixture. Where the ring includes more than one stereocenter, all of the enantiomers and diastereomers are included in the invention as individual species, unless stereochemistry is specified.

In one embodiment, C1 is C1'.

Non-limiting examples of C1' include the structures of FIG. 2.

In one embodiment, a methyl group in a structure illustrated in FIG. 2 can be replaced with a different alkyl group, as defined herein. In another embodiment, the fluoro atoms in the structures illustrated in FIG. 2 can be replaced with any other halogen. As indicated above, any of the structures illustrated in FIG. 2 or otherwise can be optionally substituted with 0, 1, 2, 3, or 4, as appropriate, and independently, with an $R^{48}$ substituent.

C2 is selected from:

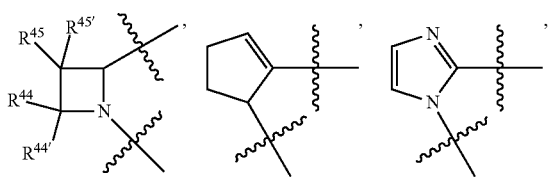

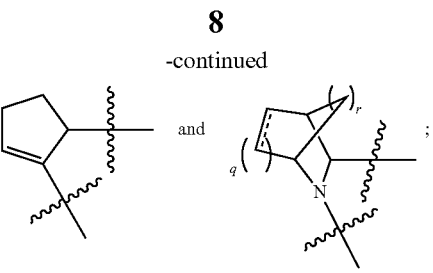

wherein q is 0, 1, 2 or 3 and r is 1, 2 or 3.

$R^{44}$, $R^{44'}$, $R^{45}$, $R^{45'}$ are independently hydrogen, hydroxyl, amino, cyano, halogen, alkyl, cycloalkyl, cycloalkylalkyl, heterocycle, heterocycloalkyl, aryl, arylalkyl, heteroaryl, or heteroarylalkyl; wherein each group can be optionally substituted, and such that a stable C2 results.

In one embodiment, $R^{44}$ and $R^{44'}$, $R^{45}$ and $R^{45'}$ or two $R^{47}$ groups can be taken together to form a carbonyl group.

In an alternate embodiment, $R^{44}$ and $R^{44'}$ or $R^{45}$ and $R^{45'}$ or $R^{46}$ and $R^{46'}$ can be taken together to form an optionally substituted 3- to 6-membered carbocyclic spiro ring or a 3- to 6-membered heterocyclic spiro ring containing 1 or 2 heteroatoms independently replaced from N, O, or S.

In one embodiment, $R^{44}$ and $R^{45}$ or $R^{44'}$ and $R^{45'}$ can be taken together to form a 4- to 6-membered carbocyclic or aryl ring or a 4- to 6-membered heterocyclic or heteroaryl ring; each of which ring may be unsubstituted or substituted with 1 or more substituents.

Non-limiting examples of C2 include the structures of FIG. 3.

C3 is selected from:

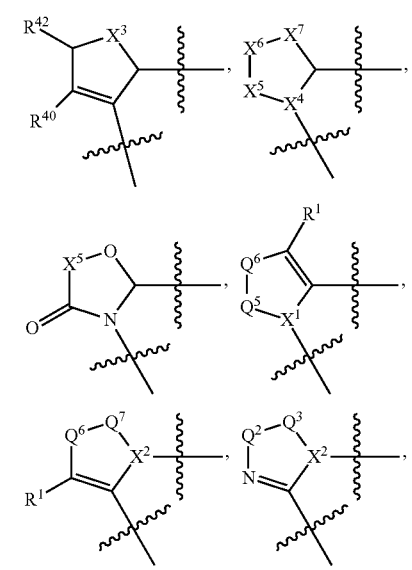

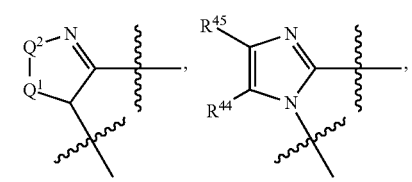

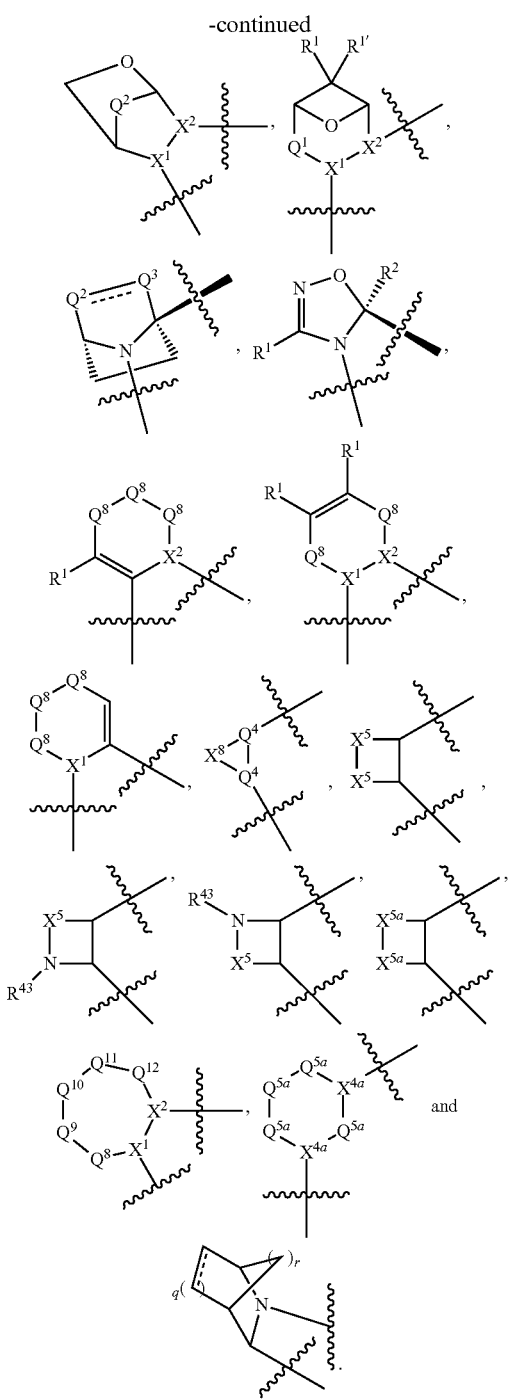

X³ is C(R¹R¹').
X⁴ is N or CH.
X⁴a is N, CH or CZ.
X⁵ and X⁶ are C(R¹R¹').
In alternative embodiments, X⁴ and X⁵ or X⁵ and X⁶ together are C=C.
X⁷ is SO or SO₂.
X⁸ is C(R¹R¹') or N(R⁴³)
X⁵a is C(R¹R¹') or O.
Q⁴ is N or CH.
Q⁵ is N(R⁴⁷) or C(R⁴⁶R⁴⁶')
Q⁵ᵃ is C(R⁴⁷R⁴⁷), N(R⁴⁷), O, S, SO, or SO₂.
Q⁶ is N(R⁴⁷), C(R⁴⁶R⁴⁶'), S, or O.
Q⁷ is C(R⁴⁶R⁴⁶'), S or N(R⁴⁷).

Q⁸, Q⁹, Q¹⁰, Q¹¹ and Q¹² are each independently C(R²R²'), S, SO, SO₂, O, N(R²) B(R⁵⁰), Si(R⁴⁹)₂, however if X¹ is N and X² is CH then L and B taken together cannot be anisole substituted in the 4 position.

In a typical embodiment, no more than one heteroatom is in a three or four membered C3 and no more than one, two or three heteroatoms can be in a five, six or seven membered C3. It is in general known by those of skill in the art which combinations of several heteroatoms will not form a stable ring system. For example, those of skill in the art would understand that the C3 ring system would not normally contain an —O—O—, —O—S—, —Si—Si—, —B—B—, —B—Si—, bond.

R⁴⁰ is hydrogen, alkyl, cycloalkyl, cycloalkylalkyl, heterocycle, heterocycloalkyl, aryl, arylalkyl, heteroaryl, heteroarylalkyl wherein each group can be optionally substituted.

R⁴² is halo, hydroxy, C₁-C₆alkoxy, C₁-C₆haloalkoxy, —SH, or —S(C₁-C₆alkyl).

R⁴³ is hydrogen, acyl, alkyl, cycloalkyl, cycloalkylalkyl, heterocycle, heterocycloalkyl, aryl, arylalkyl, heteroaryl, heteroarylalkyl wherein each group can be optionally substituted.

R⁴⁶ and R⁴⁶' are independently hydrogen, alkyl, cycloalkyl, cycloalkylalkyl, heterocycle, heterocycloalkyl, aryl, arylalkyl, heteroaryl, or heteroarylalkyl wherein each group can be optionally substituted and at least one of R⁴⁶ or R⁴⁶' is not hydrogen.

R⁴⁷ is hydrogen, acyl, alkyl, cycloalkyl, cycloalkylalkyl, heterocycle, heterocycloalkyl, aryl, arylalkyl, heteroaryl, or heteroarylalkyl wherein each group can be optionally substituted.

R⁴⁹ is halo, hydrogen, alkyl, cycloalkyl, cycloalkylalkyl, heterocycle, heterocycloalkyl, aryl, arylalkyl, heteroaryl, or heteroarylalkyl wherein each group can be optionally substituted or two R⁴⁹ groups can be taken together to form a double bond that can be optionally substituted.

R⁵⁰ is hydroxy or C₁-C₆alkyloxy.

In one embodiment, the bridged heterocyclic C3 compounds can be optionally substituted.

In one embodiment, X¹ and Q⁸ or Q⁸ and Q⁹ or Q⁹ and Q¹⁰ or Q¹⁰ and Q¹¹ or Q¹¹ and Q¹² or Q¹² and X² can form a carbon-carbon double bond.

In one embodiment, two Q⁵ᵃ groups or a X⁴ᵃ and a Q⁵ᵃ group can form a carbon-carbon double bond.

All variables, including but not limited to X¹, X², X³, X⁴, X⁵, X⁵a, X⁶, X⁷, X⁸, Q¹, Q², Q³, Q⁴, Q⁵, Q⁶, Q⁷, Q⁸, Q⁹, Q¹⁰, Q¹¹, Q¹², R¹, R⁴⁰, R⁴², R⁴³, R⁴⁴, R⁴⁴', R⁴⁵, and R⁴⁵' are independently replaced at each occurrence, as appropriate, and only where a stable compound results. For example, when C3 is a 7-membered ring and comprises silicon or boron, the ring will only comprise one Si(R⁴⁹)₂ or B(R⁵⁰) moiety. In addition, 3, 4, 5, 6 and 7-membered rings will not comprise —O—O— or —O—S— bonds.

Non-limiting examples of C3 include the structures of FIG. 4.

In one embodiment, the methyl groups in the structures illustrated in FIG. 4 can be replaced with a different alkyl group, as defined herein. In another embodiment, the fluoro atoms in the structures illustrated above can be replaced with another halo. In another embodiment, halo can be chloro. As indicated above, any of the structures in FIG. 4 or herein can be optionally substituted with 0, 1, 2, 3, or 4, as appropriate, and independently, with an R⁴⁸ substituent.

In an alternate embodiment, the central core moiety, C3, can comprise a small mimetic of a beta-turn such as a benzodiazepine, a Friedinger lactam, a 2-oxo-1,3-oxazolidine-4-caroxylate or a β-D-glucose scaffold. See, De Marco, R. et al., "In-peptide synthesis of di-oxazolidinone and dehydroamino acid-oxazolidinone motifs as β-turn inducers", J. Org. Biomol. Chem., 2013, 11, 4316-4326, Hirschmann, R. F. et al., The β-D-Glucose Scaffold as a β-Turn Mimetic, Accounts Chem. Res., 2009, 42, 1511-1520 and Smith, A. B, et al., Accounts of Chem. Res., 2011, 44, 180-193. In another embodiment, the central core moiety, C, can comprise a reverse turn mimetic that can include, but is not limited to; a non-peptidic residue, a metal chelation based mimic, or a foldamer. See, Nair, R. V. et al., "Synthetic turn mimetics and hairpin nucleators: Quo Vadimus?", Chem. Comm., 2014, 50, 13874-13884. In some embodiments, the central core moiety, C, can comprise a conformationally constrained cyclic amino acid including but not limited to a (S)- or (R)-α-trifluoromethyl pyroglutamic acid derivative. See, Chaume, G. et al., "Concise access to enantiopure (S)- or (R)-α-trifluoromethyl pyroglutamic acids from ethyl trifluoropyruvate-base chiral CF3-oxazolidines (Fox)", J. Fluor. Chem., 2008, 129, 1104-1109 and Andre, C. et al., "(S)-ABOC: A Rigid Bicyclic j-Amino Acid as Turn Inducer", Org. Lett., 2012, 14, 960-963. In some embodiments, the central core moiety, C, can comprise a monomeric unit of a foldamer such as, but not limited to an oxazolidin-2-one. See, Tomasii, C., Angelicim G. and Castellucci, N., "Foldamers Based on Oxazolidin-2-ones", Eur. J. Org. Chem., 2011, 3648-3669.

Examples of central core small mimetics of a beta-turn, beta turn inducers, reverse turn mimetics and foldamer monomers include, but are not limited to the structures of FIG. 5.

C4 is selected from

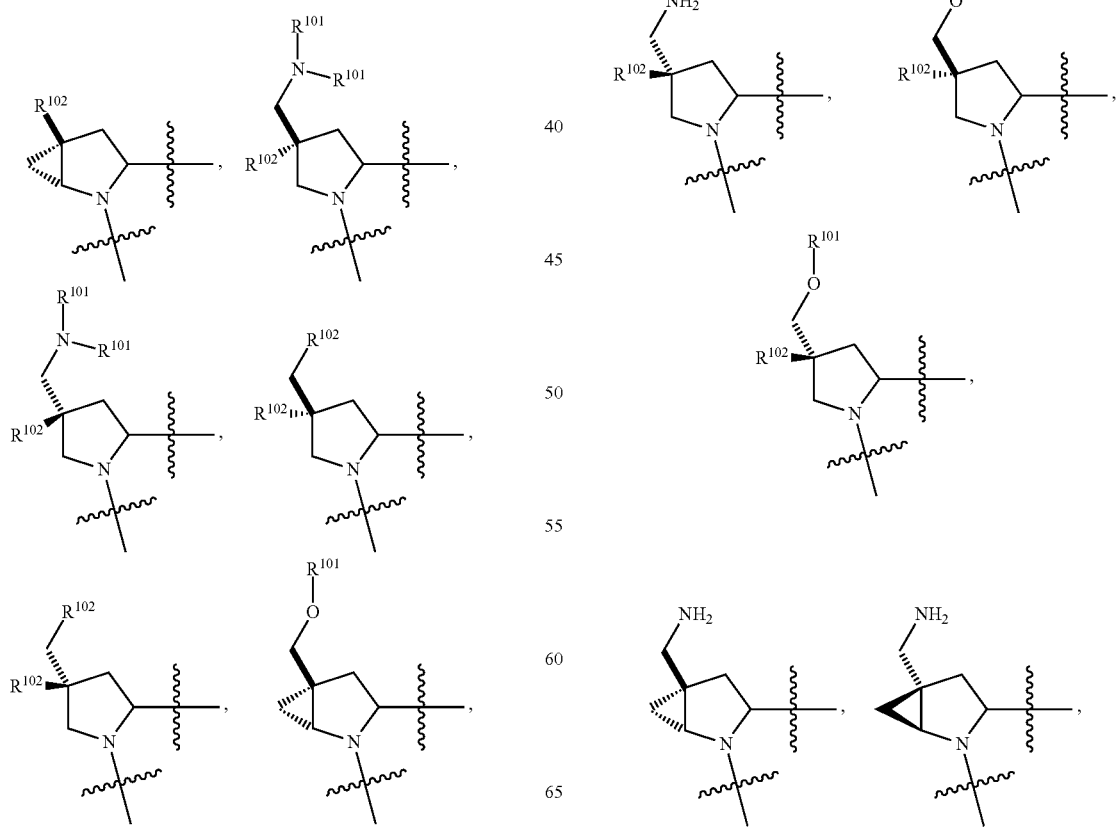

-continued
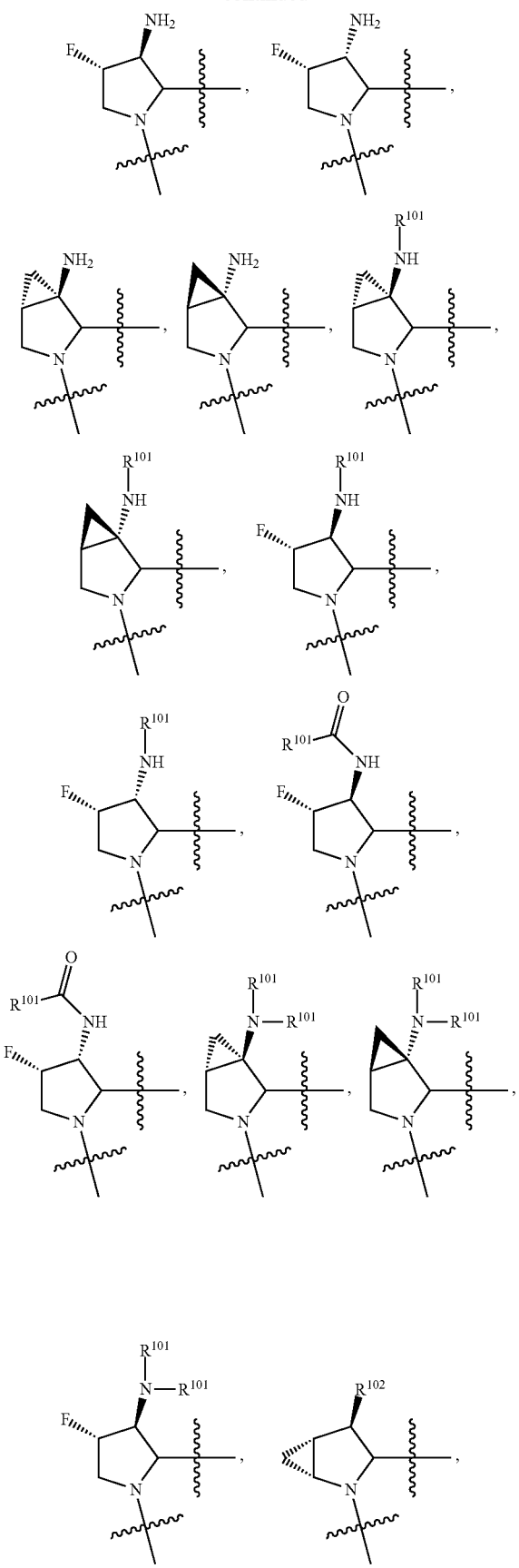
-continued
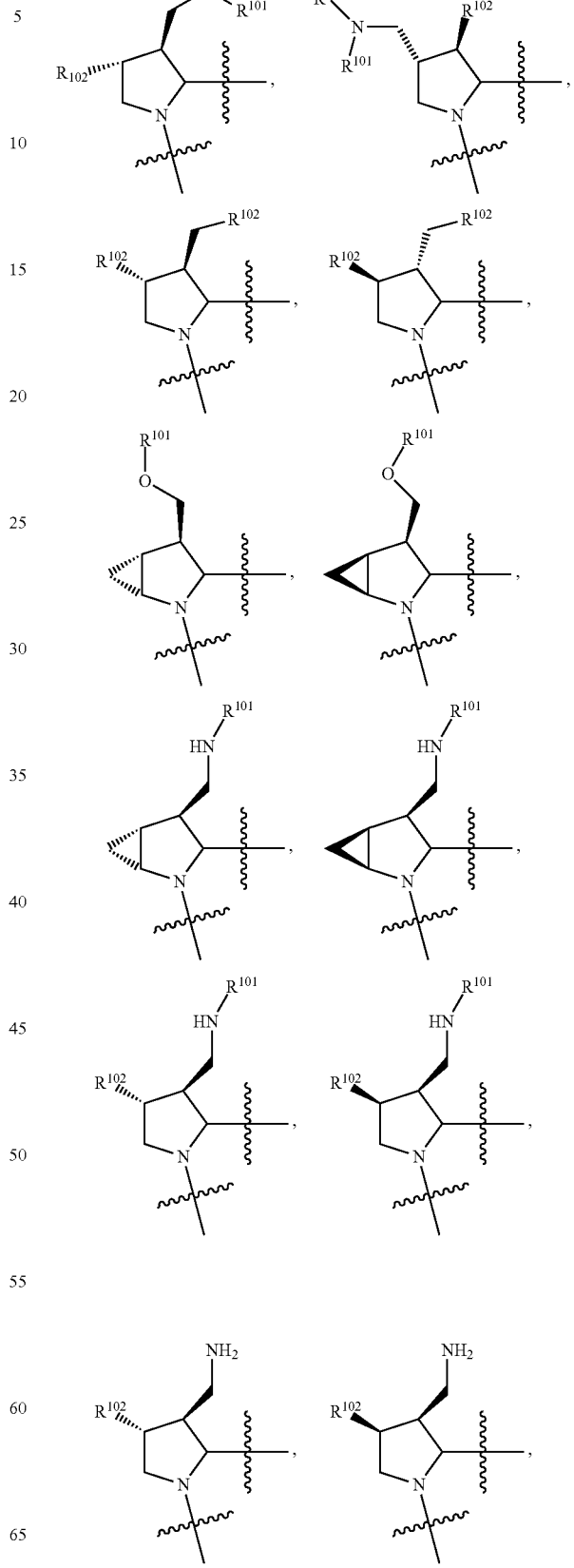

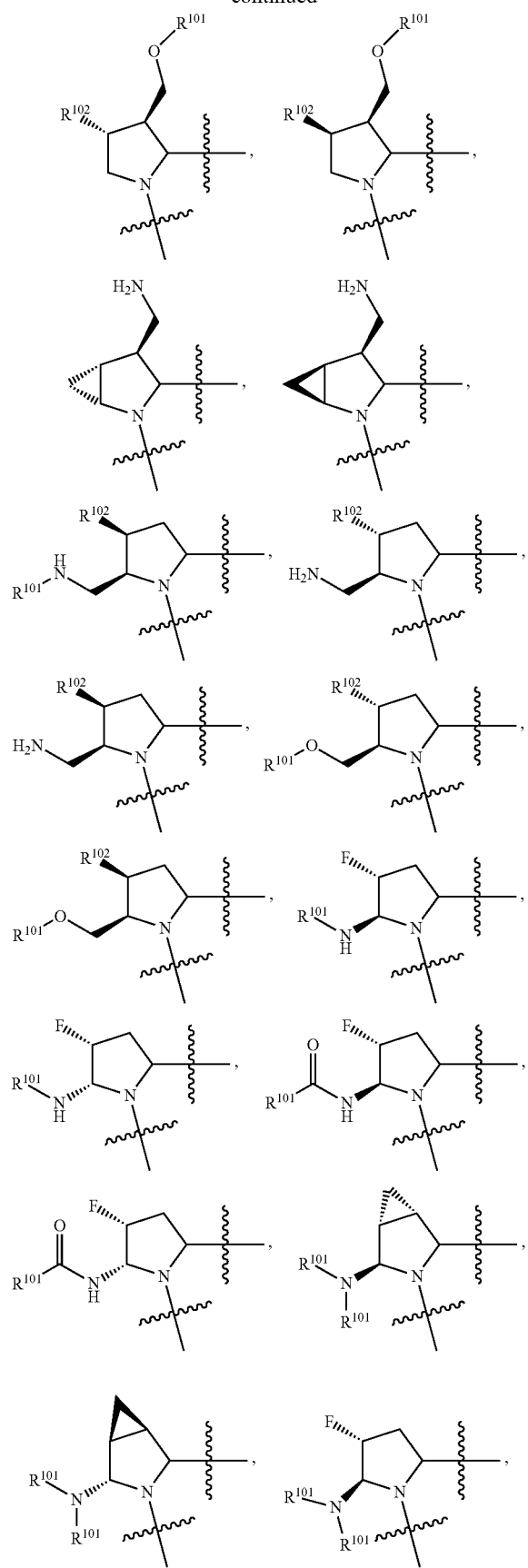
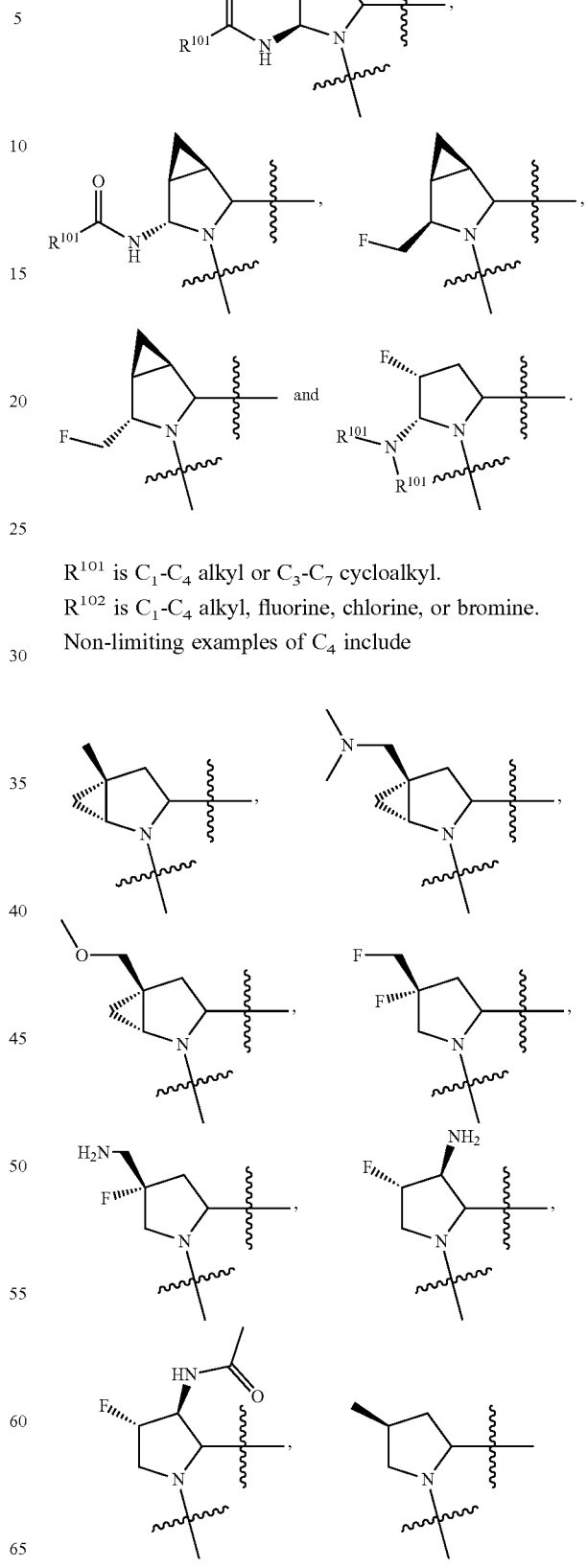
$R^{101}$ is $C_1$-$C_4$ alkyl or $C_3$-$C_7$ cycloalkyl.
$R^{102}$ is $C_1$-$C_4$ alkyl, fluorine, chlorine, or bromine.
Non-limiting examples of $C_4$ include A1 is selected from:
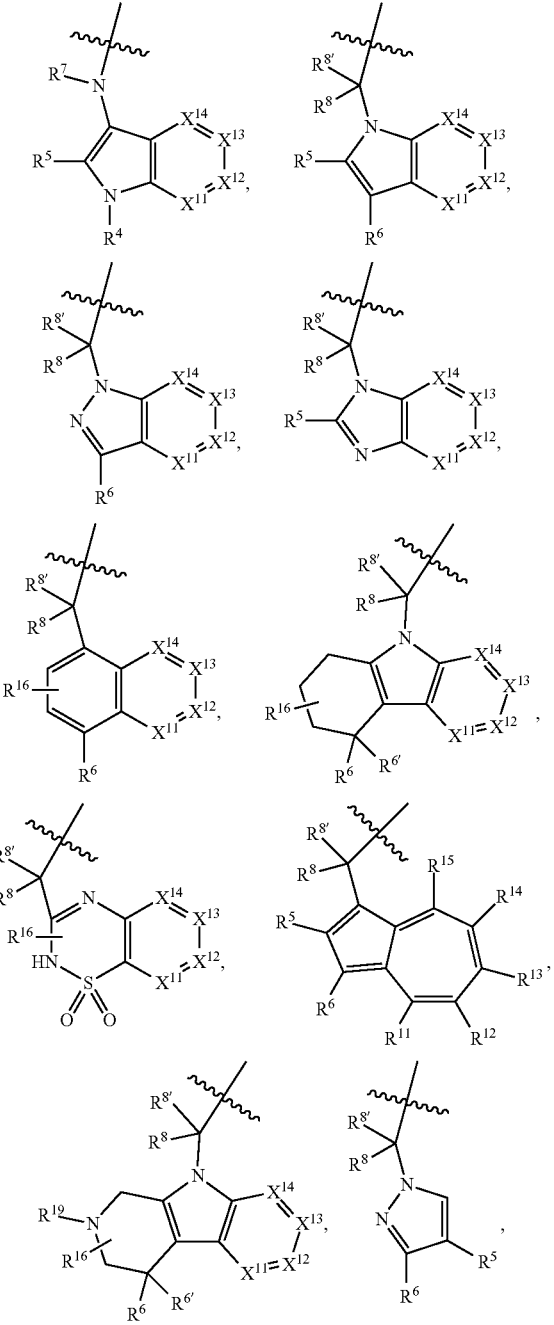
-continued
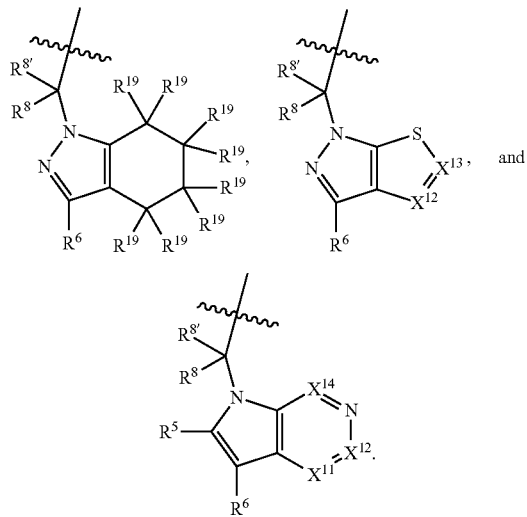
Non-limiting examples of A1 include:
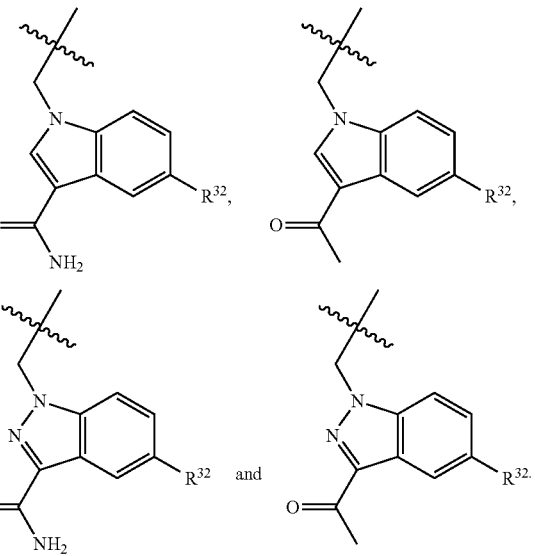
In one embodiment, A1 is A1'.
Non-limiting examples of A1' include the structures of FIG. 6.
A2 is selected from:
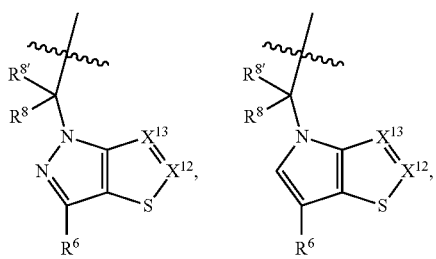
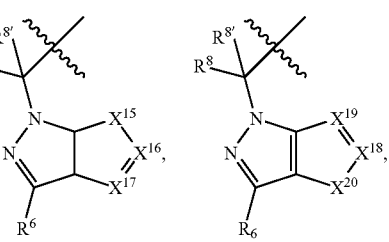

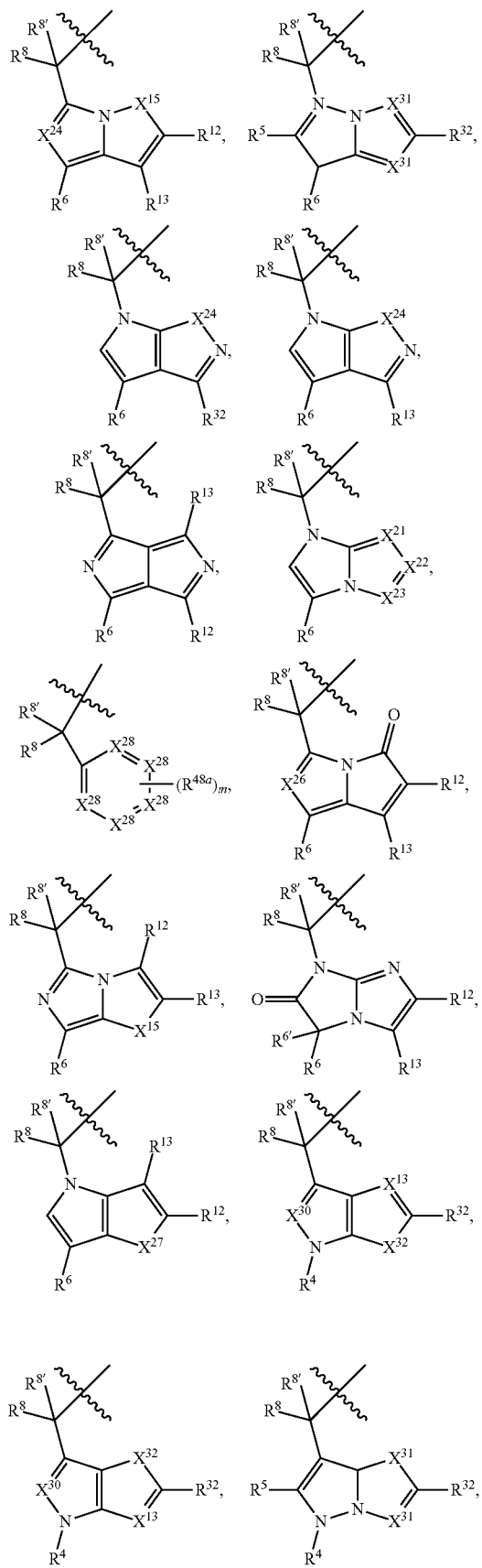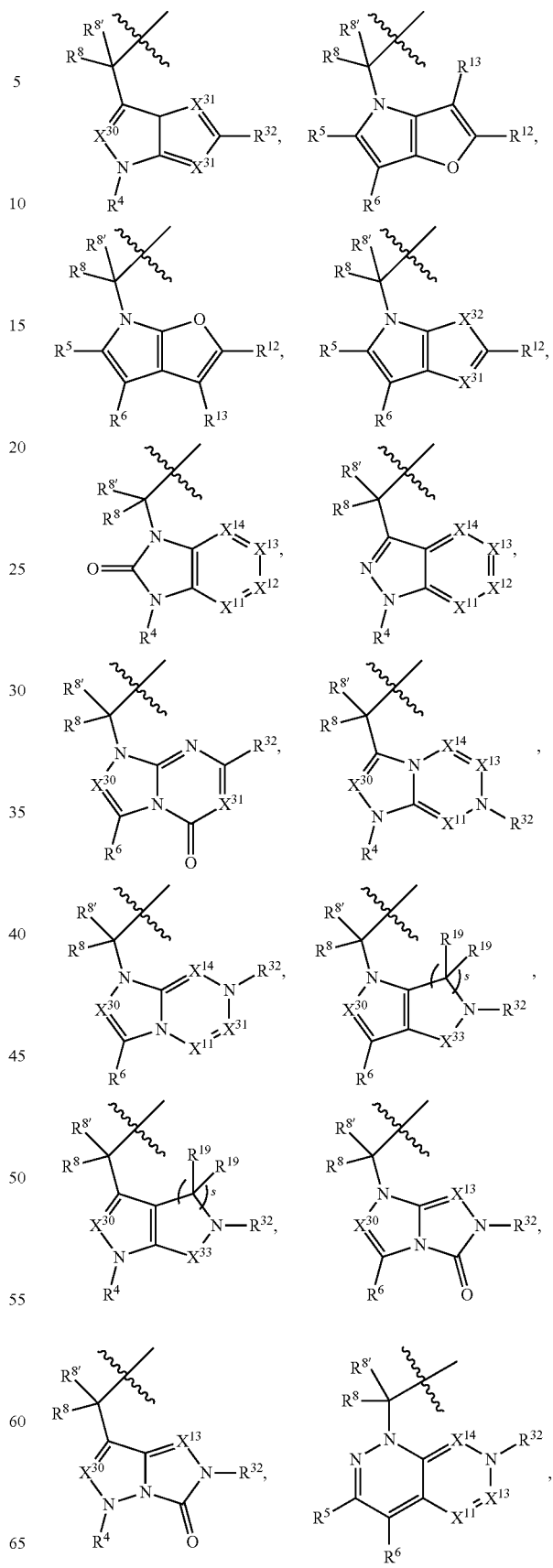

-continued

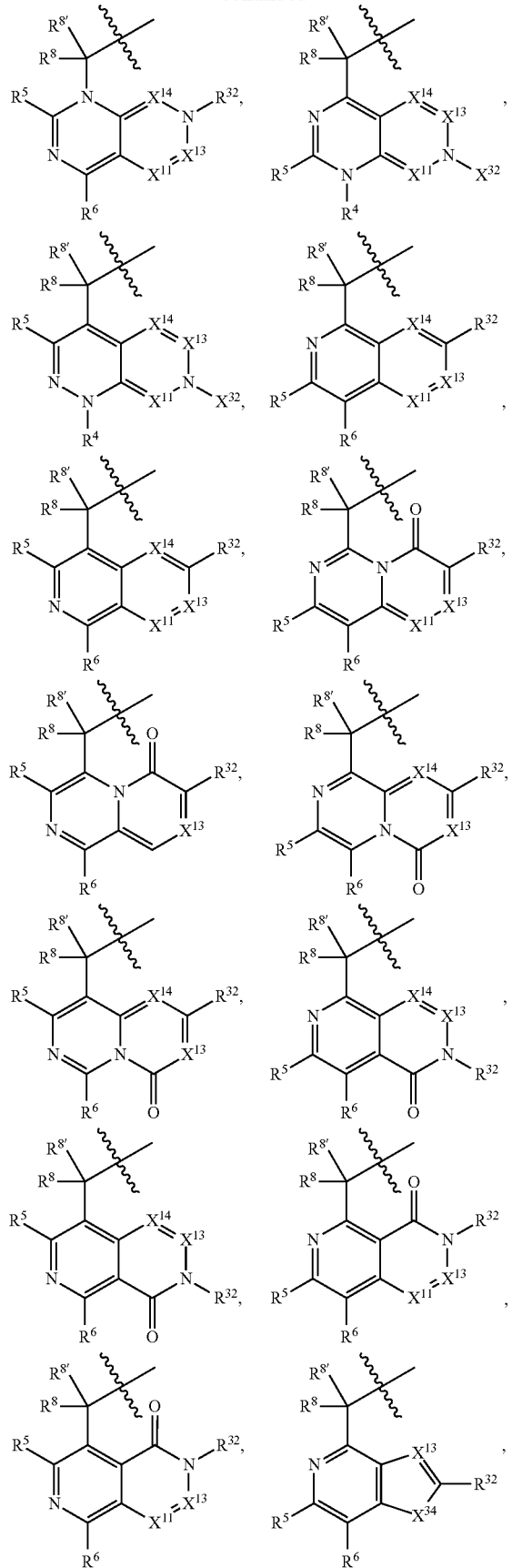

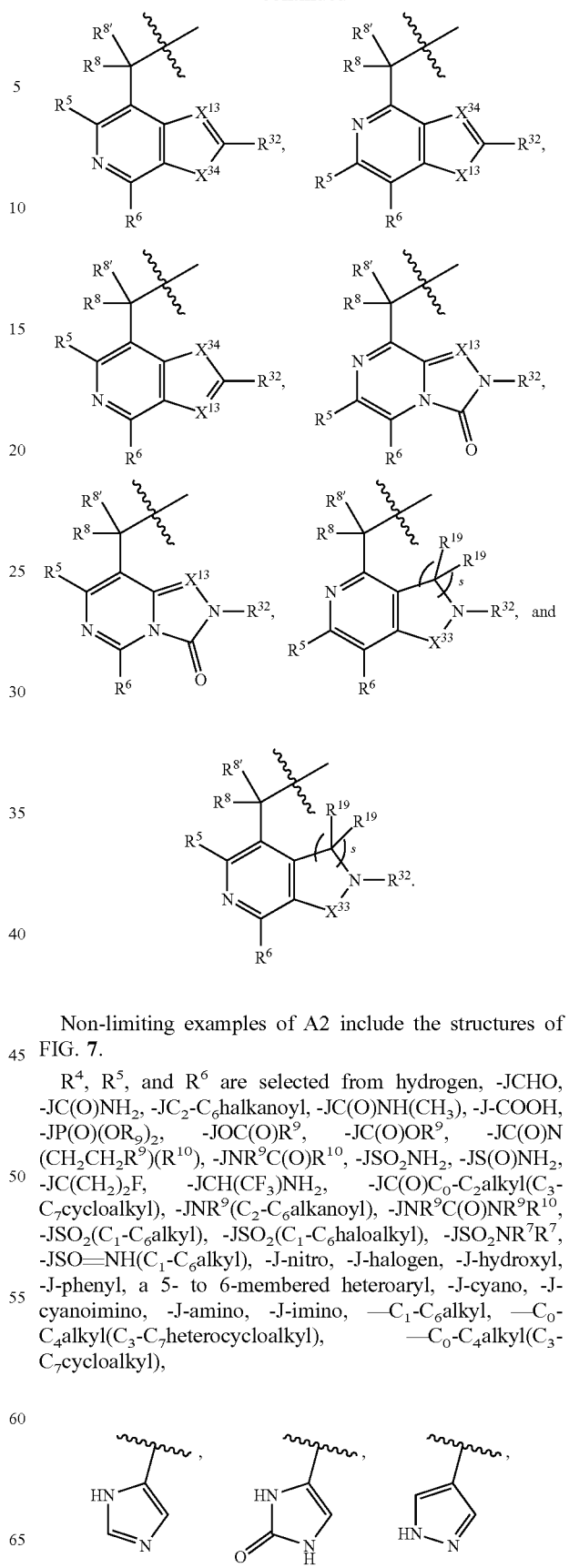

Non-limiting examples of A2 include the structures of FIG. 7.

$R^4$, $R^5$, and $R^6$ are selected from hydrogen, -JCHO, -JC(O)NH$_2$, -JC$_2$-C$_6$halkanoyl, -JC(O)NH(CH$_3$), -J-COOH, -JP(O)(OR$_9$)$_2$, -JOC(O)R$^9$, -JC(O)OR$^9$, -JC(O)N(CH$_2$CH$_2$R$^9$)(R$^{10}$), -JNR$^9$C(O)R$^{10}$, -JSO$_2$NH$_2$, -JS(O)NH$_2$, -JC(CH$_2$)$_2$F, -JCH(CF$_3$)NH$_2$, -JC(O)C$_0$-C$_2$alkyl(C$_3$-C$_7$cycloalkyl), -JNR$^9$(C$_2$-C$_6$alkanoyl), -JNR$^9$C(O)NR$^9$R$^{10}$, -JSO$_2$(C$_1$-C$_6$alkyl), -JSO$_2$(C$_1$-C$_6$haloalkyl), -JSO$_2$NR$^7$R$^7$, -JSO=NH(C$_1$-C$_6$alkyl), -J-nitro, -J-halogen, -J-hydroxyl, -J-phenyl, a 5- to 6-membered heteroaryl, -J-cyano, -J-cyanoimino, -J-amino, -J-imino, —C$_1$-C$_6$alkyl, —C$_0$-C$_4$alkyl(C$_3$-C$_7$heterocycloalkyl), —C$_0$-C$_4$alkyl(C$_3$-C$_7$cycloalkyl),

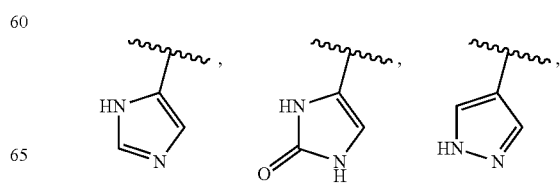

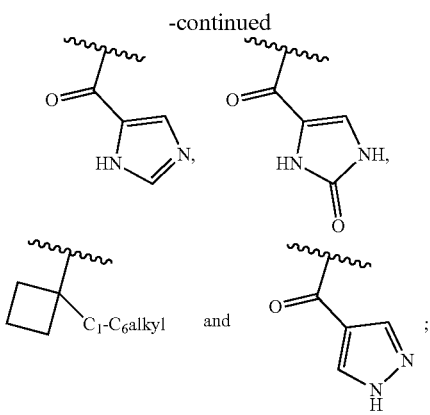

each of which R⁴, R⁵ and R⁶ other than hydrogen, nitro, halogen, cyano, cyanoimino, or —CHO, is unsubstituted or substituted with one or more of amino, imino, halogen, hydroxyl, cyano, cyanoimino, $C_1$-$C_2$alkyl, $C_1$-$C_2$alkoxy, —$C_0$-$C_2$alkyl(mono- and di-$C_1$-$C_4$alkylamino), $C_1$-$C_2$haloalkyl, and $C_1$-$C_2$haloalkoxy.

$R^{4'}$ is replaced from -JCHO, -JCONH$_2$, JC$_2$-C$_6$alkanoyl, -JSO$_2$NH$_2$, -JC(CH$_2$)$_2$F, -JCH(CF$_3$)NH$_2$, C$_1$-C$_6$alkyl, —C$_0$-C$_4$alkyl(C$_3$-C$_7$cycloalkyl), -JC(O)C$_0$-C$_2$alkyl(C$_3$-C$_7$cycloalkyl), JNR$^9$(C$_2$-C$_6$alkanoyl), JNR$^9$C(O)NR$^9$R$^{10}$,

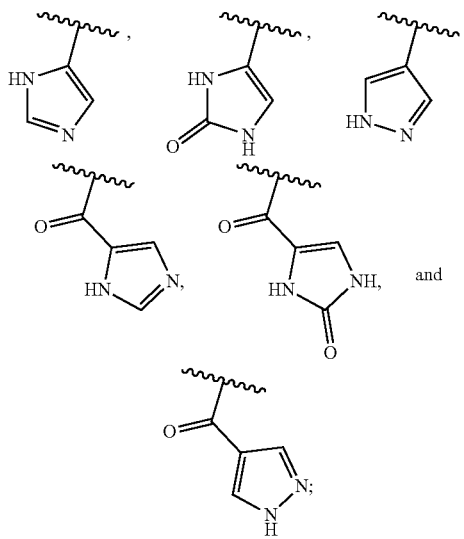

each of which $R^{4'}$ other than —CHO, is unsubstituted or substituted with one or more of amino, imino, halogen, hydroxyl, cyano, cyanoimino, $C_1$-$C_2$alkyl, $C_1$-$C_2$alkoxy, —$C_0$-$C_2$alkyl(mono- and di-$C_1$-$C_4$alkylamino), $C_1$-$C_2$haloalkyl, and $C_1$-$C_2$haloalkoxy.

$R^{6'}$ is hydrogen, halogen, hydroxyl, $C_1$-$C_4$alkyl, —$C_0$-$C_4$alkyl($C_3$-$C_7$cycloalkyl), or $C_1$-$C_4$alkoxy; or $R^6$ and $R^{6'}$ may be taken together to form an oxo, vinyl, or imino group.

$R^7$ is hydrogen, $C_1$-$C_6$alkyl, or —$C_0$-$C_4$alkyl($C_3$-$C_7$cycloalkyl).

$R^8$ and $R^{8'}$ are independently replaced from hydrogen, halogen, hydroxyl, $C_1$-$C_6$alkyl, —$C_0$-$C_4$alkyl($C_3$-$C_7$cycloalkyl), $C_1$-$C_6$alkoxy, and ($C_1$-$C_4$alkylamino)$C_0$-$C_2$alkyl; or $R^8$ and $R^{8'}$ are taken together to form an oxo group; or $R^8$ and $R^{8'}$ can be taken together with the carbon that they are bonded to form a 3-membered carbocyclic ring.

$R^{16}$ is absent or is independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, —$C_0$-$C_4$alkyl(mono- and di-$C_1$-$C_6$alkylamino), —$C_0$-$C_4$alkyl($C_3$-$C_7$cycloalkyl), $C_1$-$C_2$haloalkyl, and $C_1$-$C_2$haloalkoxy.

$R^{19}$ is hydrogen, $C_1$-$C_6$alkyl, $C_2$-$C_6$alkenyl, $C_2$-$C_6$alkanoyl, —SO$_2$C$_1$-C$_6$alkyl, (mono- and di-$C_1$-$C_6$alkylamino)$C_1$-$C_4$alkyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), $C_0$-$C_4$alkyl(heteroaryl), and wherein $R^{19}$ other than hydrogen is unsubstituted or substituted with one or more substituents independently replaced from halogen, hydroxyl, amino, —COOH, and —C(O)O$C_1$-$C_4$alkyl.

$X^{11}$ is N or $CR^{11}$.
$X^{12}$ is N or $CR^{12}$.
$X^{13}$ is N or $CR^{13}$.
$X^{14}$ is N or $CR^{14}$.

No more than 2 of $X^{11}$, $X^{12}$, $X^{13}$, and $X^{14}$ are N.

One of $R^{12}$ and $R^{13}$ is replaced from $R^{31}$ and the other of $R^{12}$ and $R^{13}$ is replaced from $R^{32}$, however, each compound has at least one $R^{32}$. In an alternative embodiment, $R^{12}$ and $R^{13}$ are each independently selected from an $R^{32}$ moiety.

$R^{31}$ is replaced from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)OR$^9$, $C_1$-$C_6$thioalkyl, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$, each of which $R^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —CONH$_2$ $C_1$-$C_2$haloalkyl, and $C_1$-$C_2$haloalkoxy, and each of which $R^{31}$ is also optionally substituted with one substituent replaced from phenyl and 4- to 7-membered heterocycle containing 1, 2, or 3 heteroatoms independently replaced from N, O, and S; which phenyl or 4- to 7-membered heterocycle is unsubstituted or substituted with one or more substituents independently replaced from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_2$haloalkyl, and $C_1$-$C_2$haloalkoxy.

$R^{32}$ is selected from aryl, heteroaryl; saturated or unsaturated heterocycle; wherein the aryl, heteroaryl, saturated or unsaturated heterocycle ring can be optionally substituted. In certain illustrations, $R^{32}$ is depicted as $Z^{32}$, which is intended to be the same moiety.

$R^{11}$, $R^{14}$, and $R^{15}$ are independently replaced at each occurrence from hydrogen, halogen, hydroxyl, nitro, cyano, —O(PO)(OR$^9$)$_2$, —(PO)(OR$^9$)$_2$, $C_1$-$C_6$alkyl, $C_2$-$C_6$alkenyl, $C_2$-$C_6$alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), $C_2$-$C_6$alkynyl, $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), $C_2$-$C_6$alkanoyl, $C_1$-$C_6$alkoxy, $C_1$-$C_6$thioalkyl, —$C_0$-$C_4$alkyl (mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, and $C_1$-$C_2$haloalkoxy.

$X^{15}$ is NH, O, or S.
$X^{16}$ is $CR^{12}$.
$X^{17}$ is N or $CR^{13}$.
$X^{18}$ is $CR^{12}$.
$X^{19}$ is N or $CR^{13}$.
$X^{20}$ is NH or O.
$X^{21}$ is N or $CR^{14}$.

$X^{22}$ is N or $CR^{13}$.
$X^{23}$ is $CR^{12}$.
$X^{24}$ and $X^{25}$ are each independently O or S.
$X^{26}$ is N or $CR^{41}$.
$X^{27}$ is $CR^{12}$, NH or O.
$X^{28}$ is N or CH.
$X^{30}$ is N or $CR^{5}$.
$X^{31}$ is N, $C(R^{54})_2$ or $CR^{54}$.
$X^{32}$ is NH, $C(R^{54})_2$ or $CR^{54}$.
$X^{33}$ is —CO— or —SO— or —SO$_2$—.
$X^{34}$ is $CHR^{13}$, NH, O, or S.
No more than 2 of $X^{28}$ are N.
$R^{41}$ is hydrogen, $C_1$-$C_6$alkyl, or —($C_0$-$C_2$alkyl)($C_3$-$C_5$cycloalkyl).
$R^{48}$ is independently replaced from hydrogen, halogen, hydroxyl, nitro, cyano, amino, $C_1$-$C_6$alkyl, $C_1$-$C_6$haloalkyl, $C_2$-$C_6$alkenyl, $C_2$-$C_6$alkynyl, $C_1$-$C_6$thioalkyl, $C_1$-$C_6$alkoxy, -J$C_3$-$C_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$) -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$) -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)=NR$^{22}$, -JCH(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)NR$^{24}$R$^{25}$, -JNR$^9$C(O)R$^{21}$, -JC(O)R$^{21}$, -JNR$^9$C(O)NR$^{10}$R$^{22}$, —CCR$^{21}$, —(CH$_2$)$_{1-4}$OC(O)R$^{21}$, -JC(O)OR$^{23}$; each of which $R^{48}$ may be unsubstituted or substituted with one or more substituents independently replaced from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, —$C_0$-$C_4$alkyl($C_3$-$C_7$cycloalkyl), $C_1$-$C_6$alkoxy, —$C_0$-$C_4$alkyl(mono- and di-$C_1$-$C_4$alkylNR$^9$R$^{10}$), $C_1$-$C_6$alkylester, $C_1$-$C_4$alkylamino, $C_1$-$C_4$hydroxylalkyl, $C_1$-$C_2$haloalkyl, $C_1$-$C_2$haloalkoxy, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, $C_1$-$C_2$haloalkyl, and $C_1$-$C_2$haloalkoxy.
$R^{48a}$ is $R^{48}$, S(O)=NHR$^{21}$, SF$_5$, and JC(R$^9$)=NR$^{21}$ and SO$_2$OR$^{21}$.
$R^{54}$ is hydrogen, $C_1$-$C_6$alkyl, $C_2$-$C_6$alkenyl, $C_2$-$C_6$alkynyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkyl($C_3$-$C_7$cycloalkyl), (phenyl)$C_0$-$C_4$alkyl-, (heterocycloalkyl)$C_0$-$C_4$alkyl and (heteroaryl)$C_0$-$C_4$alkyl- wherein the groups can be optionally substituted.
s is 1 or 2.
L is selected from L1, L1' and L2.
L1 is a bond or is replaced from the formulas -continued $R^{17}$ is hydrogen, $C_1$-$C_6$alkyl, or —$C_0$-$C_4$alkyl($C_3$-$C_7$cycloalkyl) and $R^{18}$ and $R^{18'}$, are independently replaced from hydrogen, halogen, hydroxymethyl, and methyl; and m is 0, 1, 2, or 3.

In one embodiment, L1 is L1'.

Non-limiting examples of L1' include the structures of FIG. 8.

In one embodiment, the methyl groups in the structures illustrated in FIG. 8 can be replaced with another alkyl group, as defined herein.

L2 is selected from:

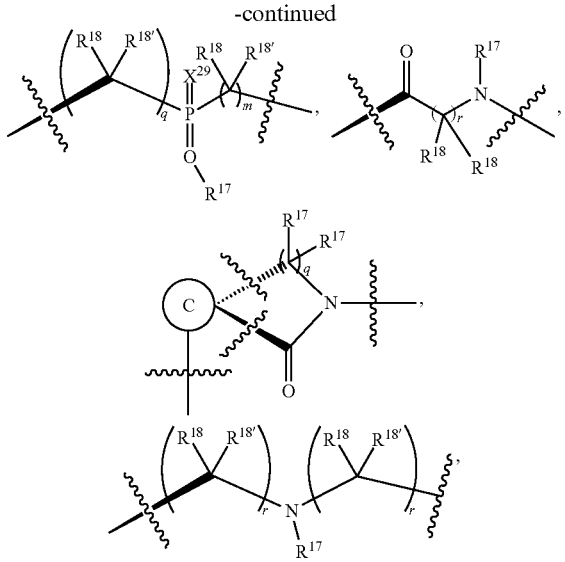

Or an optionally substituted monocyclic or bicyclic carbocyclic; an optionally substituted monocyclic or bicyclic carbocyclic-oxy group; an optionally substituted monocyclic or bicyclic heterocyclic group having 1, 2, 3, or 4 heteroatoms independently selected from N, O, and S and from 4 to 7 ring atoms per ring, an optionally substituted —($C_0$-$C_4$alkyl)(aryl); an optionally substituted —($C_0$-$C_4$alkyl)(5-membered heteroaryl) selected from pyrrole, furan, thiophene, pyrazole, oxazole, isoxazole, thiazole and isothiazole or a substituted imidazole; an optionally substituted —($C_0$-$C_4$alkyl)(6-membered heteroaryl); an optionally substituted —($C_0$-$C_4$alkyl)(8-membered heteroaryl); an optionally substituted —($C_0$-$C_4$alkyl)(9-membered heteroaryl) selected from isoindole, indazole, purine, indolizine, benzothiophene, benzothiazole, benzoxazole, benzofuran, and furopyridine; and —($C_0$-$C_4$alkyl)(10-membered heteroaryl); q is 1, 2 or 3.

L2' is selected from:

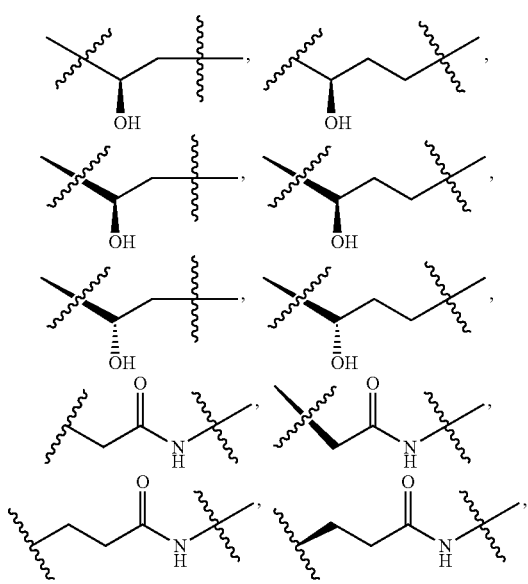

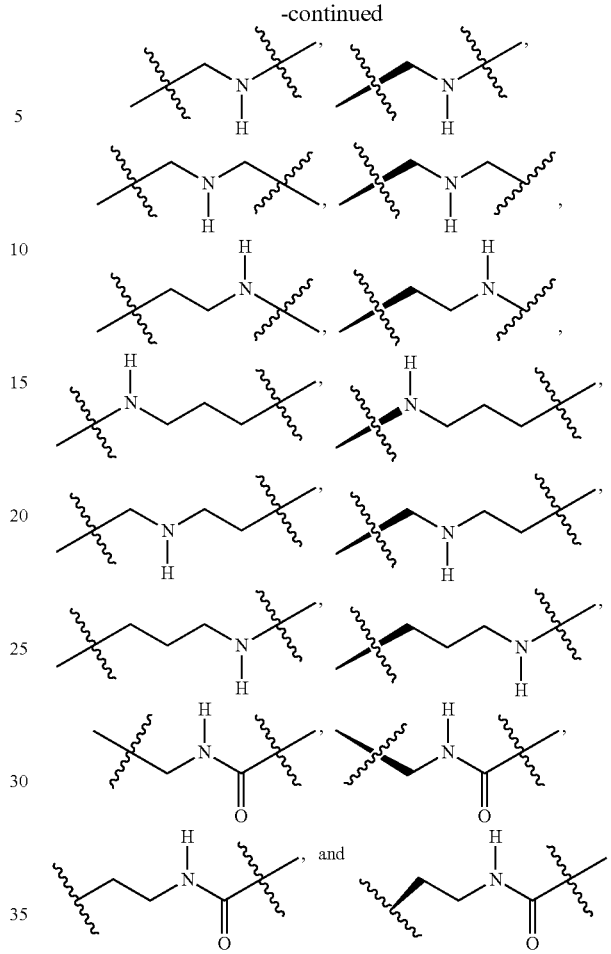

$R^{51}$ is $CH_3$, $CH_2F$, $CHF_2$ or $CF_3$.
$R^{53}$ is cyano, nitro, hydroxyl or $C_1$-$C_6$alkoxy.
$X^{29}$ can be O or S.

In certain embodiment, L2 is a bond. In certain embodiments, if L2 is heterocyclic or heteroaryl, then B can be hydrogen.

Non-limiting examples of L2 include the structures of FIG. 9.

In one embodiment, the methyl groups in the structures illustrated in FIG. 9 be replaced with another alkyl or acyl, as defined herein. In another embodiment, the carbocyclic, heterocyclic, aryl or heteroaryl rings can be optionally substituted. As indicated above, any of the structures illustrated above or below can be optionally substituted with 0, 1, 2, 3, or 4, as appropriate, and independently, of an $R^{48}$ substituent.

L3 is selected from L4 or L5.
L4 is —C(O)—.
L5 is —C(S)—, —P(O)OH—, —S(O)—, —S(O)$_2$— or —C($R^{52}$)$_2$— wherein each $R^{52}$ is independently selected from halo, hydrogen, or optionally substituted $C_1$-$C_6$alkyl. In certain embodiments the two $R^{52}$ groups can be taken together to form a 3- to 6-membered carbocyclic spiro ring or a 3- to 6-membered heterocyclic spiro ring containing 1 or 2 heteroatoms independently replaced from N, O, or S.

B1 is a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl), each of which B1 is unsubstituted or substituted with one or more substituents independently replaced from $R^{33}$ and $R^{34}$, and 0 or 1 substituents replaced from $R^{35}$ and $R^{36}$.

$R^{33}$ is independently replaced from halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, and $C_1$-$C_2$haloalkoxy.

$R^{34}$ is independently replaced from nitro, $C_2$-$C_6$alkenyl, $C_2$-$C_6$alkynyl, $C_1$-$C_6$thioalkyl, -J$C_3$-$C_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$) -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$) -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)=NR$^{22}$, -JCH(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)R$^{24}$R$^{25}$, -JNR$^9$C(O)R$^{21}$, -JC(O)R$^{21}$, -JNR$^9$C(O)NR$^{22}$OR$^{22}$, —CCR$^{21}$, —(CH$_2$)$_{1-4}$OC(O)R$^{21}$, and -JC(O)OR$^{23}$; each of which $R^{34}$ may be unsubstituted or substituted with one or more substituents independently replaced from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, —$C_0$-$C_4$alkyl($C_3$-$C_7$cycloalkyl), $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

$R^{35}$ is independently replaced from naphthyl, naphthyloxy, indanyl, (4- to 7-membered heterocycloalkyl)$C_0$-$C_4$alkyl containing 1 or 2 heteroatoms replaced from N, O, and S, and bicyclic heterocycle containing 1, 2, or 3 heteroatoms independently replaced from N, O, and S, and containing 4- to 7-ring atoms in each ring; each of which $R^{35}$ is unsubstituted or substituted with one or more substituents independently replaced from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO$_2$R$^9$, $C_1$-$C_2$haloalkyl, and $C_1$-$C_2$haloalkoxy.

$R^{36}$ is independently replaced from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently replaced from N, O, B, and S, each of which $R^{36}$ is unsubstituted or substituted with one or more substituents independently replaced from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO$_2$R$^9$, —OSi(CH$_3$)$_2$C(CH$_3$)$_3$, —Si(CH$_3$)$_2$C(CH$_3$)$_3$, $C_1$-$C_2$haloalkyl, and $C_1$-$C_2$haloalkoxy.

In one additional alternative embodiment B is selected from:

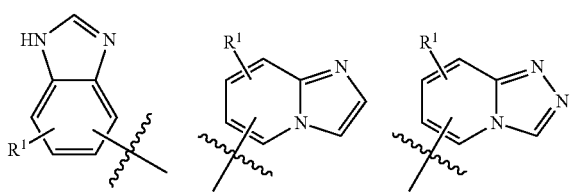

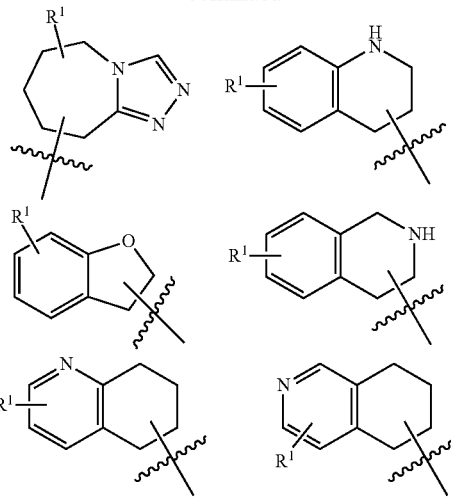

In one additional alternative embodiment $R^{36}$ is selected from:

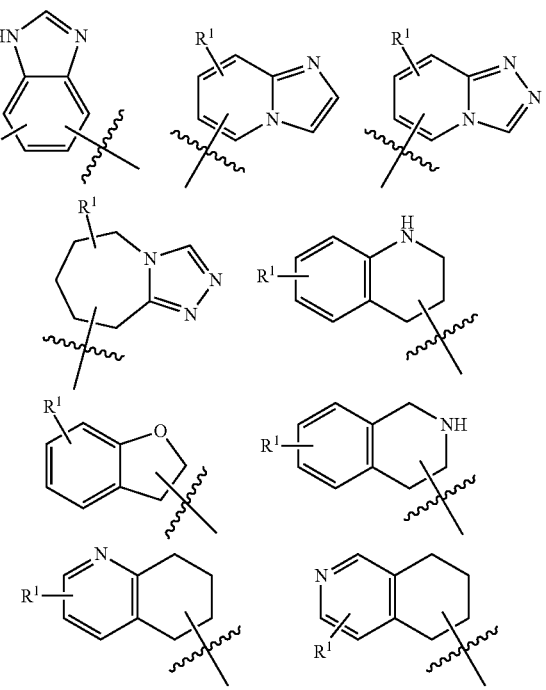

In one embodiment $R^1$ is selected from F, Cl, Br, and $C_1$-$C_6$alkyl.

In one embodiment $R^1$ is selected from hydroxyl and $C_1$-$C_6$alkoxy.

In one embodiment $R^1$ is selected from $C_2$-$C_6$alkynyl, $C_2$-$C_6$alkanoyl, and $C_1$-$C_6$thioalkyl.

In one embodiment $R^1$ is selected from amino$C_1$-$C_6$alkyl and —$C_0$-$C_4$alkylNR$^9$R$^{10}$.

$R^{21}$ and $R^{22}$ are independently replaced at each occurrence from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC$_1$-$C_6$alkyl, —$C_1$-$C_4$alkylOC(O)$C_1$-$C_6$alkyl, —$C_1$-$C_4$alkylC(O)OC$_1$-$C_6$alkyl, (4- to 7-membered heterocycloalkyl)$C_0$-

$C_4$alkyl having 1, 2, or 3 heteroatoms independently replaced from N, O, and S, and (5- or 6-membered unsaturated or aromatic heterocycle)$C_0$-$C_4$alkyl having 1, 2, or 3 heteroatoms independently replaced from N, O, and S, and each $R^{21}$ and $R^{22}$ can be optionally substituted. In one embodiment, $R^{21}$ and $R^{22}$ can be taken together to form a carbocyclic or heterocyclic ring.

$R^{23}$ is independently replaced at each occurrence from $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently replaced from N, O, and S, and (5- or 6-membered unsaturated or aromatic heterocycle)$C_0$-$C_4$alkyl having 1, 2, or 3 heteroatoms independently replaced from N, O, and S, and each $R^{23}$ can be optionally substituted.

$R^{24}$ and $R^{25}$ are taken together with the nitrogen to which they are attached to form a 4- to 7-membered monocyclic heterocycloalkyl group, or a 6- to 10-membered bicyclic heterocyclic group having fused, spiro, or bridged rings, and each $R^{24}$ and $R^{25}$ can be optionally substituted.

J is independently replaced at each occurrence from a covalent bond, $C_1$-$C_4$alkylene, —O$C_1$-$C_4$alkylene, $C_2$-$C_4$alkenylene, and $C_2$-$C_4$alkynylene.

In one embodiment, B1 is selected from FIG. 10, wherein $R^{27}$ is hydrogen, methyl, or trifluoromethyl; $R^{28}$ is hydrogen or halogen; and $R^{29}$ is hydrogen, methyl, trifluoromethyl, or —Si(CH$_3$)$_2$C(CH$_3$)$_3$.

In one embodiment, B1 is B1'. Non-limiting examples of B1' include the structures of FIG. 11 A-D.

Examples of B moieties include, but are not limited to

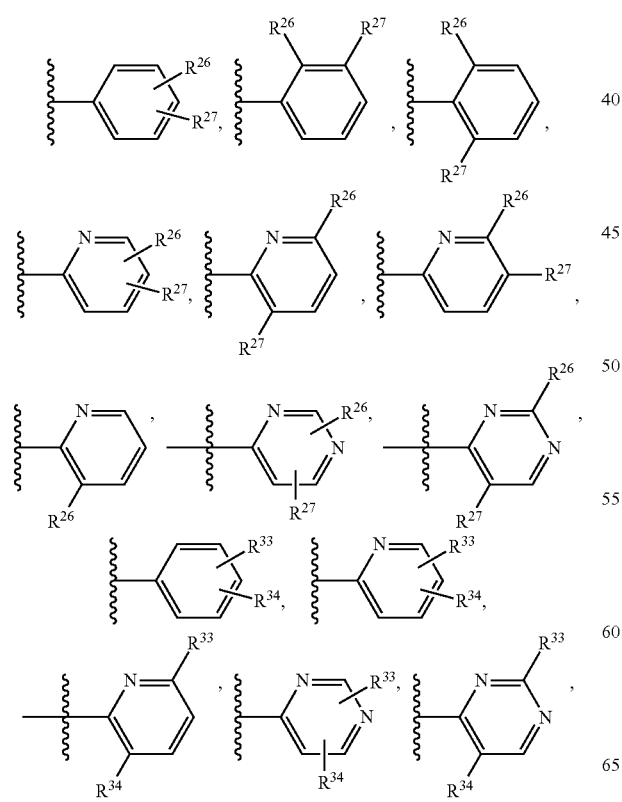
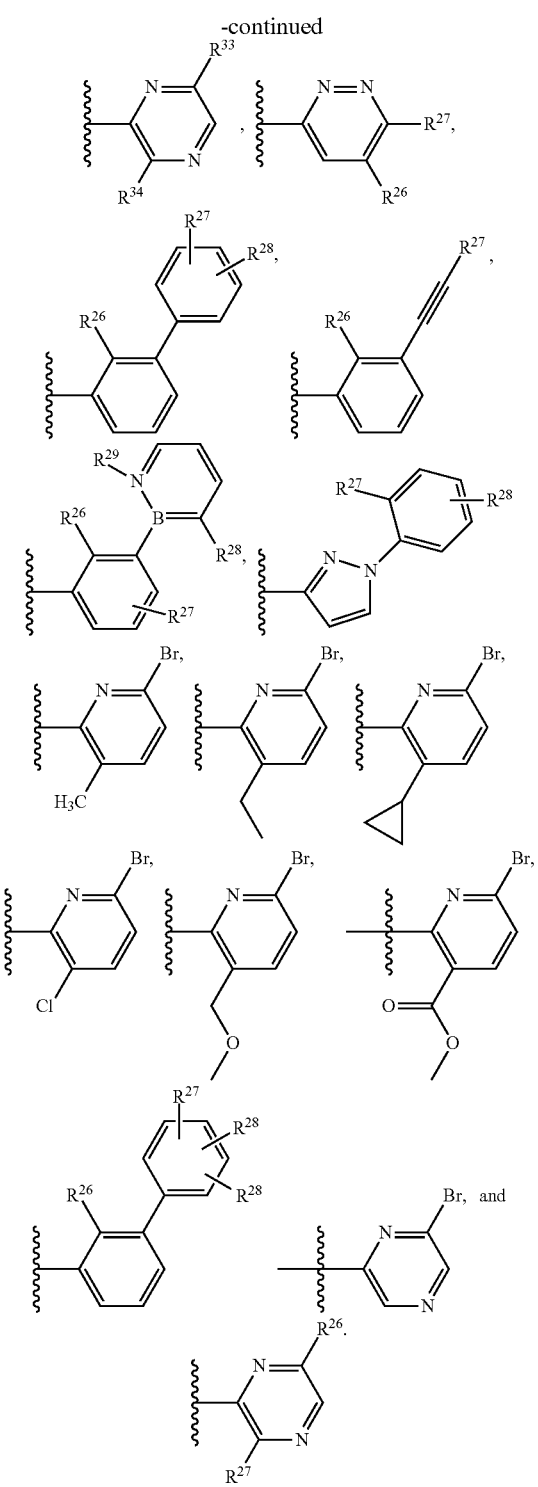

In one embodiment, B is B2 which is selected from the structures of FIG. 12.

In one embodiment B3 is:
(I) a monocyclic orbicyclic carbocyclic; a monocyclic orbicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl); each of which B3 is substituted with one or more of the following: S(O)=NHR$^{21}$, SF$_5$, and JC(R$^9$)=NR$^{21}$;

(II) a monocyclic, bicyclic, or tricyclic heterocyclic group that has at least one boron or silicon atom in the ring or a monocyclic, bicyclic, or tricyclic heteroaryl group that has at least one boron in the ring;

(III) a 6-membered aryl group fused to a 5-membered saturated cyclic group that optionally contains 1 or 2 heteroatoms independently replaced from N and S wherein one of the CH$_2$ groups of the 5-membered cyclic group is optionally substituted by oxo (i.e., =O) excluding dihydrobenzofuran;

(IV) an 8-membered monocyclic or bicyclic heteroaryl, however; when A is A1 or A1'; C is C1, C1' or C2; L is L1 or L1' and L3 is L4 the following species are excluded: 6,7-dihydro-5H-pyrrolo[1,2-a]imidazole.

(V) a 9-membered monocyclic or bicyclic heteroaryl group, however; when A is A1 or A1'; C is C1, C1' or C2; L is L1 or L1' and L3 is L4 the following species are excluded: 6-chloro-1H-benzo[d]imidazole bonded at the 7 position, 6-fluoro-1H-benzo[d]imidazole bonded at the 7 position, 6-(methylthio)-1H-benzo[d]imidazole bonded at the 7 position, and 6-(methoxy)-1H-benzo[d]imidazole bonded at the 7 position, 7-chloro-imidazo[1,2-a]pyridine substituted at the eight position, 7-(methylthio)-imidazo[1,2-a]pyridine substituted at the eight position, 7-fluoro-imidazo[1,2-a]pyridine substituted at the eight position, 7-methoxy-imidazo[1,2-a]pyridine substituted at the eight position, 4-fluoro-1H-indole substituted at the 4 position, [1,2,4]triazole[4,3-a]pyridine substituted at the 2 position, and [1,2,4]triazole[4,3-a]pyrimidine substituted at the 3 position;

(VI) a 10-membered aryl or heteroaryl group, however; when A is A1 or A1'; C is C1, C1' or C2; L is L1 or L1' and L3 is L4 the following species are excluded: an unsubstituted tetrahydroquinoline and 6,7,8,9-tetrahydro-5H-[1,2,4]triazolo[4,3-a]azepine substituted at the 3-position;

(VII) (optionally substituted alkyl)-(optionally substituted cycloalkyl), (optionally substituted alkenyl)-(optionally substituted cycloalkyl), or (optionally substituted alkynyl)-(optionally substituted cycloalkyl);

wherein B3 can be further substituted one or more times with the substituents independently selected from R$^{35}$, R$^{36}$ and R$^{48}$.

Non-limiting examples of B3 include the structures of FIG. 13.

In one embodiment, the methyl groups in the structures illustrated in FIG. 13 can be replaced by another alkyl group. In another embodiment, the B3 groups illustrated in FIG. 13 can be optionally substituted. As indicated above, any of the structures illustrated in FIG. 13 or otherwise herein can be optionally substituted with 0, 1, 2, 3, or 4, as appropriate, and independently, with an R$^{48}$ substituent.

In an alternative embodiment, B3 can also be R$^{21}$ when L2 is either an optionally substituted monocyclic or bicyclic carbocyclic; an optionally substituted monocyclic or bicyclic carbocyclic-oxy group; an optionally substituted monocyclic or bicyclic heterocyclic group having 1, 2, 3, or 4 heteroatoms independently selected from N, O, and S and from 4 to 7 ring atoms per ring, an optionally substituted —(C$_0$-C$_4$alkyl)(aryl); an optionally substituted —(C$_0$-C$_4$alkyl)(5-membered heteroaryl) selected from pyrrole, furan, thiophene, pyrazole, oxazole, isoxazole, thiazole and isothiazole or a substituted imidazole; an optionally substituted —(C$_0$-C$_4$alkyl)(6-membered heteroaryl); an optionally substituted —(C$_0$-C$_4$alkyl)(8-membered heteroaryl); an optionally substituted —(C$_0$-C$_4$alkyl)(9-membered heteroaryl) selected from isoindole, indazole, purine, indolizine, benzothiophene, benzothiazole, benzoxazole, benzofuran, and furopyridine; or an optionally substituted —(C$_0$-C$_4$alkyl)(10-membered heteroaryl)

Non-limiting examples of L2-B3 where B3 is R$^{21}$ include the structures of FIG. 14.

B4 is one of the following defined embodiments and is subject to the restriction that either A is A2, or C is C3 (or C4), or L is L2, or L3 is L5:

(I) a 4-membered carbocyclic fused to a 5- or 6-membered heteroaryl having 1, 2, or 3 heteroatoms independently replaced from N, O, and S; wherein the 4-5 or 4-6 ring system can be optionally substituted;

(II) a 4-membered carbocyclic fused to a 6-membered aryl ring wherein the 4-6 ring system can be optionally substituted;

(III) a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; C$_2$-C$_6$alkenyl; C$_2$-C$_6$alkynyl; —(C$_0$-C$_4$alkyl)(aryl); —(C$_0$-C$_4$alkyl)(heteroaryl); or —(C$_0$-C$_4$alkyl)(biphenyl); each of which B3 is substituted one or more times with S(O)$_2$OR$^{21}$ (IV) (cycloalkyl)-(optionally substituted aryl), (cycloalkyl)-(optionally substituted heteroaryl), (cycloalkyl)-(optionally substituted heterocyclic), (alkyl)-alkenyl), cycloalkyl-alkenyl;

(V) alkyl, (alkyl)-(alkenyl), alkyl(alkynyl), cycloalkyl-alkenyl each of which can be optionally substituted;

(VI) (optionally substituted alkyl)-(optionally substituted cycloalkyl), (alkenyl)-(optionally substituted cycloalkyl), (alkynyl)-(optionally substituted cycloalkyl), (optionally substituted cycloalkyl)-(optionally substituted cycloalkyl);

wherein B4 can be further substituted 1, 2, 3 or 4 times or more with the substituents independently selected from R$^{33}$, R$^{34}$, R$^{35}$ R$^{36}$ and R$^{48}$.

In an alternate embodiment, the R$^{32}$ group can be bonded to B via a linking group to form a compound of Formula I':

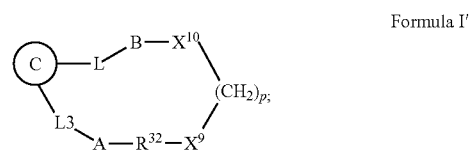

Formula I' wherein;

X$^9$ and X$^{10}$ are each independently CH$_2$, NR$^9$, O or S;

p is 2 to 10; or a pharmaceutically acceptable composition, salt, isotopic analog, or prodrug thereof.

In one embodiment, the disclosure provides a compound of Formula IM.

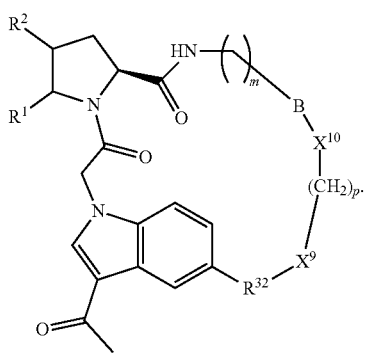

Formula IM

In one embodiment, the disclosure provides a compound of Formula IN:

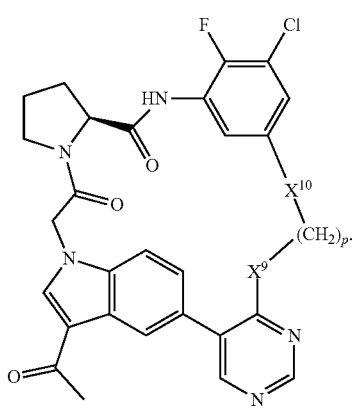

Formula IN

In one embodiment, the disclosure provides a compound of Formula IO:

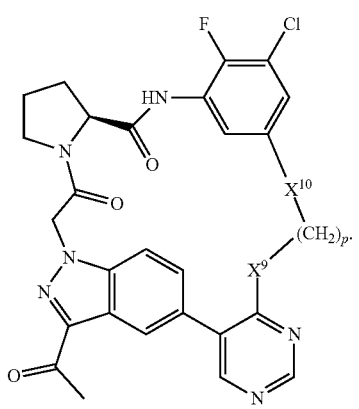

Formula IO

In one embodiment, the disclosure provides a compound of Formula IP:

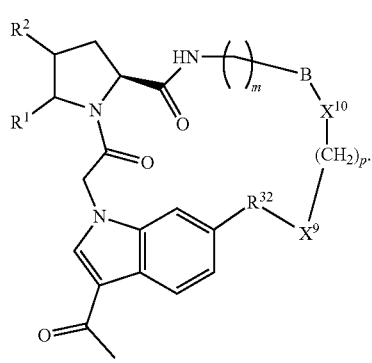

Formula IP

In one embodiment, the disclosure provides a compound of Formula IQ:

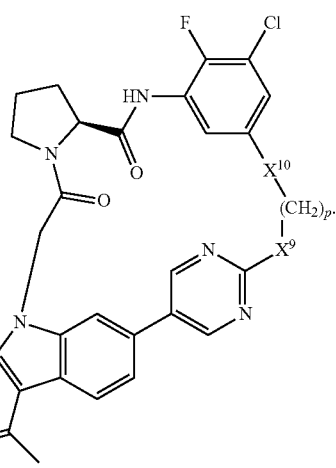

Formula IQ

In one embodiment, the disclosure provides a compound of Formula IR:

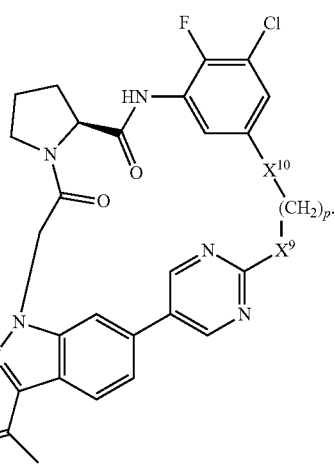

Formula IR

In an alternate embodiment, the $X^9$—$(CH_2)_p$—$X^{10}$ moiety can be saturated or partially unsaturated. In another embodiment, the $X^9$—$(CH_2)_p$—$X^{10}$ moiety can comprise one or more heteroatoms.

In an alternate embodiment, the A group can be bonded to B via a linking group to form a compound of Formula I'A:

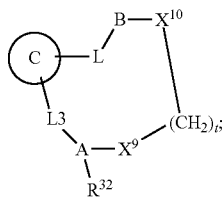

Formula I'A wherein;

$X^9$ and $X^{10}$ are each independently $CH_2$, $NR^9$, O or S;

t is 1, 2, or 3;

or a pharmaceutically acceptable composition, salt, isotopic analog, or prodrug thereof.

In one embodiment, the disclosure provides a compound of Formula IS:

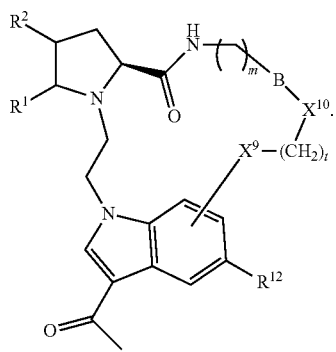

Formula IS

In one embodiment, the disclosure provides a compound of Formula IT:

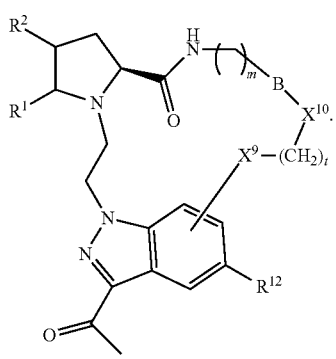

Formula IT

In an alternate embodiment, the $X^9$—$(CH_2)_t$—$X^{10}$ moiety can be saturated or partially unsaturated. In another embodiment, the $X^9$—$(CH_2)_t$—$X^{10}$ moiety can comprise one or more heteroatoms.

In an alternate embodiment, the disclosure provides compounds of Formula I''

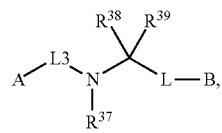

(I'')

or a pharmaceutically acceptable composition, salt, isotopic analog, or prodrug thereof.

A is selected from A1, A1' and A2.
B is selected from B1, B1', B2, B3, and B4.
L is selected from L1, L1', L2 and L2'.
L3 is selected from L4 and L5.
$R^{37}$ is hydrogen, $C_1$-$C_6$alkyl or —$(C_0$-$C_2$alkyl)($C_3$-$C_6$cycloalkyl).

$R^{38}$ and $R^{39}$ are independently hydrogen (which as in any other location can be deuterium), $C_1$-$C_6$alkyl (including $C_1$-$C_3$ alkyl), $C_1$-$C_6$haloalkyl, $C_1$-$C_6$hydroxyalkyl, $C_2$-$C_6$alkenyl, $C_2$-$C_6$alkynyl, $C_1$-$C_6$alkoxy, ($C_3$-$C_6$cycloalkyl)$C_0$-$C_4$alkyl-, (aryl)$C_0$-$C_2$alkyl-, (heteroaryl)$C_0$-$C_2$alkyl-, or a side chain of an amino acid (i.e., a moiety which is found on the carbon linking the amino group and the carboxyl group in an amino acid) or its isomer; each of which is optionally substituted. The $R^{38}$ and $R^{39}$ substituents independently include but are not limited to any corresponding $R^{38}$ and $R^{39}$ positions found in natural amino acids (or their D-counterpart) (i.e., the substituents on the carbon between the carbonyl and the amino group) and non-proteogenic amino acids, such as serine, threonine, asparagine, glutamine, cysteine, selenocysteine, glycine (e.g., hydrogen), alanine, valine, isoleucine, methionine, phenylalanine, tyrosine, tryptophan, ornithine, glutamine, arginine, histidine, proline, hydroxyproline, selenomethionine, lanthionine, 2-aminoisobutyric acid or dehydroalanine (i.e., $R^{38}$ or $R^{39}$ is an exo-double bond), with optional protection of functional groups such as hydroxyl, amino, thiol, etc.

Pharmaceutical compositions comprising a compound or salt of Formula I, Formula I' or Formula I'' together with a pharmaceutically acceptable carrier are also disclosed.

The present invention thus includes at least the following features:

(a) a compound of Formula I, Formula I' or Formula I'' or a pharmaceutically acceptable salt or prodrug thereof, for use in treating or preventing a disorder listed in the Detailed Description, Part IV, including but not limited to the development of fatty liver and conditions stemming from fatty liver, such as nonalcoholic steatohepatitis (NASH), liver inflammation, cirrhosis, or liver failure; dermatomyocitis; amyotrophic lateral sclerosis; cytokine or inflammatory reactions in response to biotherapeutics (e.g. CAR T-cell therapy); paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

(b) a pharmaceutically acceptable composition of a compound of Formula I, Formula I' or Formula I'' or its pharmaceutically acceptable salt in a pharmaceutically acceptable carrier;

(c) a compound selected from Formula I, Formula I' or Formula I'' or a pharmaceutically acceptable salt or prodrug thereof, for use in treating or preventing a disorder mediated by the complement pathway, and for example, cascade Factor D;

(d) use of a compound of Formula I, Formula I' or Formula I", as described herein, or a pharmaceutically acceptable salt or prodrug thereof, in the manufacture of a medicament for treating or preventing a disorder listed in the Detailed Description, Part IV, including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; cytokine or inflammatory reactions in response to biotherapeutics (e.g. CAR T-cell therapy); paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

(e) a process for manufacturing a medicament intended for the therapeutic use for treating or preventing a disorder listed in the Detailed Description, Part IV, or generally for treating or preventing disorders mediated by complement cascade Factor D, characterized in that a compound selected from Formula I, Formula I' or Formula I" or an embodiment of the active compound is used in the manufacture;

(f) a compound selected from Formula I, Formula I' or Formula I" or a salt thereof as described herein in substantially pure form (e.g., at least 90 or 95%):

(g) a compound of Formula I, Formula I' or Formula I" as described herein, or a pharmaceutically acceptable salt or prodrug thereof, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

(h) For each of (a) through (g) above, and otherwise herein, each assembly of moieties in the Figures and each active compound made therefrom or its use is considered and deemed specifically and individually disclosed, as such depiction is for convenience of space only and not intended to describe a only a genus or even a subgenus for such indication.

DETAILED DESCRIPTION

I. Terminology

Figure 1:
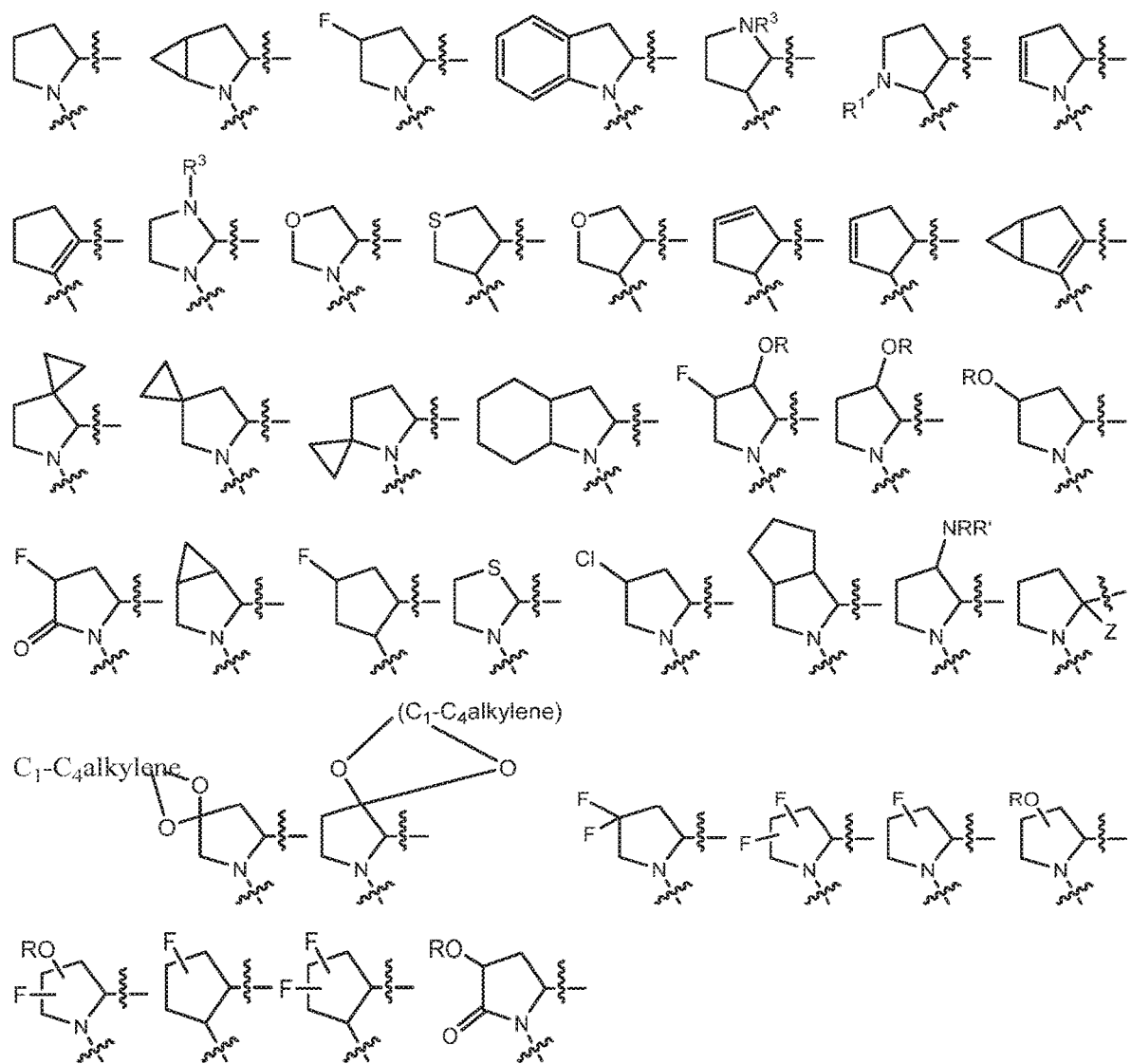
FIG. 1 provides non-limiting specific embodiments of the Central Core ring, wherein R, R', and $R^3$ are defined below.
Figure 2A:
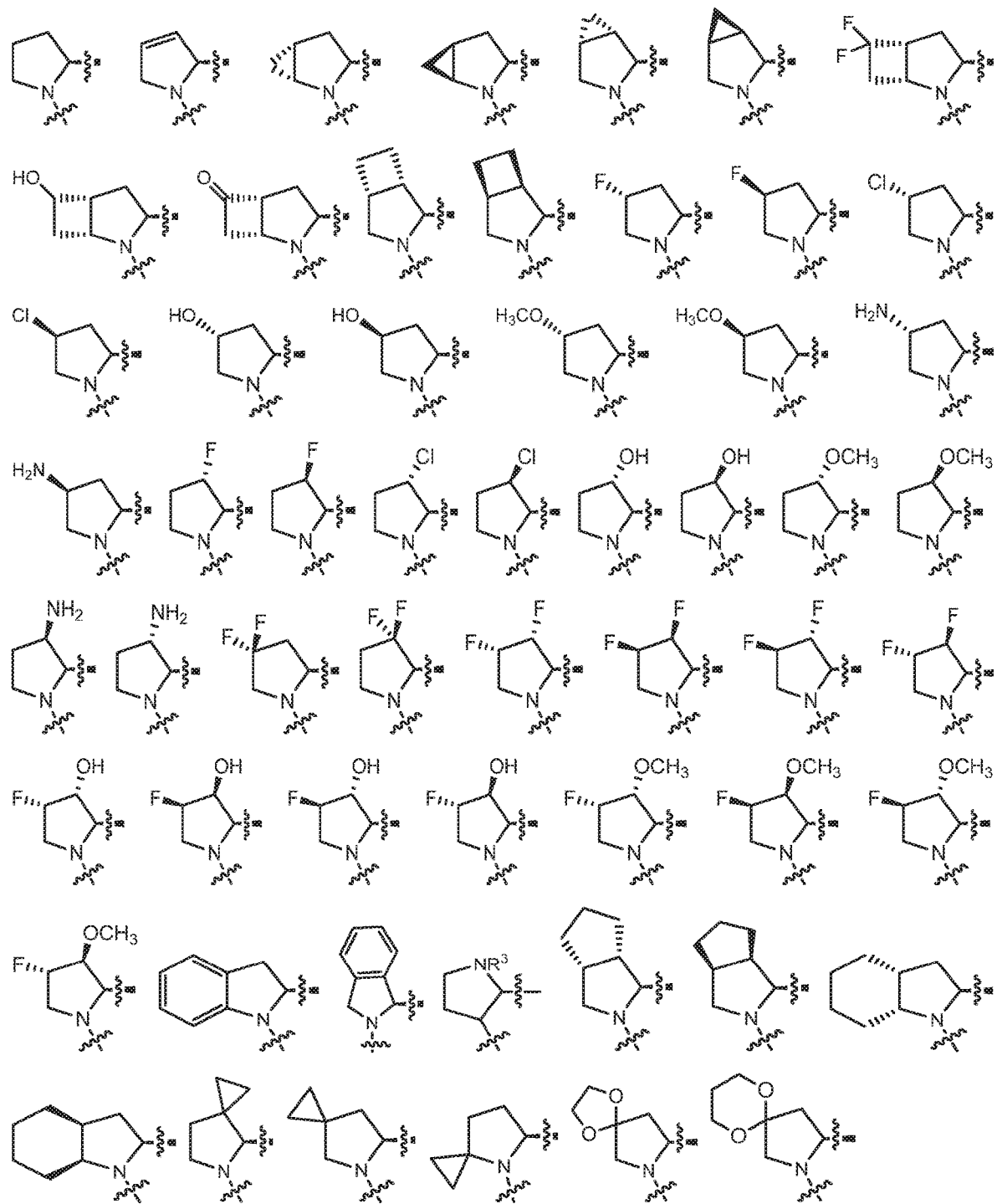
FIGS. 2A, 2B, 2C, 2D, 2E, 2F, 2G, 2H, 2I, 2J, 2K, 2L, and 2M, provide non-limiting embodiments of C1', wherein $R^3$ is as defined herein.
Figure 2B:
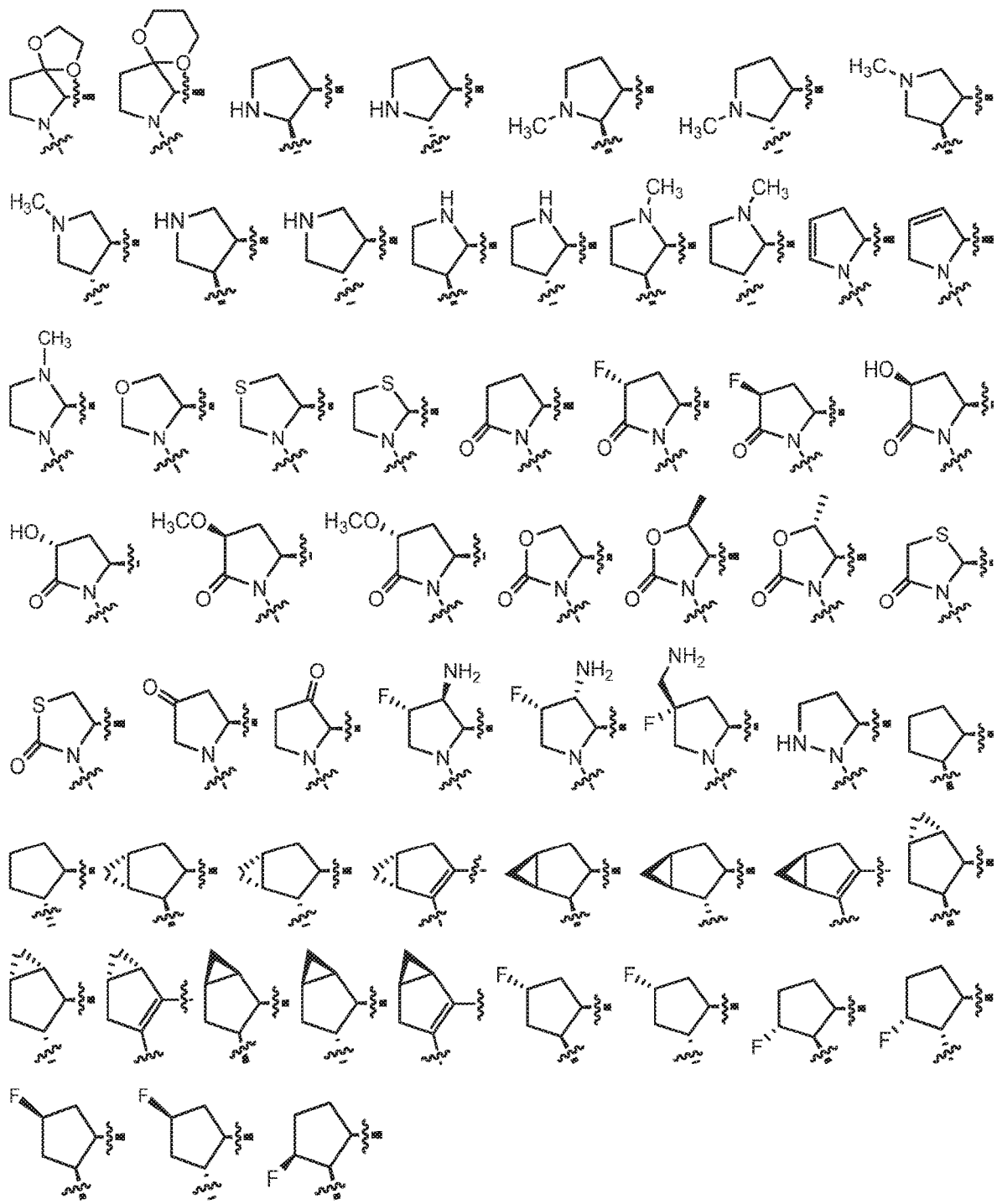
Figure 2C:
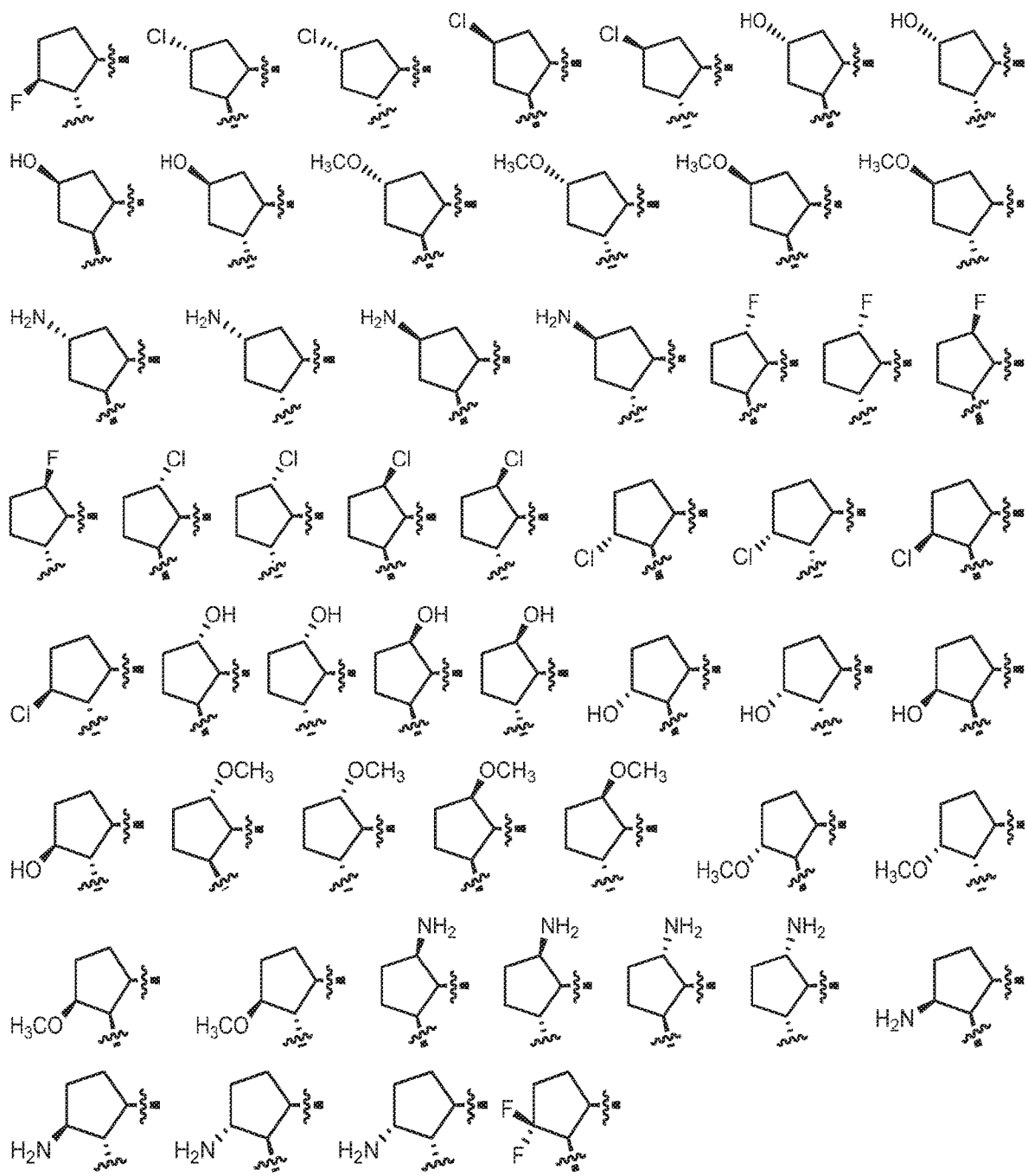
Figure 2D:
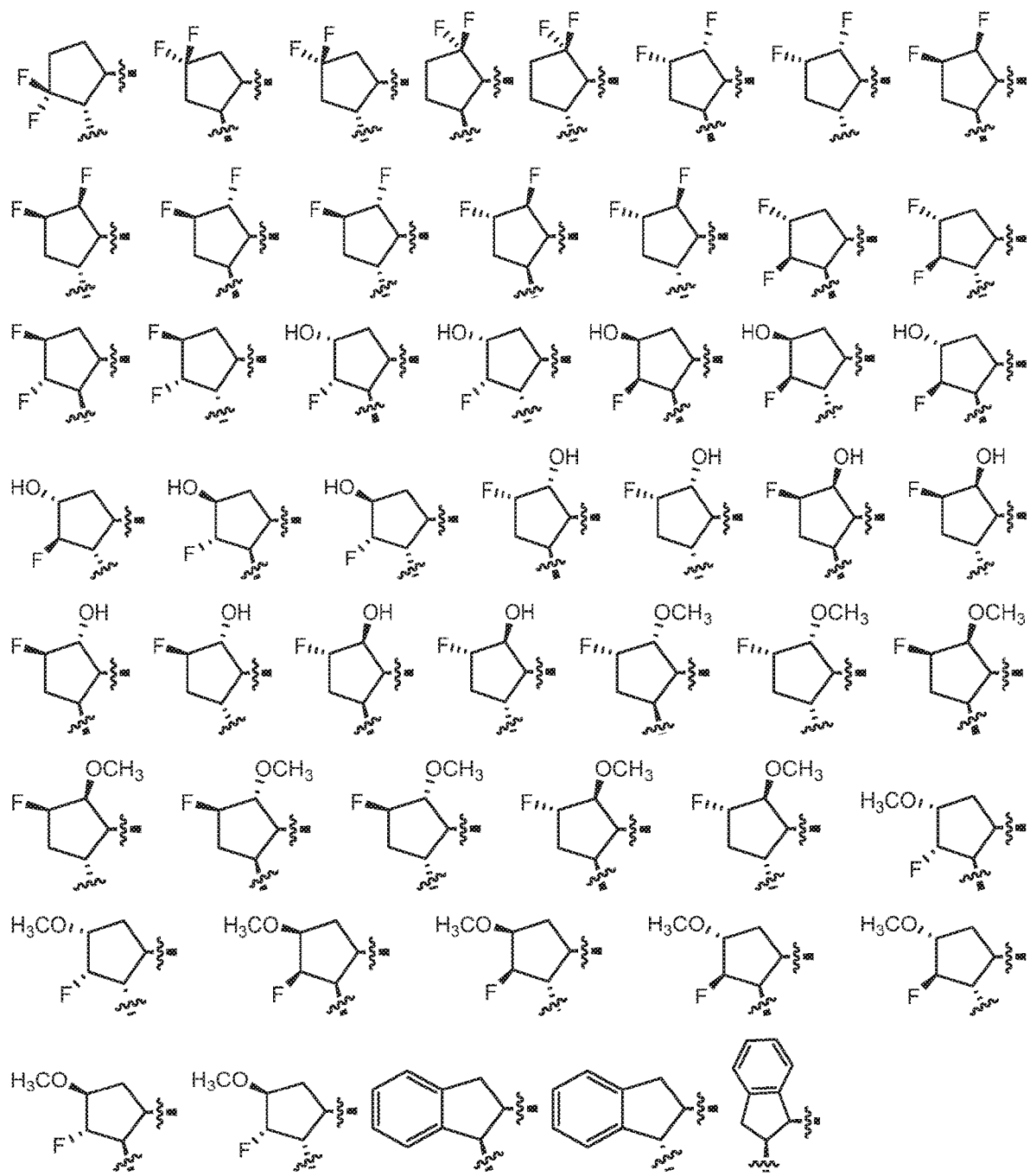
Figure 2E:
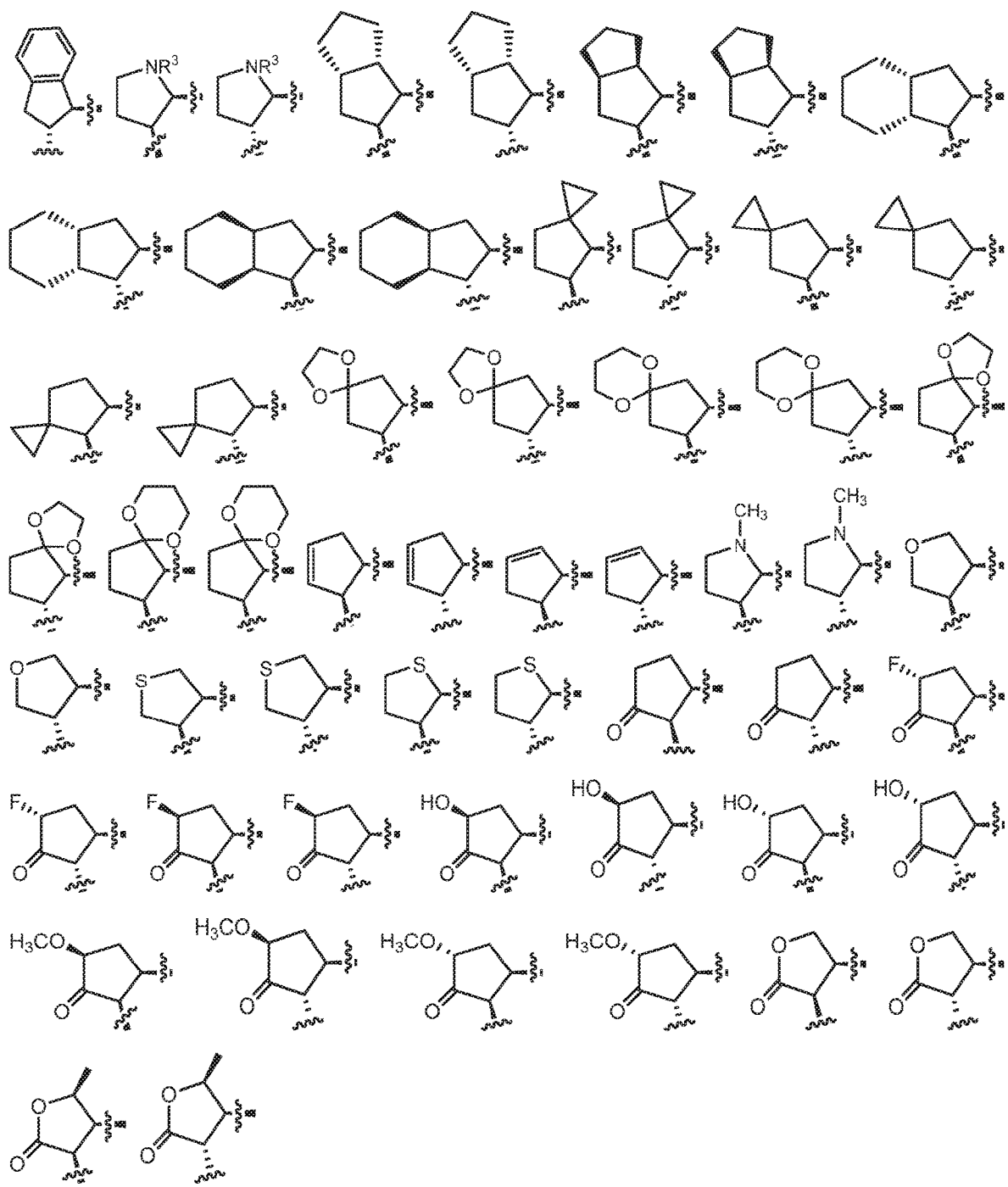
Figure 2F:
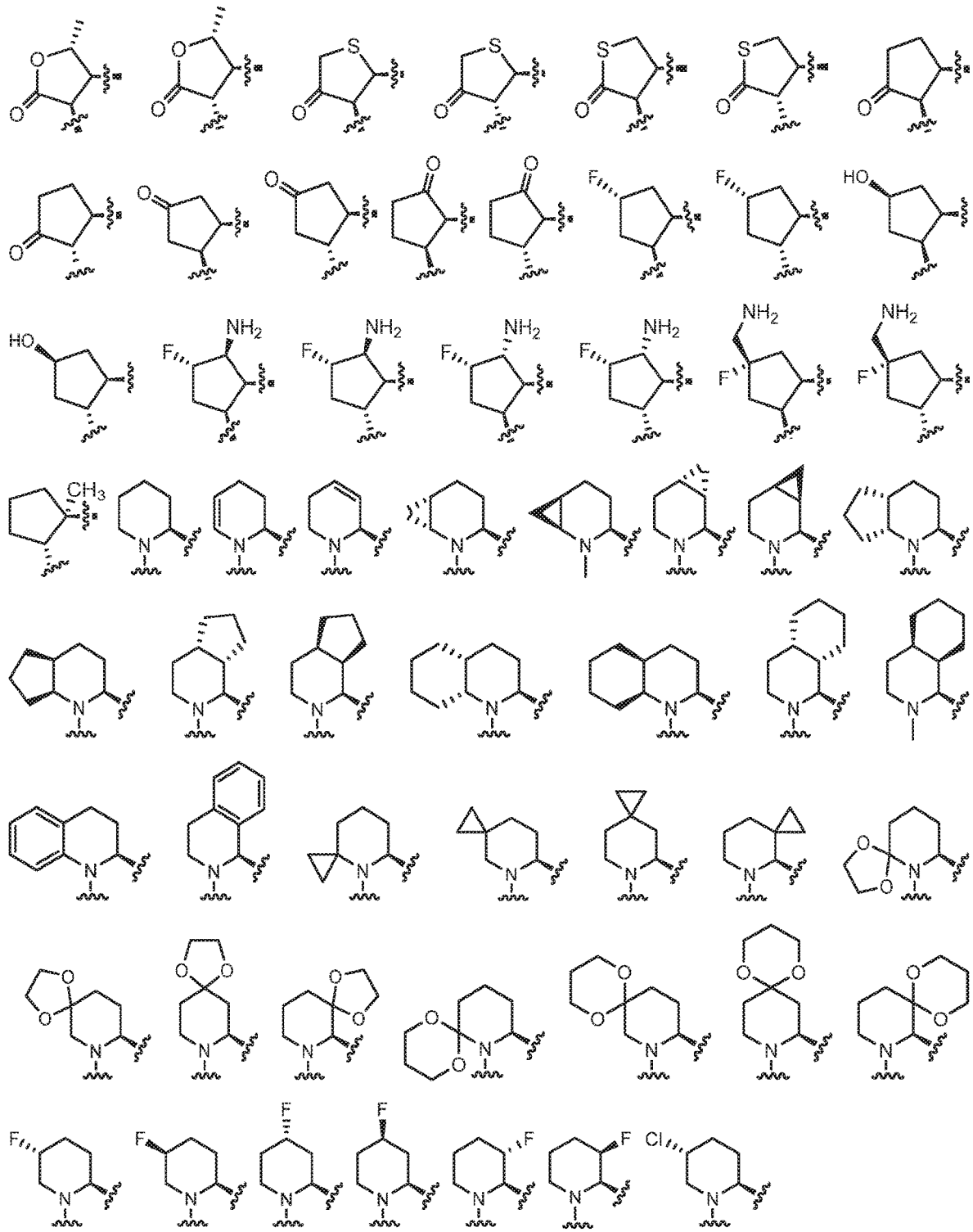
Figure 2G:
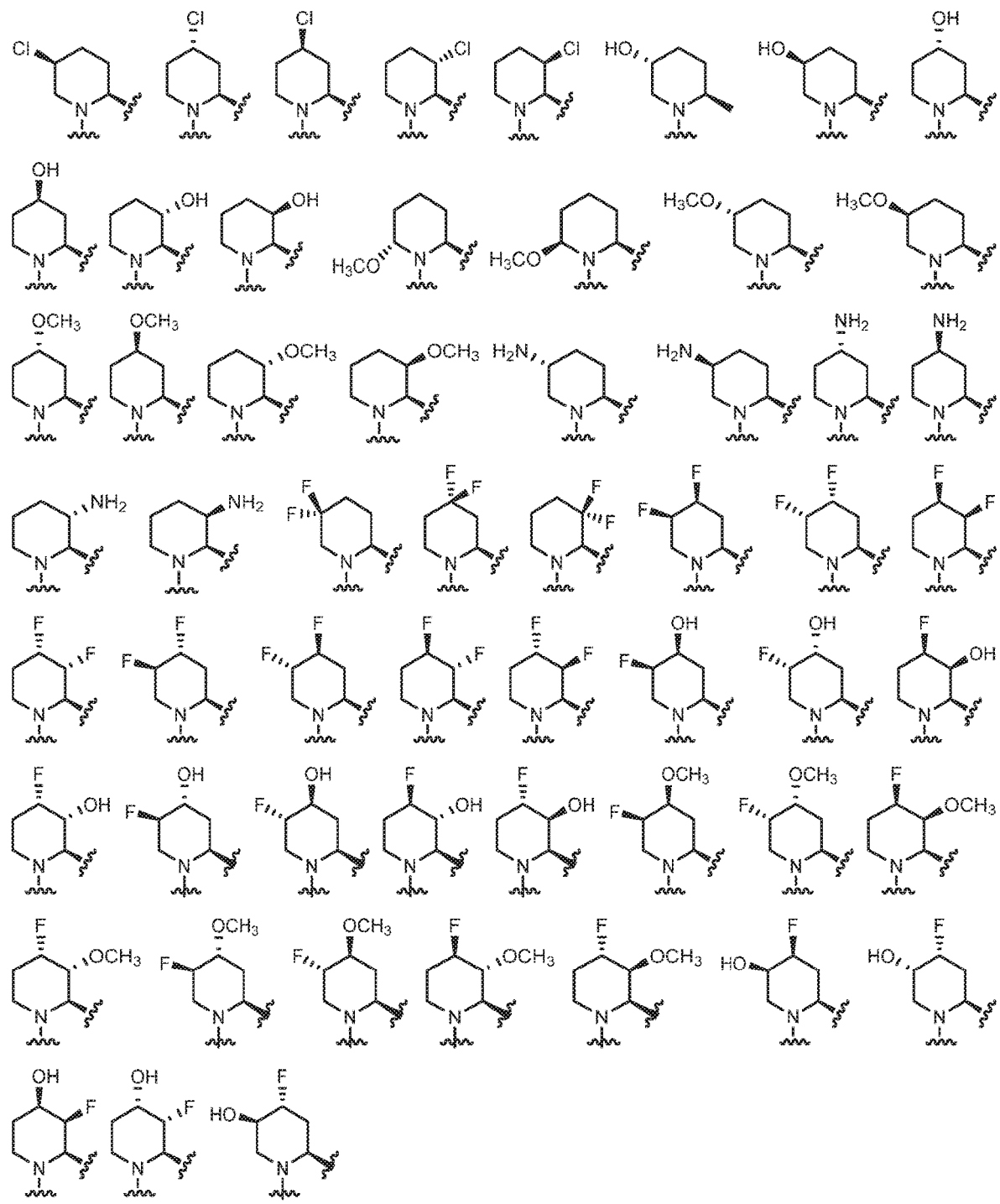
Figure 2H:
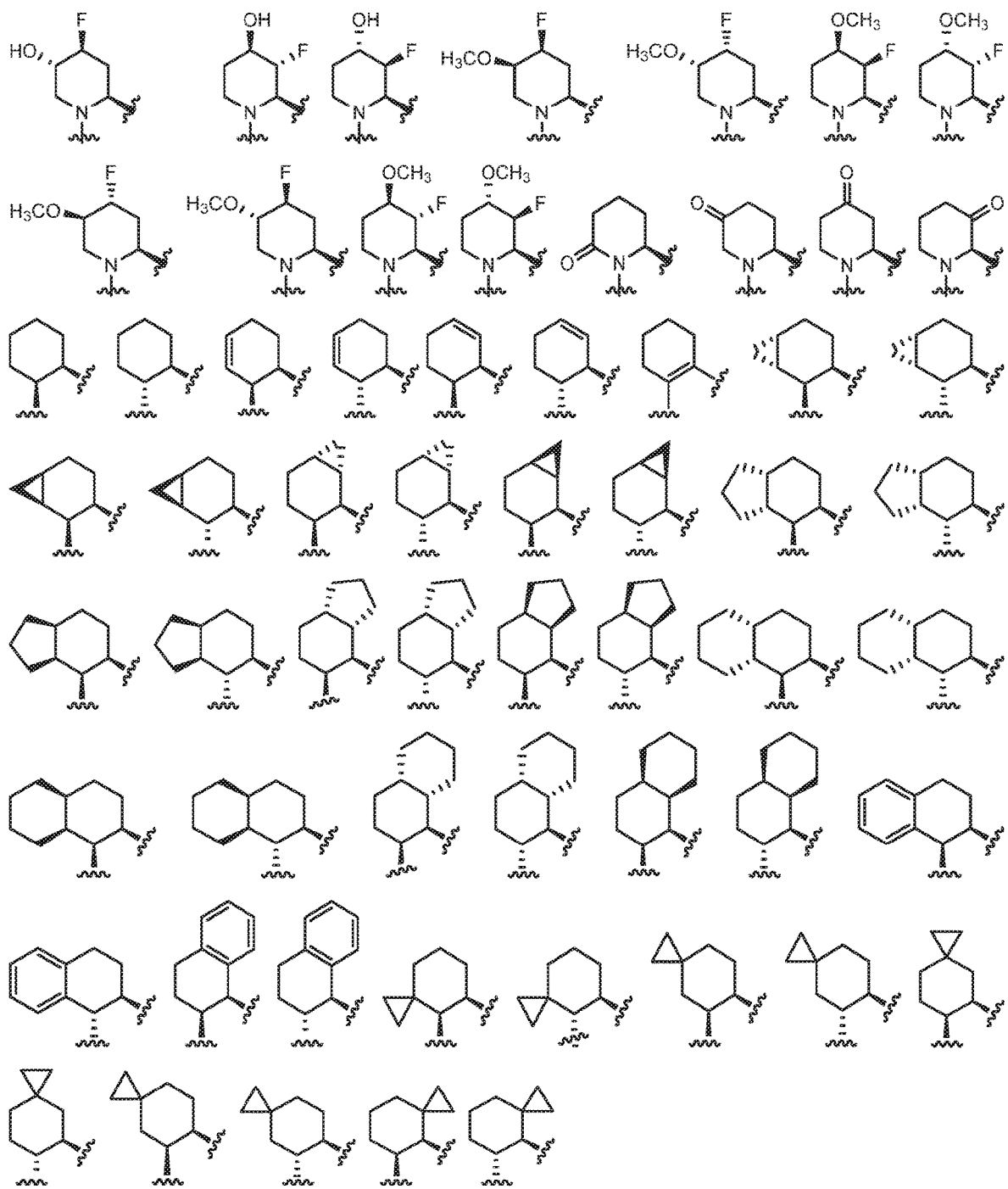
Figure 2I:
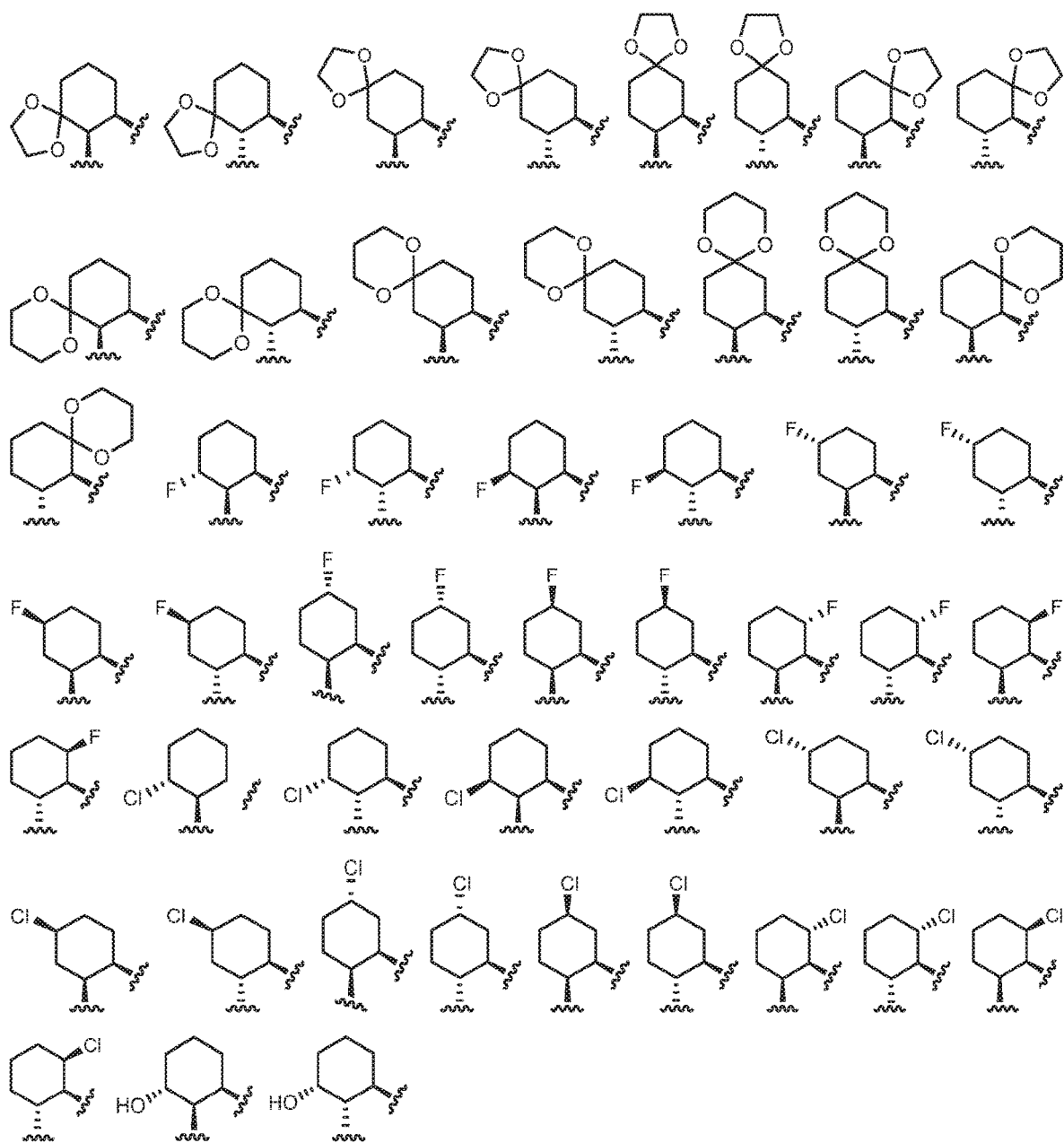
Figure 2J:
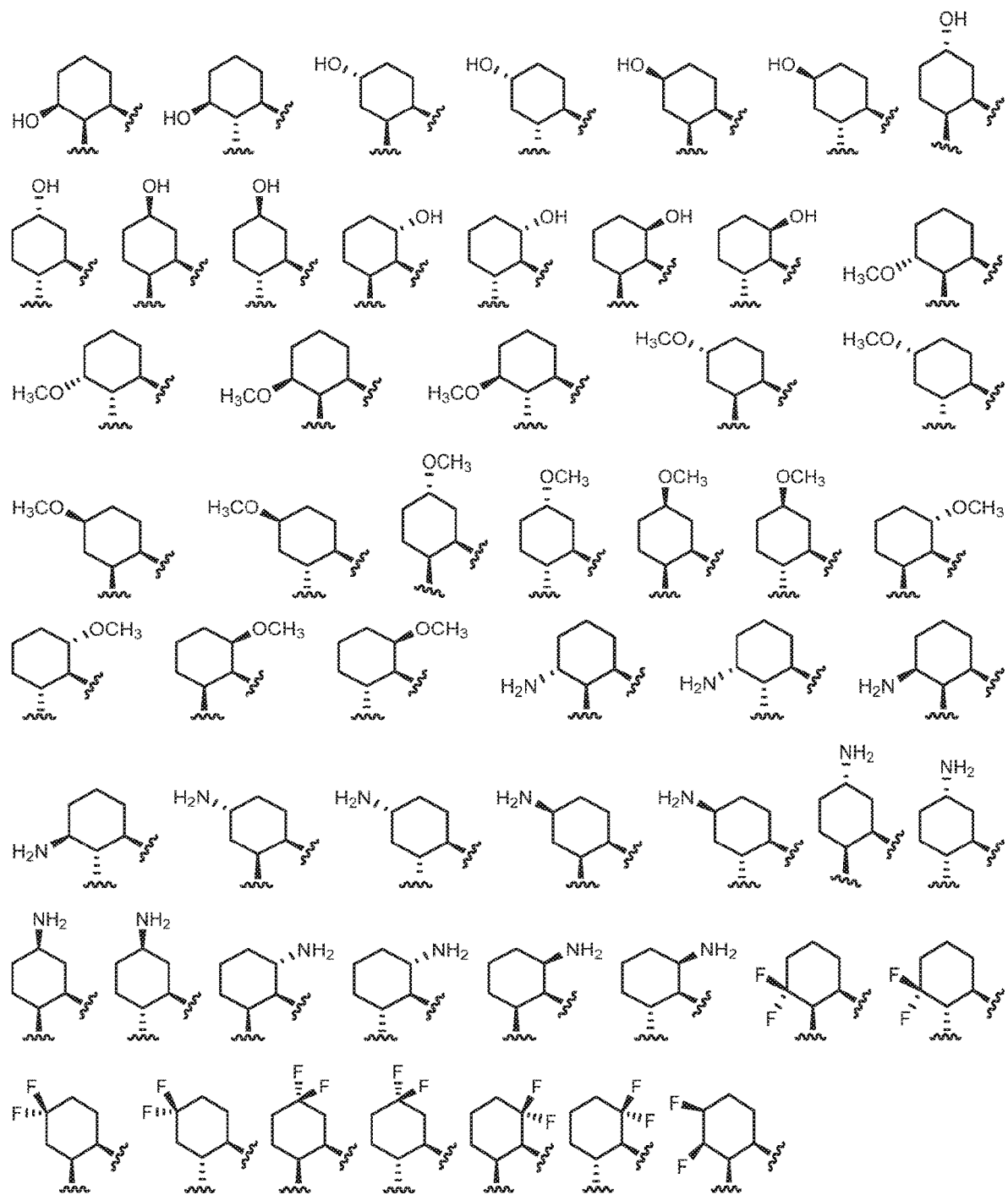
Figure 2K:
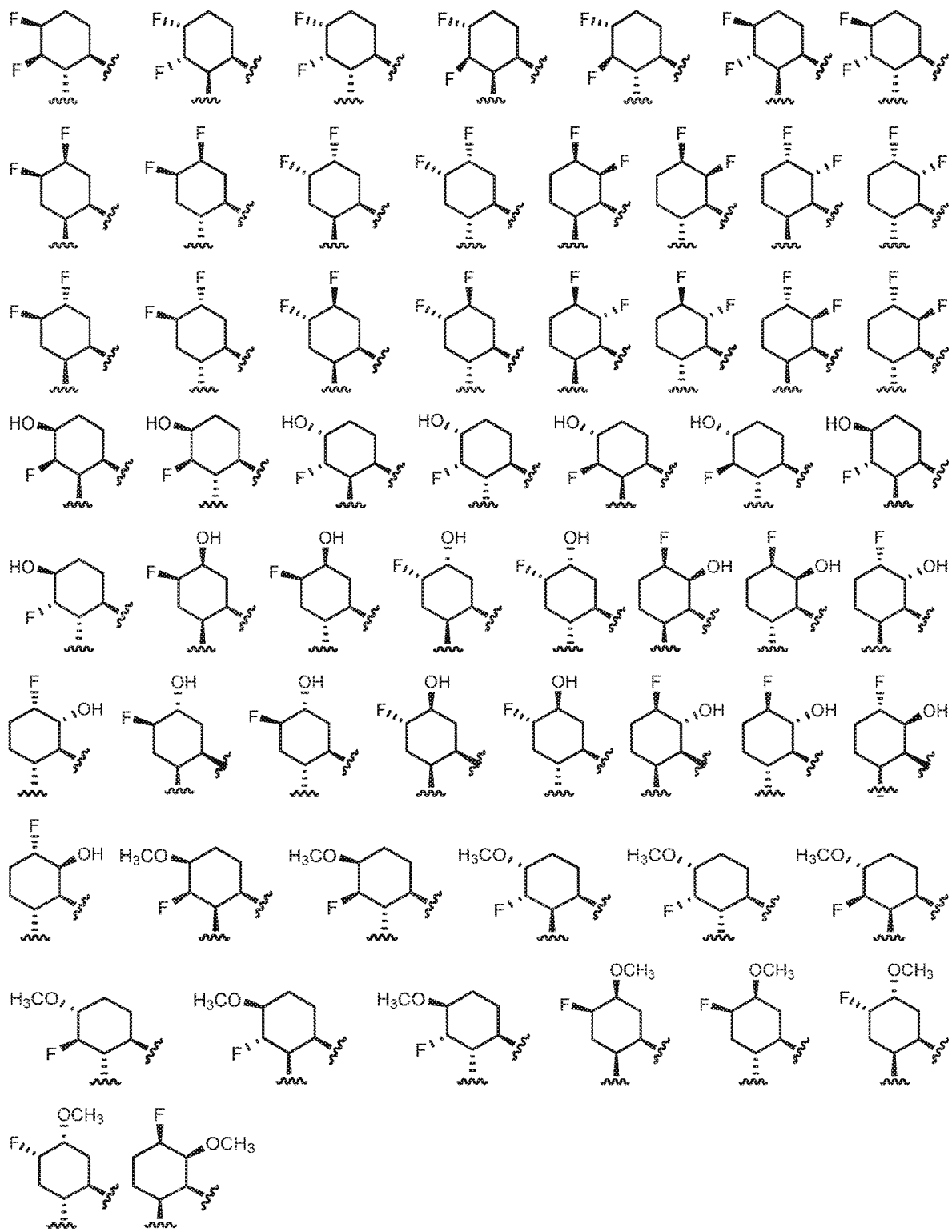
Figure 2L:
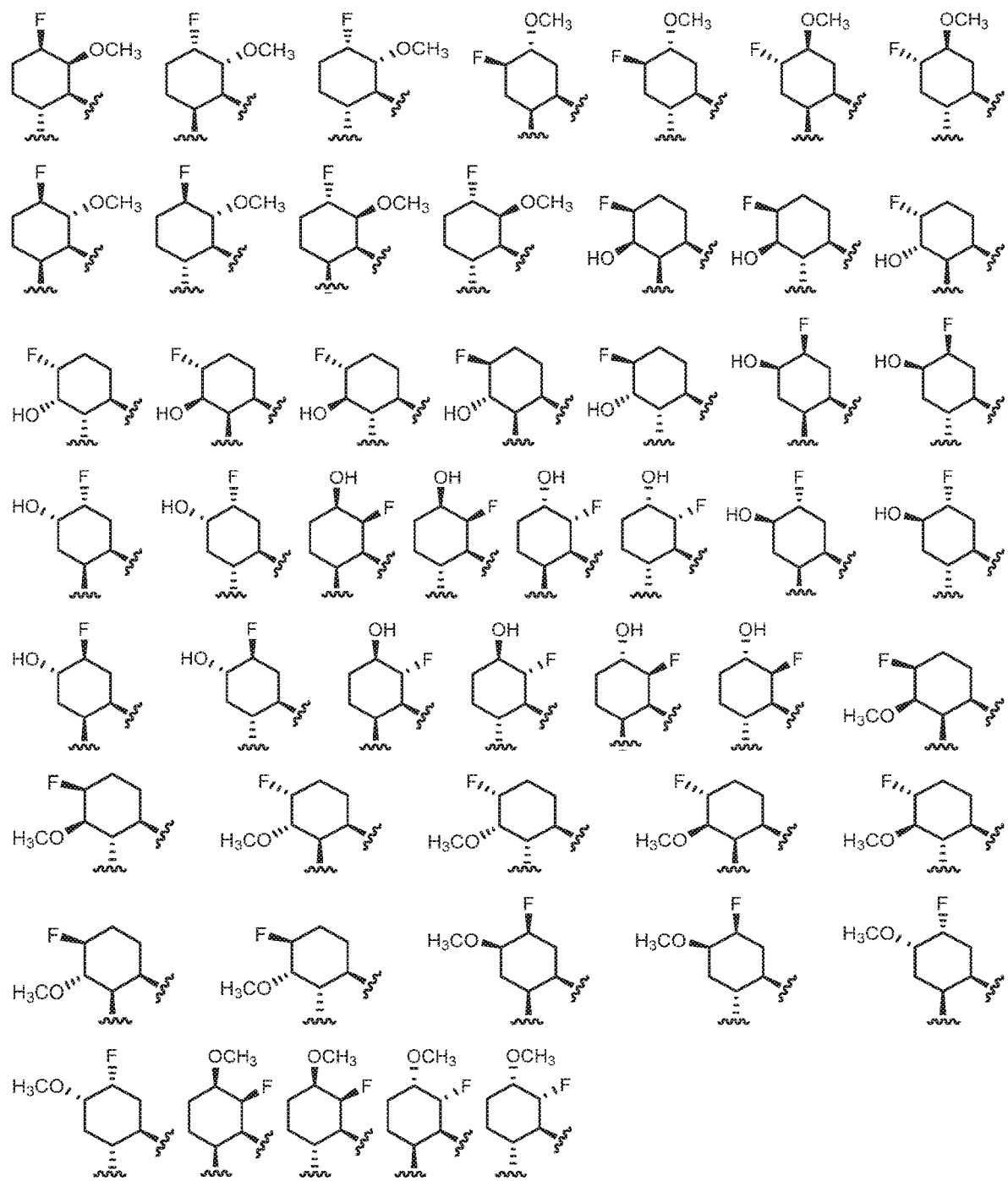
Figure 2M:
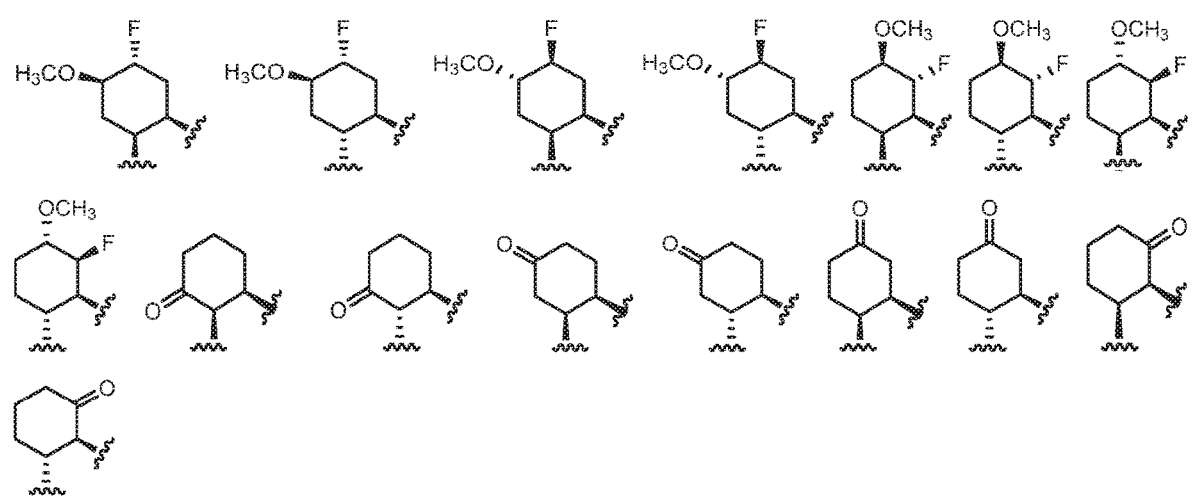
Figure 3:
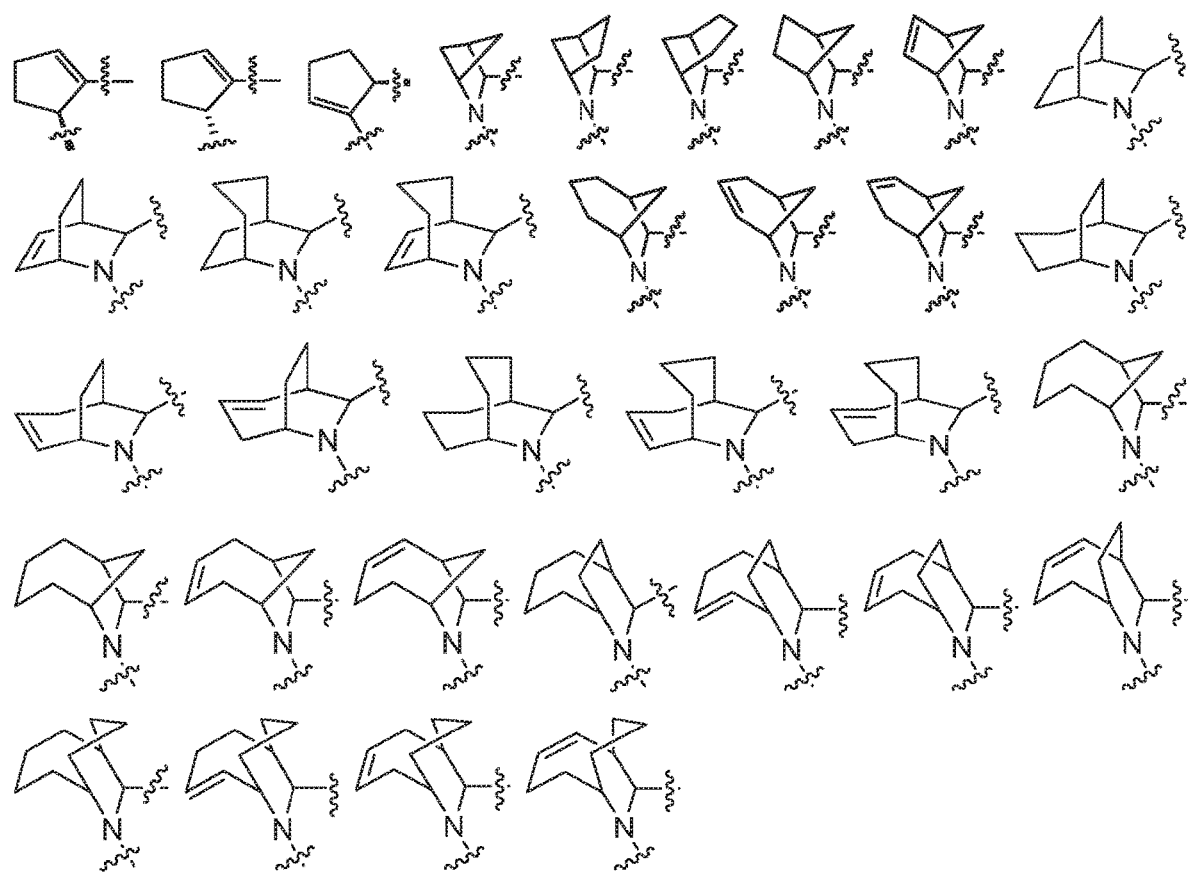
FIG. 3 provides non-limiting embodiments of C2.
Figure 4A:
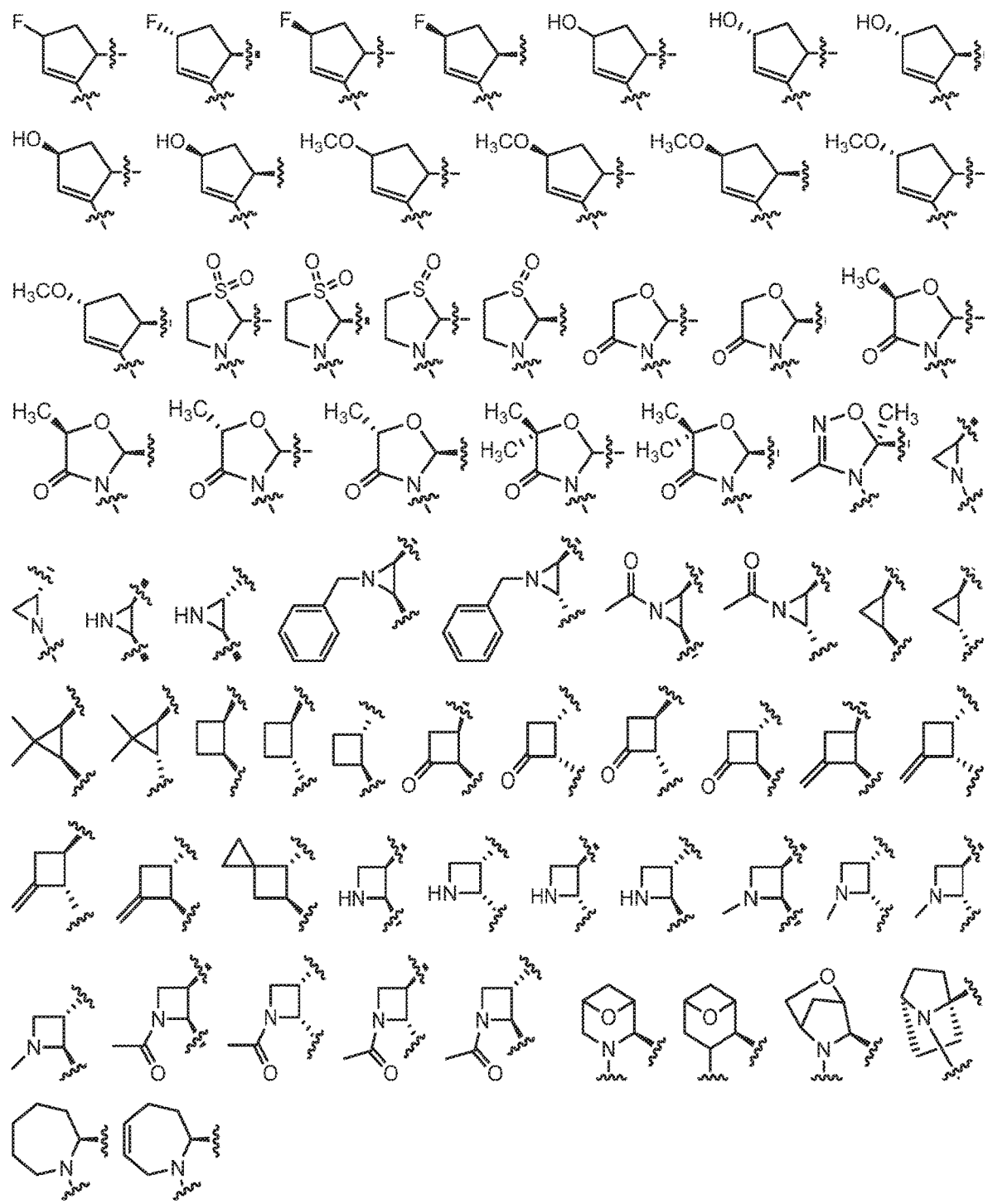
FIGS. 4A, 4B, 4C, 4D, 4E, 4F, 4G, 4H, 4I, 4J, 4K, 4L, 4M, and 4N, provide non-limiting embodiments of C3.
Figure 4B:
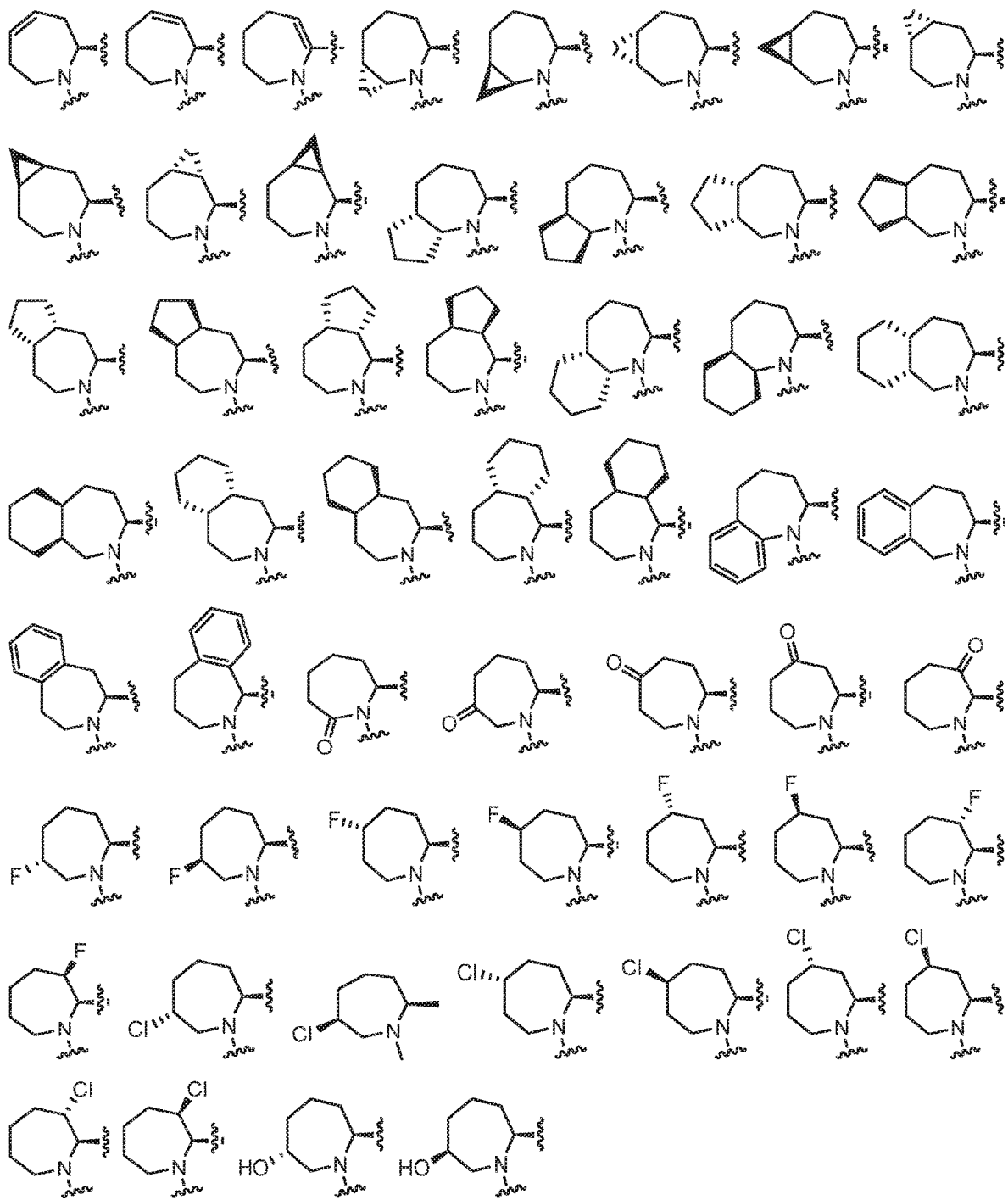
Figure 4C:
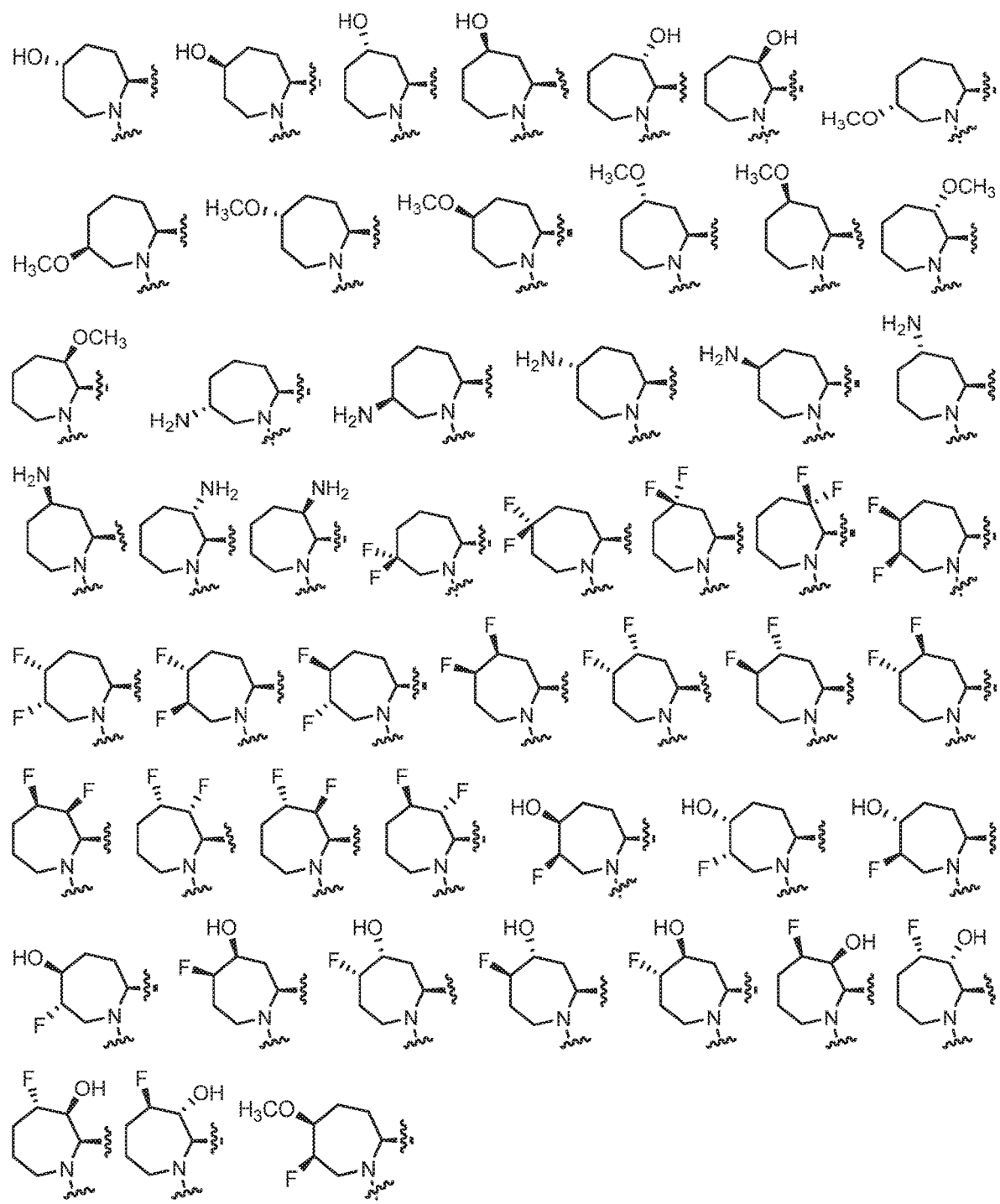
Figure 4D:
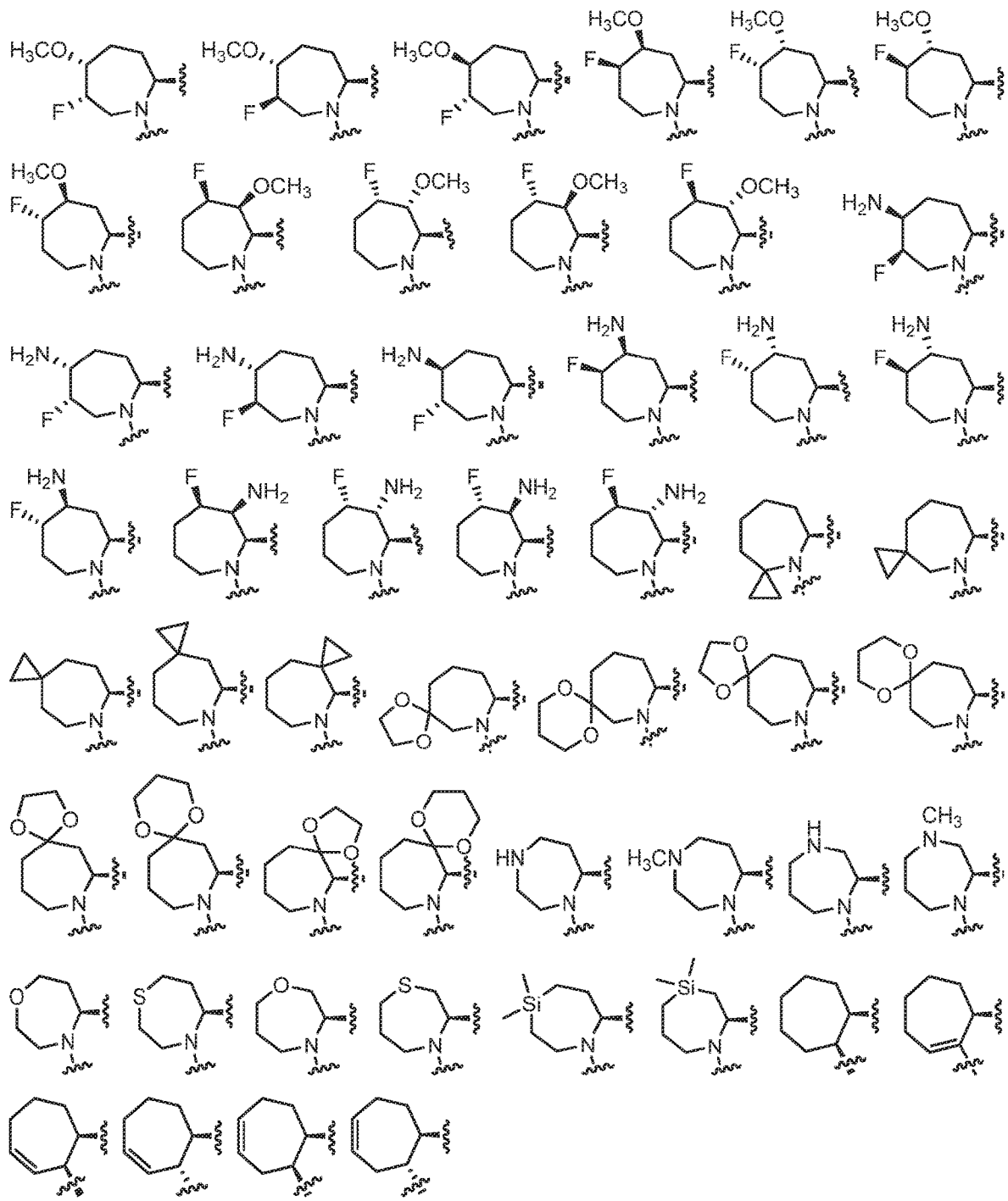
Figure 4E:
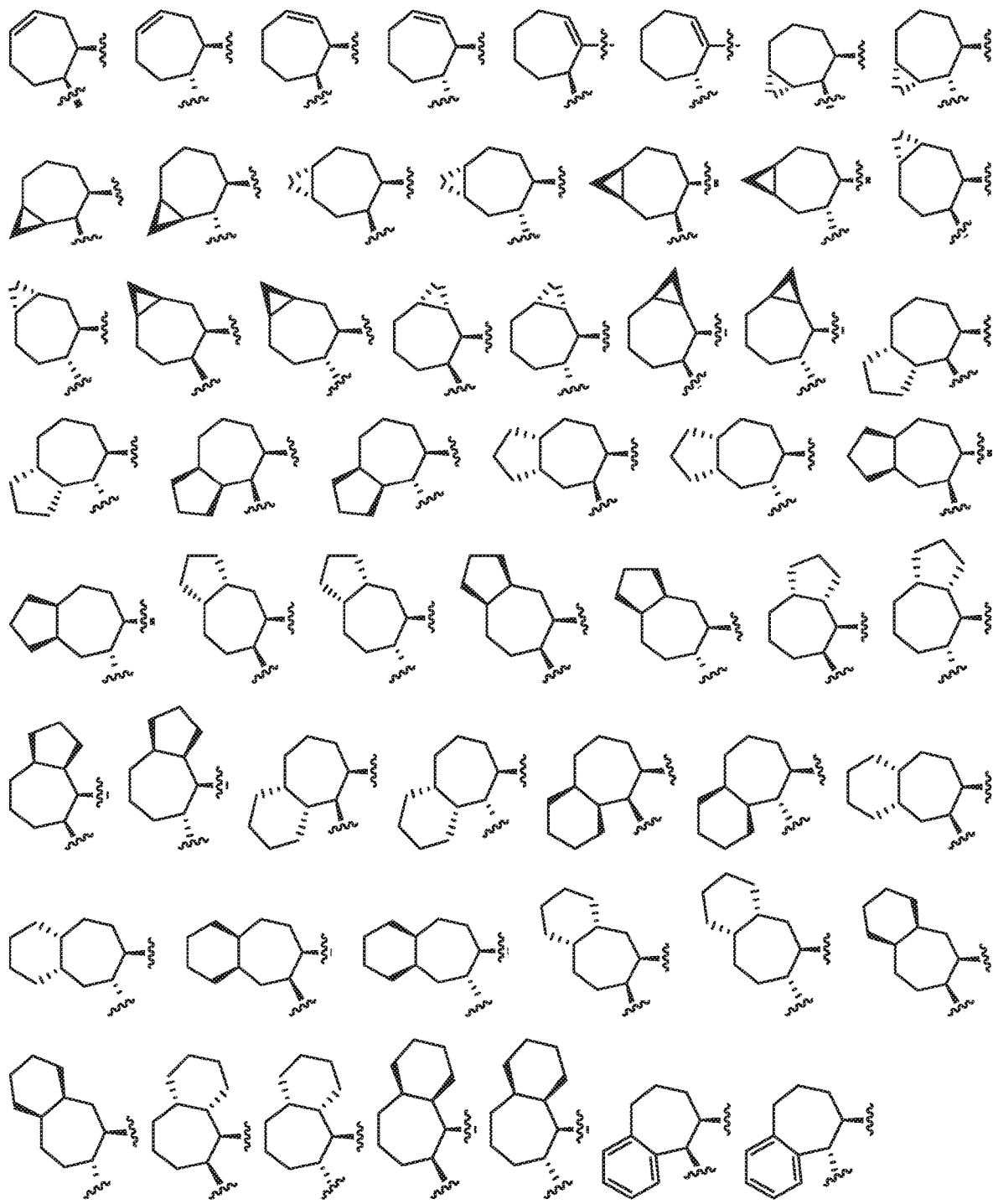
Figure 4F:
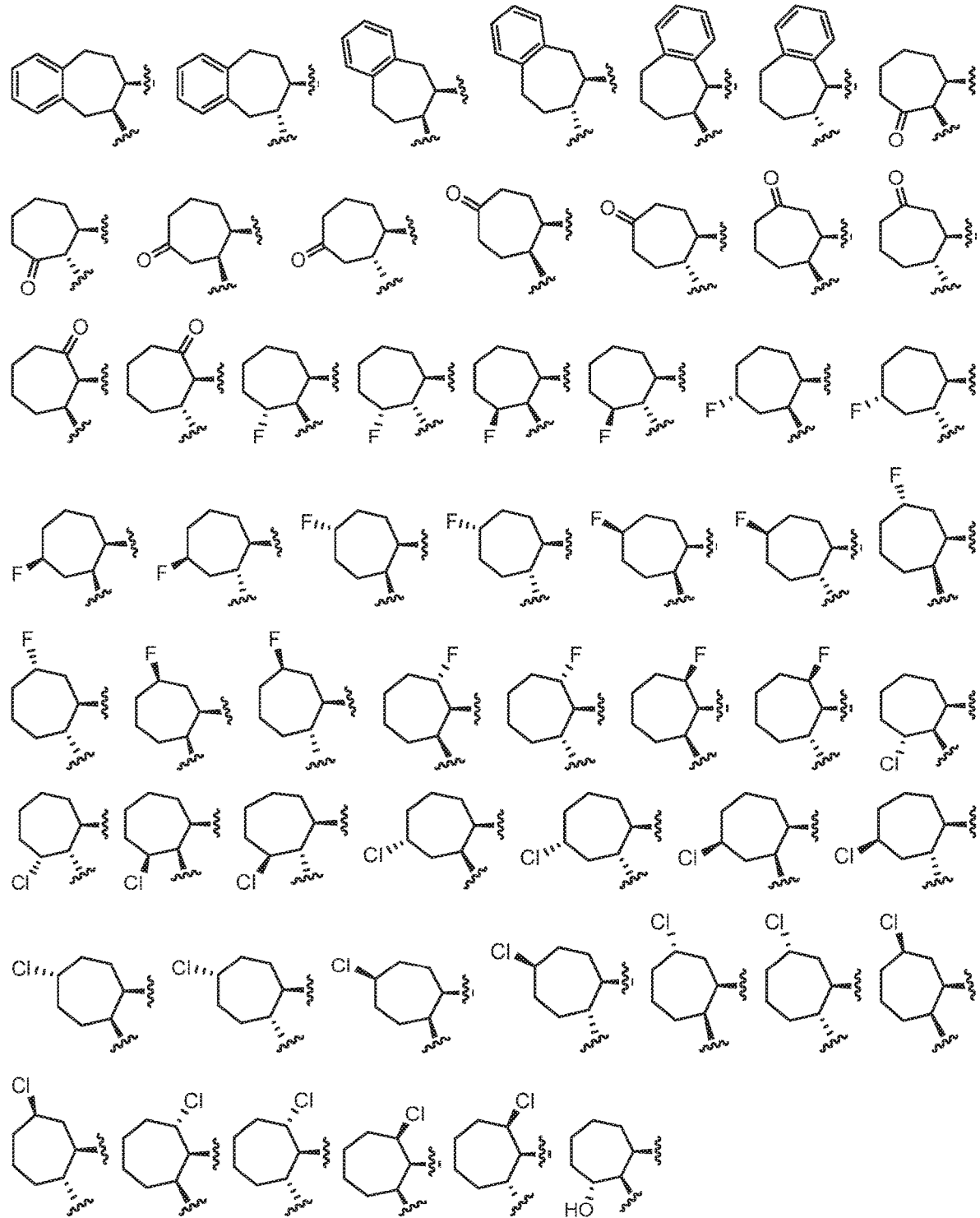
Figure 4G:
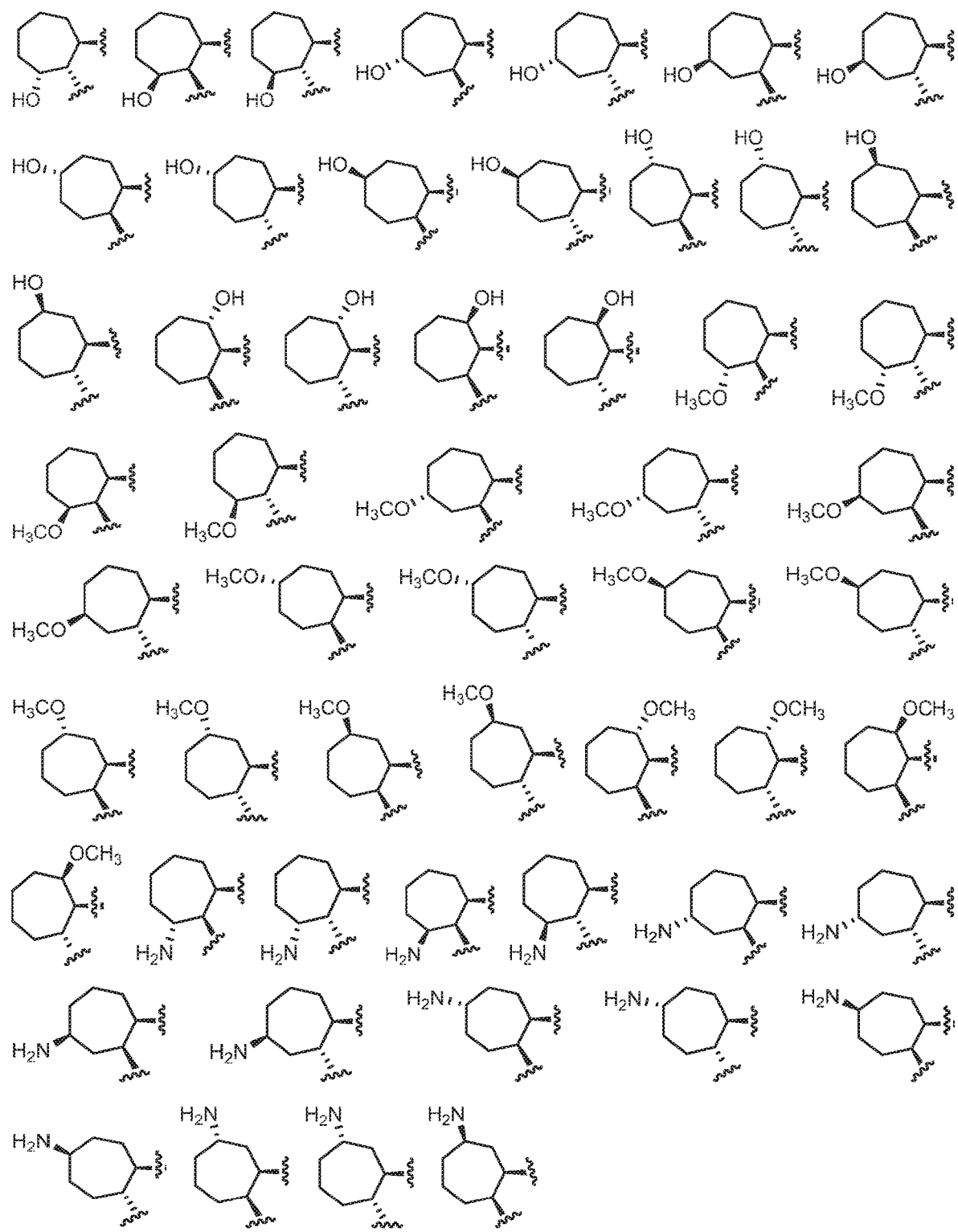
Figure 4H:
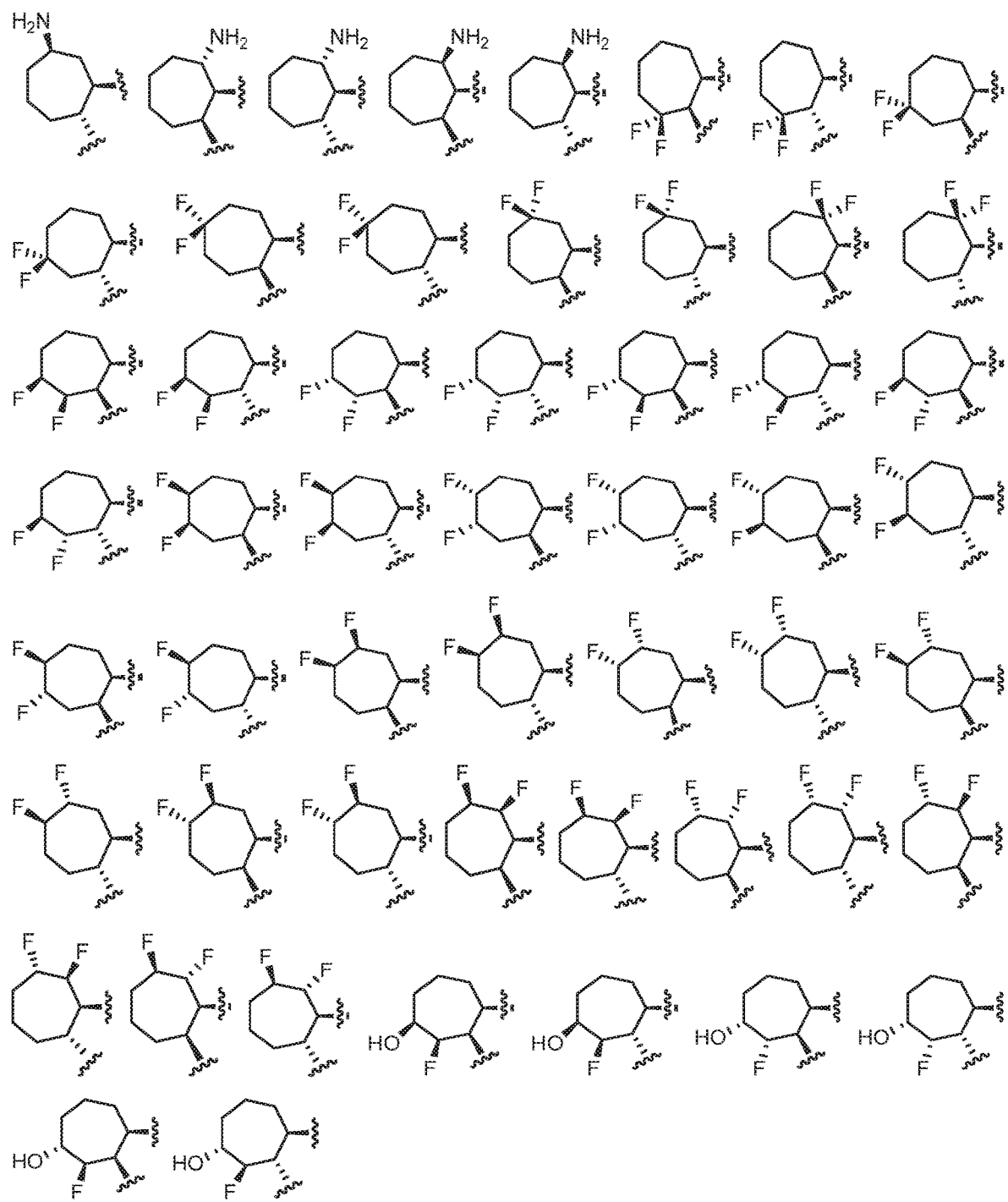
Figure 4I:
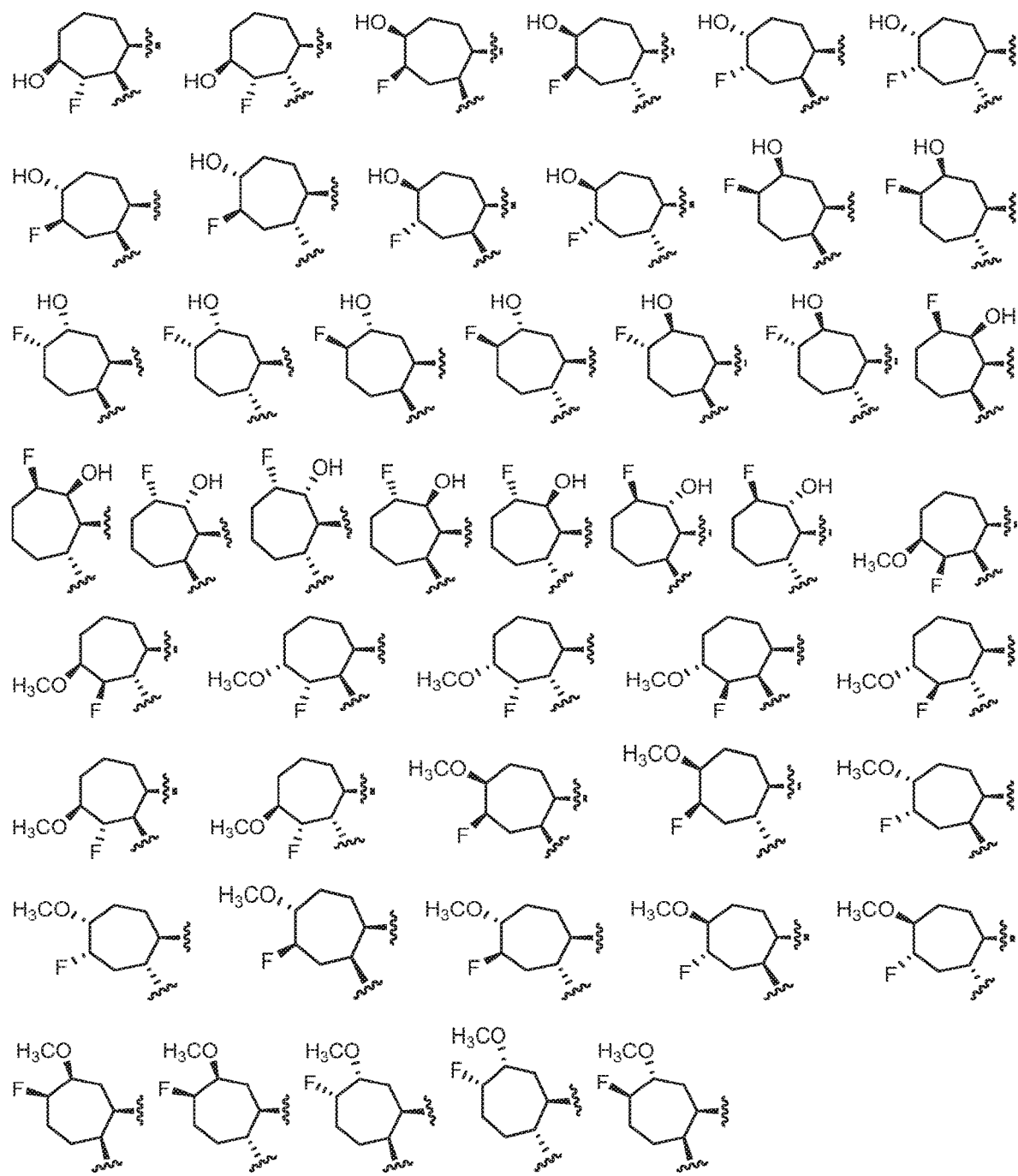
Figure 4J:
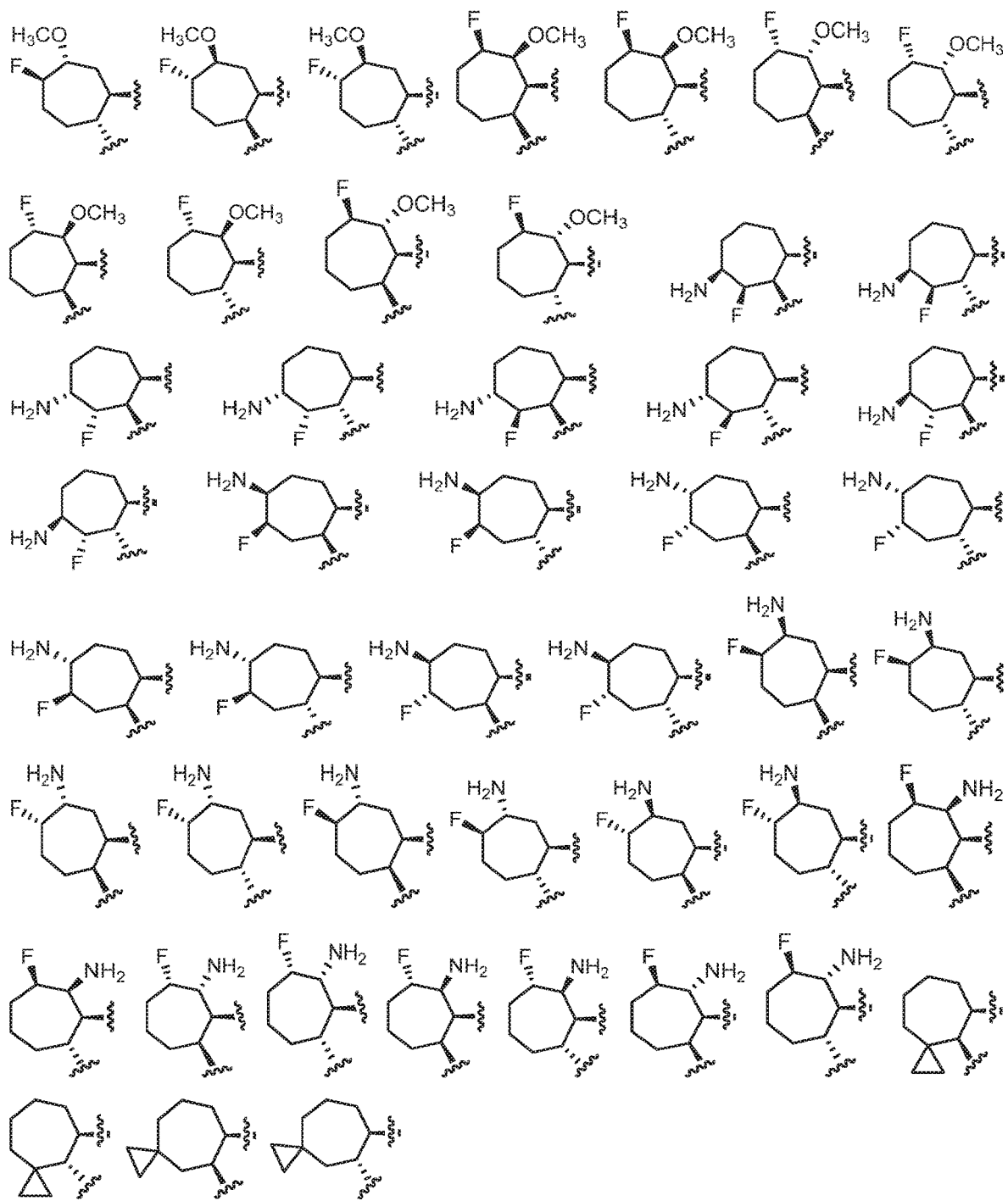
Figure 4K:
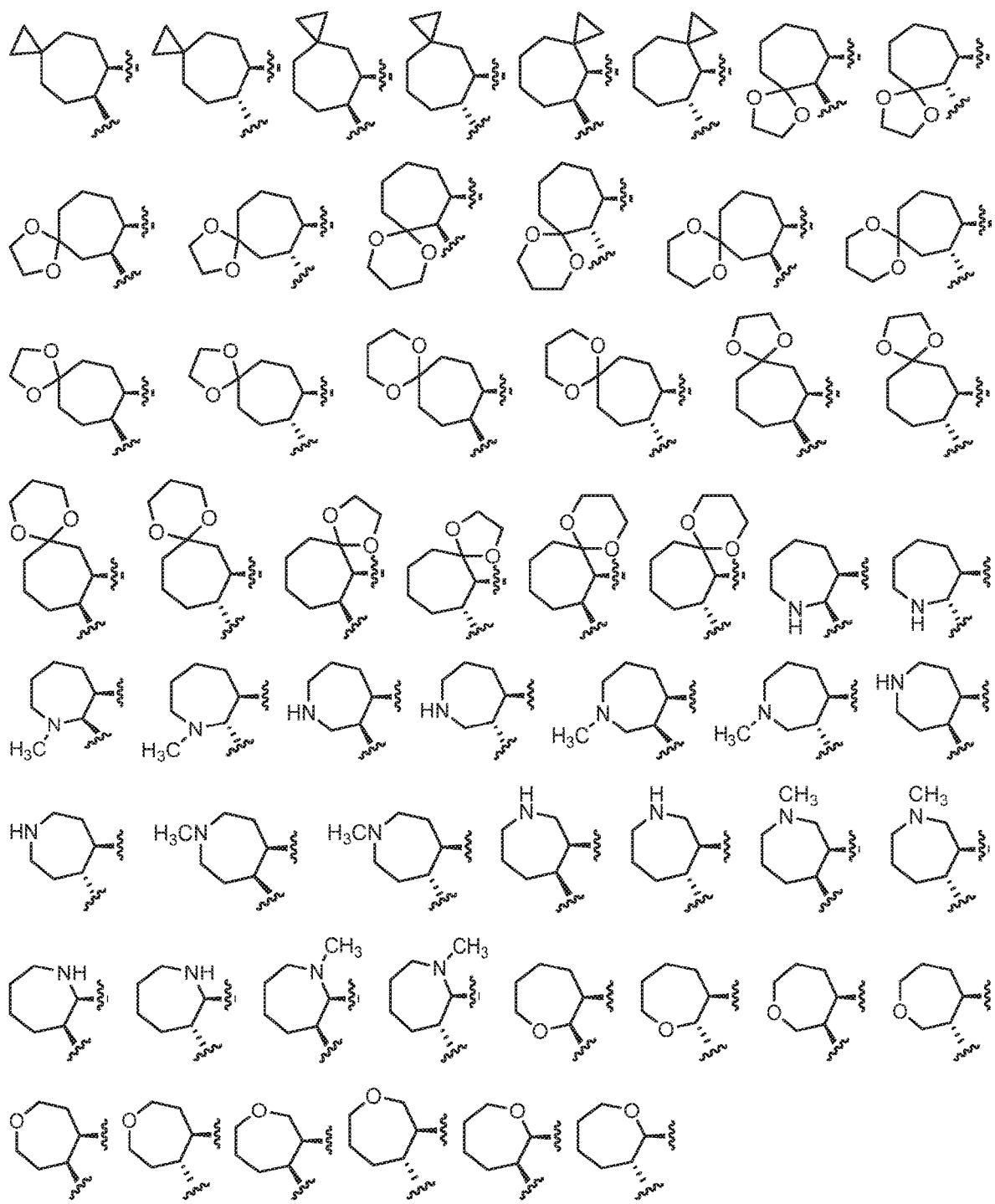
Figure 4L:
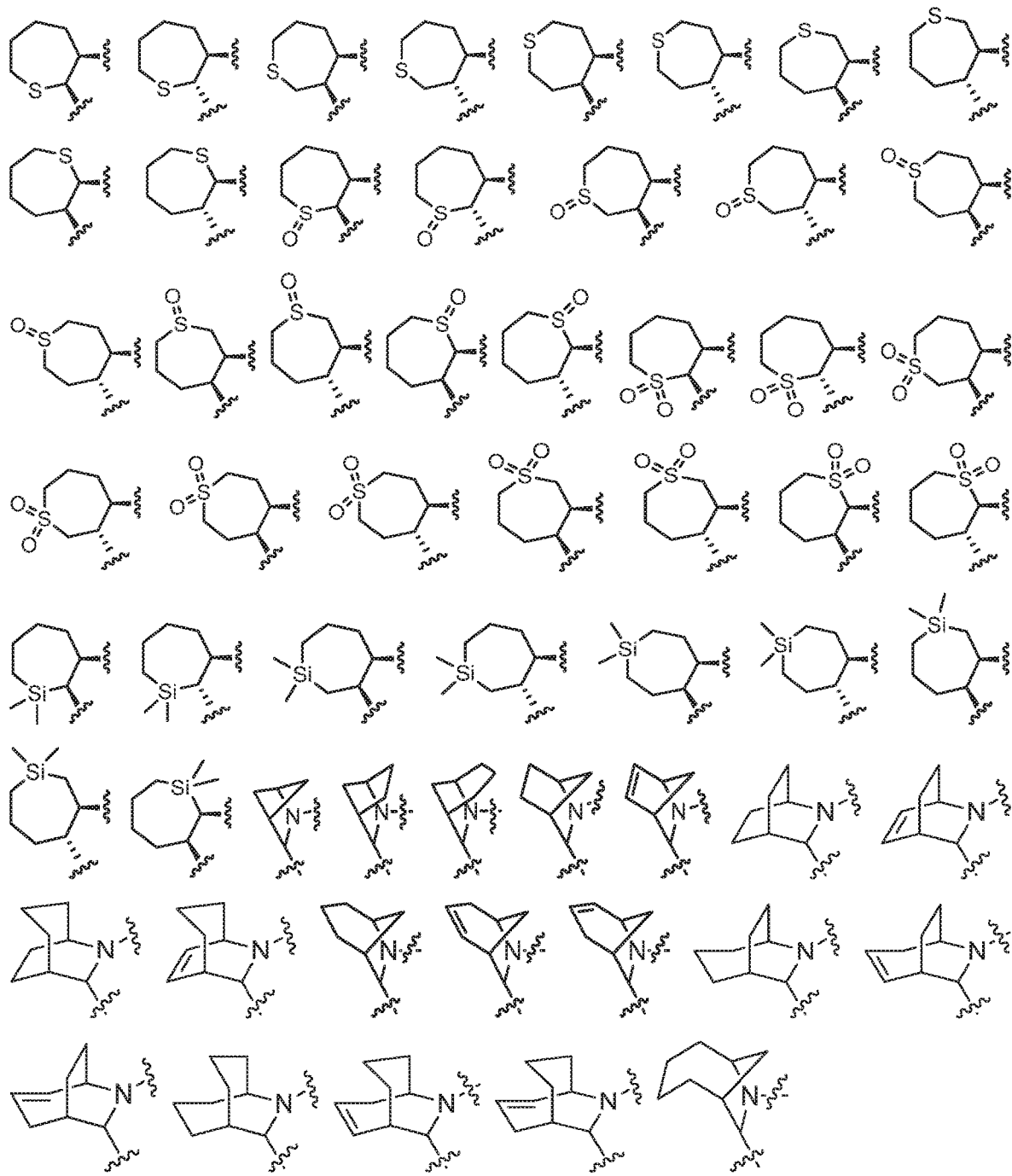
Figure 4M:
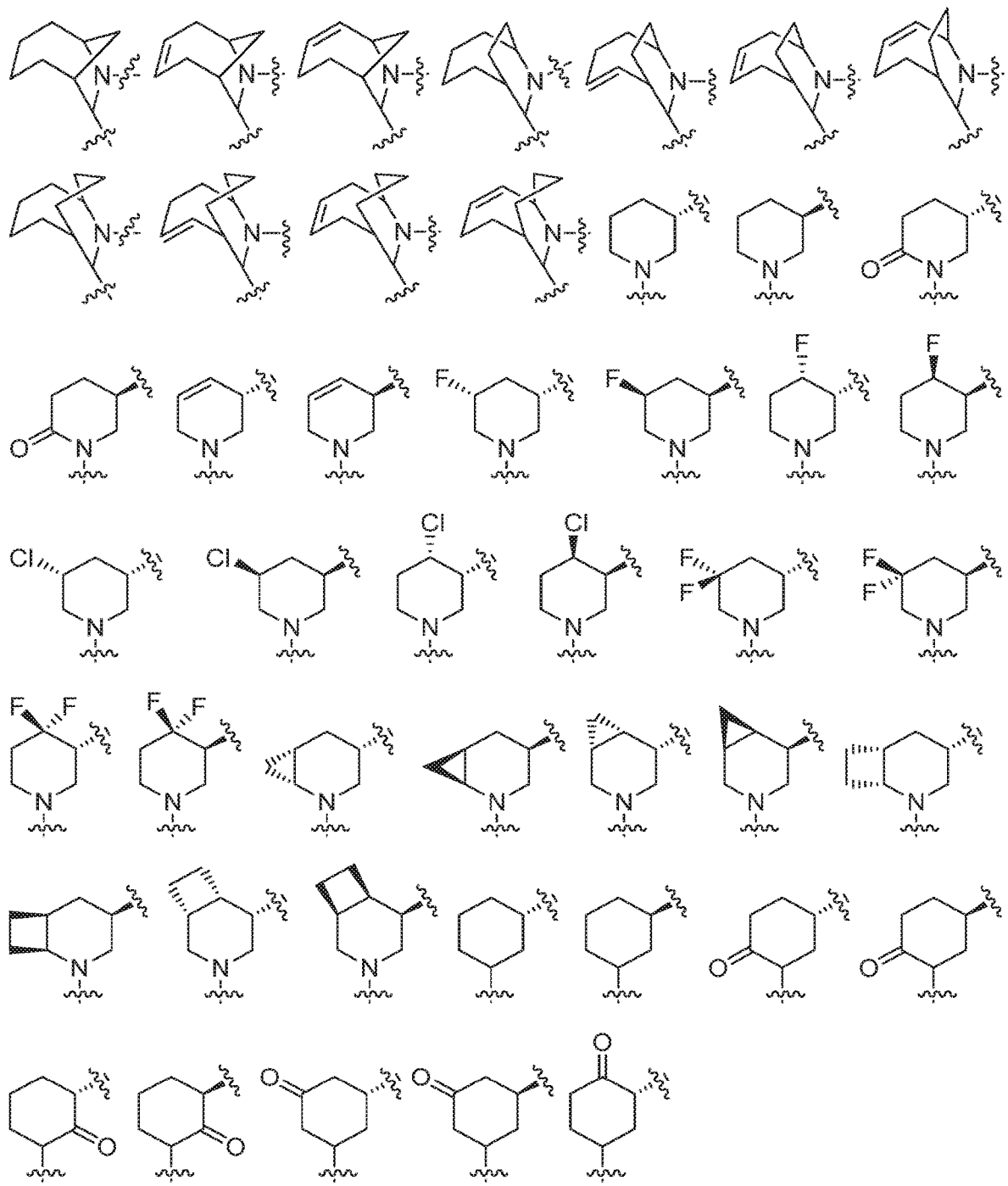
Figure 4N:
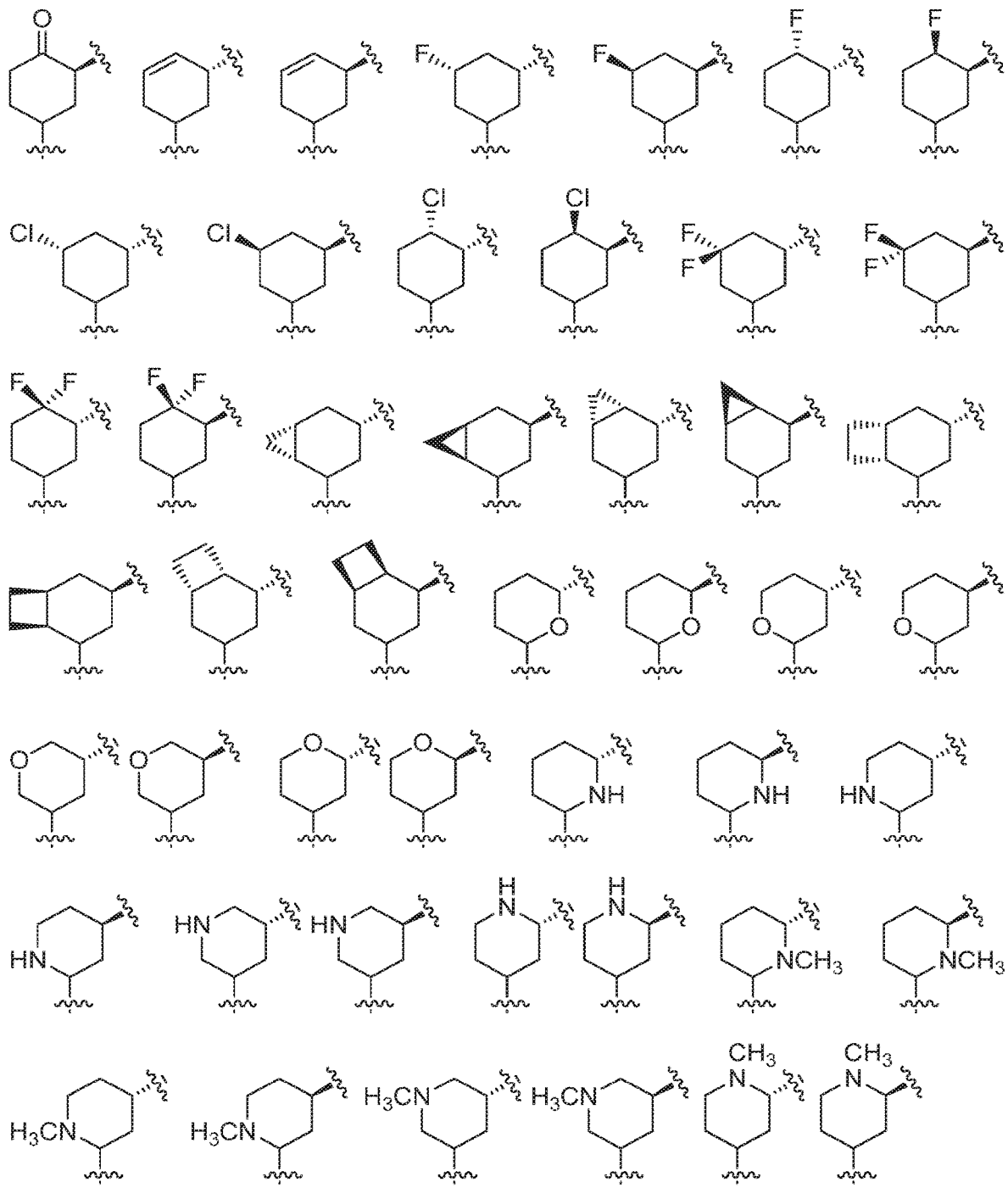
Figure 5:
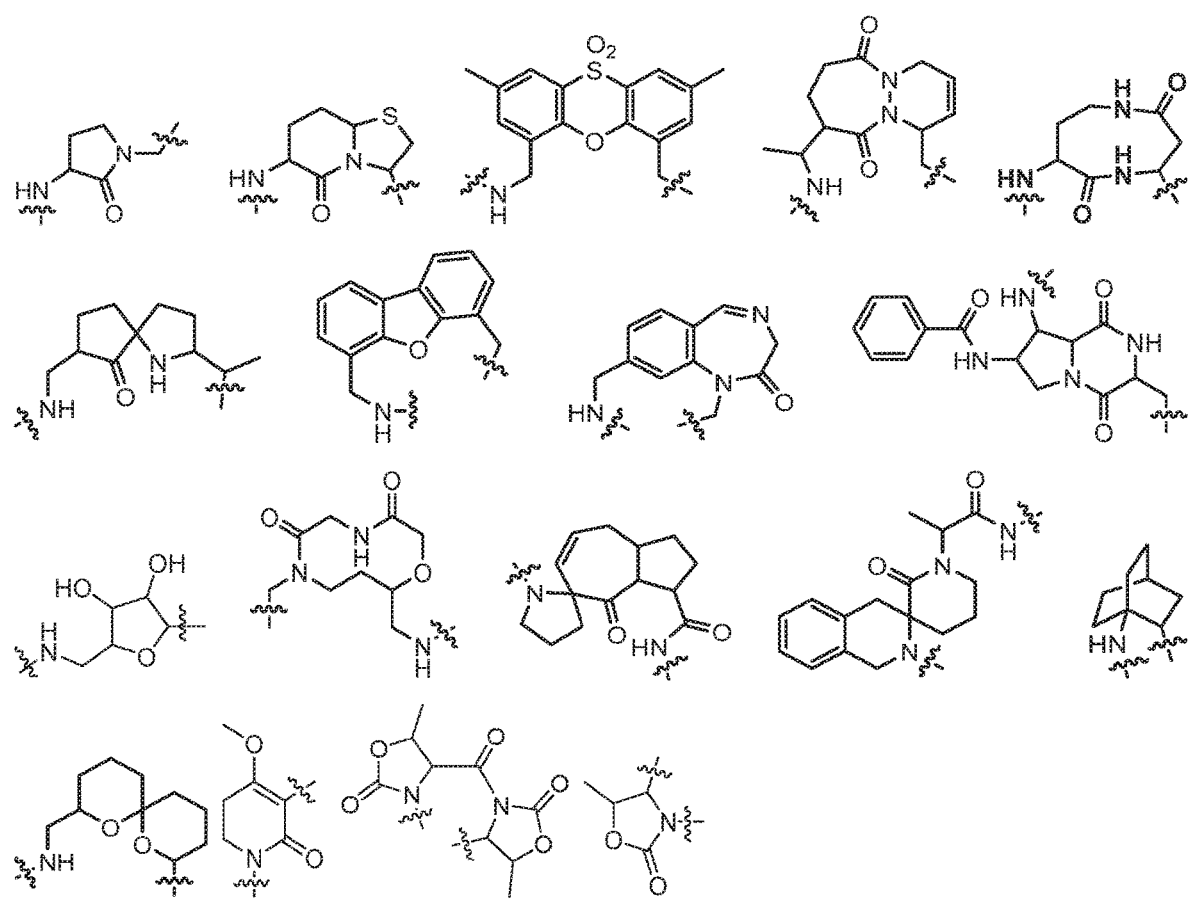
FIG. 5 provides non-limiting embodiments of central core small mimetics of a beta-turn, beta turn inducers, reverse turn mimetics and foldamer monomers.
Figure 6:
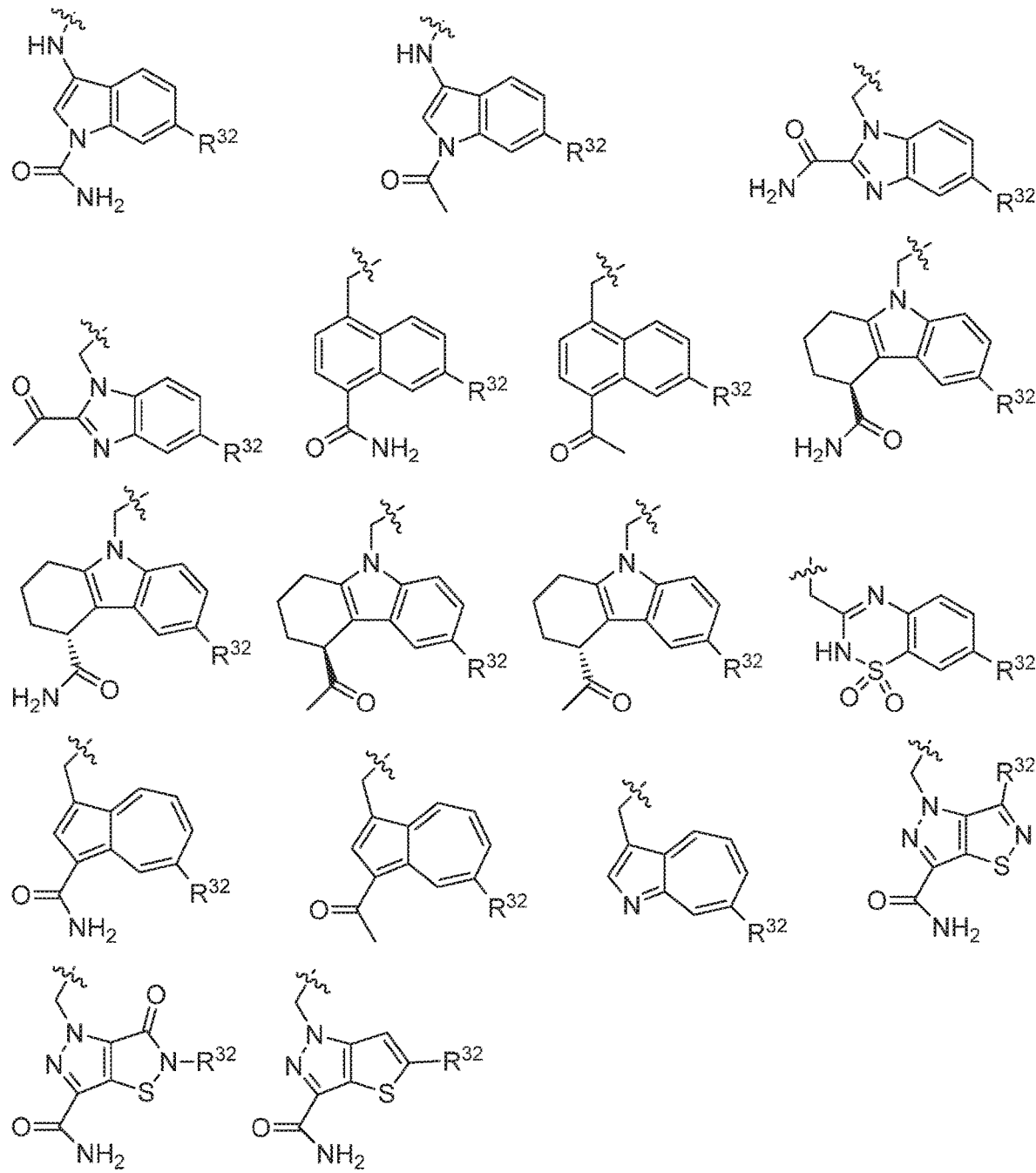
FIG. 6 provides non-limiting embodiments of A1', wherein $R^{32}$ is defined below.
Figure 7A:
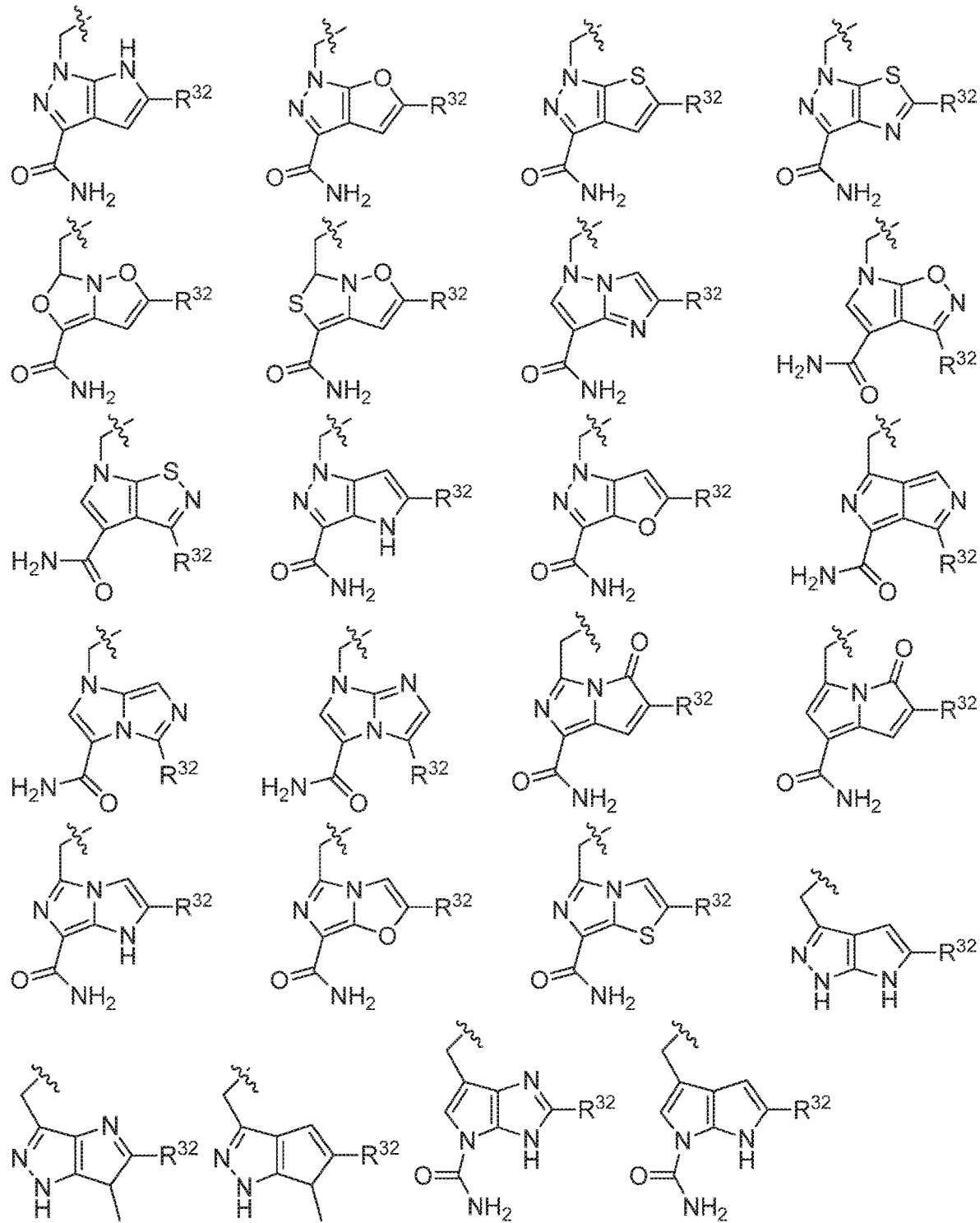
FIGS. 7A, 7B, 7C, 7D, and 7E, provide non-limiting embodiments of A2, wherein $R^{32}$ is defined below.
Figure 7B:
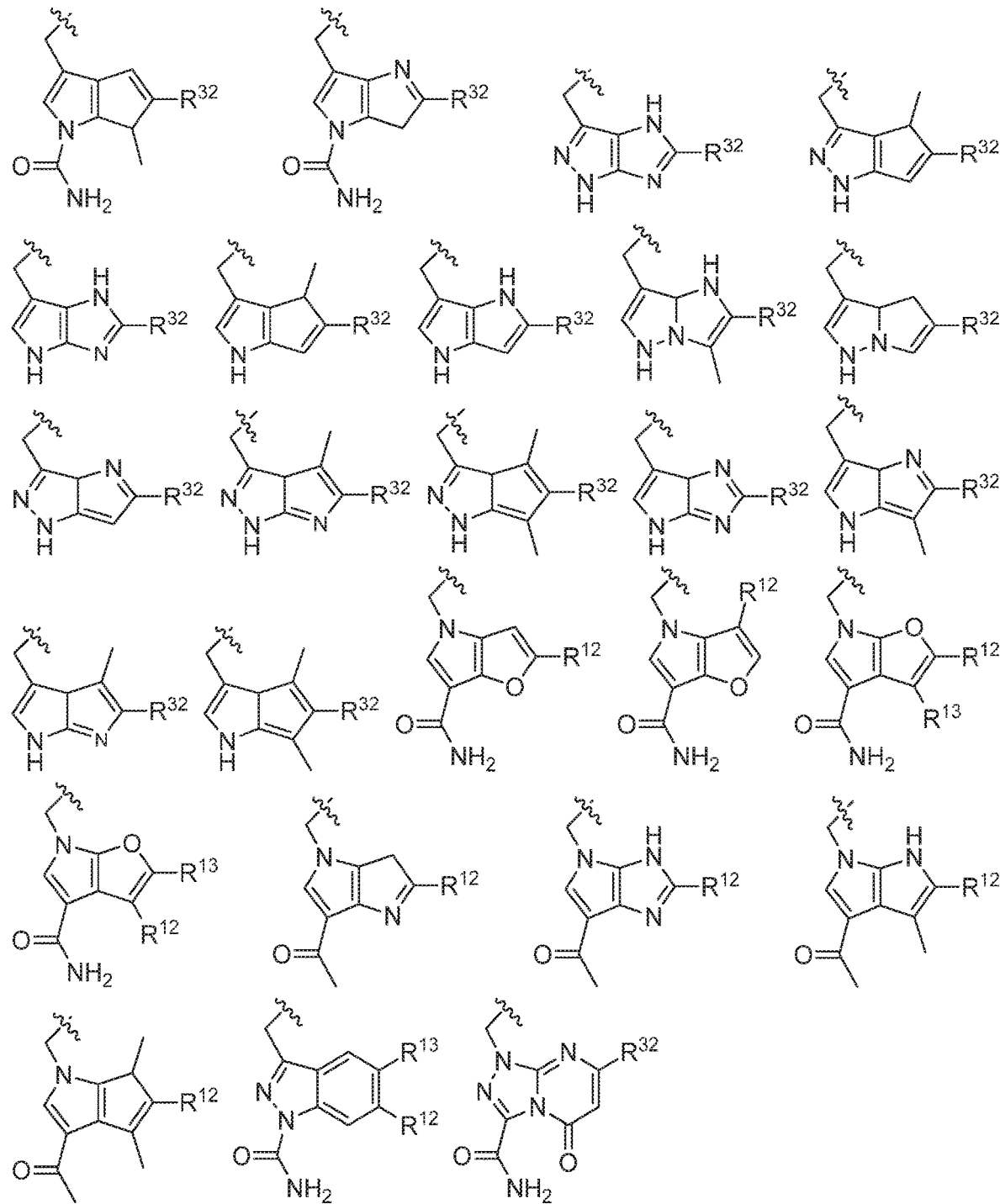
Figure 7C:
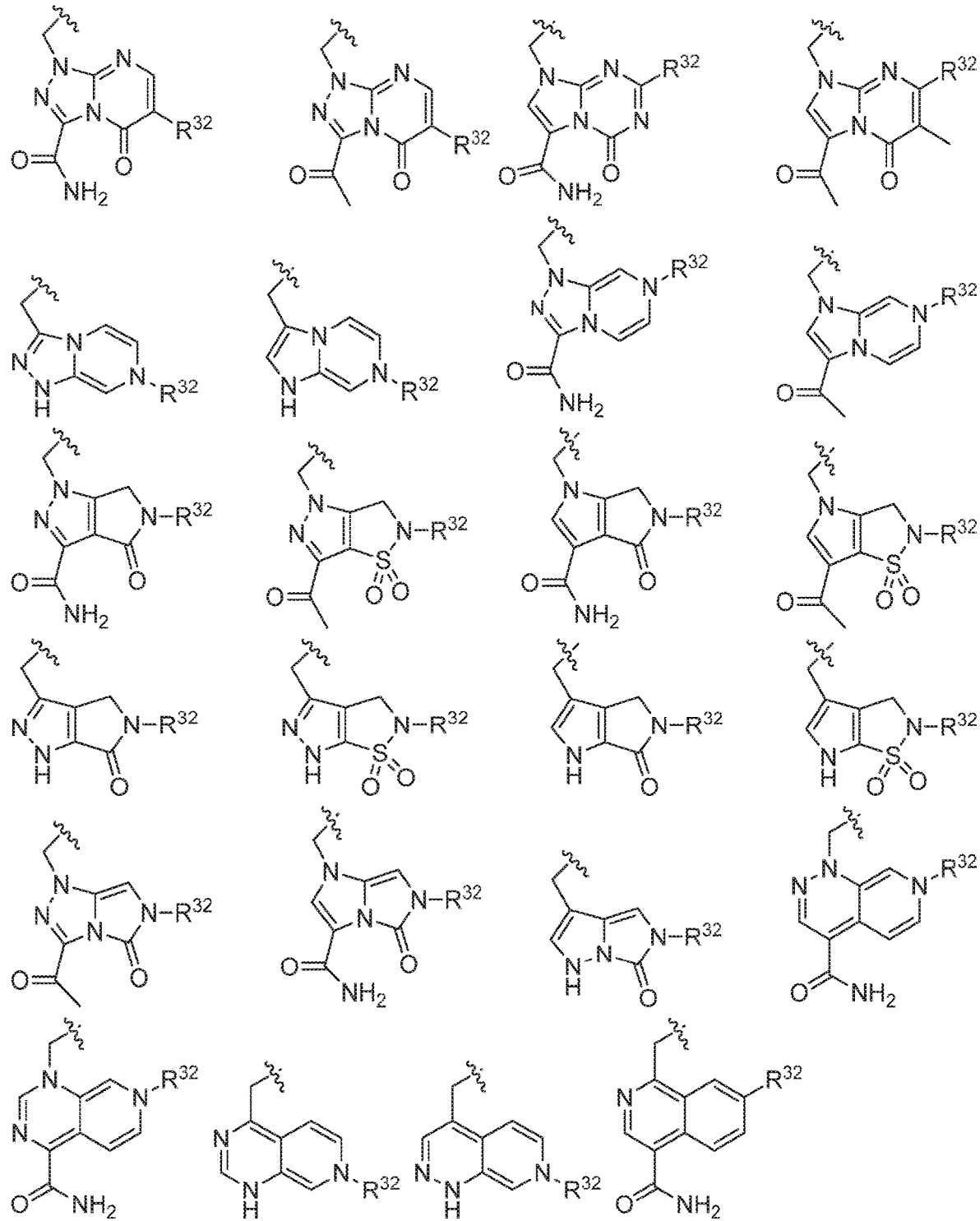
Figure 7D:
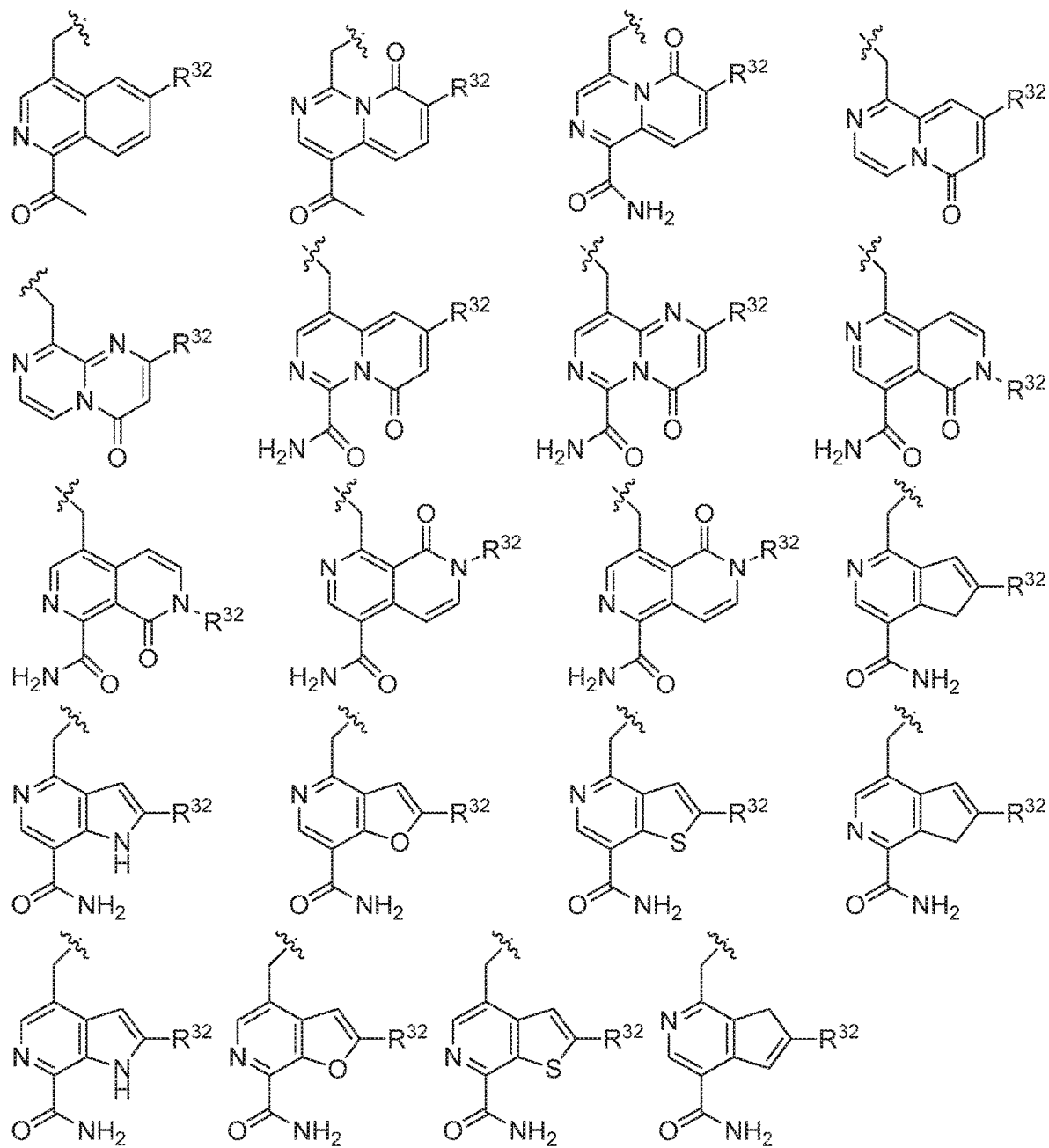
Figure 7E:
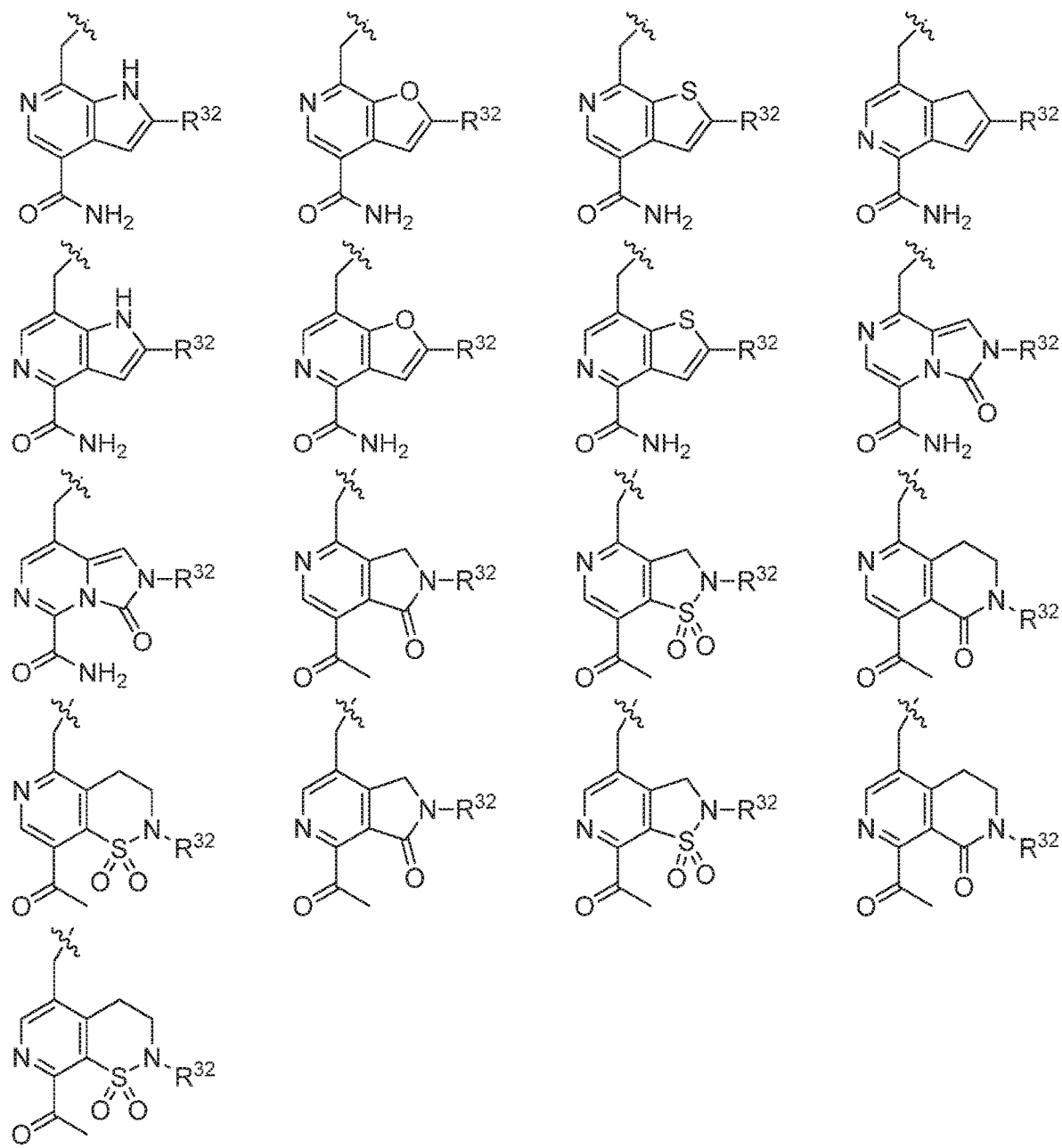
Figure 8A:
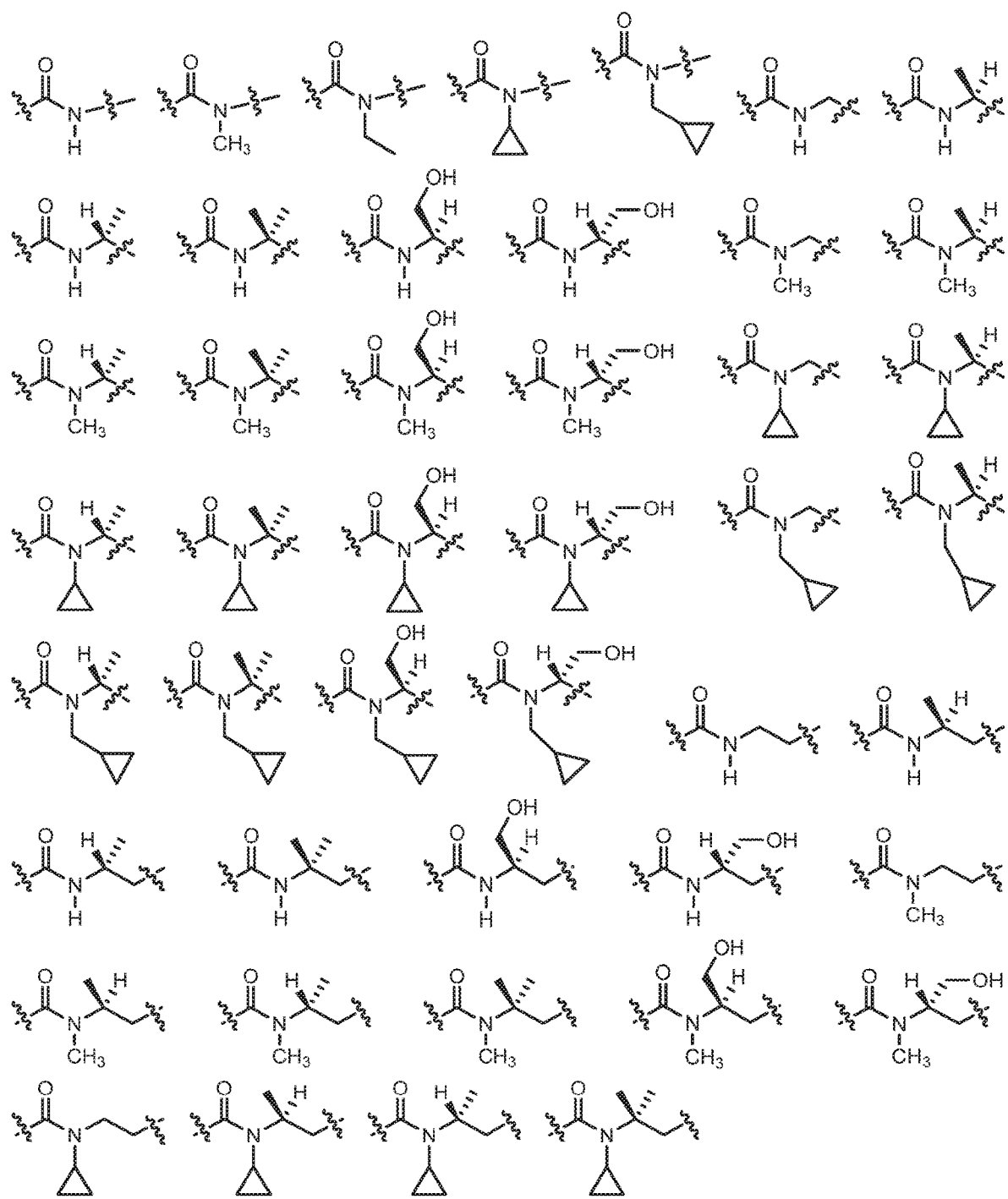
FIGS. 8A, 8B, 8C, and 8D, provide non-limiting embodiments of L1'.
Figure 8B:
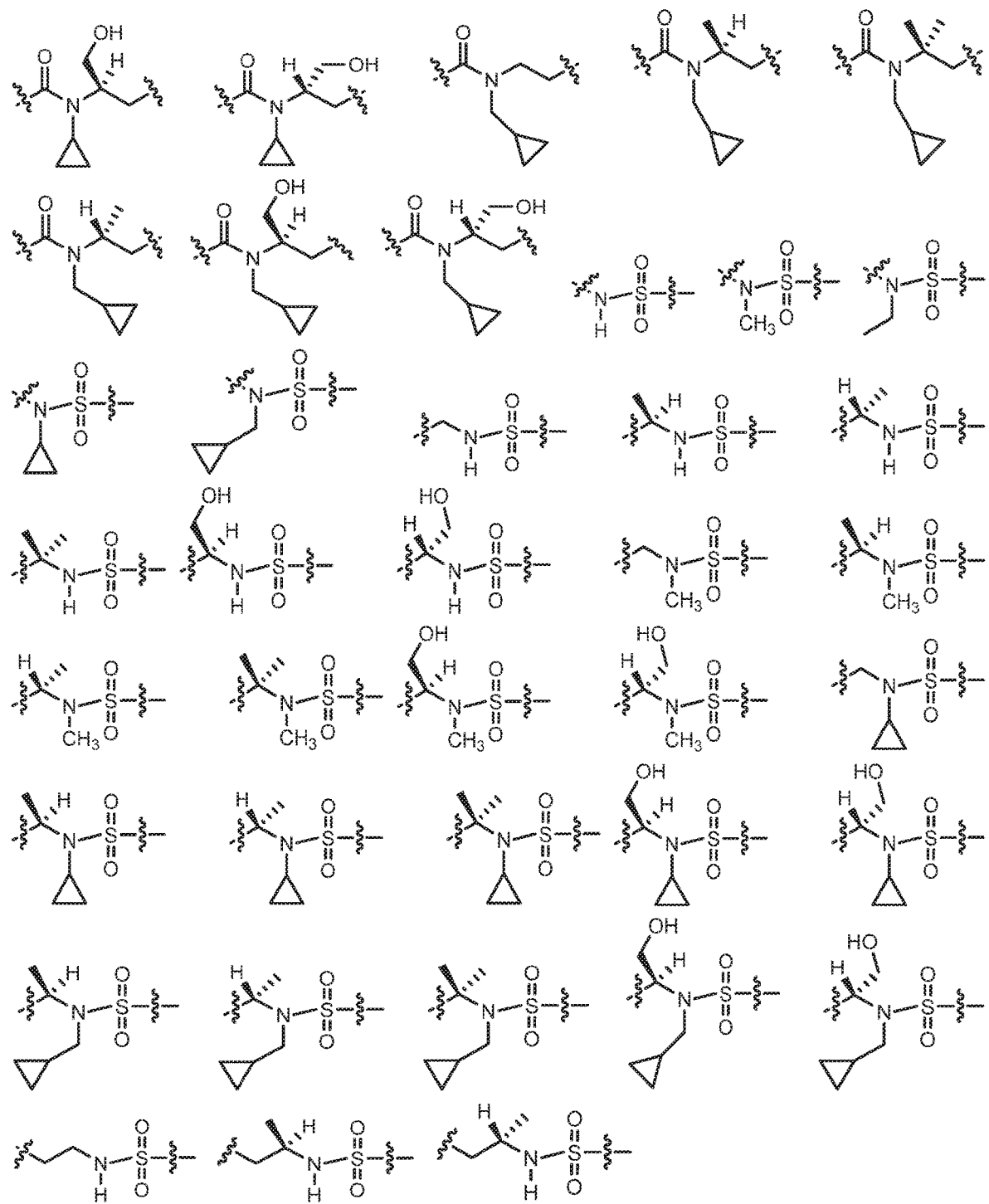
Figure 8C:
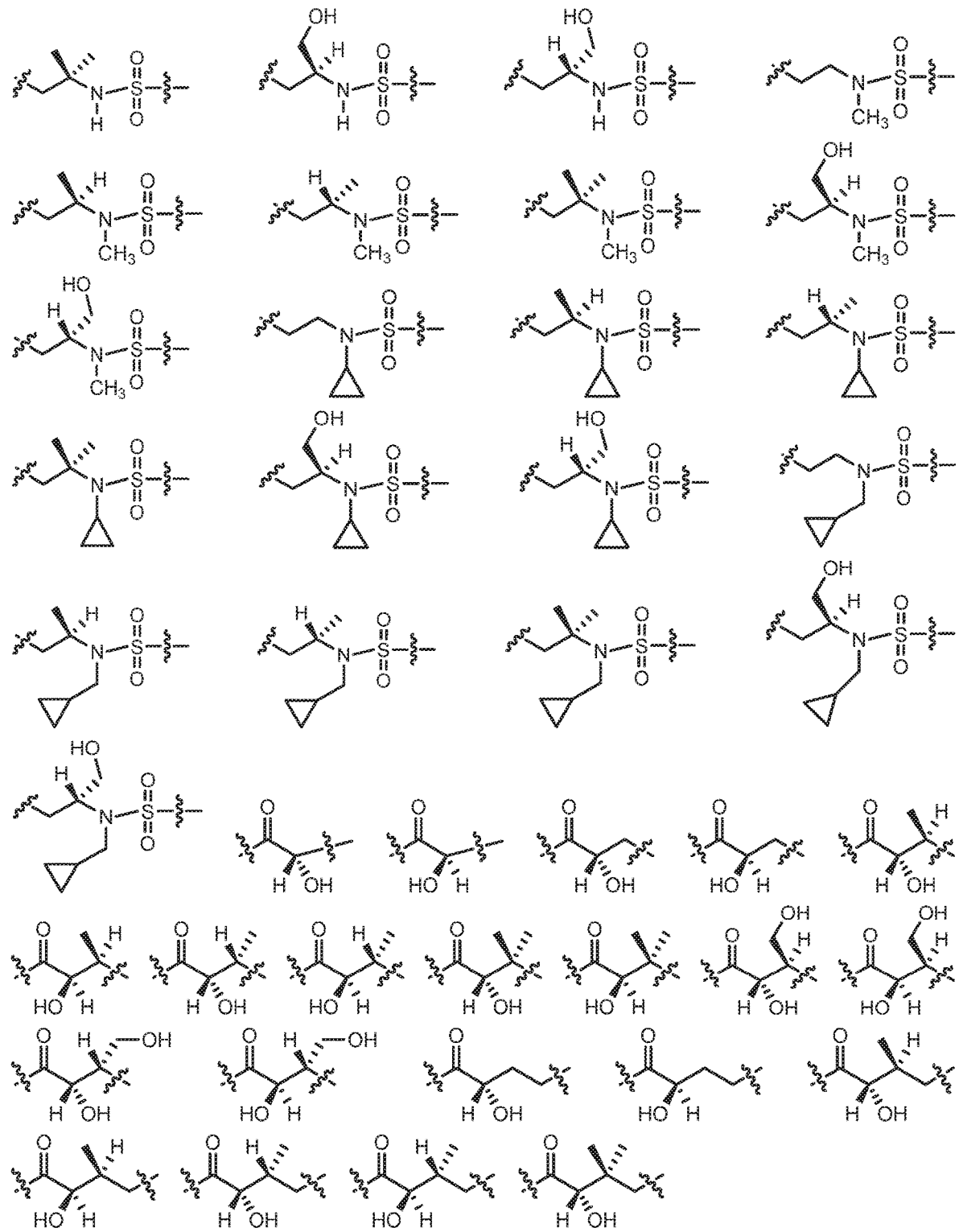
Figure 8D:
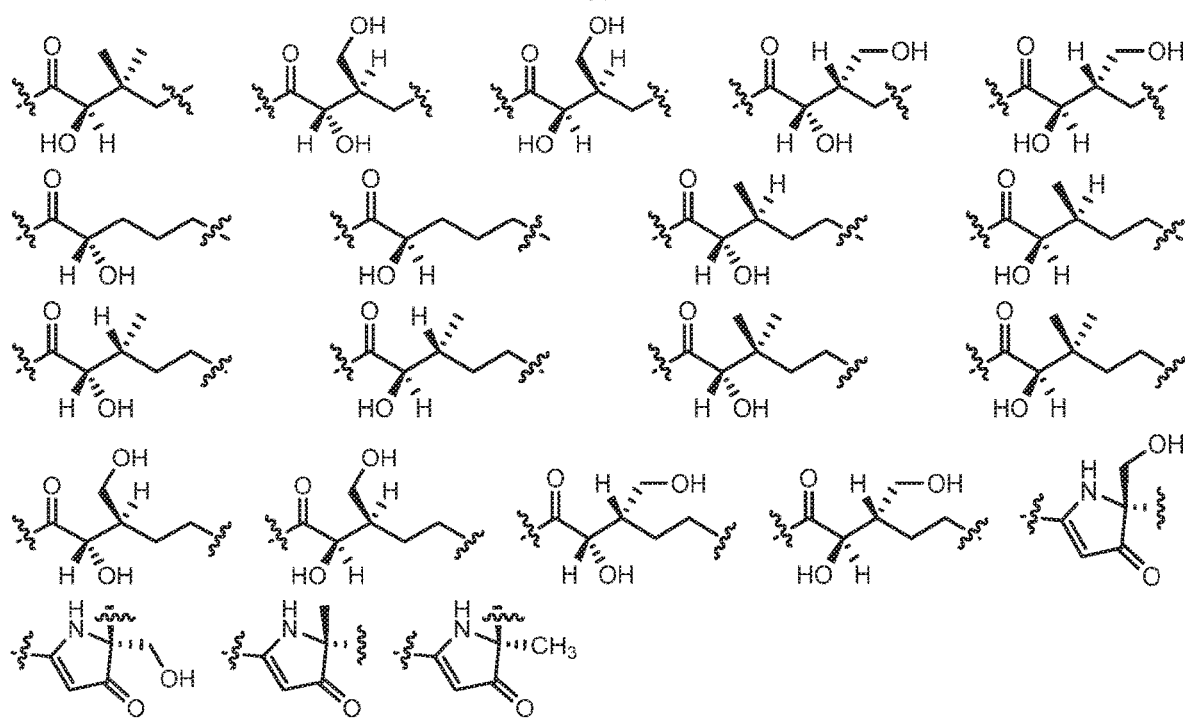
Figure 9A:
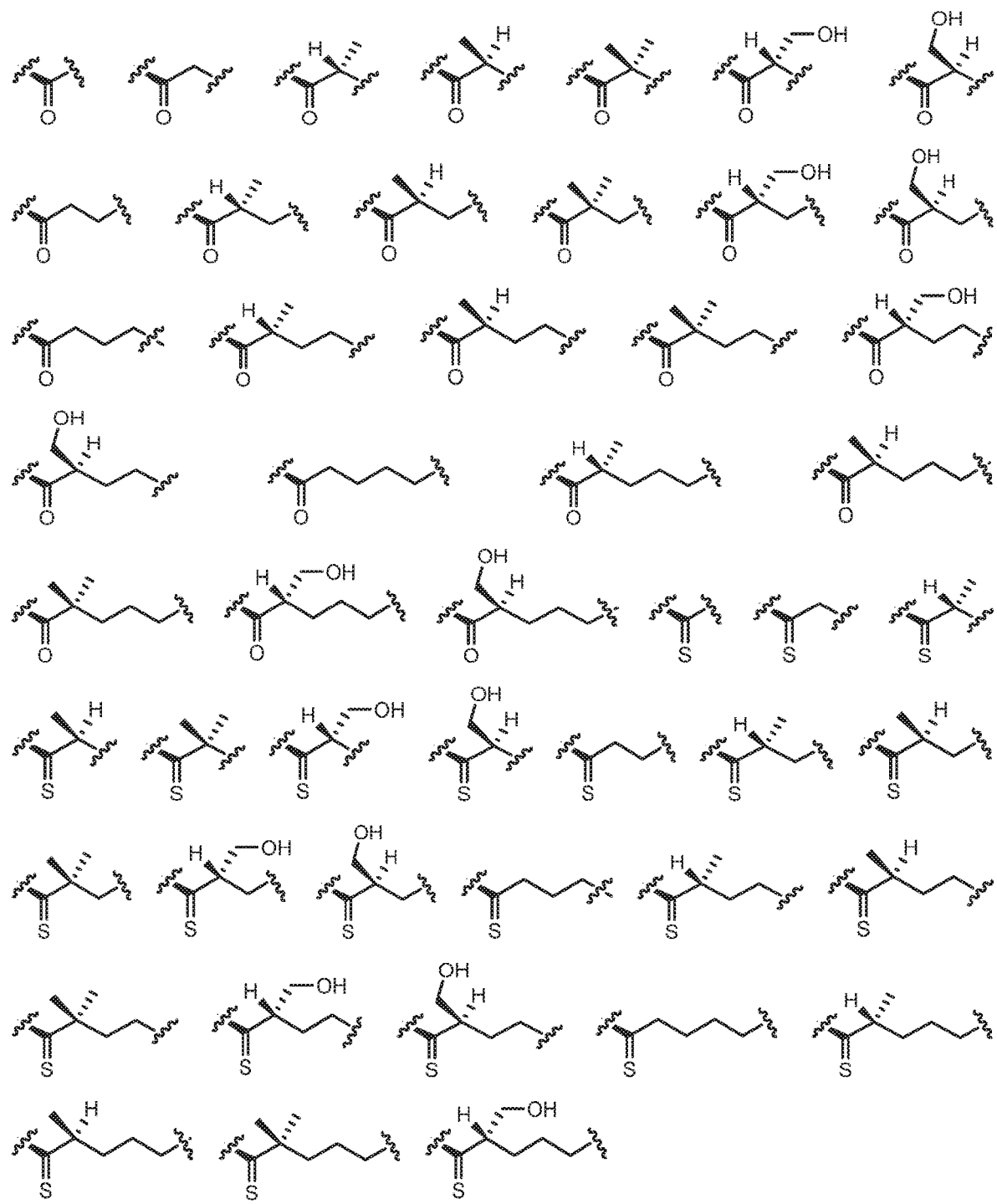
FIGS. 9A, 9B, 9C, 9D, 9E, 9F, 9G, 9H, 9I, and 9J, provide non-limiting embodiments of L2.
Figure 9B:
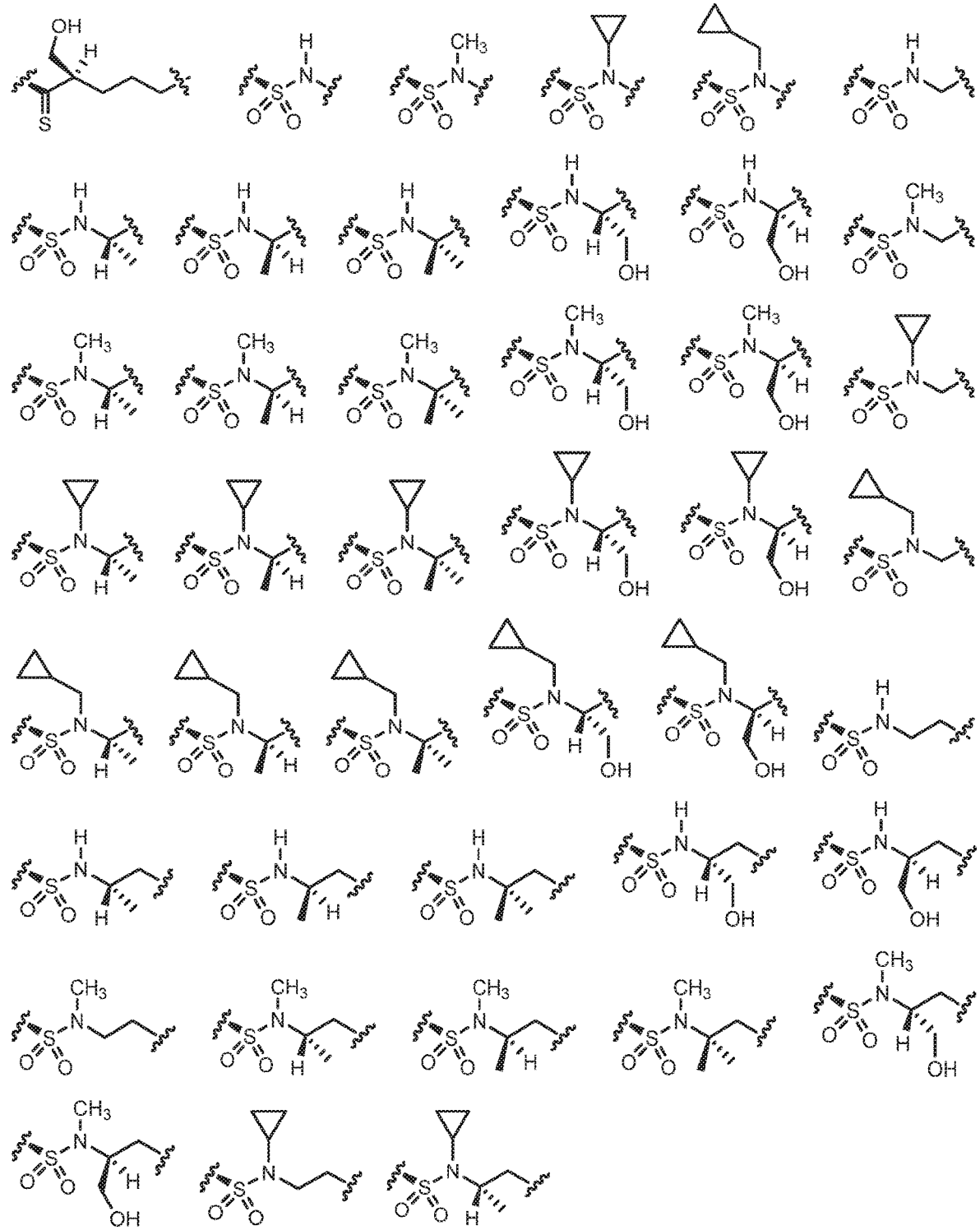
Figure 9C:
Figure 9D:
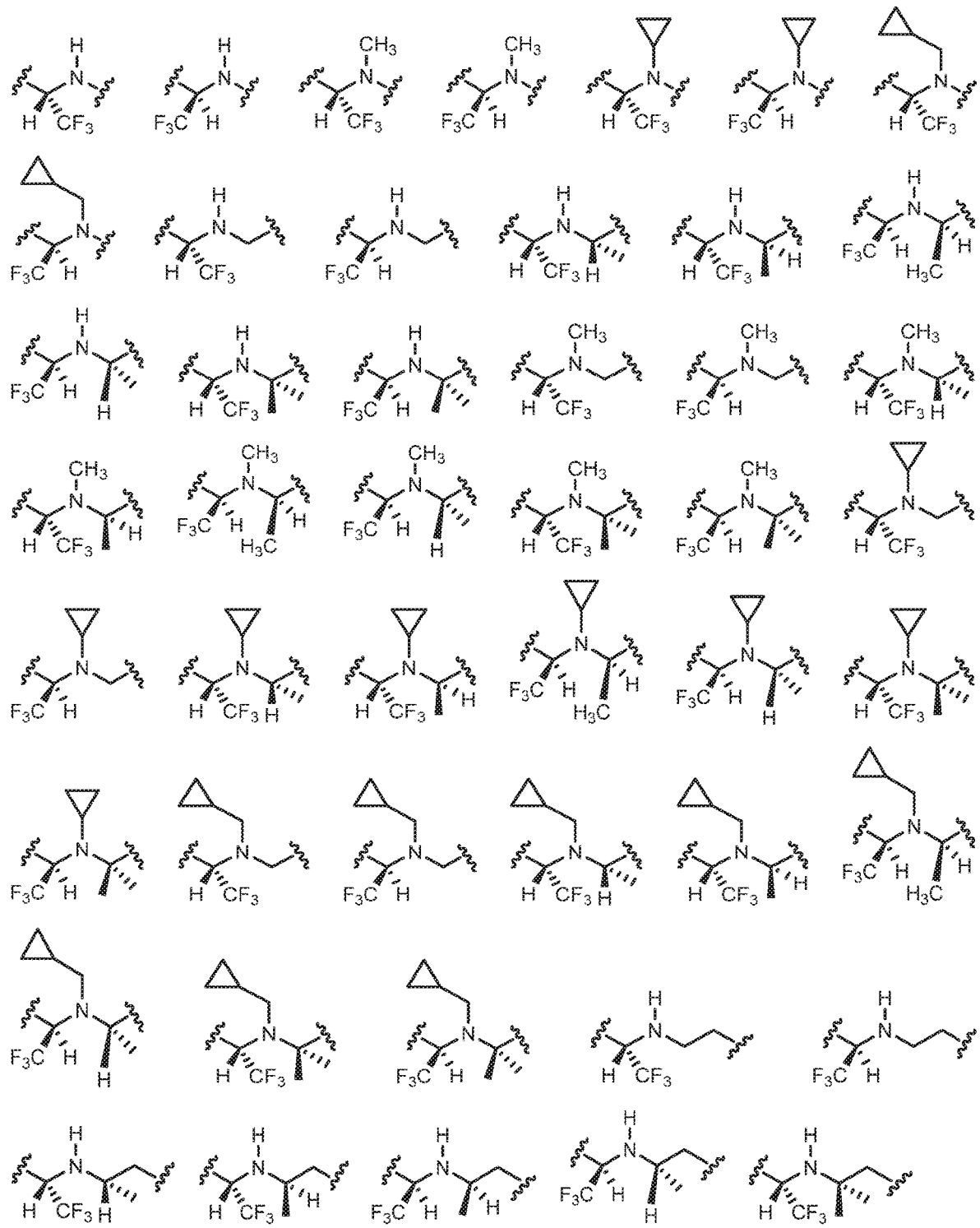
Figure 9E:
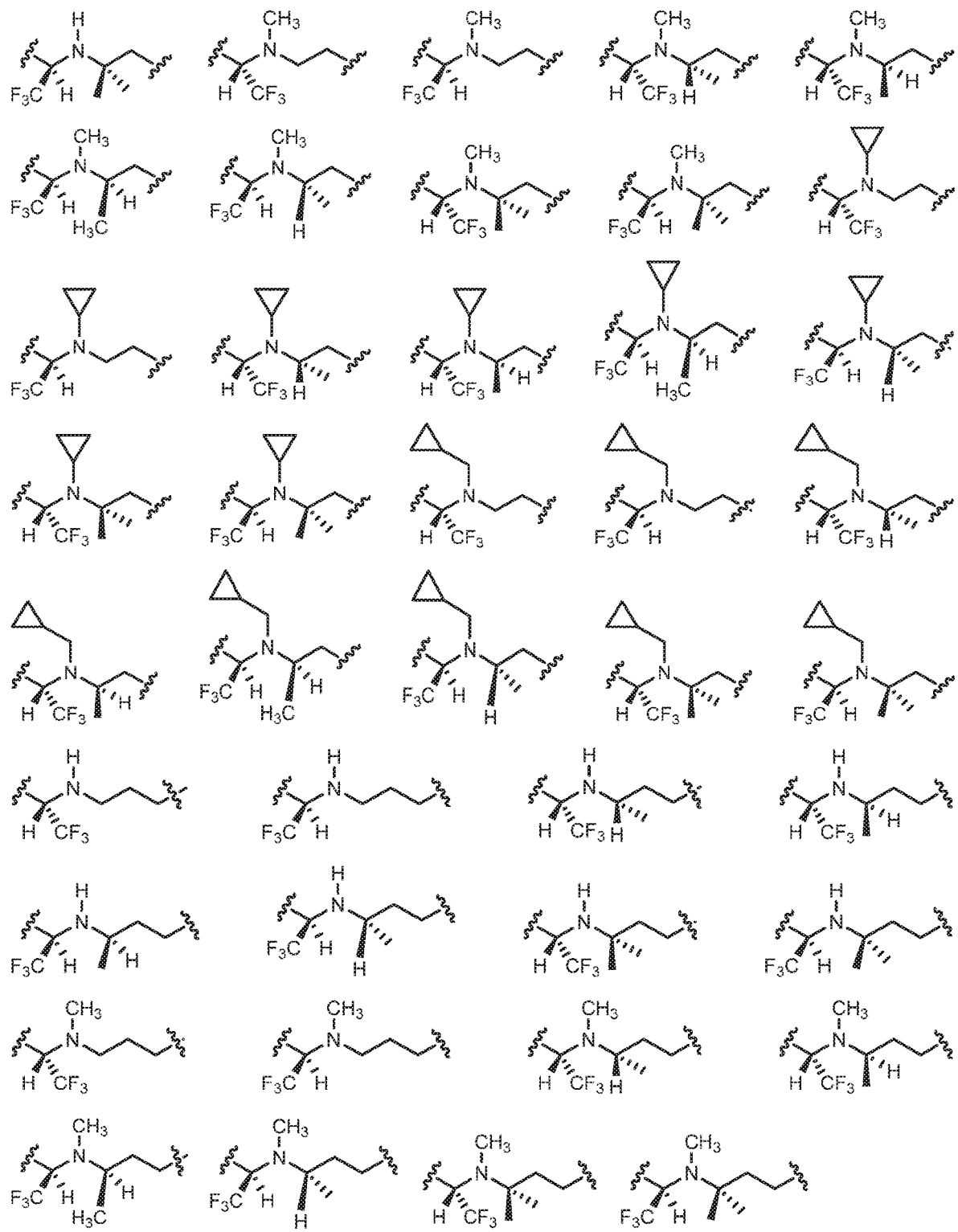
Figure 9F:
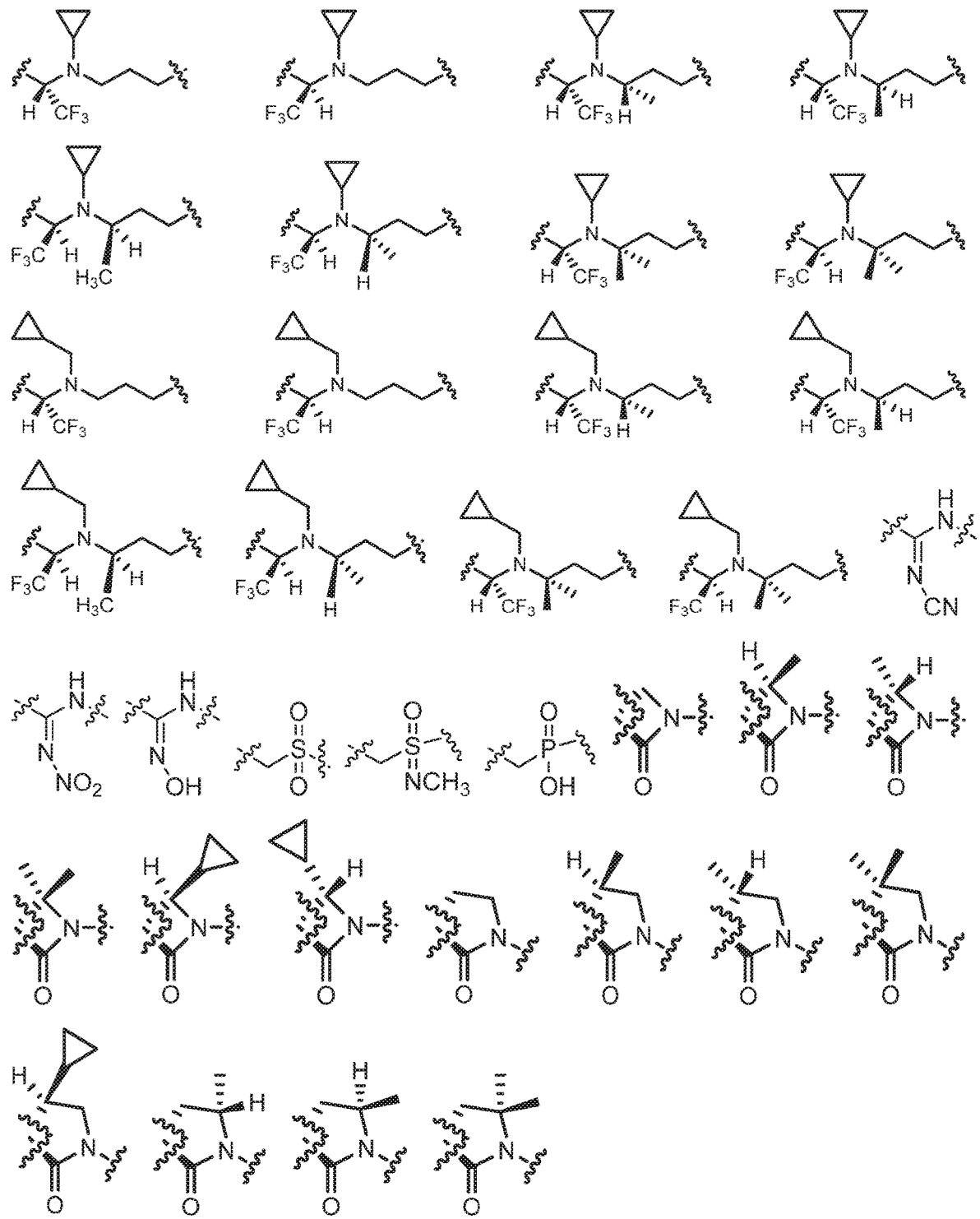
Figure 9G:
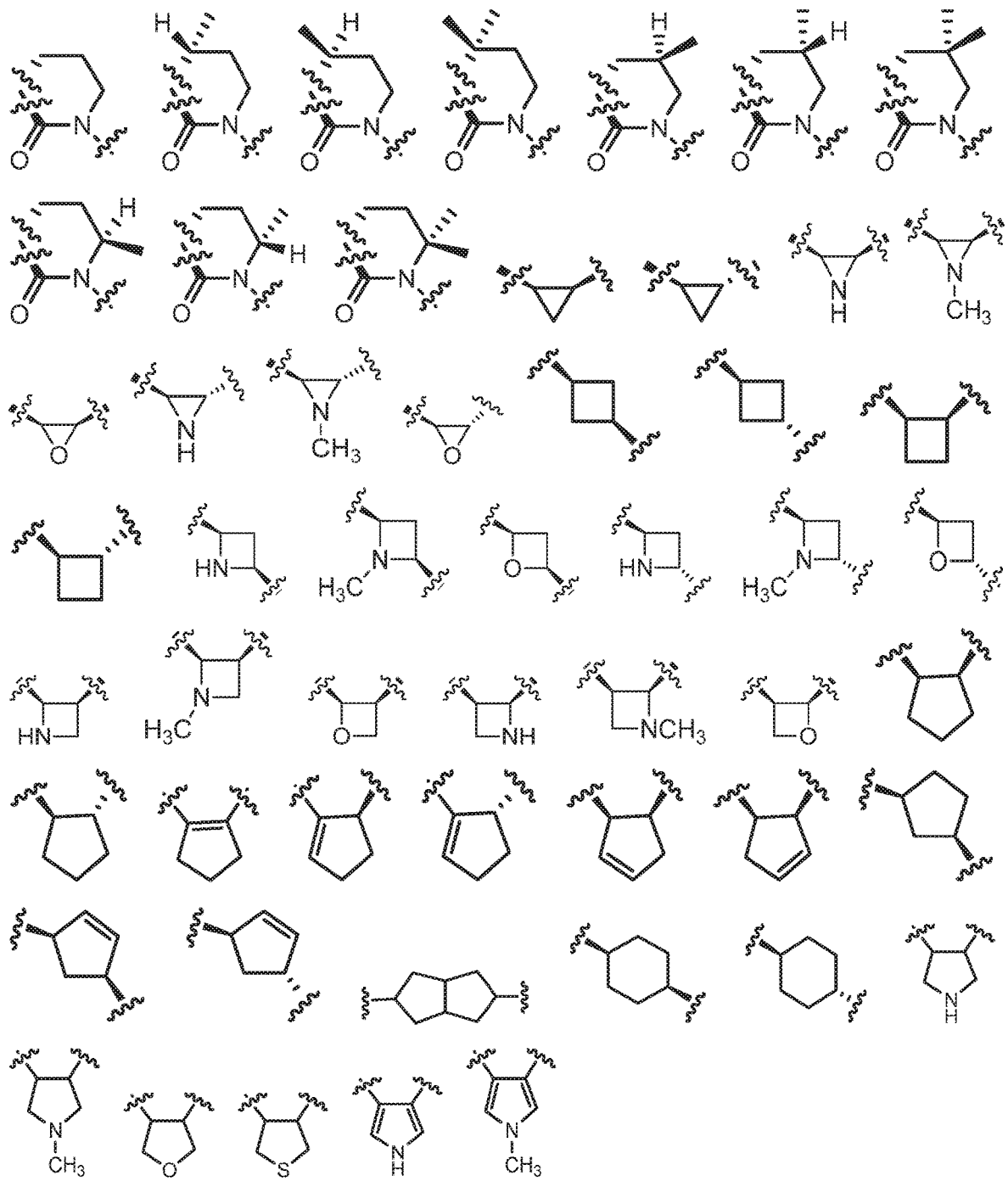
Figure 9H:
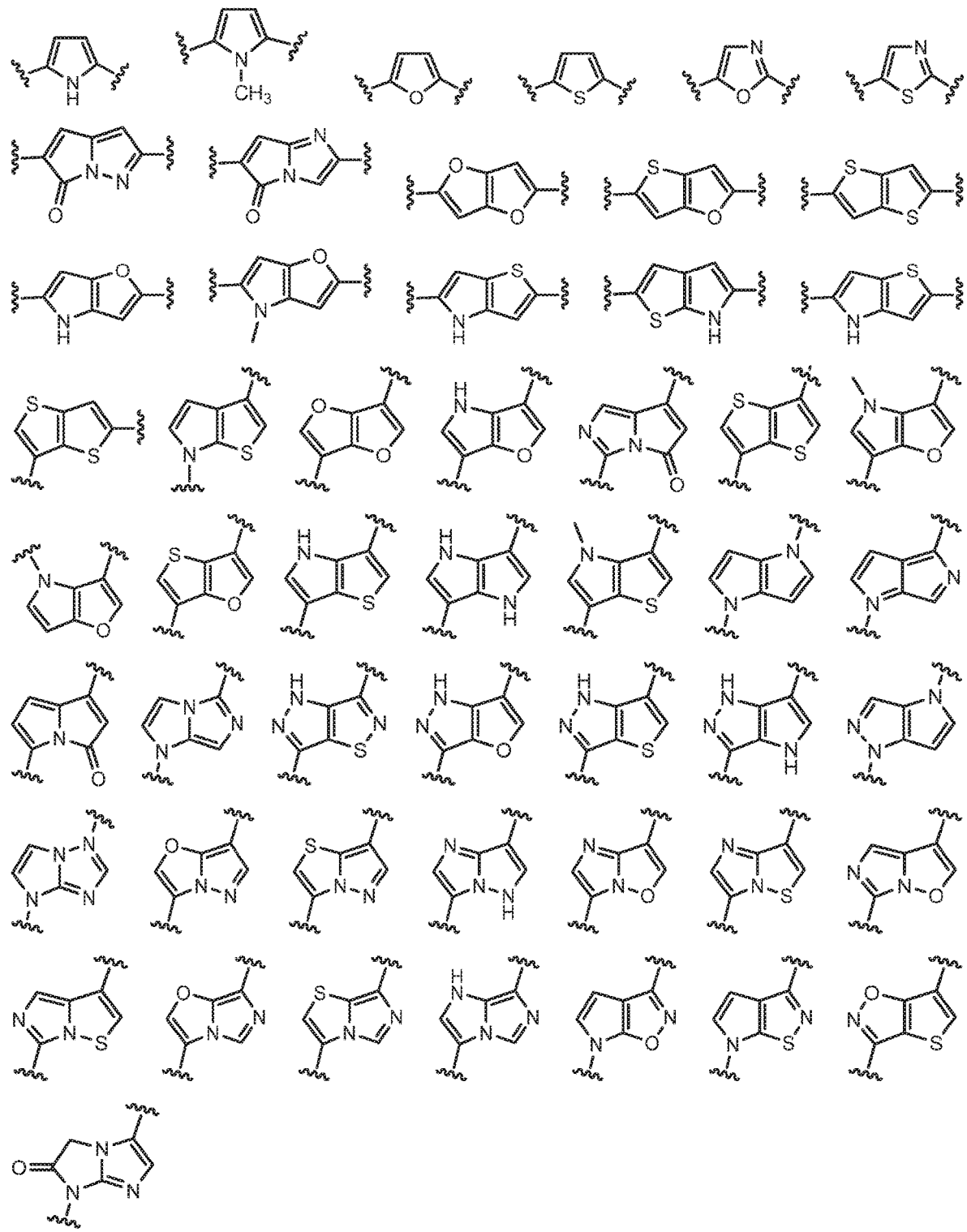
Figure 9I:
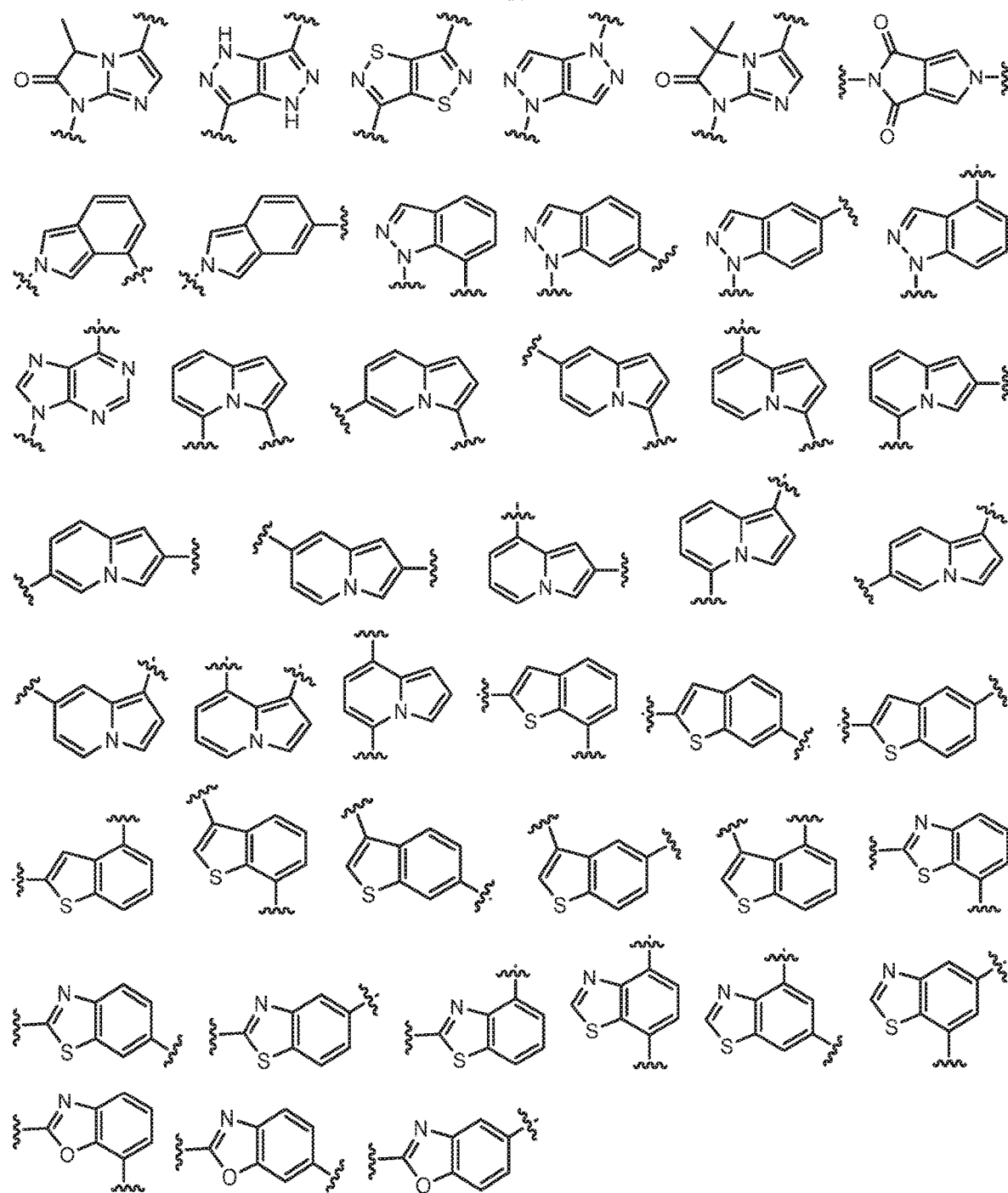
Figure 9J:
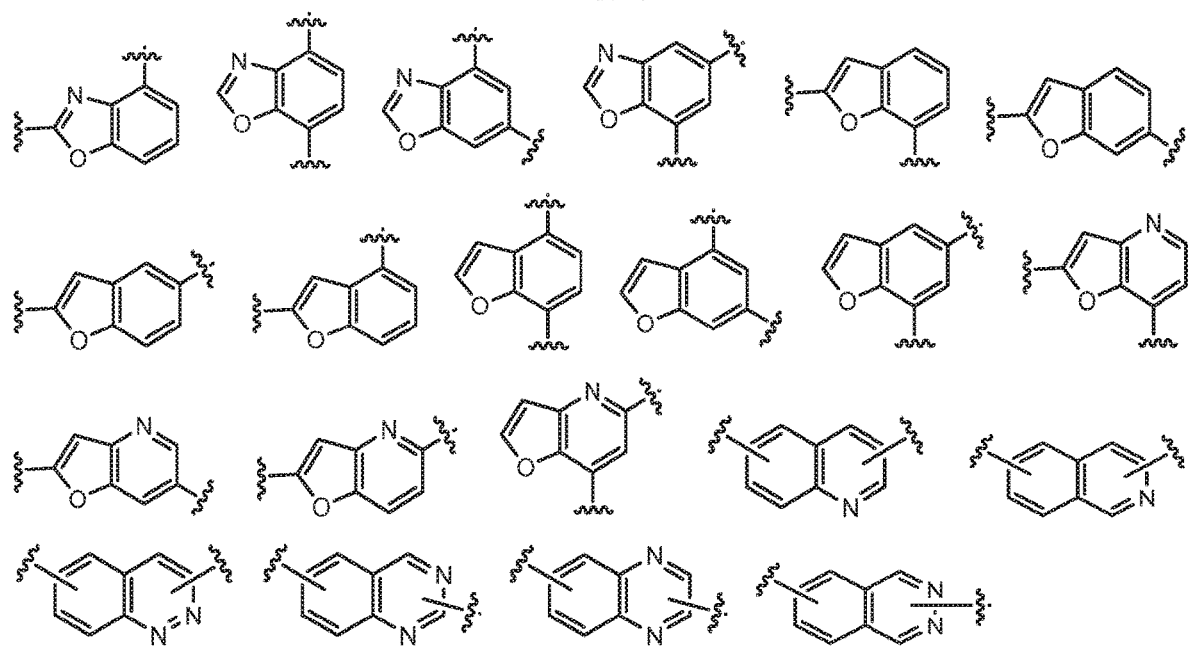
Figure 10A:
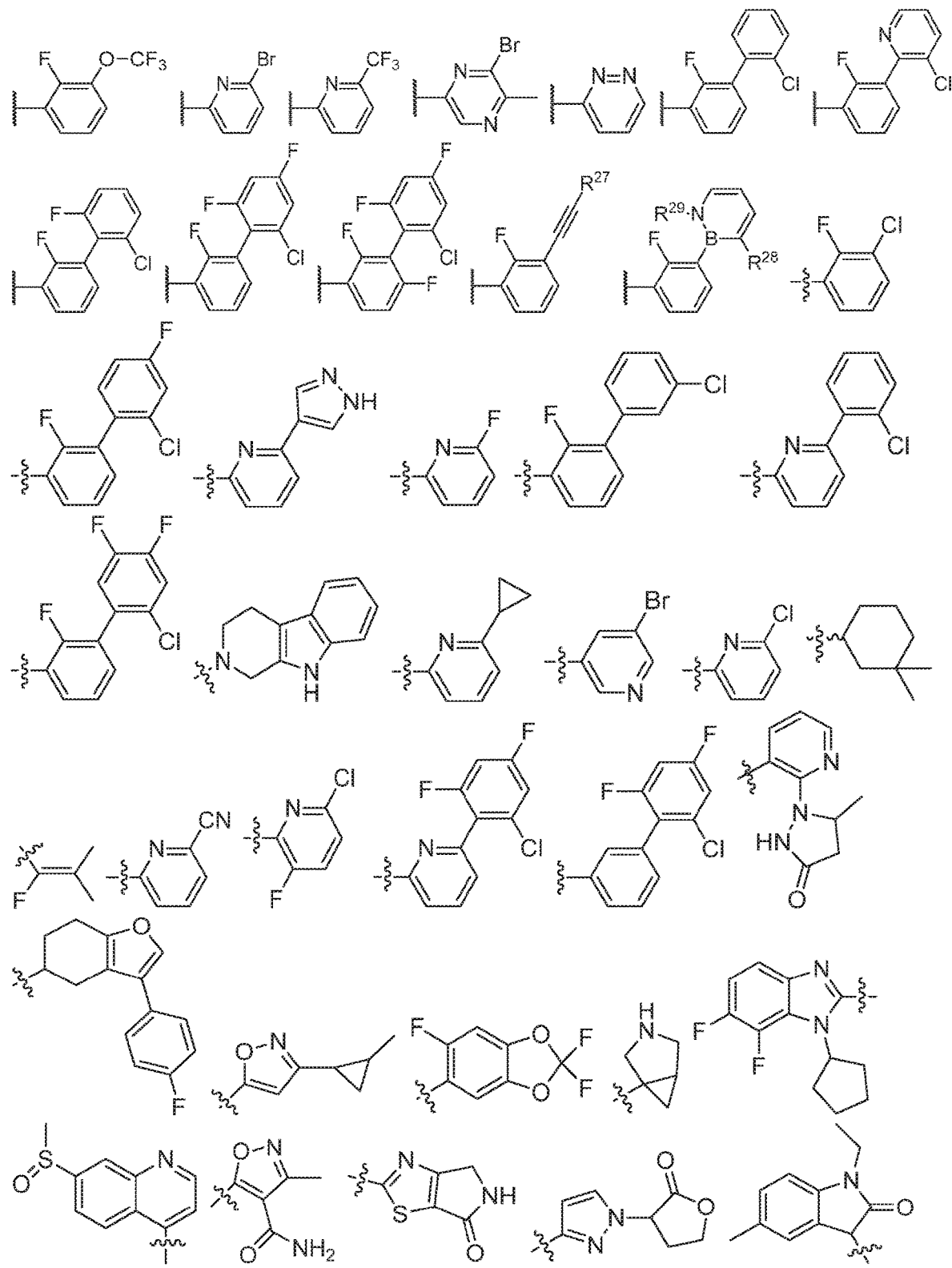
FIGS. 10A, 10B, 10C, and 10D, provide non-limiting specific embodiments of B1 rings, wherein $R^{27}$, $R^{28}$, and $R^{29}$ are defined below.
Figure 10B:
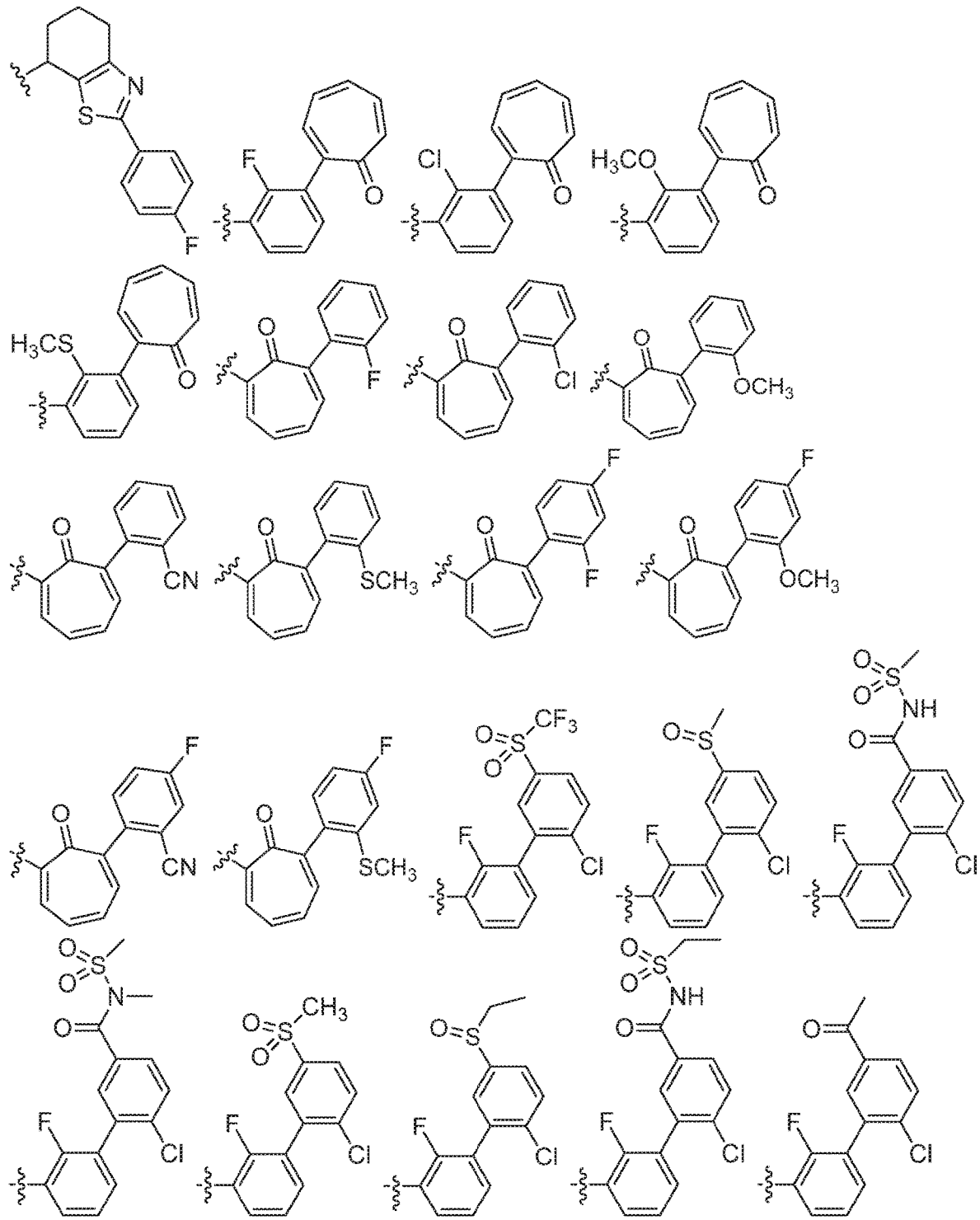
Figure 10C:
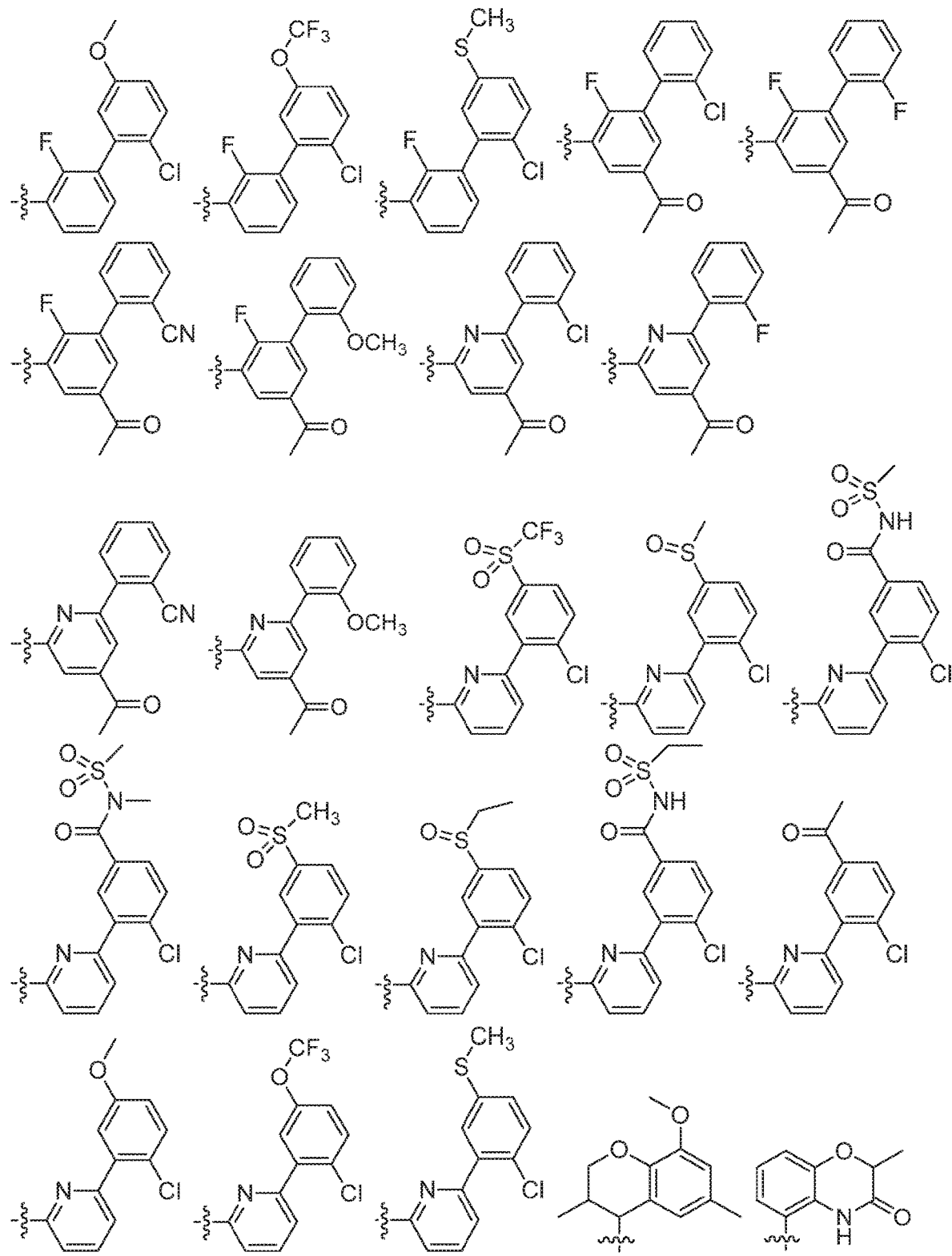
Figure 10D:
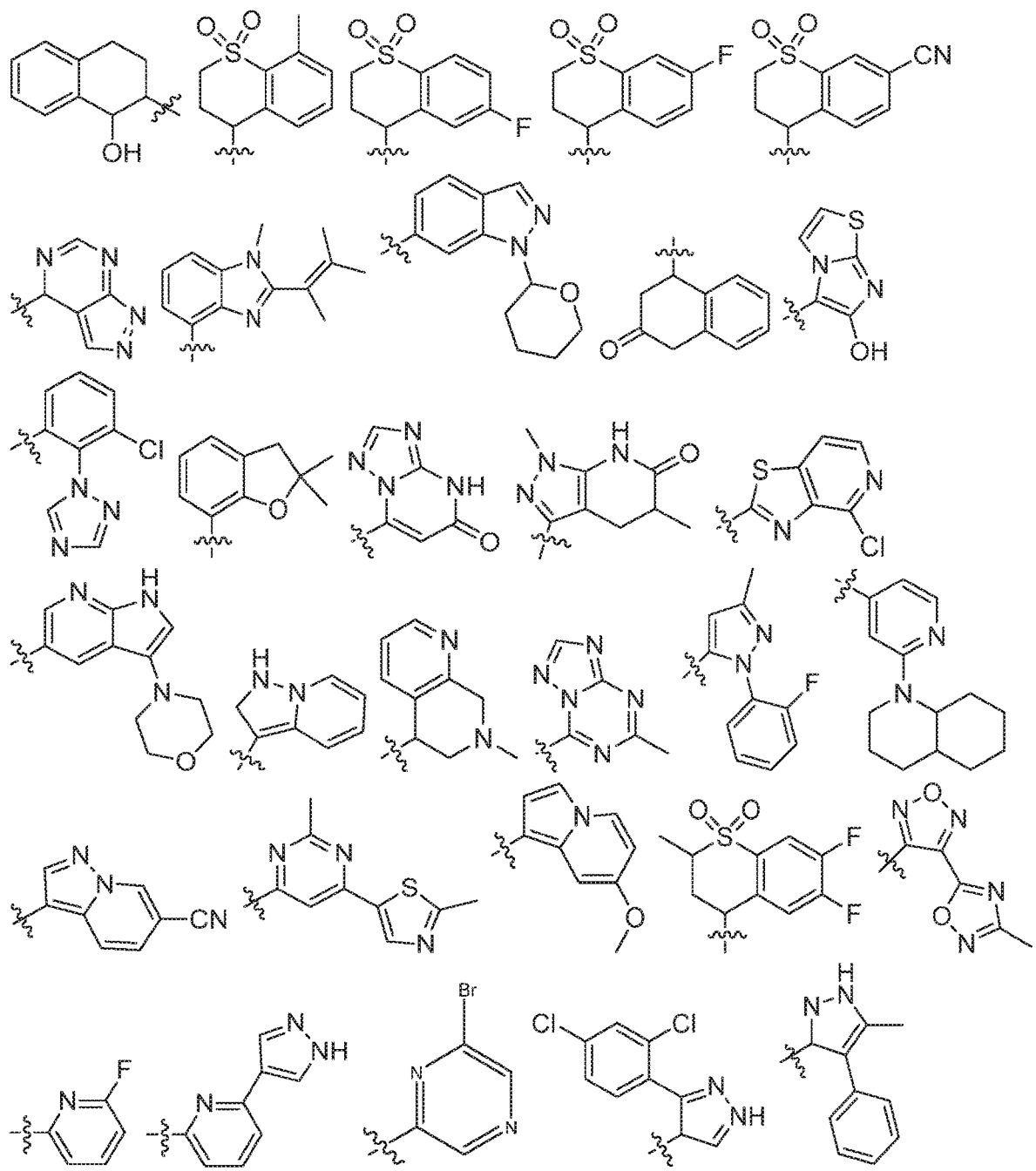
Figure 11A:
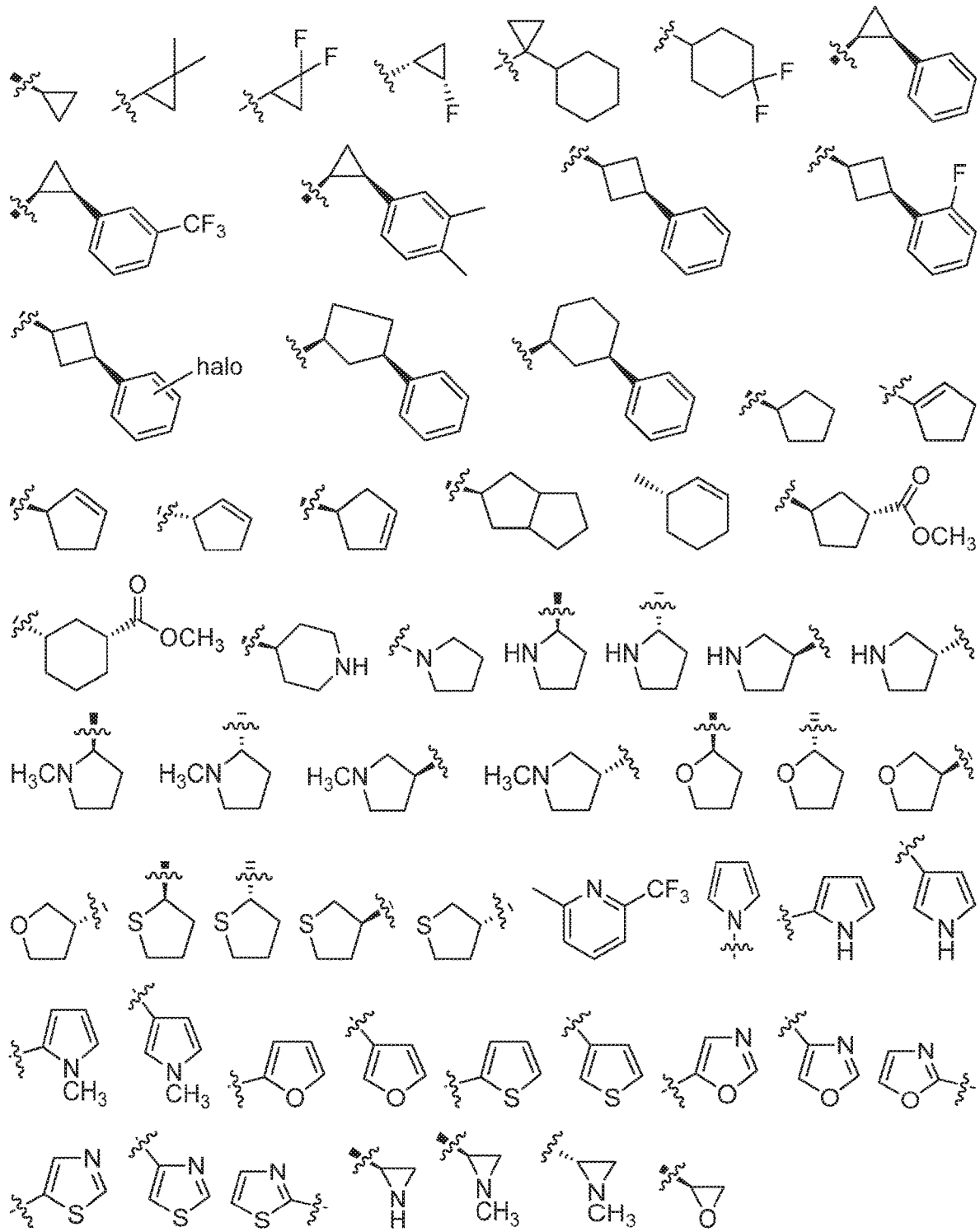
FIGS. 11A, 11B, 11C, and 11D, provide non-limiting specific embodiments of B1' rings, wherein halo is selected from F, Cl, Br, or I.
Figure 11B:
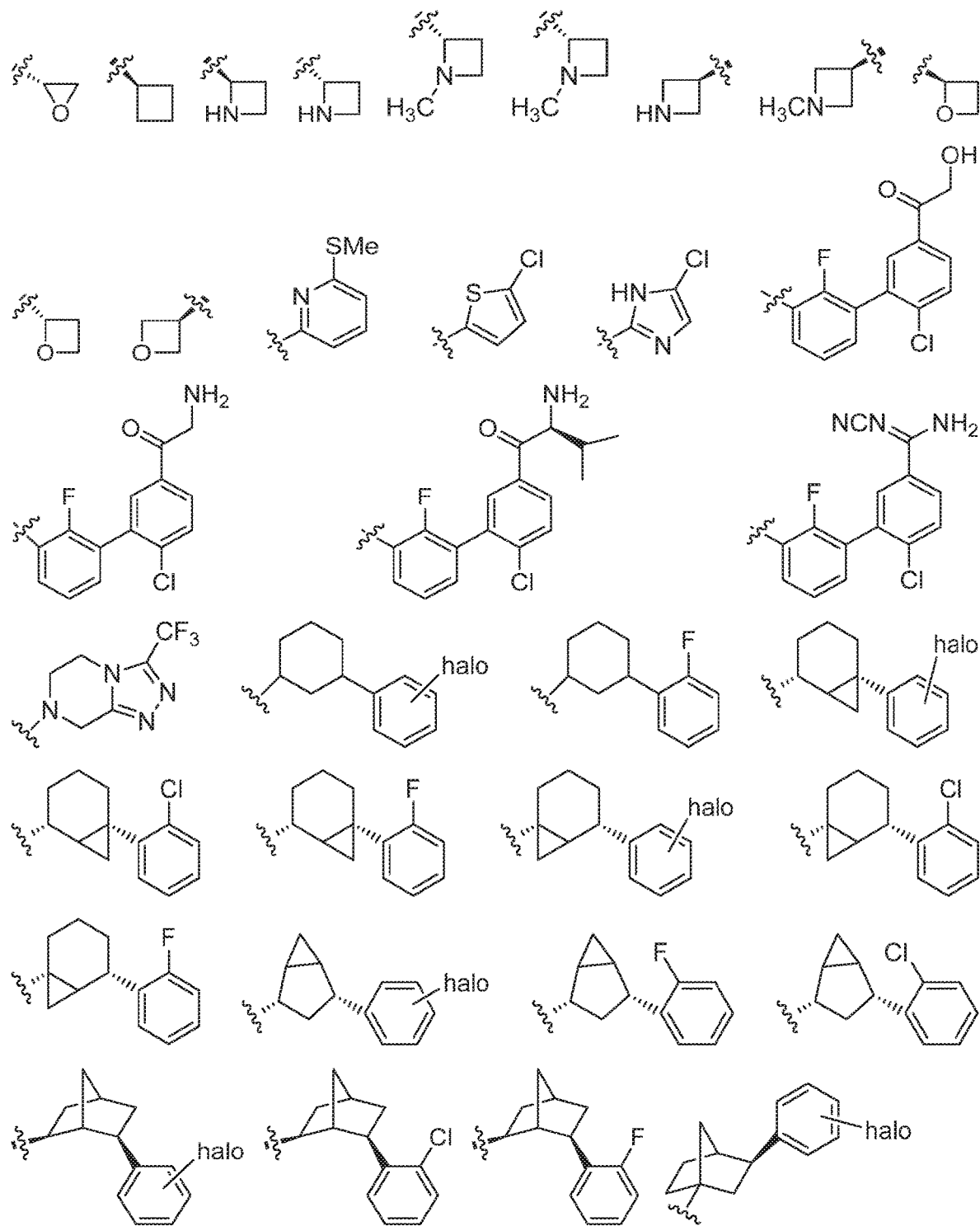
Figure 11C:
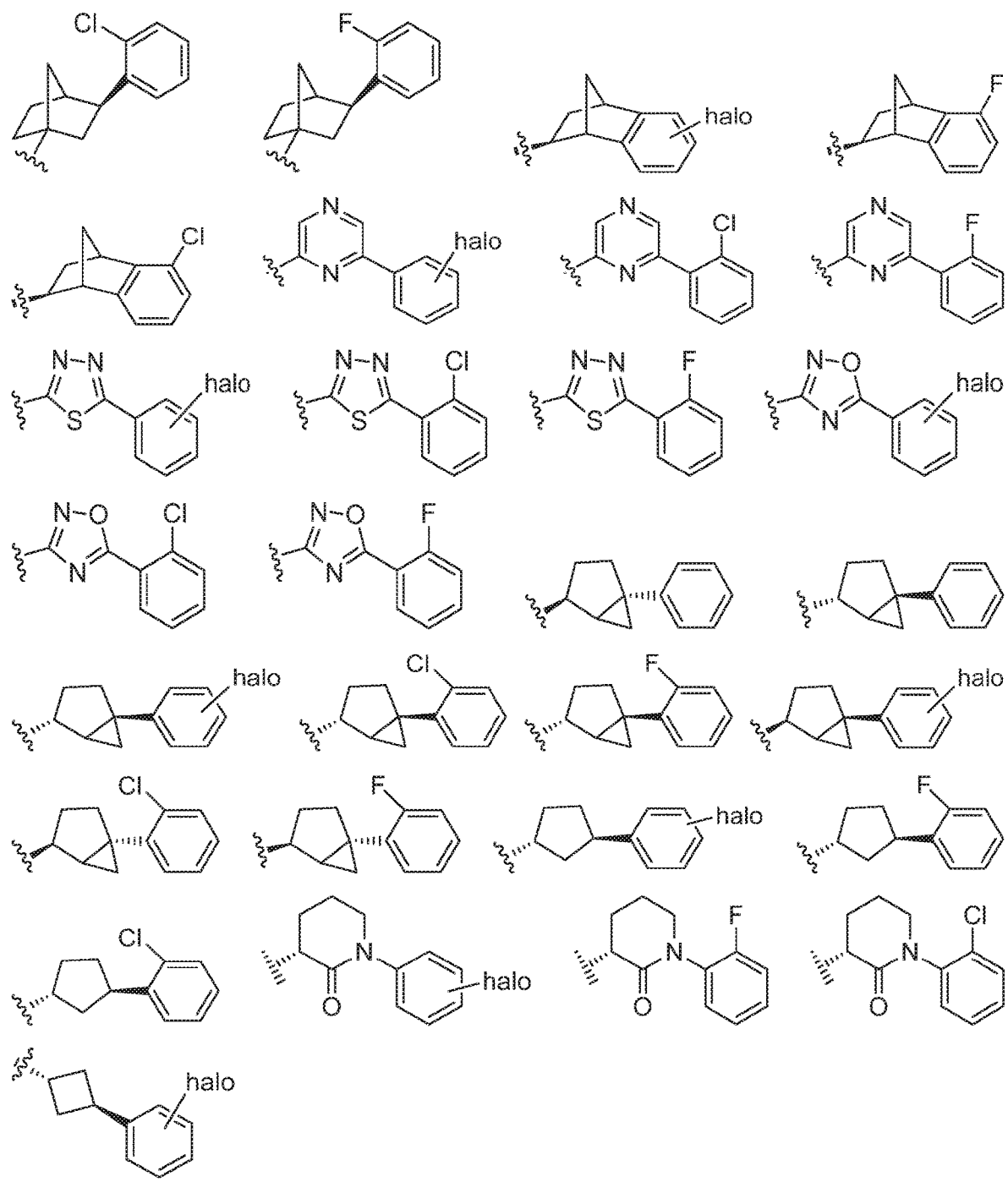
Figure 11D:
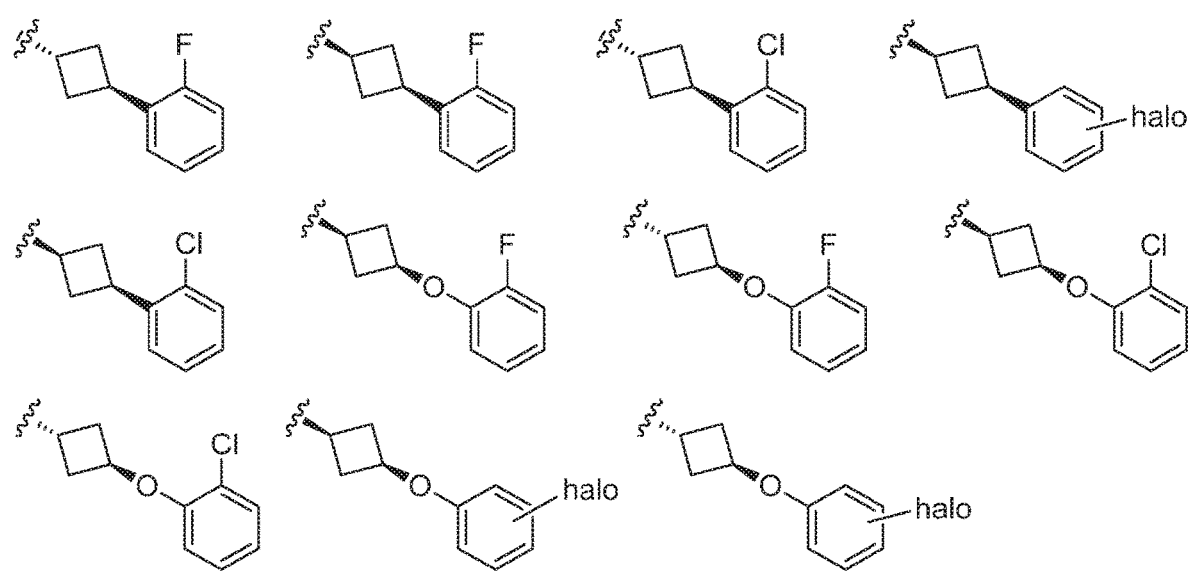
Figure 12:
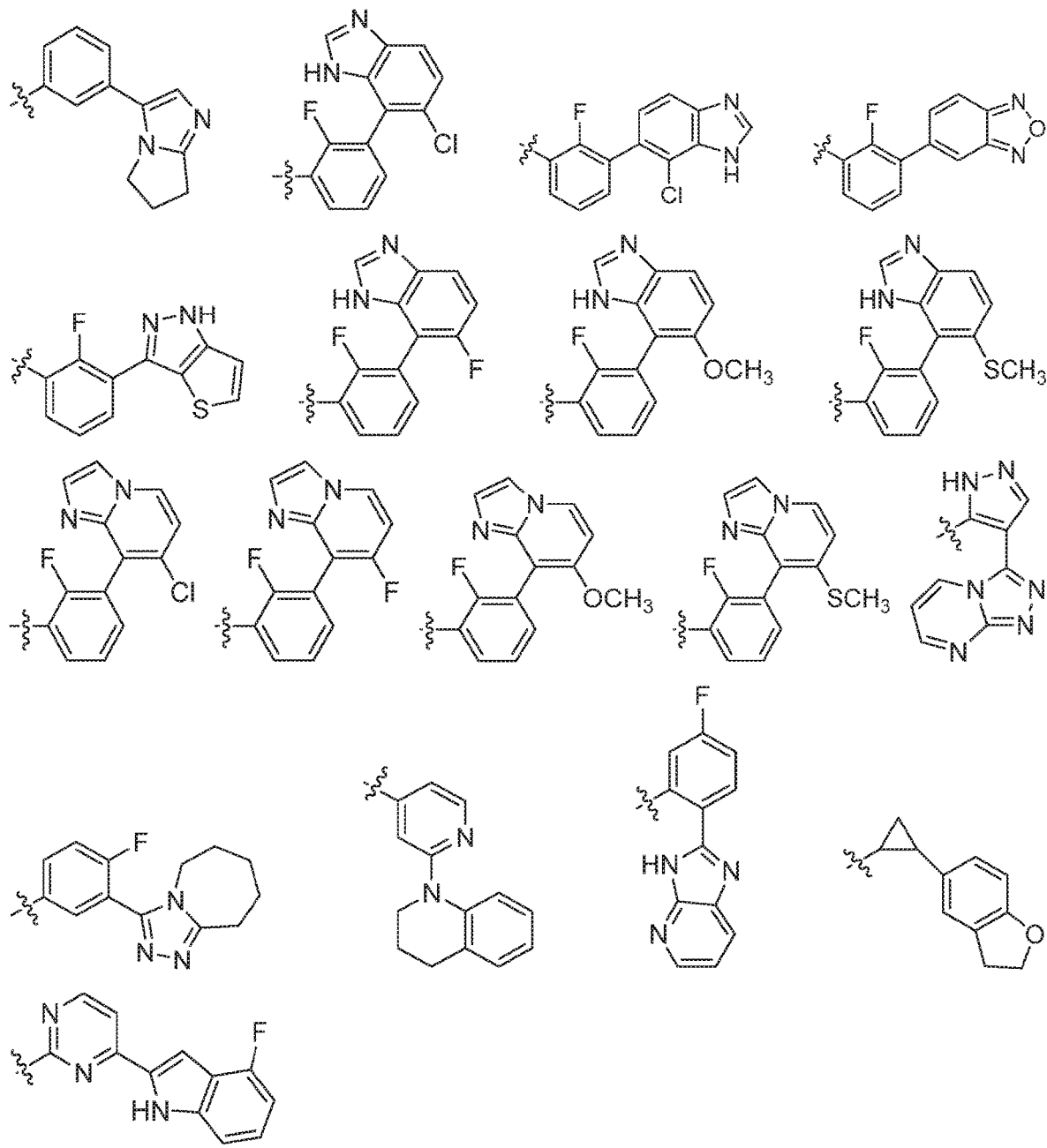
FIG. 12 provides specific embodiments of B2 rings.
Figure 13A:
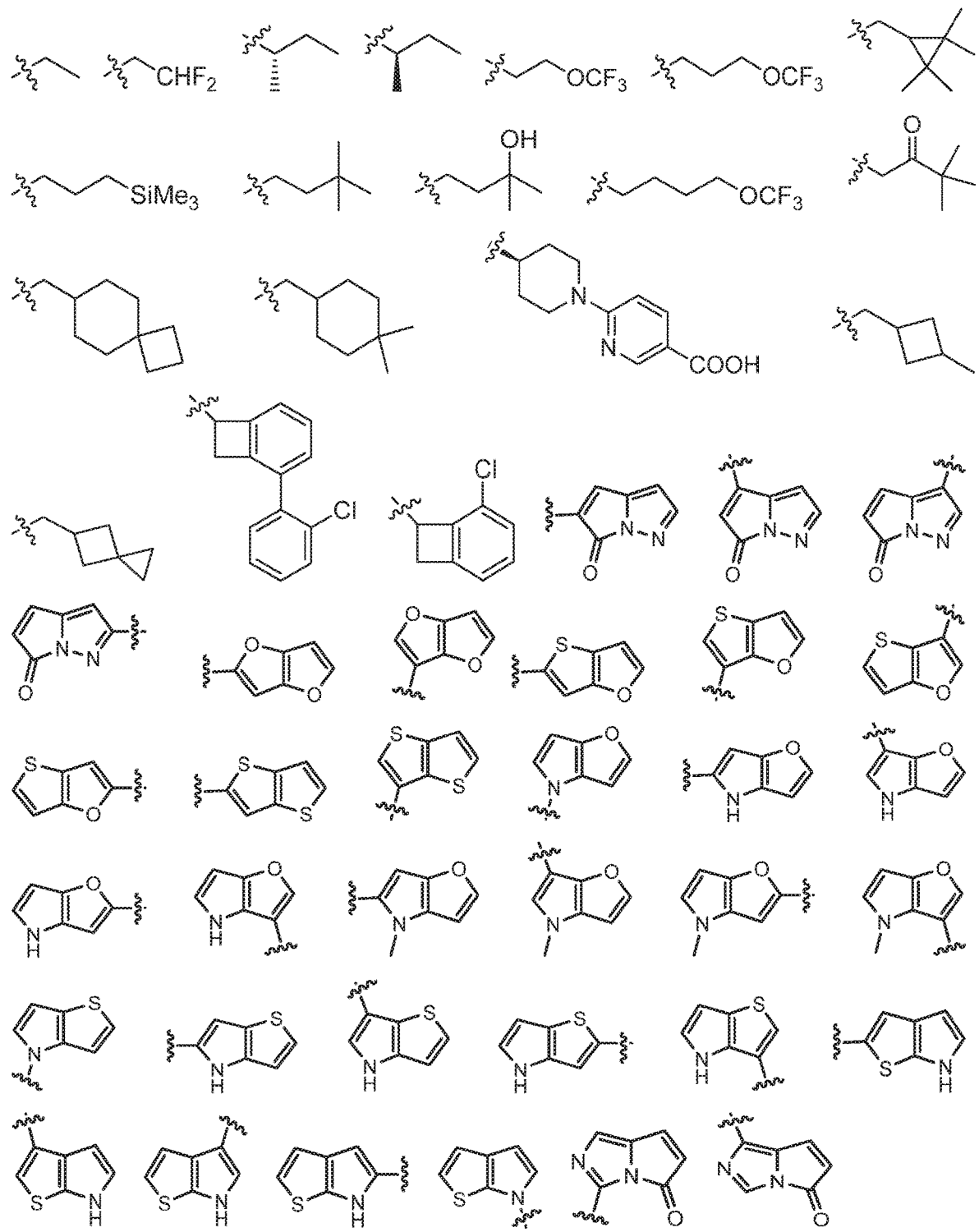
FIGS. 13A, 13B, 13C, 13D, 13E, 13F, 13G, 13H, 13I, 13J, 13K, 13L, 13M, 13N, 13O, 13P, 13Q, 13R, 13S, 13T, 13U, 13V, 13W, 13X, 13Y, and 13Z, provide specific embodiments of B3 moieties.
Figure 13B:
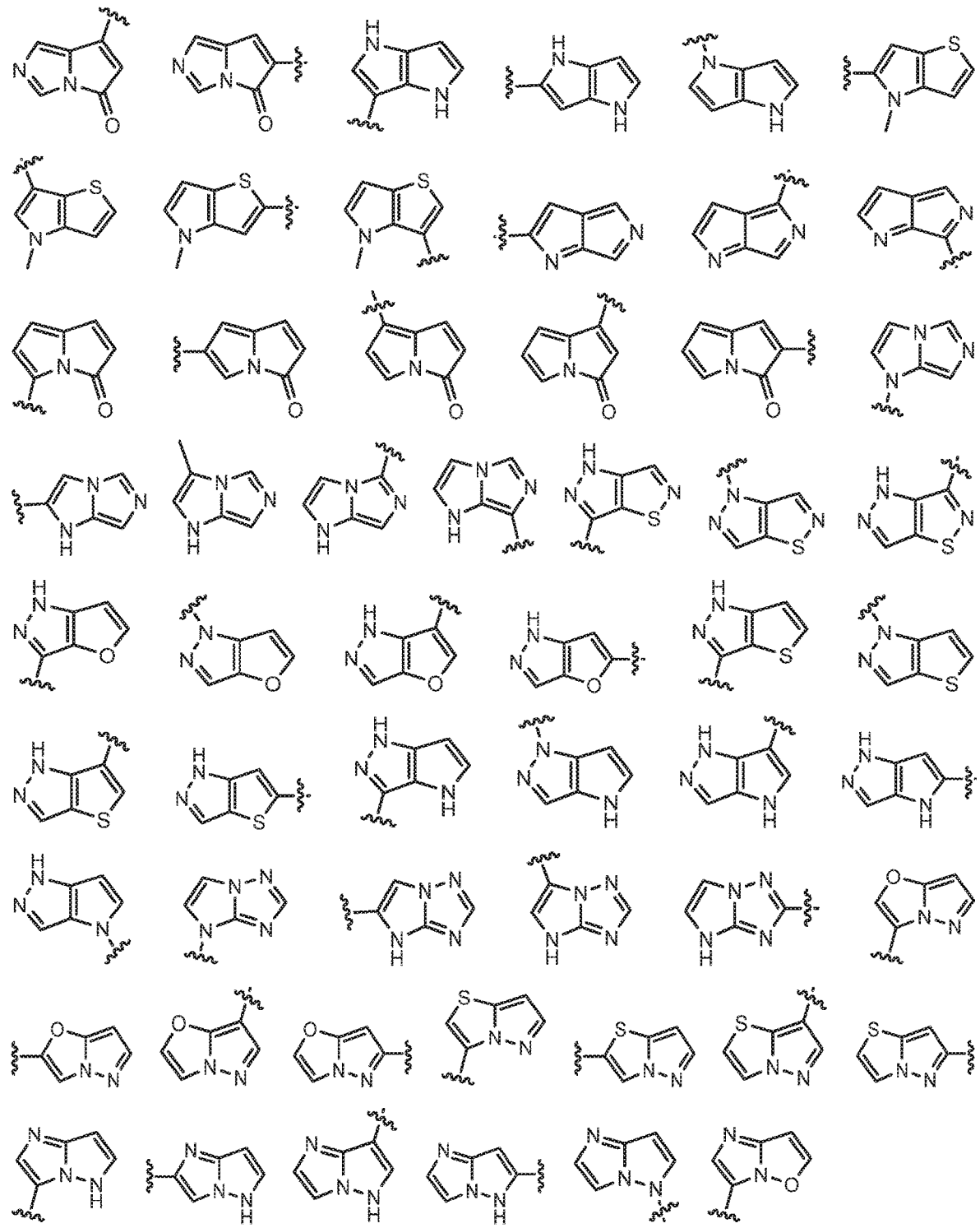
Figure 13C:
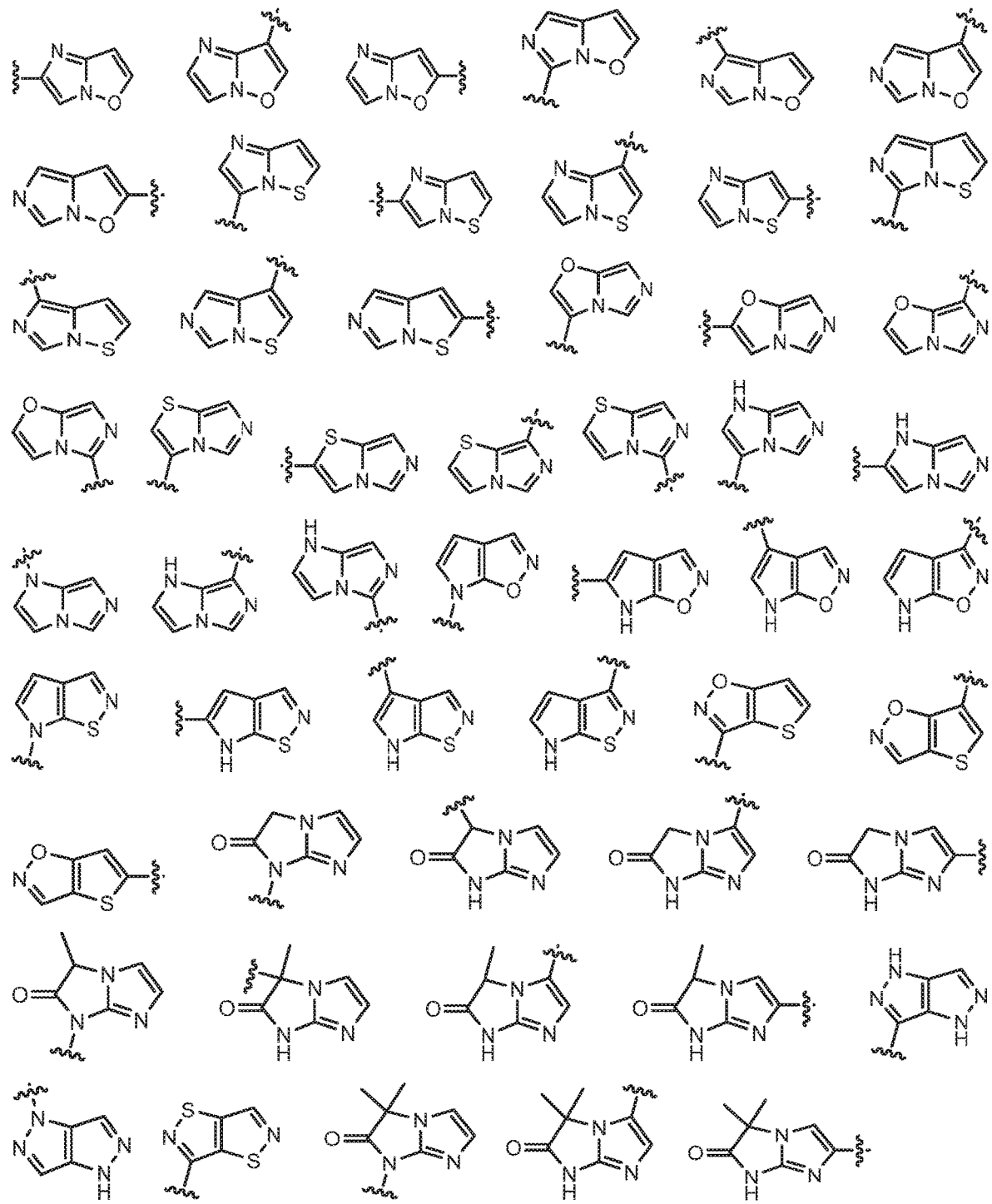
Figure 13D:
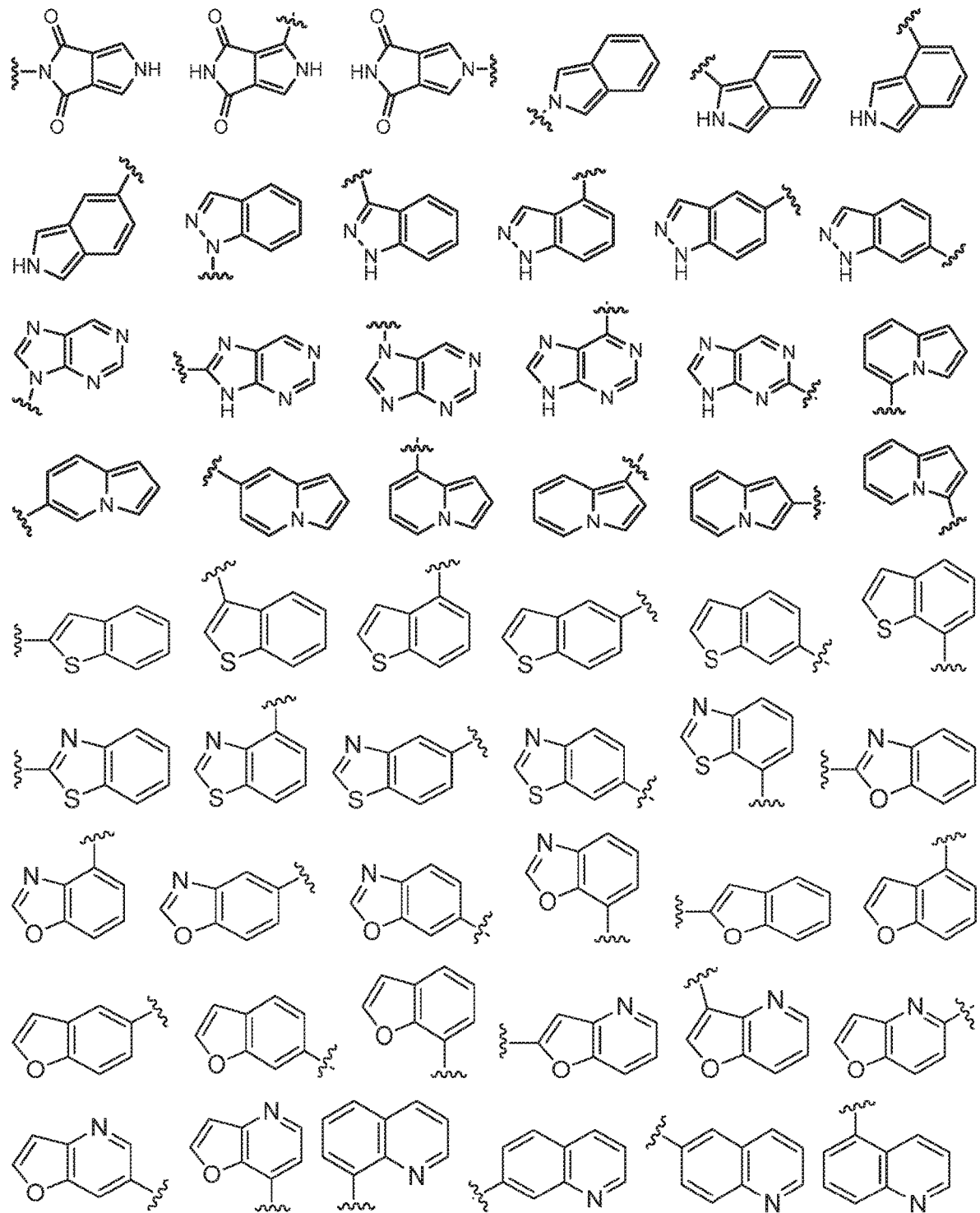
Figure 13E:
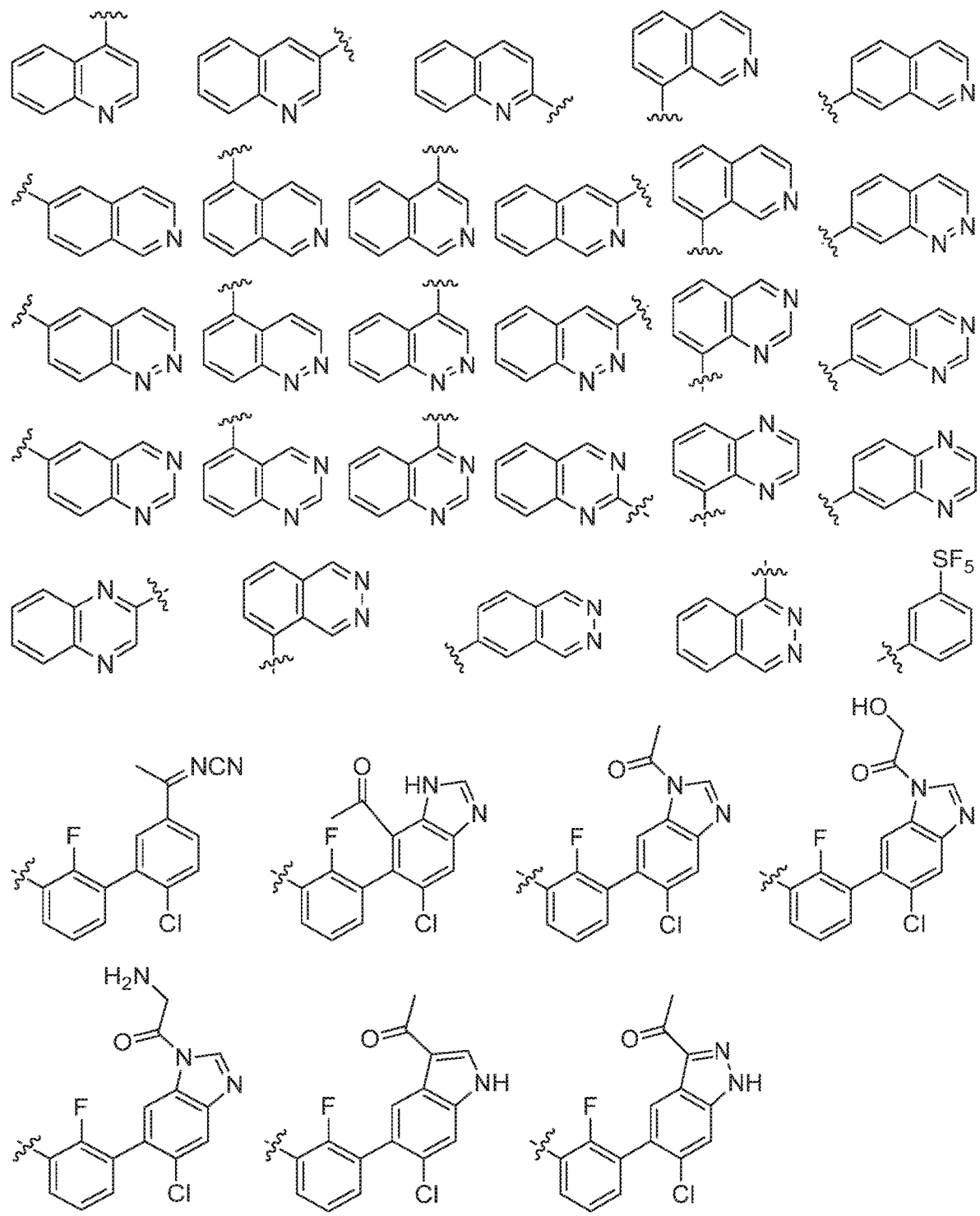
Figure 13F:
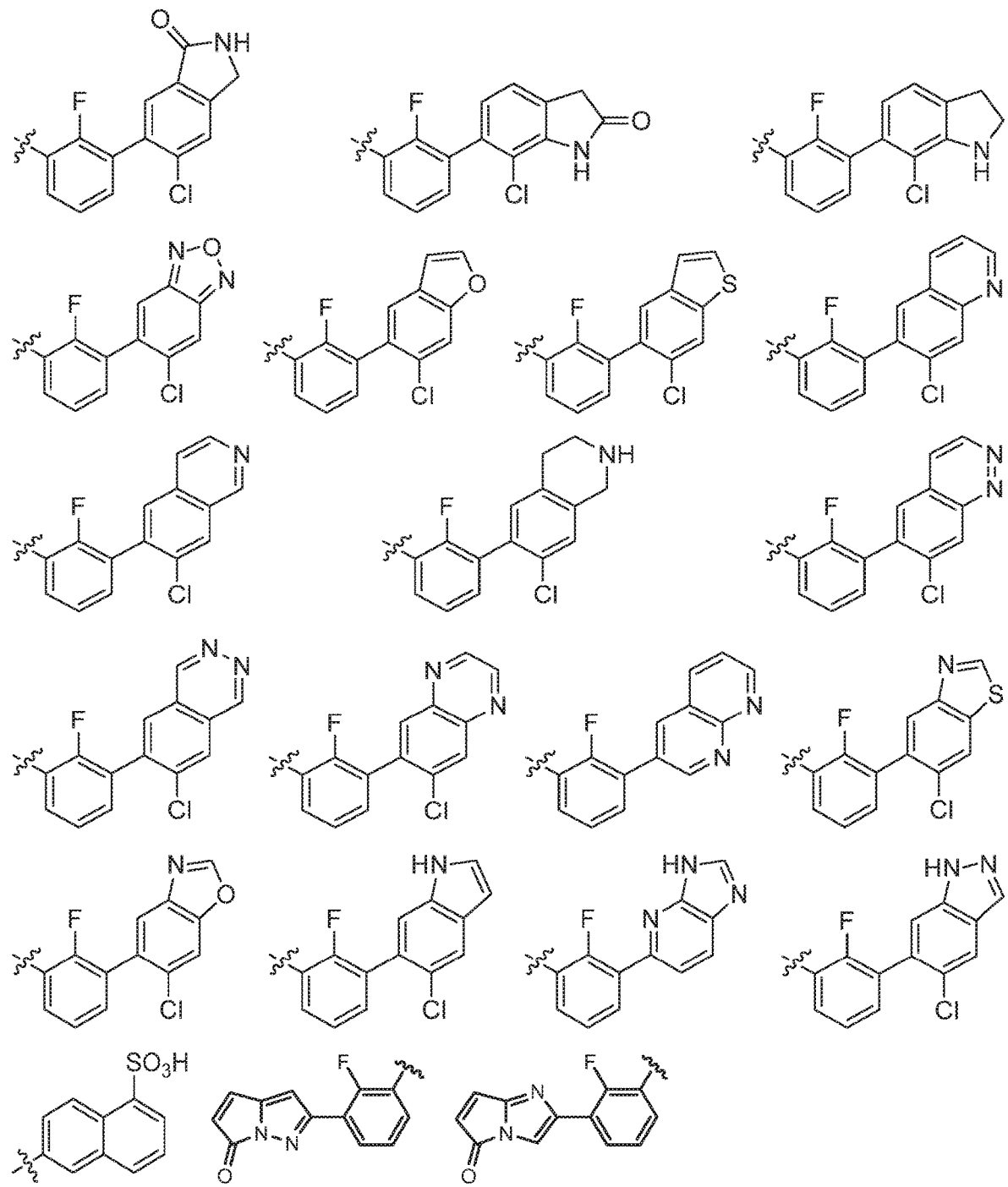
Figure 13G:
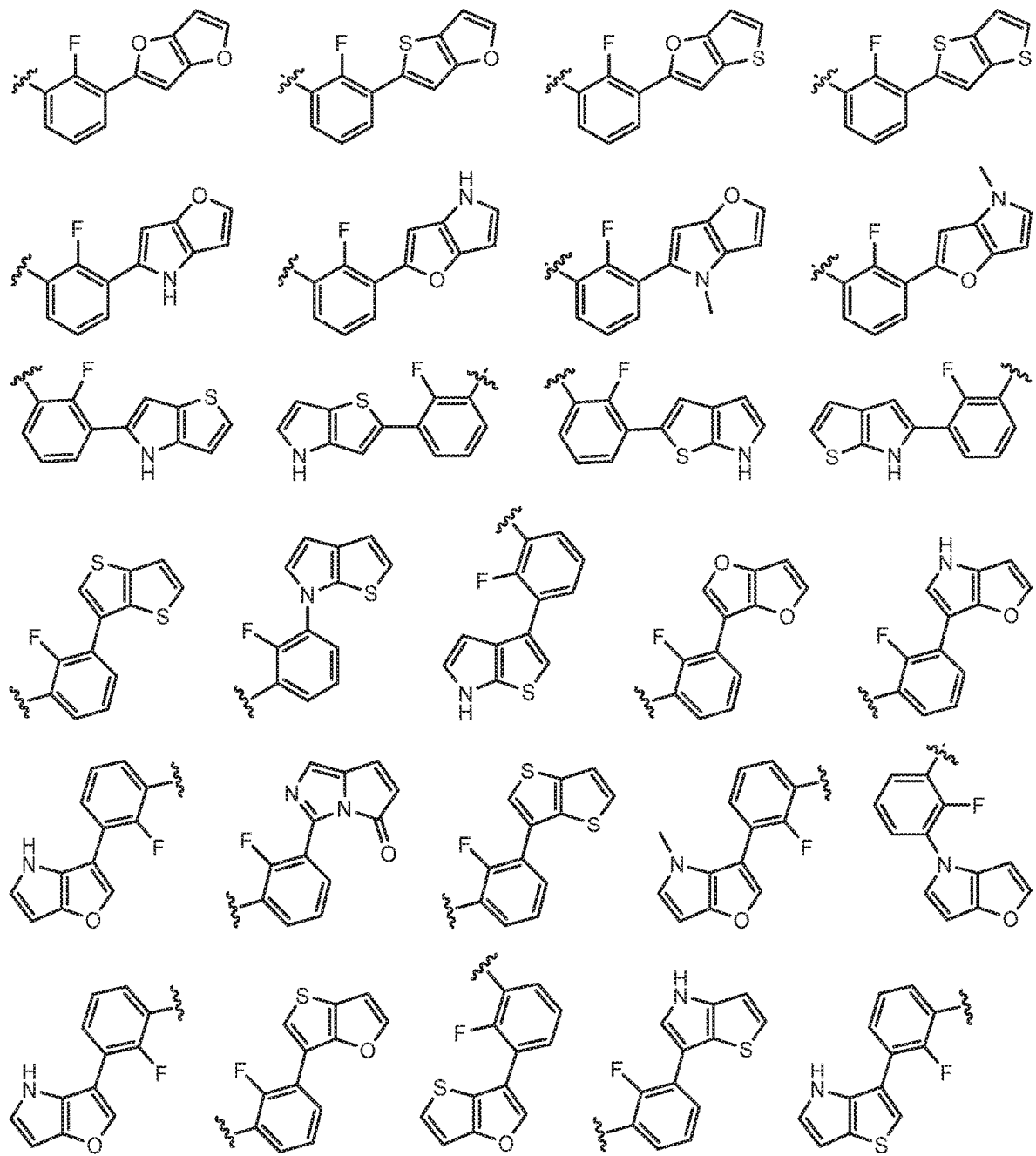
Figure 13H:
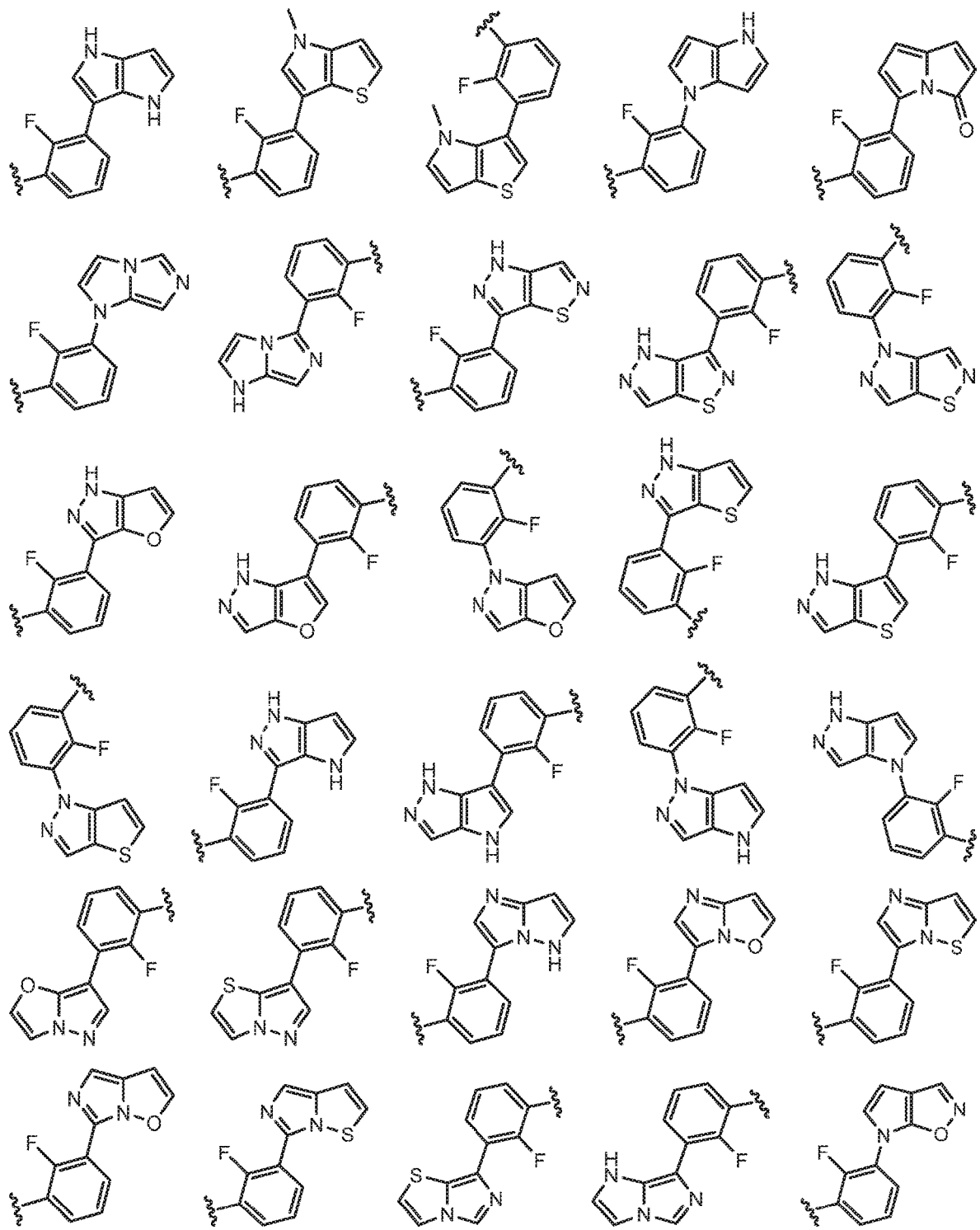
Figure 13I:
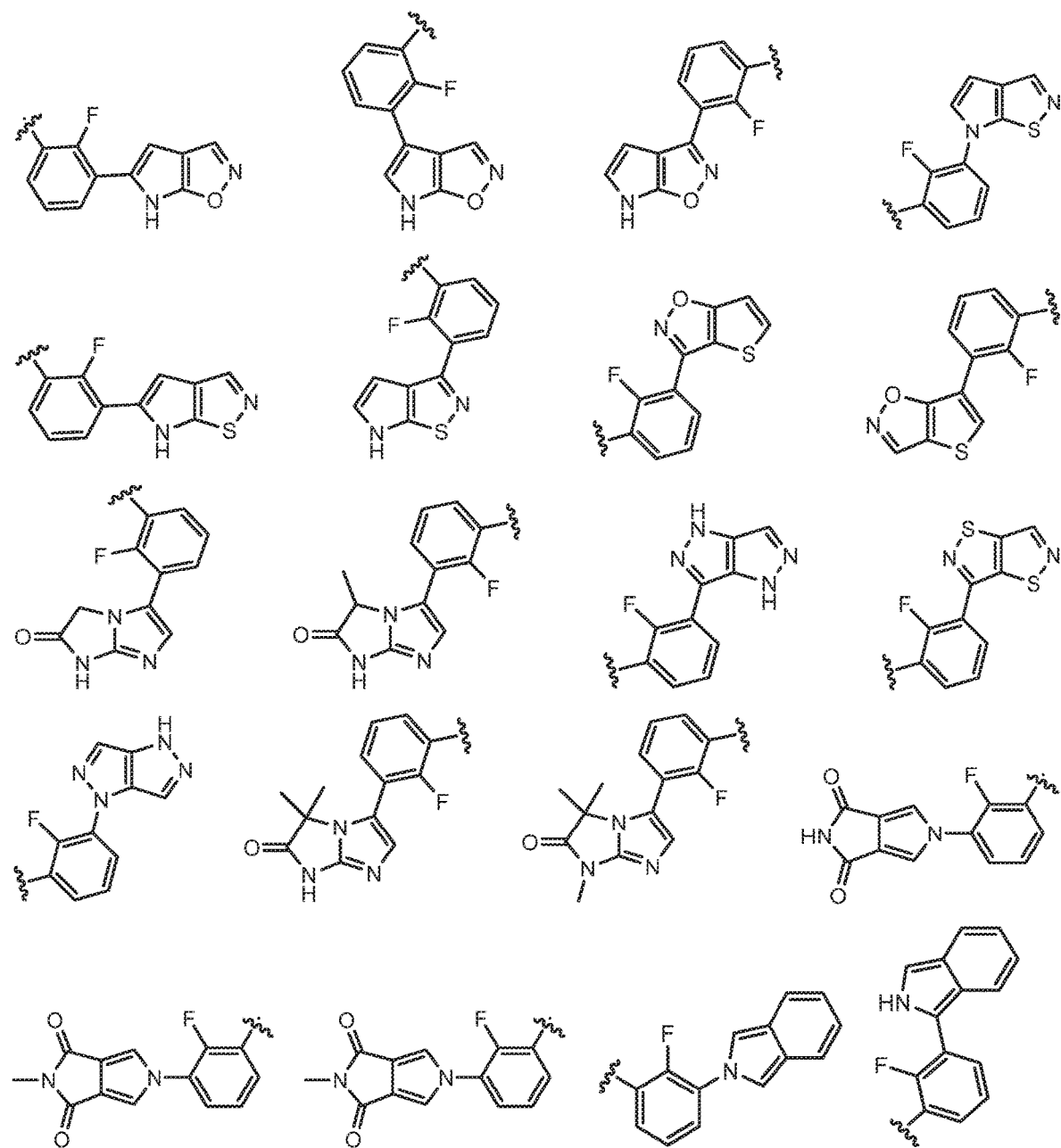
Figure 13J:
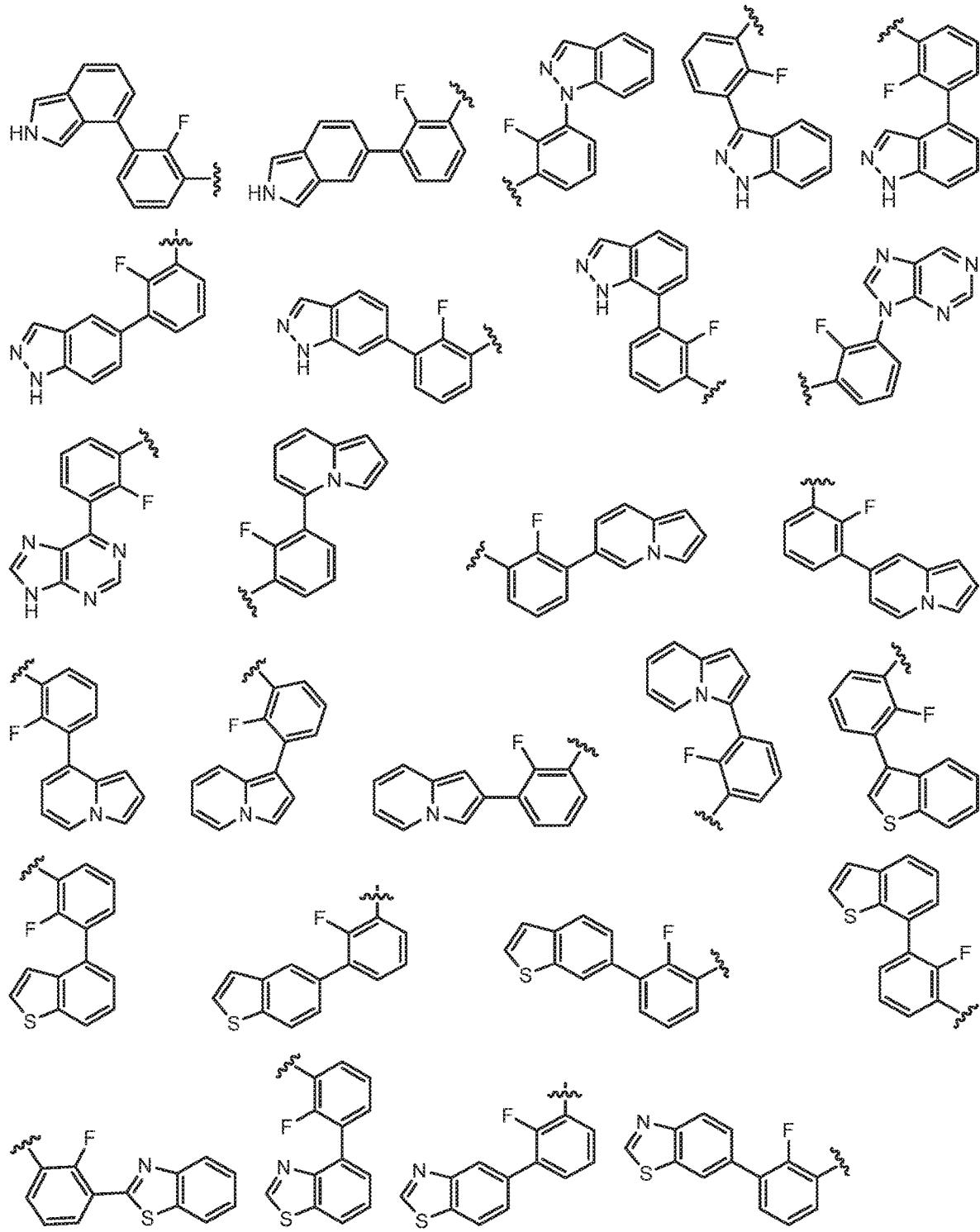
Figure 13K:
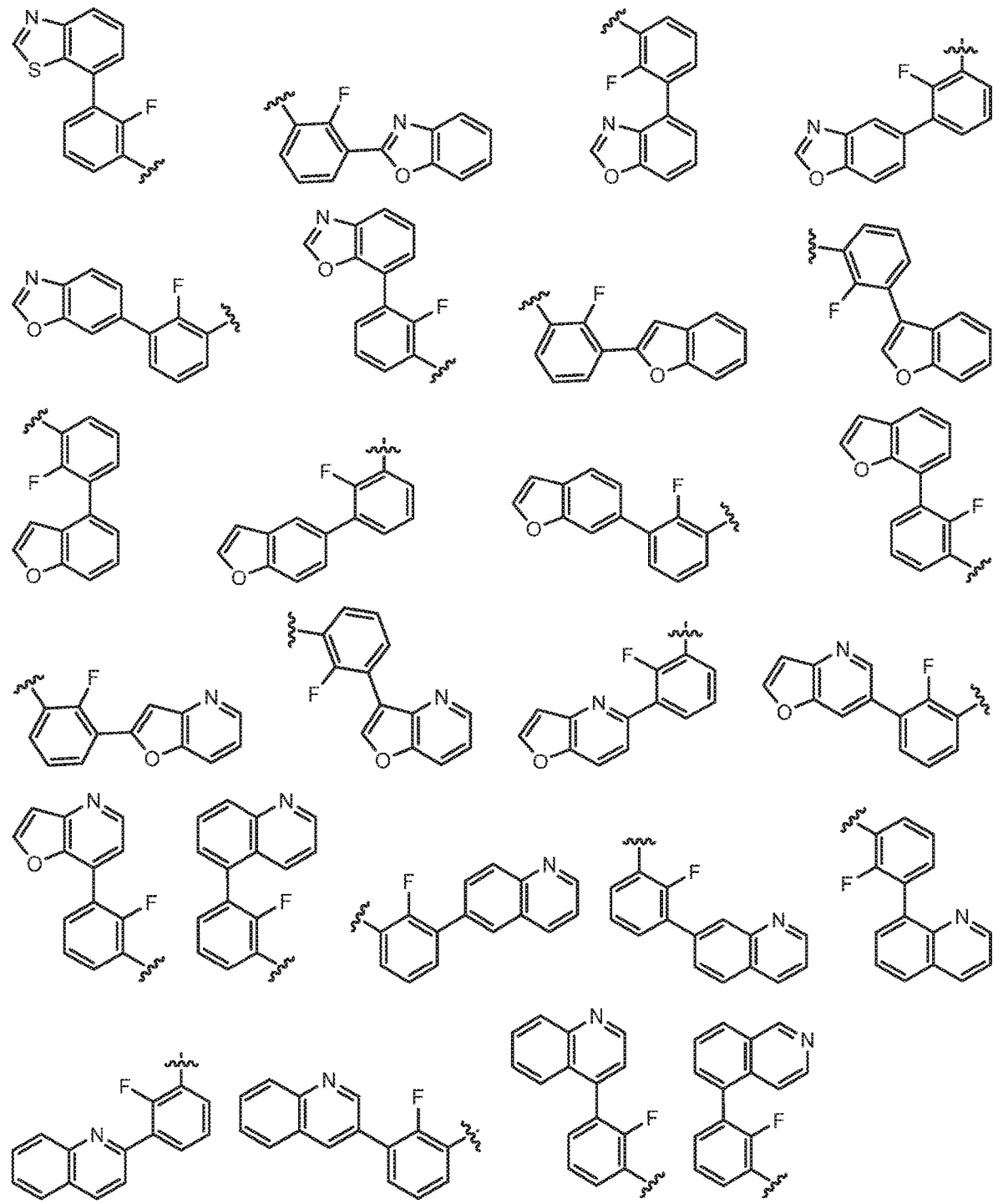
Figure 13L:
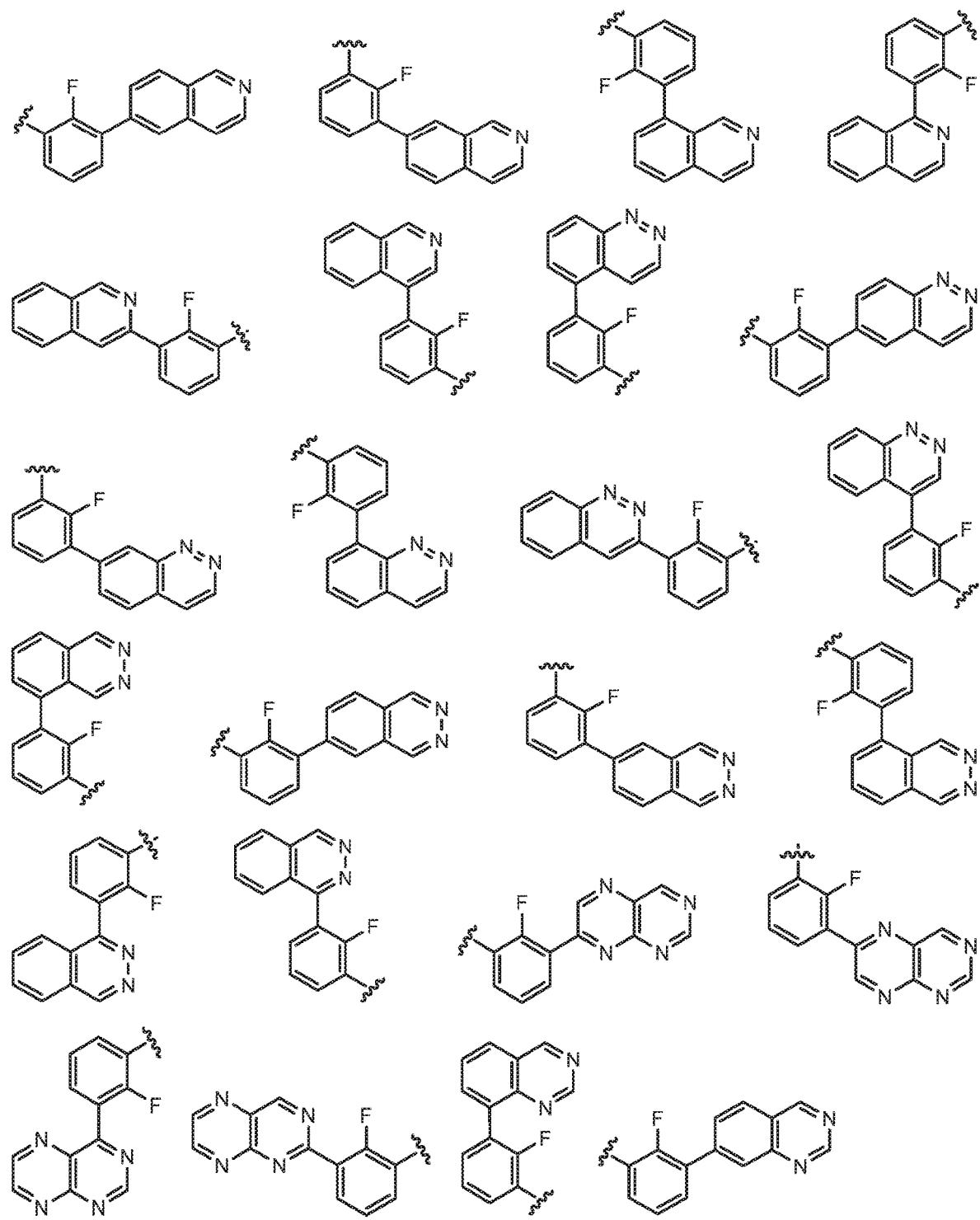
Figure 13M:
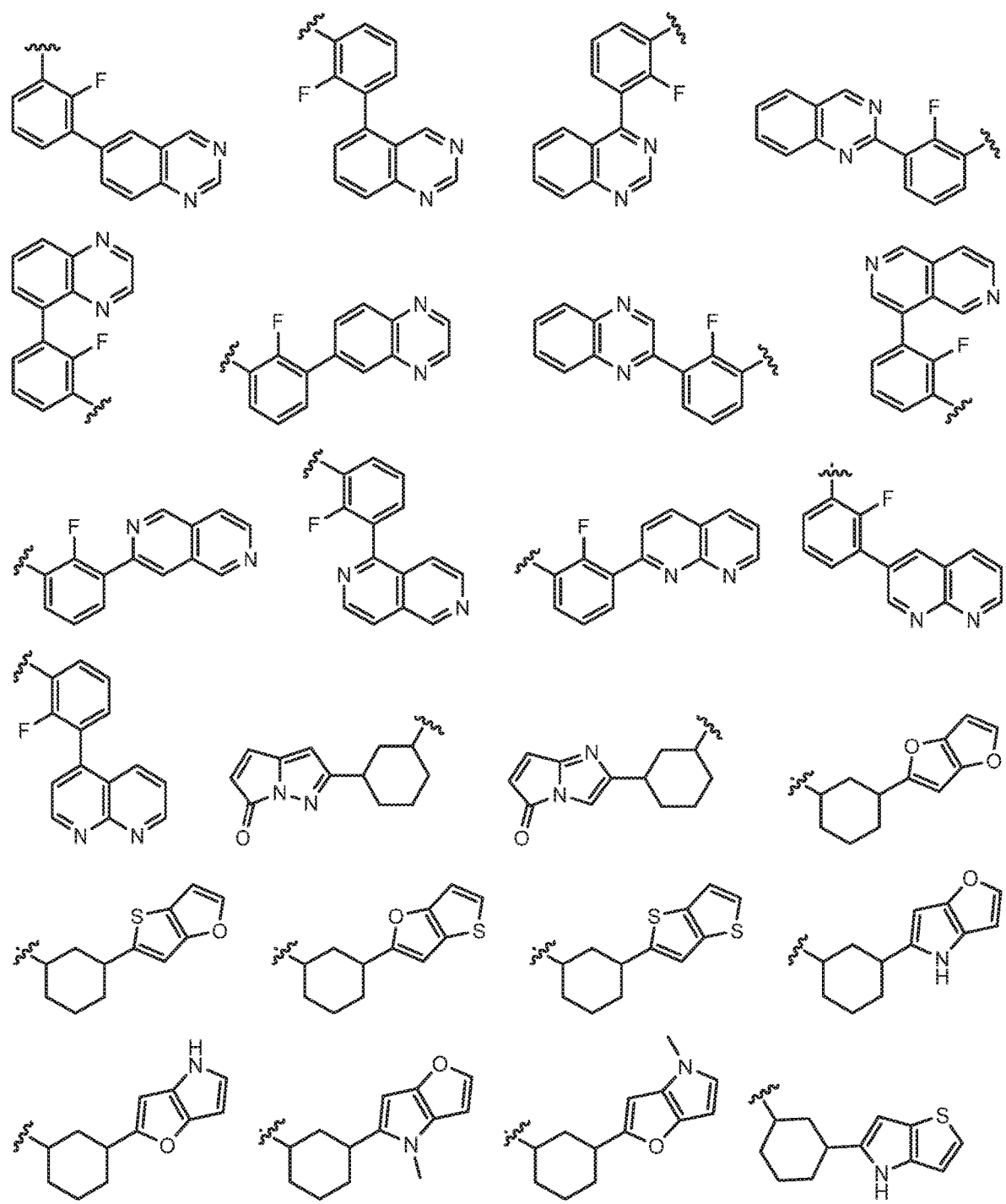
Figure 13N:
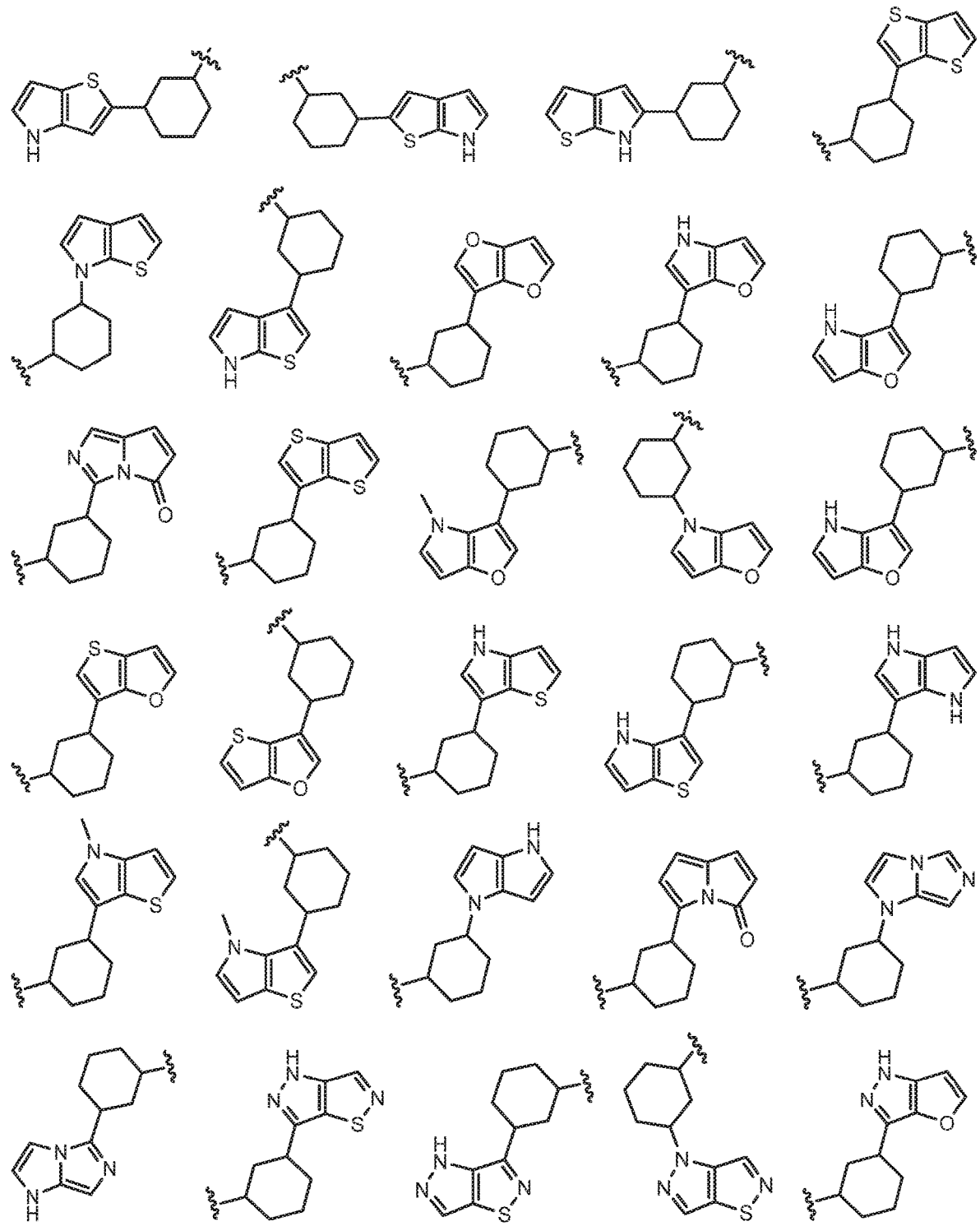
Figure 13O:
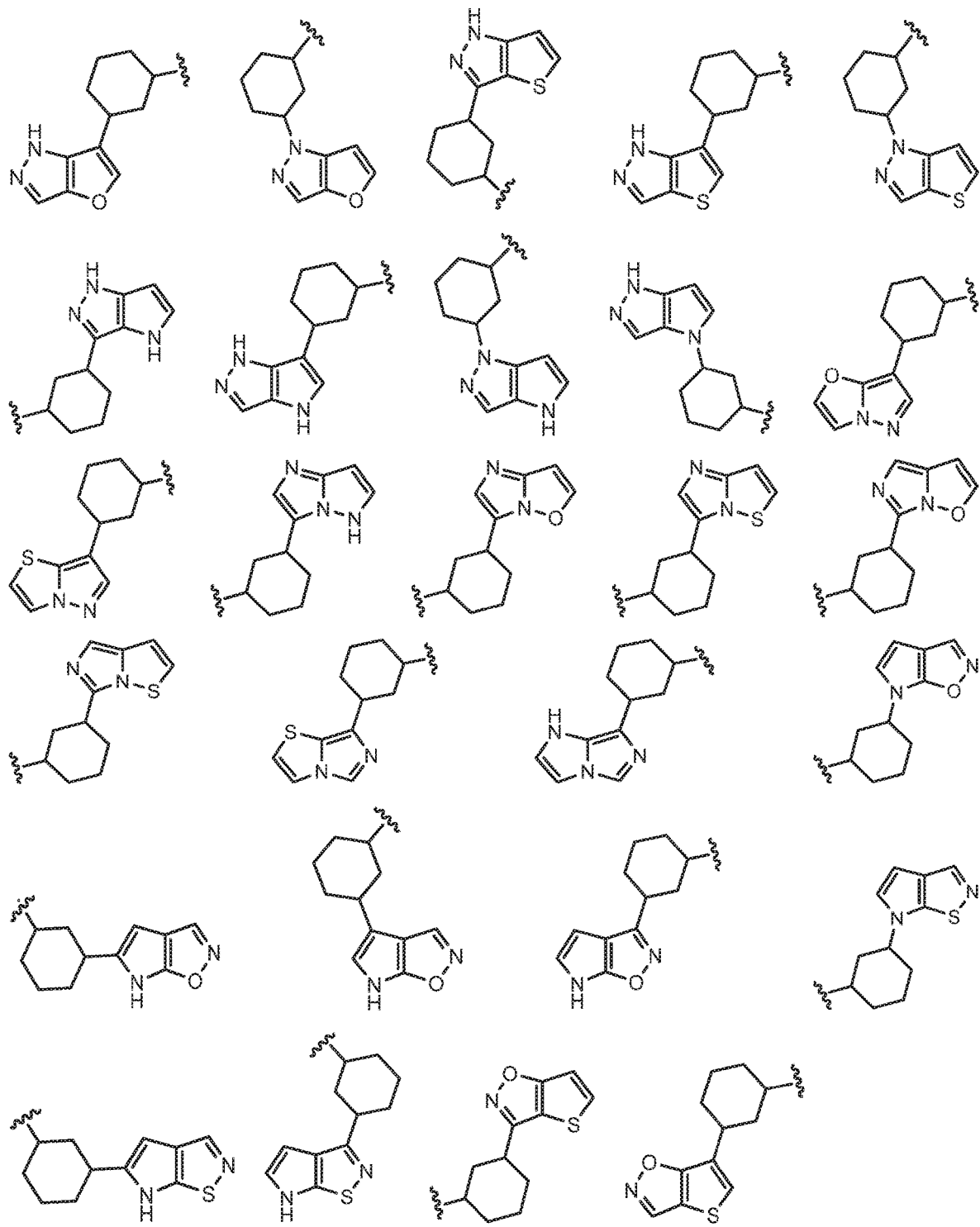
Figure 13P:
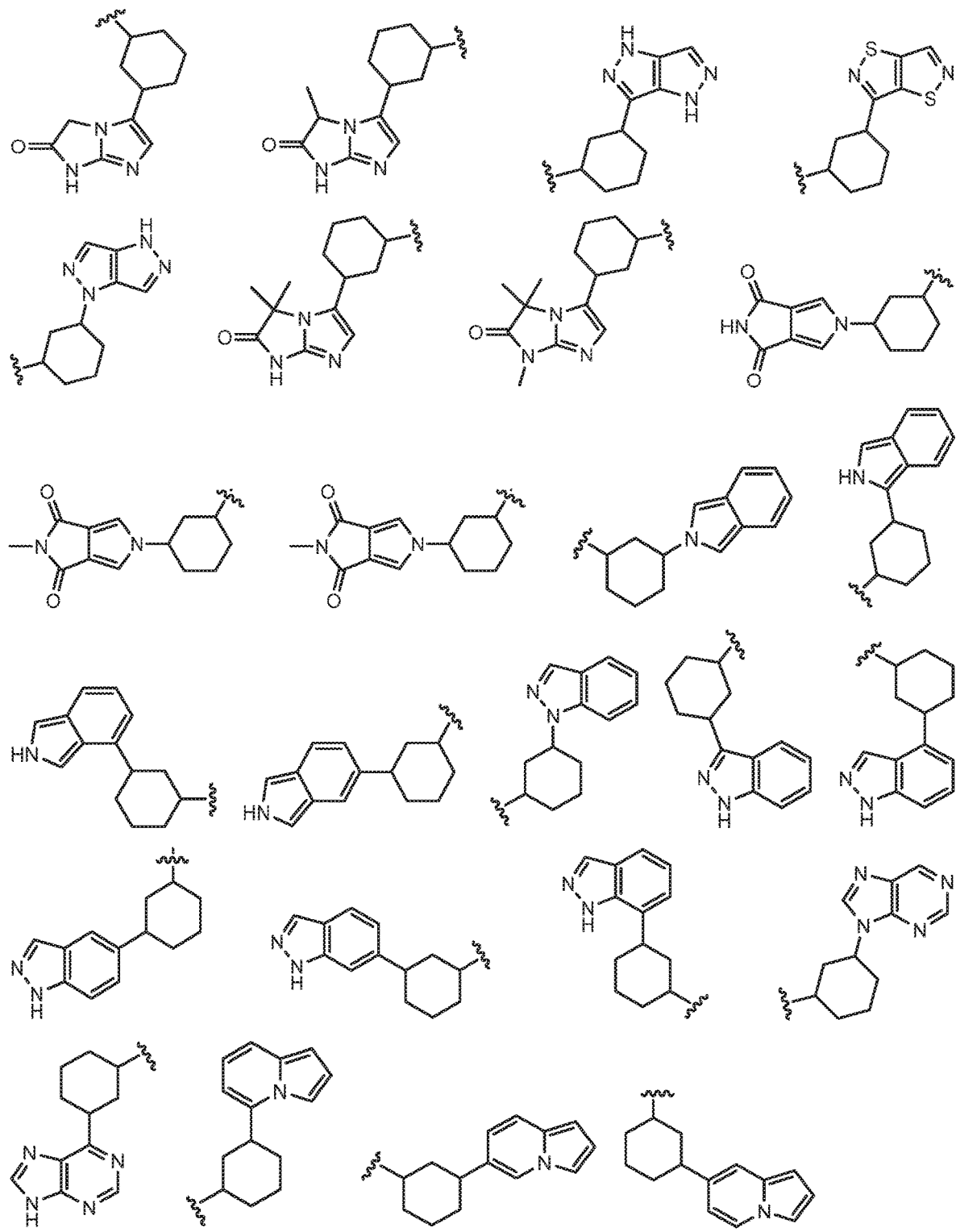
Figure 13Q:
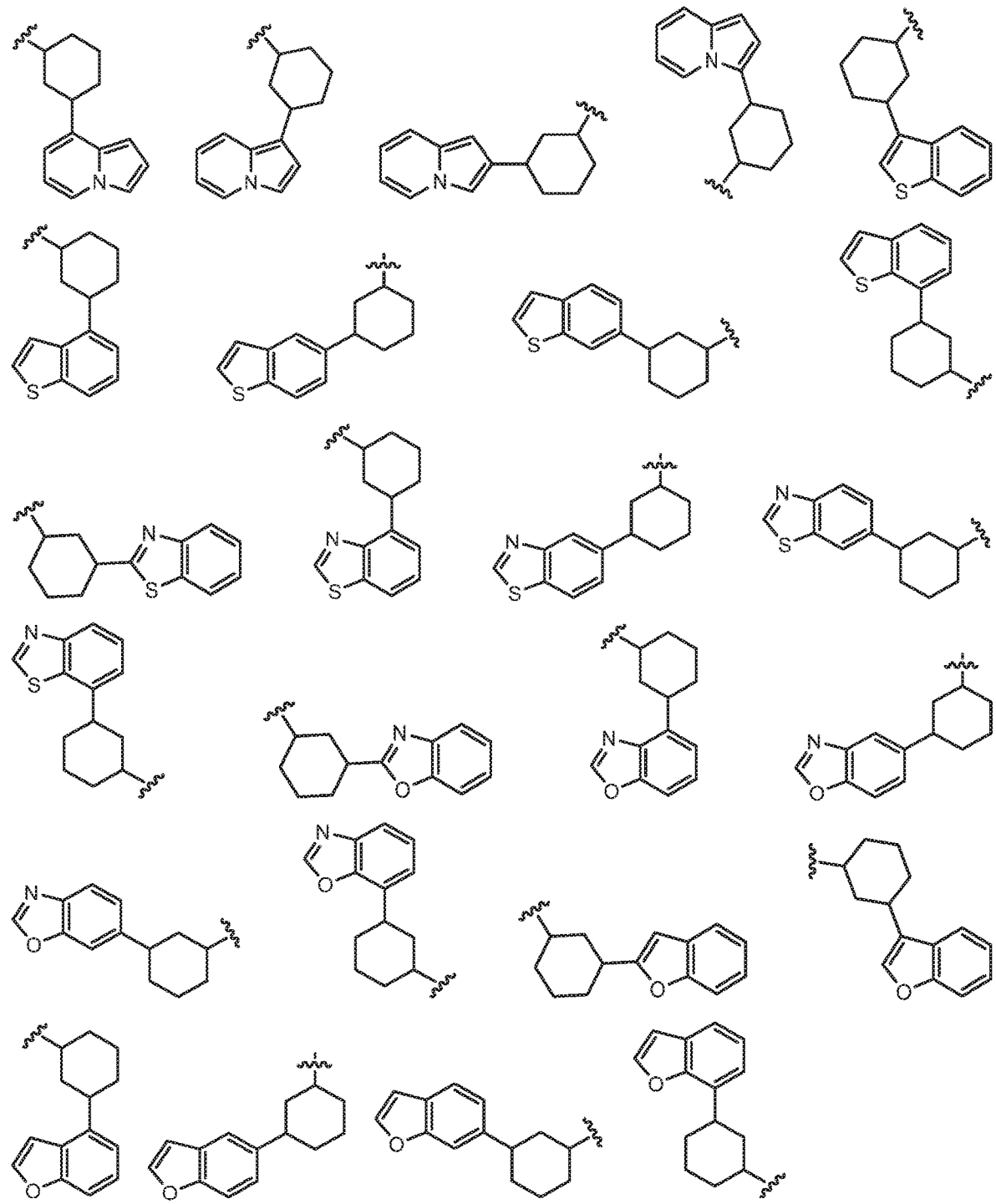
Figure 13R:
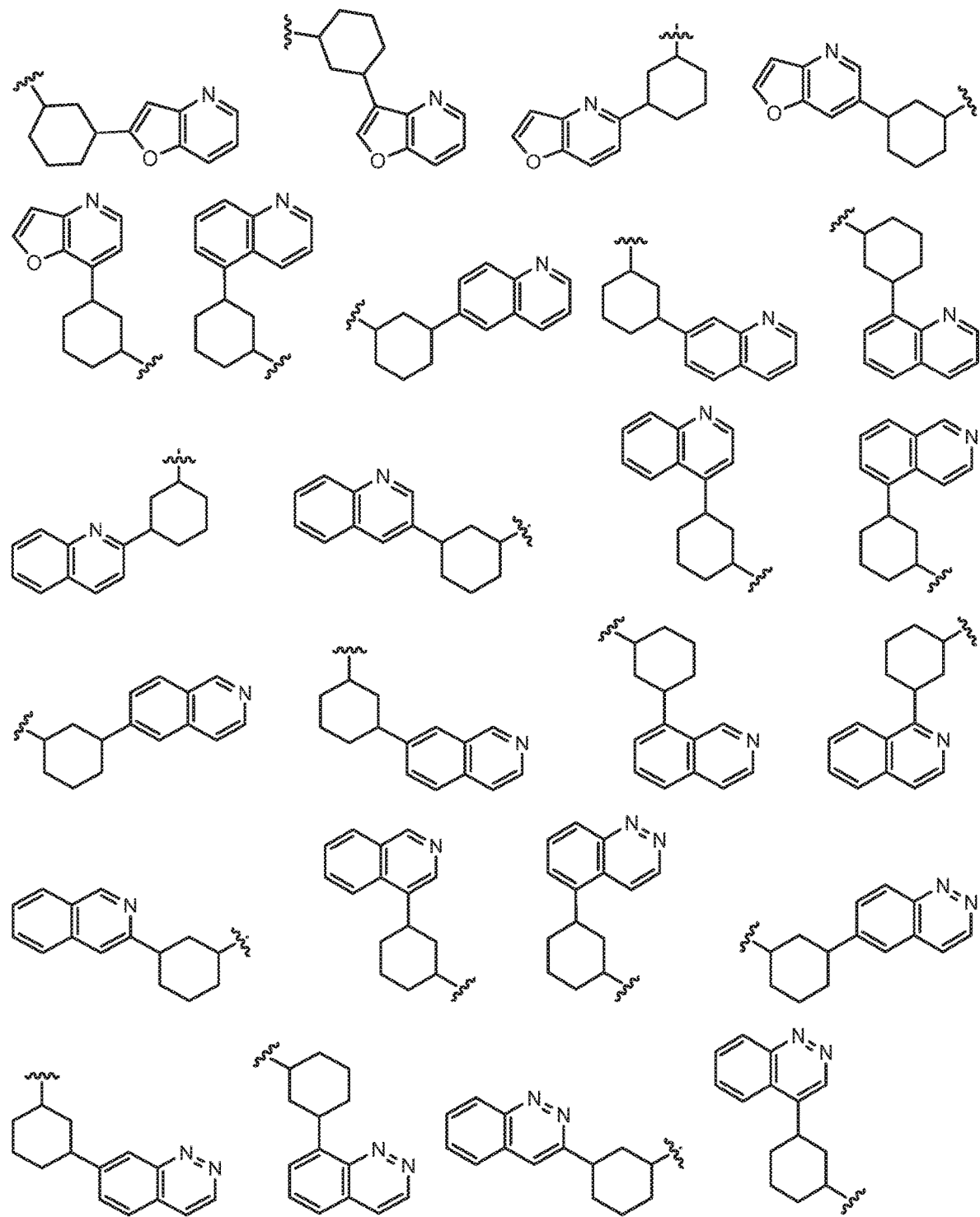
Figure 13S:
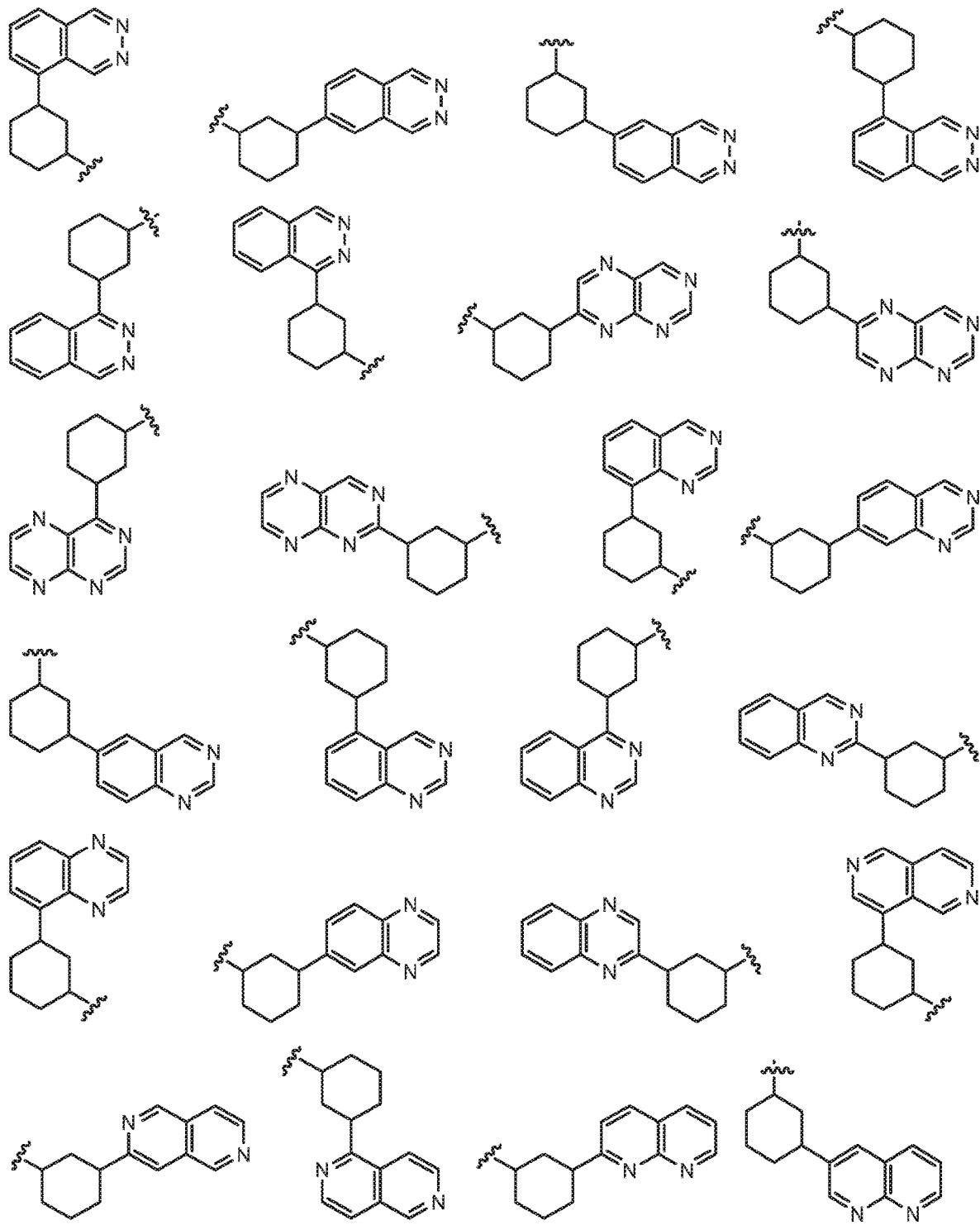
Figure 13T:
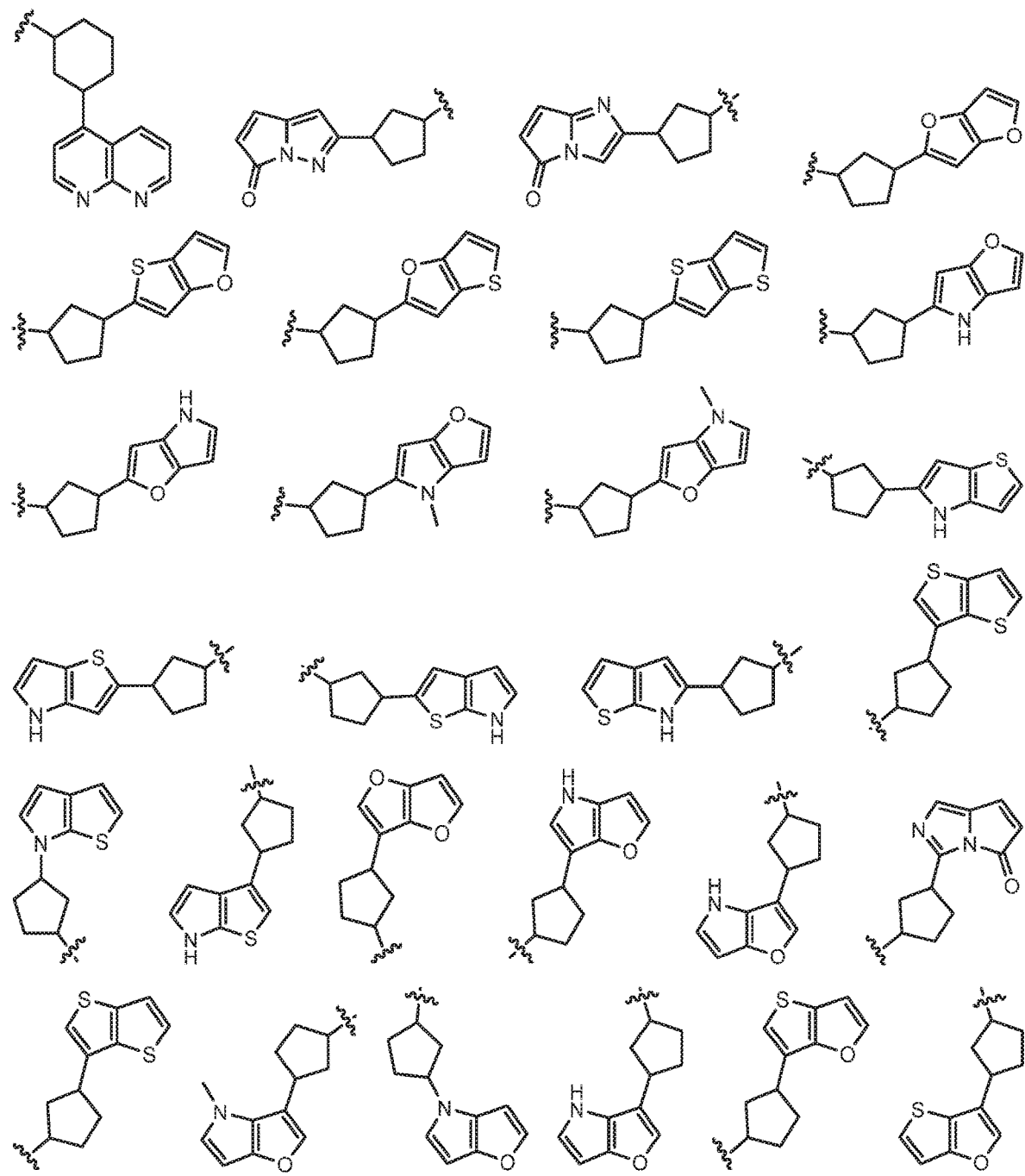
Figure 13U:
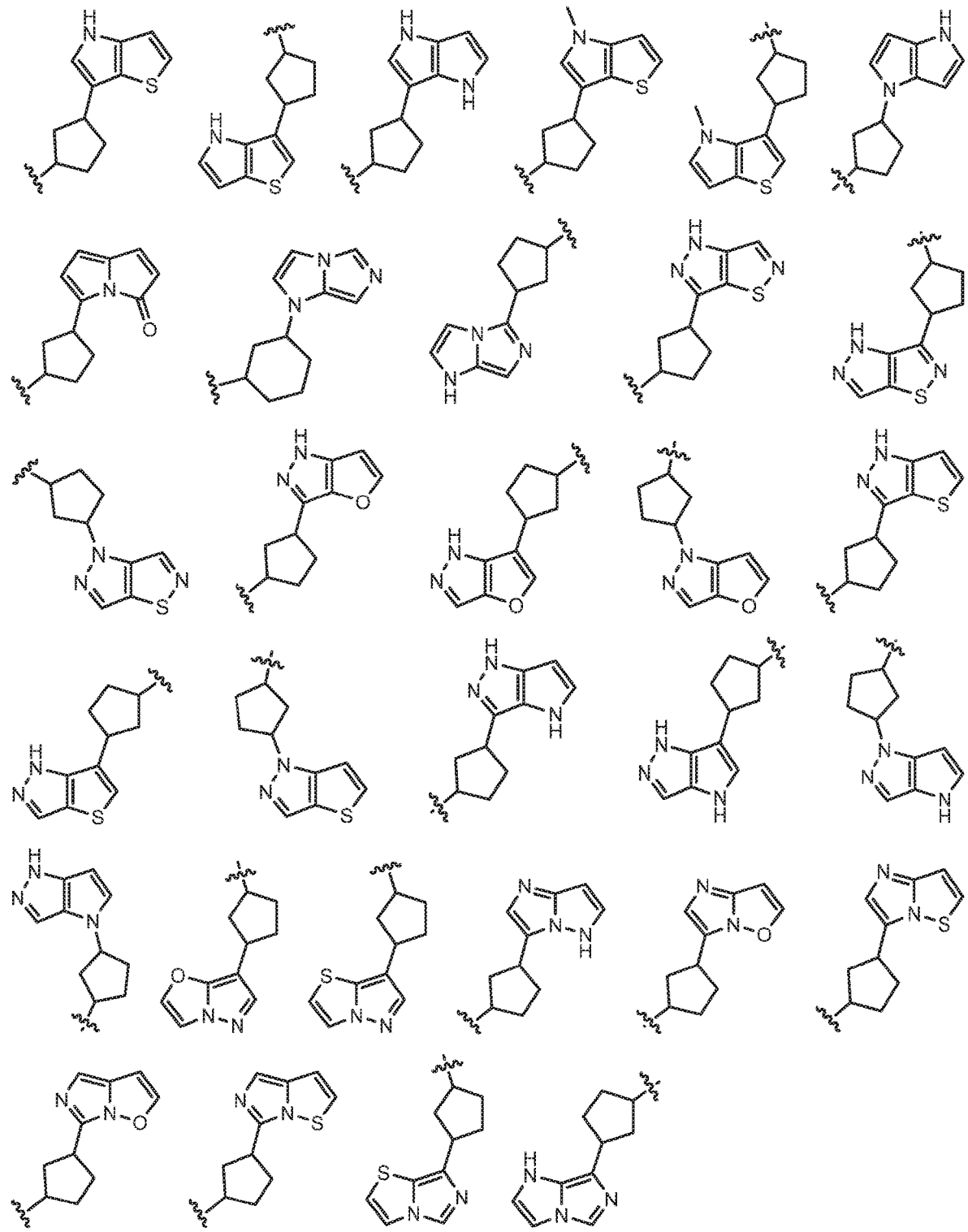
Figure 13V:
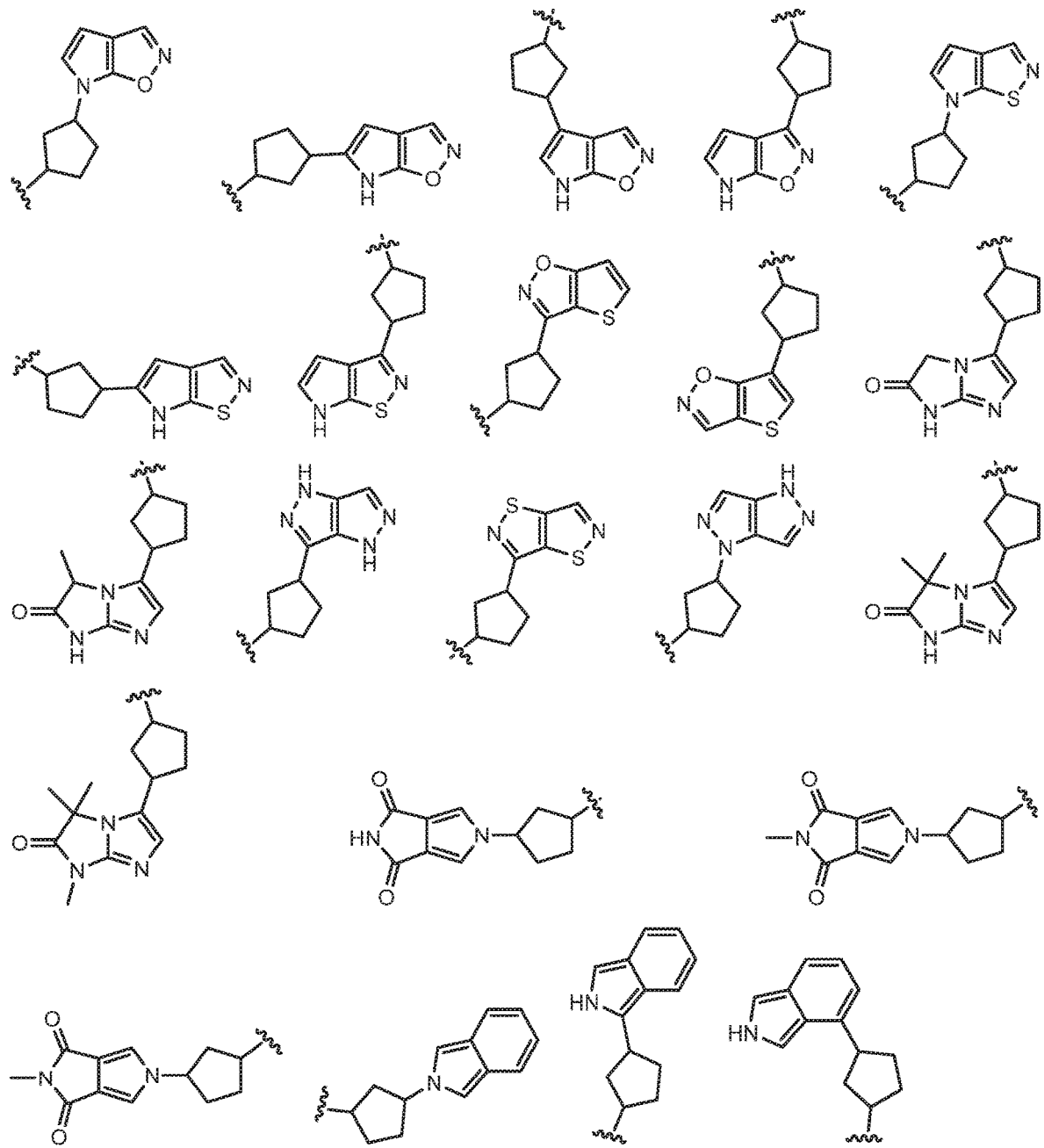
Figure 13W:
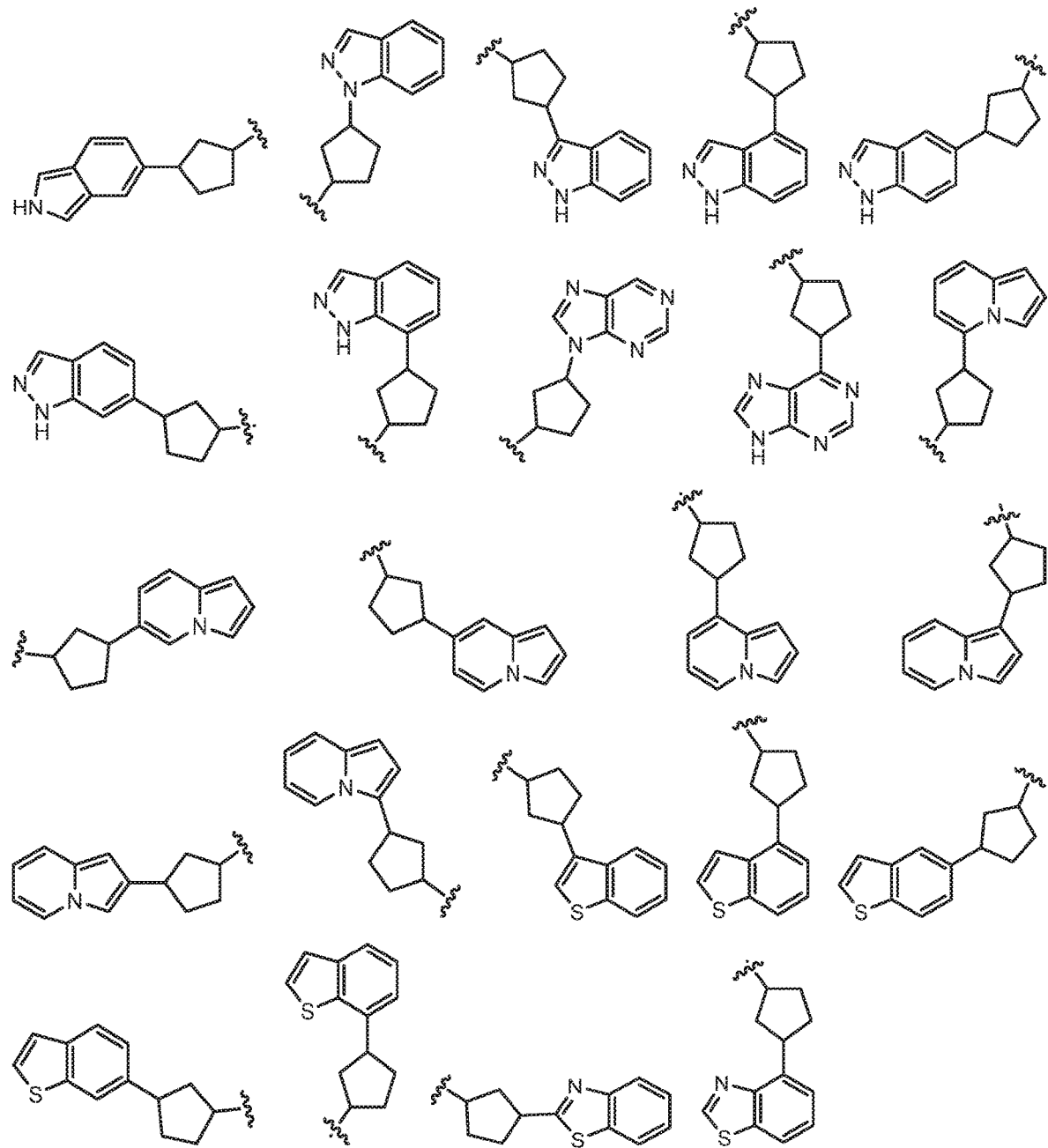
Figure 13X:
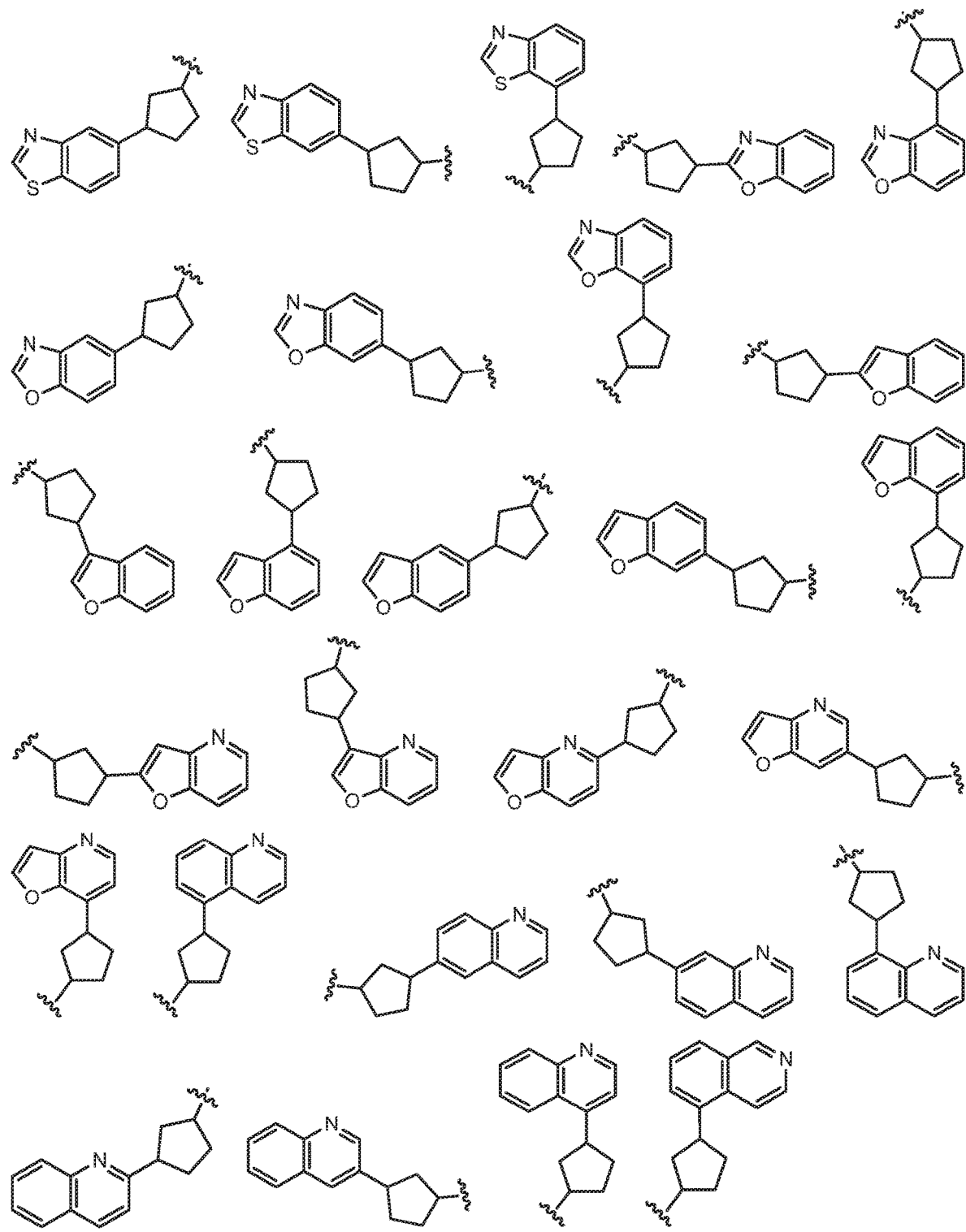
Figure 13Y:
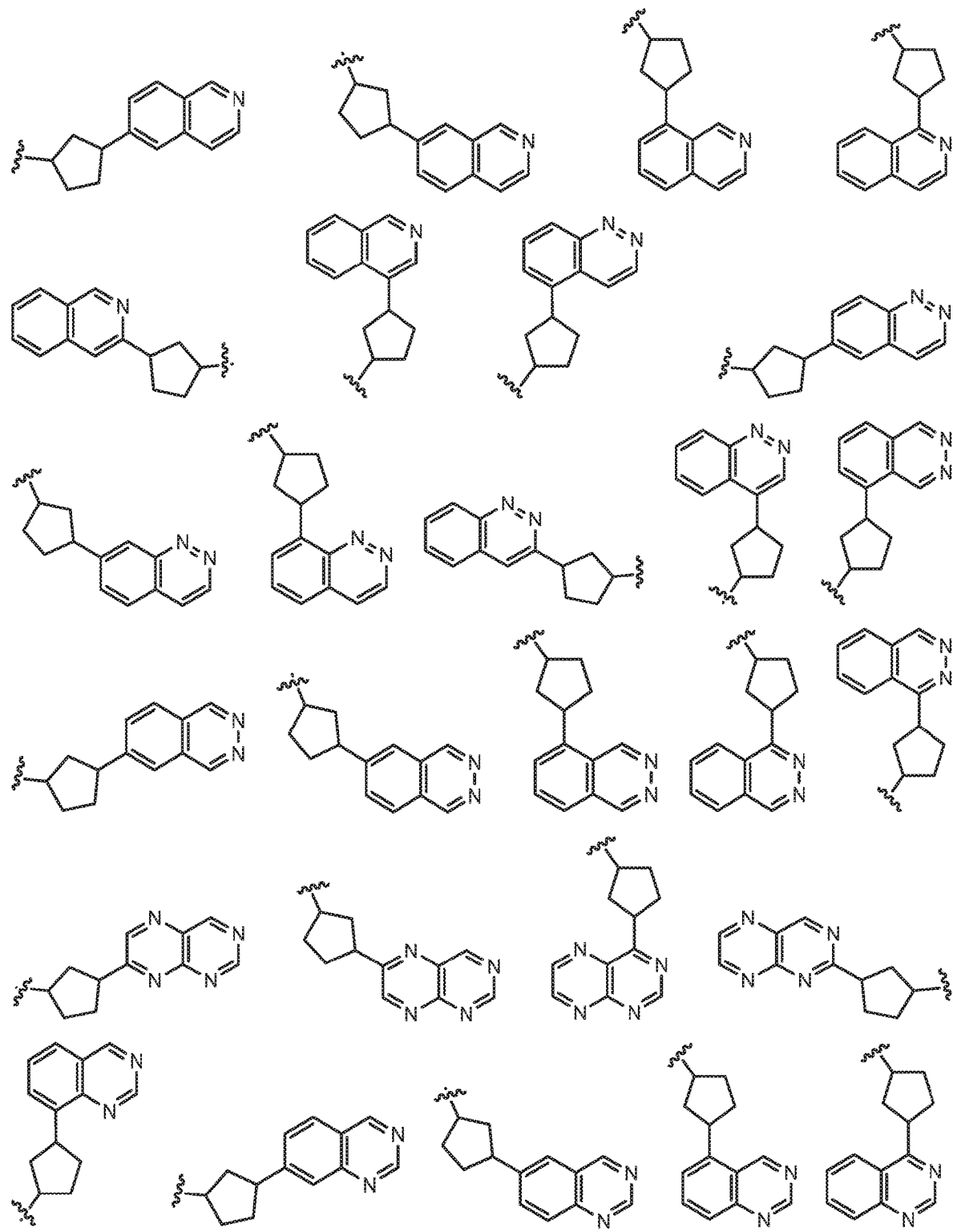
Figure 13Z:
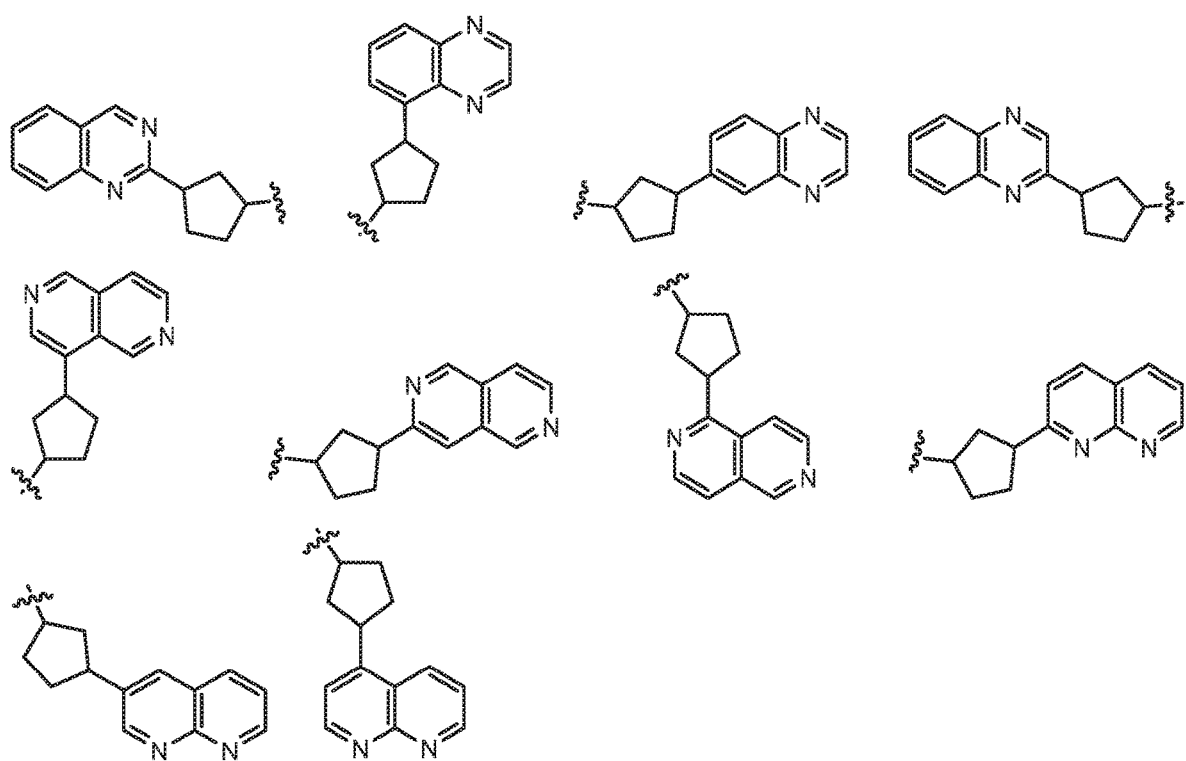
Figure 14:
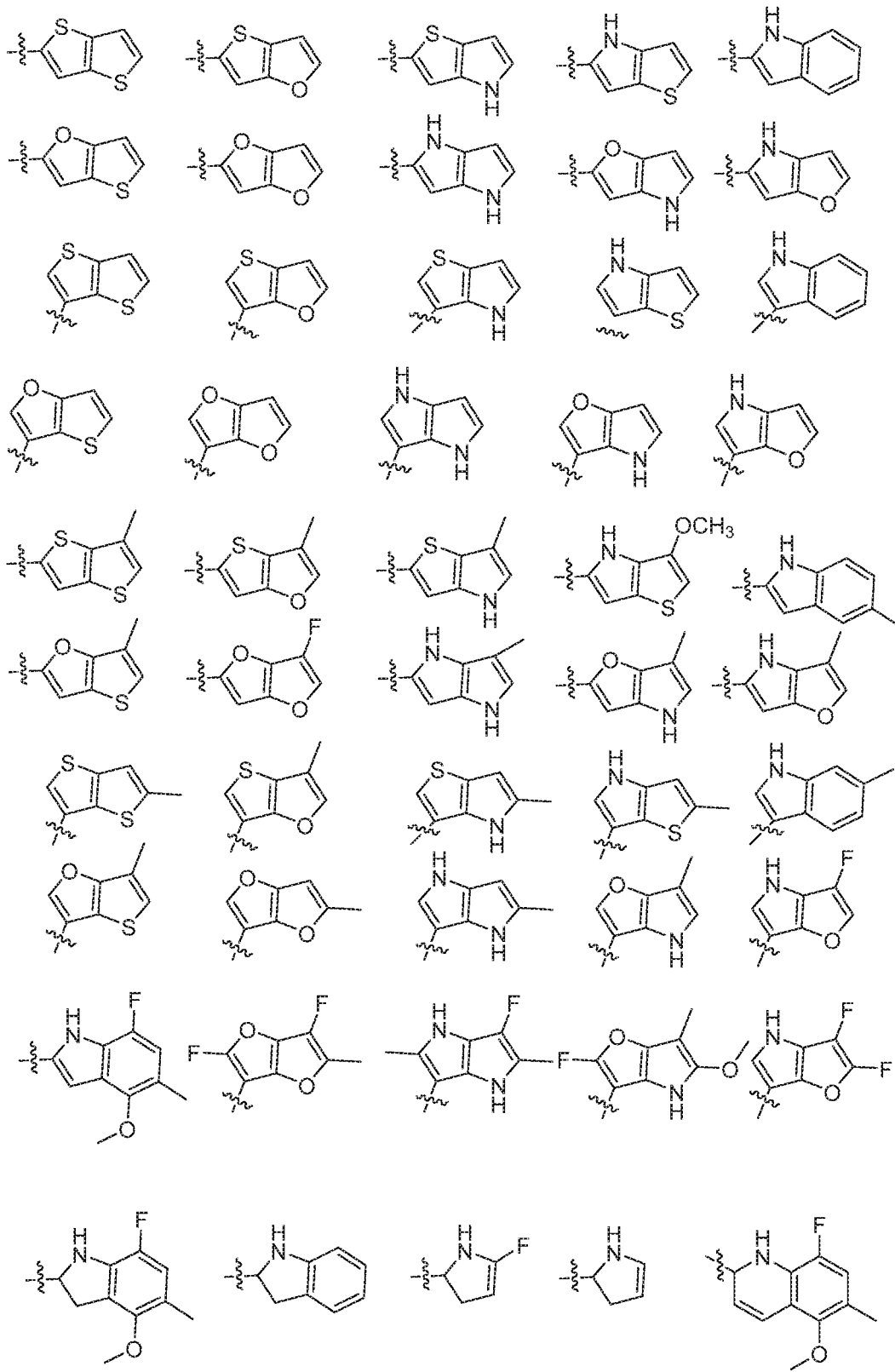
FIG. 14 provides non-limiting embodiments of L2-B3 wherein B3 is $R^{21}$, and $R^{21}$ is defined below.

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixtures of enantiomers, diastereomers, tautomers, racemates and other isomers, such as rotamers, as if each is specifically described, unless otherwise indicated or otherwise unclear from the context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds of Formula I, Formula I' or Formula I" with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. In one embodiment, isotopically labelled compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively or in addition, isotopes of carbon, e.g., $^{13}C$ and $^{14}C$, may be used. In one embodiment, the isotopic substitution is deuterium for hydrogen at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one embodiments deuterium is 90, 95 or 99% enriched at a desired location. Unless otherwise stated, the enrichment at any point is above natural abundance and enough to alter a detectable property of the drug in a human.

In one embodiment, the substitution of a hydrogen atom for a deuterium atom can be provided in any of A1, A1', A2, B1, B1', B2, B3, B4, C1, C1', C2, C3, C4, L1, L1', L2, L2', L4 or L5. In one embodiment, the substitution of a hydrogen atom for a deuterium atom occurs within an R group selected from any of R, R', $R^1$, $R^{1'}$, $R^2$, $R^{2'}$, $R^3$, $R^{3'}$, $R^{4'}$ $R^5$, $R^6$, $R^{6'}$, $R^7$, R, $R^{8'}$, $R^{11}$, $R^{12}$, $R^{13}$, $R^{14}$, $R^{15}$, $R^{16}$, $R^{19}$, $R^{21}$, $R^{22}$, $R^{23}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{71}$, $R^{101}$, or $R^{102}$. For example, when any of R groups are, or contain for example through substitution, methyl, ethyl, or methoxy, the alkyl residue may be deuterated (in non-limiting embodiments, $CD_3$, $CH_2CD_3$, $CD_2CD_3$, $CDH_2$, $CD_2H$, $CD_3$, $CHDCH_2D$, $CH_2CD_3$, $CHDCHD_2$, $OCDH_2$, $OCD_2H$, or $OCD_3$ etc.). In certain other embodiments, an R group has a """ or an "a" designation, which in one embodiment can be deuterated. In certain other embodiments, when two substituents of the central core ring are combined to form a cyclopropyl ring, the unsubstituted methylene carbon may be deuterated.

The compound of the present invention may form a solvate with solvents (including water). Therefore, in one embodiment, the invention includes a solvated form of the active compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C=O)NH$_2$ is attached through carbon of the keto (C=O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., =O) then two hydrogens on the atom are replaced. For example a pyridyl group substituted by oxo is a pyridone. Combinations of substituents and/or variables are permissible only if such combinations result in stable compounds or useful synthetic intermediates.

A stable active compound refers to a compound that can be isolated and can be formulated into a dosage form with a shelf life of at least one month. A stable manufacturing intermediate or precursor to an active compound is stable if it does not degrade within the period needed for reaction or other use. A stable moiety or substituent group is one that does not degrade, react or fall apart within the period necessary for use. Nonlimiting examples of unstable moieties are those that combine heteroatoms in an unstable arrangement, as typically known and identifiable to those of skill in the art.

Any suitable group may be present on a "substituted" or "optionally substituted" position that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; alkylthio including those having one or more thioether linkages; alkylsulfinyl; alkylsulfonyl groups including those having one or more sulfonyl linkages; aminoalkyl groups including groups having one or more N atoms; aryl (e.g., phenyl, biphenyl, naphthyl, or the like, each ring either substituted or unsubstituted aromatic); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated, unsaturated, or aromatic heterocyclic group having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino. In certain embodiments "optionally substituted" includes one or more substituents independently replaced from halogen, hydroxyl, amino, cyano, —CHO, —COOH, —CONH$_2$, $C_1$-$C_6$alkyl, $C_2$-$C_6$alkenyl, $C_2$-$C_6$alkynyl, —$C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, hydoxy$C_1$-$C_6$alkyl, ester, carbamate, urea, sulfonamide, —$C_1$-$C_6$alkyl (heterocyclo), $C_1$-$C_6$alkyl(heteroaryl), —$C_1$-$C_6$alkyl($C_3$-$C_7$cycloalkyl), O—$C_1$-$C_6$alkyl($C_3$-$C_7$cycloalkyl), B(OH)$_2$, phosphate, phosphonate and $C_1$-$C_2$haloalkoxy.

"Alkyl" is a branched or straight chain saturated aliphatic hydrocarbon group. In one embodiment, the alkyl contains from 1 to about 12 carbon atoms, more generally from 1 to about 6 carbon atoms or from 1 to about 4 carbon atoms. In one embodiment, the alkyl contains from 1 to about 8 carbon atoms. In certain embodiments, the alkyl is $C_1$-$C_2$, $C_1$-$C_3$, $C_1$-$C_4$, $C_1$-$C_5$ or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$cycloalkyl)$C_0$-$C_4$ alkyl, or —$C_0$-$C_4$alkyl($C_3$-$C_7$cycloalkyl), the indicated group, in this case cycloalkyl, is either directly bound by a single covalent bond ($C_0$alkyl), or attached by an alkyl chain in this case 1, 2, 3, or 4 carbon atoms. Alkyls can also be attached via other groups such as heteroatoms as in —O—$C_0$-$C_4$alkyl ($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, 2,3-dimethylbutane, and hexyl. In one embodiment, the alkyl group is optionally substituted as described above. In one embodiment, trimethylsilyl can be used instead of t-butyl.

In one embodiment, when a term is used that includes "alk" it should be understood that "cycloalkyl" or "carbocyclic" can be considered part of the definition, unless unambiguously excluded by the context. For example and without limitation, the terms alkyl, alkenyl, alkynyl, alkoxy, alkanoyl, alkenloxy, haloalkyl, aminoalkyl, alkylene, alkenylene, alkynylene, etc. can all be considered to include the cyclic forms of alkyl, unless unambiguously excluded by context.

"Alkenyl" is a branched or straight chain aliphatic hydrocarbon group having one or more carbon-carbon double bonds that may occur at a stable point along the chain. Nonlimiting examples are $C_2$-$C_8$alkenyl, $C_2$-$C_7$alkenyl, $C_2$-$C_6$alkenyl, $C_2$-$C_5$alkenyl and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl. In one embodiment, the alkenyl group is optionally substituted as described above.

"Alkynyl" is a branched or straight chain aliphatic hydrocarbon group having one or more carbon-carbon triple bonds that may occur at any stable point along the chain, for example, $C_2$-$C_8$alkynyl or $C_2$-$C_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In one embodiment, the alkynyl group is optionally substituted as described above.

"Alkylene" is a bivalent saturated hydrocarbon. Alkylenes, for example, can be a 1, 2, 3, 4, 5, 6, 7 to 8 carbon moiety, 1 to 6 carbon moiety, or an indicated number of carbon atoms, for example $C_1$-$C_2$alkylene, $C_1$-$C_3$alkylene, $C_1$-$C_4$alkylene, $C_1$-$C_6$alkylene, or $C_1$-$C_6$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Alkenyloxy" is an alkenyl group as defined covalently bound to the group it substitutes by an oxygen bridge (—O—).

"Alkanoyl" is an alkyl group as defined above covalently bound through a carbonyl (C═O) bridge. The carbonyl carbon is included in the number of carbons, that is $C_2$alkanoyl is a CH$_3$(C═O)— group. In one embodiment, the alkanoyl group is optionally substituted as described above.

"Alkylester" is an alkyl group as defined herein covalently bound through an ester linkage. The ester linkage may be in either orientation, e.g., a group of the formula —O(C═O)alkyl or a group of the formula —(C═O)Oalkyl.

"Amide" or "carboxamide" is —C(O)NR$^a$R$^b$ wherein R$^a$ and R$^b$ are each independently selected from hydrogen, alkyl, for example, $C_1$-$C_6$alkyl, alkenyl, for example, $C_2$-$C_6$alkenyl, alkynyl, for example, $C_2$-$C_6$alkynyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), and —$C_0$-$C_4$alkyl (heteroaryl); or together with the nitrogen to which they are bonded, R$^a$ and R$^b$ can form a $C_3$-$C_7$heterocyclic ring. In one embodiment, the R$^a$ and R$^b$ groups are each independently optionally substituted as described herein.

"Carbocyclic group", "carbocyclic ring", or "cycloalkyl" is a saturated or partially unsaturated (i.e., not aromatic) group containing all carbon ring atoms. A carbocyclic group typically contains 1 ring of 3 to 7 carbon atoms or 2 fused rings each containing 3 to 7 carbon atoms. Cycloalkyl substituents may be pendant from a substituted nitrogen or carbon atom, or a substituted carbon atom that may have two substituents can have a cycloalkyl group, which is attached as a spiro group. Examples of carbocyclic rings include cyclohexenyl, cyclohexyl, cyclopentenyl, cyclopentyl, cyclobutenyl, cyclobutyl and cyclopropyl rings. In one embodiment, the carbocyclic ring is optionally substituted as described above. In one embodiment, the cycloalkyl is a partially unsaturated (i.e., not aromatic) group containing all carbon ring atoms. In another embodiment, the cycloalkyl is a saturated group containing all carbon ring atoms.

"Carbocyclic-oxy group" is a monocyclic carbocyclic ring or a mono- or bi-cyclic carbocyclic group as defined above attached to the group it substitutes via an oxygen, —O—, linker.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Hydroxyalkyl" is an alkyl group as previously described, substituted with at least one hydroxyl substituent.

"Aminoalkyl" is an alkyl group as previously described, substituted with at least one amino substituent.

"Halo" or "halogen" indicates independently, any of fluoro, chloro, bromo or iodo.

"Aryl" indicates an aromatic group containing only carbon in the aromatic ring or rings. In one embodiment, the aryl group contains 1 to 3 separate or fused rings and is 6 to about 14 or 18 ring atoms, without heteroatoms as ring members. When indicated, such aryl groups may be further substituted with carbon or non-carbon atoms or groups. Such substitution may include fusion to a 4 to 7 or a 5 to 7-membered saturated or partially unsaturated cyclic group that optionally contains 1, 2 or 3 heteroatoms independently replaced from N, O, B, P, Si and/or S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described above.

The term "heterocycle," or "heterocyclic ring" as used herein refers to a saturated or a partially unsaturated (i.e., having one or more double and/or triple bonds within the ring without aromaticity) carbocyclic moiety of 3 to about 12, and more typically 3, 4, 5, 6, 7, 8 to 10 ring atoms in which at least one ring atom is a heteroatom selected from nitrogen, oxygen, phosphorus sulfur, silicon and boron, the remaining ring atoms being C, where one or more ring atoms is optionally substituted independently with one or more substituents described above. A heterocycle may be a monocycle having 3 to 7 ring members (2 to 6 carbon atoms and 1 to 4 heteroatoms selected from N, O, P, S, Si and B) or a bicycle having 6 to 10 ring members (4 to 9 carbon atoms and 1 to 6 heteroatoms selected from N, O, P, S, Si and B), for example: a bicyclo [4,5], [5,5], [5,6], or [6,6] system. In one embodiment, the only heteroatom is nitrogen. In one embodiment, the only heteroatom is oxygen. In one embodiment, the only heteroatom is sulfur, boron or silicon. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, pyrrolidinyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyco[3.1.0]hexanyl, 3-azabicyclo[4.1.0]heptanyl, azabicyclo[2.2.2]hexanyl, 3H-indolyl, quinolizinyl, N-pyridyl ureas, and pyrrolopyrimidine. Spiro moieties are also included within the scope of this definition. Examples of a heterocyclic group wherein 1 or 2 ring carbon atoms are substituted with oxo (=O) moieties are pyrimidinonyl and 1,1-dioxo-thiomorpholinyl. The heterocycle groups herein are optionally substituted independently with one or more substituents described herein, for example, 1, 2, or 3 substituents.

"Heterocyclicoxy group" is a monocyclic heterocyclic ring or a bicyclic heterocyclic group as described previously linked to the group it substitutes via an oxygen, —O—, linker.

"Heteroaryl" refers to a stable monocyclic aromatic ring which contains from 1 to 3, or in some embodiments from 1, 2 or 3 heteroatoms replaced from N, O, S, B or P with remaining ring atoms being carbon, or a stable bicyclic or tricyclic system containing at least one 5, 6, or 7 membered aromatic ring which contains from 1 to 3, or in some embodiments from 1 to 2, heteroatoms replaced from N, O, S, B or P with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5, 6, or 7 ring atoms. In some embodiments bicyclic heteroaryl groups are 8- to 10-membered heteroaryl groups, that is, groups containing 8 or 10 ring atoms in which one 5, 6, or 7 member aromatic ring is fused to a second aromatic or non-aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. Heteroaryl groups are optionally substituted independently with one or more substituents described herein. "Heteroaryloxy" is a heteroaryl group as described bound to the group it substituted via an oxygen, —O—, linker.

"Heterocycloalkyl" is a saturated ring group. It may have, for example, 1, 2, 3, or 4 heteroatoms independently replaced from N, S, O, Si and B with remaining ring atoms being carbon. In a typical embodiment, nitrogen is the heteroatom. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl.

The term "mono- and/or di-alkylamino" indicate a secondary or tertiary alkylamino group, wherein the alkyl groups are independently replaced alkyl groups, as defined herein. The point of attachment of the alkylamino group is on the nitrogen. Examples of mono- and di-alkylamino groups include ethylamino, dimethylamino, and methyl-propyl-amino.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

"Pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

A "pharmaceutically acceptable salt" is a derivative of the disclosed compound in which the parent compound is modified by making inorganic and organic, pharmaceutically acceptable, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, including but not limited to by modulation of the complement Factor D pathway. Typically the host is a human. A "patient" or "host" or "subject" also refers to for example, a mammal, primate (e.g., human), cows, sheep, goat, horse, dog, cat, rabbit, rat, mice, fish, bird and the like.

A "prodrug" as used herein, means a compound which when administered to a host in vivo is converted into a parent drug. As used herein, the term "parent drug" means any of the presently described chemical compounds described herein. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

"Providing a compound with at least one additional active agent," for example, in one embodiment can mean that the compound and the additional active agent(s) are provided simultaneously in a single dosage form, provided concomitantly in separate dosage forms, or provided in separate dosage forms for administration. In one embodiment, the compound administrations are separated by some amount of time that is within the time in which both the compound and the at least one additional active agent are within the blood stream of a patient. In certain embodiments the compound and the additional active agent need not be prescribed for a patient by the same medical care worker. In certain embodiments the additional active agent or agents need not require a prescription. Administration of the compound or the at least one additional active agent can occur via any appropriate route, for example, oral tablets, oral capsules, oral liquids, inhalation, injection, suppositories, parenteral, sublingual, buccal, intravenous, intraaortal, transdermal, polymeric controlled delivery, non-polymeric controlled delivery, nano or microparticles, liposomes, and/or topical contact. In one embodiment, the instructions for administration in a form of combination therapy is provided in the drug labeling.

A "therapeutically effective amount" of a pharmaceutical composition/combination of this invention means an amount effective, when administered to a host, to provide a therapeutic benefit such as an amelioration of symptoms or reduction or diminution of the disease itself. In one embodiment, a therapeutically effective amount is an amount sufficient to prevent a significant increase or will significantly reduce the detectable level of complement Factor D in the patient's blood, serum, or tissues.

II. Detailed Description of the Active Compounds

According to the present invention, a compound of Formula I is provided:

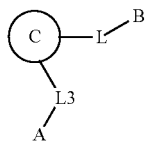
(I)

as well as the pharmaceutically acceptable salts and compositions thereof. Formula I can be considered to have a central core C, an L substituent, a B substituent, and an L3-A substituent. Formula I comprises at least one of the A2, B3, C3, L2, L2', or L5 (and in certain embodiments, C4) moieties described herein. The invention includes a compound of Formula I, or a pharmaceutically acceptable salt or composition thereof, wherein $R^{12}$ or $R^{13}$ on the A group is an aryl, heteroaryl or heterocycle, for example an $R^{32}$. In one embodiment, the compound is an inhibitor of complement factor D, and therefore can be used as an effective amount to treat a host in need of complement factor D modulation. In another embodiment, the compound acts through a mechanism other than inhibition of complement D to treat a disorder described herein in a host, typically a human.

The present invention also includes a compound of Formula I':

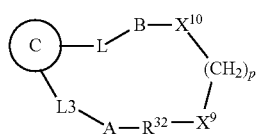
(I')

as well as the pharmaceutically acceptable salts and compositions thereof. Formula I' has a central core C moiety, an A substituent, a L3 substituent, an L substituent, a B substituent and a $—X^9—(CH_2)_p—X^{10}$ linker; wherein $R^{12}$ or $R^{13}$ on the A1 or A2 group is an amide substituent, for example a divalent $R^{32}$ moiety. In one embodiment, this compound is an inhibitor of complement factor D, and therefore can be used as an effective amount to treat a host in need of complement factor D modulation. Alternatively, the compound may act through a different mechanism of action to treat the disorders described herein.

In addition, the present invention provides a compound of Formula I":

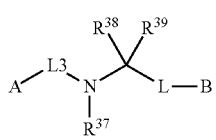
(I")

as well as the pharmaceutically acceptable salts and compositions thereof. Formula I" has an

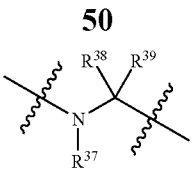

moiety, an A substituent, a L3 substituent, a L substituent and a B substituent. Compounds of Formula I", or a pharmaceutically acceptable salt or composition thereof, wherein $R^{12}$ or $R^{13}$ on the A1 or A2 group is an heteroaryl, aryl, or heterocycle substituent, for example an $R^{32}$. In one embodiment, this compound is an inhibitor of complement factor D, and therefore can be used as an effective amount to treat a host in need of complement factor D modulation. Alternatively, the compound may act through a different mechanism of action to treat the disorders described herein.

Non-limiting examples of compounds falling within Formula I and Formula I' with variations in the variables e.g., A, B, $R^1$-$R^{3'}$, and L, are described below.

Non-limiting examples of compounds falling within Formula I" with variations in the variables e.g., $R^{37}$, $R^{38}$, $R^{39}$, A, B, L and L3 are described below. The disclosure includes all combinations of these definitions as long as a stable compound results.

In certain embodiments, any of the active compounds can be provided in its N-oxide form to a patient in need thereof. In a different embodiment, an N-oxide of one of the active compounds or a precursor of the active compound is used in a manufacturing scheme. In yet another embodiment, the N-oxide is a metabolite of administration of one of the active compounds herein, and may have independent activity. The N-oxide can be formed by treating the compound of interest with an oxidizing agent, for example a suitable peroxyacid or peroxide, to generate an N-oxide compound. For example, a heteroaryl group, for example a pyridyl group, can be treated with an oxidizing agent such as sodium percarbonate in the presence of a rhenium-based catalyst under mild reaction conditions to generate an N-oxide compound. A person skilled in the art will understand that appropriate protecting groups may be necessary to carry out the chemistry. See, Jain, S. L. et al., "Rhenium-Catalyzed Highly Efficient Oxidations of Tertiary Nitrogen Compounds to N-Oxides Using Sodium Percarbonate as Oxygen Source, Synlett, 2261-2663, 2006.

In other embodiments, any of the active compounds with a sulfur can be provided in its sulfoxide or sulfone form to a patient in need thereof. In a different embodiment, a sulfoxide or sulfone of one of the active compounds or a precursor of the active compound is used in a manufacturing scheme. A sulfur atom in a selected compound as described herein can be oxidized to form a sulfoxide

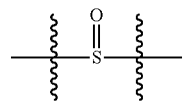

or a sulfone

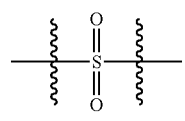 [SMILES: *S(*)(=O)=O]

using known methods. For example, the compound 1,3,5-triazo-2,4,6-triphosphorine-2,2,4,4,6,6-tetrachloride (TAPC) is an efficient promoter for the oxidation of sulfides to sulfoxides. See, Bahrami, M. et al., "TAPC-Promoted Oxidation of sulfides and Deoxygenation of Sulfoxides", J. Org. Chem., 75, 6208-6213 (2010). Oxidation of sulfides with 30% hydrogen peroxide catalyzed by tantalum carbide provides sulfoxides in high yields, see, Kirihara, A., et al., "Tantalum Carbide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Sulfides can be oxidized to sulfones using, for example, niobium carbide as the catalyst, see, Kirihara, A., et al., "Tantalum Cardide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Urea-hydrogen peroxide adduct is a stable inexpensive and easily handled reagent for the oxidation of sulfides to sulfones, see Varma, R S. and Naicker, K. P., "The Urea-Hydrogen Peroxide Complex: Solid-State Oxidative Protocols for Hydroxylated Aldehydes and Ketones (Dakin Reaction), Nitriles, Sulfides, and Nitrogen Heterocycles", Org. Lett., 1, 189-191 (1999). One skilled in the art will appreciate that other heteroatoms, such as nitrogen, may need to be protected and then deprotected while carrying out the oxidation of a sulfur atom to produce the desired compound.

Formulas 2 Through 654

In one aspect, the disclosure includes compounds and salts of Formulas 2-654 for any use and in any composition described in this application.

TABLE 1

Exemplary Compounds within the Present Invention.

| Formula No. | Formula |
|---|---|
| 2 | A1L4C1L1B3 |
| 3 | A1L4C1L1'B3 |
| 4 | A1L4C1L2B1 |
| 5 | A1L4C1L2B1' |
| 6 | A1L4C1L2B2 |
| 7 | A1L4C1L2B3 |
| 8 | A1L4C1'L1B3 |
| 9 | A1L4C1'L1'B3 |
| 10 | A1L4C1'L2B1 |
| 11 | A1L4C1'L2B1' |
| 12 | A1L4C1'L2B2 |
| 13 | A1L4C1'L2B3 |
| 14 | A1L4C2L1B3 |
| 15 | A1L4C2L1'B3 |
| 16 | A1L4C2L2B1 |
| 17 | A1L4C2L2B1' |
| 18 | A1L4C2L2B2 |
| 19 | A1L4C2L2B3 |
| 20 | A1L4C3L1B1 |
| 21 | A1L4C3L1B1' |
| 22 | A1L4C3L1B2 |
| 23 | A1L4C3L1B3 |
| 24 | A1L4C3L1'B1 |
| 25 | A1L4C3L1'B1' |
| 26 | A1L4C3L1'B2 |
| 27 | A1L4C3L1'B3 |
| 28 | A1L4C3L2B1 |
| 29 | A1L4C3L2B1' |
| 30 | A1L4C3L2B2 |
| 31 | A1L4C3L2B3 |
| 32 | A1L5C1L1B1 |
| 33 | A1L5C1L1B1' |
| 34 | A1L5C1L1B2 |
| 35 | A1L5C1L1B3 |
| 36 | A1L5C1L1'B1 |
| 37 | A1L5C1L1'B1' |
| 38 | A1L5C1L1'B2 |
| 39 | A1L5C1L1'B3 |
| 40 | A1L5C1L2B1 |
| 41 | A1L5C1L2B1' |
| 42 | A1L5C1L2B2 |
| 43 | A1L5C1L2B3 |
| 44 | A1L5C1'L1B1 |
| 45 | A1L5C1'L1B1' |
| 46 | A1L5C1'L1B2 |
| 47 | A1L5C1'L1B3 |
| 48 | A1L5C1'L1'B1 |
| 49 | A1L5C1'L1'B1' |
| 50 | A1L5C1'L1'B2 |
| 51 | A1L5C1'L1'B3 |
| 52 | A1L5C1'L2B1 |
| 53 | A1L5C1'L2B1' |
| 54 | A1L5C1'L2B2 |
| 55 | A1L5C1'L2B3 |
| 56 | A1L5C2L1B1 |
| 57 | A1L5C2L1B1' |
| 58 | A1L5C2L1B2 |
| 59 | A1L5C2L1B3 |
| 60 | A1L5C2L1'B1 |
| 61 | A1L5C2L1'B1' |
| 62 | A1L5C2L1'B2 |
| 63 | A1L5C2L1'B3 |
| 64 | A1L5C2L2B1 |
| 65 | A1L5C2L2B1' |
| 66 | A1L5C2L2B2 |
| 67 | A1L5C2L2B3 |
| 68 | A1L5C3L1B1 |
| 69 | A1L5C3L1B1' |
| 70 | A1L5C3L1B2 |
| 71 | A1L5C3L1B3 |
| 72 | A1L5C3L1'B1 |
| 73 | A1L5C3L1'B1' |
| 74 | A1L5C3L1'B2 |
| 75 | A1L5C3L1'B3 |
| 76 | A1L5C3L2B1 |
| 77 | A1L5C3L2B1' |
| 78 | A1L5C3L2B2 |
| 79 | A1L5C3L2B3 |
| 80 | A1'L4C1L1B3 |
| 81 | A1'L4C1L1'B3 |
| 82 | A1'L4C1L2B1 |
| 83 | A1'L4C1L2B1' |
| 84 | A1'L4C1L2B2 |
| 85 | A1'L4C1L2B3 |
| 86 | A1'L4C1'L1B3 |
| 87 | A1'L4C1'L1'B3 |
| 88 | A1'L4C1'L2B1 |
| 89 | A1'L4C1'L2B1' |
| 90 | A1'L4C1'L2B2 |
| 91 | A1'L4C1'L2B3 |
| 92 | A1'L4C2L1B3 |
| 93 | A1'L4C2L1'B3 |
| 94 | A1'L4C2L2B1 |
| 95 | A1'L4C2L2B1' |
| 96 | A1'L4C2L2B2 |
| 97 | A1'L4C2L2B3 |
| 98 | A1'L4C3L1B1 |
| 99 | A1'L4C3L1B1' |
| 100 | A1'L4C3L1B2 |
| 101 | A1'L4C3L1B3 |
| 102 | A1'L4C3L1'B1 |
| 103 | A1'L4C3L1'B1' |
| 104 | A1'L4C3L1'B2 |
| 105 | A1'L4C3L1'B3 |
| 106 | A1'L4C3L2B1 |
| 107 | A1'L4C3L2B1' |
| 108 | A1'L4C3L2B2 |
| 109 | A1'L4C3L2B3 |
| 110 | A1'L5C1L1B1 |
| 111 | A1'L5C1L1B1' |

TABLE 1-continued

Exemplary Compounds within the Present Invention.

| Formula No. | Formula |
|---|---|
| 112 | A1'L5C1L1B2 |
| 113 | A1'L5C1L1B3 |
| 114 | A1'L5C1L1'B1 |
| 115 | A1'L5C1L1'B1' |
| 116 | A1'L5C1L1'B2 |
| 117 | A1'L5C1L1'B3 |
| 118 | A1'L5C1L2B1 |
| 119 | A1'L5C1L2B1' |
| 120 | A1'L5C1L2B2 |
| 121 | A1'L5C1L2B3 |
| 122 | A1'L5C1'L1B1 |
| 123 | A1'L5C1'L1B1' |
| 124 | A1'L5C1'L1B2 |
| 125 | A1'L5C1'L1B3 |
| 126 | A1'L5C1'L1'B1 |
| 127 | A1'L5C1'L1'B1' |
| 128 | A2L4C1L1B4 |
| 129 | A2L4C1L1'B4 |
| 130 | A2L4C1L2B4 |
| 131 | A2L4C1'L1B4 |
| 132 | A2L4C1'L1'B4 |
| 133 | A2L4C1'L2B4 |
| 134 | A2L4C2L1B4 |
| 135 | A2L4C2L1'B4 |
| 136 | A2L4C2L2B4 |
| 137 | A2L4C3L1B4 |
| 138 | A2L4C3L1'B4 |
| 139 | A2L4C3L2B4 |
| 140 | A2L5C1L1B4 |
| 141 | A2L5C1L1'B4 |
| 142 | A2L5C1L2B4 |
| 143 | A2L5C1'L1B4 |
| 144 | A2L5C1'L1'B4 |
| 145 | A2L5C1'L2B4 |
| 146 | A2L5C2L1B4 |
| 147 | A2L5C2L1'B4 |
| 148 | A2L5C2L2B4 |
| 149 | A2L5C3L1B4 |
| 150 | A2L5C3L1'B4 |
| 151 | A2L5C3L2B4 |
| 152 | A1L4C3L1B4 |
| 153 | A1L4C3L1'B4 |
| 154 | A1L4C3L2B4 |
| 155 | A1L5C3L1B4 |
| 156 | A1L5C3L1'B4 |
| 157 | A1L5C3L2B4 |
| 158 | A1L4C4L2B1 |
| 159 | A1L4C4L2B1' |
| 160 | A1L4C4L2B2 |
| 161 | A1L4C4L2B3 |
| 162 | A1L5C4L2B1 |
| 163 | A1L5C4L2B1' |
| 164 | A1L5C4L2B2 |
| 165 | A1L5C4L2B3 |
| 166 | A1'L4C4L2B1 |
| 167 | A1'L4C4L2B1' |
| 168 | A1'L4C4L2B2 |
| 169 | A1'L4C4L2B3 |
| 170 | A2L4C4L2B4 |
| 171 | A2L5C4L2B4 |
| 172 | A1L4C4L2B4 |
| 173 | A1L5C4L2B4 |
| 174 | A1L4C4L2'B1 |
| 175 | A1L4C4L2'B1' |
| 176 | A1L4C4L2'B2 |
| 177 | A1L4C4L2'B3 |
| 178 | A1L5C4L2'B1 |
| 179 | A1L5C4L2'B1' |
| 180 | A1L5C4L2'B2 |
| 181 | A1L5C4L2'B3 |
| 182 | A1'L4C4L2'B1 |
| 183 | A1'L4C4L2'B1' |
| 184 | A1'L4C4L2'B2 |
| 185 | A1'L4C4L2'B3 |
| 186 | A2L4C4L2'B4 |
| 187 | A2L5C4L2'B4 |
| 188 | A1L4C4L2'B4 |
| 189 | A1L5C4L2'B4 |
| 190 | A1L4C1L2B1 |
| 191 | A1L4C1L2B1' |
| 192 | A1L4C1L2B2 |
| 193 | A1L4C1L2B3 |
| 194 | A1L4C1'L2B1 |
| 195 | A1L4C1'L2B1' |
| 196 | A1L4C1'L2B2 |
| 197 | A1L4C1'L2B3 |
| 198 | A1L4C2L2B1 |
| 199 | A1L4C2L2B1' |
| 200 | A1L4C2L2B2 |
| 201 | A1L4C2L2B3 |
| 202 | A1L5C1L2B1 |
| 203 | A1L5C1L2B1' |
| 204 | A1L5C1L2B2 |
| 205 | A1L5C1L2B3 |
| 206 | A1L5C1'L2B1 |
| 207 | A1L5C1'L2B1' |
| 208 | A1L5C1'L2B2 |
| 209 | A1L5C1'L2B3 |
| 210 | A1L5C2L2B1 |
| 211 | A1L5C2L2B1' |
| 212 | A1L5C2L2B2 |
| 213 | A1L5C2L2B3 |
| 214 | A1'L4C1L2B1 |
| 215 | A1'L4C1L2B1' |
| 216 | A1'L4C1L2B2 |
| 217 | A1'L4C1L2B3 |
| 218 | A1'L4C1'L2B1 |
| 219 | A1'L4C1'L2B1' |
| 220 | A1'L4C1'L2B2 |
| 221 | A1'L4C1'L2B3 |
| 222 | A1'L4C2L2B1 |
| 223 | A1'L4C2L2B1' |
| 224 | A1'L4C2L2B2 |
| 225 | A1'L4C2L2B3 |
| 226 | A1'L5C1L2B1 |
| 227 | A1'L5C1L2B1' |
| 228 | A1'L5C1L2B2 |
| 229 | A1'L5C1L2B3 |
| 230 | A2L4C1L2B4 |
| 231 | A2L4C1'L2B4 |
| 232 | A2L4C2L2B4 |
| 233 | A2L5C1L2B4 |
| 234 | A2L5C1'L2B4 |
| 235 | A2L5C2L2B4 |
| 236 | A1L4C1L2'B1 |
| 237 | A1L4C1L2'B1' |
| 238 | A1L4C1L2'B2 |
| 239 | A1L4C1L2'B3 |
| 240 | A1L4C1'L2'B1 |
| 241 | A1L4C1'L2'B1' |
| 242 | A1L4C1'L2'B2 |
| 243 | A1L4C1'L2'B3 |
| 244 | A1L4C2L2'B1 |
| 245 | A1L4C2L2'B1' |
| 246 | A1L4C2L2'B2 |
| 247 | A1L4C2L2'B3 |
| 248 | A1L5C1L2'B1 |
| 249 | A1L5C1L2'B1' |
| 250 | A1L5C1L2'B2 |
| 251 | A1L5C1L2'B3 |
| 252 | A1L5C1'L2'B1 |
| 253 | A1L5C1'L2'B1' |
| 254 | A1L5C1'L2'B2 |
| 255 | A1L5C1'L2'B3 |
| 256 | A1L5C2L2'B1 |
| 257 | A1L5C2L2'B1' |
| 258 | A1L5C2L2'B2 |
| 259 | A1L5C2L2'B3 |
| 260 | A1'L4C1L2'B1 |
| 261 | A1'L4C1L2'B1' |

TABLE 1-continued

Exemplary Compounds within the Present Invention.

| Formula No. | Formula |
|---|---|
| 262 | A1'L4C1L2'B2 |
| 263 | A1'L4C1L2'B3 |
| 264 | A1'L4C1'L2'B1 |
| 265 | A1'L4C1'L2'B1' |
| 266 | A1'L4C1'L2'B2 |
| 267 | A1'L4C1'L2'B3 |
| 268 | A1'L4C2L2'B1 |
| 269 | A1'L4C2L2'B1' |
| 270 | A1'L4C2L2'B2 |
| 271 | A1'L4C2L2'B3 |
| 272 | A1'L5C1L2'B1 |
| 273 | A1'L5C1L2'B1' |
| 274 | A1'L5C1L2'B2 |
| 275 | A1'L5C1L2'B3 |
| 276 | A2L4C1L2'B4 |
| 277 | A2L4C1'L2'B4 |
| 278 | A2L4C2L2'B4 |
| 279 | A2L5C1L2'B4 |
| 280 | A2L5C1'L2'B4 |
| 281 | A2L5C2L2'B4 |
| 282 | A2L4C4L1B1 |
| 283 | A2L4C4L1B1' |
| 284 | A2L4C4L1B2 |
| 285 | A2L4C4L1B3 |
| 286 | A2L4C4L1'B1 |
| 287 | A2L4C4L1'B1' |
| 288 | A2L4C4L1'B2 |
| 289 | A2L4C4L1'B3 |
| 290 | A2L5C4L1B1 |
| 291 | A2L5C4L1B1' |
| 292 | A2L5C4L1B2 |
| 293 | A2L5C4L1B3 |
| 294 | A2L5C4L1'B1 |
| 295 | A2L5C4L1'B1' |
| 296 | A2L5C4L1'B2 |
| 297 | A2L5C4L1'B3 |
| 298 | A1'L4C4L1B3 |
| 299 | A1'L4C4L1'B3 |
| 300 | A1'L5C1'L1'B2 |
| 301 | A1'L5C1'L1'B3 |
| 302 | A1'L5C1'L2B1 |
| 303 | A1'L5C1'L2B1' |
| 304 | A1'L5C1'L2B2 |
| 305 | A1'L5C1'L2B3 |
| 306 | A1'L5C2L1B1 |
| 307 | A1'L5C2L1B1' |
| 308 | A1'L5C2L1B2 |
| 309 | A1'L5C2L1B3 |
| 310 | A1'L5C2L1'B1 |
| 311 | A1'L5C2L1'B1' |
| 312 | A1'L5C2L1'B2 |
| 313 | A1'L5C2L1'B3 |
| 314 | A1'L5C2L2B1 |
| 315 | A1'L5C2L2B1' |
| 316 | A1'L5C2L2B2 |
| 317 | A1'L5C2L2B3 |
| 318 | A1'L5C3L1B1 |
| 319 | A1'L5C3L1B1' |
| 320 | A1'L5C3L1B2 |
| 321 | A1'L5C3L1B3 |
| 322 | A1'L5C3L1'B1 |
| 323 | A1'L5C3L1'B1' |
| 324 | A1'L5C3L1'B2 |
| 325 | A1'L5C3L1'B3 |
| 326 | A1'L5C3L2B1 |
| 327 | A1'L5C3L2B1' |
| 328 | A1'L5C3L2B2 |
| 329 | A1'L5C3L2B3 |
| 330 | A2L4C1L1B1 |
| 331 | A2L4C1L1B1' |
| 332 | A2L4C1L1B2 |
| 333 | A2L4C1L1B3 |
| 334 | A2L4C1L1'B1 |
| 335 | A2L4C1L1'B1' |
| 336 | A2L4C1L1'B2 |
| 337 | A2L4C1L1'B3 |
| 338 | A2L4C1L2B1 |
| 339 | A2L4C1L2B1' |
| 340 | A2L4C1L2B2 |
| 341 | A2L4C1L2B3 |
| 342 | A2L4C1'L1B1 |
| 343 | A2L4C1'L1B1' |
| 344 | A2L4C1'L1B2 |
| 345 | A2L4C1'L1B3 |
| 346 | A2L4C1'L1'B1 |
| 347 | A2L4C1'L1'B1' |
| 348 | A2L4C1'L1'B2 |
| 349 | A2L4C1'L1'B3 |
| 350 | A2L4C1'L2B1 |
| 351 | A2L4C1'L2B1' |
| 352 | A2L4C1'L2B2 |
| 353 | A2L4C1'L2B3 |
| 354 | A2L4C2L1B1 |
| 355 | A2L4C2L1B1' |
| 356 | A2L4C2L1B2 |
| 357 | A2L4C2L1B3 |
| 358 | A2L4C2L1'B1 |
| 359 | A2L4C2L1'B1' |
| 360 | A2L4C2L1'B2 |
| 361 | A2L4C2L1'B3 |
| 362 | A2L4C2L2B1 |
| 363 | A2L4C2L2B1' |
| 364 | A2L4C2L2B2 |
| 365 | A2L4C2L2B3 |
| 366 | A2L4C3L1B1 |
| 367 | A2L4C3L1B1' |
| 368 | A2L4C3L1B2 |
| 369 | A2L4C3L1B3 |
| 370 | A2L4C3L1'B1 |
| 371 | A2L4C3L1'B1' |
| 372 | A2L4C3L1'B2 |
| 373 | A2L4C3L1'B3 |
| 374 | A2L4C3L2B1 |
| 375 | A2L4C3L2B1' |
| 376 | A2L4C3L2B2 |
| 377 | A2L4C3L2B3 |
| 378 | A2L5C1L1B1 |
| 379 | A2L5C1L1B1' |
| 380 | A2L5C1L1B2 |
| 381 | A2L5C1L1B3 |
| 382 | A2L5C1L1'B1 |
| 383 | A2L5C1L1'B1' |
| 384 | A2L5C1L1'B2 |
| 385 | A2L5C1L1'B3 |
| 386 | A2L5C1L2B1 |
| 387 | A2L5C1L2B1' |
| 388 | A2L5C1L2B2 |
| 389 | A2L5C1L2B3 |
| 390 | A2L5C1'L1B1 |
| 391 | A2L5C1'L1B1' |
| 392 | A2L5C1'L1B2 |
| 393 | A2L5C1'L1B3 |
| 394 | A2L5C1'L1'B1 |
| 395 | A2L5C1'L1'B1' |
| 396 | A2L5C1'L1'B2 |
| 397 | A2L5C1'L1'B3 |
| 398 | A2L5C1'L2B1 |
| 399 | A2L5C1'L2B1' |
| 400 | A2L5C1'L2B2 |
| 401 | A2L5C1'L2B3 |
| 402 | A2L5C2L1B1 |
| 403 | A2L5C2L1B1' |
| 404 | A2L5C2L1B2 |
| 405 | A2L5C2L1B3 |
| 406 | A2L5C2L1'B1 |
| 407 | A2L5C2L1'B1' |
| 408 | A2L5C2L1'B2 |
| 409 | A2L5C2L1'B3 |
| 410 | A2L5C2L2B1 |
| 411 | A2L5C2L2B1' |

TABLE 1-continued

Exemplary Compounds within the Present Invention.

| Formula No. | Formula |
|---|---|
| 412 | A2L5C2L2B2 |
| 413 | A2L5C2L2B3 |
| 414 | A2L5C3L1B1 |
| 415 | A2L5C3L1B1' |
| 416 | A2L5C3L1B2 |
| 417 | A2L5C3L1B3 |
| 418 | A2L5C3L1'B1 |
| 419 | A2L5C3L1'B1' |
| 420 | A2L5C3L1'B2 |
| 421 | A2L5C3L1'B3 |
| 422 | A2L5C3L2B1 |
| 423 | A2L5C3L2B1' |
| 424 | A2L5C3L2B2 |
| 425 | A2L5C3L2B3 |
| 426 | A1'L4C3L1B4 |
| 427 | A1'L4C3L1'B4 |
| 428 | A1'L4C3L2B4 |
| 429 | A1'L5C3L1B4 |
| 430 | A1'L5C3L1'B4 |
| 431 | A1'L5C3L2B4 |
| 432 | A1L4C1L2B4 |
| 433 | A1L4C1'L2B4 |
| 434 | A1L4C2L2B4 |
| 435 | A1L5C1L2B4 |
| 436 | A1L5C1'L2B4 |
| 437 | A1L5C2L2B4 |
| 438 | A1'L4C1L2B4 |
| 439 | A1'L4C1'L2B4 |
| 440 | A1'L4C2L2B4 |
| 441 | A1'L5C1L2B4 |
| 442 | A1'L5C1'L2B4 |
| 443 | A1'L5C2L2B4 |
| 444 | A1L5C1L1B4 |
| 445 | A1L5C1L1'B4 |
| 446 | A1L5C1'L1B4 |
| 447 | A1L5C1'L1'B4 |
| 448 | A1L5C2L1B4 |
| 449 | A1L5C2L1'B4 |
| 450 | A1'L5C1L1B4 |
| 451 | A1'L5C1L1'B4 |
| 452 | A1'L5C1'L1B4 |
| 453 | A1'L5C1'L1'B4 |
| 454 | A1'L5C2L1B4 |
| 455 | A1'L5C2L1'B4 |
| 456 | A1'L5C4L2B1 |
| 457 | A1'L5C4L2B1' |
| 458 | A1'L5C4L2B2 |
| 459 | A1'L5C4L2B3 |
| 460 | A2L4C4L2B1 |
| 461 | A2L4C4L2B1' |
| 462 | A2L4C4L2B2 |
| 463 | A2L4C4L2B3 |
| 464 | A2L5C4L2B1 |
| 465 | A2L5C4L2B1' |
| 466 | A2L5C4L2B2 |
| 467 | A2L5C4L2B3 |
| 468 | A1'L4C4L2B4 |
| 469 | A1'L5C4L2B4 |
| 470 | A1'L5C4L2'B1 |
| 471 | A1'L5C4L2'B1' |
| 472 | A1'L5C4L2'B2 |
| 473 | A1'L5C4L2'B3 |
| 474 | A2L4C4L2'B1 |
| 475 | A2L4C4L2'B1' |
| 476 | A2L4C4L2'B2 |
| 477 | A2L4C4L2'B3 |
| 478 | A2L5C4L2'B1 |
| 479 | A2L5C4L2'B1' |
| 480 | A2L5C4L2'B2 |
| 481 | A2L5C4L2'B3 |
| 482 | A1'L4C4L2'B4 |
| 483 | A1'L5C4L2'B4 |
| 484 | A1'L5C1L2B1 |
| 485 | A1'L5C1L2B1' |
| 486 | A1'L5C1L2B2 |
| 487 | A1'L5C1L2B3 |
| 488 | A1'L5C2L2B1 |
| 489 | A1'L5C2L2B1' |
| 490 | A1'L5C2L2B2 |
| 491 | A1'L5C2L2B3 |
| 492 | A2L4C1L2B1 |
| 493 | A2L4C1L2B1' |
| 494 | A2L4C1L2B2 |
| 495 | A2L4C1L2B3 |
| 496 | A2L4C1'L2B1 |
| 497 | A2L4C1'L2B1' |
| 498 | A2L4C1'L2B2 |
| 499 | A2L4C1'L2B3 |
| 500 | A2L4C2L2B1 |
| 501 | A2L4C2L2B1' |
| 502 | A2L4C2L2B2 |
| 503 | A2L4C2L2B3 |
| 504 | A2L5C1L2B1 |
| 505 | A2L5C1L2B1' |
| 506 | A2L5C1L2B2 |
| 507 | A2L5C1L2B3 |
| 508 | A2L5C1'L2B1 |
| 509 | A2L5C1'L2B1' |
| 510 | A2L5C1'L2B2 |
| 511 | A2L5C1'L2B3 |
| 512 | A2L5C2L2B1 |
| 513 | A2L5C2L2B1' |
| 514 | A2L5C2L2B2 |
| 515 | A2L5C2L2B3 |
| 516 | A1L4C1L2B4 |
| 517 | A1L4C1'L2B4 |
| 518 | A1L4C2L2B4 |
| 519 | A1L5C1L2B4 |
| 520 | A1L5C1'L2B4 |
| 521 | A1L5C2L2B4 |
| 522 | A1'L4C1L2B4 |
| 523 | A1'L4C1'L2B4 |
| 524 | A1'L4C2L2B4 |
| 525 | A1'L5C1L2B4 |
| 526 | A1'L5C1'L2B4 |
| 527 | A1'L5C2L2B4 |
| 528 | A1'L5C1L2'B1 |
| 529 | A1'L5C1L2'B1' |
| 530 | A1'L5C1L2'B2 |
| 531 | A1'L5C1L2'B3 |
| 532 | A1'L5C2L2'B1 |
| 533 | A1'L5C2L2'B1' |
| 534 | A1'L5C2L2'B2 |
| 535 | A1'L5C2L2'B3 |
| 536 | A2L4C1L2'B1 |
| 537 | A2L4C1L2'B1' |
| 538 | A2L4C1L2'B2 |
| 539 | A2L4C1L2'B3 |
| 540 | A2L4C1'L2'B1 |
| 541 | A2L4C1'L2'B1' |
| 542 | A2L4C1'L2'B2 |
| 543 | A2L4C1'L2'B3 |
| 544 | A2L4C2L2'B1 |
| 545 | A2L4C2L2'B1' |
| 546 | A2L4C2L2'B2 |
| 547 | A2L4C2L2'B3 |
| 548 | A2L5C1L2'B1 |
| 549 | A2L5C1L2'B1' |
| 550 | A2L5C1L2'B2 |
| 551 | A2L5C1L2'B3 |
| 552 | A2L5C1'L2'B1 |
| 553 | A2L5C1'L2'B1' |
| 554 | A2L5C1'L2'B2 |
| 555 | A2L5C1'L2'B3 |
| 556 | A2L5C2L2'B1 |
| 557 | A2L5C2L2'B1' |
| 558 | A2L5C2L2'B2 |
| 559 | A2L5C2L2'B3 |
| 560 | A1L4C1L2'B4 |
| 561 | A1L4C1'L2'B4 |

TABLE 1-continued

Exemplary Compounds within the Present Invention.

| Formula No. | Formula |
|---|---|
| 562 | A1L4C2L2'B4 |
| 563 | A1L5C1L2'B4 |
| 564 | A1L5C1'L2'B4 |
| 565 | A1L5C2L2'B4 |
| 566 | A1'L4C1L2'B4 |
| 567 | A1'L4C1'L2'B4 |
| 568 | A1'L4C2L2'B4 |
| 569 | A1'L5C1L2'B4 |
| 570 | A1'L5C1'L2'B4 |
| 571 | A1'L5C2L2'B4 |
| 572 | A2L4C4L1B4 |
| 573 | A2L4C4L1'B4 |
| 574 | A2L5C4L1B4 |
| 575 | A2L5C4L1'B4 |
| 576 | A1'L5C4L1B1 |
| 577 | A1'L5C4L1B1' |
| 578 | A1'L5C4L1B2 |
| 579 | A1'L5C4L1B3 |
| 580 | A1'L5C4L1'B1 |
| 581 | A1'L5C4L1'B1' |
| 582 | A1'L5C4L1'B2 |
| 583 | A1'L5C4L1'B3 |
| 584 | A1'L5C4L1B4 |
| 585 | A1'L5C4L1'B4 |
| 586 | A1L5C4L1B1 |
| 587 | A1L5C4L1B1' |
| 588 | A1L5C4L1B2 |
| 589 | A1L5C4L1B3 |
| 590 | A1L5C4L1'B1 |
| 591 | A1L5C4L1'B1' |
| 592 | A1L5C4L1'B2 |
| 593 | A1L5C4L1'B3 |
| 594 | A1L5C4L1B4 |
| 595 | A1L5C4L1'B4 |
| 596 | A1L4C4L1B3 |
| 597 | A1L4C4L1'B3 |

TABLE 2

Additional Exemplary Compounds within the Present Invention.

Formula 598

Formula 599

TABLE 2-continued

Additional Exemplary Compounds within the Present Invention.

Formula 600

Formula 601

Formula 602

Formula 603

Formula 604

Formula 605

TABLE 2-continued
Additional Exemplary Compounds within the Present Invention.
Formula 606
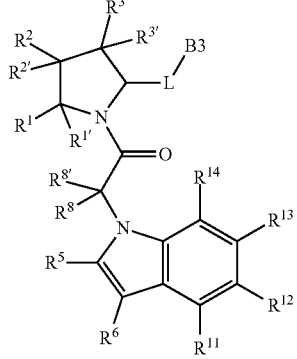
Formula 607
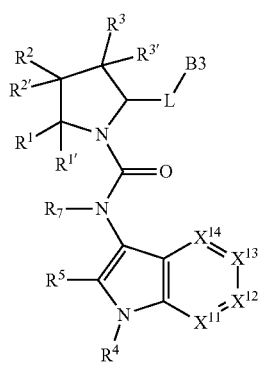
Formula 608
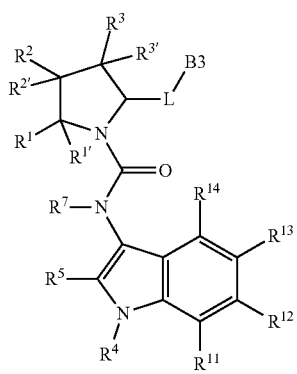
Formula 609
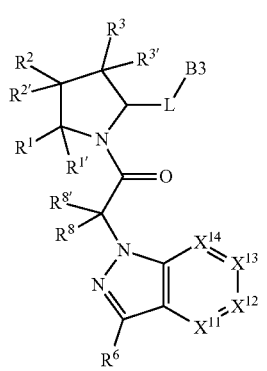
TABLE 2-continued
Additional Exemplary Compounds within the Present Invention.
Formula 610
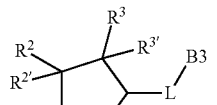
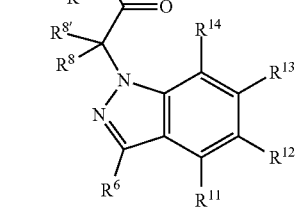
Formula 611
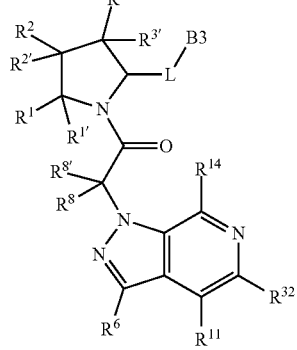
Formula 612
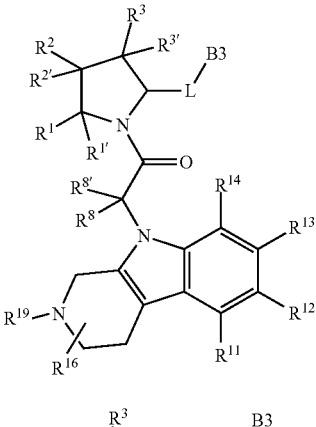
Formula 613
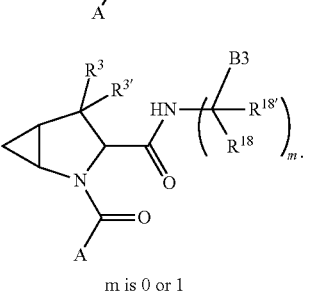
Formula 614
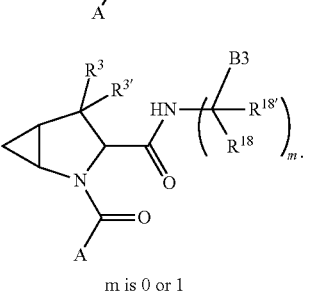
m is 0 or 1

TABLE 2-continued
Additional Exemplary Compounds within the Present Invention.
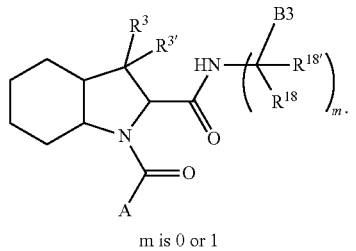
Formula 615
m is 0 or 1
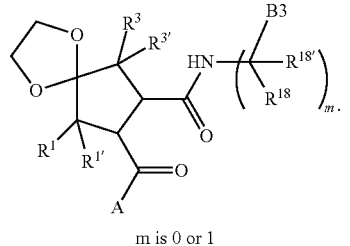
Formula 616
m is 0 or 1
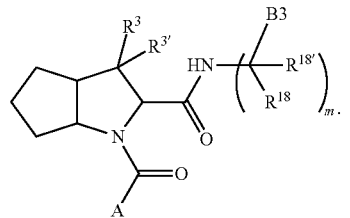
Formula 617
m is 0 or 1
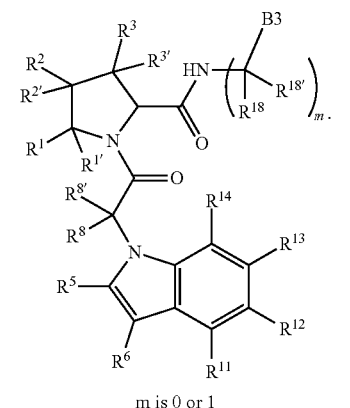
Formula 618
m is 0 or 1
TABLE 2-continued
Additional Exemplary Compounds within the Present Invention.
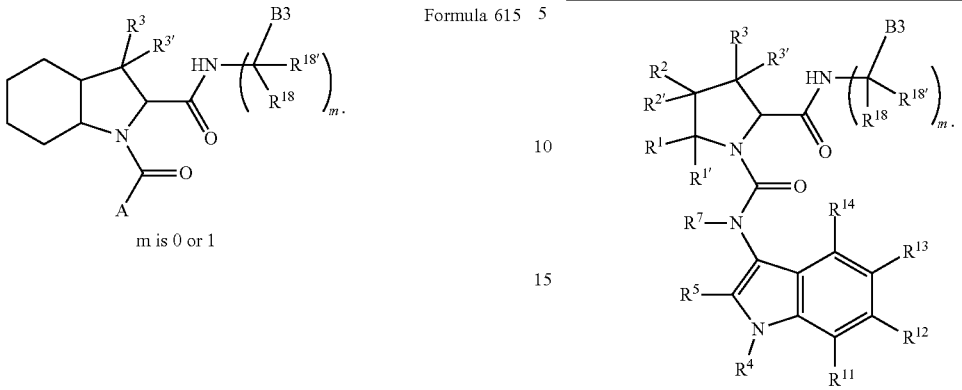
Formula 619
m is 0 or 1
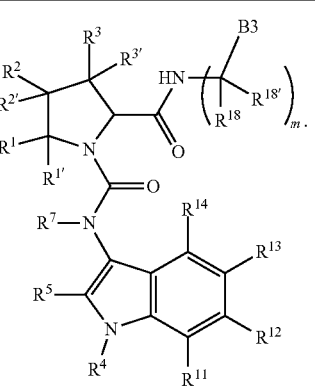
Formula 620
m is 0 or 1
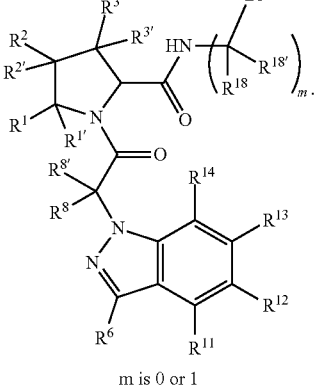
Formula 621
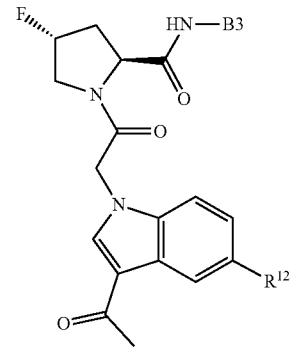
Formula 622

TABLE 2-continued
Additional Exemplary Compounds within the Present Invention.
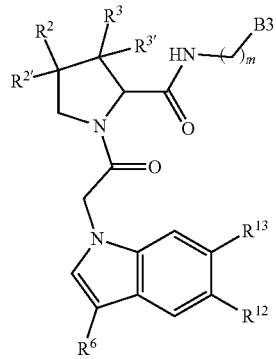
Formula 623
m is 0 or 1
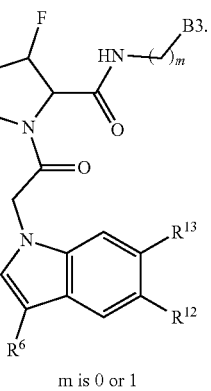
Formula 624
m is 0 or 1
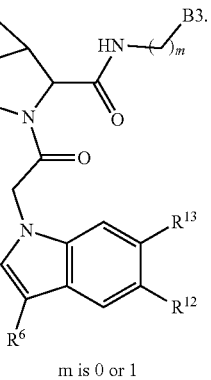
Formula 625
m is 0 or 1
Formula 626
m is 0 or 1
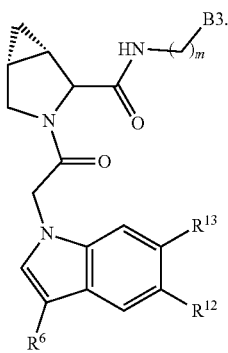
Formula 627
m is 0 or 1
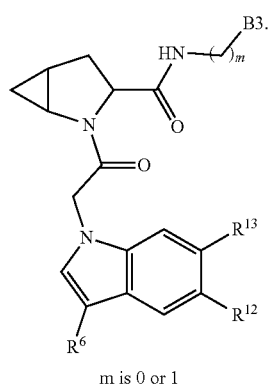
Formula 628
m is 0 or 1
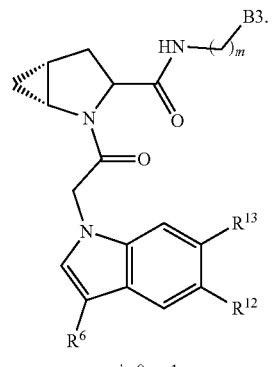
Formula 629
m is 0 or 1
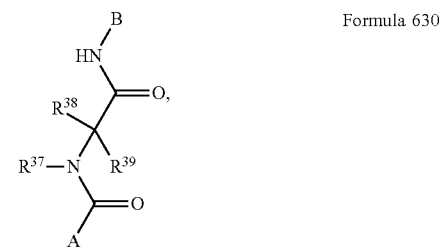
Formula 630

TABLE 2-continued
Additional Exemplary Compounds within the Present Invention.
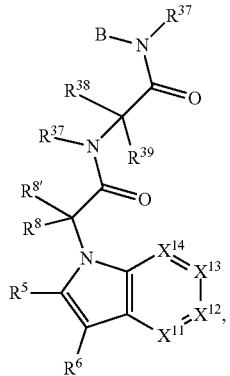
Formula 631
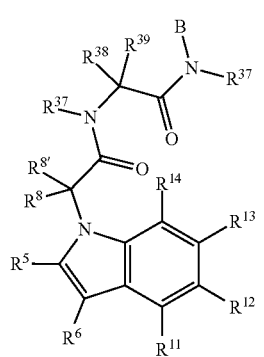
Formula 632
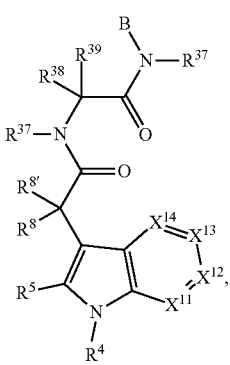
Formula 633
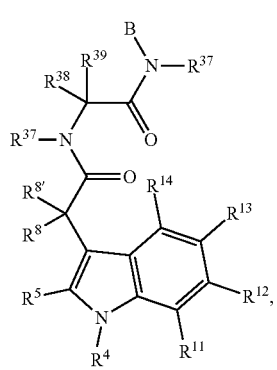
Formula 634
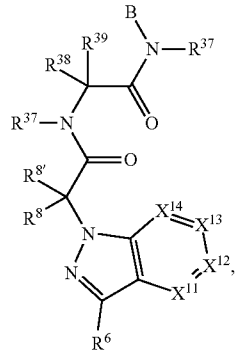
Formula 635
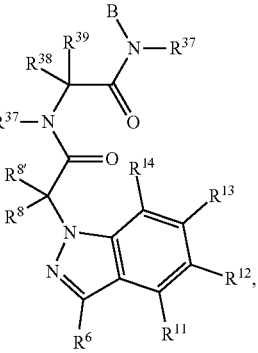
Formula 636
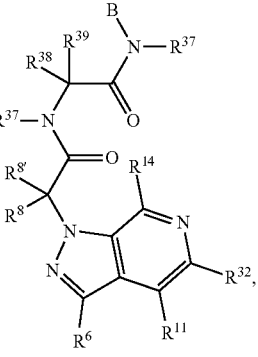
Formula 637
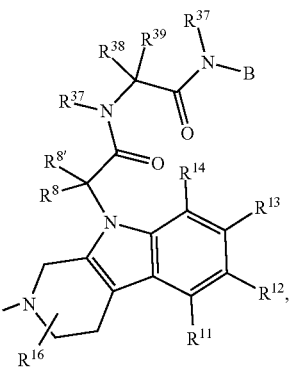
Formula 638

TABLE 2-continued
Additional Exemplary Compounds within the Present Invention.
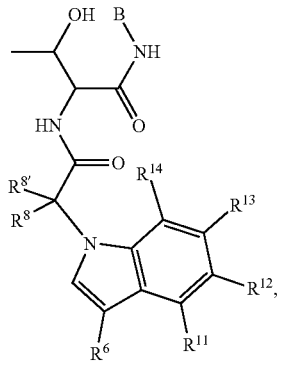
Formula 639
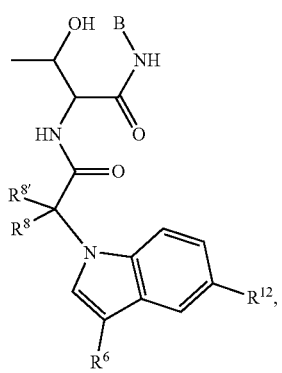
Formula 640
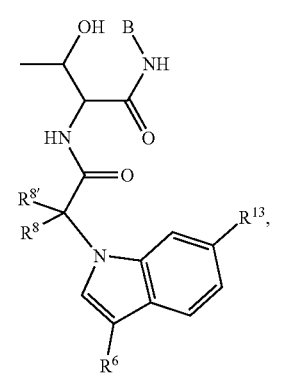
Formula 641
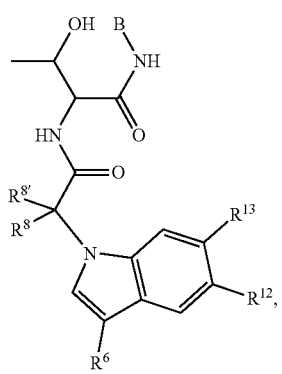
Formula 642
TABLE 2-continued
Additional Exemplary Compounds within the Present Invention.
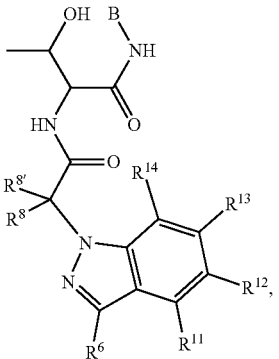
Formula 643
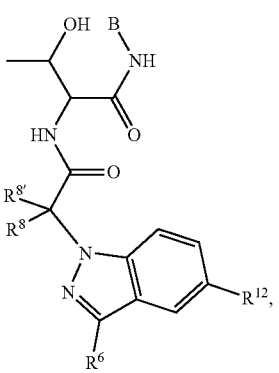
Formula 644
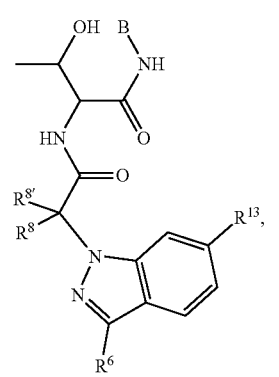
Formula 645
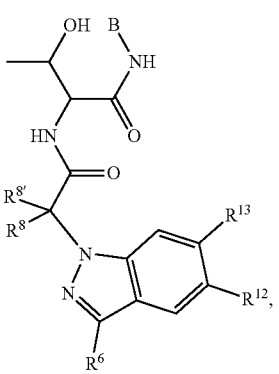
Formula 646

TABLE 2-continued

Additional Exemplary Compounds within the Present Invention.

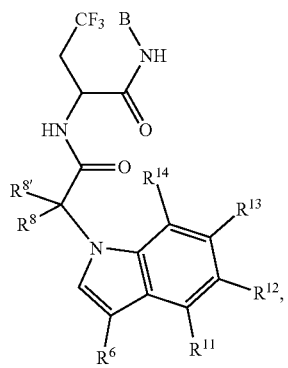

Formula 647

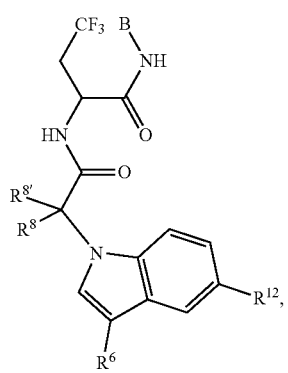

Formula 648

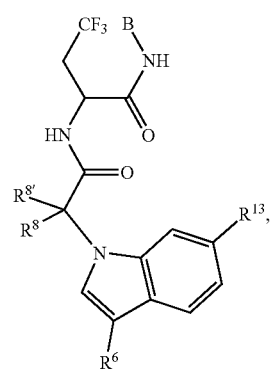

Formula 649

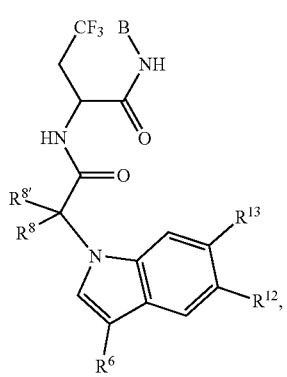

Formula 650

TABLE 2-continued

Additional Exemplary Compounds within the Present Invention.

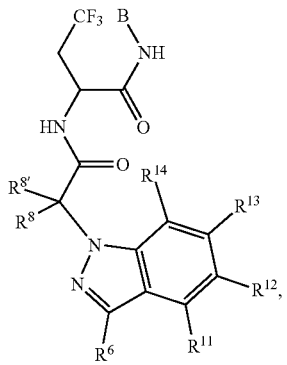

Formula 651

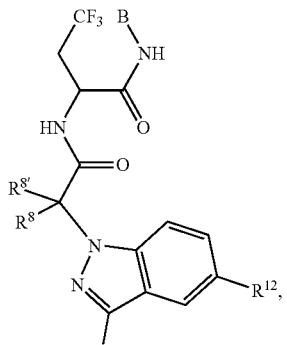

Formula 652

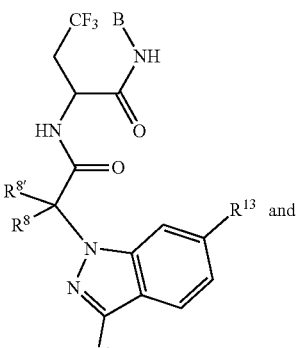

Formula 653 and

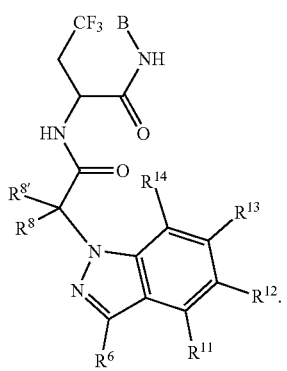

Formula 654

Additionally, the disclosure includes compounds and salts of Formula I, Formula I' and Formula I" pharmaceutically acceptable compositions thereof, and any of their subformulae (2-654) in which at least one of the following conditions is met in the embodiments described below.

The $R^{12}$ and $R^{13}$ Aryl, Heteroaryl, and Heterocycle Substituents

The invention includes a compound of Formula I, Formula I' or Formula I", a pharmaceutically acceptable salt or composition thereof, wherein at least one of $R^{12}$ or $R^{13}$ on the A1 or A2 group is an aryl, heteroaryl, or heterocycle for example, $R^{32}$.

One of $R^{12}$ and $R^{13}$ is selected from $R^{31}$ and the other of $R^{12}$ and $R^{13}$ is replaced from $R^{32}$. In another embodiment, each of $R^{12}$ and $R^{13}$ can be independently selected from $R^{32}$.

$R^{31}$ is selected from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)OR$^9$, $C_1$-$C_6$thioalkyl, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$, each of which $R^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —CONH$_2$ $C_1$-$C_2$haloalkyl, and $C_1$-$C_2$haloalkoxy, and each of which $R^{31}$ is also optionally substituted with one substituent replaced from phenyl and 4- to 7-membered heterocycle containing 1, 2, or 3 heteroatoms independently replaced from N, O, and S; which phenyl or 4- to 7-membered heterocycle is unsubstituted or substituted with one or more substituents independently replaced from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_2$haloalkyl, and $C_1$-$C_2$haloalkoxy;

$R^{32}$ is selected from aryl, heteroaryl; saturated or unsaturated heterocycle; wherein the aryl, heteroaryl, saturated or unsaturated heterocycle ring can be optionally substituted.

Figure 15:
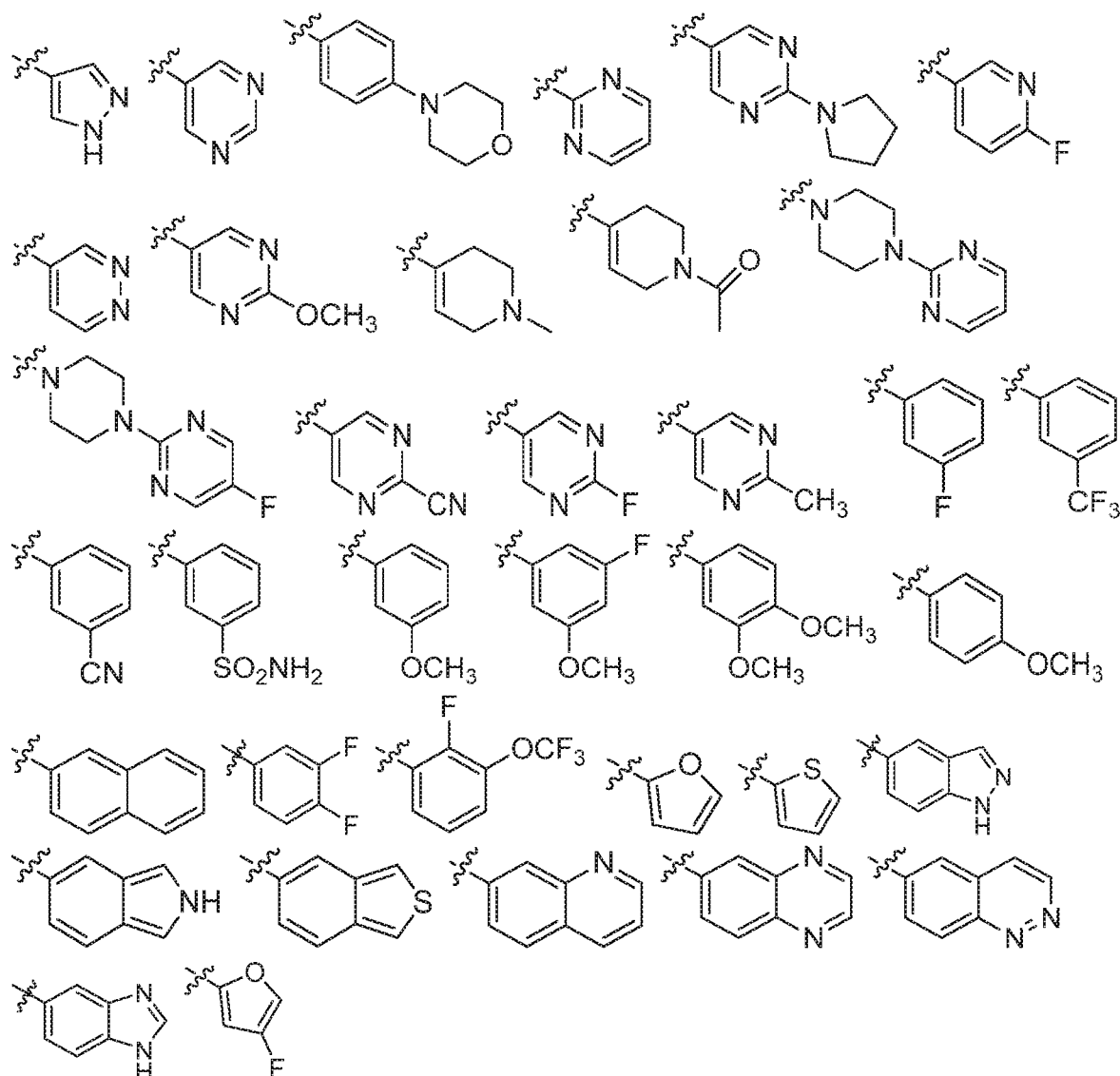
FIG. 15 provides non-limiting embodiments of $R^{32}$.

Non-limiting examples of $R^{32}$ include the moieties of FIG. 15.

In one embodiment, $R^{32}$ is $R^{32'}$.

Figure 16:
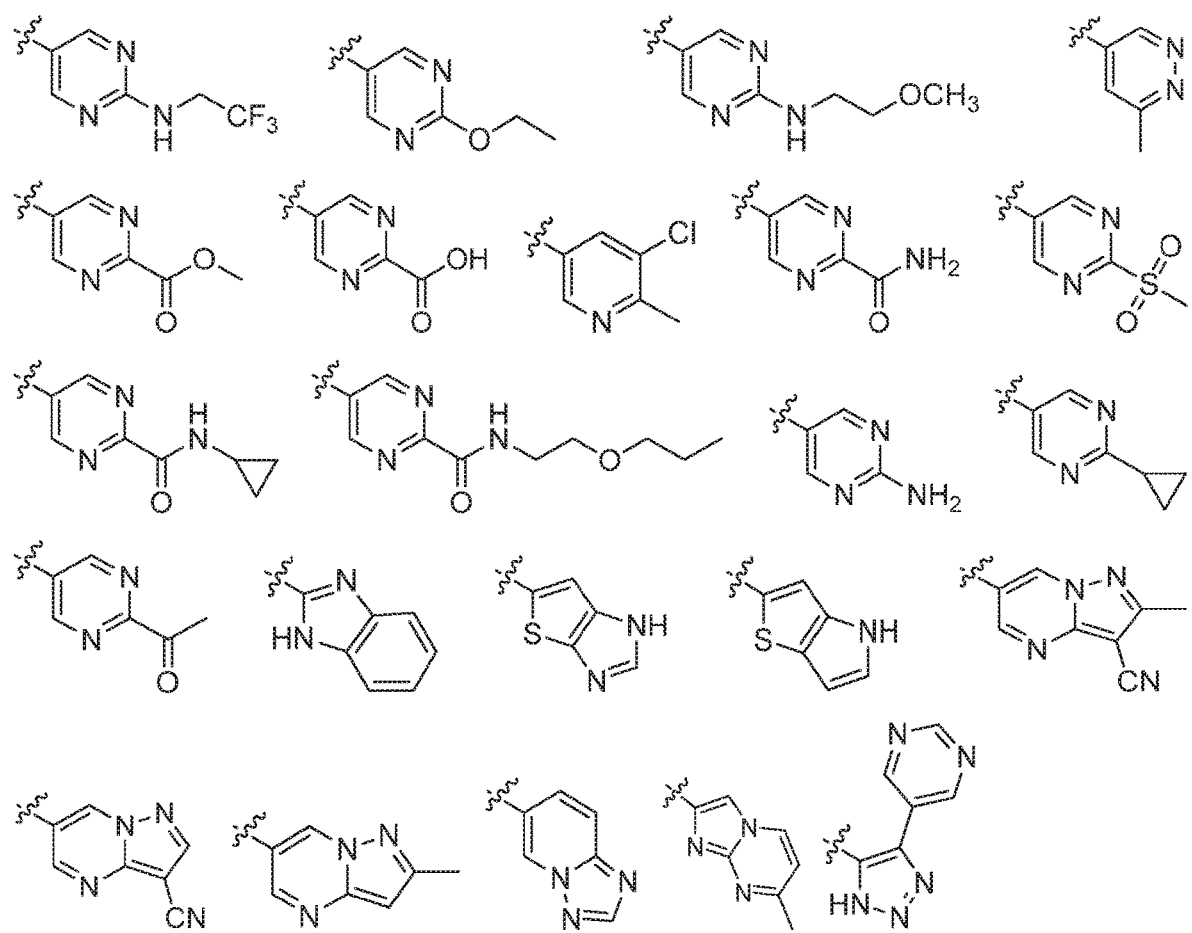
FIG. 16 provides non-limiting specific embodiments of $R^{32'}$.
Figure 17A:
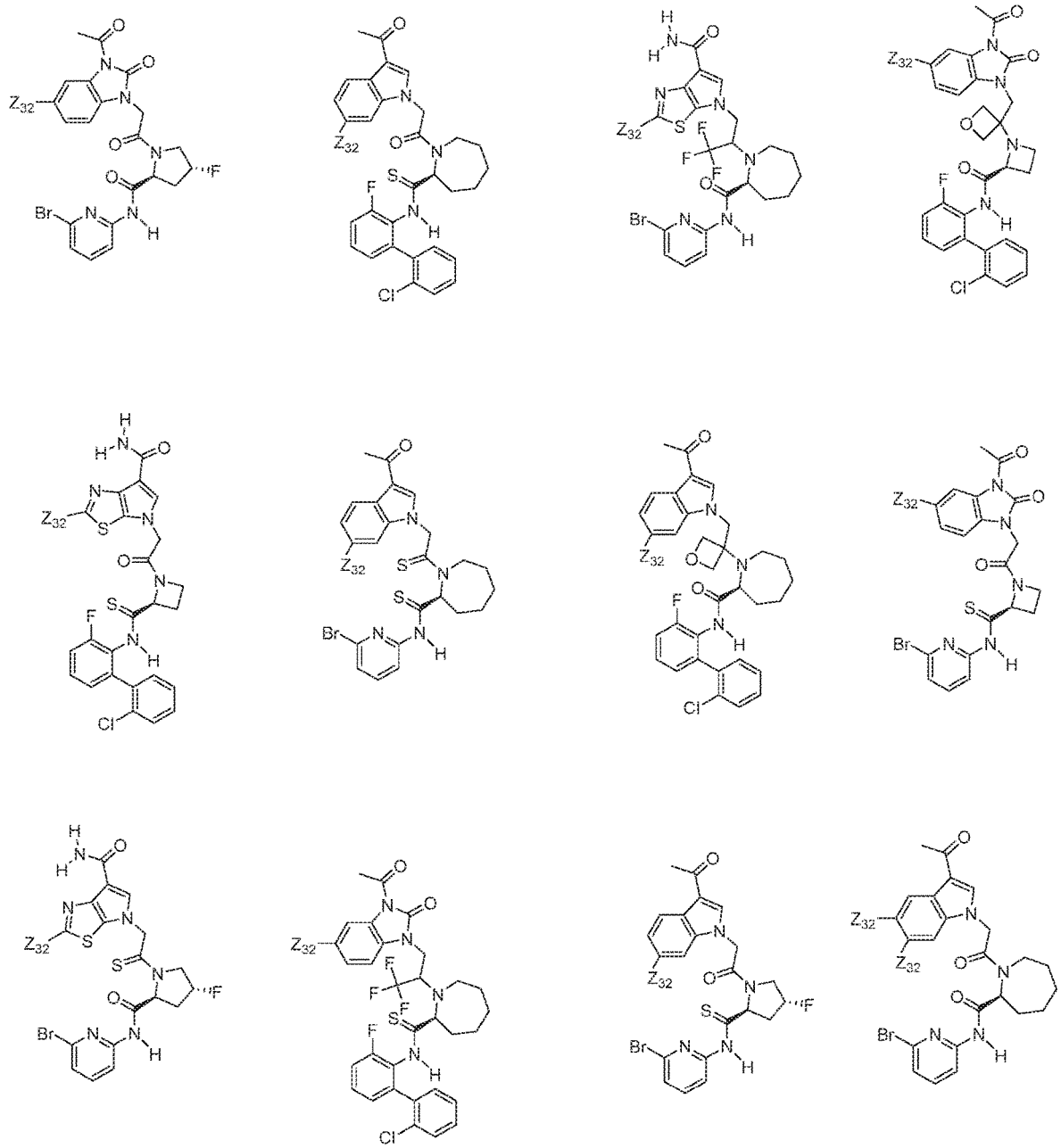
FIGS. 17A, 17B, 17C, 17D, 17E, 17F, 17G, 17H, 17I, 17J, 17K, 17L, 17M, and 17N, provide non-limiting examples of compounds included in the present invention, wherein $Z_{32}$ is the same as $R^{32}$ as used herein.
Figure 17B:
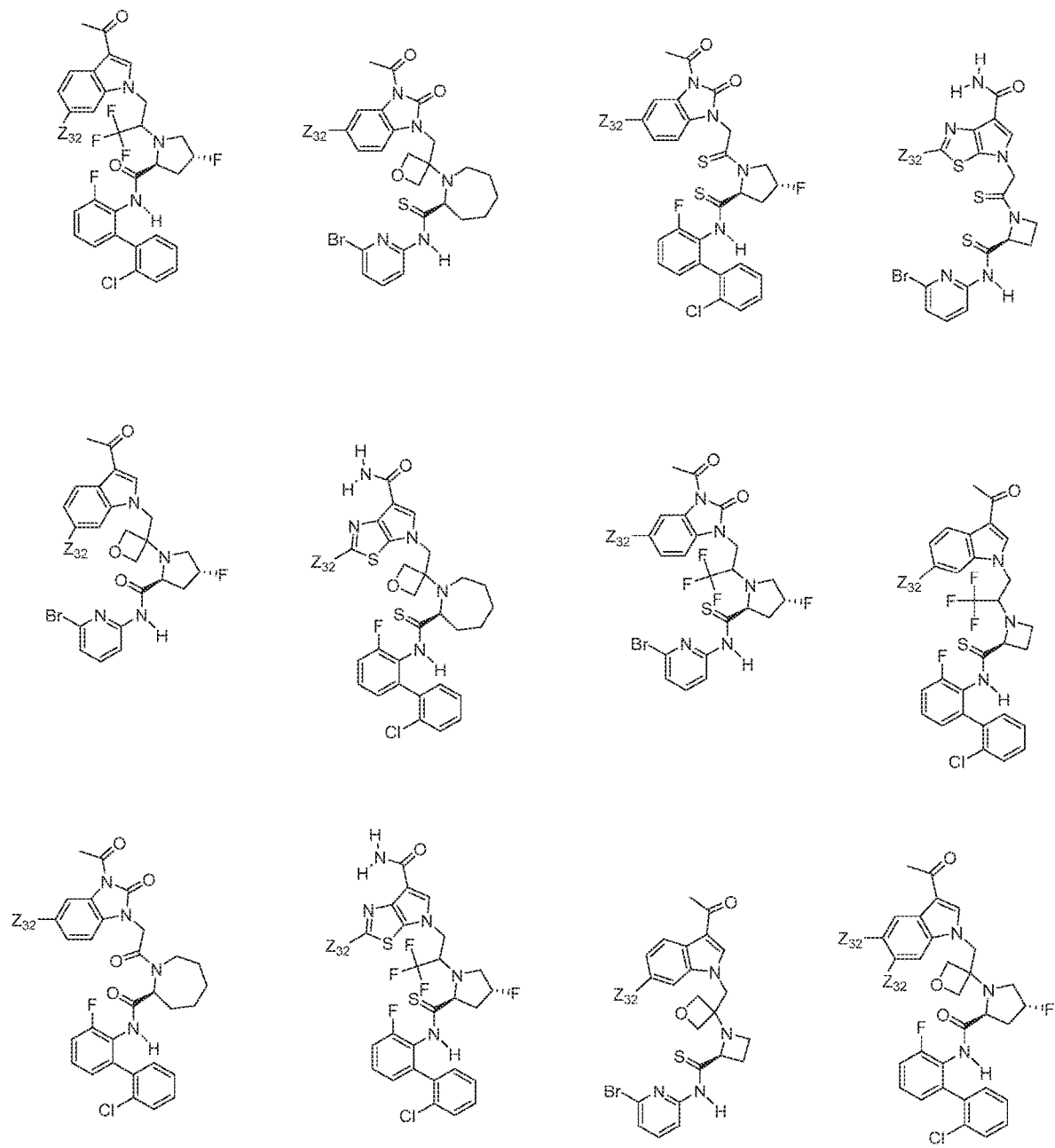
Figure 17C:
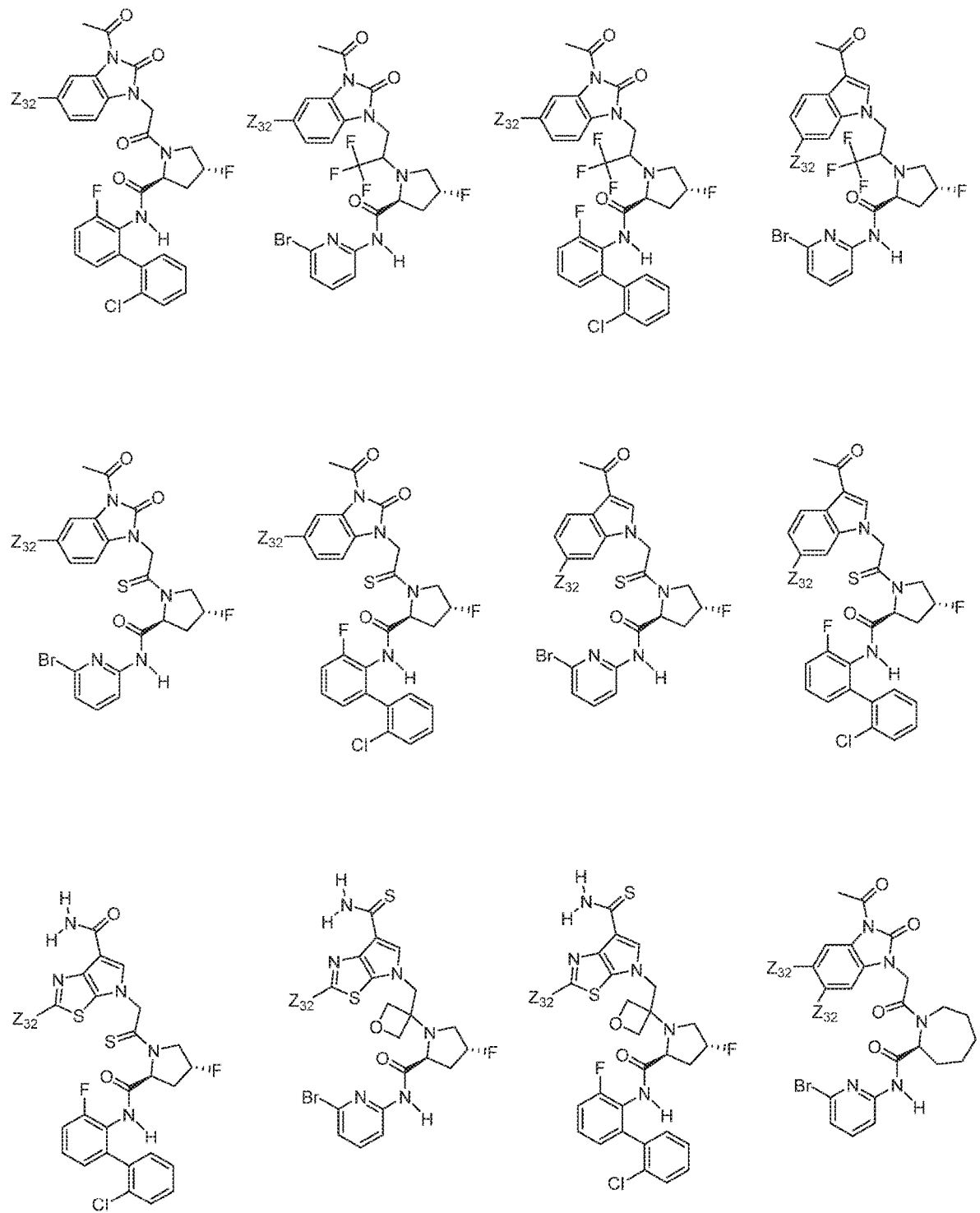
Figure 17D:
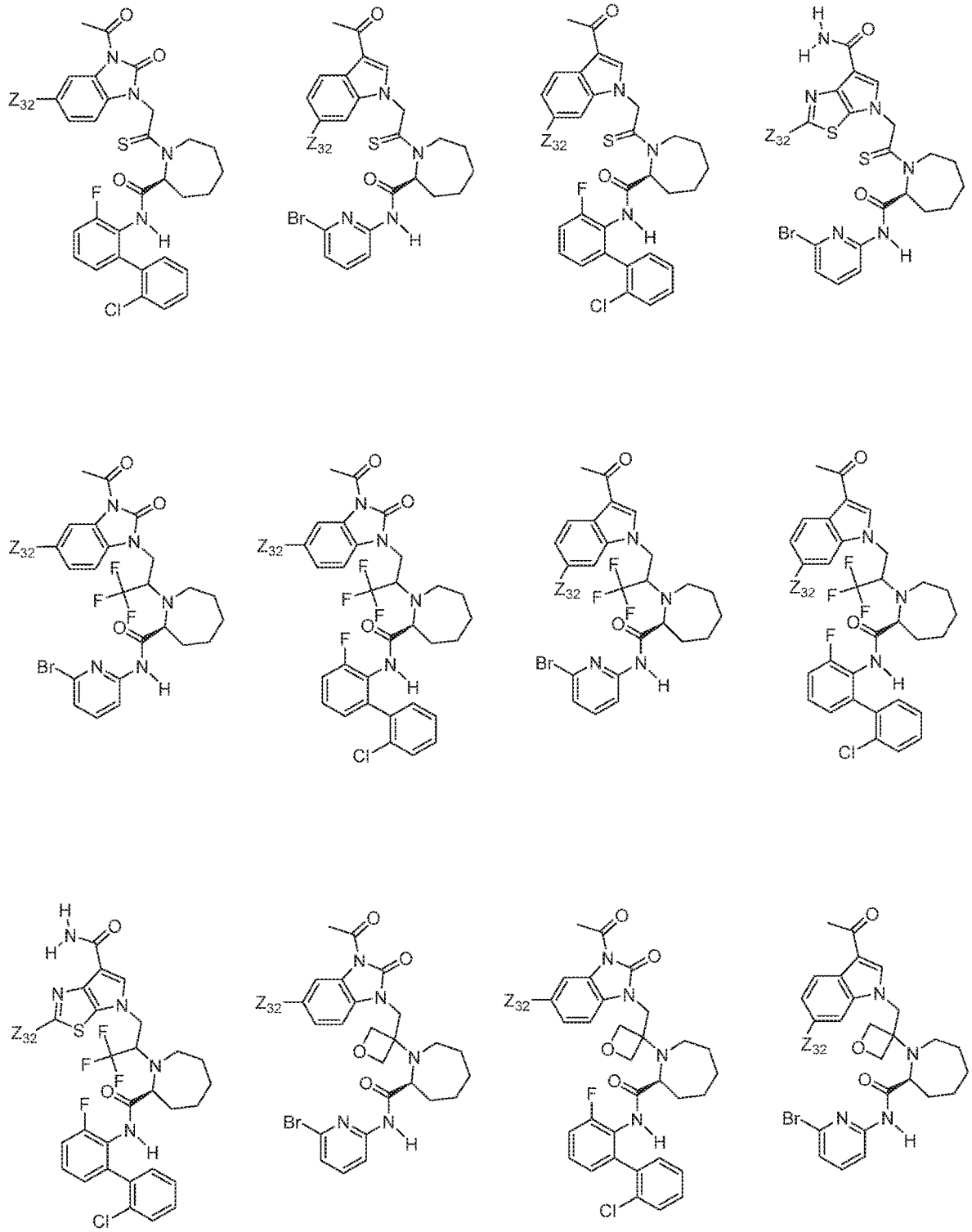
Figure 17E:
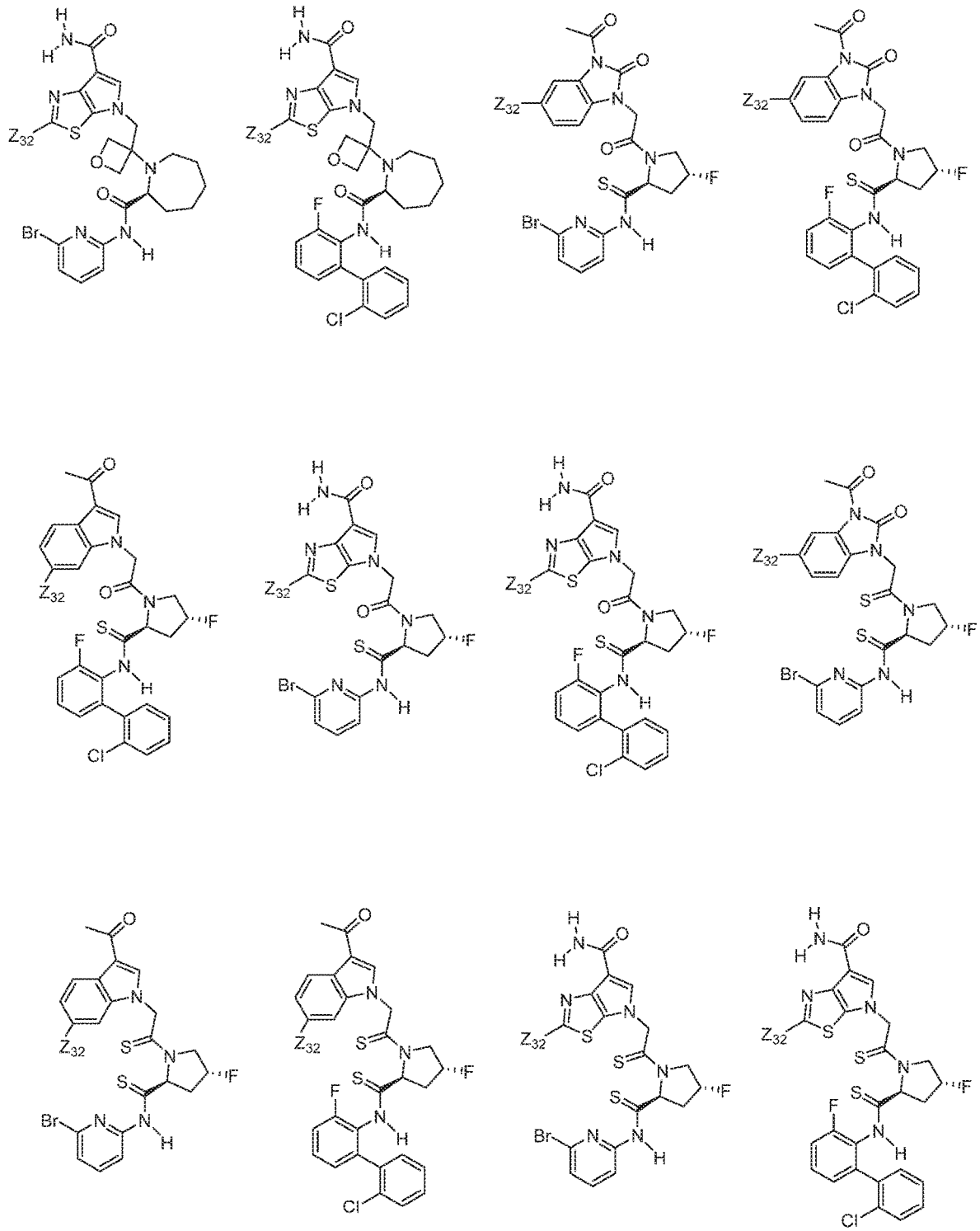
Figure 17F:
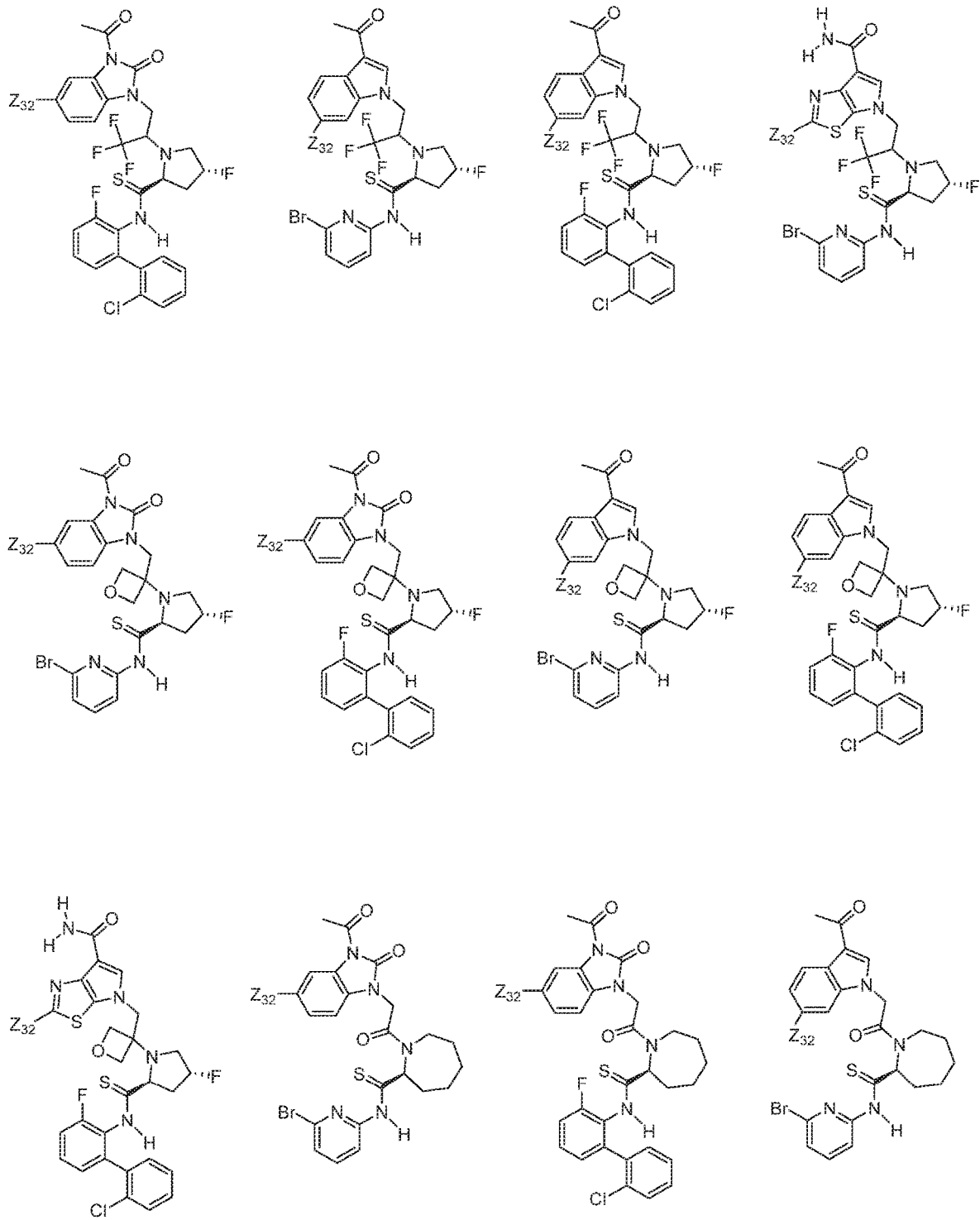
Figure 17G:
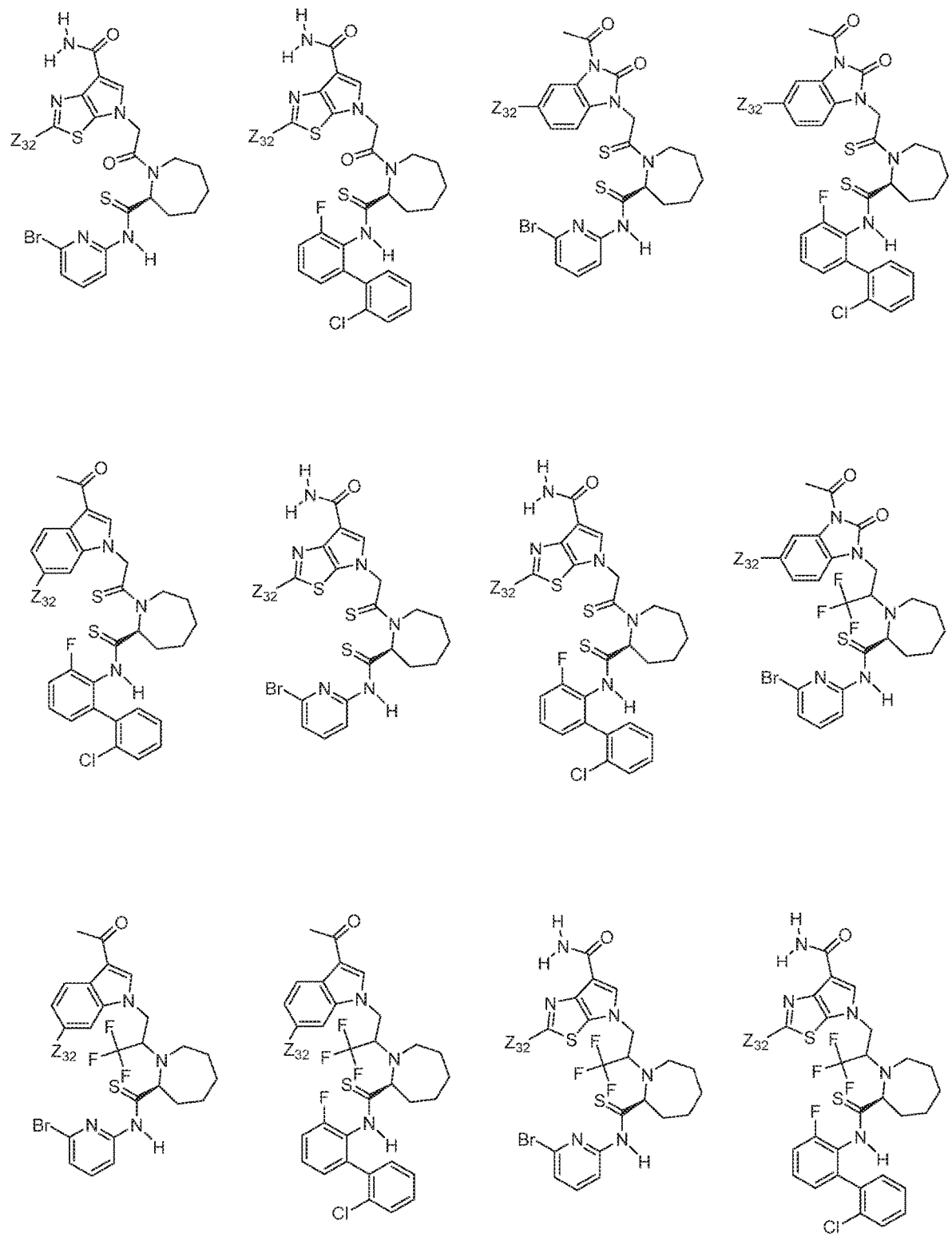
Figure 17H:
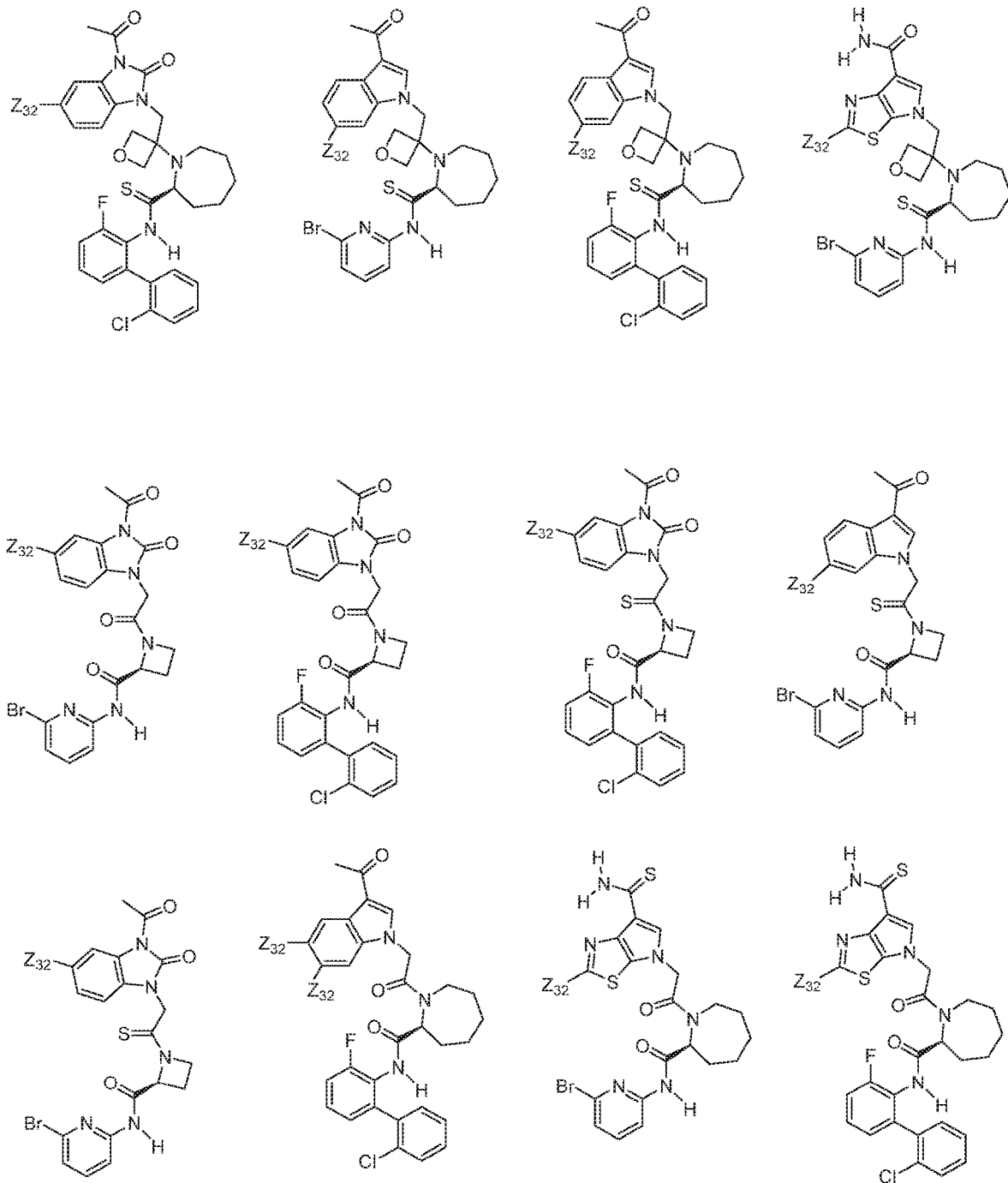
Figure 17I:
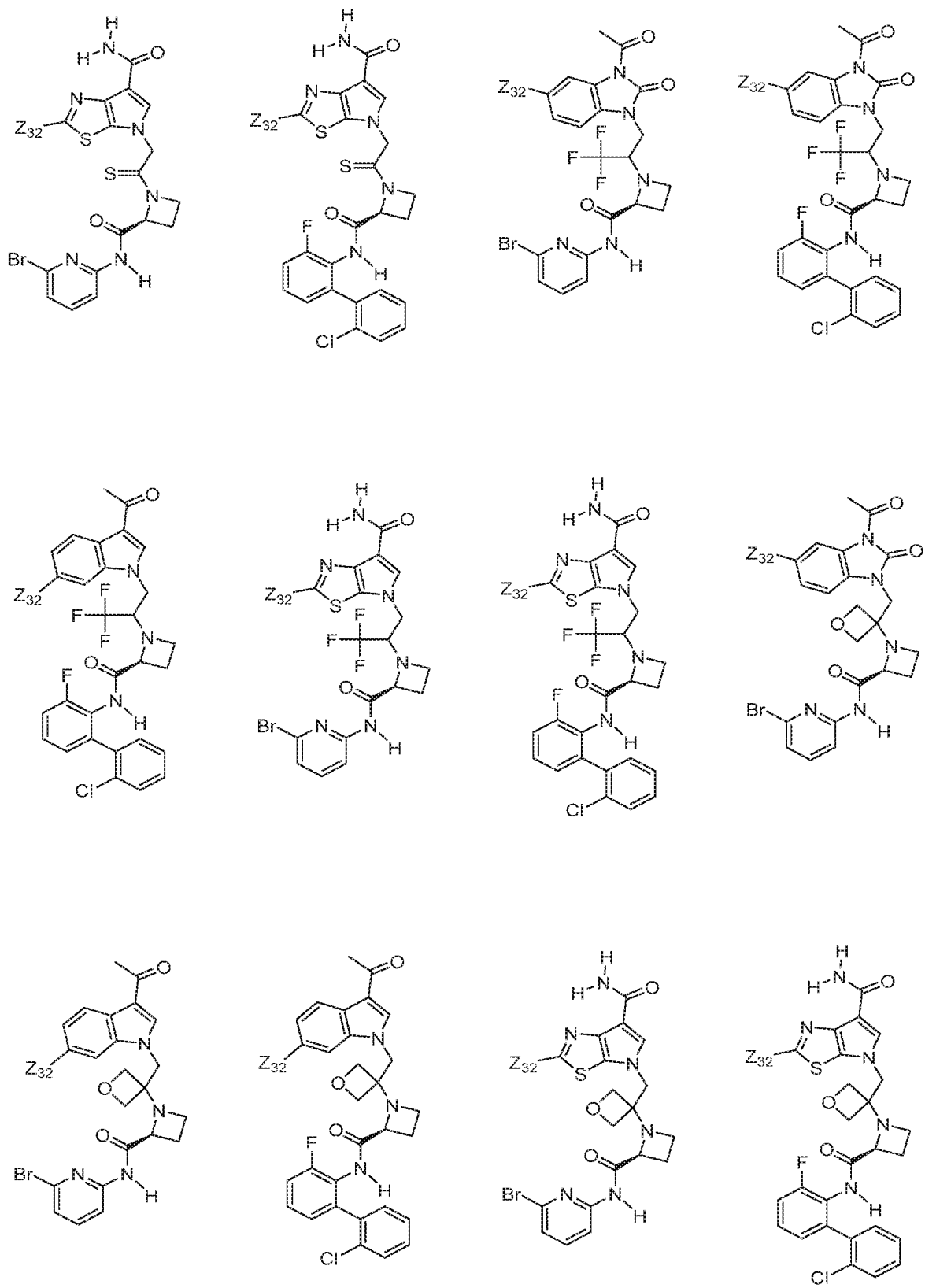
Figure 17J:
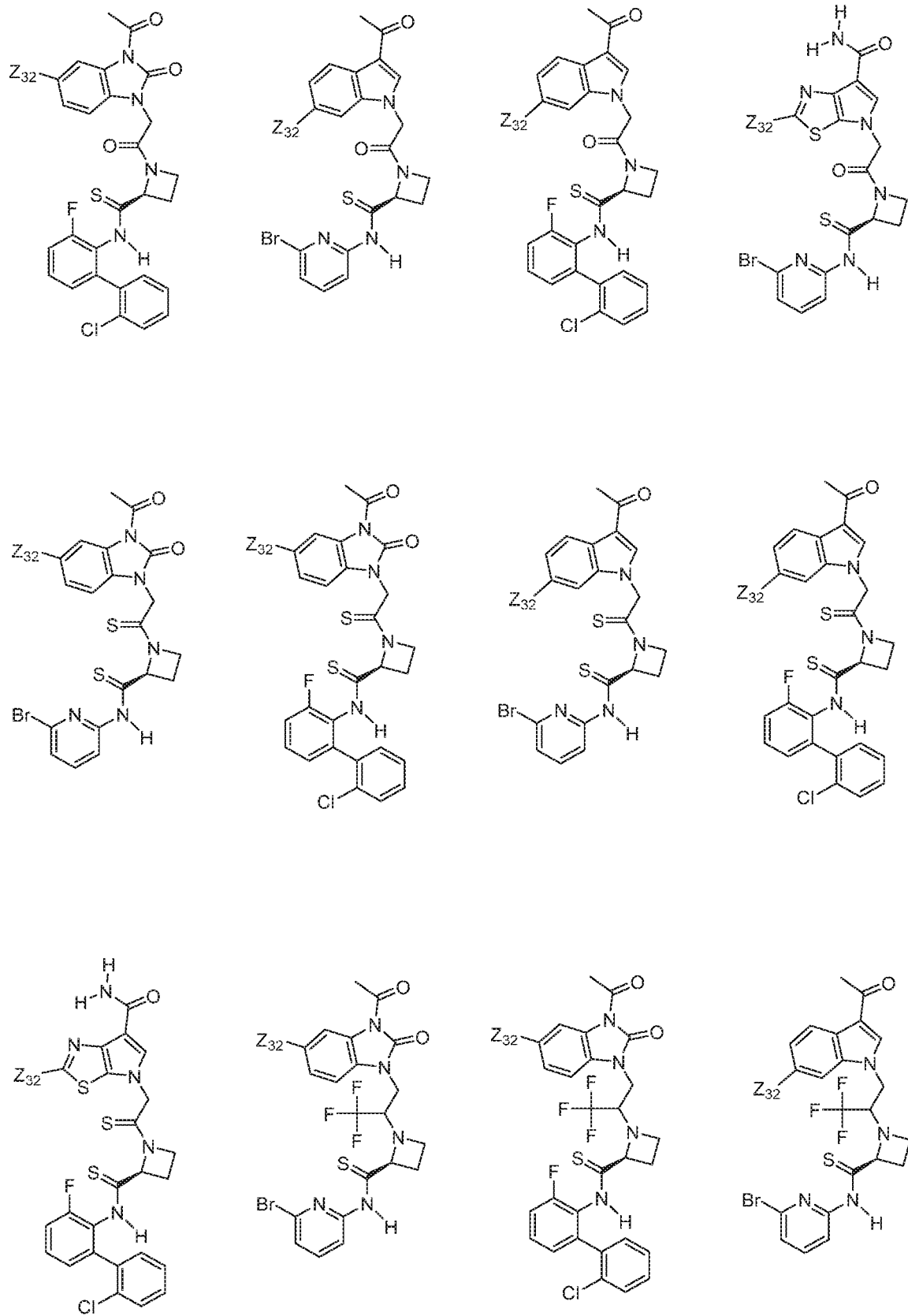
Figure 17K:
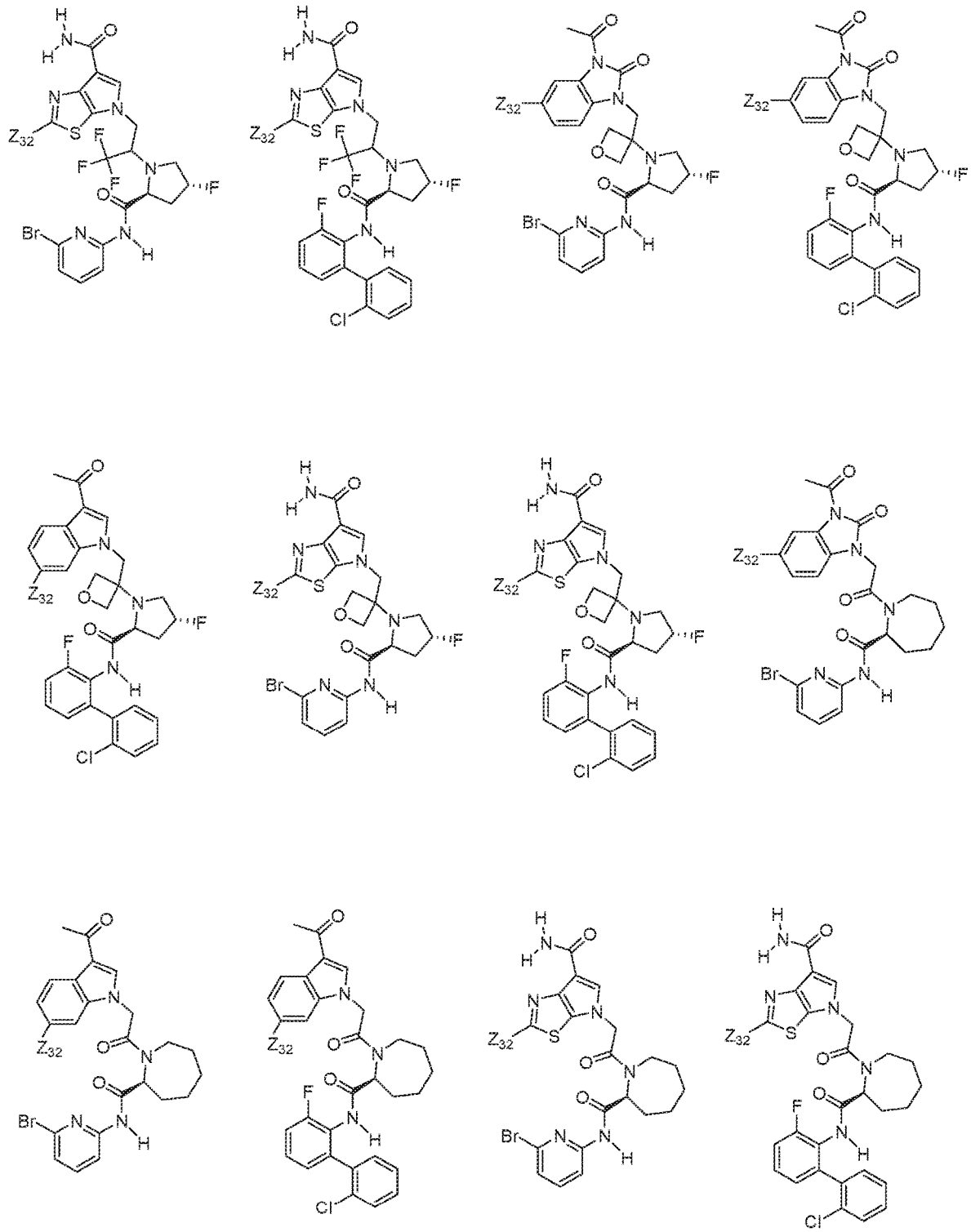
Figure 17L:
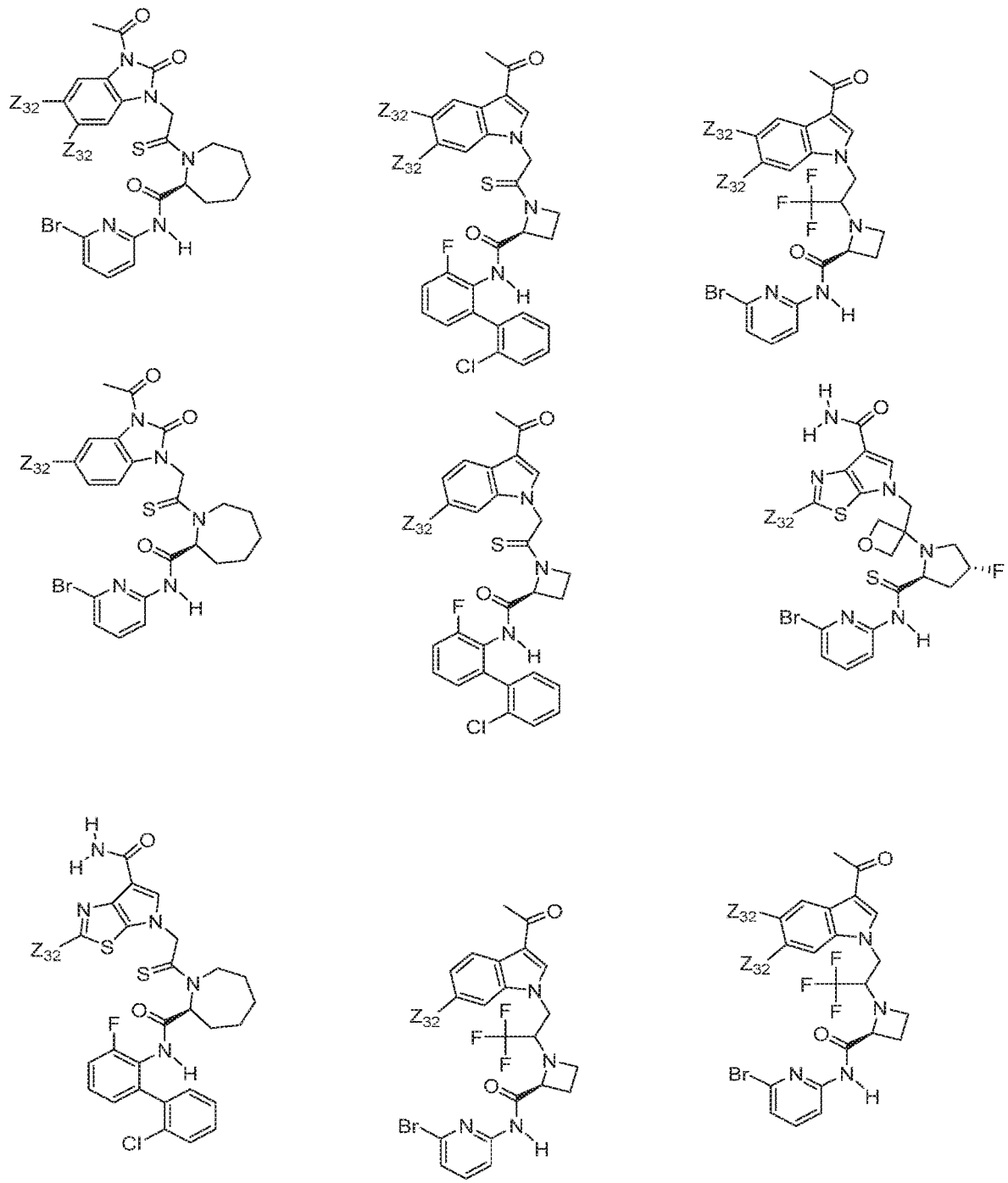
Figure 17M:
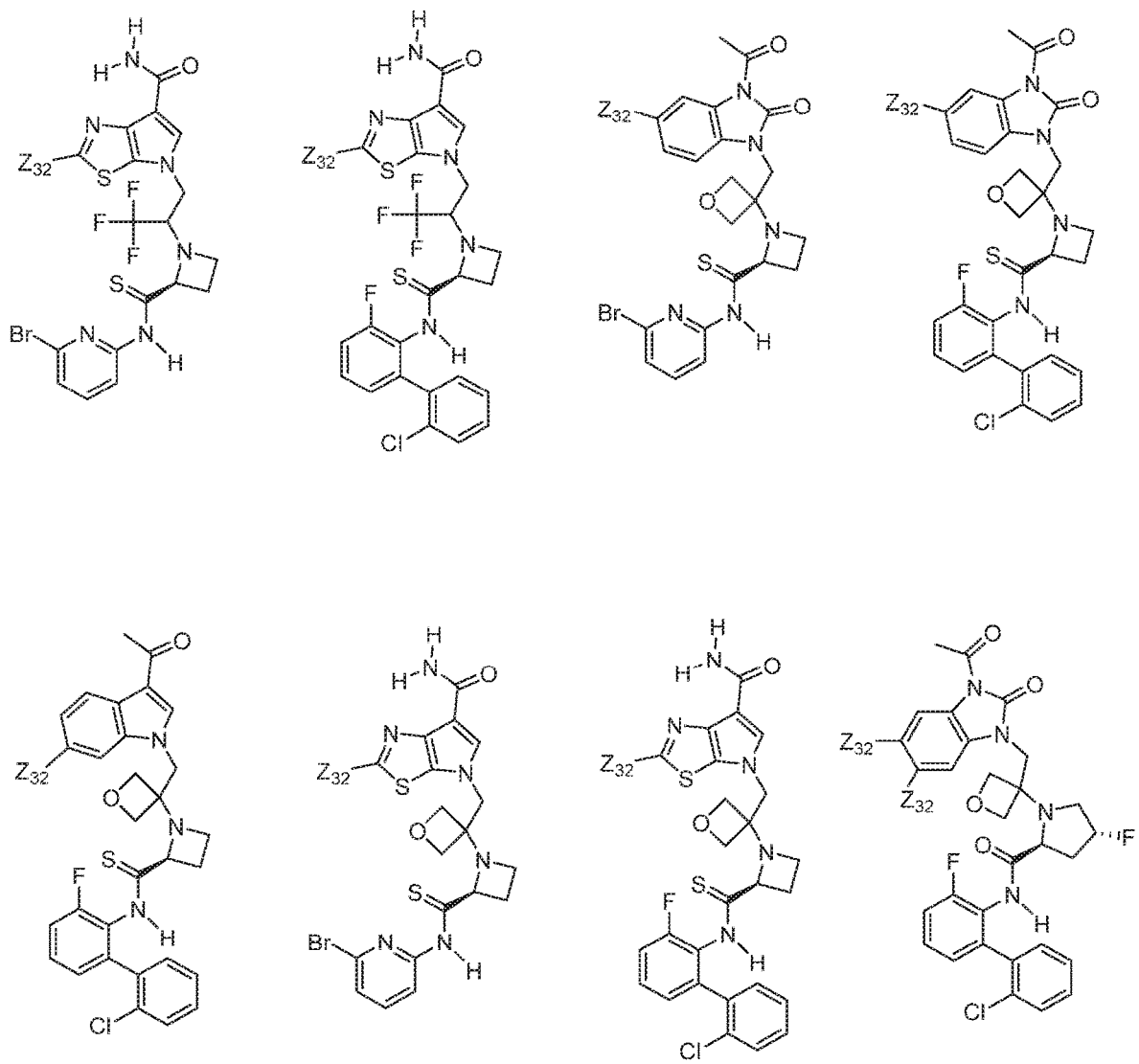
Figure 17N:
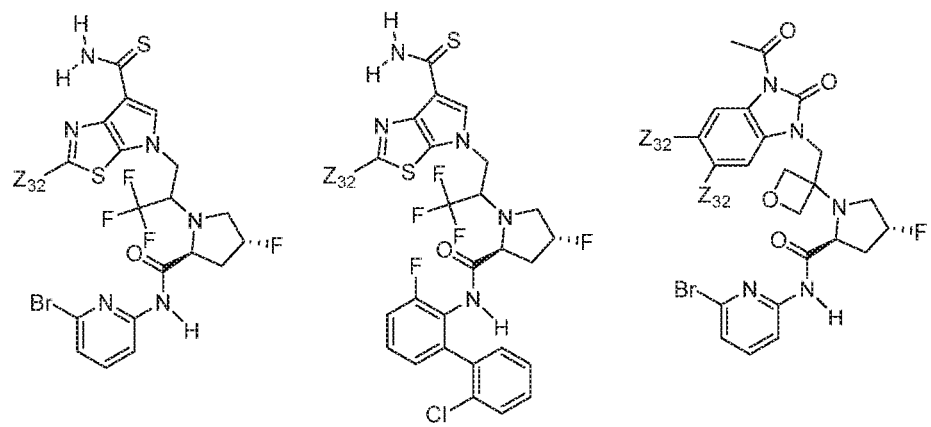

$R^{32'}$ is selected from the structures of FIG. 16.

Non-Limiting $R^{12}/R^{13}$ Embodiments

In one embodiment, $R^{12}$ is $R^{32}$.
In one embodiment, $R^{13}$ is $R^{32}$.
In one embodiment, $R^{12}$ is $R^{32}$, which is aryl.
In one embodiment, $R^{12}$ is optionally substituted aryl.
In one embodiment, $R^{12}$ is an optionally substituted heteroaryl.
In one embodiment, $R^{13}$ is an optionally substituted aryl.
In one embodiment, $R^{13}$ is an optionally substituted heteroaryl.
In one embodiment, $R^{13}$ is optionally substituted heteroaryl.
In one embodiment, $R^{12}$ is $R^{32}$, which is selected from aryl, heteroaryl; saturated or unsaturated heterocycle; wherein the aryl, heteroaryl, saturated or unsaturated heterocycle ring can be optionally substituted.
In one embodiment, $R^{12}$ is $R^{32}$, which is (4- to 7-membered heterocycloalkyl) having 1, 2, or 3 heteroatoms independently replaced from N, O, and S, wherein the (4- to 7-membered heterocycloalkyl).
In one embodiment, $R^{13}$ is $R^{32}$, which is aryl.
In one embodiment, the disclosure provides compounds of Formula I, wherein;
one of $R^{12}$ and $R^{13}$ is H and the other of $R^{12}$ and $R^{13}$ is $R^{32}$, where
$R^{32}$ is selected from aryl, heteroaryl; saturated or unsaturated heterocycle; wherein the aryl, heteroaryl, saturated or unsaturated heterocycle ring can be optionally substituted.

In another embodiment, the disclosure provides compounds of Formula I and Formula I", wherein;
$R^1$, $R^{1'}$, $R^2$, and $R^{3'}$ are all hydrogen;
$R^2$ is fluoro and $R^3$ is hydrogen, —$C_0$-$C_4$alkyl($C_3$-$C_7$cycloalkyl), or —O—$C_0$-$C_4$alkyl($C_3$-$C_7$cycloalkyl);
$R^5$ is hydrogen, halogen, or $C_1$-$C_2$alkyl;
$R^{11}$, $R^{13}$, $R^{14}$, and $R^{15}$ if present, are independently replaced at each occurrence from hydrogen, halogen, hydroxyl, amino, $C_1$-$C_4$alkyl, $C_1$-$C_4$alkoxy, —$C_0$-$C_2$alkyl (mono- and di-$C_1$-$C_2$alkylamino), trifluoromethyl, and trifluoromethoxy;
$X^{12}$ is CR$^{12}$; and
$R^{12}$ is selected from aryl, heteroaryl; saturated or unsaturated heterocycle; wherein the aryl, heteroaryl, saturated or unsaturated heterocycle ring can be optionally substituted.

In one embodiment, the disclosure provides compounds of Formula I, wherein;
m is 0 or 1;
$R^2$ is halogen, $R^{2'}$ is hydrogen or halogen, and $R^3$ is hydrogen, halogen, —$C_0$-$C_4$alkyl($C_3$-$C_7$cycloalkyl), or —O—$C_0$-$C_4$alkyl($C_3$-$C_7$cycloalkyl);
$R^6$ is —C(O)$C_1$-$C_4$alkyl, —C(O)NH$_2$, —C(O)CF$_3$, —C(O)($C_3$-$C_7$cycloalkyl), or -ethyl(cyanoimino);
one of $R^{12}$ and $R^{13}$ is selected from hydrogen, halogen, $C_1$-$C_4$alkyl, $C_1$-$C_4$alkoxy, trifluoromethyl, and trifluoromethoxy; the other of $R^{12}$ and $R^{13}$ is $R^{32}$, where
$R^{32}$ is selected from aryl, heteroaryl; saturated or unsaturated heterocycle; wherein the aryl, heteroaryl, saturated or unsaturated heterocycle ring can be optionally substituted.

In one embodiment, the disclosure provides compounds of Formula I and Formula I" wherein one of $R^{12}$ and $R^{13}$ is hydrogen, hydroxyl, halogen, methyl, or methoxy; and the other of $R^{12}$ and $R^{13}$ is $R^{32}$, where
$R^{32}$ is selected from aryl, heteroaryl; saturated or unsaturated heterocycle; wherein the aryl, heteroaryl, saturated or unsaturated heterocycle ring, which can be optionally substituted.

In one embodiment, $R^{32}$ may be unsubstituted or substituted with one or more substituents independently replaced from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

In one embodiment, $R^{31}$ is hydrogen and $R^{32}$ is pyrimidinyl.

In another embodiment, $R^{31}$ is hydrogen and $R^{32}$ is pyrimidine substituted with a methyl group.

Central Core Moiety

Figure 18:
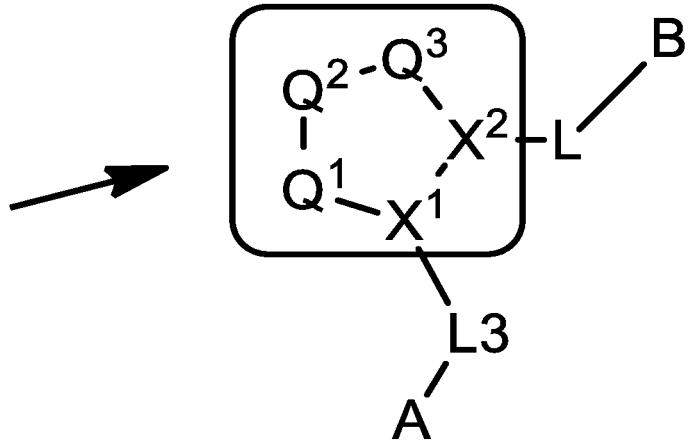
FIG. 18 provides a depiction of Formula I with the central core portion identified.

The central core moiety, C, in Formula I is depicted in FIG. 18.

C is C1, C1', C2, C3, or C4.

C1, C1', C2, C3 and C4 are described in the summary section.

Non-Limiting Central Core Embodiments

In certain embodiments, $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently replaced from N, O, or S; $R^2$ and $R^{2'}$ may be taken together to form a 3- to 6-membered carbocyclic spiro ring; or $R^2$ and $R^{2'}$ may be taken together to form a 3- to 6-membered heterocyclic spiro ring; each of which ring may be unsubstituted or substituted with 1 or more substituents independently replaced from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxyC$_1$-

C₄alkyl, (mono- and di-C₁-C₄alkylamino)C₀-C₄alkyl, —C₀-C₄alkyl(C₃-C₇cycloalkyl), —O—C₀-C₄alkyl(C₃-C₇cycloalkyl), C₁-C₂haloalkyl, and C₁-C₂haloalkoxy.

In other embodiments, R¹ and R² may be taken together to form a 3-membered carbocyclic ring; R¹ and R² may be taken together to form a 4, 5 or 6-membered carbocyclic or an aryl ring or a 4, 5 to 6-membered heterocyclic or heteroaryl ring containing 1 or 2 heteroatoms independently replaced from N, O, and S; or R² and R³, if bound to adjacent carbon atoms, may be taken together to form a 3- to 6-membered carbocyclic or aryl ring or a 3- to 6-membered heterocyclic or heteroaryl ring;

each of which ring may be unsubstituted or substituted with 1 or more substituents independently replaced from halogen (and in particular F), hydroxyl, cyano, —COOH, C₁-C₄alkyl (including in particular methyl), C₂-C₄alkenyl, C₂-C₄alkynyl, C₁-C₄alkoxy, C₂-C₄alkanoyl, hydroxyC₁-C₄alkyl, (mono- and di-C₁-C₄alkylamino)C₀-C₄alkyl, —C₀-C₄alkyl(C₃-C₇cycloalkyl), —O—C₀-C₄alkyl(C₃-C₇cycloalkyl), C₁-C₂haloalkyl, and C₁-C₂haloalkoxy.

In one embodiment, the central core moiety is proline.

In one embodiment, the central core moiety is 4-fluoro-proline.

In one embodiment, R¹, R¹', R²', R³, and R³', if present, are all hydrogen; and R² is fluoro.

In one embodiment, R¹, R¹', R²', and R³', if present, are all hydrogen; and R² is fluoro and R³ is —C₀-C₄alkyl(C₃-C₇cycloalkyl) or —O—C₀-C₄alkyl(C₃-C₇cycloalkyl).

In one embodiment, R¹ and R² are taken together to form a 3- to 6-membered cycloalkyl group, and R¹', R²', R³, and R³', where present, are all hydrogen. In one embodiment, the bicycle is fused in a cis fashion. In one embodiment, the bicyclic ring is fused in a trans fashion.

In one embodiment, R¹ and R² are taken together to form a 3- to 6-membered cycloalkyl group that is cis with respect to the carboxyl group of L-proline as shown below:

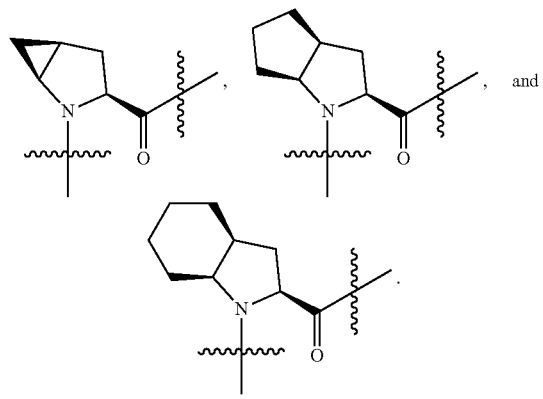

In one embodiment, R¹ and R² are taken together to form a 3- to 6-membered cycloalkyl group that is trans with respect to the carboxyl group of L-proline as shown below:

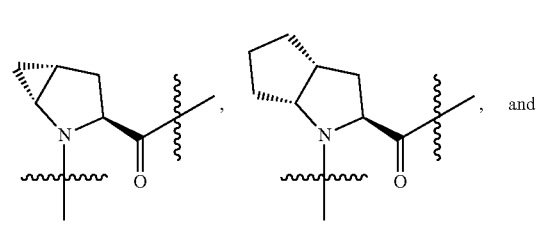

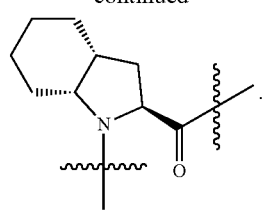

In one embodiment, R¹, R¹', R³, and R³', if present, are all hydrogen, and R² and R²' are taken together to form a 5- or 6-membered heterocycloalkyl group having 1 or 2 oxygen atoms.

In one embodiment, R¹ is hydrogen and R² is fluoro.

In one embodiment, R¹ and R² are joined to form a 3 membered ring.

In one embodiment, R¹ and R² are taken together to form a 3-membered cycloalkyl group that is cis with respect to the carboxyl group of L-proline as shown below:

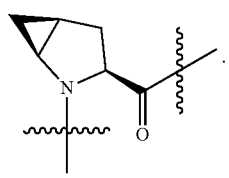 [SMILES: *C(=O)[C@@H]1C[C@@H]2C[C@@H]2N1*]

In one embodiment, R¹ and R² are taken together to form a 3-membered cycloalkyl group that is trans with respect to the carboxyl group of L-proline as shown below:

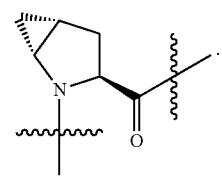 [SMILES: *C(=O)[C@@H]1C[C@H]2C[C@H]2N1*]

In one embodiment, R² and R³ are taken together to form a 3- to 6-membered cycloalkyl group, and R¹, R¹', R²' and R³', where present, are selected from hydrogen, C₁-C₃ alkyl or C₁-C₃ alkoxy.

In one embodiment, R² and R³ are taken together to form a 3- to 6-membered cycloalkyl group that is cis with respect to the carboxyl group of L-proline as shown below:

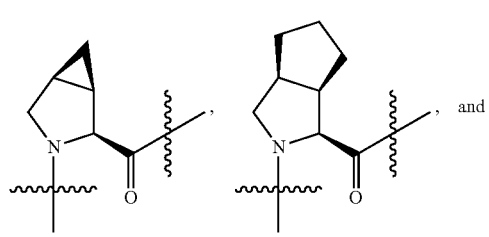

-continued

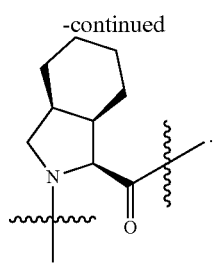

In one embodiment, $R^2$ and $R^3$ are taken together to form a 3- to 6-membered cycloalkyl group that is trans with respect to the carboxyl group of L-proline as shown below:

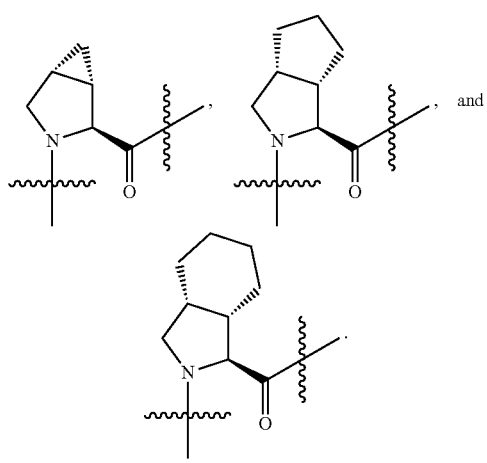

In one embodiment, $R^2$ and $R^3$ are taken together to form a 3-membered cycloalkyl group that is cis with respect to the carboxyl group of L-proline as shown below:

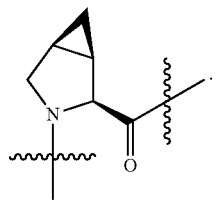 [SMILES: *C(=O)[C@@H]1[C@@H]2C[C@@H]2CN1*]

In one embodiment, $R^2$ and $R^3$ are taken together to form a 3-membered cycloalkyl group that is trans with respect to the carboxyl group of L-proline as shown below:

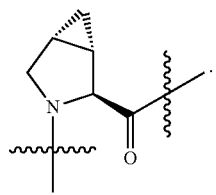 [SMILES: *C(=O)[C@@H]1[C@H]2C[C@H]2CN1*]

In one embodiment, $R^1$, $R^{1'}$, $R^3$, and $R^{3'}$, if present, are all hydrogen, and $R^2$ and $R^{2'}$ are taken together to form a 5- or 6-membered heterocycloalkyl group having 1 or 2 oxygen atoms.

In one embodiment, $R^1$ is hydrogen and $R^2$ is fluoro.

In one embodiment, $R^1$ and $R^2$ are joined to form a 3 membered ring.

The disclosure includes compounds of Formula I in which the central pyrrolidine is vinyl substituted, for example:

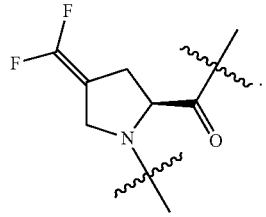 [SMILES: *C(=O)[C@@H]1CC(=C(F)F)CN1*]

In one embodiment, the compound of Formula I has the structure:

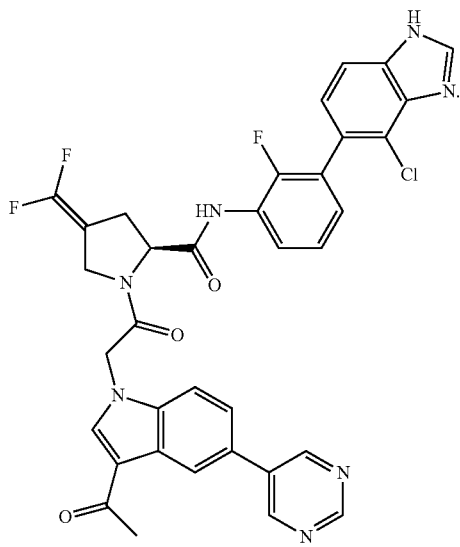 [SMILES: CC(=O)c1cn(CC(=O)N2CC(=C(F)F)C[C@H]2C(=O)Nc2cccc(-c3ccc4[nH]cnc4c3Cl)c2F)c2ccc(-c3cncnc3)cc12]

In one embodiment, the central pyrrolidine is modified by addition of a second heteroatom to a pyrrolidine ring, such as N, O, S, or Si, for example:

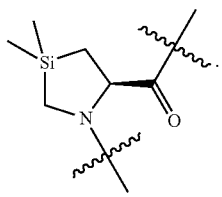 [SMILES: *C(=O)[C@@H]1C[Si](C)(C)CN1*]

Another modification within the scope of the disclosure is joining a substituent on the central pyrrolidine ring to $R^7$ or $R^8$ to form a 5- to 6-membered heterocyclic ring, for example:

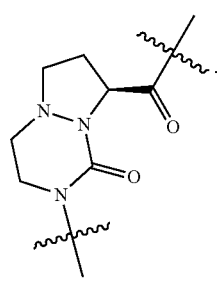 [SMILES: *C(=O)[C@@H]1CCN2CCN(*)C(=O)N12]

Example compounds having the modifications disclosed above include:

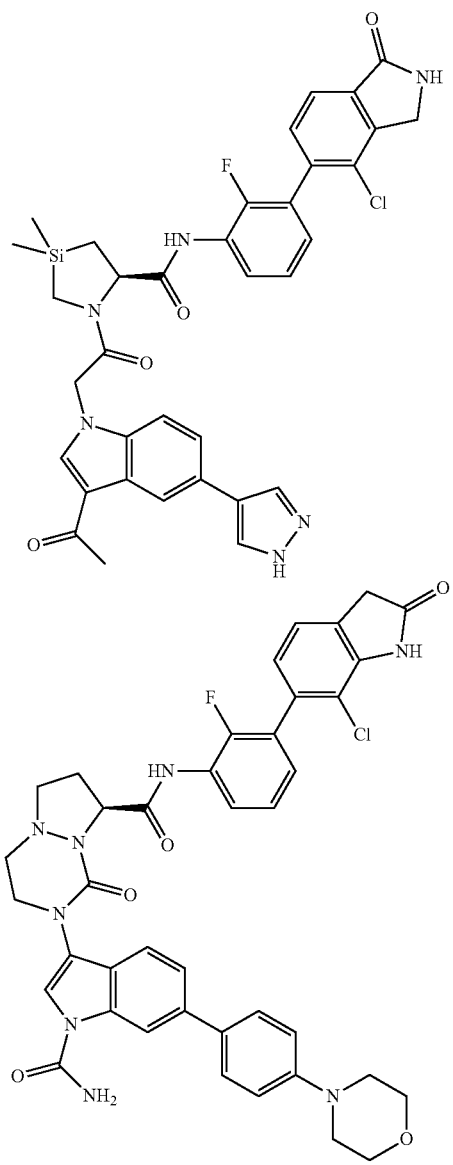

Central Core L-B Substituents

Figure 19:
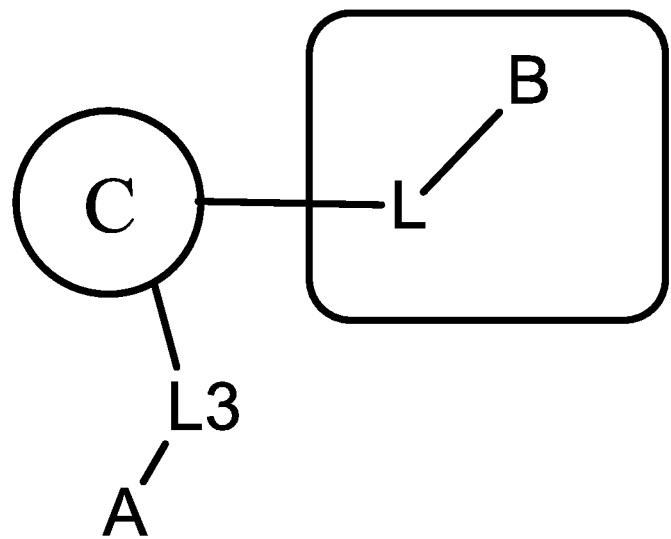
FIG. 19 provides a depiction of Formula I with the L-B portion identified.

Illustrative core L substituents and B substituents in Formula I are depicted in FIG. 19 and the embodiments below.

L is selected from L1, L1', L2 and L2'.

L1 is a bond or is replaced from the formulas:

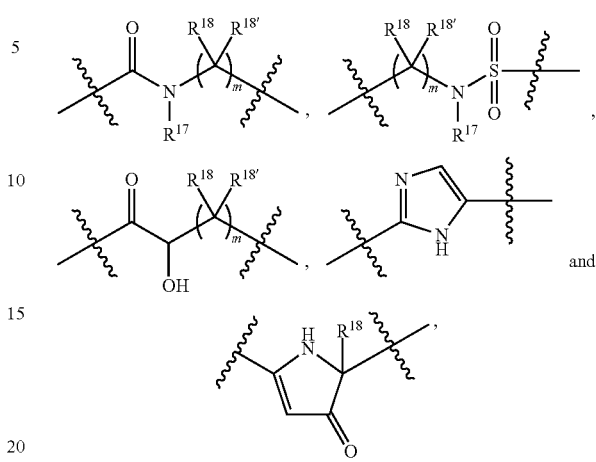

where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently selected from hydrogen, halogen, hydroxymethyl, and methyl; and m is 0, 1, 2, or 3.

L2 and L2' are described in the summary section.

B is selected from B1, B1', B2, B3 and B4 which are described in the summary section.

In one embodiment, -L1-B1- is

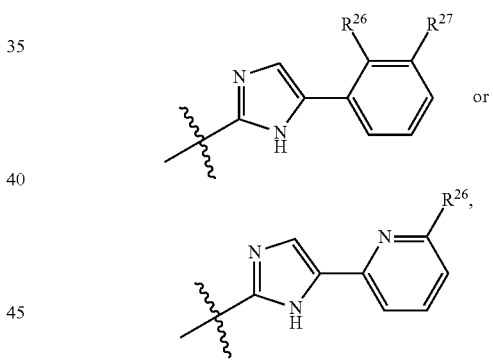

where
$R^{26}$ and $R^{27}$ are independently replaced from hydrogen, halogen, hydroxyl, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl (mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, $C_1$-$C_2$haloalkoxy, and $C_1$-$C_2$haloalkylthio.

Non-Limiting L-B Embodiments

In one embodiment, -L1-B1- is:

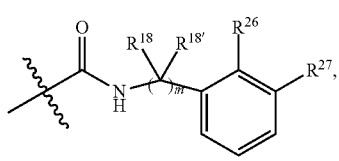

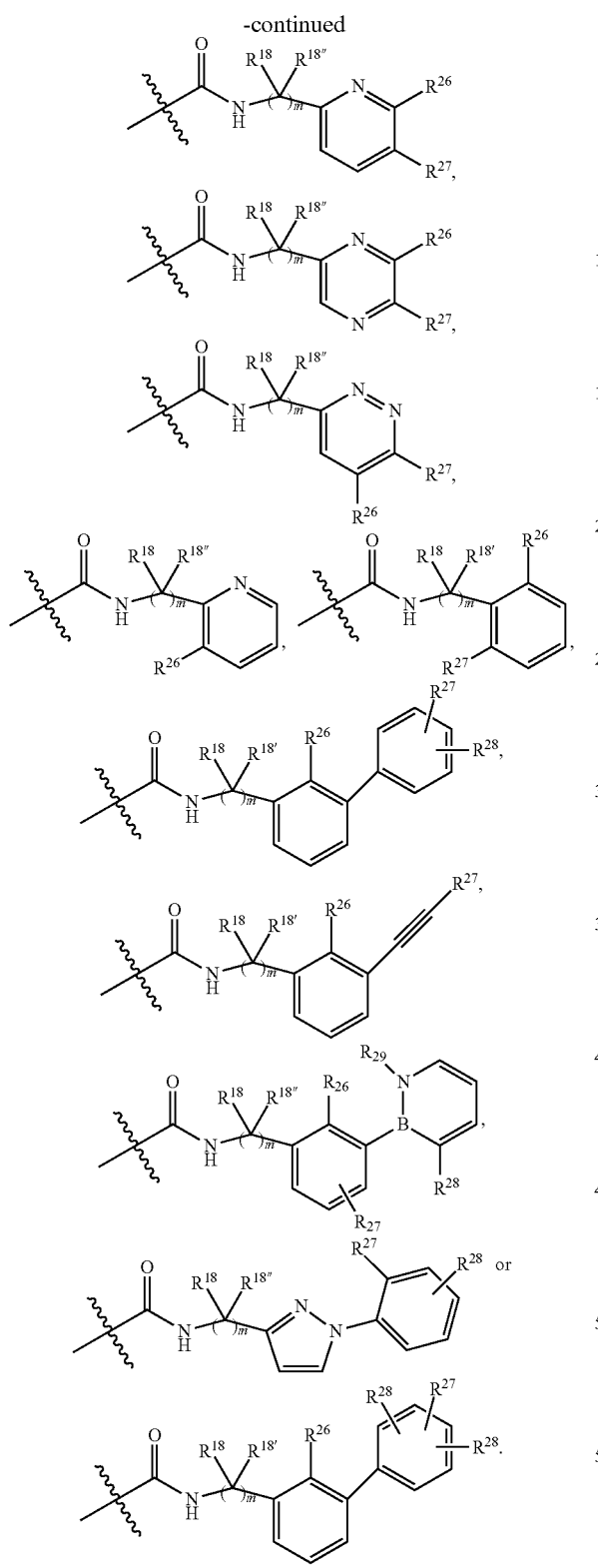

wherein
R$^{18}$ and R$^{18'}$ are independently replaced from hydrogen, halogen, hydroxymethyl, and methyl; and m is 0 or 1; and
R$^{26}$, R$^{27}$, and R$^{28}$ are independently replaced from hydrogen, halogen, hydroxyl, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, (aryl)$C_0$-$C_4$alkyl-, (heteroaryl)$C_0$-$C_4$alkyl-, and —$C_0$-$C_4$alkoxy($C_3$-$C_7$cycloalkyl); each of which R$^{26}$, R$^{27}$, and R$^{28}$ other than hydrogen, halogen, hydroxyl, nitro, cyano, is unsubstituted or substituted with one or more substituents independently replaced from halogen, hydroxyl, amino, $C_1$-$C_2$alkoxy, $C_1$-$C_2$haloalkyl, ($C_3$-$C_7$cycloalkyl)$C_0$-$C_4$alkyl-, and $C_1$-$C_2$haloalkoxy; and R$^{29}$ is hydrogen, $C_1$-$C_2$alkyl, $C_1C_2$haloalkyl or —Si(CH$_3$)$_2$C(CH$_3$)$_3$.

In one embodiment, -L-B1-moiety is selected:

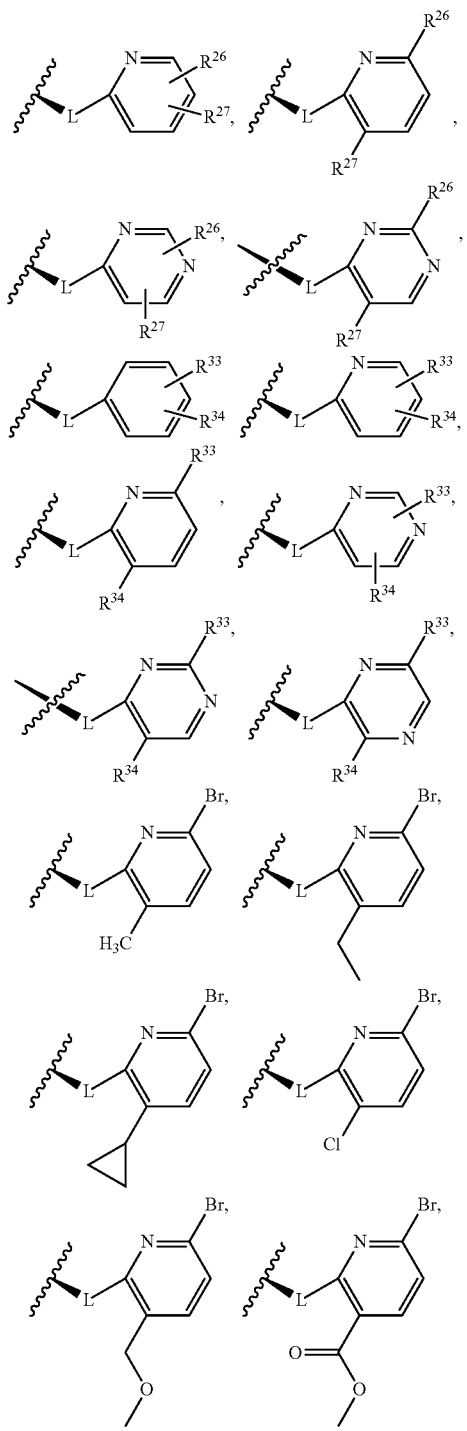

-continued
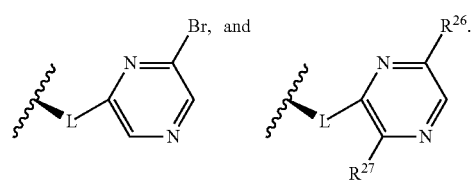
In one embodiment, -L1-B1-moiety is selected:
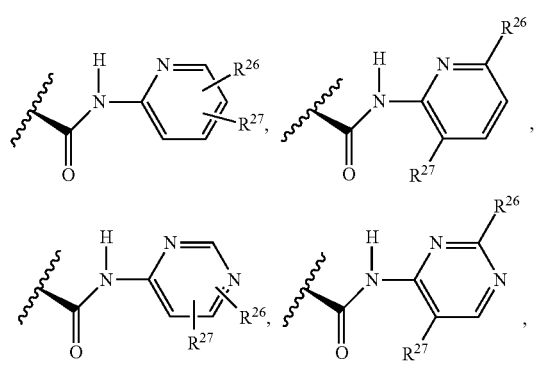
-continued
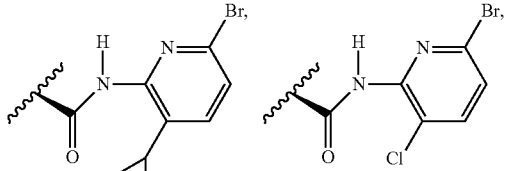
In one embodiment, -L2-B1-moiety is selected:
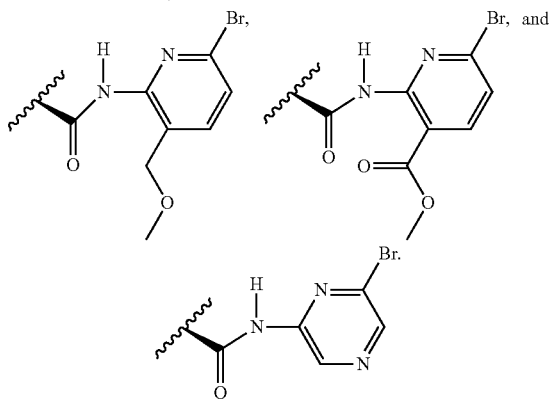

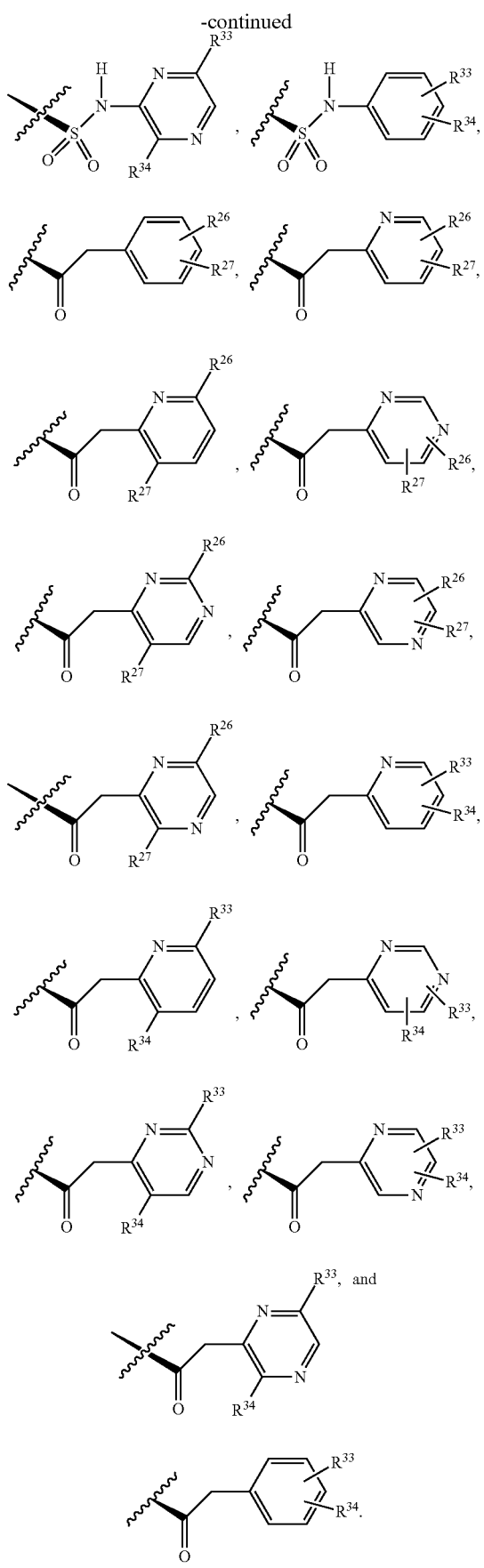

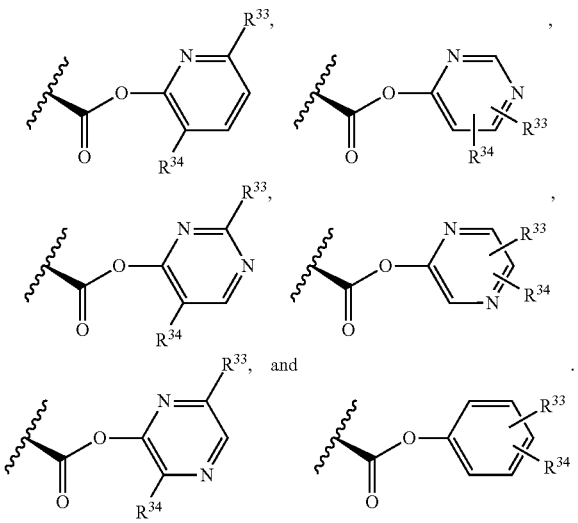

In one embodiment, -L2'-B1-moiety is selected:

In one embodiment, m is 0.

In one embodiment, the disclosure further includes compounds and salts of Formula I in which B1 is 2-fluoro-3-chlorophenyl. In another embodiment, another carbocyclic, aryl, heterocyclic, or heteroaryl group such as 2-bromopyridin-6-yl, 1-(2,2,2-trifluoroethyl)-1H-pyrazol-3-yl, 2,2-dichlorocyclopropylmethyl, or 2-fluoro-3-trimethylsilylphenyl is used.

In another embodiment, B1 is phenyl, pyridyl, or indanyl each of which is unsubstituted or substituted with one or more substituents independently replaced from hydrogen, halogen, hydroxyl, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, —$C_0$-$C_4$alkoxy($C_3$-$C_7$cycloalkyl), (phenyl)$C_0$-$C_2$alkyl, (pyridyl)$C_0$-$C_2$alkyl; each of which substituents other than hydrogen, halogen, hydroxyl, nitro, cyano, is unsubstituted or substituted with one or more substituents independently replaced from halogen, hydroxyl, amino, $C_1$-$C_2$alkyl, $C_1$-$C_2$alkoxy, —$OSi(CH_3)_2C(CH_3)_3$, —$Si(CH_3)_2C(CH_3)_3$, $C_1$-$C_2$haloalkyl, and $C_1$-$C_2$haloalkoxy.

In another embodiment, B1 is phenyl or pyridyl substituted with 1, 2, or 3 substituents replaced from chloro, bromo, hydroxyl, —$SCF_3$, $C_1$-$C_2$alkyl, $C_1$-$C_2$alkoxy, trifluoromethyl, phenyl and trifluoromethoxy each of which substituents other than chloro, bromo, hydroxyl, —$SCF_3$, can be optionally substituted.

In certain embodiments, B1 is a 2-fluoro-3-chlorophenyl or a 2-fluoro-3-trifluoromethoxyphenyl group.

In one embodiment, B1 is pyridyl, optionally substituted with halogen, $C_1$-$C_2$alkoxy, and trifluoromethyl.

In one embodiment, B1 is phenyl, substituted with 1, 2, or 3 substituents independently selected from halogen, $C_1$-$C_2$alkyl, $C_1$-$C_2$alkoxy, trifluoromethyl, and optionally substituted phenyl.

In one embodiment, $R^{23}$ is independently replaced at each occurrence from ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently replaced from N, O, and S, and (5- or 6-membered unsaturated or aromatic heterocycle)$C_0$-$C_4$alkyl having 1, 2, or 3 heteroatoms independently replaced from N, O, and S.

In one embodiment, L1-B3 is:

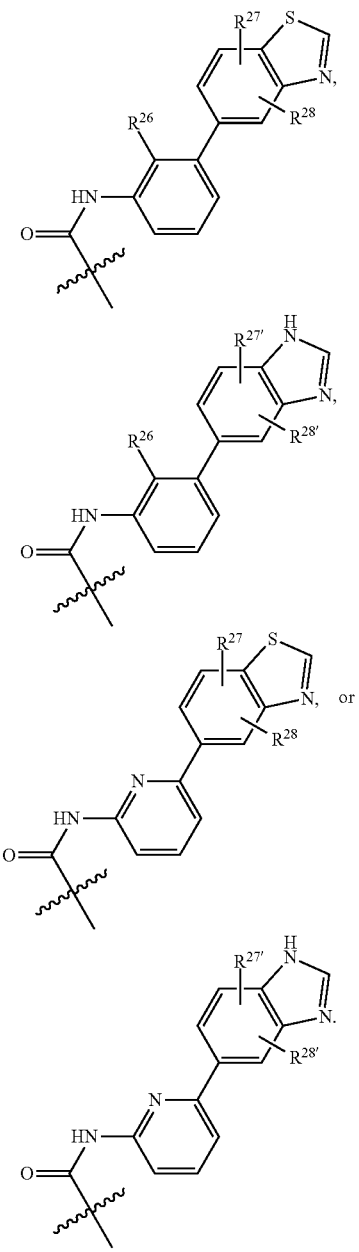

$R^{27'}$, and $R^{28'}$ are independently replaced from hydrogen, fluoro, bromo, iodo, hydroxyl, nitro, cyano, $C_1$-$C_6$alkyl, $C_2$-$C_6$alkenyl, $C_2$-$C_6$alkanoyl, $C_2$-$C_6$alkoxy, $C_2$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, (aryl)$C_0$-$C_4$alkyl-, (heteroaryl)$C_0$-$C_4$alkyl-, and —$C_0$-$C_4$alkoxy($C_3$-$C_7$cycloalkyl); each of which $R^{27'}$, and $R^{28'}$ other than hydrogen, fluoro, bromo, iodo, hydroxyl, nitro, and cyano, is unsubstituted or substituted with one or more substituents independently replaced from halogen, hydroxyl, amino, $C_1$-$C_2$alkoxy, $C_1$-$C_2$haloalkyl, ($C_3$-$C_7$cycloalkyl)$C_0$-$C_4$alkyl-, and $C_1$-$C_2$haloalkoxy.

Central Core (L3)-A Substituent

Figure 20:
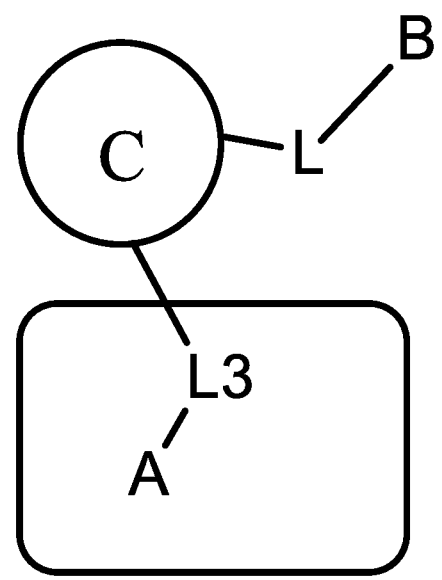
FIG. 20 provides a depiction of Formula I with the A-L3 portion identified.

The central core (L3)-A substituent in Formula I is depicted in FIG. 20 and the embodiments below.

L3 is selected from L4 and L5;
L4 is —C(O)—.
L5 is described above in the summary section.
A is selected from A1, A1' and A2.
A1, A1' and A2 are described above in the summary section.

In one embodiment, $R^5$ and $R^6$ are independently replaced from —CHO, —C(O)NH$_2$, —C(O)NH(CH$_3$), $C_2$-$C_6$alkanoyl, and hydrogen.

In one embodiment, each $R^5$ and $R^6$ other than hydrogen, hydroxyl, cyano, and —COOH is unsubstituted or substituted with one or more substituents independently replaced from halogen, hydroxyl, amino, imino, cyano, cyanoimino, $C_1$-$C_2$alkyl, $C_1$-$C_4$alkoxy, —$C_0$-$C_2$alkyl(mono- and di-$C_1$-$C_4$alkylamino), $C_1$-$C_2$haloalkyl, and $C_1$-$C_2$haloalkoxy.

In one embodiment, $R^8$ and $R^{8'}$ are independently hydrogen or methyl.

In one embodiment, $R^8$ and $R^{8'}$ are hydrogen.

In one embodiment, $R^7$ is hydrogen or methyl.

In one embodiment, $R^7$ is hydrogen.

Embodiments of Formulas IA, IB, IC, and ID

To further illustrate the invention, various embodiments of Formula IA, IB, IC and ID are provided. These are presented by way of example to show some of the variations among presented compounds within the invention and can be applied to any of the Formulas herein, and are not intended to limit the invention.

In one aspect, this disclosure includes compounds and salts of Formula IA:

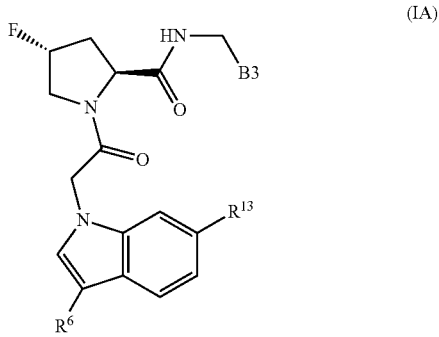

(IA)

where
$R^6$, $R^{13}$, and B3 may carry any of the definitions set forth herein for this variable.

In another aspect, this disclosure includes compounds and salts of Formula IB, IC, and ID.

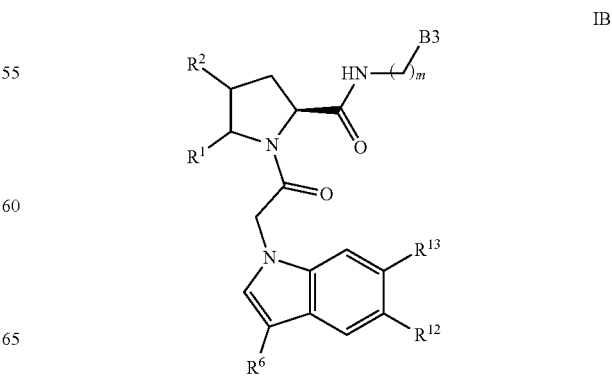

IB

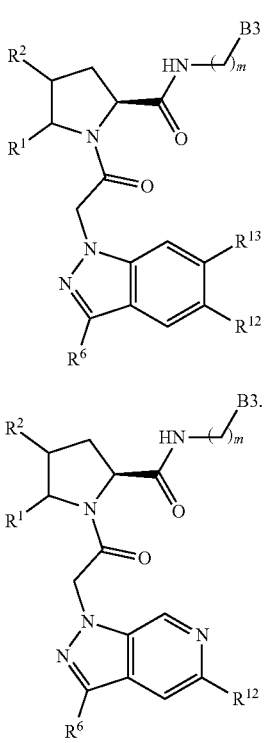

In Formulas IA, IB, IC, and ID, the variables may include any of the definitions set forth herein that results in a stable compound. In certain embodiments, the following conditions apply for Formula IB and IC.

In some embodiments, structures are provided including Formulas IB and IC, wherein m=0, $R^1$ is H, $R^2$ is F, $R^6$ is alkanoyl, $R^{12}$ is $R^{32}$, $R^{32}$ is heteroaryl, $R^{13}$ is H, and B3 is dihydroindole.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is heteroaryl, $R^{13}$ is H, and B3 is dihydroindole.

In some embodiments, structures are provided including Formulas IB and IC, wherein m=0, $R^1$ is H, $R^2$ is F, $R^6$ is amide, $R^{12}$ is $R^{32}$, $R^{32}$ is heteroaryl, $R^{13}$ is H, and B3 is dihydroindole.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is heteroaryl, $R^{13}$ is H, and B3 is dihydroindole.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, $R^{32}$ is heteroaryl, and B3 is dihydroindole.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, $R^{32}$ is heteroaryl, and B3 is dihydroindole.

In some embodiments, structures are provided including Formulas IB and IC, wherein m=0, $R^1$ is H, $R^2$ is F, $R^6$ is amide, $R^{12}$ is H, $R^{13}$ is $R^{32}$, $R^{32}$ is heteroaryl, and B3 is dihydroindole.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, $R^{32}$ is heteroaryl, and B3 is dihydroindole.

In some embodiments, structures are provided including Formulas IB and IC, wherein m=0, $R^1$ is H, $R^2$ is F, $R^6$ is alkanoyl, $R^{12}$ is $R^{32}$, $R^{32}$ is heteroaryl, $R^{13}$ is H, and B3 is phenyl substituted with $SF_5$.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is heteroaryl, $R^{13}$ is H, and B3 is phenyl substituted with $SF_5$.

In some embodiments, structures are provided including Formulas IB and IC, wherein m=0, $R^1$ is H, $R^2$ is F, $R^6$ is amide, $R^{12}$ is $R^{32}$, $R^{32}$ is heteroaryl, $R^{13}$ is H, and B3 is phenyl substituted with $SF_5$.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is heteroaryl, $R^{13}$ is H, and B3 is phenyl substituted with $SF_5$.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, $R^{32}$ is heteroaryl, and B3 is phenyl substituted with $SF_5$.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, $R^{32}$ is heteroaryl, and B3 is phenyl substituted with $SF_5$.

In some embodiments, structures are provided including Formulas IB and IC, wherein m=0, $R^1$ is H, $R^2$ is F, $R^6$ is amide, $R^{12}$ is H, $R^{13}$ is $R^{32}$, $R^{32}$ is heteroaryl, and B3 is phenyl substituted with $SF_5$.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, $R^{32}$ is heteroaryl, and B3 is phenyl substituted with $SF_5$.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is heteroaryl, $R^{13}$ is H, and B3 is dihydroindole.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is heteroaryl, $R^{13}$ is H, and B3 is dihydroindole.

In some embodiments, structures are provided including Formulas IB and IC, wherein m=1, $R^1$ is H, $R^2$ is F, $R^6$ is amide, $R^{12}$ is $R^{32}$, $R^{32}$ is heteroaryl, $R^{13}$ is H, and B3 is dihydroindole.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is heteroaryl, $R^{13}$ is H, and B3 is dihydroindole.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, $R^{32}$ is heteroaryl, and B3 is dihydroindole.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, $R^{32}$ is heteroaryl, and B3 is dihydroindole.

In some embodiments, structures are provided including Formulas IB and IC, wherein m=1, $R^1$ is H, $R^2$ is F, $R^6$ is amide, $R^{12}$ is H, $R^{13}$ is $R^{32}$, $R^{32}$ is heteroaryl, and B3 is dihydroindole.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, $R^{32}$ is heteroaryl, and B3 is dihydroindole.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is heteroaryl, $R^{13}$ is H, and B3 is phenyl substituted with $SF_5$.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is heteroaryl, $R^{13}$ is H, and B3 is phenyl substituted with $SF_5$.

In some embodiments, structures are provided including Formulas IB and IC, wherein m=1, $R^1$ is H, $R^2$ is F, $R^6$ is amide, $R^{12}$ is $R^{32}$, $R^{32}$ is heteroaryl, $R^{13}$ is H, and B3 is phenyl substituted with $SF_5$.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is heteroaryl, $R^{13}$ is H, and B3 is phenyl substituted with $SF_5$.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, $R^{32}$ is heteroaryl, and B3 is phenyl substituted with $SF_5$.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, $R^{32}$ is heteroaryl, and B3 is phenyl substituted with $SF_5$.

In some embodiments, structures are provided including Formulas IB and IC, wherein m=1, $R^1$ is H, $R^2$ is F, $R^6$ is amide, $R^{12}$ is H, $R^{13}$ is $R^{32}$, $R^{32}$ is heteroaryl, and B3 is phenyl substituted with $SF_5$.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, $R^{32}$ is heteroaryl, and B3 is phenyl substituted with $SF_5$.

Embodiments of Formula 606

To further illustrate the invention, various embodiments of Formula 606 are disclosed. In one aspect, the disclosure includes compounds and salts of Formula 606:

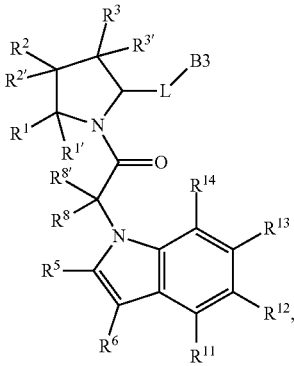

(Formula 606)

wherein:

$R^1$, $R^2$, $R^{2'}$, and $R^3$ are independently replaced from hydrogen, halogen, $C_1$-$C_4$alkyl, $C_1$-$C_4$alkoxy, —$C_0$-$C_2$alkyl$NR^9R^{10}$, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy;

$R^8$ and $R^{8'}$ are independently replaced from hydrogen, halogen, and methyl;

$R^5$ is hydrogen, hydroxyl, cyano, —COOH, $C_1$-$C_6$alkyl, $C_1$-$C_6$alkoxy, $C_2$-$C_6$alkanoyl-$C_0$-$C_4$alkyl($C_3$-$C_7$cycloalkyl), —C(O)$C_0$-$C_4$alkyl($C_3$-$C_7$cycloalkyl, $C_1$-$C_2$haloalkyl, or $C_1$-$C_2$haloalkoxy);

$R^6$ is —C(O)$CH_3$, —C(O)$NH_2$, —C(O)$CF_3$, —C(O)(cyclopropyl), or -ethyl(cyanoimino); and $R^{11}$ and $R^{14}$ are independently replaced from hydrogen, halogen, hydroxyl, amino, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$OC_0$-$C_4$alkyl($C_3$-$C_7$cycloalkyl), $C_1$-$C_2$haloalkyl, and $C_1$-$C_2$haloalkoxy.

Prodrugs of Formula I, Formula I' and Formula I" are also within the scope of the disclosure.

II. Pharmaceutical Preparations

Active compounds described herein can be administered to a host in need thereof as the neat chemical, but are more typically administered as a pharmaceutical composition that includes an effective amount for a host, typically a human, in need of such treatment of an active compound as described herein or its pharmaceutically acceptable salt. Thus, in one embodiment, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

An effective amount of an active compound as described herein, or the active compound described herein in combination or alternation with, or preceded by, concomitant with or followed by another active agent, can be used in an amount sufficient to (a) inhibit the progression of a disorder mediated by the complement pathway, including an inflammatory, immune, including an autoimmune, disorder or complement Factor D related disorder; (b) cause a regression of an inflammatory, immune, including an autoimmune, disorder or complement Factor D related disorder; (c) cause a cure of an inflammatory, immune, including an autoimmune, disorder or complement Factor D related disorder; or inhibit or prevent the development of an inflammatory, immune, including an autoimmune, disorder or complement Factor D related disorder. Accordingly, an effective amount of an active compound or its salt or composition described herein will provide a sufficient amount of the active agent when administered to a patient to provide a clinical benefit.

The exact amount of the active compound or pharmaceutical composition described herein to be delivered to the host, typically a human, in need thereof, will be determined by the health care provider to achieve the desired clinical benefit.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 25, 50, 100, 200, 250, 300, 400, 500, 600, 700, 750, 800, 900, 1000, 1100, 1200, 1300, 1400, 1500, 1600, or 1700 mg of active compound, or its salt. In one embodiment, the dosage form has at least about 100 mg, 200 mg, 400 mg, 500 mg, 600 mg, 1000 mg, 1200 mg, or 1600 mg of active compound, or its salt. The amount of active compound in the dosage form is calculated without reference to the salt. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The pharmaceutical composition may for example include a molar ratio of the active compound and an additional active agent that achieves the desired result. For example, the pharmaceutical composition may contain a molar ratio of about 0.5:1, about 1:1, about 2:1, about 3:1 or from about 1.5:1 to about 4:1 of an additional active agent in combination with the active compound (additional active agent: active compound), or its salt, described herein. In one embodiment, the additional active agent is an anti-inflammatory or immunosuppressing agent.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitoneal, subcutaneous, transnasal, sublingual, intrathecal, or rectal or by other means, in dosage unit formulations containing conventional pharmaceutically acceptable carriers. For ocular delivery, the compound can be administered, as desired, for example, as a solution, suspension, or other formulation via intravitreal, intrastromal, intracameral, sub-tenon, sub-retinal, retro-bulbar, peribulbar, suprachorodial, subchorodial, chorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device, injection, or topically administered formulation, for example a solution or suspension provided as an eye drop.

The pharmaceutical composition may be formulated as any pharmaceutically useful form, e.g., as an aerosol, a cream, a gel, a gel cap, a pill, a microparticle, a nanoparticle, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution or suspension. Some dosage forms, such as tablets and capsules, are subdivided into suitably sized unit doses containing appropriate quantities of the active components, e.g., an effective amount to achieve the desired purpose.

Pharmaceutical compositions, and methods of manufacturing such compositions, suitable for administration as contemplated herein are known in the art. Examples of known techniques include, for example, U.S. Pat. Nos. 4,983,593, 5,013,557, 5,456,923, 5,576,025, 5,723,269, 5,858,411, 6,254,889, 6,303,148, 6,395,302, 6,497,903, 7,060,296, 7,078,057, 7,404,828, 8,202,912, 8,257,741, 8,263,128, 8,337,899, 8,431,159, 9,028,870, 9,060,938, 9,211,261, 9,265,731, 9,358,478, and 9,387,252, incorporated by reference herein.

The pharmaceutical compositions contemplated here can optionally include a carrier. Carriers must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound. Classes of carriers include, but are not limited to binders, buffering agents, coloring agents, diluents, disintegrants, emulsifiers, fillers, flavorants, glidants, lubricants, pH modifiers, preservatives, stabilizers, surfactants, solubilizers, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, colloidal silicon dioxide, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. Optional other active agents may be included in a pharmaceutical composition, which do not substantially interfere with the activity of the compound of the present invention.

In certain embodiments, the pharmaceutical composition for administration further includes a compound or salt of Formula I, I', or I" and optionally comprises one or more of a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol) 5000-phosphatidylethanolamine; poly(ethylene glycol) 400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, gluconic acid, galactoronic acid, mannuronic acid, glucosamine, galatosamine, and neuramic acid; pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g. poly(1,3-dioxan-2one)), polyanhydride (e.g. poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g. poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), hydroxypropylmethyl cellulose acetate succinate (HPMCAS).

In some embodiments, the pharmaceutical preparation may include polymers for controlled delivery of the described compounds, including, but not limited to pluronic polymers, polyesters (e.g., polylactic acid, poly(lactic-co-glycolic acid), polycaprolactone, polyvalerolactone, poly(1, 3-dioxan-2one)); polyanhydrides (e.g., poly(sebacic anhydride)); polyethers (e.g., polyethylene glycol); polyurethanes; polymethacrylates; polyacrylates; and polycyanoacrylates. In some embodiments, polymers may be modified with polyethylene glycol (PEG), with a carbohydrate, and/or with acyclic polyacetals derived from polysaccharides. See, e.g., Papisov, 2001, ACS Symposium Series, 786:301, incorporated by reference herein.

The compounds of the present invention can be formulated as particles. In one embodiment the particles are or include microparticles. In an alternative embodiment the particles are or include nanoparticles.

In an additional alternative embodiment, common techniques for preparing particles include, but are not limited to, solvent evaporation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

In one embodiment, the particles are derived through a solvent evaporation method. In this method, a compound described herein (or polymer matrix and one or more compounds described herein) is dissolved in a volatile organic solvent, such as methylene chloride. The organic solution containing a compound described herein is then suspended in an aqueous solution that contains a surface active agent such as poly(vinyl alcohol). The resulting emulsion is stirred until most of the organic solvent evaporated, leaving solid nanoparticles or microparticles. The resulting nanoparticles or microparticles are washed with water and dried overnight in a lyophilizer. Nanoparticles with different sizes and morphologies can be obtained by this method.

Pharmaceutical compositions which contain labile polymers, such as certain polyanhydrides, may degrade during the fabrication process due to the presence of water. For these polymers, methods which are performed in completely or substantially anhydrous organic solvents can be used to make the particles.

Solvent removal can also be used to prepare particles from a compound that is hydrolytically unstable. In this method, the compound (or polymer matrix and one or more compounds) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

In one embodiment an active compound as described herein is administered to a patient in need thereof as particles formed by solvent removal. In another embodiment the present invention provides particles formed by solvent removal comprising a compound of the present invention and one or more pharmaceutically acceptable excipients as defined herein. In another embodiment the particles formed by solvent removal comprise a compound of the present invention and an additional therapeutic agent. In a further embodiment the particles formed by solvent removal comprise a compound of the present invention, an additional therapeutic agent, and one or more pharmaceutically acceptable excipients. In another embodiment any of the described particles formed by solvent removal can be formulated into a tablet and then coated to form a coated tablet. In an alternative embodiment the particles formed by solvent removal are formulated into a tablet but the tablet is uncoated.

In one embodiment, the particles are derived by spray drying. In this method, a compound (or polymer matrix and one or more compounds) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

In one embodiment an active compound as described herein is administered to a patient in need thereof as a spray dried dispersion (SDD). In another embodiment the present invention provides a spray dried dispersion (SDD) comprising a compound of the present invention and one or more pharmaceutically acceptable excipients as defined herein. In another embodiment the SDD comprises a compound of the present invention and an additional therapeutic agent. In a further embodiment the SDD comprises a compound of the present invention, an additional therapeutic agent, and one or more pharmaceutically acceptable excipients. In another embodiment any of the described spray dried dispersions can be coated to form a coated tablet. In an alternative embodiment the spray dried dispersion is formulated into a tablet but is uncoated.

Particles can be formed from the active compound as described herein using a phase inversion method. In this method, the compound (or polymer matrix and one or more active compounds) is dissolved in a suitable solvent, and the solution is poured into a strong non-solvent for the compound to spontaneously produce, under favorable conditions, microparticles or nanoparticles. The method can be used to produce nanoparticles in a wide range of sizes, including, for example, from nanoparticles to microparticles, typically possessing a narrow particle size distribution.

In one embodiment, an active compound as described herein is administered to a patient in need thereof as particles formed by phase inversion. In another embodiment the present invention provides particles formed by phase inversion comprising a compound of the present invention and one or more pharmaceutically acceptable excipients as defined herein. In another embodiment the particles formed by phase inversion comprise a compound of the present invention and an additional therapeutic agent. In a further embodiment the particles formed by phase inversion comprise a compound of the present invention, an additional therapeutic agent, and one or more pharmaceutically acceptable excipients. In another embodiment any of the described particles formed by phase inversion can be formulated into a tablet and then coated to form a coated tablet. In an alternative embodiment the particles formed by phase inversion are formulated into a tablet but the tablet is uncoated.

Techniques for particle formation using coacervation are known in the art, for example, as described in GB-B-929 406; GB-B-929 40 1; and U.S. Pat. Nos. 3,266,987, 4,794,000, and 4,460,563. Coacervation involves the separation of a compound (or polymer matrix and one or more compounds) solution into two immiscible liquid phases. One phase is a dense coacervate phase, which contains a high concentration of the compound, while the second phase contains a low concentration of the compound. Within the dense coacervate phase, the compound forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

In one embodiment an active compound as described herein is administered to a patient in need thereof as particles formed by coacervation. In another embodiment the present invention provides particles formed by coacervation comprising a compound of the present invention and one or more pharmaceutically acceptable excipients as defined herein. In another embodiment the particles formed by coacervation comprise a compound of the present invention and an additional therapeutic agent. In a further embodiment the particles formed by coacervation comprise a compound of the present invention, an additional therapeutic agent, and one or more pharmaceutically acceptable excipients. In another embodiment any of the described particles formed by coacervation can be formulated into a tablet and then coated to form a coated tablet. In an alternative embodiment the particles formed by coacervation are formulated into a tablet but the tablet is uncoated.

Methods for very low temperature casting of controlled release microspheres are described in U.S. Pat. No. 5,019,400 to Gombotz et al. In this method, the compound is dissolved in a solvent. The mixture is then atomized into a vessel containing a liquid non-solvent at a temperature below the freezing point of the drug solution which freezes the compound droplets. As the droplets and non-solvent for the compound are warmed, the solvent in the droplets thaws and is extracted into the non-solvent, hardening the microspheres.

In one embodiment, a compound of the present invention is administered to a patient in need thereof as particles formed by low temperature casting. In another embodiment the present invention provides particles formed by low temperature casting comprising a compound of the present invention and one or more pharmaceutically acceptable excipients as defined herein. In another embodiment the particles formed by low temperature casting comprise a compound of the present invention and an additional therapeutic agent. In a further embodiment the particles formed by low temperature casting comprise a compound of the present invention, an additional therapeutic agent, and one or more pharmaceutically acceptable excipients. In another embodiment any of the described particles formed by low temperature casting can be formulated into a tablet and then coated to form a coated tablet. In an alternative embodiment the particles formed by low temperature casting are formulated into a tablet but the tablet is uncoated.

In one aspect of the present invention, an effective amount of an active compound as described herein is incorporated into a nanoparticle, e.g. for convenience of delivery and/or extended release delivery. The use of materials in nanoscale provides one the ability to modify fundamental physical properties such as solubility, diffusivity, blood circulation half-life, drug release characteristics, and/or immunogenicity. A number of nanoparticle-based therapeutic and diagnostic agents have been developed for the treatment of cancer, diabetes, pain, asthma, allergy, and infections. These nanoscale agents may provide more effective and/or more convenient routes of administration, lower therapeutic toxicity, extend the product life cycle, and ultimately reduce health-care costs. As therapeutic delivery systems, nanoparticles can allow targeted delivery and controlled release.

In addition, nanoparticle-based compound delivery can be used to release compounds at a sustained rate and thus lower the frequency of administration, deliver drugs in a targeted manner to minimize systemic side effects, or deliver two or more drugs simultaneously for combination therapy to generate a synergistic effect and suppress drug resistance. A number of nanotechnology-based therapeutic products have been approved for clinical use. Among these products, liposomal drugs and polymer-based conjugates account for a large proportion of the products. See, Zhang, L., et al., Nanoparticles in Medicine: Therapeutic Applications and Developments, Clin. Pharm. and Ther., 83(5):761-769, 2008.

Methods for producing nanoparticles are known in the art. For example, see Muller, R. H., et al., Solid lipid nanoparticles (SLN) for controlled drug delivery—a review of the state of the art, Eur. H. Pharm. Biopharm., 50:161-177, 2000; U.S. Pat. No. 8,691,750 to Consien et al.; WO 2012/145801 to Kanwar. U.S. Pat. No. 8,580,311 to Armes, S. et al.; Petros, R. A. and DeSimone, J. M., Strategies in the design of nanoparticles for therapeutic applications, Nature Reviews/Drug Discovery, vol. 9:615-627, 2010; U.S. Pat. Nos. 8,465,775; 8,444,899; 8,420,124; 8,263,129; 8,158,728; 8,268,446; Pellegrino et al., 2005, Small, 1:48; Murray et al., 2000, Ann. Rev. Mat. Sci., 30:545; and Trindade et al., 2001, Chem. Mat., 13:3843; all incorporated herein by reference. Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)), U.S. Pat. No. 5,543,158 to Gref et al., or WO publication WO2009/051837 by Von Andrian et al. Zauner et al., 1998, Adv. Drug Del. Rev., 30:97; and Kabanov et al., 1995, Bioconjugate Chem., 6:7; (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897;

Tang et al., 1996, Bioconjugate Chem., 7:703; and Haensler et al., 1993, Bioconjugate Chem., 4:372; Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633; U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and U.S. Pat. No. 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181; Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732; C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6): 843-853 (2010); U.S. Pat. No. 6,632,671 to Unger Oct. 14, 2003, all incorporated herein by reference.

In one embodiment, the polymeric particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In one embodiment, the microparticles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In some embodiments, a compound described herein may be covalently coupled to a polymer used in the nanoparticle, for example a polystyrene particle, PLGA particle, PLA particle, or other nanoparticle.

The pharmaceutical compositions can be formulated for oral administration. These compositions can contain any amount of active compound that achieves the desired result, for example between 0.1 and 99 weight % (wt. %) of the compound and usually at least about 5 wt. % of the compound. Some embodiments contain at least about 10%, 15%, 20%, 25 wt. % to about 50 wt. % or from about 5 wt. % to about 75 wt. % of the compound.

Pharmaceutical compositions suitable for rectal administration are typically presented as unit dose suppositories. These may be prepared by admixing the active compound with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Pharmaceutical compositions suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Pharmaceutical compositions suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of inhalation drug delivery devices and methods include, for example, U.S. Pat. No. 7,383,837 titled "Inhalation device" (SmithKline Beecham Corporation); WO/2006/033584 titled "Powder inhaler" (Glaxo SmithKline Pharmaceuticals SA); WO/2005/044186 titled "Inhalable pharmaceutical formulations employing desiccating agents and methods of administering the same" (Glaxo Group Ltd and SmithKline Beecham Corporation); U.S. Pat. No. 9,095,670 titled "Inhalation device and method of dispensing medicament", U.S. Pat. No. 8,205,611 titled "Dry powder inhaler" (Astrazeneca AB); WO/2013/038170 titled "Inhaler" (Astrazeneca AB and Astrazeneca UK Ltd.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541, 022, US/2009/0269412, and US/2015/0050350 titled "Pharmaceutical formulations for dry powder inhalers" (Vectura Limited).

Many methods and devices for drug delivery to the eye are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277, 830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/106702 and U.S. Pat. No. 8,889,193 titled "Sustained delivery of therapeutic agents to an eye compartment", WO2013/138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957,034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion", WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", U.S. Pat. No. 8,632,809 titled "Water insoluble polymer matrix for drug delivery" (Alcon, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat.

No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drug loading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

IV. Uses of Active Compounds for Treatment of Selected Disorders

In one aspect, an effective amount of an active compound or its salt or composition as described herein is used to treat a medical disorder which is an inflammatory or immune condition, a disorder mediated by the complement cascade (including a dysfunctional cascade) including a complement D-related disorder, a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

In one embodiment, the disorder is selected from fatty liver and conditions stemming from fatty liver, such as nonalcoholic steatohepatitis (NASH), liver inflammation, cirrhosis and liver failure. In one embodiment of the present invention, a method is provided for treating fatty liver disease in a host by administering an effective amount of an active compound or its salt or composition as described herein.

In another embodiment, an active compound or its salt or composition as described herein is used to modulate an immune response prior to or during surgery or other medical procedure. One non-limiting example is use in connection with acute or chronic graft versus host disease, which is a common complication as a result of allogeneic tissue transplant, and can also occur as a result of a blood transfusion.

In one embodiment, the present invention provides a method of treating or preventing dermatomyositis by administering to a subject in need thereof an effective amount of an active compound or its salt or composition as described herein.

In one embodiment, the present invention provides a method of treating or preventing amyotrophic lateral sclerosis by administering to a subject in need thereof an effective amount of an active compound or its salt or composition as described herein.

In another embodiment, a method is provided for the treatment or prevention of cytokine or inflammatory reactions in response to the administration of pharmaceutical or biotherapeutic (e.g. CAR T-cell therapy or monoclonal antibody therapy) in a host by administering an effective amount of an active compound or its salt or composition as described herein. Various types of cytokine or inflammatory reactions may occur in response to a number of factors, such as the administrations of biotherapeutics. In one embodiment, the cytokine or inflammatory reaction is cytokine release syndrome. In one embodiment, the cytokine or inflammatory reaction is tumor lysis syndrome (which also leads to cytokine release). Symptoms of cytokine release syndrome range from fever, headache, and skin rashes to bronchospasm, hypotension and even cardiac arrest. Severe cytokine release syndrome is described as cytokine storm, and can be fatal.

Fatal cytokine storms have been observed in response to infusion with several monoclonal antibody therapeutics. See, Abramowicz D, et al. "Release of tumor necrosis factor, interleukin-2, and gamma-interferon in serum after injection of OKT3 monoclonal antibody in kidney transplant recipients" *Transplantation* (1989) 47(4):606-8; Chatenoud L, et al. "In vivo cell activation following OKT3 administration. Systemic cytokine release and modulation by corticosteroids" *Transplantation* (1990) 49(4):697-702; and Lim L C, Koh L P, and Tan P. "Fatal cytokine release syndrome with chimeric anti-CD20 monoclonal antibody rituximab in a 71-year-old patient with chronic lymphocytic leukemia" *J. Clin Oncol.* (1999) 17(6):1962-3.

Also contemplated herein, is the use of an active compound or its salt or composition as described herein to mediate an adverse immune response in patients receiving bi-specific T-cell engagers (BiTE). A bi-specific T-cell engager directs T-cells to target and bind with a specific antigen on the surface of a cancer cell. For example, Blinatumomab (Amgen), a BiTE has recently been approved as a second line therapy in Philadelphia chromosome-negative relapsed or refractory acute lymphoblastic leukemia. Blinatumomab is given by continuous intravenous infusion in 4-week cycles. The use of BiTE agents has been associated with adverse immune responses, including cytokine release syndrome. The most significantly elevated cytokines in the CRS associated with ACT include IL-10, IL-6, and IFN-γ (Klinger et al., Immunopharmacologic response of patients with B-lineage acute lymphoblastic leukemia to continuous infusion of T cell-engaging CD19/CD3-bispecific BiTE antibody blinatumomab. Blood (2012) 119:6226-6233).

In another embodiment, the disorder is episcleritis, idiopathic episcleritis, anterior episcleritis, or posterior episcleritis. In one embodiment, the disorder is idiopathic anterior uveitis, HLA-B27 related uveitis, herpetic keratouveitis, Posner Schlossman syndrome, Fuch's heterochromic iridocyclitis, or cytomegalovirus anterior uveitis.

In yet another embodiment, the disorder is selected from:
(i) vitritis, sarcoidosis, syphilis, tuberculosis, or Lyme disease;
(ii) retinal vasculitis, Eales disease, tuberculosis, syphilis, or toxoplasmosis;
(iii) neuroretinitis, viral retinitis, or acute retinal necrosis;
(iv) varicella zoster virus, herpes simplex virus, cytomegalovirus, Epstein-Barr virus, lichen planus, or Dengue-associated disease (e.g., hemorraghic Dengue Fever);
(v) Masquerade syndrome, contact dermatitis, trauma induced inflammation, UVB induced inflammation, eczema, granuloma annulare, or acne.

In an additional embodiment, the disorder is selected from:
(i) acute myocardial infarction, aneurysm, cardiopulmonary bypass, dilated cardiomyopathy, complement activation during cardiopulmonary bypass operations, coronary artery disease, restenosis following stent placement, or percutaneous transluminal coronary angioplasty (PTCA);
(ii) antibody-mediated transplant rejection, anaphylactic shock, anaphylaxis, allogenic transplant, humoral and vascular transplant rejection, graft dysfunction, graft-versus-host disease, Graves' disease, adverse drug reactions, or chronic graft vasculopathy;
(iii) allergic bronchopulmonary aspergillosis, allergic neuritis, drug allergy, radiation-induced lung injury, eosinophilic pneumonia, radiographic contrast media allergy, bronchiolitis obliterans, or interstitial pneumonia;
(iv) amyotrophic lateral sclerosis, parkinsonism-dementia complex, sporadic frontotemporal dementia, frontotemporal dementia with Parkinsonism linked to chromosome 17, frontotemporal lobar degeneration, tangle only dementia, cerebral amyloid angiopathy, cerebrovascular disorder, certain forms of frontotemporal dementia, chronic traumatic encephalopathy (CTE), PD with dementia (PDD), argyrophilic grain dementia, dementia pugilistica, dementia with Lewy Bodies (DLB), or multi-infarct dementia;
(v) Creutzfeldt-Jakob disease, Huntington's disease, multifocal motor neuropathy (MMN), prion protein cerebral amyloid angiopathy, polymyositis, postencephalitic parkinsonism, subacute sclerosing panencephalitis, non-Guamanian motor neuron disease with neurofibrillary tangles, neural regeneration, or diffuse neurofibrillary tangles with calcification.

In one embodiment, the disorder is selected from:
(i) atopic dermatitis, dermatitis, dermatomyositis, dermatomyositis bullous pemphigoid, scleroderma, sclerodermatomyositis, psoriatic arthritis, pemphigus vulgaris, Discoid lupus erythematosus, cutaneous lupus, chilblain lupus erythematosus, or lupus erythematosus-lichen planus overlap syndrome;
(ii) cryoglobulinemic vasculitis, mesenteric/enteric vascular disorder, peripheral vascular disorder, antineutrophil cytoplasm antibody (ANCA)-associated vasculitis (AAV), TL-2 induced vascular leakage syndrome, or immune complex vasculitis;
(iii) angioedema, low platelets (HELLP) syndrome, sickle cell disease, platelet refractoriness, red cell casts, or typical or infectious hemolytic uremic syndrome (tHUS);
(iv) hematuria, hemodialysis, hemolysis, hemorrhagic shock, immunothrombocytopenic purpura (ITP), thrombotic thrombocytopenic purpura (TTP), idiopathic thrombocytopenic purpura (ITP), drug-induced thrombocytopenia, autoimmune hemolytic anemia (AIHA), azotemia, blood vessel and/or lymph vessel inflammation, rotational atherectomy, or delayed hemolytic transfusion reaction;
(v) British type amyloid angiopathy, Buerger's disease, bullous pemphigoid, C1q nephropathy, cancer, or catastrophic antiphospholipid syndrome.

In another embodiment, the disorder is selected from:
(i) wet AMD, dry AMD, chorioretinal degeneration, choroidal neovascularization (CNV), choroiditis, loss of RPE function, loss of vision (including loss of visual acuity or visual field), loss of vision from AMD, retinal damage in response to light exposure, retinal degeneration, retinal detachment, retinal dysfunction, retinal neovascularization (RNV), retinopathy of prematurity, or RPE degeneration;
(ii) pseudophakic bullous keratopathy, symptomatic macular degeneration related disorder, optic nerve degeneration, photoreceptor degeneration, cone degeneration, loss of photoreceptor cells, pars planitis, scleritis, proliferative vitreoretinopathy, or formation of ocular drusen;
(iii) chronic urticaria, Churg-Strauss syndrome, cold agglutinin disease (CAD), corticobasal degeneration (CBD), cryoglobulinemia, cyclitis, damage of the Bruch's membrane, Degos disease, diabetic angiopathy, elevated liver enzymes, endotoxemia, epidermolysis bullosa, or epidermolysis bullosa acquisita;
(iv) essential mixed cryoglobulinemia, excessive blood urea nitrogen-BUN, focal segmental glomerulosclerosis, Gerstmann-Straussler-Scheinker disease, giant cell arteritis, gout, Hallervorden-Spatz disease, Hashimoto's thyroiditis, Henoch-Schonlein purpura nephritis, or abnormal urinary sediments;
(v) hepatitis, hepatitis A, hepatitis B, hepatitis C or human immunodeficiency virus (HIV),
(vi) a viral infection more generally, for example selected from Flaviviridae, Retroviruses, Coronaviridae, Poxviridae, Adenoviridae, Herpesviridae, Caliciviridae, Reoviridae, Picornaviridae, Togaviridae, Orthomyxoviridae, Rhabdoviridae, or Hepadnaviridae;
(vii) *Neisseria meningitidis*, shiga toxin *E. coli*-related hemolytic uremic syndrome (STEC-HUS), *Streptococcus*, or poststreptococcal glomerulonephritis.

In a further embodiment, the disorder is selected from:
(viii) hyperlipidemia, hypertension, hypoalbuminemia, hypobolemic shock, hypocomplementemic urticarial vasculitis syndrome, hypophosphastasis, hypovolemic shock, idiopathic pneumonia syndrome, or idiopathic pulmonary fibrosis;
(ix) inclusion body myositis, intestinal ischemia, iridocyclitis, iritis, juvenile chronic arthritis, Kawasaki's disease (arteritis), or lipiduria;

(x) membranoproliferative glomerulonephritis (MPGN) I, microscopic polyangiitis, mixed cryoglobulinemia, molybdenum cofactor deficiency (MoCD) type A, pancreatitis, panniculitis, Pick's disease, polyarteritis nodosa (PAN), progressive subcortical gliosis, proteinuria, reduced glomerular filtration rate (GFR), or renovascular disorder;

(xi) multiple organ failure, multiple system atrophy (MSA), myotonic dystrophy, Niemann-Pick disease type C, chronic demyelinating diseases, or progressive supranuclear palsy;

(xii) spinal cord injury, spinal muscular atrophy, spondyloarthropathies, Reiter's syndrome, spontaneous fetal loss, recurrent fetal loss, pre-eclampsia, synucleinopathy, Takayasu's arteritis, post-partum thryoiditis, thyroiditis, Type I cryoglobulinemia, Type II mixed cryoglobulinemia, Type III mixed cryoglobulinemia, ulcerative colitis, uremia, urticaria, venous gas embolus (VGE), or Wegener's granulomatosis;

In one embodiment, an active compound or its salt or composition as described herein is useful for treating or preventing a disorder selected from autoimmune oophoritis, endometriosis, autoimmune orchitis, Ord's thyroiditis, autoimmune enteropathy, coeliac disease, Hashimoto's encephalopathy, antiphospholipid syndrome (APLS) (Hughes syndrome), aplastic anemia, autoimmune lymphoproliferative syndrome (Canale-Smith syndrome), autoimmune neutropenia, Evans syndrome, pernicious anemia, pure red cell aplasia, thrombocytopenia, adipose dolorosa (Dercum's disease), adult onset Still's disease, ankylosing spondylitis, CREST syndrome, drug-induced lupus, eosinophilic fasciitis (Shulman's syndrome), Felty syndrome, IgG4-related disease, mixed connective tissue disease (MCTD), palindromic rheumatism (Hench-Rosenberg syndrome), Parry-Romberg syndrome, Parsonage-Turner syndrome, relapsing polychondritis (Meyenburg-Altherr-Uehlinger syndrome), retroperitonial fibrosis, rheumatic fever, Schnitzler syndrome, fibromyalgia, neuromyotonia (Isaac's disease), paraneoplastic degeneration, autoimmune inner ear disease, Meniere's disease, interstitial cystitis, autoimmune pancreatitis, zika virus-related disorders, chikungunya virus-related disorders, subacute bacterial endocarditis (SBE), IgA nephropathy, IgA vasculitis, polymyalgia rheumatic, rheumatoid vasculitis, alopecia areata, autoimmune progesterone dermatitis, dermatitis herpetiformis, erythema nodosum, gestational pemphigoid, hidradenitis suppurativa, lichen sclerosus, linear IgA disease (LAD), morphea, myositis, *Pityriasis lichenoides* et varioliformis *acuta*, vitiligo post-myocardial infarction syndrome (Dressler's syndrome), post-pericardiotomy syndrome, autoimmune retinopathy, Cogan syndrome, Graves opthalmopathy, ligneous conjunctivitis, Mooren's ulcer, opsoclonus myoclonus syndrome, optic neuritis, retinocochleocerebral vasculopathy (Susac's syndrome), sympathetic opthalmia, Tolosa-Hunt syndrome, interstitial lung disease, antisynthetase syndrome, Addison's disease, autoimmune polyendocrine syndrome (APS) type I, autoimmune polyendocrine syndrome (APS) type II, autoimmune polyendocrine syndrome (APS) type III, disseminated sclerosis (multiple sclerosis, pattern II), rapidly progressing glomerulonephritis (RPGN), juvenile rheumatoid arthritis, enthesitis-related arthritis, reactive arthritis (Reiter's syndrome), autoimmune hepatitis or lupoid hepatitis, primary biliary cirrhosis (PBS), primary sclerosing cholangitis, microscopic colitis, latent lupus (undifferentiated connective tissue disease (UCTD)), acute disseminated encephalomyelitis (ADEM), acute motor axonal neuropathy, anti-n-methyl-D-aspartate receptor encephalitis, Balo concentric sclerosis (Schilders disease), Bickerstaff's encephalitis, chronic inflammatory demyelinating polyneuropathy, idiopathic inflammatory demyelinating disease, Lambert-Eaton mysathenic syndrome, Oshtoran syndrome, pediatric autoimmune neuropsychiatric disorder associated with *Streptococcus* (PANDAS), progressive inflammatory neuropathy, restless leg syndrome, stiff person syndrome, Sydenhem syndrome, transverse myelitis, lupus vasculitis, leukocytoclastic vasculitis, Microscopic Polyangiitis, polymyositis or ischemic-reperfusion injury of the eye.

In one embodiment, an active compound or its salt or composition as described herein is useful for treating or preventing a disorder that is mediated by the complement pathway, and in particular, a pathway that is modulated by complement Factor D. In another embodiment, the compound is effective to treat the disorder, albeit through a different mechanism.

In certain embodiments, the disorder is an inflammatory disorder, an immune disorder, an autoimmune disorder, or complement Factor D related disorders in a host. In one embodiment, the disorder is an ocular disorder or an eye disorder.

Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, anterior uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

In a further embodiment, the disorder is selected from age-related macular degeneration, glaucoma, diabetic retinopathy, neuromyelitis optica (NMO), vasculitis, hemodialysis, blistering cutaneous diseases (including bullous pemphigoid, pemphigus, and epidermolysis bullosa), ocular cicatrical pemphigoid, uveitis, adult macular degeneration, diabetic retinopa retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, postoperative inflammation, and retinal vein occlusion, or uveitis (including Behcet's disease and other sub-types of uveitis).

In some embodiments, complement mediated diseases include ophthalmic diseases (including early or neovascular age-related macular degeneration and geographic atrophy), autoimmune diseases (including arthritis, rheumatoid arthritis), respiratory diseases, cardiovascular diseases. In other embodiments, the compounds of the invention are suitable for use in the treatment of diseases and disorders associated with fatty acid metabolism, including obesity and other metabolic disorders.

Disorders that may be treated or prevented by an active compound or its salt or composition as described herein also include, but are not limited to:

(i) paroxysmal nocturnal hemoglobinuria (PNH), hereditary angioedema, capillary leak syndrome, atypical hemolytic uremic syndrome (aHUS), hemolytic uremic syndrome (HUS), abdominal aortic aneurysm, hemodialysis complications, hemolytic anemia, or hemodialysis;

(ii) myasthenia gravis, multiple sclerosis, C3 glomerulonephritis (C3GNs), MPGN II (dense deposit disease), neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome;

(iii) inflammatory effects of sepsis, systemic inflammatory response syndrome (SIRS), disorders of inappropriate or undesirable complement activation, interleukin-2 induced toxicity during IL-2 therapy, inflammatory disorders, inflammation of autoimmune diseases, system lupus erythematosus (SLE), Crohn's disease, rheumatoid arthritis, inflammatory bowel disease, lupus nephritis, arthritis, immune complex disorders and autoimmune diseases, systemic lupus, or lupus erythematosus;

(iv) ischemia/reperfusion injury (I/R injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes;

(v) Alzheimer's dementia, stroke, schizophrenia, traumatic brain injury, trauma, Parkinson's disease, epilepsy, transplant rejection, prevention of fetal loss, biomaterial reactions (e.g. in hemodialysis, implants), hyperacute allograft rejection, xenograft rejection, transplantation, psoriasis, burn injury, thermal injury including burns or frostbite;

(vi) asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, or immune complex-associated inflammation.

In one embodiment, a method for the treatment of paroxysmal nocturnal hemoglobinuria (PNH) in a host is provided that includes the administration of an effective amount of an active compound or its salt or composition as described herein. In another embodiment, a method for the treatment of age-related macular degeneration (AMD) in a host is provided that includes the administration of an effective amount an active compound or its salt or composition as described herein. In another embodiment, a method for the treatment of rheumatoid arthritis in a host is provided that includes the administration of an effective amount of an active compound or its salt or composition as described herein. In another embodiment, a method for the treatment of multiple sclerosis in a host is provided that includes the administration of an effective amount of an active compound or its salt or composition as described herein. In another embodiment, a method for the treatment of myasthenia gravis in a host is provided that includes the administration of an effective amount of an active compound or its salt or composition as described herein. In another embodiment, a method for the treatment of atypical hemolytic uremic syndrome (aHUS) in a host is provided that includes the administration of an effective amount of an active compound or its salt or composition as described herein. In another embodiment, a method for the treatment of C3 glomerulonephritis in host is provided that includes the administration of an effective amount of an active compound or its salt or composition as described herein. In another embodiment, a method for the treatment of abdominal aortic aneurysm in host is provided that includes the administration of an effective amount of an active compound or its salt or composition as described herein. In another embodiment, a method for the treatment of neuromyelitis optica (NMO) in a host is provided that includes the administration of an effective amount of an active compound or its salt or composition as described herein.

In one embodiment, a method for the treatment of sickle cell in a host is provided that includes the administration of an effective amount of an active compound or its salt or composition as described herein. In one embodiment, a method for the treatment of immunothrombocytopenic purpura (ITP), thrombotic thrombocytopenic purpura (TTP), or idiopathic thrombocytopenic purpura (ITP) in a host is provided that includes the administration of an effective amount of an active compound or its salt or composition as described herein. In one embodiment, a method for the treatment of ANCA-vasculitis in a host is provided that includes the administration of an effective amount of an active compound or its salt or composition as described herein. In one embodiment, a method for the treatment of IgA nephropathy in a host is provided that includes the administration of an effective amount of an active compound or its salt or composition as described herein. In one embodiment, a method for the treatment of rapidly progressing glomerulonephritis (RPGN), in a host is provided that includes the administration of an effective amount of an active compound or its salt or composition as described herein. In one embodiment, a method for the treatment of lupus nephritis, in a host is provided that includes the administration of an effective amount of an active compound or its salt or composition as described herein. In one embodiment, a method for the treatment of hemorraghic dengue fever, in a host is provided that includes the administration of an effective amount of an active compound or its salt or composition as described herein.

In some embodiments, the present invention provides methods of treating or preventing an inflammatory disorder or a complement related disease, by administering to a host in need thereof an effective amount of an active compound or its salt or composition as described herein. In some embodiments, the present invention provides methods of treating or preventing an inflammatory disorder more generally, an immune disorder, autoimmune disorder, or complement Factor D related disease in a host, by providing an effective amount of a compound or pharmaceutically acceptable salt of an active compound or its salt or composition as described herein to patient with a Factor D mediated inflammatory disorder. An active compound or its salt or composition as described herein as the only active agent or may be provided together with one or more additional active agents.

In one embodiment, a method for the treatment of a disorder associated with a dysfunction in the complement cascade in a host is provided that includes the administration of an effective amount of an active compound or its salt or composition as described herein. In one embodiment, a method of inhibiting activation of the alternative complement pathway in a subject is provided that includes the administration of an effective amount of an active compound or its salt or composition as described herein. In one embodiment, a method of modulating Factor D activity in a subject is provided that includes the administration of an effective amount of an active compound or its salt or composition as described herein.

In an additional alternative embodiment, an active compound or its salt or composition as described herein is used in the treatment of an autoimmune disorder.

The complement pathway enhances the ability of antibodies and phagocytic cells to clear microbes and damaged cells from the body. It is part of the innate immune system and in healthy individuals is an essential process. Inhibiting the complement pathway will decrease the body's immune system response. Therefore, it is an object of the present invention to treat autoimmune disorders by administering an effective does of an active compound or its salt or composition as described herein to a subject in need thereof.

In one embodiment the autoimmune disorder is caused by activity of the complement system. In one embodiment the autoimmune disorder is caused by activity of the alternative complement pathway. In one embodiment the autoimmune disorder is caused by activity of the classical complement pathway. In another embodiment the autoimmune disorder is caused by a mechanism of action that is not directly related to the complement system, such as the over-proliferation of T-lymphocytes or the over-production of cytokines.

Non-limiting examples of autoimmune disorders include: lupus, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), diabetes, multiple sclerosis, pernicious anemia, psoriasis, rheumatoid arthritis, sarcoidosis, and scleroderma.

In one embodiment, an active compound or its salt or composition as described herein is used in the treatment of lupus. Non-limiting examples of lupus include lupus erythematosus, cutaneous lupus, discoid lupus erythematosus, chilblain lupus erythematosus, or lupus erythematosus-lichen planus overlap syndrome.

Lupus erythematosus is a general category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Multiple Sclerosis is an autoimmune demyelinating disorder that is believed to be T lymphocyte dependent. MS generally exhibits a relapsing-remitting course or a chronic progressive course. The etiology of MS is unknown, however, viral infections, genetic predisposition, environment, and autoimmunity all appear to contribute to the disorder. Lesions in MS patients contain infiltrates of predominantly T lymphocyte mediated microglial cells and infiltrating macrophages. CD4+ T lymphocytes are the predominant cell type present at these lesions. The hallmark of the MS lesion is plaque, an area of demyelination sharply demarcated from the usual white matter seen in MRI scans. Histological appearance of MS plaques varies with different stages of the disease. In active lesions, the blood-brain barrier is damaged, thereby permitting extravasation of serum proteins into extracellular spaces. Inflammatory cells can be seen in perivascular cuffs and throughout white matter. CD4+ T-cells, especially Th1, accumulate around postcapillary venules at the edge of the plaque and are also scattered in the white matter. In active lesions, up-regulation of adhesion molecules and markers of lymphocyte and monocyte activation, such as IL2-R and CD26 have also been observed. Demyelination in active lesions is not accompanied by destruction of oligodendrocytes. In contrast, during chronic phases of the disease, lesions are characterized by a loss of oligodendrocytes and hence, the presence of myelin oligodendrocyte glycoprotein (MOG) antibodies in the blood.

Diabetes can refer to either type 1 or type 2 diabetes. In one embodiment an active compound or its salt or composition as described herein is provided at an effective dose to treat a patient with type 1 diabetes. In one embodiment an active compound or its salt or composition as described herein is provided at an effective dose to treat a patient with type 2 diabetes.

Type 1 diabetes is an autoimmune disease. An autoimmune disease results when the body's system for fighting infection (the immune system) turns against a part of the body. The pancreas then produces little or no insulin.

V. Combination Therapy

In one embodiment an active compound or its salt or composition as described herein may be provided in combination or alternation with or preceded by, concomitant with or followed by, an effective amount of at least one additional therapeutic agent, for example, for treatment of a disorder listed herein. Non-limiting examples of second active agents for such combination therapy are provided below.

In one embodiment, an active compound or its salt or composition as described herein may be provided in combination or alternation with at least one additional inhibitor of the complement system or a second active compound with a different biological mechanism of action. In the description below and herein generally, whenever any of the terms referring to an active compound or its salt or composition as described herein are used, it should be understood that pharmaceutically acceptable salts, prodrugs or compositions are considered included, unless otherwise stated or inconsistent with the text.

In non-limiting embodiments, an active compound or its salt or composition as described herein may be provided together with a protease inhibitor, a soluble complement regulator, a therapeutic antibody (monoclonal or polyclonal), complement component inhibitor, receptor agonist, or siRNA.

In other embodiments, an active compound described herein is administered in combination or alternation with an antibody against tumor necrosis factor (TNF), including but not limited to infliximab (Remicade), adalimumab, certolizumab, golimumab, or a receptor fusion protein such as etanercept (Embrel).

In another embodiment, an active compound as described herein can be administered in combination or alternation with an anti-CD20 antibody, including but not limited to rituximab (Rituxan), adalimumab (Humira), ofatumumab (Arzerra), tositumomab (Bexxar), obinutuzumab (Gazyva), or ibritumomab (Zevalin).

In an alternative embodiment, an active compound as described herein can be administered in combination or alternation with an anti-IL6 antibody, including but not limited to tocilizumab (Actemra) and siltuximab (Sylvant).

In an alternative embodiment, an active compound as described herein can be administered in combination or alternation with an IL17 inhibitor, including but not limited to secukibumab (Cosentyx).

In an alternative embodiment, an active compound as described herein can be administered in combination or alternation with a p40 (IL12/IL23) inhibitor, including but not limited to ustekinumab (Stelara).

In an alternative embodiment, an active compound as described herein can be administered in combination or alteration with an TL23 inhibitor, including but not limited to risankizumab.

In an alternative embodiment, an active compound as described herein can be administered in combination or alteration with an anti-interferon α antibody, for example but not limited to sifalimumab.

In an alternative embodiment, an active compound as described herein can be administered in combination or alteration with a kinase inhibitor, for example but not limited to a JAK1/JAK3 inhibitor, for example but not limited to tofacitinib (Xelianz). In an alternative embodiment, an active compound as described herein can be administered in combination or alteration with a JAK1/JAK2 inhibitor, for example but not limited to baracitibib.

In another embodiment, an active compound as described herein can be administered in combination or alternation with an immune checkpoint inhibitor. Non-limiting examples of checkpoint inhibitors are anti-PD-1 or anti-PDL1 antibodies (for example, Nivolumab, Pembrolizumab, Pidilizumab and Atezolizumab) and anti-CTLA4 antibodies (Ipilimumab and Tremelimumab).

Non-limiting examples of active agents that can be used in combination with active compounds described herein are:

Protease inhibitors: plasma-derived C1-INH concentrates, for example Cetor® (Sanquin), Berinert-P® (CSL Behring, Lev Pharma), and Cinryze®; recombinant human C1-inhibitors, for example Rhucin®; ritonavir (Norvir®, Abbvie, Inc.);

Soluble complement regulators: Soluble complement receptor 1 (TP10) (Avant Immunotherapeutics); sCR1-sLe$^x$/TP-20 (Avant Immunotherapeutics); MLN-2222/CAB-2 (Millenium Pharmaceuticals); Mirococept (Inflazyme Pharmaceuticals);

Therapeutic antibodies: Eculizumab/Soliris (Alexion Pharmaceuticals); Pexelizumab (Alexion Pharmaceuticals); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-CD38 (Genmab A/S);

Complement component inhibitors: Compstatin/POT-4 (Potentia Pharmaceuticals); ARC1905 (Archemix);

Receptor agonists: PMX-53 (Peptech Ltd.); JPE-137 (Jerini); JSM-7717 (Jerini);

Others: Recombinant human MBL (rhMBL; Enzon Pharmaceuticals);

Imides and glutarimide derivatives such as thalidomide, lenalidomide, pomalidomide;

Additional non-limiting examples that can be used in combination or alternation with an active compound or its salt or composition as described herein include the following.

| Non-limiting examples of potential therapeutics for combination therapy | | | |
|---|---|---|---|
| Name | Target | Company | Class of Molecule |
| LFG316 | C5 | Novartis/Morphosys | Monoclonal antibody |
| 4(1MEW)APL-1, APL-2 | C3/C3b | Apella | Compstatin Family |
| 4(1MeW)POT-4 | C3/C3b | Potentia | Compstatin Family |
| Anti-C5 siRNA | C5 | Alnylam | Si-RNA |
| Anti-FB siRNA | CFB | Alnylam | SiRNA |
| ARC1005 | C5 | Novo Nordisk | Aptamers |
| ATA | C5 | N.A. | Chemical |
| Coversin | C5 | Volution Immuno-Pharmaceuticals | Small animal protein |
| CP40/AMY-101, PEG-Cp40 | C3/C3b | Amyndas | Compstatin Family |
| CRIg/CFH | CAP C3 convertase | NA | CFH-based protein |

Non-limiting examples of potential therapeutics for combination therapy

| Name | Target | Company | Class of Molecule |
| --- | --- | --- | --- |
| Cynryze | C1n/C1s | ViroPharma/Baxter | Human purified protein |
| FCFD4514S | CFD | Genentech/Roche | Monoclonal antibody |
| H17 | C3 (C3b/iC3b) | EluSys Therapeutics | Monoclonal antibody |
| Mini-CFH | CAP C3 convertase | Amyndas | CFH-based protein |
| Mirococept (APT070) | CAP and CCP C3 | NA | CR1-based protein |
| Mubodine | C5 | Adienne | Monoclonal antibody |
| RA101348 | C5 | Rapharma | Small molecule |
| sCR1 (CDX-1135) | CAP and CP C3 | Celldex | CR1-based protein |
| SOBI002 | C5 | Swedish Orphan Biovitrum | Affibody |
| SOMAmers | C5 | SomaLogic | Aptamers |
| SOMAmers | CFB and CFD | SomaLogic | Aptamers (SELEX) |
| TA106 | CFB | Alexion Pharmaceuticals | Monoclonal antibody |
| TNT003 | C1s | True North | Monoclonal antibody |
| TT30 (CR2/CFH) | CAP C3 convertase | Alexion | CFH-based protein |
| TT32 (CR2/CR1) | CAP and CCP C3 | Alexion Pharmaceuticals | CR1-based protein |
| Nafamostat (FUT-175, Futhan) | C1s, CFD, other proteases | Torri Pharmaceuticals | Small molecule |
| OMS721 | MASP-2 | Omeros | Monoclonal antibody |
| OMS906 | MASP-2 | Omeros | Monoclonal antibody |
| Bikaciomab, NM9308 | CFB | Novelmed | Monoclonal antibody |
| NM9401 | Properdin | Novelmed | Monoclonal antibody |
| CVF, HC-1496 | C3 | InCode | Recombinant peptide |
| ALXN1102/ALXN1103 (TT30) | C3-conv, C3b | Alexion Pharmaceuticals | Regulator |
| rFH | C3-conv, C3b | Optherion | Regulator |
| 5C6, AMY-301 | CFH | Amyndas | Regulator |
| Erdigna | C5 | Adienne Pharma | Antibody |
| ARC 1905 | C5 | Opthotech | Monoclonal Antibody |
| MEDI7814 | C5/C5a | MedImmune | Monoclonal Antibody |
| NOX-D19 | C5a | Noxxon | Aptamer (Spiegelmer) |
| IFX-1, CaCP29 | C5a | InflaRx | Monoclonal Antibody |
| PMX53, PMX205 | C5aR | Cephalon, Teva | Peptidomimetic |
| CCX168 | C5aR | ChemoCentryx | Small molecule |
| ADC-1004 | C5aR | Alligator Bioscience | Small molecule |
| Anti-C5aR-151, NN8209; Anti-C5aR-215, NN8210 | C5aR | Novo Nordisk | Monoclonal Antibody |
| Imprime PGG | CR3 | Biothera | Soluble beta-glucan |

In one embodiment, an active compound or its salt or composition as described herein may be provided together with a compound that inhibits an enzyme that metabolizes an administered protease inhibitor. In one embodiment, a compound or salt may be provided together with ritonavir.

In one embodiment, an active compound or its salt or composition as described herein may be provided in combination with a complement C5 inhibitor or C5 convertase inhibitor. In another embodiment, an active compound or its salt or composition as described herein may be provided in combination with eculizumab, a monoclonal antibody directed to the complement factor C5 and manufactured and marketed by Alexion Pharmaceuticals under the tradename Soliris. Eculizumab has been approved by the U.S. FDA for the treatment of PNH and aHUS.

In one embodiment, an active compound or its salt or composition as described herein may be provided together with a compound that inhibits complement factor D. In one embodiment of the invention, an active compound or its salt or composition as described herein as described herein can be used in combination or alternation with a compound described in Biocryst Pharmaceuticals U.S. Pat. No. 6,653, 340 titled "Compounds useful in the complement, coagulate and kallikrein pathways and method for their preparation" describes fused bicyclic ring compounds that are potent inhibitors of Factor D; Novartis PCT patent publication WO2012/093101 titled "Indole compounds or analogues thereof useful for the treatment of age-related macular degeneration" describes certain Factor D inhibitors; Novartis PCT patent publications WO2014/002051, WO2014/002052, WO2014/002053, WO2014/002054, WO2014/002057, WO2014/002058, WO2014/002059, WO2014/005150, WO2014/009833, WO 2013/164802, WO 2015/009616, WO 2015/066241, Bristol-Myers Squibb PCT patent publication WO2004/045518 titled "Open chain prolyl urea-related modulators of androgen receptor function"; Japan Tobacco Inc. PCT patent publication WO1999/048492 titled "Amide derivatives and nociceptin antagonists"; Ferring B. V. and Yamanouchi Pharmaceutical Co. LTD. PCT patent publication WO1993/020099 titled "CCK and/or gastrin receptor ligands"; Alexion Pharmaceuticals PCT patent publication WO1995/029697 titled "Methods and compositions for the treatment of glomerulonephritis and other inflammatory diseases"; or Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders."

In one embodiment, an active compound or its salt or composition as described herein is administered in combination with an anti-inflammatory drug, antimicrobial agent, anti-angiogenesis agent, immunosuppressant, antibody, steroid, ocular antihypertensive drug or combinations thereof. Examples of such agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluoromethalone, rimexolone, anecortave, cyclosporine, methotrexate, tacrolimus and combinations thereof.

In one embodiment of the present invention, an active compound or its salt or composition as described herein can be administered in combination or alternation with at least one immunosuppressive agent. The immunosuppressive agent as non-limiting examples, may be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, tocilizumab (Actemra), siltuximab (Sylvant), secukibumab (Cosentyx), ustekinumab (Stelara), risankizumab, sifalimumab, aspirin and ibuprofen.

Examples of anti-inflammatory agents include methotrexate, dexamethasone, dexamethasone alcohol, dexamethasone sodium phosphate, fluromethalone acetate, fluromethalone alcohol, lotoprendol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flubiprofen, naproxan, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucocorticoids, diclofenac, and any combination thereof. In one embodiment, an active compound or its salt or composition as described herein is combined with one or more non-steroidal anti-inflammatory drugs (NSAIDs) selected from naproxen sodium (Anaprox), celecoxib (Celebrex), sulindac (Clinoril), oxaprozin (Daypro), salsalate (Disalcid), diflunisal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

In one embodiment, an active compound or its salt or composition as described herein is administered in combination or alteration with an omega-3 fatty acid or a peroxisome proliferator-activated receptor (PPARs) agonist. Omega-3 fatty acids are known to reduce serum triglycerides by inhibiting DGAT and by stimulating peroxisomal and mitochondrial beta oxidation. Two omega-3 fatty acids, eicosapentaenoic acid (EPA) and docosahexaenoic acid (DHA), have been found to have high affinity for both PPAR-alpha and PPAR-gamma. Marine oils, e.g., fish oils, are a good source of EPA and DHA, which have been found to regulate lipid metabolism. Omega-3 fatty acids have been found to have beneficial effects on the risk factors for cardiovascular diseases, especially mild hypertension, hypertriglyceridemia and on the coagulation factor VII phospholipid complex activity. Omega-3 fatty acids lower serum triglycerides, increase serum HDL-cholesterol, lower systolic and diastolic blood pressure and the pulse rate, and lower the activity of the blood coagulation factor VII-phospholipid complex. Further, omega-3 fatty acids seem to be well tolerated, without giving rise to any severe side effects. One such form of omega-3 fatty acid is a concentrate of omega-3, long chain, polyunsaturated fatty acids from fish oil containing DHA and EPA and is sold under the trademark Omacor®. Such a form of omega-3 fatty acid is described, for example, in U.S. Pat. Nos. 5,502,077, 5,656,667 and 5,698,594, the disclosures of which are incorporated herein by reference.

Peroxisome proliferator-activated receptors (PPARs) are members of the nuclear hormone receptor superfamily ligand-activated transcription factors that are related to retinoid, steroid and thyroid hormone receptors. There are three distinct PPAR subtypes that are the products of different genes and are commonly designated PPAR-alpha, PPAR-beta/delta (or merely, delta) and PPAR-gamma. General classes of pharmacological agents that stimulate peroxisomal activity are known as PPAR agonists, e.g., PPAR-alpha agonists, PPAR-gamma agonists and PPAR-delta agonists. Some pharmacological agents are combinations of PPAR agonists, such as alpha/gamma agonists, etc., and some other pharmacological agents have dual agonist/antagonist activity. Fibrates such as fenofibrate, bezafibrate, clofibrate and gemfibrozil, are PPAR-alpha agonists and are used in patients to decrease lipoproteins rich in triglycerides, to increase HDL and to decrease atherogenic-dense LDL. Fibrates are typically orally administered to such patients. Fenofibrate or 2-[4-(4-chlorobenzoyl)phenoxy]-2-methyl-propanoic acid, 1-methylethyl ester, has been known for many years as a medicinally active principle because of its efficacy in lowering blood triglyceride and cholesterol levels.

In one embodiment, the present invention provides a method of treating or preventing age-related macular degeneration (AMD) by administering to a subject in need thereof an effective amount of an active compound or its salt or composition as described herein in combination with an anti-VEGF agent. Non-limiting examples of anti-VEGF agents include, but are not limited to, aflibercept (Eylea®; Regeneron Pharmaceuticals); ranibizumab (Lucentis®: Genentech and Novartis); and pegaptanib (Macugen®; OSI Pharmaceuticals and Pfizer); Bevacizumab (Avastin; Genentech/Roche); anecortane acetate, squalamine lactate, and corticosteroids, including, but not limited to, triamcinolone acetonide.

In one embodiment, the present invention provides a method of treating or preventing paroxysmal nocturnal hemoglobinuria (PNH) by administering to a subject in need thereof an effective amount of an active compound or its salt or composition as described herein with an additional inhibitor of the complement system or another active compound with a different biological mechanism of action. In another embodiment, the present invention provides a method of treating or preventing paroxysmal nocturnal hemoglobinuria (PNH) by administering to a subject in need thereof an effective amount of an active compound or its salt or composition as described herein in combination or alternation with eculizumab. In another embodiment, the present invention provides a method of treating or preventing paroxysmal nocturnal hemoglobinuria (PNH) by administering to a subject in need thereof an effective amount of an active compound or its salt or composition as described herein in combination or alternation with CP40. In one embodiment, the additional agent is PEGylated-CP40. CP40 is a peptide inhibitor that shows a strong binding affinity for C3b and inhibits hemolysis of paroxysmal nocturnal hemoglobinuria (PNH) erythrocytes.

In one embodiment, the present invention provides a method of treating or preventing rheumatoid arthritis by administering to a subject in need thereof an effective amount of a composition comprising an active compound or its salt or composition as described herein in combination or alternation with an additional inhibitor of the complement system, or an active agent that functions through a different mechanism of action. In another embodiment, the present invention provides a method of treating or preventing rheumatoid arthritis by administering to a subject in need thereof an effective amount of an active compound or its salt or composition as described herein in combination or alternation with methotrexate. In certain embodiments, an active compound or its salt or composition as described herein is administered in combination or alternation with at least one additional therapeutic agent selected from: salicylates including aspirin (Anacin, Ascriptin, Bayer Aspirin, Ecotrin) and salsalate (Mono-Gesic, Salgesic); nonsteroidal anti-inflammatory drugs (NSAIDs); nonselective inhibitors of the cyclo-oxygenase (COX-1 and COX-2) enzymes, including diclofenac (Cataflam, Voltaren), ibuprofen (Advil, Motrin), ketoprofen (Orudis), naproxen (Aleve, Naprosyn), piroxicam (Feldene), etodolac (Lodine), indomethacin, oxaprozin (Daypro), nabumetone (Relafen), and meloxicam (Mobic); selective cyclo-oxygenase-2 (COX-2) inhibitors including Celecoxib (Celebrex); disease-modifying anti-rheumatic drugs (DMARDs), including azathioprine (Imuran), cyclosporine (Sandimmune, Neoral), gold salts (Ridaura, Solganal, Aurolate, Myochrysine), hydroxychloroquine (Plaquenil), leflunomide (Arava), methotrexate (Rheumatrex), penicillamine (Cuprimine), and sulfasalazine (Azulfidine); biologic drugs including abatacept (Orencia), etanercept (Enbrel), infliximab (Remicade), adalimumab (Humira), and anakinra (Kineret); corticosteroids including betamethasone (Celestone Soluspan), cortisone (Cortone), dexamethasone (Decadron), methylprednisolone (SoluMedrol, DepoMedrol), prednisolone (Delta-Cortef), prednisone (Deltasone, Orasone), and triamcinolone (Aristocort); gold salts, including Auranofin (Ridaura); Aurothioglucose (Solganal); Aurolate; Myochrysine; or any combination thereof.

In one embodiment, the present invention provides a method of treating or preventing multiple sclerosis by administering to a subject in need thereof an effective amount of an active compound or its salt or composition as described herein in combination or alternation with an additional inhibitor of the complement system, or an active agent that functions through a different mechanism of action. In another embodiment, the present invention provides a method of treating or preventing multiple sclerosis by administering to a subject in need thereof an effective amount of an active compound or its salt or composition as described herein in combination or alternation with a corticosteroid. Examples of corticosteroids include, but are not limited to, prednisone, dexamethasone, solumedrol, and methylprednisolone. In one embodiment, an active compound or its salt or composition as described herein is combined with at least one anti-multiple sclerosis drug, for example, selected from: Aubagio (teriflunomide), Avonex (interferon beta-1a), Betaseron (interferon beta-1b), Copaxone (glatiramer acetate), Extavia (interferon beta-1b), Gilenya (fingolimod), Lemtrada (alemtuzumab), Novantrone (mitoxantrone), Plegridy (peginterferon beta-1a), Rebif (interferon beta-1a), Tecfidera (dimethyl fumarate), Tysabri (natalizumab), Solu-Medrol (methylprednisolone), High-dose oral Deltasone (prednisone), H. P. Acthar Gel (ACTH), or a combination thereof.

In one embodiment, an active compound or its salt or composition as described herein is useful in a combination with another pharmaceutical agent to ameliorate or reduce a side effect of the agent. For example, in one embodiment, an active compound or its salt or composition as described herein may be used in combination with adoptive cell transfer therapies to reduce an associated inflammatory response associated with such therapies, for example, a cytokine mediated response such as cytokine release syndrome. In one embodiment, the adoptive cell transfer therapy includes the use of a chimeric antigen receptor T-Cell (CAR T). In one embodiment, the adoptive cell transfer therapy includes the use of a chimeric antigen receptor T-Cell (CAR T) or a dendritic cell to treat a hematologic or solid tumor, for example, a B-cell related hematologic cancer. In one embodiment, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19.

In an additional alternative embodiment, an active compound or its salt or composition as described herein may be provided in combination with eculizumab for the treatment of PNH, aHUSs, STEC-HUS, ANCA-vasculitis, AMD, CAD, chronic hemolysis, neuromyelitis optica, or transplantation rejection. In one embodiment, an active compound or its salt or composition as described herein may be provided in combination with compstatin or a compstatin derivative for the treatment of PNH, aHUSs, STEC-HUS, ANCA-vasculitis, AMD, CAD, chronic hemolysis, neuromyelitis optica, or transplantation rejection.

In one embodiment, an active compound or its salt or composition as described herein may be provided in combination with rituxan for the treatment of a complement mediated disorder. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, an active compound or its salt or composition as described herein may be provided in combination with cyclophosphamide for the treatment of a complement mediated disorder. In one embodiment, the disorder is an autoimmune disease. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, an active compound or its salt or composition as described herein is dosed in combination with a conventional DLE treatment for the treatment of lupus to a subject in need thereof.

Examples of conventional DLE treatments include topical corticosteroid ointments or creams, such as triamcinolone acetonide, fluocinolone, flurandrenolide, betamethasone valerate, or betamethasone dipropionate. Resistant plaques can be injected with an intradermal corticosteroid. Other potential DLE treatments include calcineurin inhibitors such as pimecrolimus cream or tacrolimus ointment. Particularly resistant cases can be treated with systemic antimalarial drugs, such as hydroxychloroquine (PLAQUENIL).

In one embodiment, an active compound or its salt or composition as described herein may be provided in combination with methotrexate for the treatment of Lupus.

In one embodiment, an active compound or its salt or composition as described herein may be provided in combination with azathioprine for the treatment of Lupus.

In one embodiment, an active compound or its salt or composition as described herein may be provided in combination with a non-steroidal anti-inflammatory drug for the treatment of Lupus.

In one embodiment, an active compound or its salt or composition as described herein may be provided in combination with a corticosteroid for the treatment of Lupus.

In one embodiment, an active compound or its salt or composition as described herein may be provided in combination with a belimumab (Benlysta) for the treatment of Lupus.

In one embodiment, an active compound or its salt or composition as described herein may be provided in combination with hydroxychloroquine (Plaquenil) for the treatment of Lupus.

In one embodiment, an active compound or its salt or composition as described herein may be provided in combination with sifalimumab for the treatment of Lupus.

In one embodiment, an active compound or its salt or composition as described herein may be provided in combination with OMS721 (Omeros) for the treatment of a complement mediated disorder. In one embodiment, an active compound or its salt or composition as described herein may be provided in combination with OMS906 (Omeros) for the treatment of a complement mediated disorder. In one embodiment, the complement mediated disorder is, for example, thrombotic thrombocytopenic purpura (TTP) or aHUS.

In one embodiment, an active compound or its salt or composition as described herein may be provided in combination with an anti-inflammatory agent, immunosuppressive agent, or anti-cytokine agent for the treatment or prevention of cytokine or inflammatory reactions in response to the administration of pharmaceuticals or biotherapeutics (e.g. adoptive T-cell therapy (ACT) such as CAR T-cell therapy, or monoclonal antibody therapy). In one embodiment, an active compound or its salt or composition as described herein may be provided in combination with a corticosteroid, for example prednisone, dexamethasone, solumedrol, and methylprednisolone, and/or anti-cytokine compounds targeting, e.g., IL-4, IL-10, IL-11, IL-13 and TGFβ. In one embodiment, an active compound or its salt or composition as described herein may be provided in combination with an anti-cytokine inhibitor including, but are not limited to, adalimumab, infliximab, etanercept, protopic, efalizumab, alefacept, anakinra, siltuximab, secukibumab, ustekinumab, golimumab, and tocilizumab, or a combination thereof. Additional anti-inflammatory agents that can be used in combination with an active compound or its salt or composition as described herein include, but are not limited to, non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline); DAB 486-IL-2 and/or DAB 389-IL-2 (IL-2 fusion proteins; Seragen); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein); R973401 (phosphodiesterase Type IV inhibitor); MK-966 (COX-2 Inhibitor); Iloprost, leflunomide (anti-inflammatory and cytokine inhibition); tranexamic acid (inhibitor of plasminogen activation); T-614 (cytokine inhibitor); prostaglandin E1; Tenidap (non-steroidal anti-inflammatory drug); Naproxen (non-steroidal anti-inflammatory drug); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine; Azathioprine; ICE inhibitor (inhibitor of the enzyme interleukin-1β converting enzyme); zap-70 and/or lck inhibitor (inhibitor of the tyrosine kinase zap-70 or lck); TNF-convertase inhibitors; anti-IL-12 antibodies; anti-IL-18 antibodies; interleukin-11; interleukin-13; interleukin-17 inhibitors; gold; penicillamine; chloroquine; chlorambucil; hydroxychloroquine; cyclosporine; cyclophosphamide; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine).

In a specific embodiment, an active compound or its salt or composition as described herein may be provided in combination with a corticosteroid for the treatment or prevention of cytokine or inflammatory reactions in response to the administration of pharmaceuticals or biotherapeutics. In another embodiment, an active compound or its salt or composition as described herein may be provided in combination with etarnercept for the treatment or prevention of cytokine or inflammatory reactions in response to the administration of pharmaceuticals or biotherapeutics. In another embodiment, an active compound or its salt or composition as described herein may be provided in combination with tocilizumab for the treatment or prevention of cytokine or inflammatory reactions in response to the administration of pharmaceuticals or biotherapeutics. In another embodiment, an active compound or its salt or composition as described herein may be provided in combination with etarnercept and tocilizumab for the treatment or prevention of cytokine or inflammatory reactions in response to the administration of pharmaceuticals or biotherapeutics. In another embodiment, an active compound or its salt or composition as described herein may be provided in combination with infliximab for the treatment or prevention of cytokine or inflammatory reactions in response to the administration of pharmaceuticals or biotherapeutics. In another embodiment, an active compound or its salt or composition as described herein may be provided in combination with golimumab for the treatment or prevention of cytokine or inflammatory reactions in response to the administration of pharmaceuticals or biotherapeutics.

VI. Combinations for Prophylactic or Concommitant Anti-Bacterial Therapy

In one aspect of the present invention, a method is provided for treating a host in need thereof that comprises administering an effective amount of a prophylactic anti-bacterial vaccine prior to administration of an active compound or its salt or composition for any of the disorders described herein. In another aspect of the present invention, a method is provided for treating a host in need thereof that comprises administering an effective amount of a prophylactic anti-bacterial drug, such as a pharmaceutical drug, prior to administration of an active compound or its salt or composition for any of the disorders described herein. In one aspect of the present invention, a method is provided for treating a host in need thereof that comprises administering an effective amount of an anti-bacterial vaccine after administration of an active compound or its salt or composition for any of the disorders described herein. In another aspect of the present invention, a method is provided for treating a host in need thereof that comprises administering an effective amount of an anti-bacterial drug, such as a pharmaceutical drug, after administration of an active compound or its salt or composition for any of the disorders described herein. In one embodiment, the disorder is PNH or aHUS. In one embodiment, the host has received an organ or other tissue or biological fluid transplant. In one embodiment, the host is also administered eculizumab.

In one aspect of the present invention, an active compound or its salt or composition as described herein is administered to a host concomitantly to a subject following the prophylactic administration of a vaccine against a bacterial infection. In one embodiment, the complement mediated disorder is PNH or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject concomitantly with the prophylactic administration of a vaccine against a bacterial infection. In one embodiment, the complement mediated disorder is PNH or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject and, during the administration period of the compound or salt, a vaccine against a bacterial infection is administered to the subject. In one embodiment, the complement mediated disorder is PNH or aHUS. In one embodiment, the subject has received an organ or other tissue or biological fluid transplant. In one embodiment, the subject is also administered eculizumab.

In one aspect of the present invention, the subject is administered an active compound or its salt or composition as described herein in combination with an antibiotic compound for the duration of factor D inhibitor administration. In one embodiment, the complement mediated disorder is PNH or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject following the prophylactic administration of a vaccine against a bacterial infection, and in combination with an antibiotic compound for the duration of factor D inhibitor administration. In one embodiment, the complement mediated disorder is PNH or aHUS. In one embodiment, the subject has received an organ or other tissue or biological fluid transplant. In one embodiment, the subject is also administered eculizumab.

In one embodiment, the subject, prior to receiving an active compound or its salt or composition as described herein, is vaccinated against a bacterial infection caused by the bacterium *Neisseria meningitidis*. In one embodiment, the subject is vaccinated against a bacterial infection caused by the bacterium *Haemophilus influenzae*. In one embodiment, the *Haemophilus influenzae* is *Haemophilus influenzae* serotype B (Hib). In one embodiment, the subject is vaccinated against a bacterial infection caused by *Streptococcus pneumoniae*. In one embodiment, the subject is vaccinated against a bacterial infection caused by the bacterium *Nisseria meningitidis, Haemophilus influenzae*, or *Streptococcus pneumoniae*, or a combination of one or more of *Nisseria meningitidis, Haemophilus influenzae*, or *Streptococcus pneumoniae*. In one embodiment, the subject is vaccinated against a bacterial infection caused by the bacterium *Nisseria meningitidis, Haemophilus influenzae*, and *Streptococcus pneumoniae*.

In other embodiments, the subject is vaccinated against a bacterial infection caused by a bacterium selected from a Gram-negative bacterium. In one embodiment, the subject is vaccinated against a bacterial infection caused by a bacterium selected from a Gram-positive bacterium. In one embodiment, the subject is vaccinated against a bacterial infection caused by the bacterium *Nisseria meningitidis, Haemophilus influenzae*, or *Streptococcus pneunemoniae*, or a combination of one or more of *Nisseria meningitidis, Haemophilus influenzae*, or *Streptococcus pneumoniae*, and one or more of, but not limited to, *Bacillus anthracis, Bordetella pertussis, Clostridium tetani, Corynebacterium diphtheria, Coxiella burnetii, Mycobacterium tuberculosis, Salmonella typhi, Vibrio cholerae, Anaplasma phagocytophilum, Ehrlichia ewingii, Ehrlichia chaffeensis, Ehrlichia canis, Neorickettsia sennetsu, Mycobacterium leprae, Borrelia burgdorferi, Borrelia mayonii, Borrelia afzelii, Borrelia garinii, Mycobacterium bovis, Staphylococcus aureus, Streptococcus pyogenes, Treponema pallidum, Francisella tularensis, Yersinia pestis,*

In one embodiment, the subject is vaccinated with one or more vaccines selected from, but not limited to, typhoid vaccine, live (Vivotif Berna Vaccine, PaxVax), typhoid Vi polysaccharide vaccine (Typhim Vi, Sanofi), pneumococcal 23-polyvalent vaccine, PCV13 (Pneumovax 23, Merck), pneumococcal 7-valent vaccine, PCV7 (Prevnar, Pfizer), pneumococcal 13-valent vaccine, PCV13 (Prevnar 13, Pfizer), *Haemophilus* b conjugate (prp-t) vaccine (ActHIB, Sanofi; Hibrix, GSK), *Haemophilus* b conjugate (hboc) vaccine (HibTITER, Neuron Biotech), *Haemophilus* b conjugate (prp-omp) vaccine (PedvaxHIB, Merck), *Haemophilus* b conjugate (prp-t) vaccine/meningococcal conjugate vaccine (MenHibrix, GSK), *Haemophilus* b conjugate (prp-t) vaccine/meningococcal conjugate vaccine/Hepatitis B vaccine (Comvax, Merck), meningococcal polysaccharide vaccine (Menomune A/C/Y/W-135, Sanofi), meningococcal conjugate vaccine/diphtheria CRM197 conjugate (Menveo, GSK; Menactra, Sanofi), meningococcal group B vaccine (Bexsero, GSK; Trumenba, Pfizer), anthrax vaccine adsorbed (Biothrax, Emergent Biosolutions), tetanus toxoid (Te Anatoxal Berna, Hendricks Regional Health), Bacillus Calmette and Guérin, live, intravesical (TheraCys, Sanofi; Tice BCG, Organon), cholera vaccine, live, oral (Vachora, Sanofi; Dukoral, SBL Vaccines; ShanChol, Shantha Biotec; Micromedex, Truven Health), tetanus toxoids and diphtheria absorbed (Tdap; Decavac, Sanofi; Tenivac, Sanofi; td, Massachusetts Biological Labs), diphtheria and tetanus toxois and pertussis (DTap; Daptacel, Sanofi; Infanrix, GSK; Tripedia, Sanofi), diphtheria and tetanus toxois and pertussis/polio (Kinrix, GSK; Quadracel, Sanofi), diphtheria and tetanus toxois and pertussis tetanus/hepatitis B/polio (Pediarix, GSK), diphtheria and tetanus toxois and pertussis/polio, *Haemophilus* influenza tybe b (Pentacel, Sanofi), and/or diphtheria, and pertussis (Tdap; Boostrix, GSK; Adacel, Sanofi), or a combination thereof.

As described above, a subject receiving a compound of the present invention to treat a disorder is prophylactically administered an antibiotic compound in addition to a factor D inhibitor described herein. In one embodiment, the subject is administered an antibiotic compound for the duration of administration of the active compound to reduce the development of a bacterial infection. Antibiotic compounds for concomitant administration with a factor D inhibitor described herein can be any antibiotic useful in preventing or reducing the effect of a bacterial infection. Antibiotics are well known in the art and include, but are not limited to, amikacin (Amikin), gentamicin (Garamycin), kanamycin (Kantrex), neomycin (Neo-Fradin), netilmicin (Netromycin), tobramycin (Nebcin), paromomycin (Humatin), streptomycin, spectinomycin (Trobicin), geldanamycin, herbimycin, rifaximin (Xifaxan), loracarbef (Lorabid), ertapenem (Invanz), doripenem (Doribax), imipenem/cilastatin (Primaxin), meropenem (Merrem), cefadroxil (Duricef), cefazolin (Ancef), cefalotin/cefalothin (Keflin), cephalexin (Keflex), cefaclor (Distaclor), cefamandole (Mandol), cefoxitin (Mefoxin), cefprozil (Cefzil), cefuroxime (Ceftin, Zinnat), cefixime (Cefspan), cefdinir (Omnicef, Cefdiel), cefditoren (Spectracef, Meiact), cefoperazone (Cefobid), cefotaxime (Claforan), cefpodoxime (Vantin) ceftazidime (Fortaz), ceftibuten (Cedax), ceftizoxime (Cefizox), ceftriaxone (Rocephin), cefepime (Maxipime), ceftaroline fosamil (Teflaro), ceftobiprole (Zeftera), teicoplanin (Targocid), vancomycin (Vancocin), telavancin (Vibativ), dalbavancin (Dalvance), oritavancin (Orbactiv), clindamycin (Cleocin), lincomycin (Lincocin), daptomycin (Cubicin), azithromycin (Zithromax, Surnamed, Xithrone), clarithromycin (Biaxin), dirithromycin (Dynabac), erythromycin (Erythocin, Erythroped), roxithromycin, troleandomycin (Tao), telithromycin (Ketek), spiramycin (Rovamycine), aztreonam (Azactam), furazolidone (Furoxone), nitrofurantoin (Macrodantin, Macrobid), linezolid (Zyvox), posizolid, radezolid, torezolid, amoxicillin (Novamox, Amoxil), ampicillin (Principen), azlocillin, carbenicillin (Geocillin), cloxacillin (Tegopen), dicloxacillin (Dynapen), flucloxacillin (Floxapen), mezlocillin (Mezlin), methicillin (Staphcillin), nafcillin (Unipen), oxacillin (Prostaphlin), penicillin G (Pentids), penicillin V (Veetids (Pen-Vee-K), piperacillin (Pipracil), penicillin G (Pfizerpen), temocillin (Negaban), ticarcillin (Ticar), amoxicillin/clavulanate (Augmentin), ampicillin/sulbactam (Unasyn), piperacillin/tazobactam (Zosyn), ticarcillin/clavulanate (Timentin), bacitracin, colistin (Coly-Mycin-S), polymyxin B, ciprofloxacin (Cipro, Ciproxin, Ciprobay), enoxacin (Penetrex), gatifloxacin (Tequin), gemifloxacin (Factive), levofloxacin (Levaquin), lomefloxacin (Maxaquin), moxifloxacin (Avelox), nalidixic acid (NegGram), norfloxacin (Noroxin), ofloxacin (Floxin, Ocuflox), trovafloxacin (Trovan), grepafloxacin (Raxar), sparfloxacin (Zagam), temafloxacin (Omniflox), mafenide (Sulfamylon), sulfacetamide (Sulamyd, Bleph-10), sulfadiazine (Micro-Sulfon), silver sulfadiazine (Silvadene), sulfadimethoxine (Di-Methox, Albon), sulfamethizole (Thiosulfil Forte), sulfamethoxazole (Gantanol), sulfanilamide, sulfasalazine (Azulfidine), sulfisoxazole (Gantrisin), trimethoprim-sulfamethoxazole (Co-trimoxazole) (TMP-SMX) (Bactrim, Septra), sulfonamidochrysoidine (Prontosil), demeclocycline (Declomycin), doxycycline (Vibramycin), minocycline (Minocin), oxytetracycline (Terramycin), tetracycline (Sumycin, Achromycin V, Steclin), clofazimine (Lamprene), dapsone (Avlosulfon), capreomycin (Capastat), cycloserine (Seromycin), ethambutol (Myambutol), ethionamide (Trecator), isoniazid (I.N.H.), pyrazinamide (Aldinamide), rifampicin (Rifadin, Rimactane), rifabutin (Mycobutin), rifapentine (Priftin), streptomycin, arsphenamine (Salvarsan), chloramphenicol (Chloromycetin), fosfomycin (Monurol, Monuril), fusidic acid (Fucidin), metronidazole (Flagyl), mupirocin (Bactroban), platensimycin, quinupristin/dalfopristin (Synercid), thiamphenicol, tigecycline (Tigacyl), tinidazole (Tindamax Fasigyn), trimethoprim (Proloprim, Trimpex), and/or teixobactin, or a combination thereof.

In one embodiment, the subject is administered a prophylactic antibiotic selected from cephalosporin, for example, ceftriaxone or cefotaxime, ampicillin-sulbactam, Penicillin G, ampicillin, chloramphenicol, fluoroquinolone, aztreonam, levofloxacin, moxifloxacin, gemifloxacin, vancomycin, clindamycin, cefazolin, azithromycin, meropenem, ceftaroline, tigecycline, clarithromycin, moxifloxacin, trimethoprim/sulfamethoxazole, cefuroxime, axetil, ciprofloxacin, rifampin, minocycline, spiramycin, and cefixime, or a combination of two or more thereof.

VII. Process of Preparation of Compounds of Formula I, Formula I' and Formula I"

Abbreviations
  ACN Acetonitrile
  Ac Acetyl
  $Ac_2O$ Acetic anhydride
  AcOEt, EtOAc ethyl acetate
  AcOH Acetic acid
  $Boc_2O$ di-tert-butyl dicarbonate
  Bu Butyl
  CAN Ceric ammonium nitrate
  CBz Carboxybenzyl
  CDI Carbonyldiimidazole
  $CH_3OH$, MeOH Methanol
  CsF Cesium fluoride
  CuI Cuprous iodide
  DCM, $CH_2Cl_2$ Dichloromethane
  DIEA, DIPEA N,N-diisopropylethylamine
  DMA N,N-dimethylacetamide
  DMAP 4-Dimethylaminopyridine
  DMF N,N-dimethylformamide
  DMS Dimethyl sulfide
  DMSO Dimethylsulfoxide
  DPPA Diphenyl phosphoryl azide
  EDCI 1-Ethyl-3-(3-dimethylaminopropyl)carbodiimide
  Et Ethyl
  $Et_3N$, TEA Triethylamine
  EtOAc Ethylacetate
  EtOH Ethanol
  HATU 1-[Bis(dimethylamino)methylene]-1H-1,2,3-triazolo[4,5-b]pyridinium3-oxide hexafluorophosphate
  HCl Hydrochloric acid
  HOBT Hydroxybenzotriazole
  iBu, i-Bu, isoBu Isobutyl
  iPr, i-Pr, isoPr Isopropyl
  $^iPr_2NEt$ N,N-diisopropylethylamine
  $K_2CO_3$ Potassium carbonate
  $K_2CO_3$ Potassium carbonate
  LiOH Lithium hydroxide
  Me Methyl
  MeI Methyl iodide
  Ms Mesyl
  MsCl Mesylchloride
  MTBE Methyl $^t$butylether
  $Na_2SO_4$ Sodium sulfate
  NaCl Sodium chloride
  NaH Sodium hydride
  $NaHCO_3$ Sodium bicarbonate
  NBS N-bromo succinimide
  NCS N-chloro succinimide
  $NEt_3$ Trimethylamine
  NMP N-Methyl-2-pyrrolidone
  PCC Pyridinium chlorochromate
  Pd $(OAc)_2$ Palladium acetate
  $Pd(dppf)Cl_2$ [1,1'-Bis(diphenylphosphino) ferrocene]dichloropalladium(II)
  $Pd(PPh_3)_2Cl_2$ Bis(triphenylphosphine)palladium(II) dichloride
  $Pd(PPh_3)_4$ Tetrakis(triphenylphosphine)palladium(0)
  Pd/C Palladium on carbon
  $Pd_2(dba)_3$ Tris(dibenzylideneacetone)dipalladium(0)
  PMB 4-Methoxybenzyl ether
  $PPh_3$ Triphenylphosphine
  Pr Propyl
  Py, py Pyridine
  RT Room temperature
  TBAF Tetra-n-butylammonium fluoride
  TBAT Tetrabutylammonium difluorotriphenylsilicate
  tBu, t-Bu tertbutyl
  tBuOK Potassium tert-butoxide
  TEA Trimethylamine
  $Tf_2O$ Trifluoromethanesulfonic anhydride
  TFA Trifluoroacetic acid
  THF Tetrahydrofuran
  TMS Trimethylsilane
  TMSBr Bromotrimethylsilane
  $t_R$ Retention time
  Troc 2,2,2-Trichlorethoxycarbonyl chloride
  Zn $(CN)_2$ Zinc cyanide
General Methods All nonaqueous reactions were performed under an atmosphere of dry argon or nitrogen gas using anhydrous solvents. The progress of reactions and the purity of target compounds were determined using one of the two liquid chromatography (LC) methods listed below. The structure of starting materials, intermediates, and final products was confirmed by standard analytical techniques, including NMR spectroscopy and mass spectrometry.
  LC Method A
  Instrument: Waters Acquity Ultra Performance LC
  Column: ACQUITY UPLC BEH C18 2.1×50 mm, 1.7 m
  Column Temperature: 40° C.
  Mobile Phase: Solvent A: $H_2O$+0.05% FA; Solvent B: $CH_3CN$+0.05% FA
  Flow Rate: 0.8 mL/min
  Gradient: 0.24 min @ 15% B, 3.26 min gradient (15-85% B), then 0.5 min @ 85% B.
  Detection: UV (PDA), ELS, and MS (SQ in EI mode)
  LC Method B
  Instrument: Shimadzu LC-2010A HT
  Column: Athena, C18-WP, 50×4.6 mm, 5 m
  Column Temperature: 40° C.
  Mobile Phase: Solvent A: $H_2O/CH_3OH/FA$=90/10/0.1; Solvent B: $H_2O/CH_3OH/FA$=10/90/0.1
  Flow Rate: 3 mL/min
  Gradient: 0.4 min @ 30% B, 3.4 min gradient (30-100% B), then 0.8 min @ 100% B
  Detection: UV (220/254 nm)
  LC Method C
  Instrument: Agilent 1100/1200 series LC system with DAD detector
  Column: Atlantis dC18 (250×4.6) mm, 5 μm
  Column Temperature: Ambient Mobile Phase A: 0.1% TFA in water, Mobile Phase B: Acetonitrile
Flow Rate: 1.0 mL/min
Gradient:

| Time (min) | 0.0 | 15 | 20 | 23 | 30 |
|---|---|---|---|---|---|
| % B | 10 | 100 | 100 | 10 | 10 |

Detection: (210-400 nm)
LC Method D
Instrument: Shimadzu LC 20AD system with PDA detector
Column: Phenomenex Gemini NX C18 (150×4.6) mm, 5 µm
Column Temperature: Ambient
Mobile Phase A: 10 mM $NH_4OAC$ in water, Mobile Phase B: Acetonitrile
Flow Rate: 1.0 mL/min
Gradient:

| Time (min) | 0.0 | 15 | 20 | 23 | 30 |
|---|---|---|---|---|---|
| % B | 10 | 100 | 100 | 10 | 10 |

Detection: (210-400 nm)

Example 1. General Route of Synthesis

A compound of the present invention can be prepared, for example, from a central core. In one embodiment, for example, the central core Structure 1 is an N-protected amino acid where $X^1$ is nitrogen and PG=protecting group. In one embodiment, the central core is coupled to an amine to generate an amide of Structure 2 (wherein L-B includes a C(O)N moiety). Structure 2 can then be deprotected to generate Structure 3. Structure 3 is coupled to Structure 4 (A-COOH) to generate a second amide bond, forming a compound within Formula I. The chemistry is illustrated in Route 1.

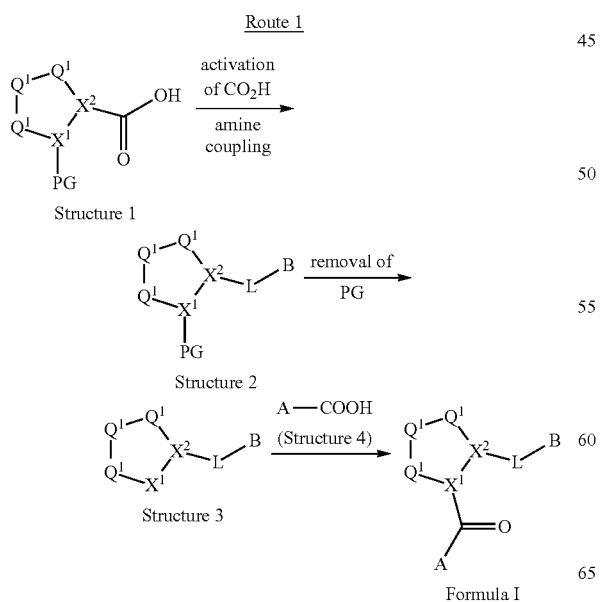

In an alternative embodiment, central core Structure 5 is reacted with a heterocyclic or heteroaryl compound to generate a compound of Structure 6. In one embodiment, Structure 6 is deprotected to generate a carboxylic acid, Structure 7. In one embodiment, Structure 7 is coupled to an amine to generate a compound of Formula I. This chemistry is illustrated in Route 2.

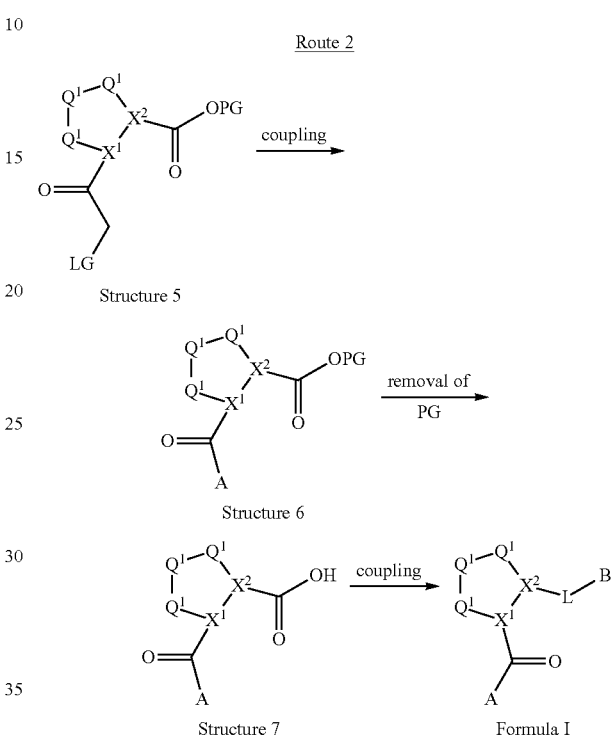

In an alternative embodiment, Structure 8 is deprotected to generate an amine which is Structure 9. Structure 9 is then coupled to generate an amide which is Structure 6. Structure 6 is then deprotected to generate a carboxylic acid which is Structure 7. Structure 7 is then coupled to form the amide which falls within Formula I. The chemistry is illustrated in Route 3.

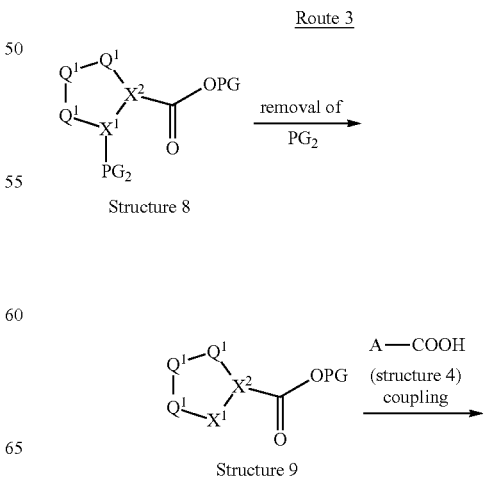

-continued

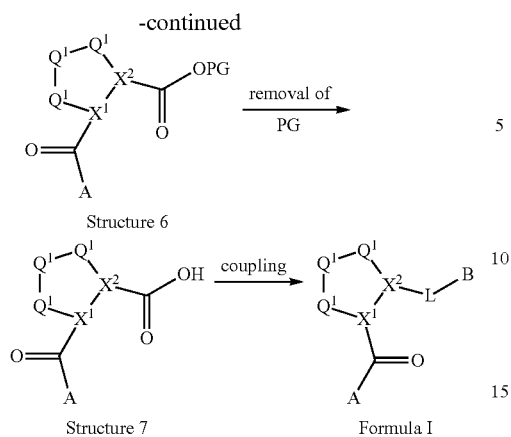

In an alternate embodiment, a heteroaryl or aryl moiety, 4-1, is coupled to a central core to generate 4-2. The protected acid, 4-2 is deblocked to form the carboxylic acid, 4-3. The carboxylic acid is then coupled to form an amide (L-B) which is 4-4. The heteroaryl or aryl moiety, A', can then be further derivitized to add substituents at the $X^{11}$, $X^{12}$, $X^{13}$ and $X^{14}$ positions to generate compounds of Formula I. This chemistry is illustrated in Route 4.

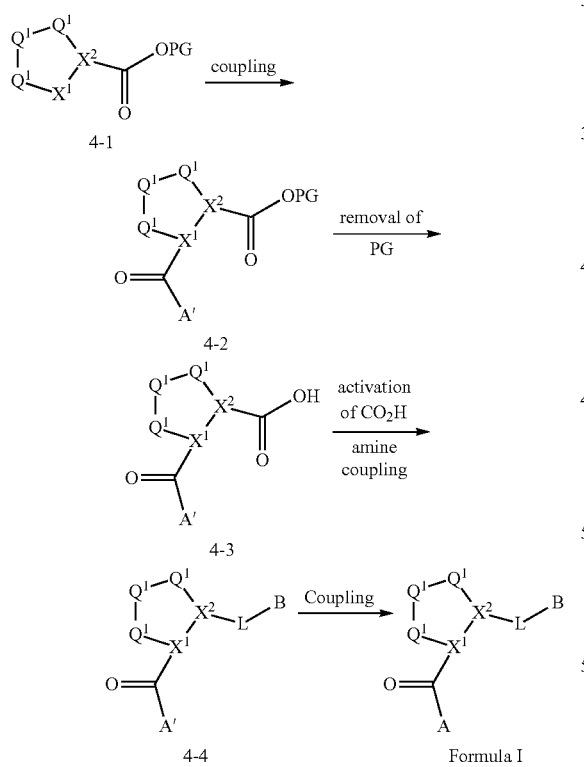

In an alternate embodiment, Structure 5-1 is coupled to an acid, Structure 5-2, to generate Structure 5-3. The carboxylic acid, Structure 5-3, is deblocked to generate a carboxylic acid which is Structure 5-4. Carboxylic acid Structure 5-4 is coupled to an amine to form the product amide (L-B) which is a compound within Formula I. This chemistry is illustrated in Route 5.

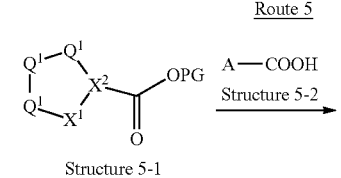

In an alternate embodiment, a heteroaryl compound of Structure 10 is acylated to generate a compound of Structure 11, wherein LG is a leaving group. As an example, the leaving group can be a halide, for example bromide. Structure 11 is coupled to Structure 12 to generate Structure 13. In some embodiments, $LG_1$ is a leaving group. In some embodiments, the $LG_1$ is a halide. Structure 13 is coupled to an aryl, heteroaryl or heterocylic compound to generate Structure 14. In some embodiments, Structure 13 is treated with an aryl, heteroaryl or heterocylic boronic acid, an organometallic catalyst, a base and an organic solvent. In some embodiments, the organometallic catalyst is tetrakis (triphenylphosphine)palladium (0). In some embodiments, the base is cesium carbonate. In some embodiments, the organic solvent is DMF. Structure 14 is treated with an organic acid such as, but not limited to, trifluoroacetic acid to generate Structure 15. Structure 15 is coupled to Structure 3 from Route 1 to generate a compound within Formula I. This chemistry is illustrated in Route 6.

Route 6

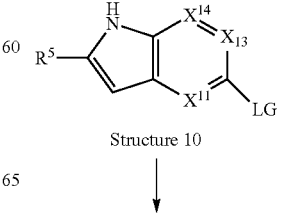

Structure 10

↓

-continued

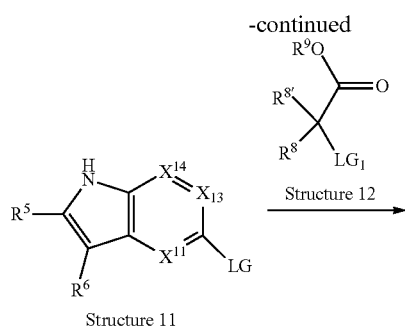
Structure 11

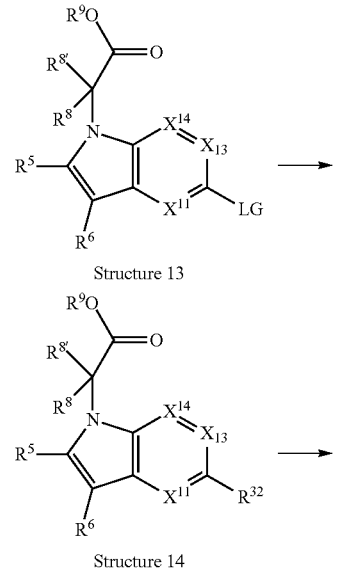
Structure 13

Structure 14

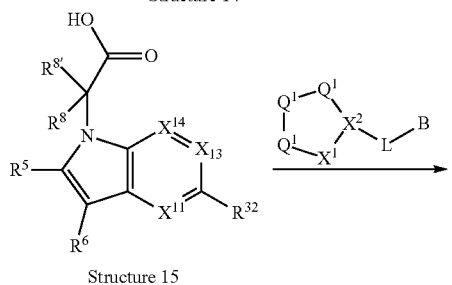
Structure 15

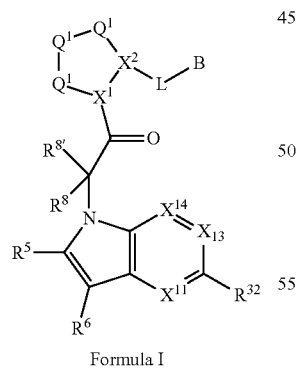
Formula I

In an alternate embodiment, a heteroaryl compound of Structure 17 is acylated to generate a compound of Structure 18, wherein LG is a leaving group. As an example, the leaving group can be a halide, for example bromide. Structure 18 is coupled to an activated ester, Structure 12 from Route 6, wherein $LG_1$ can be a halogen to generate Structure 19.

Structure 19 is coupled to an aryl, heteroaryl or heterocylic compound to generate Structure 20. In some embodiments, Structure 19 is treated with an aryl, heteroaryl or heterocylic boronic acid, an organometallic catalyst, a base and an organic solvent. In some embodiments, the organometallic catalyst is tetrakis(triphenylphosphine)palladium (0). In some embodiments, the base is cesium carbonate. In some embodiments, the organic solvent is DMF. Structure 20 is treated with an organic acid such as, but not limited to, trifluoroacetic acid to generate Structure 21. Structure 21 is coupled to Structure 3 from Route 1 to generate a compound within Formula I. This chemistry is illustrated in Route 7.

Route 7

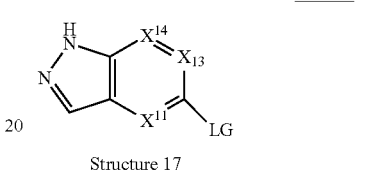
Structure 17

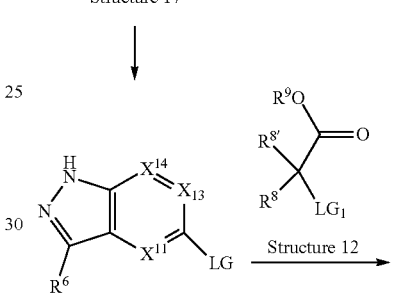
Structure 18

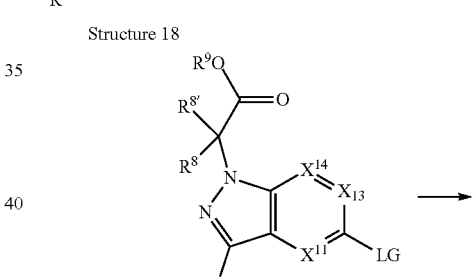
Structure 19

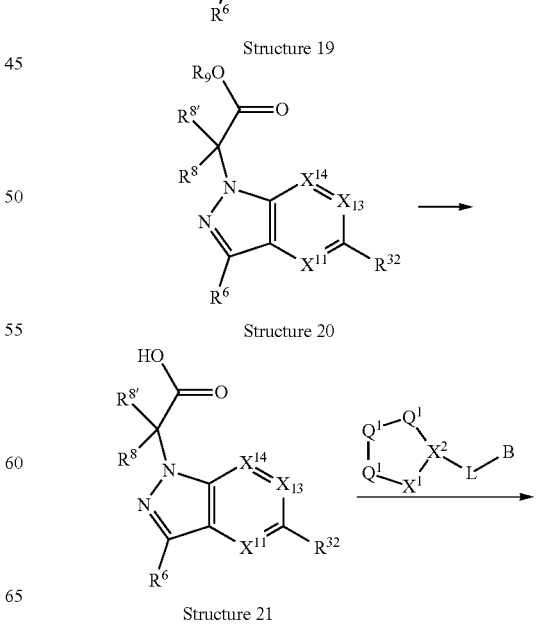
Structure 20

Structure 21

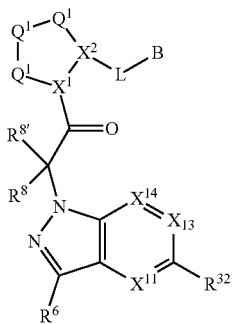

Formula I

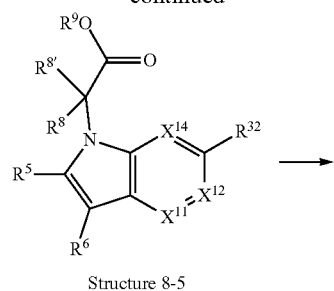

Structure 8-5

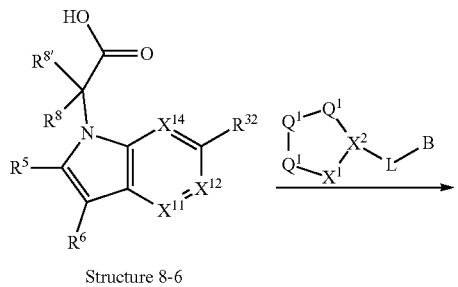

Structure 8-6

In an alternate embodiment, a heteroaryl compound of Structure 8-1 is acylated to generate a compound of Structure 8-2, wherein LG is a leaving group. As an example, the leaving group can be a halide, for example bromide. Structure 8-2 is coupled to Structure 8-3 to generate Structure 8-4. In some embodiments, $LG_1$ is a leaving group. In some embodiments, the $LG_1$ is a halide.

Structure 8-4 is coupled to an aryl, heteroaryl or heterocylic compound to generate Structure 8-5. In some embodiments, Structure 8-4 is treated with an aryl, heteroaryl or heterocylic boronic acid, an organometallic catalyst, a base and an organic solvent. In some embodiments, the organometallic catalyst is tetrakis(triphenylphosphine)palladium (0). In some embodiments, the base is cesium carbonate. In some embodiments, the organic solvent is DMF. Structure 8-5 is treated with an organic acid such as, but not limited to, trifluoroacetic acid to generate Structure 8-6. Structure 8-6 is coupled to Structure 3 from Route 1 to generate a compound within Formula I. This chemistry is illustrated in Route 8.

Route 8

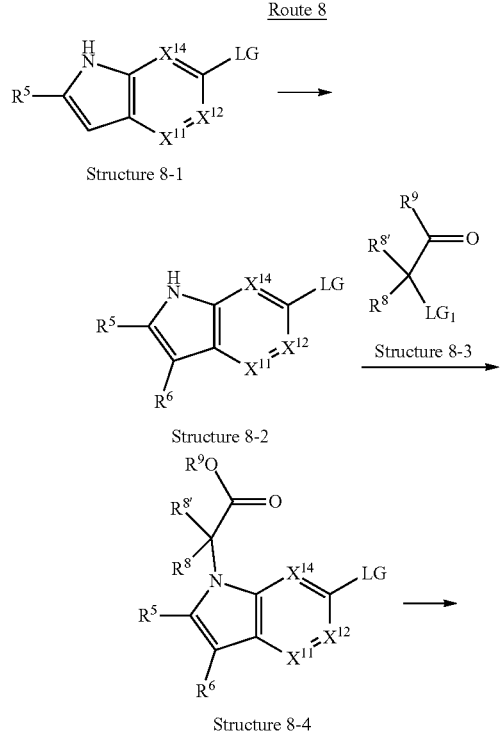

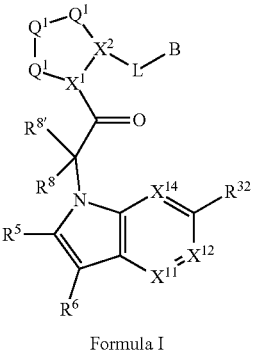

Formula I

In an alternate embodiment, a heteroaryl compound of Structure 9-1 is acylated to generate a compound of Structure 9-2, wherein LG is a leaving group. As an example, the leaving group can be a halide, for example bromide. Structure 9-2 is coupled to an activated ester, Structure 9-3, wherein $LG_1$ can be a halide to generate Structure 9-4. Structure 9-4 is coupled to an aryl, heteroaryl or heterocylic compound to generate Structure 9-5. In some embodiments, Structure 9-4 is treated with an aryl, heteroaryl or heterocylic boronic acid, an organometallic catalyst, a base and an organic solvent. In some embodiments, the organometallic catalyst is tetrakis(triphenylphosphine)palladium (0). In some embodiments, the base is cesium carbonate. In some embodiments, the organic solvent is DMF. Structure 9-5 is treated with an organic acid such as, but not limited to, trifluoroacetic acid to generate Structure 9-6. Structure 9-6 is coupled to Structure 3 from Route 1 to generate a compound within Formula I. This chemistry is illustrated in Route 9.

Route 9
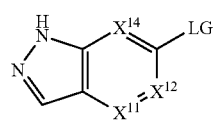
Structure 9-1
↓
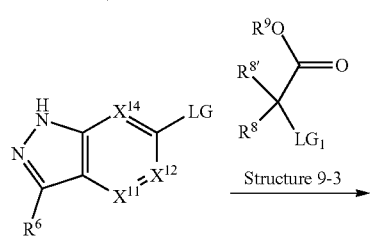
Structure 9-2
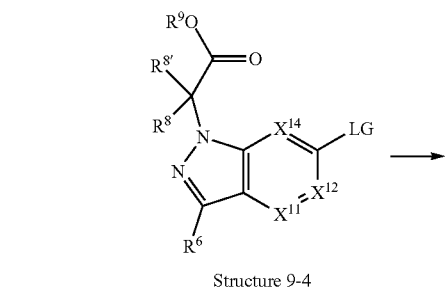
Structure 9-4
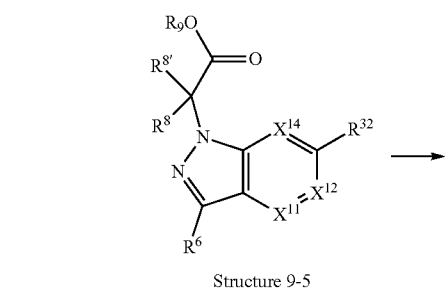
Structure 9-5
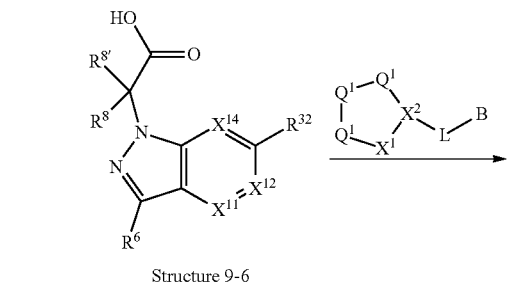
Structure 9-6
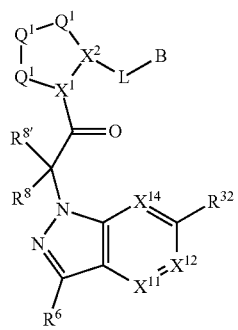
Formula I
In an alternate embodiment, Structure 10-1 is coupled to an amine to generate an amide (L-B), and Structure 10-2. Structure 10-2, is coupled to an amine to generate compounds within Formula I. This chemistry is illustrated in Route 10.
Route 10
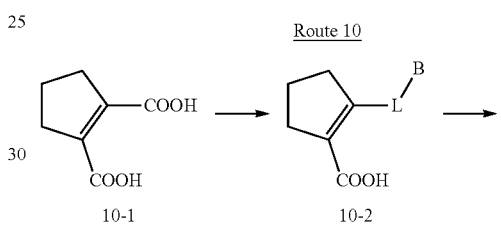
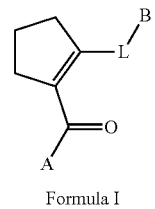
Formula I
Example 2. Examples of Central Synthons
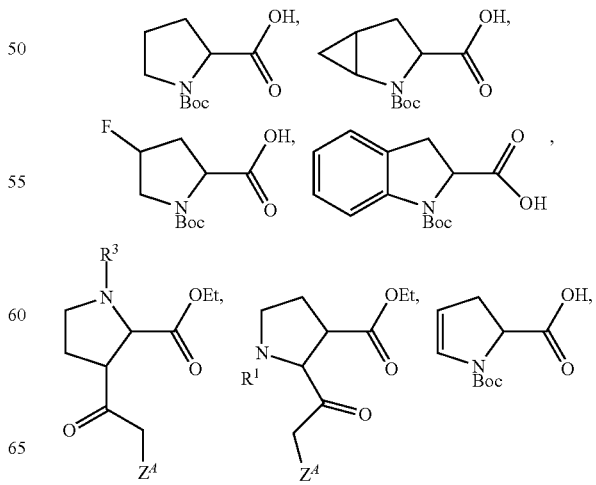

-continued
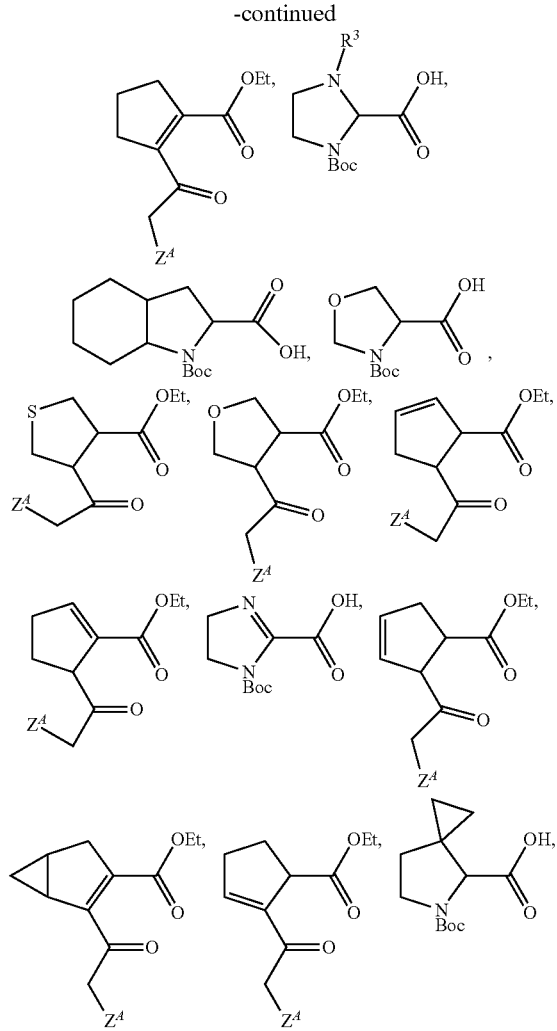
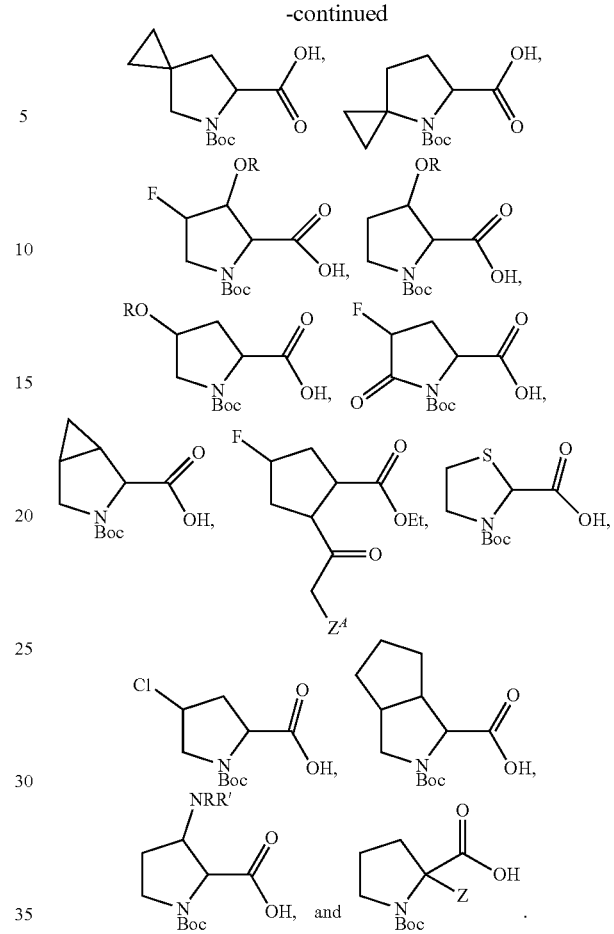
$Z^A$ is halogen.
In one embodiment, deuterated L-proline synthons are disclosed. Deuterated synthons include, but are not limited to, for example, the following compounds:
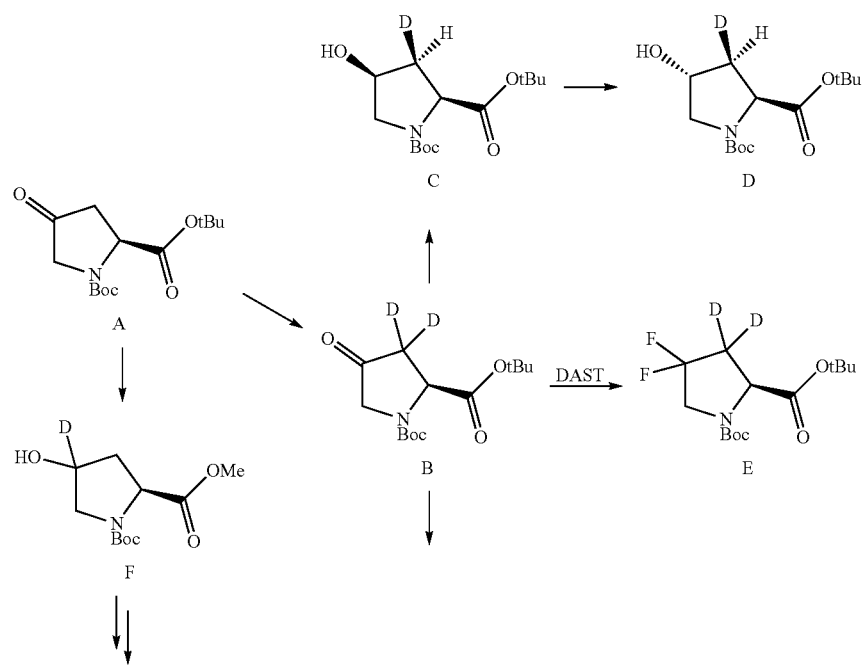

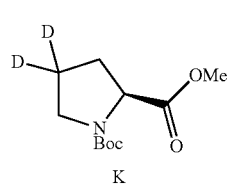

K

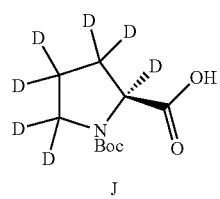

J

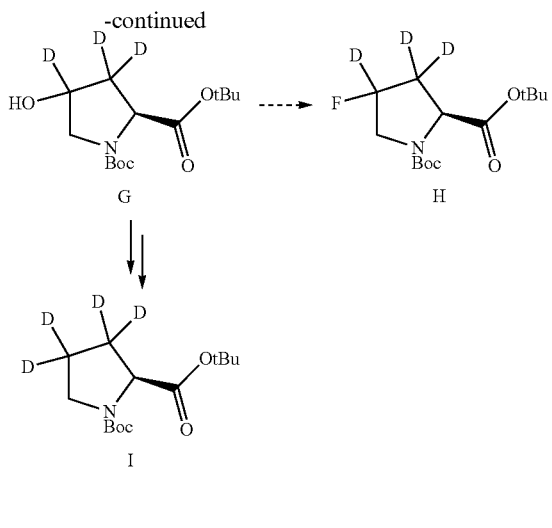

G    H

I

Structure A can be treated with deuterium oxide to generate Structure B. See, Barraclough, P. et al. Tetrahedron Lett. 2005, 46, 4653-4655; Barraclough, P. et al. Org. Biomol. Chem. 2006, 4, 1483-1491 and WO 2014/037480 (p. 103). Structure B can be reduced to generate Structure C. See, Barraclough, P. et al. Tetrahedron Lett. 2005, 46, 4653-4655; Barraclough, P. et al. Org. Biomol. Chem. 2006, 4, 1483-1491. Structure C can be treated with Mitsunobu reaction conditions to generate Structure D. Structure B can be treated with DAST to generate Structure E. See, WO 2014/037480. Structure A can be treated with sodium borodeuteride to generate Structure F. See, Dormoy, J.-R.; Castro, B. *Synthesis* 1986, 81-82. Compound F can be used to generate Structure K. See, Dormoy, J.-R.; Castro, B. *Synthesis* 1986, 81-82. Structure B can be treated with a deuterated reducing agent, for example sodium borodeuteride to generate Structure G. Structure G can be treated with DAST to generate Structure H. Structure F can be used to generate Structure K. See, Dormoy, J.-R.; Castro, B. *Synthesis* 1986, 81-82. Structure G can be used to generate Structure I. Structure J can be prepared according to Hruby, V. J. et al. *J. Am. Chem. Soc.* 1979, 101, 202-212. Structures A-J can be used to prepare compounds of Formula I.

Example 3. Preparation of Central-L-B Synthons

Routes 1a, 1b and 1c.

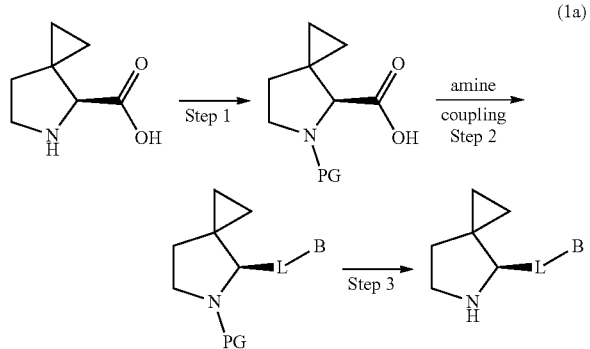

In Route 1a, 5-azaspiro[2.4]heptane-4,5-dicarboxylic acid, 5-(1,1-dimethylethyl) ester, (4S)—, CAS 209269-08-9, can be prepared as described in Tandon, M. et al. Bioorg. Med. Chem. Lett. 1998, 8, 1139-1144. In Step 2, the protected azaspiro[2.4]heptane is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1b, (4S) 4-oxazolidinecarboxylic acid, hydrochloride is treated with an amine protecting reagent. In one embodiment, the amine protecting reagent is di-tert-butyl dicarbonate. In another embodiment, 3,4-oxazolidinedicarboxylic acid, 3-(1,1-dimethylethyl) ester, (4S)—, is commercially available from JPM2 Pharmaceuticals. In one embodiment the reaction is carried out in an organic solvent in the presence of a base. In one embodiment, the organic solvent is acetonitrile. In one embodiment, the base is 4-dimentylaminopyridine (DMAP). In Step 2, the protected 4-oxazolidinecarboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1c, (S)-5-(tert-Butoxycarbonyl)-5-azaspiro[2.4]heptane-6-caboxylic acid, CAS 1129634-44-1, is commercially available from Ark Pharm. In Step 2, the carboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

Routes 2a, 2b, 2c, and 2d.

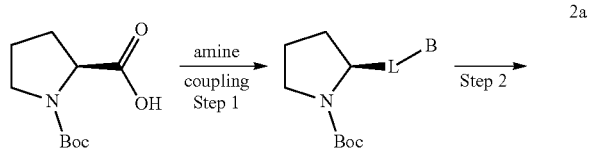

2a

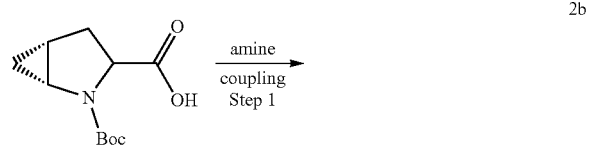

2b

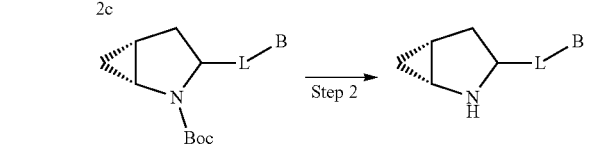

2c

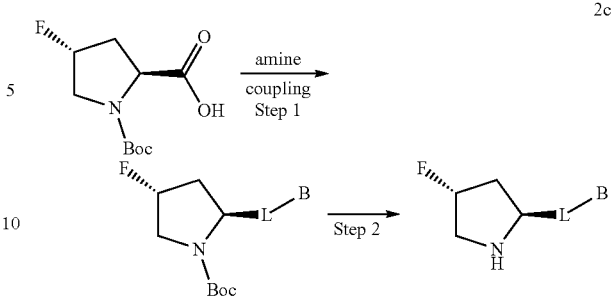

2c

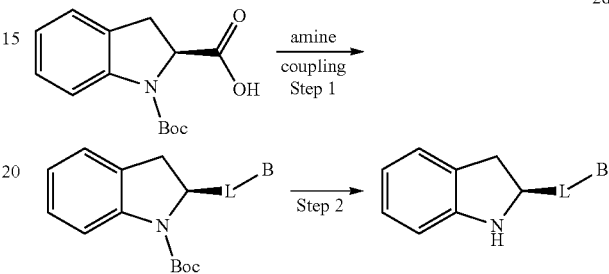

2d

In Route 2a, commercially available Boc-L-proline is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2b, commercially available (1R, 3S, 5R)-2-[(tert-butoxy)carbonyl]-2-azabicyclo[3.1.0]hexane-3-carboxylic acid, from Enamine, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2c, commercially available (2S,4R)-1-(tert-butoxycarbonyl)-4-fluoropyrrolidine-2-carboxylic acid, from Manchester Organics, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2d, commercially available (S)-1-(tert-butoxycarbonyl)indoline-2-carboxylic acid, from Chem-Impex, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane. This chemistry is illustrated in Scheme 2.

Additional starting materials that can readily be converted to Central-L-B-Synthons include, but are not limited to: (S)-1-(tert-butoxycarbonyl)-2,3-dihydro-1H-pyrrole-2-carboxylic acid, CAS 90104-21-5, available from Ark Pharm; cyclopent-1-ene-1,2-dicarboxylic acid, CAS 3128-15-2, purchased from Ark Pharm; imidazole, 1H-imidazole-1,2-dicarboxylic acid, 1-(1,1-dimethylethyl) 2-ethyl ester, CAS 553650-00-3, commercially available from FCH Group; Boc-L-octahydroindole-2-carboxylic acid can be purchased from Chem Impex. The compound,

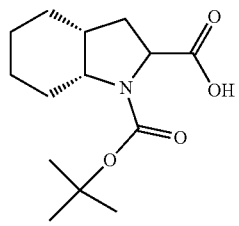 [SMILES: CC(C)(C)OC(=O)N1C(C(=O)O)C[C@H]2CCCC[C@H]21]

can be prepared according to the procedures disclosed in WO 2004/111041; (S)-Boc-5-oxopyrrolidine-2-carboxylic acid is available from the Aldrich Chemical Co.; (1S,2S,5R)-3-(tert-butoxycarbonyl)-3-azabicyclo[3.3.0]hexane-2-carboxylic acid is available from Ark Pharm; (S)-3-Boc-thiazolidine-2-carboxylic acid is available from Alfa Aesar; (2S,4R)-1-(tert-butoxycarbonyl)-4-chloropyrrolidine-2-carboxylic acid is available from Arch Bioscience; (1S,3aR,6aS)-2-(tert-butoxycarbonyl)octahydrocyclopenta[c]pyrrole-1-carboxylic acid is available from Ark Pharm; 1,2-pyrrolidinedicarboxylic acid, 3-[[(phenylmethoxy)carbonyl]amino]-, 1-(1,1-dimethylethyl) ester, (2S,3R) can be prepared as disclosed in WO 2004/007501. The Cbz group can be removed and the amino group can be alkylated to generate central core compounds of the present invention.

The compound

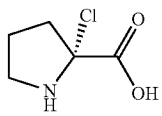

can be prepared as disclosed by Braun, J. V.; Heymons, Albrecht Berichte der Deutschen Chemischen Gesellschaft [Abteilung] B: Abhandlungen (1930) 63B, 502-7.

The compounds (2S,3S,4S)-4-fluoro-3-methoxy-pyrrolidine-1,2-dicarboxylic acid 1-tert-butyl ester and (2R,3R,4R)-3-fluoro-4-methoxy-pyrrolidine-1,2-dicarboxylic acid 1-tert-butyl ester can be prepared as a mixture according to WO 2012/093101 to Novartis and the regioisomers can be ultimately separated once coupled to generate the central core-L-B synthons. The compound (S)-Boc-5-oxopyrrolidine-2-carboxylic acid is available from the Aldrich Chemical Co.

Example 4. Synthesis of L-B Moieties

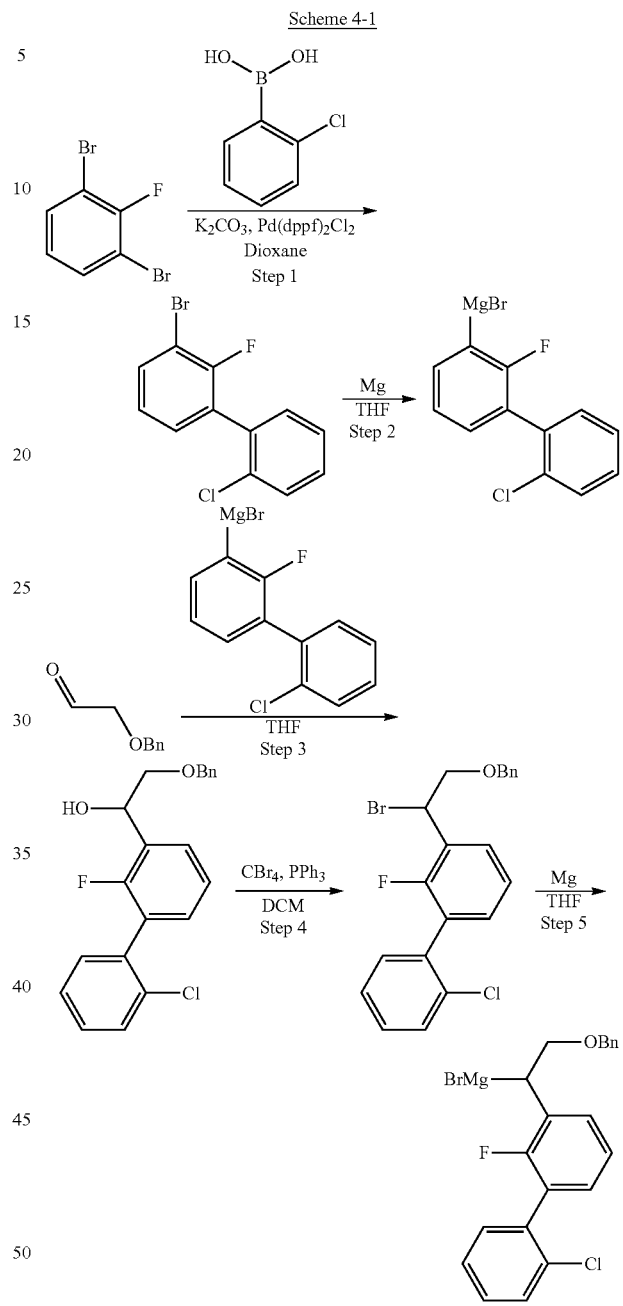

Scheme 4-1: In Step 1 the appropriately substituted dibromo species is coupled with an appropriate boronic acid as known in the art to form a mixture of biaryl and triaryl products from which the desired biaryl compound is isolated. In Step 2 the appropriately substituted biaryl species is converted to the Grignard reagent with activated magnesium. In Step 3 the appropriately substituted aldehyde is treated with the previously prepared Grignard reagent to form an alcohol. In Step 4 the appropriately substituted alcohol is converted to a bromide as known in the art with carbon tetrabromide and triphenyl phosphine. In Step 5 the appropriately substituted bromide is converted to the Grignard reagent with activated magnesium.

Example 5. Synthesis of C-L-B Moieties
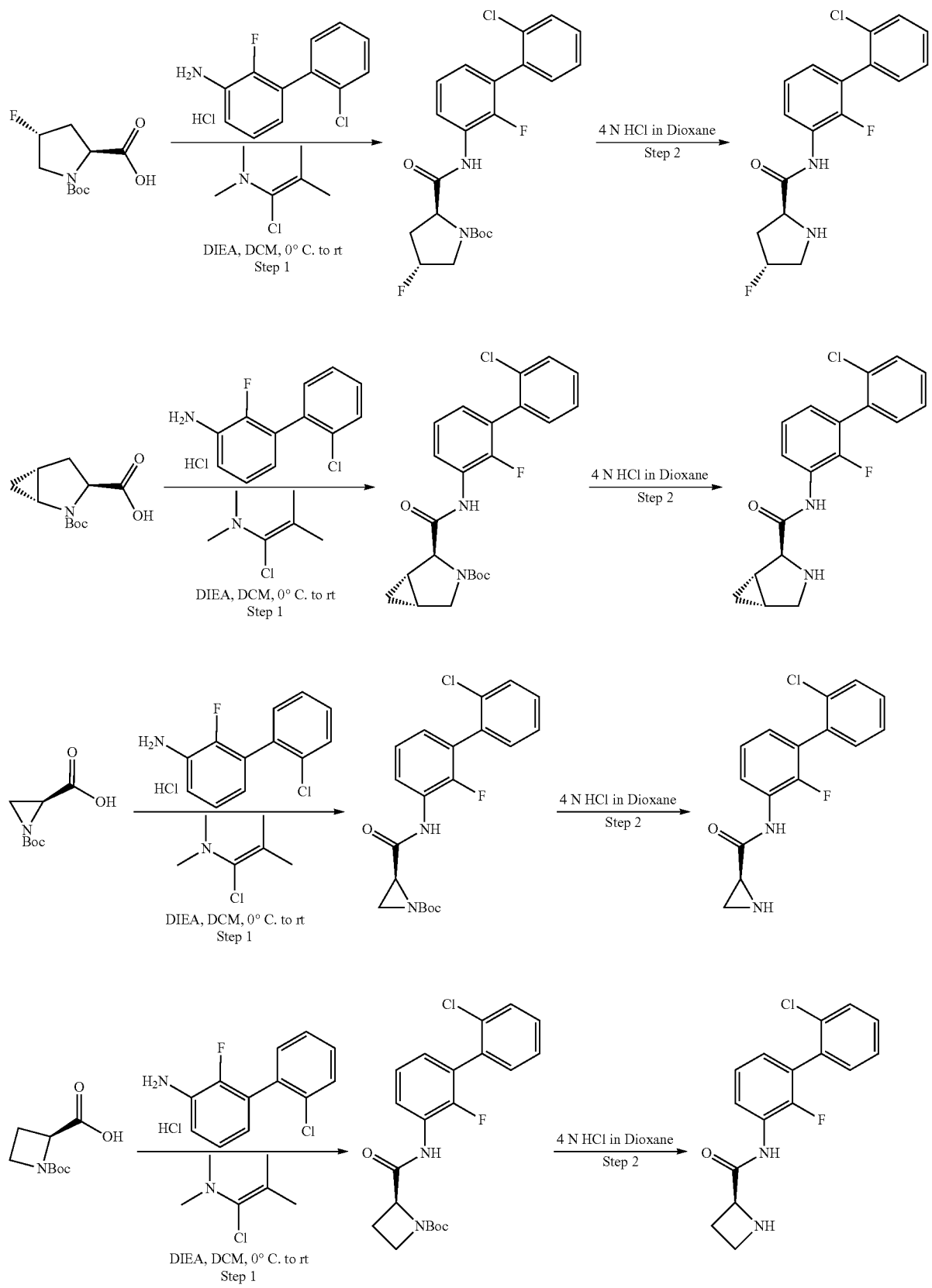
Scheme 5-1

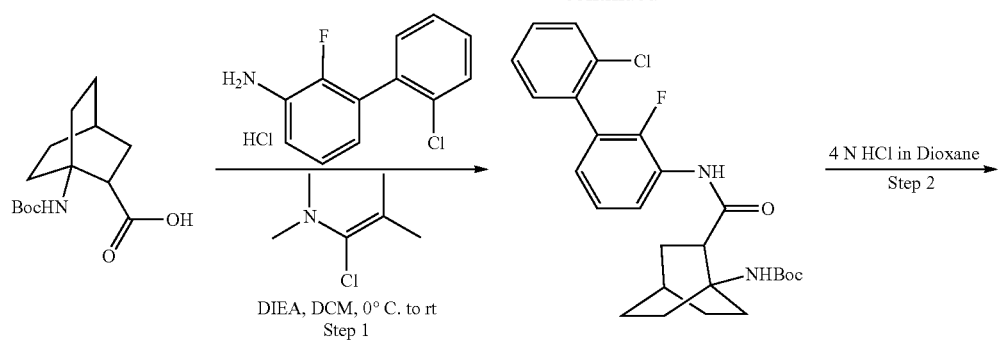
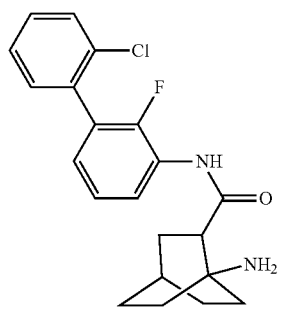
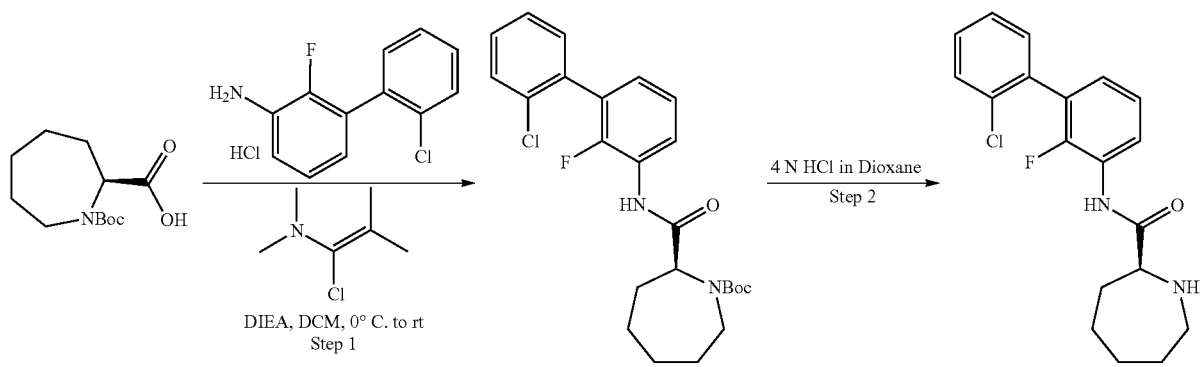
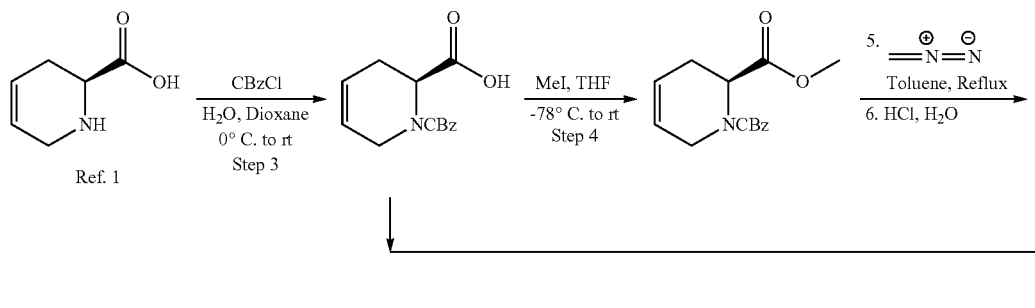

151 152

-continued

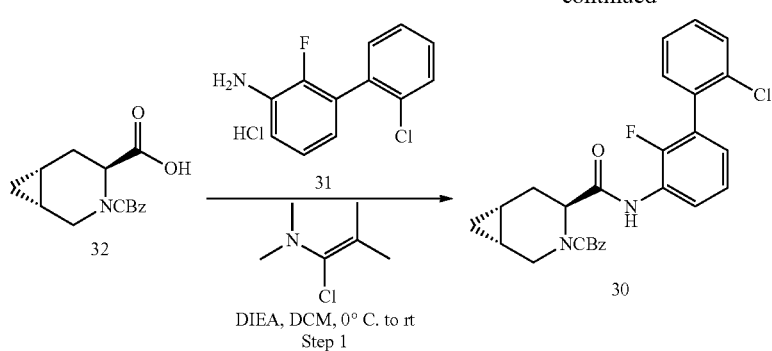

Step 1
DIEA, DCM, 0° C. to rt

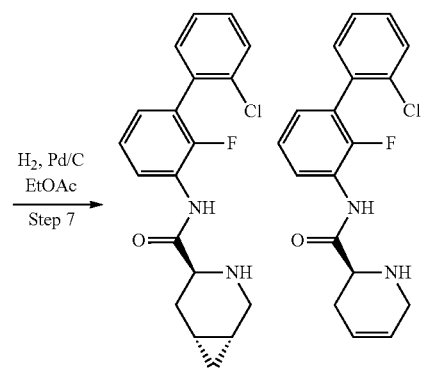

Step 7
H₂, Pd/C
EtOAc

1. Herdeis, C., et al. (1994). Liebigs Ann. Chem. (11): 1117-1120.

Scheme 5-1: In Step 1 the appropriately substituted carboxylic acid is coupled to the appropriately substituted amine as known in the art to form an amide. In Step 2 the appropriately substituted Boc-protected species is deprotected with acid to liberate the free amine. In Step 3 the appropriately substituted amine is Cbz-protected as known in the art to form a protected carboxylic acid. In Step 4 the appropriately substituted carboxylic acid can be orthogonally protected as known in the art to form an ester. In Step 5 the appropriately substituted and protected alkene is subjected to a carbene to form a bicyclic ring. In Step 6 the appropriately substituted ester is saponified with acid to liberate the carboxylic acid. In Step 7 the appropriately substituted Cbz-protected species is deprotected with hydrogen to liberate the free amine.

Scheme 5-2

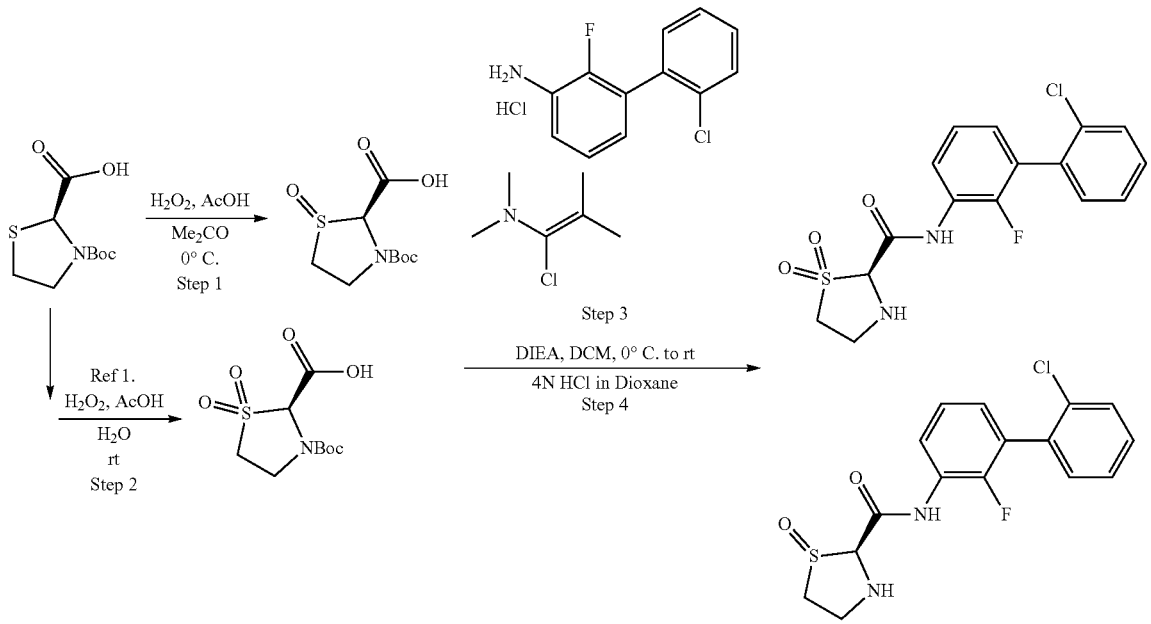

1. Vasil'eva, T. P. (2003). Russ. Chem. Bull. 52(4): 958-960.

Scheme 5-2: In Step 1 the appropriately substituted sulfide is oxidized to a sulfoxide as known in the art. Alternatively, in Step 2 the appropriately substituted sulfide is oxidized to a sulfone as known in the art. In Step 3 the appropriately substituted carboxylic acid is coupled to the appropriately substituted amine as known in the art to form an amide. In Step 4 the appropriately substituted Boc-protected species is deprotected with acid to liberate the free amine.

Scheme 5-3

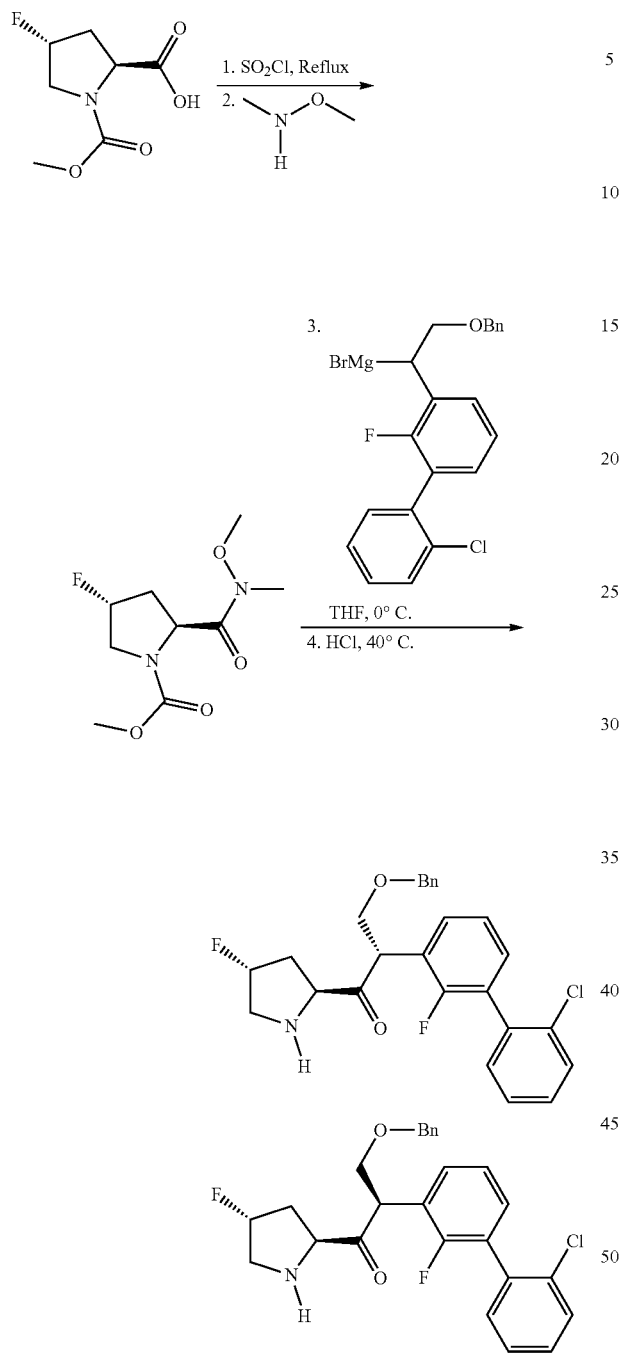

Scheme 5-3: In Step 1 the appropriately substituted carboxylic acid is converted to the acyl chloride as known in the art. In Step 2 the appropriately substituted acyl chloride is converted to the Weinreb amide as known in the art. In Step 3 the appropriately substituted Weinreb amide is reacted with a Grignard reagent to afford a ketone. The synthesis of complex Grignard reagents is described in Example 4. In Step 4 the appropriately substituted carbamate protected amine is deprotected to liberate the free amine.

Scheme 5-4

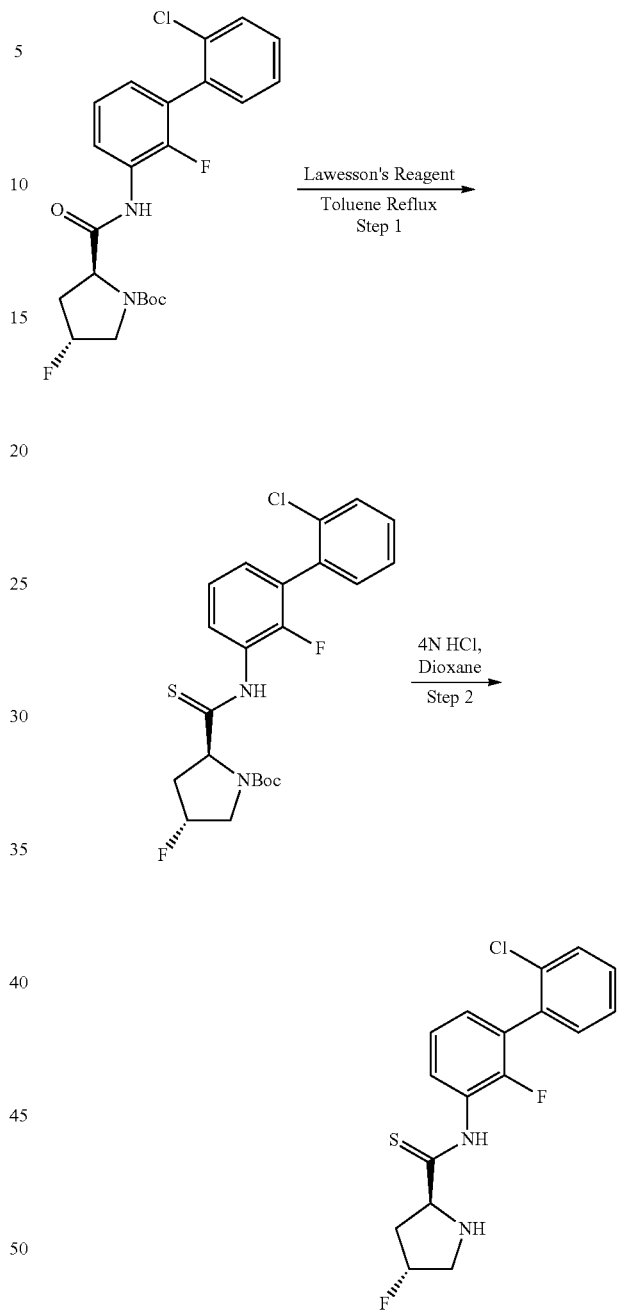

Scheme 5-4: In Step 1 the appropriately substituted amide is converted to a thioamide with Lawesson's reagent. In Step 2 the appropriately substituted Boc-protected amine is deprotected with acid to liberate the free amine.

Scheme 5-5

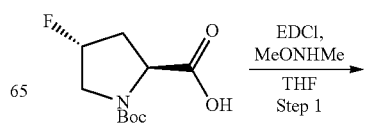

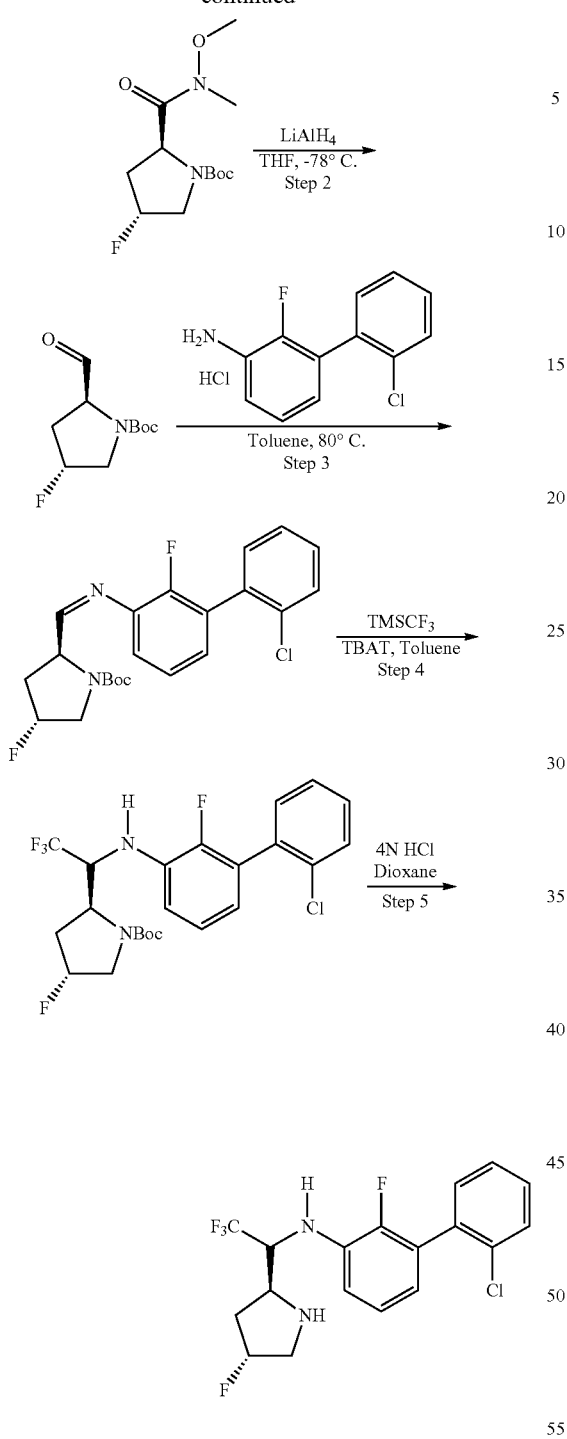
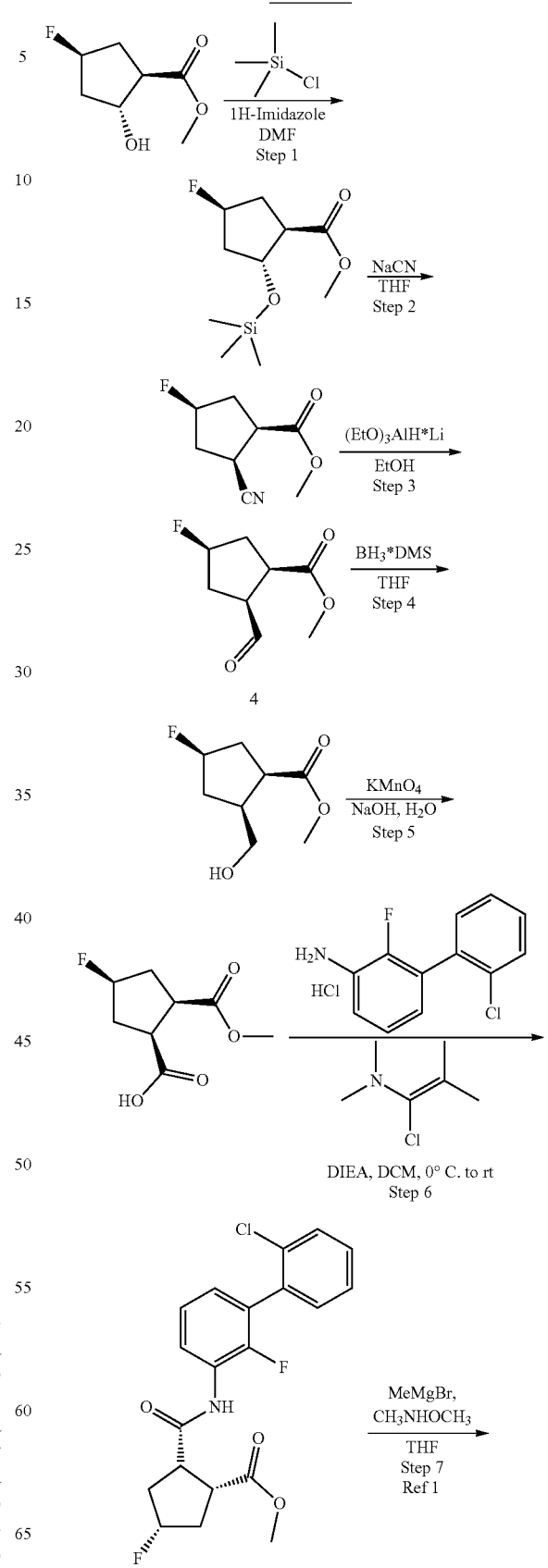

Scheme 5-5: In Step 1 the appropriately substituted carboxylic acid is converted to a Weinreb amide as known in the art. In Step 2 the appropriately substituted Weinreb amide is reduced as known in the art to afford an aldehyde. In Step 3 the appropriately substituted aldehyde is subjected to an amine to form a Schiff base which is subsequently quenched in Step 4. In Step 4 the appropriately substituted Schiff base is subjected to an appropriate nucleophile to form a complex amine. In Step 5 the appropriately substituted Boc-protected species is deprotected with acid to liberate the free amine.

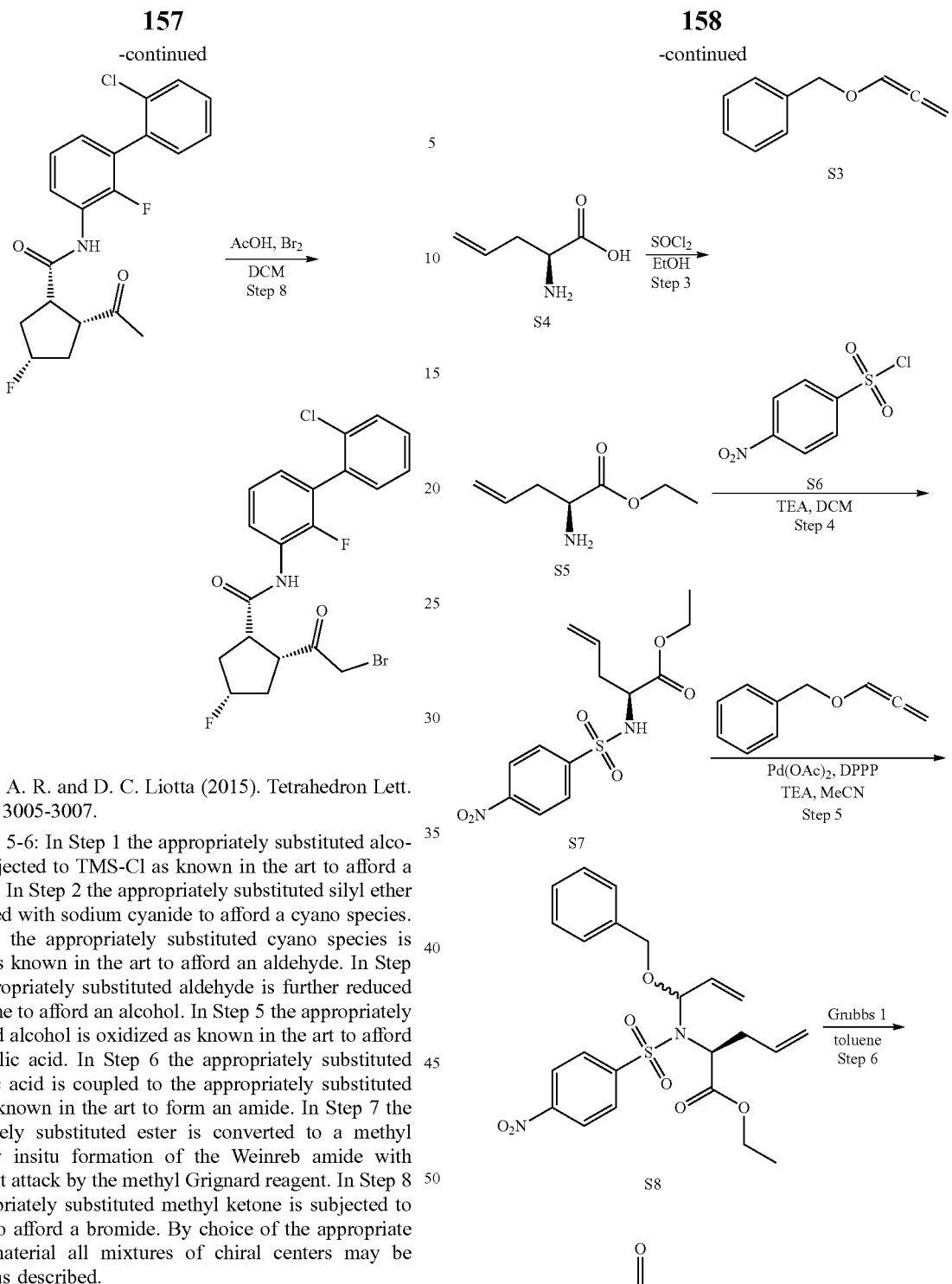

1. Prosser, A. R. and D. C. Liotta (2015). Tetrahedron Lett. 56(23): 3005-3007.

Scheme 5-6: In Step 1 the appropriately substituted alcohol is subjected to TMS-Cl as known in the art to afford a silyl ether. In Step 2 the appropriately substituted silyl ether is subjected with sodium cyanide to afford a cyano species. In Step 3 the appropriately substituted cyano species is reduced as known in the art to afford an aldehyde. In Step 4 the appropriately substituted aldehyde is further reduced with borane to afford an alcohol. In Step 5 the appropriately substituted alcohol is oxidized as known in the art to afford a carboxylic acid. In Step 6 the appropriately substituted carboxylic acid is coupled to the appropriately substituted amine as known in the art to form an amide. In Step 7 the appropriately substituted ester is converted to a methyl ketone by insitu formation of the Weinreb amide with subsequent attack by the methyl Grignard reagent. In Step 8 the appropriately substituted methyl ketone is subjected to bromine to afford a bromide. By choice of the appropriate starting material all mixtures of chiral centers may be prepared as described.

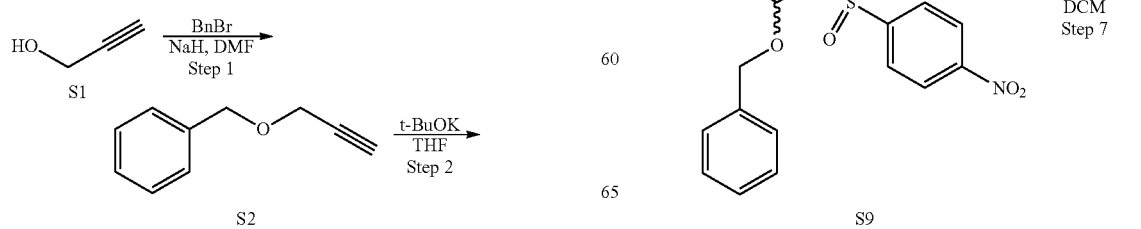

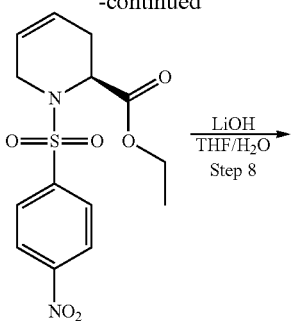

S10

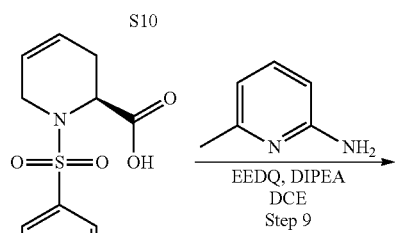

S11

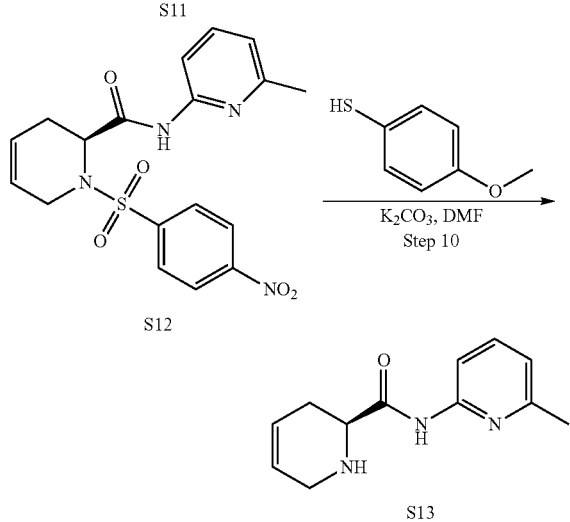

S12

S13

Step 1: ((Prop-2-ynyloxy)methyl)benzene (S2)

To a solution of scheme 5-7 compound S1 (15.5 g, 0.277 mol) in dry DMF (150 mL) was added NaH (12 g, 305 mol) at 0° C. slowly. After stirring at 0° C. for 1 h, BnBr (52 g, 305 mol) was added to the mixture at 0° C. The reaction was stirred at room temperature for 16 h. Then the mixture was quenched with saturated aqueous NH₄Cl solution (150 mL) and extracted with DCM (300 mL). The organic layer was washed with aqueous LiCl solution (150 mL×3), dried over anhydrous $Na_2SO_4$, and concentrated. The residue was purified by column chromatography on silica gel (eluted with petroleum ether:ethyl acetate=100:0 to 100:1) to afford the title compound (21 g, 53.1% yield) as a colorless oil.

Step 2: ((Propa-1,2-dienyloxy)methyl)benzene (S3)

To a solution of scheme 5-7 compound S2 (21 g, 0.144 mol) in dry THF (120 ml) was added t-BuOK (4.84 g, 0.0432 mol). The reaction mixture was stirred at room temperature for 3 h and then concentrated under reduced pressure. Et₂O (200 mL) was added and the resulting mixture was filtered. The filtrate was concentrated and purified by column chromatography on silica gel (eluted with petroleum ether) to afford the title compound (13.8 g, 66.3% yield) as a colorless oil.

Step 3: (S)-Ethyl 2-aminopent-4-enoate (S5)

To a solution of scheme 5-7 compound S4 (5 g, 43.5 mmol) in EtOH (70 mL) was added $SOCl_2$ (15.52 g, 130.5 mmol) dropwise at 0° C. The reaction was stirred at room temperature for 16 h and concentrated. The residue was triturated with Et₂O (60 mL) and filtered to afford the title compound (7 g, yield 89%) as a white powder, which was directly used in the next reaction without further purification. LC/MS (ESI) m/z: 144 (M+H)⁺.

Step 4: (S)-Ethyl 2-(4-nitrophenylsulfonamido)pent-4-enoate (S7)

To a mixture of scheme 5-7 compound S5 (7 g, 39 mmol) and TEA (9.85 g, 97.5 mmol) in DCM (80 mL) was added 4-nitrobenzene-1-sulfonyl chloride (8.63 g, 39 mmol). The reaction mixture was stirred at room temperature overnight and then quenched with saturated aq.$NaHCO_3$ solution (100 mL). The resulting mixture was extracted with DCM (50 mL×2). The combined organic phases were washed with brine, dried over anhydrous $Na_2SO_4$, filtered and then concentrated. The residue was purified by column chromatography on silica gel (eluted with petroleum ether:ethyl acetate=15:1 to 8:1) to afford the title compound (9.2 g, 71.84% yield) as a yellow oil. LC/MS (ESI) m/z: 327 (M−H)⁺.

Step 5: (S)-Ethyl 2-(N-(1-(benzyloxy)allyl)-4-nitrophenylsulfonamido)pent-4-enoate (S8)

To a solution of scheme 5-7 compound S7 (8.4 g, 25.6 mmol) in MeCN (90 mL) was added ((propa-1,2-dienyloxy)methyl)benzene (4.2 g, 28.17 mmol), DPPP (1.06 g, 2.56 mmol), TEA (5.17 g, 51.2 mmol) and Pd(OAc)₂ (576 mg, 2.56 mmol). The reaction was degassed and stirred at room temperature for 16 h under N₂ atmosphere. The mixture was concentrated to dryness and the residue was purified by column chromatography on silica gel (eluted with petroleum ether:ethyl acetate=30:1 to 20:1) to afford the title compound (8.1 g, 66.67% yield) as a yellow solid.

Step 6: (S)-Ethyl 6-(benzyloxy)-1-(4-nitrophenylsulfonyl)-1,2,3,6-tetrahydropyridine-2-carboxylate (S9)

To a solution of scheme 5-7 compound S8 (8 g, 16.88 mmol) in dry degassed toluene (80 mL) was added Grubbs I catalyst (707 mg, 0.844 mmol) under N₂ atmosphere. The resulting mixture was degassed three times and stirred at 80° C. for 20 h under N₂ atmosphere. After cooling to room temperature, the reaction mixture was concentrated and the residue was purified by column chromatography on silica gel (eluted with petroleum ether:ethyl acetate=15:1 to 6:1) to afford the title compound (6.58 g, 87.31% yield) as a yellow oil. LC/MS (ESI) m/z: 447 (M−H)⁺.

Step 7: (S)-Ethyl 1-(4-nitrophenylsulfonyl)-1,2,3,6-tetrahydropyridine-2-carboxylate (S10)

To a mixture of scheme 5-7 compound S9 (6.58 g, 14.72 mmol) and triethylsilane (5.17 g, 44.16 mmol) in dry DCM (80 mL) was added boron trifluoride etherate (6.27 g, 44.16 mmol) at −75° C. under N₂ atmosphere dropwise. The reaction was stirred at −75° C. for 1 h and then at room temperature for 3 h. The mixture was quenched with saturated NaHCO₃ solution (100 mL) and extracted with DCM (60 mL×2). The combined organic phases were washed with brine, dried over anhydrous Na₂SO₄, filtered and then concentrated. The residue was purified by column chromatography on silica gel (eluted with petroleum ether:ethyl acetate=15:1 to 8:1) to afford the title compound (4.5 g, 89.8% yield) as a colorless oil.

Step 8: (S)-1-(4-Nitrophenylsulfonyl)-1,2,3,6-tetrahydropyridine-2-carboxylic acid (S11)

To a mixture of scheme 5-7 compound S10 (4.5 g, 13.22 mmol) in EtOH/THF/H₂O (40 mL, 1:2:1, V/V) was added LiOH (1.66 g, 39.66 mmol). The reaction mixture was stirred at room temperature for 4 h and then acidified with aqueous HCl solution (1 M) to pH=5. The resulting mixture was extracted with DCM/MeOH (40 mL×2, 20:1, V/V). The combined organic phases were washed with brine, dried over anhydrous Na₂SO₄, filtered and concentrated to afford the title compound (3.3 g, 79.9% yield) as a yellow solid, which was directly used in the next reaction without further purification. LC/MS (ESI) m/z: 311 (M−H)⁺.

Step 9: (S)—N-(6-methylpyridin-2-yl)-1-(4-nitrophenylsulfonyl)-1,2,3,6-tetrahydropyridine-2-carboxamide (S12)

To a solution of scheme 5-7 compound S11 (1.77 g, 5.76 mmol) in dichloroethane (30 mL) was added 6-methylpyridin-2-amine (674 mg, 6.24 mmol), EEDQ (2.82 g, 11.34 mmol) and DIPEA (2.22 g, 17 mmol). The reaction was stirred at reflux overnight under N₂ atmosphere. After cooling, the mixture was concentrated and purified by column chromatography on silica gel (eluted with petroleum ether:ethyl acetate=8:1 to 2:1) to afford the title compound (1.4 g, 60.4% yield) as a yellow solid. LC/MS (ESI) m/z: 403 (M+H)⁺.

Step 10: (S)—N-(6-methylpyridin-2-yl)-1,2,3,6-tetrahydropyridine-2-carboxamide (S13)

To a solution of scheme 5-7 compound S12 (740 mg, 1.84 mmol) in DMF (8 mL) was added K₂CO₃ (762 mg, 5.52 mmol) and 4-methoxybenzenethiol (335 mg, 2.4 mmol). The reaction was stirred at room temperature for 24 h. Then the mixture was diluted with 10% of LiCl solution (40 ml) and extracted with DCM/MeOH (40 mL×2, 20:1, V/V). The combined organic phases were washed with brine, dried over anhydrous Na₂SO₄, filtered and then concentrated. The residue was purified by column chromatography on silica gel (eluted with DCM:MeOH=100:0 to 50:1) to afford scheme 5-7 compound S13 (310 mg, 77.54% yield) as a yellow solid. LC/MS (ESI) m/z: 218 (M+H)⁺.

Scheme 5-8

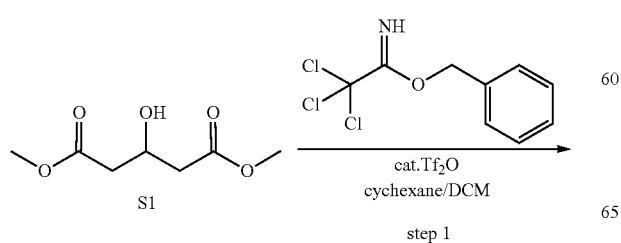

step 1

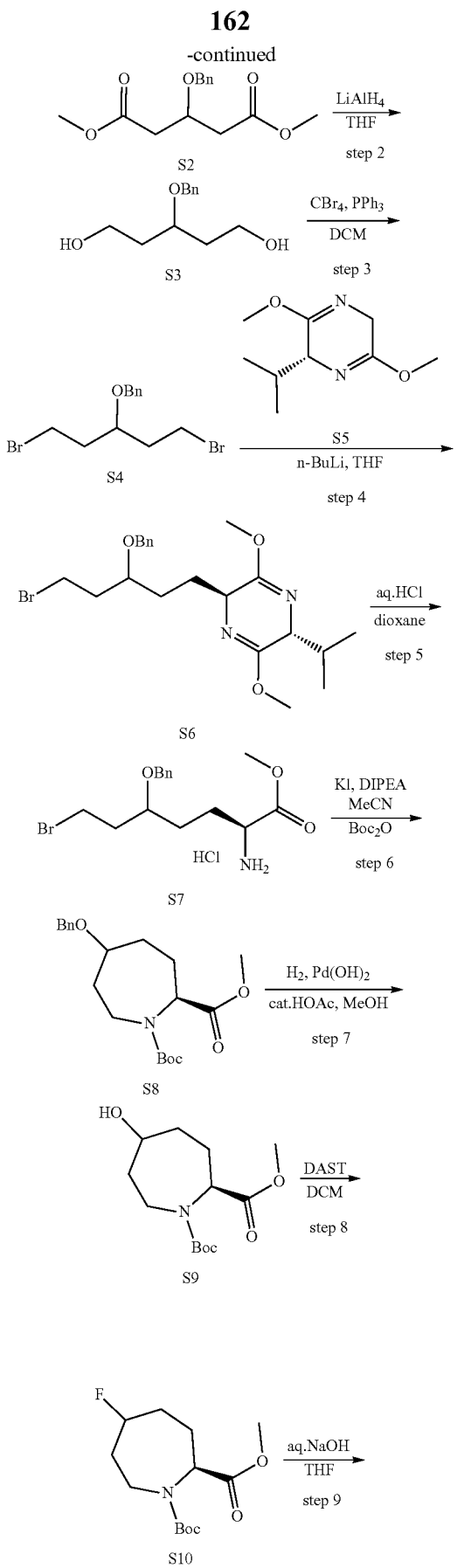

-continued

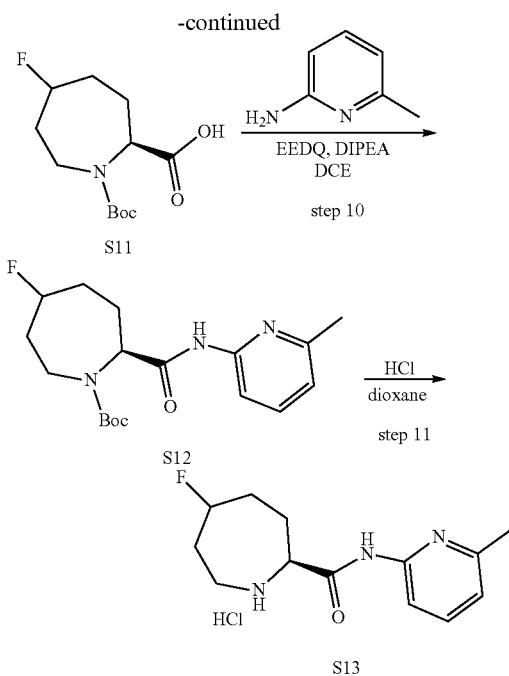

Step 1: Dimethyl 3-(benzyloxy)pentanedioate (S2)

To a solution of scheme 5-8 compound S1 (24 g, 0.136 mol) and benzyl 2,2,2-trichloroacetimidate (51.3 g, 0.204 mol) in cyclohexane/dichloromethane (600 mL/120 mL) at room temperature was added trifluoromethanesulfonic anhydride (cat. 1.2 mL) dropwise. The reaction mixture was stirred at room temperature overnight and filtered. The filtrate was washed with sat. NaHCO$_3$ and brine, dried over anhydrous Na$_2$SO$_4$, filtered and concentrated. The residue was purified by column chromatography on silica gel (eluted with petroleum ether:ethyl acetate=10:1) to afford the title compound (35 g, 93.3% yield) as a yellow oil.

Step 2: 3-(Benzyloxy)pentane-1,5-diol (S3)

To a solution of scheme 5-8 compound S2 (35 g, 0.13 mol) in THF (anhydrous, 200 mL) was added lithium aluminium hydride (15 g, 0.39 mol) in portions at 0° C. The mixture was heated to 65° C. for 4 h. The mixture was quenched by aqueous sodium hydroxide solution (15 mL, 15% wt) and water (15 mL+45 mL). The slurry was filtered and the filter cake was washed with dichloromethane twice. The combined filtrates were dried over sodium sulfate and concentrated to afford the title compound (22 g, 79.7% yield) as a yellow oil.

Step 3:
((1,5-Dibromopentane-3-yloxy)methyl)benzene (S4)

To a mixture of scheme 5-8 compound S3 (22 g, 0.10 mol) and PPh$_3$ (82.3 g, 0.31 mol) in dry dichloromethane (200 mL) was added perbromomethane (86.95 g, 0.26 mol) in dry dichloromethane (50 mL) dropwise at 0° C. The reaction was stirred at room temperature overnight and concentrated under reduced pressure. The residue was purified by silica gel chromatography (petroleum ether:ethyl acetate=80:1) to afford the title compound (23 g, 66.7% yield) as a yellow oil.

Step 4: (2S,5R)-2-(3-(Benzyloxy)-5-bromopentyl)-5-isopropyl-3,6-dimethoxy-2,5-dihydropyrazine (S6)

To a dry-ice/acetone cooled solution of scheme 5-8 compound S5 (5 g, 0.027 mol) in THF (50 ml), n-BuLi (2.5 M, 14.1 mL, 0.035 mol) was added dropwise for 30 min. After addition, the reaction was stirred at this temperature for 30 min, followed by dropwise addition of a solution of compound S4 (13.6 g, 0.04 mol) in THF (20 mL). The reaction mixture was stirred at this temperature for another 30 min and allowed to stir at room temperature for 16 h. Then the reaction was quenched with aqueous NH$_4$Cl (50 mL) and extracted with ethyl acetate (60 mL×2). The combined organic layers were washed with brine, dried over anhydrous Na$_2$SO$_4$, filtered and then concentrated. The residue was purified by column chromatography on silica gel (eluted with petroleum ether:ethyl acetate=10:1) to afford the title compound (6 g, yield 50.4%) and scheme 5-8 compound S4 (4.8 g) was recovered.

Step 5: (2S)-Methyl 2-amino-5-(benzyloxy)-7-bromoheptanoate Hydrochloride Salt (S7)

To a mixture of scheme 5-8 compound S6 (6 g, 0.01 mol) in dioxane (30 mL) was added 0.5 M HCl (30 mL, dropwise at 0° C. The reaction was stirred at room temperature overnight and concentrated under reduced pressure to afford a residue, which was co-evaporated with toluene (15 mL×2) to afford the title compound (crude HCl salt, 8 g) as a brown oil. The residue was directly used in the next reaction without purification.

Step 6: (2S)-1-tert-Butyl 2-methyl 5-(benzyloxy)azepane-1,2-dicarboxylate (S8)

To a mixture of scheme 5-8 compound S7 (8 g crude) in acetonitrile (80 mL) was added DIPEA (9.03 mL, 0.054 mol), followed by sodium iodide (2.05 g, 0.013 mol). The reaction was stirred at 90° C. for 16 h. Then (Boc)$_2$O (5.97 g, 0.027 mol) was added and the reaction mixture was stirred at room temperature for 3 h. The resulting mixture was diluted with ethyl acetate (100 mL) and washed twice with brine (30 mL×2). The organic layer was dried over anhydrous Na$_2$SO$_4$, filtered and concentrated. The crude product was purified by silica gel chromatography (petroleum ether:ethyl acetate=20:1) to afford the title compound (3.6 g, 72.4% yield) as a colorless oil.

Step 7: tert-Butyl (2S)-1-tert-butyl 2-methyl 5-hydroxyazepane-1,2-dicarboxylate (S9)

A solution of scheme 5-8 compound S8 (1.6 g, 4.40 mmol) and cat. HOAc (1.5 mL) in methanol (35 mL) was degassed three times under N$_2$ atmosphere, and Pd(OH)$_2$ (240 mg) was added. The mixture was degassed again and stirred under a H$_2$ balloon at 50° C. over 12 h. The reaction was filtered through celite, and the filtrate was concentrated to afford the title compound (1.1 g, 91.3% yield) as a light yellow oil.

Step 8: (2S)-1-tert-Butyl 2-methyl 5-fluoroazepane-1,2-dicarboxylate (S10)

To a dry-ice/ethanol cooled solution of scheme 5-8 compound S9 (1.1 g, 4.03 mmol) in DCM (20 mL) was added DAST (0.79 mL, 6.04 mmol) dropwise. The reaction mixture was warmed up slowly and stirred at room temperature overnight. After quenching with saturated aq.NaHCO₃ solution, the mixture was extracted with DCM (20 mL×2). The combined organic phases were washed with water and brine, dried over anhydrous Na₂SO₄, filtered and concentrated to afford crude product. The crude product was purified by silica gel chromatography (petroleum ether:ethyl acetate=10:1) to afford the title compound (750 mg, 68.1% yield) as a colorless oil.

Step 9: (2S)-1-(tert-Butoxycarbonyl)-5-fluoro-azepane-2-carboxylic acid (S11)

To a mixture of scheme 5-8 compound S10 (750 mg, 2.72 mmol) in THF (7 mL) was added aqueous NaOH solution (4 M, 2.7 mL, 10.8 mmol). The reaction was stirred at 40° C. overnight and concentrated under reduced pressure. The residue was diluted with water (10 mL) and washed with Et₂O (3 ml×2). The aqueous layer was acidified with diluted hydrochloric acid (1 M) to pH=3. The resulting mixture was extracted with DCM (10 mL×2). The combined organic layers were washed with brine, dried over anhydrous Na₂SO₄ and concentrated under reduced pressure to afford the title compound (700 mg, 98.4% yield) as a white solid.

Step 10: (2S)-tert-Butyl 5-fluoro-2-(6-methylpyridin-2-ylcarbamoyl)azepane-1-carboxylate (S12)

To a solution of scheme 5-8 compound S11 (500 mg, 1.91 mmol) and 6-methylpyridin-2-amine (248 mg, 2.29 mmol) in DCE (10 ml) was added DIPEA (0.95 mL, 5.73 mmol) and EEDQ (943.5 mg, 3.82 mmol). The reaction mixture was stirred at 90° C. overnight and concentrated under high vacuum. The residue was purified by silica gel chromatography (petroleum ether:ethyl acetate=10:1) to afford the title compound (500 mg, 74.4% yield) as a white solid.

Step 11: (2S)-5-Fluoro-N-(6-methylpyridin-2-yl)azepane-2-carboxamide hydrochloride (S13)

To a mixture of scheme 5-8 compound S12 (500 mg, 1.42 mmol) in dioxane (2 mL) was added HCl/dioxane (4 M, 5 mL) dropwise at 0° C. The reaction mixture was stirred at room temperature for 2 h and concentrated under reduced pressure to afford scheme 5-8 S13 (550 mg, 100% yield) as a white solid, which was directly used in the next reaction without purification.

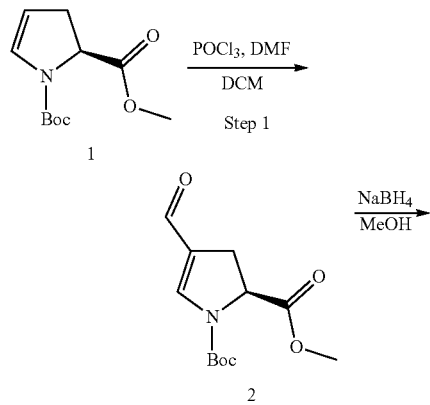

Scheme 5-9

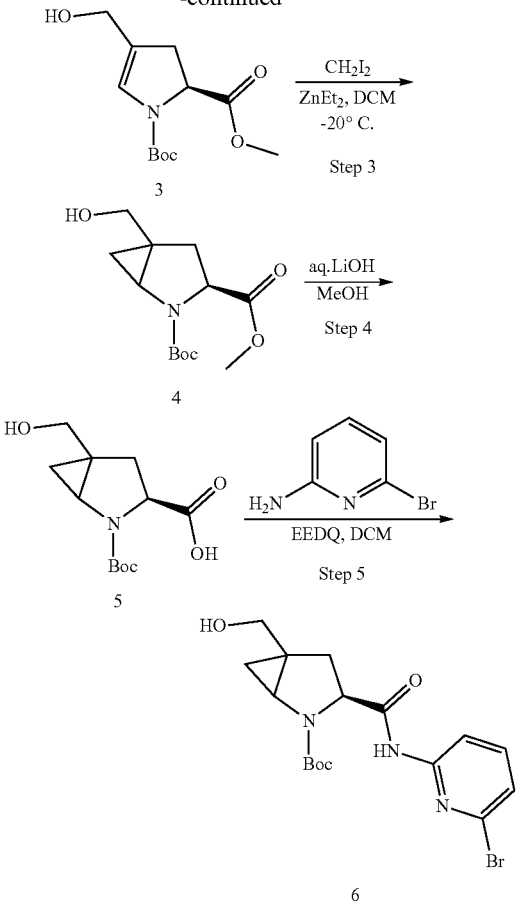

Step 1: (S)-Methyl 4-formyl-2,3-dihydro-1H-pyrrole-2-carboxylate (S2)

POCl₃ (2.7 g, 17.6 mmol) was added dropwise to ice-cooled DMF (2.6 g, 35.2 mmol) under N₂ atmosphere. The reaction was stirred at 0° C. for 30 min and then diluted with dry DCM (50 mL). A solution of scheme 5-8 compound S1 (2 g, 8.8 mmol) in DCM (20 mL) was added to the above mixture dropwise at 0° C. for 30 min. The reaction mixture was stirred at room temperature for 1 h and slowly poured into ice cooled 2 M aqueous NaOH solution. The resulting mixture was extracted with DCM (50 mL×2). The combined organic layers were washed with water and brine, dried, and concentrated to afford a residue that was purified by silica gel column chromatography (eluted with petroleum ether: ethyl acetate=10:1 to 5:1) to afford the title compound (1.9 g, 84.6% yield) as a light yellow oil.

Step 2: (S)-1-tert-Butyl 2-methyl 4-(hydroxymethyl)-2,3-dihydro-1H-pyrrole-1,2-dicarboxylate (S3)

To a solution of the scheme 5-8 compound S2 (1.9 g, 7.44 mmol) in DCM (20 mL) and MeOH (10 mL) was added NaBH₄ (23 mg, 1.44 mmol) in portions at −70° C. The reaction was stirred at 0° C. for 30 min and quenched with saturated aqueous NH₄Cl solution (10 mL). The resulting mixture was extracted with DCM twice and the combined organic layers were washed with brine, dried over anhydrous Na₂SO₄, filtered, and concentrated. The residue was purified by silica gel column chromatography (eluted with petroleum ether:ethyl acetate=10:1 to 3:1) to afford the title compound (1.7 g, 88.8% yield) as a colorless oil.

Step 3: (3S)-2-tert-Butyl 3-methyl 5-(hydroxymethyl)-2-azabicyclo[3.1.0]hexane-2,3-dicarboxylate (S4)

To a solution of the scheme 5-8 compound S3 (1.5 g, 5.83 mmol) in DCM (20 mL) was added diethylzinc hexane solution (1 M, 17.5 mL, 17.5 mmol) dropwise followed by diiodomethane (4.68 g, 17.5 mmol) at −20° C. under N₂ atmosphere. The reaction was stirred at −20° C. for 2 h and quenched with aqueous NH₄Cl solution. The resulting mixture was extracted with DCM twice. The combined organic layers were washed with water and brine, dried over anhydrous Na₂SO₄, filtered and concentrated to afford a residue. This residue was purified by silica gel column chromatography (eluted with petroleum ether:ethyl acetate=10:1 to 3:1) to afford the title compound (1.2 g, 75.8% yield) as a colorless oil.

Step 4: (3S)-2-(tert-Butoxycarbonyl)-5-(hydroxymethyl)-2-azabicyclo[3.1.0]hexane-3-carboxylic Acid (S5)

To a solution of scheme 5-8 compound S4 (150 mg, 0.55 mmol) in THF (5 mL) was added aqueous LiOH solution (3 mL, 3 mmol). The reaction was stirred at room temperature for 2 h and concentrated. The residue was acidified with 1 N HCl solution to pH=~3. The resulting mixture was extracted with EtOAc twice. The combined organic layer was washed with brine, dried over anhydrous Na₂SO₄, filtered and concentrated to afford the title compound (110 mg, 78.2% yield) as a white solid.

Step 5: (3S)-tert-Butyl 3-(6-bromopyridin-2-ylcarbamoyl)-5-(hydroxymethyl)-2-azabicyclo[3.1.0]hexane-2-carboxylate (S6)

To a mixture of the scheme 5-8 compound S5 (110 mg, 0.43 mmol), 6-bromopyridin-2-amine (74 mg, 0.43 mmol and EEDQ (210 mg, 0.85 mmol) in 1,2-DCE (5 mL) was added DIPEA (165 mg, 1.29 mmol). The reaction was stirred at 90° C. for 16 h and concentrated. The residue was purified by silica gel column chromatography (eluted with petroleum ether:ethyl acetate=10:1 to 2:1) to afford the title scheme 5-8 compound S6 (120 mg, 67.7% yield) as a yellow solid. LC/MS (ESI) m/z: 412 (M+H)⁺.

Scheme 5-10

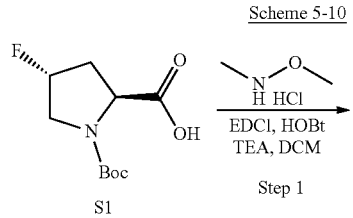

S1

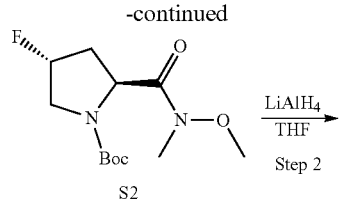

S2

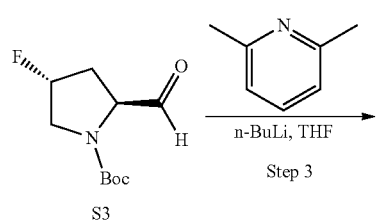

S3

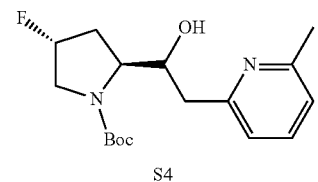

S4

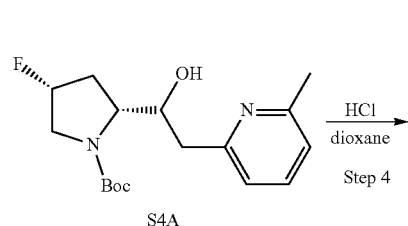

S4A

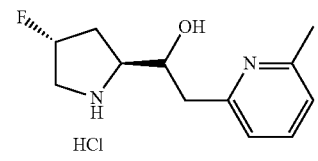

5

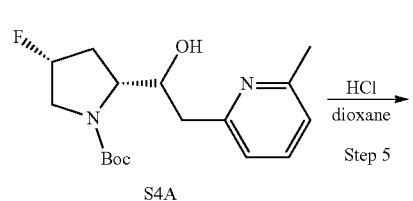

S4A

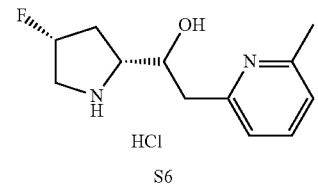

S6

Step 1: (2S,4R)-tert-Butyl 4-fluoro-2-(methoxy(methyl)carbamoyl)pyrrolidine-1-carboxylate (S2)

To a solution of scheme 5-10 compound S1 (5 g, 21.43 mmol) in DCM (100 mL) was added N,O-dimethylhydroxylamine hydrochloride (2.5 g, 25.72 mmol), EDCI (6.16 g, 32.14 mmol) and HOBt (2.9 g, 21.43 mmol) followed by TEA (5.4 g, 53.58 mmol) at 0° C. The reaction mixture was stirred at room temperature for 16 h. The mixture was diluted with DCM and washed with water and brine, dried over anhydrous $Na_2SO_4$ and concentrated to afford crude product that was washed with petroleum ether/EtOAc (2/1) to afford the title compound (5.5 g, 92.88% yield) as a white solid.

Step 2: (2S,4R)-tert-Butyl 4-fluoro-2-formylpyrrolidine-1-carboxylate (S3)

To a solution of scheme 5-10 compound S2 (5 g, 18.12 mmol) in THF (40 mL) was added $LiAlH_4$ (1.38 g, 36.23 mmol). The reaction was stirred at 0° C. for 2 h. The reaction was quenched with water (1.38 mL), aqueous NaOH solution (1.38 mL, 15% wt) and water (4 mL) successively. The mixture was filtered and the filter cake was washed with THF twice. The combined filtrates were concentrated to dryness to afford crude product. The crude product was purified by silica gel column chromatography (eluted with petroleum ether:ethyl acetate=30:1 to 10:1) to afford the title compound (2.7 g, 68.7% yield) as a white solid.

Step 3: (2S,4R)-tert-Butyl 4-fluoro-2-((R)-1-hydroxy-2-(6-methylpyridin-2-yl)ethyl)pyrrolidine-1-carboxylate (S4A) & (2R,4R)-tert-butyl 4-fluoro-2-((S)-1-hydroxy-2-(6-methylpyridin-2-yl)ethyl)pyrrolidine-1-carboxylate (S4)

To a stirred solution of 2,6-dimethylpyridine (2.46 g, 23.04 mmol) in THF (50 mL) was added n-butyllithium (1.6 M in THF, 7.2 mL, 11.52 mmol) dropwise at −70° C. The reaction mixture was stirred at this temperature for 1 h. and then scheme 5-10 compound S3 (2.5 g, 1.52 mmol) in THF (10 mL) was added at −70° C. for 30 min. The mixture was continued to stir at this temperature for 1 h and quenched with aqueous $NH_4Cl$ solution. The resulting mixture was extracted with EtOAc (100 mL). The organic phase was washed with brine, dried with anhydrous $Na_2SO_4$ and concentrated. The residue was purified by silica gel column chromatography (eluted with petroleum ether:ethyl acetate=20:1 to 10:1) to afford the title compound S4 (1.2 g, 26.3% yield) and S4A (1.3 g, 28.56% yield) as a white solid.

Step 4: (R)-1-((2S,4R)-4-Fluoropyrrolidin-2-yl)-2-(6-methylpyridin-2-yl)ethanol (S5)

To a solution of scheme 5-10 compound S4 (1.2 g, 3.7 mmol) in dioxane (10 mL) was added HCl/dioxane (4 M, 5 mL). The reaction mixture was stirred at room temperature for 1 h. The reaction solution was concentrated to afford scheme 5-10 compound S5 (1.3 g, 100% yield) as a white solid. This compound was carried forward without any further purification.

Step 5: (S)-1-((2R,4R)-4-Fluoropyrrolidin-2-yl)-2-(6-methylpyridin-2-yl)ethan-1-ol (S6)

To a solution of scheme 5-10 compound S4A (1.3 g, 4 mmol) in dioxane (10 mL) was added HCl/dioxane (4 M, 5 mL). The reaction mixture was stirred at room temperature for 1 hr and concentrated to dryness to afford scheme 5-10 compound S6 (1.4 g, 100% yield) as a white solid. This compound was carried forward without further purification.

Example 6. Synthesis of a Moieties

Scheme 6-1

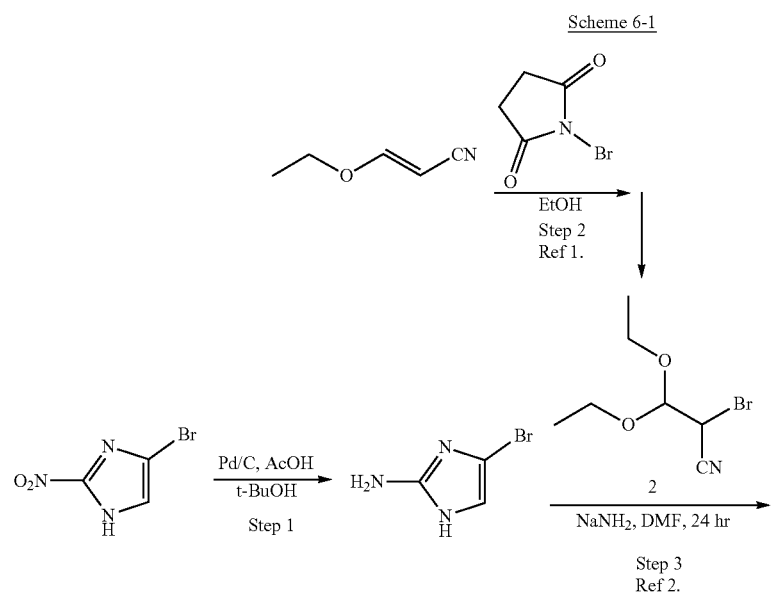

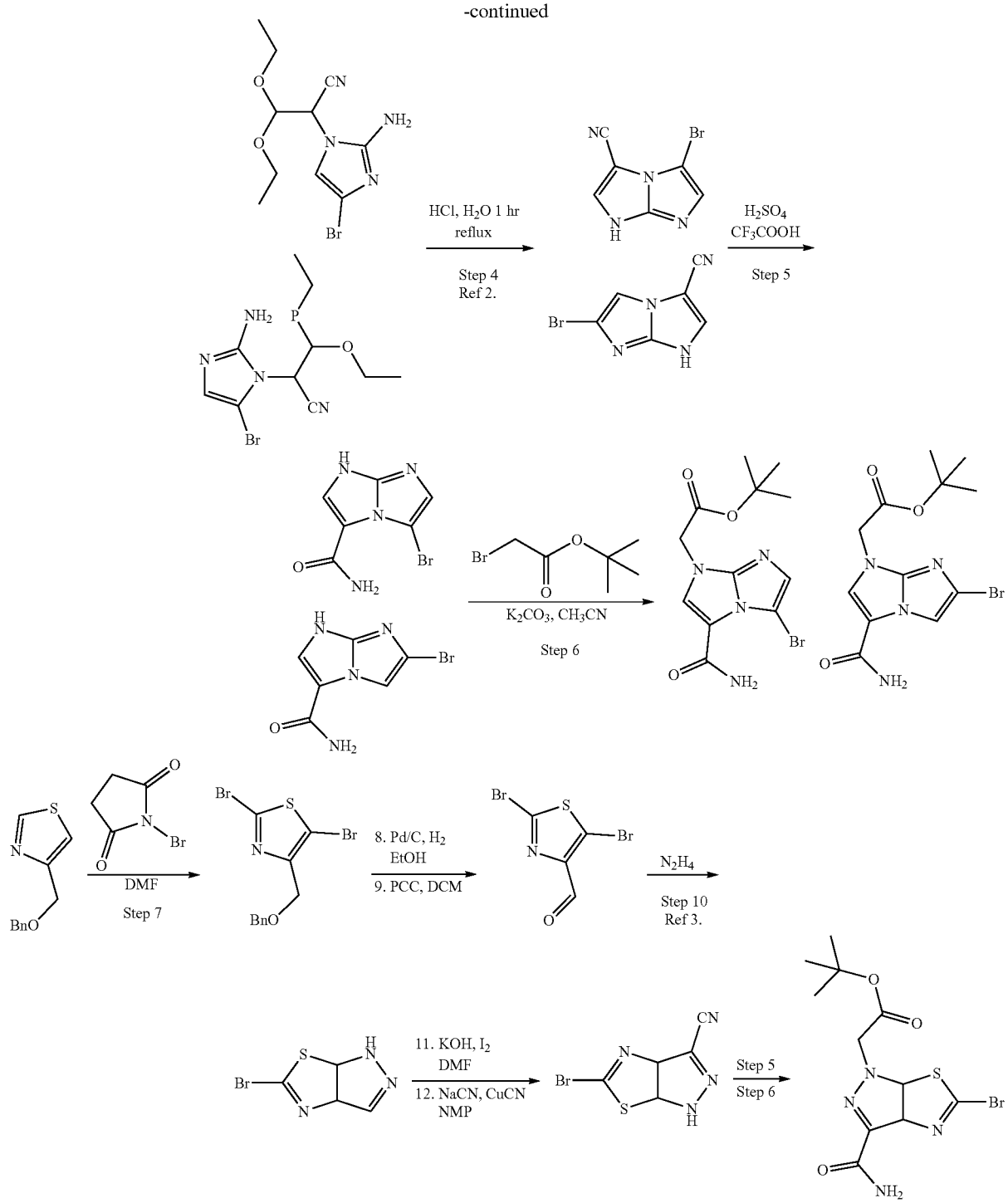

1. Babler, J.H. (1987). Synth. Commun. 17(1): 77-84.
2. Mas, T., et al. (2002). ARKIVOC (Gainesville, FL, U. S.) (5): 48-61.
3. Lebedev, A. Y., et al. (2005). J. Org. Chem. 70(2): 596-602.

Scheme 6-1: In Step 1 the appropriately substituted nitro species is reduced with palladium as known in the art to afford an amine. In Step 2 the appropriately substituted alkene species is brominated with concurrent addition of ethanol as known in the art to afford the bromide species. In Step 3 the appropriately substituted mixture of tautomers is subjected to the previously prepared bromide species as known in the art to afford the two isomers. The appropriately substituted isomers corresponding to each tautomer may either be separated or used as a mixture in the subsequent reactions with separation at a later step. In Step 4 the appropriately substituted ketal species is deprotected and subsequently cyclized in the presence of acid as known in the art. In Step 5 the appropriately substituted cyano species is subjected to strong acid to afford a primary amide. In Step 6 the appropriately substituted heterocycle is subjected to a bromide species of the appropriate linker to afford the appropriately protected species. Various 5-5 fused bicyclic systems can be appropriately prepared by slight modifications of this synthetic protocol, another non-limiting example is presented in Steps 5 through 12 with the same conditions for formation of a primary amide and installation of linker. In Step 7 the appropriately substituted aryl species is brominated as known in the art. In Step 8 the appropriately substituted ether species is deprotected with palladium as known in the art to afford an alcohol. In Step 9 the appropriately substituted alcohol is oxidized as known in the art to afford an aldehyde. In Step 10 the appropriately substituted aldehyde is subjected to hydrazine to first form a Schiff base and subsequently cyclize to afford a bicyclic system. In Step 11 the appropriately substituted bicyclic system is iodinated as known in the art. In Step 12 the appropriately substituted iodide is subjected to sodium cyanide to afford the cyano species.

Scheme 6-2

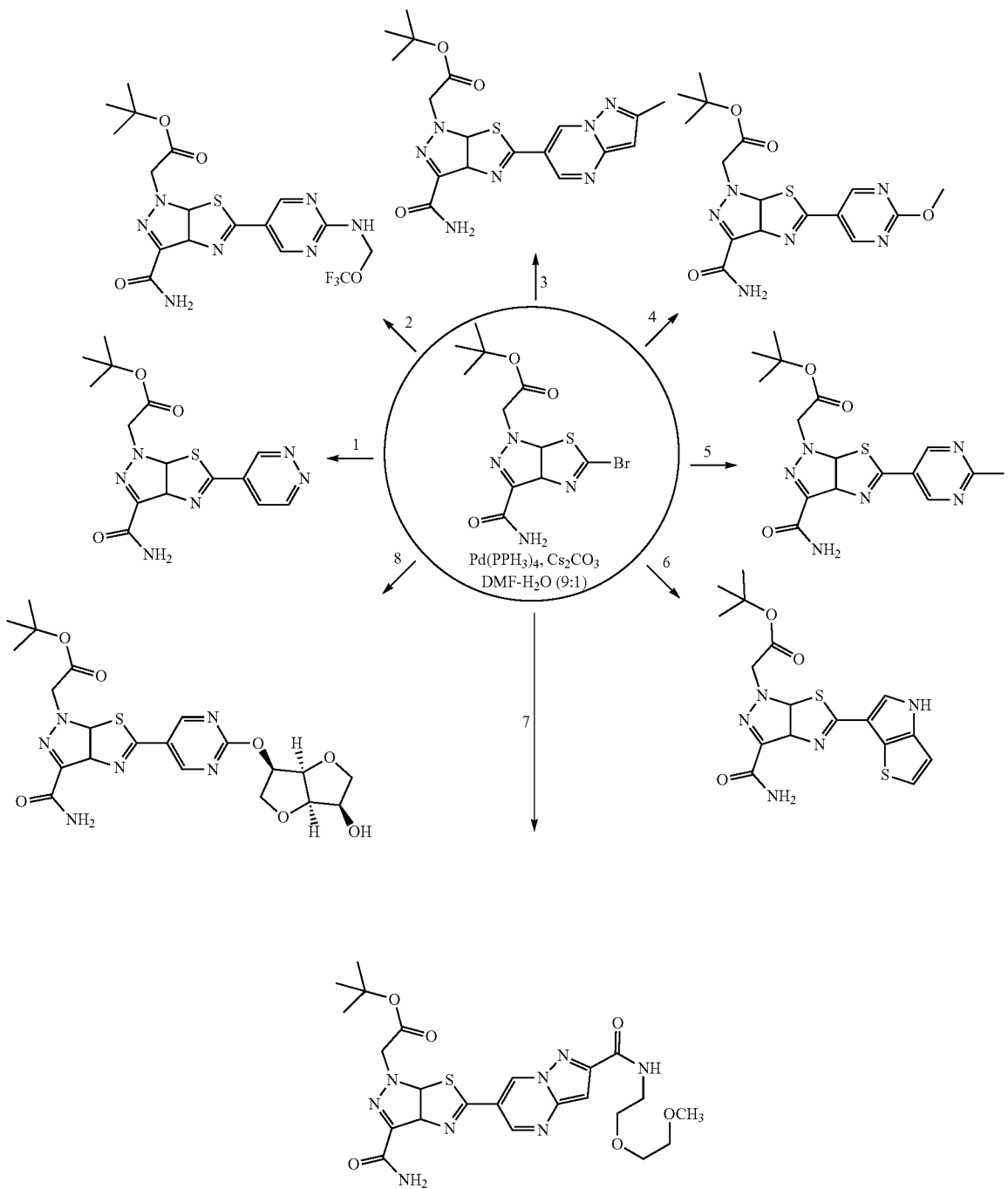

-continued
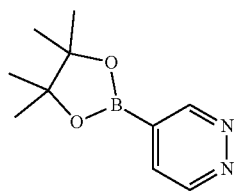
1
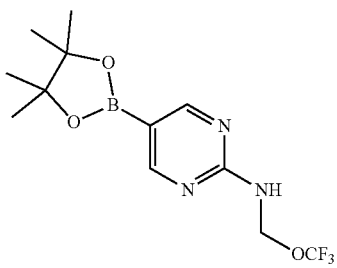
2
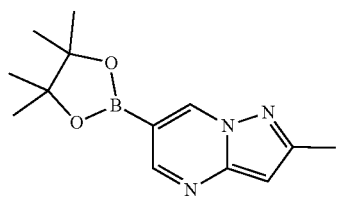
3
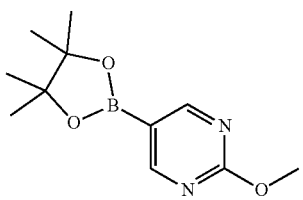
4
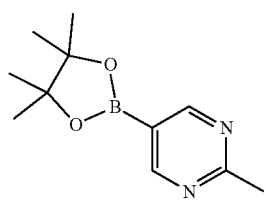
5
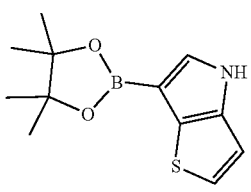
6
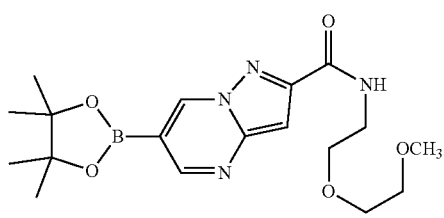
7
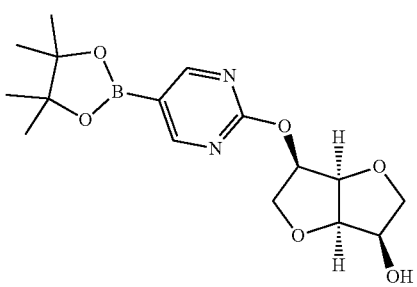
8
Scheme 6-2: Non-limiting examples of aryl substituents are provided demonstrating the robust nature of the synthetic protocol. Boronic acids 1-8 are subjected to an appropriately substituted aryl bromide to afford a biaryl system.
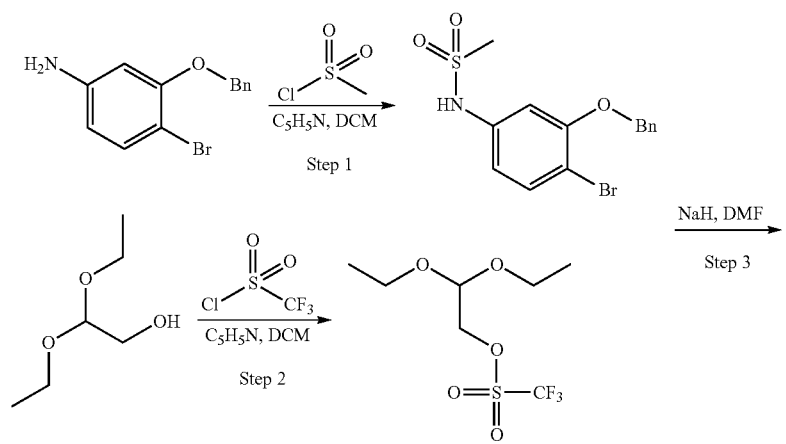
Scheme 6-3

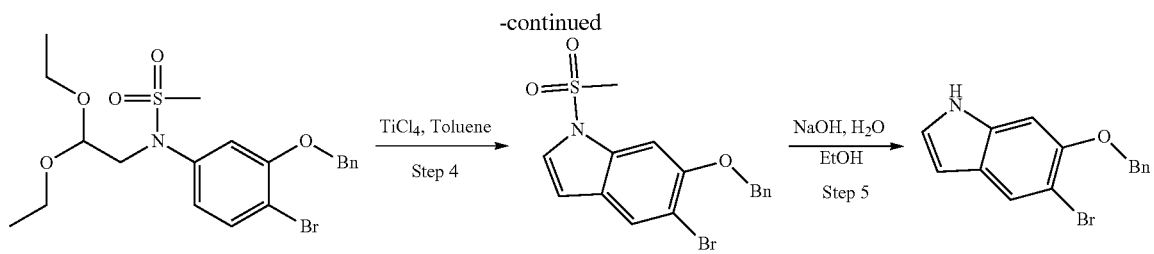

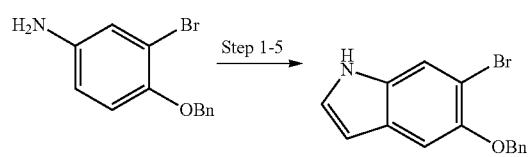

Scheme 6-3: In Step 1 the appropriately substituted and protected aniline is converted as known in the art to a sulfonamide. In Step 2 the appropriately substituted alcohol is converted as known in the art to a triflouro sulfonamide. In Step 3 the previously prepared reagents are subjected to sodium hydride to afford their adduct. In Step 4 the appropriately substituted ketal is subjected to a strong lewis acid to afford deprotection and subsequent cyclization to a biaryl species. In Step 5 the appropriately substituted sulfonamide is deprotected in the presence of base to afford a free amine. In an alternative embodiment this synthetic protocol can be applied to other aniline isomers to afford substituents on alternative positions.

Scheme 6-4

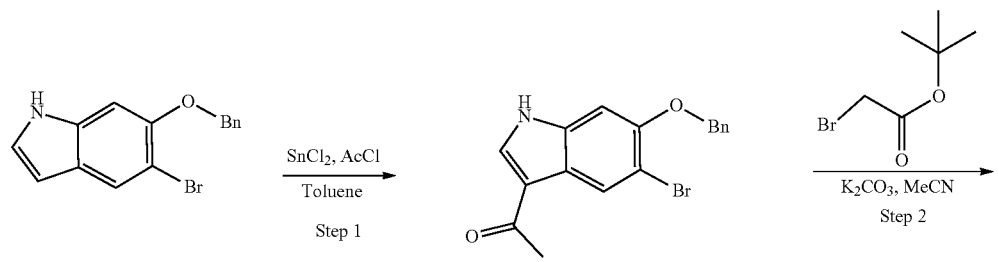

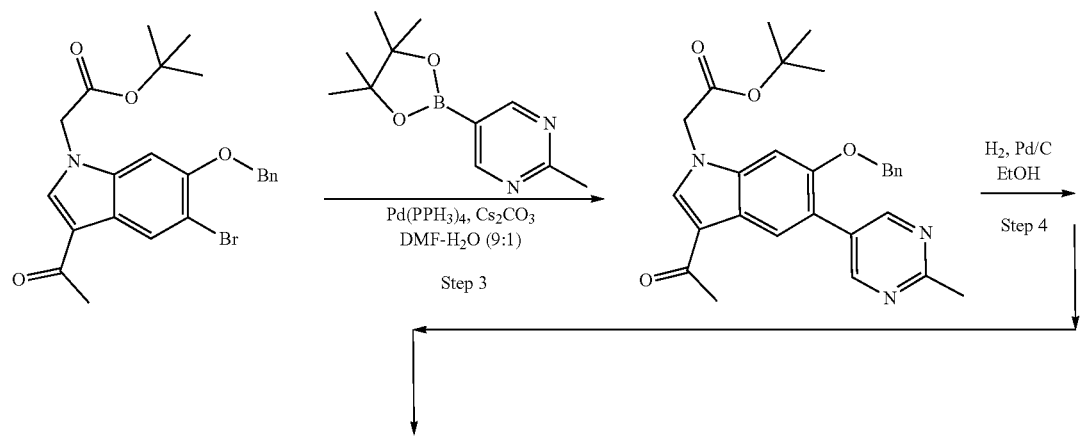

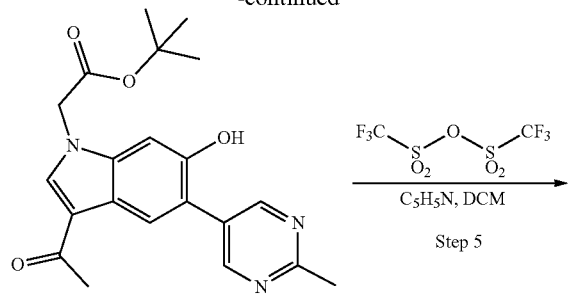

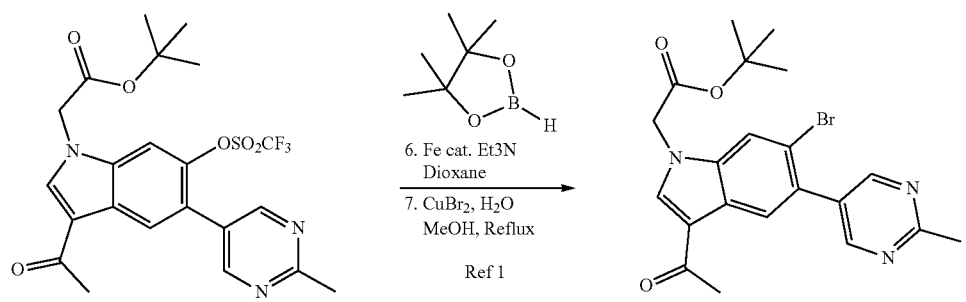

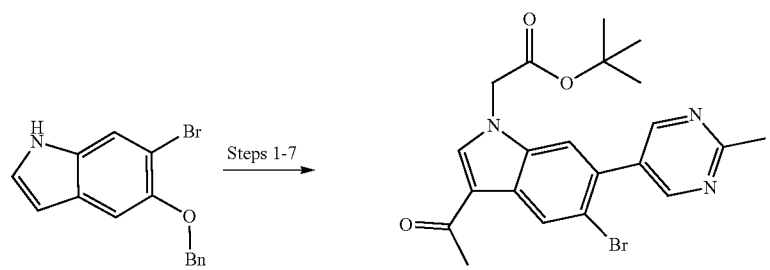

1. Thompson, A. L. S., et al. (2005). Synthesis (4): 547-550.

Scheme 6-4: In Step 1 the appropriately substituted indole is acylated as known in the art. In Step 2 the appropriately substituted heterocycle is subjected to a bromide species of the appropriate linker to afford the appropriately protected species. In Step 3 the appropriately substituted aryl bromide is subjected to a boronic acid to afford an aryl species. In Step 4 the appropriately substituted benzyl alcohol is deprotected in the presence of hydrogen gas and palladium to afford a free alcohol. In Step 5 the appropriately substituted phenol is subjected to a sulfonic anhydride to afford a leaving group. In Step 6 the appropriately substituted aryl species is converted to a boronic acid as known in the art. In Step 7 the appropriately substituted boronic acid is subjected to copper bromide to afford an aryl bromide species. In an alternative embodiment this synthetic protocol can simply be applied to other indole isomers to afford substituents on alternative positions.

Scheme 6-5
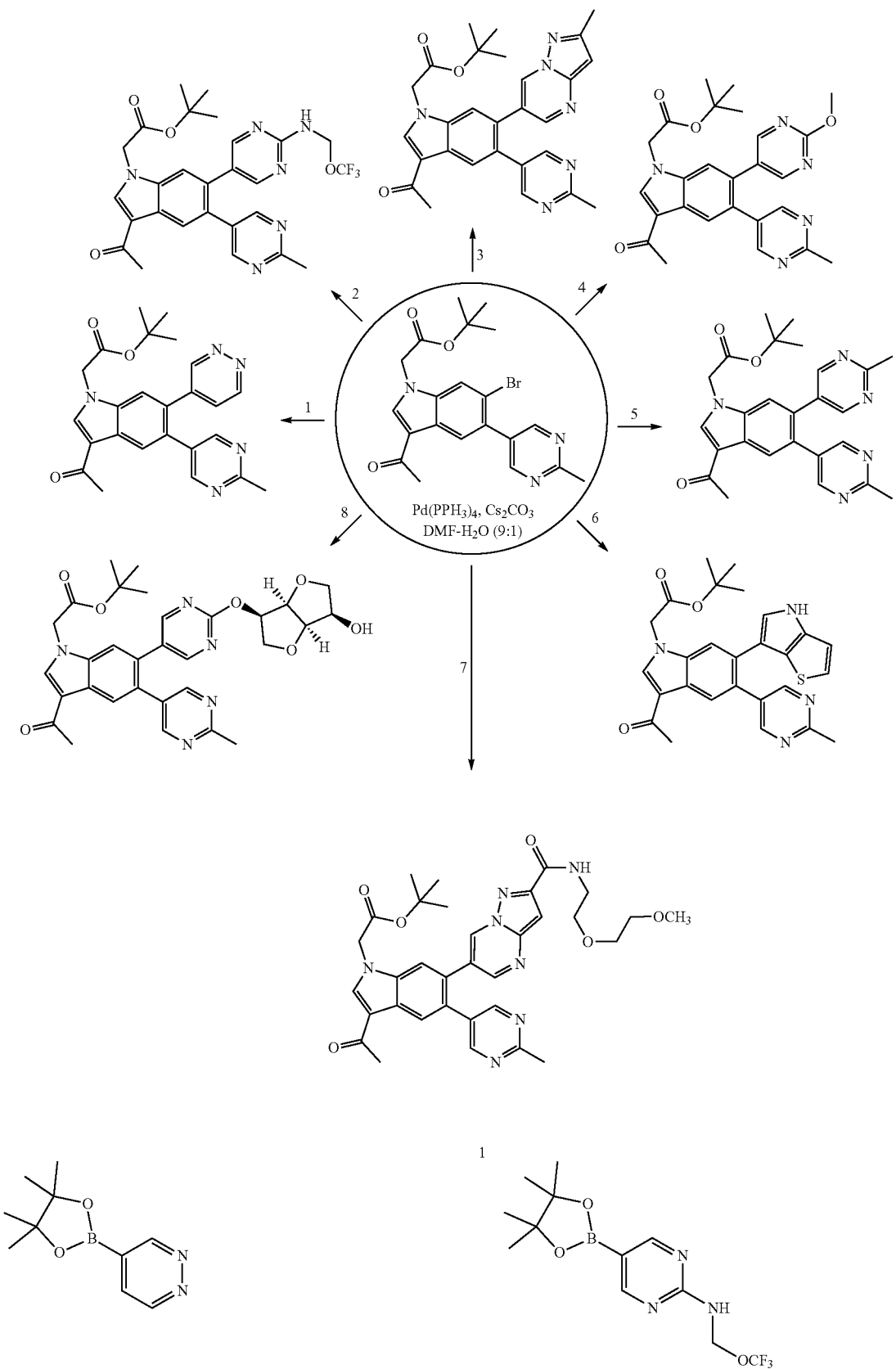

1
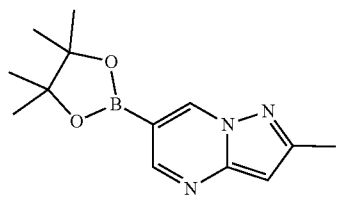
2
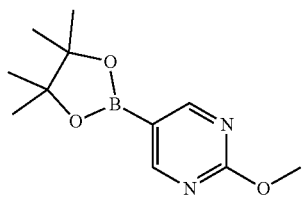
3
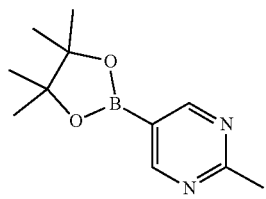
4
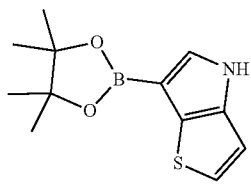
5
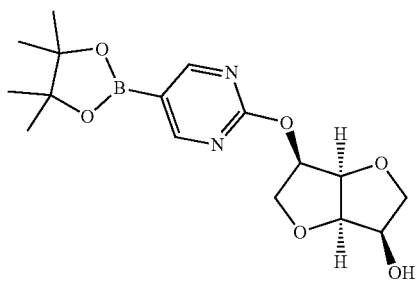
6
7
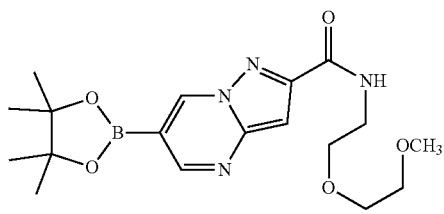
8
Scheme 6-5: Non-limiting examples of aryl substituents are provided demonstrating the robust nature of the synthetic protocol. Boronic acids 1-8 are subjected to an appropriately substituted aryl bromide to afford an aryl system.
-continued
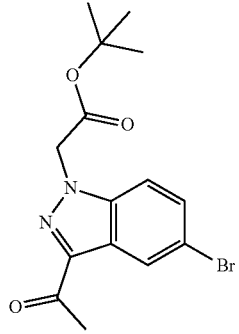
Scheme 6-6
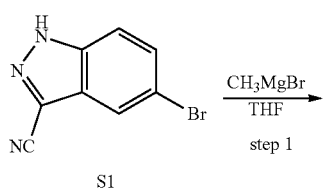
S1
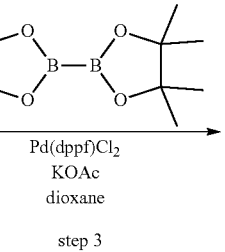
step 3
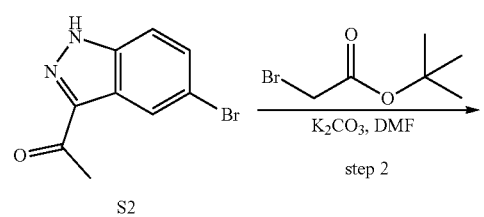
S2
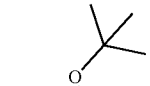
S4
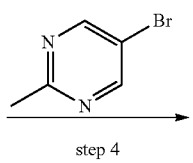
step 4

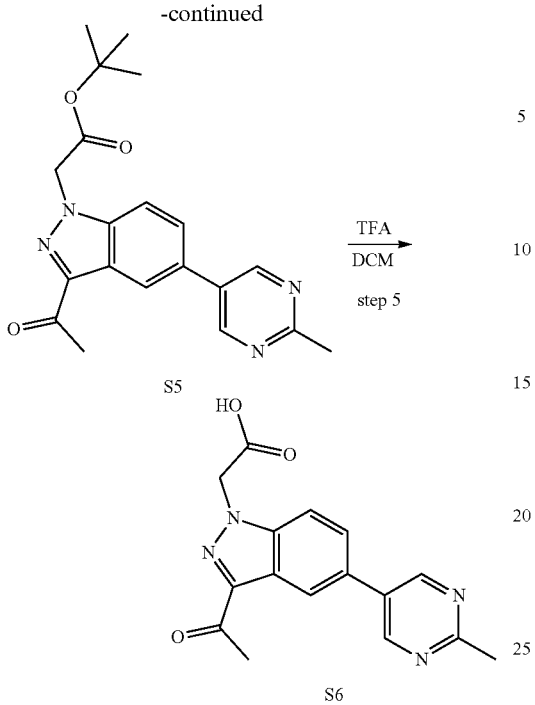

Step 1: 1-(5-Bromo-1H-indazol-3-yl)ethanone (S2)

To a stirred solution of scheme 6-6 compound S1 (10 g, 57.5 mmol) in THF (150 mL) under nitrogen was added methyl magnesium bromide solution (63.2 mL, 126.5 mmol) dropwise at 0° C. under $N_2$ atmosphere. The reaction mixture was stirred at room temperature for 16 h. The mixture was quenched with saturated aqueous $NH_4Cl$ solution and extracted with EtOAc (200 mL). The organic phase was washed with brine, dried with anhydrous $Na_2SO_4$ and concentrated. The residue was purified by silica gel column chromatography (eluted with petroleum ether:ethyl acetate=10:1 to 5:1) to afford the title compound (5.1 g, 37.1% yield) as a white solid.

Step 2: tert-Butyl 2-(3-acetyl-5-bromo-1H-indazol-1-yl)acetate (S3)

To a mixture of scheme 6-6 compound S2 (5 g, 20.9 mmol) and tert-butyl bromoacetate (4.9 g, 25.1 mmol) in DMF (40 mL) was added $K_2CO_3$ (5.78 g, 41.8 mmol). The reaction was stirred at room temperature overnight. The mixture was diluted with water and extracted with ethyl acetate (100 mL). The organic phase was washed with brine, dried with anhydrous $Na_2SO_4$ and concentrated, the residue was purified by silica gel column chromatography (eluted with petroleum ether:ethyl acetate=50:1 to 5:1) to afford the title compound (6.5 g, 88.0% yield) as a white solid.

Step 3: tert-Butyl 2-(3-acetyl-5-(4,4,5,5-tetramethyl-1,3,2-dioxaborolan-2-yl)-1H-indazol-1-yl)acetate (S4)

A mixture of scheme 6-6 compound S3 (5.5 g, 15.57 mmol), 4,4,4',4',5,5,5',5'-octamethyl-2,2'-bi(1,3,2-dioxaborolane) (3.99 g, 18.67 mmol), KOAc (4.58 g, 46.71 mmol) in dioxane (70 mL) was degassed under $N_2$ for three times. Pddppf (1.14 g, 1.56 mmol) was added to the mixture and the resulting mixture was degassed again and stirred at 120° C. under $N_2$ atmosphere for 2 h. The mixture was diluted with EtOAc and washed with water and brine, dried, and concentrated to afford a residue. The crude material was purified by silica gel column chromatography (eluted with petroleum ether:ethyl acetate=10:1 to 1:1) to afford the title compound (3.5 g, 56.2% yield) as a white solid.

Step 4: tert-Butyl 2-(3-acetyl-5-(2-methylpyrimidin-5-yl)-1H-indazol-1-yl)acetate (S5)

The mixture of scheme 6-6 compound S4 (3.5 g, 8.744 mmol), 5-Bromo-2-methylpyrimidine (1.666 g, 9.681 mmol), $Pd(PPh_3)_4$ (1 g, 0.87 mmol) and $K_2CO_3$ (3.63 g, 26.23 mmol) in dioxane (150 mL) and water (50 mL) was degassed under $N_2$ atmosphere for three times and then stirred at 100° C. for 4 h under $N_2$ atmosphere. The mixture was diluted with EtOAc, washed with water and brine, dried over anhydrous $Na_2SO_4$, filtered, and concentrated. The residue was purified by silica gel column chromatography (eluted with petroleum ether:ethyl acetate=50:1 to 5:1) to afford the title compound (2.4 g, 74.9% yield) as a white solid.

Step 5: 2-(3-Acetyl-5-(2-methylpyrimidin-5-yl)-1H-indazol-1-yl)acetic Acid (S6)

To a solution of scheme 6-6 compound S5 (2 g, 5.46 mmol) in DCM (20 mL) was added TFA (10 mL). The reaction was stirred at room temperature for 2 h. Then the reaction solution was concentrated to afford scheme 6-6 compound S6 (1.6 g, 100% yield) as a yellow solid. This compound was carried forward without any further purification.

Scheme 6-7

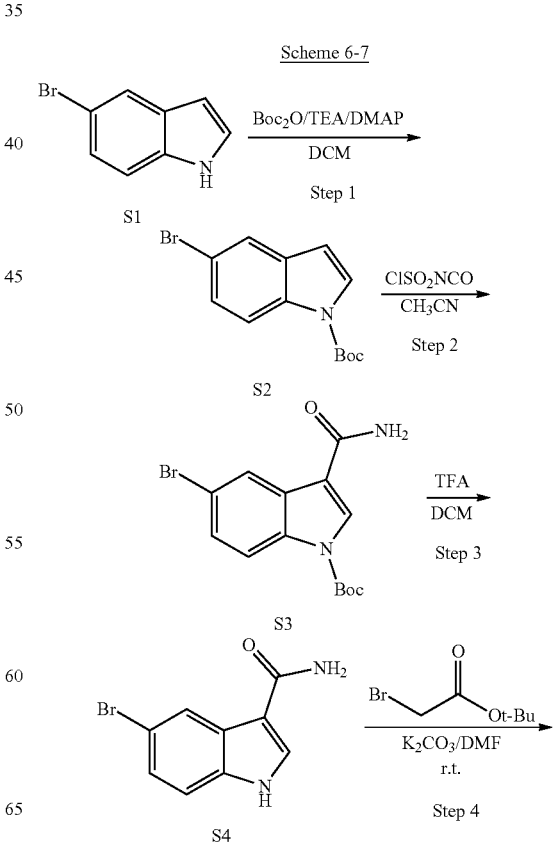

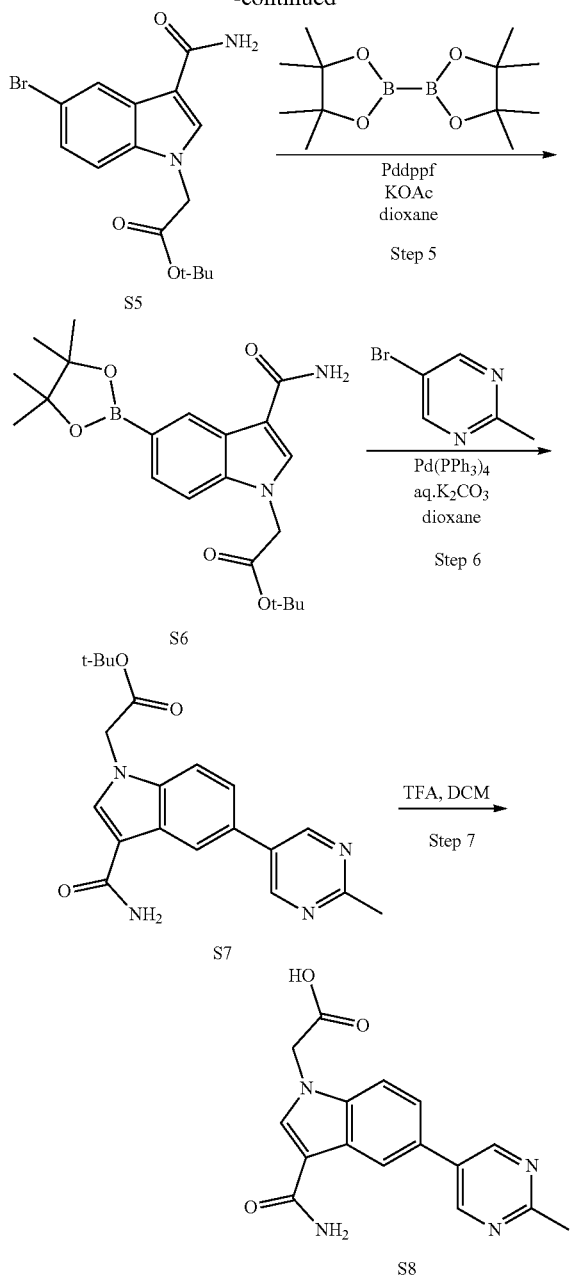

Step 1: tert-Butyl 5-bromo-1H-indole-1-carboxylate (S2)

To a solution of scheme 6-7 compound S1 (30 g, 0.15 mol) in DCM (300 mL) at 0° C. was added Et₃N (64 mL, 0.46 mol) and DMAP (5.6 g, 0.046 mol). This was followed by portion-wise addition of Boc₂O (50 g, 0.23 mol) and the reaction mixture was stirred at room temperature for 16 h. The mixture was diluted with DCM (200 mL) and washed with water and brine, dried over anhydrous Na₂SO₄, filtered and concentrated. The residue was purified by column chromatography on silica gel (eluted with petroleum ether: ethyl acetate=50:1) to afford the title compound (44 g, 97% yield) as a white solid. LC/MS (ESI) m/z: 240 (M−56+H)+.

Step 2: tert-Butyl 5-bromo-3-carbamoyl-1H-indole-1-carboxylate (S3)

To a solution of scheme 6-7 compound S2 (10 g, 33.7 mmol) in MeCN (100 mL) was added chlorosulfonyl isocyanate (3.1 mL, 35.6 mmol) dropwise at 0° C. The reaction was stirred at room temperature overnight. Acetone (200 mL) and H₂O (25 mL) was dropwise added at 0° C., followed by dropwise addition of aqueous KOH solution (5 mL, 10% wt). The reaction was stirred at room temperature for 30 min and extracted with EtOAc (50 mL×2). The combined organic phases are washed with brine, dried over anhydrous Na₂SO₄, and then concentrated to afford the title compound (7.4 g, 64.8% yield) as a white solid. LC/MS (ESI) m/z: 339 (M+H)+.

Step 3: 5-Bromo-1H-indole-3-carboxamide (S4)

To a solution of scheme 6-7 compound S3 (7.4 g, 21.8 mmol) in DCM (100 mL) was dropwise added TFA (15 mL) and the reaction was stirred at room temperature for 2 h. The reaction mixture was concentrated, and co-evaporated with toluene twice to afford the title compound (7.5 g, 100% yield) as a yellow solid, which was directly used in the next reaction without further purification. LC/MS (ESI) m/z: 239 (M+H)+

Step 4: tert-Butyl 2-(5-bromo-3-carbamoyl-1H-indol-1-yl)acetate (S5)

To a mixture of scheme 6-7 compound S4 (7.5 g, 21.8 mmol) and K₂CO₃ (9.04 g, 65.45 mmol) in DMF (100 mL) was added tert-butyl 2-bromoacetate (6.2 mL, 43.5 mmol) dropwise at 0° C. The reaction mixture was stirred at room temperature overnight. The mixture was diluted with EtOAc and washed with water and brine, dried over anhydrous Na₂SO₄, filtered and concentrated to afford crude product, which was washed with petroleum ether and dried under vacuum to afford the title compound (6.7 g, 87.0% yield) as a white solid. LC/MS (ESI) m/z: 353 (M+H)+.

Step 5: tert-Butyl 2-(3-carbamoyl-5-(4,4,5,5-tetramethyl-1,3,2-dioxaborolan-2-yl)-1H-indol-1-yl)acetate (S6)

To a solution of scheme 6-7 compound S5 (4 g, 11.36 mmol) in dioxane (40 mL) was added 4,4,4',4',5,5,5',5'-octamethyl-2,2'-bi(1,3,2-dioxaborolane) (4.4 g, 17.04 mmol), KOAc (2.2 g, 22.72 mmol), and PdCl₂(dppf) (416 mg, 0.568 mmol). The reaction mixture was stirred at 90° C. under N₂ for overnight. After filtration, water was added and the resulting mixture was extracted with ethyl acetate (20 mL×3). The organic phase was washed with brine, dried over anhydrous Na₂SO₄, filtered and then concentrated. The residue was purified by column chromatography on silica gel (eluted with DCM/MeOH=50:1 to 30:1) to afford scheme 5-7 compound S6 (4.2 g, 92.3% yield) as a white solid. LC/MS (ESI) m/z: 401 (M+H)+.

Step 6: tert-Butyl 2-(3-carbamoyl-5-(2-methylpyrimidin-5-yl)-1H-indol-1-yl)acetate (S7)

To a mixture of scheme 6-7 compound S6 (2 g, 4.99 mmol) and 5-bromo-2-methyl pyrimidine (1.04 g, 5.98 mmol) in dioxane (20 mL) was added aq.K₂CO₃ solution (7.5 mL, 7.5 mmol, 1 M) and the mixture was degassed under N₂ atmosphere three times. Pd(PPh₃)₄ (289 mg, 0.25 mmol) was added under N₂ atmosphere and the reaction was stirred at 100° C. under N₂ atmosphere for 16 h. The reaction mixture was cooled and diluted with EtOAc, washed with water and brine, dried and concentrated to dryness. The residue was purified by column chromatography on silica gel eluted with petroleum ether/EtOAc (10:1 to 1:1) to afford the title compound (1.49 g, 81.6% yield) as a white solid. LC/MS (ESI) m/z: 367 (M+H)⁺.

Step 7: tert-Butyl 2-(3-carbamoyl-5-(2-methylpyrimidin-5-yl)-1H-indol-1-yl)acetate (S8)

To a solution of scheme 6-7 compound S7 (1.49 g, 4.06 mmol) in DCM was added TFA dropwise at 0° C. The reaction mixture was stirred at room temperature for 2 h. The mixture was concentrated to dryness and washed with diethyl ether and dried under vacuum to afford scheme 6-7 compound S8 (1.1 g, 87.3% yield) as a yellow solid. LC/MS (ESI) m/z: 311 (M+H)⁺.

Scheme 6-8

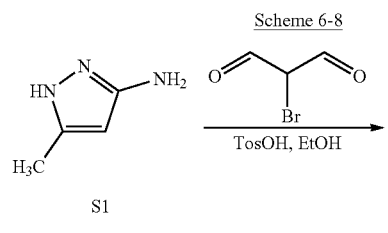

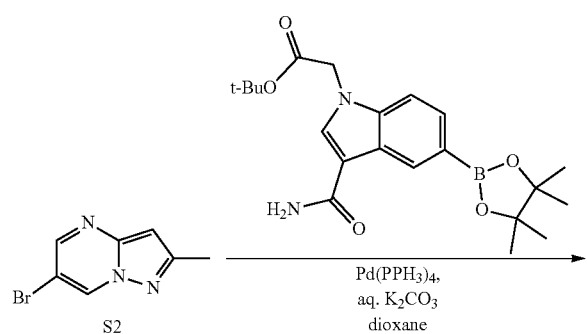

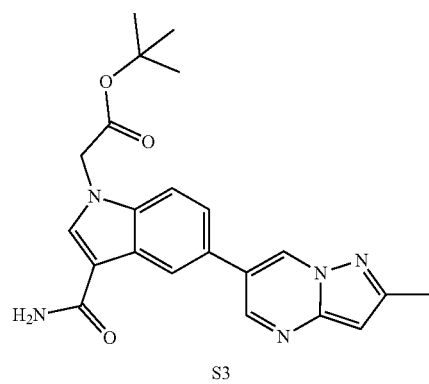

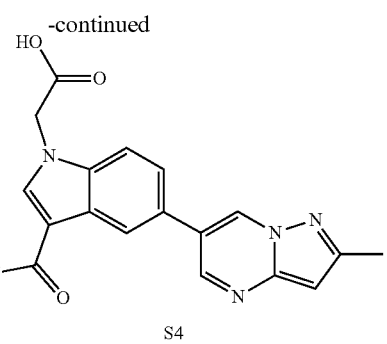

Step 1: 6-Bromo-2-methylpyrazolo [1,5-a] pyrimidine (S2)

To a solution of 5-methyl-1H-pyrazol-3-amine (1.0 g, 10.31 mmol) in EtOH (2 mL) was added 2-bromomalonaldehyde (1.56 g, 10.31 mmol), followed by 4-methylbenzenesulfonic acid (91 mg, 0.52 mmol). The reaction mixture was stirred at 80° C. overnight and concentrated. The residue was purified by column chromatography on silica gel eluted with petroleum ether/EtOAc (50:1 to 5:1) to afford the title compound (540 mg, 25.0% yield); LC/MS (ESI) m/z: 212 [M+H]⁺.

Step 2: tert-Butyl 2-(3-carbamoyl-5-(2-methylpyrazolo[1,5-a]pyrimidin-6-yl)-1H-indol-1-yl)acetate (S3)

To a mixture of scheme 6-8 compound S2 (490 mg, 1.22 mmol) and 6-bromo-2-methylpyrazolo [1,5-a] pyrimidine (286 mg, 1.35 mmol) in dioxane (10 mL) was added aqueous K₂CO₃ solution (2 mL, 2 mmol, 1 M) and the mixture was degassed under N₂ atmosphere for three times. After addition of Pd(PPh₃)₄ (70 mg, 0.06 mmol) under N₂ atmosphere, the reaction mixture was stirred at 100° C. under N₂ atmosphere for 16 h. The reaction mixture was cooled and diluted with EtOAc. The resulting mixture was washed with water and brine, dried over anhydrous Na₂SO₄ and concentrated to dryness. The residue was purified by column chromatography on silica gel eluted with DCM/MeOH (100:1 to 40:1) to afford the title compound (290 mg, 58.6% yield) as a white solid. LC/MS (ESI) m/z: 406 (M+H)⁺.

Step 3: 2-(3-Carbamoyl-5-(2-methylpyrazolo[1,5-a]pyrimidin-6-yl)-1H-indol-1-yl)acetic acid (S4)

To a solution of tert-butyl 2-(3-carbamoyl-5-(2-methylpyrazolo [1,5-a]pyrimidin-6-yl)-1H-indol-1-yl) acetate (290 mg, 0.72 mmol) in DCM (2 mL) was added TFA (2 mL). The reaction mixture was stirred at room temperature for 2 h and concentrated to dryness to afford scheme 6-8 compound S4 (240 mg, 96% yield) as a yellow solid, which was used directly in the next step; LC-MS: LC/MS (ESI) m/z: 350 [M+H]⁺.

Scheme 6-9

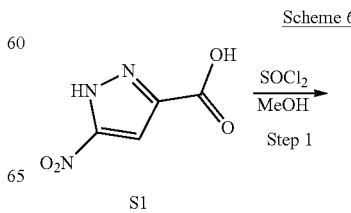

Step 1

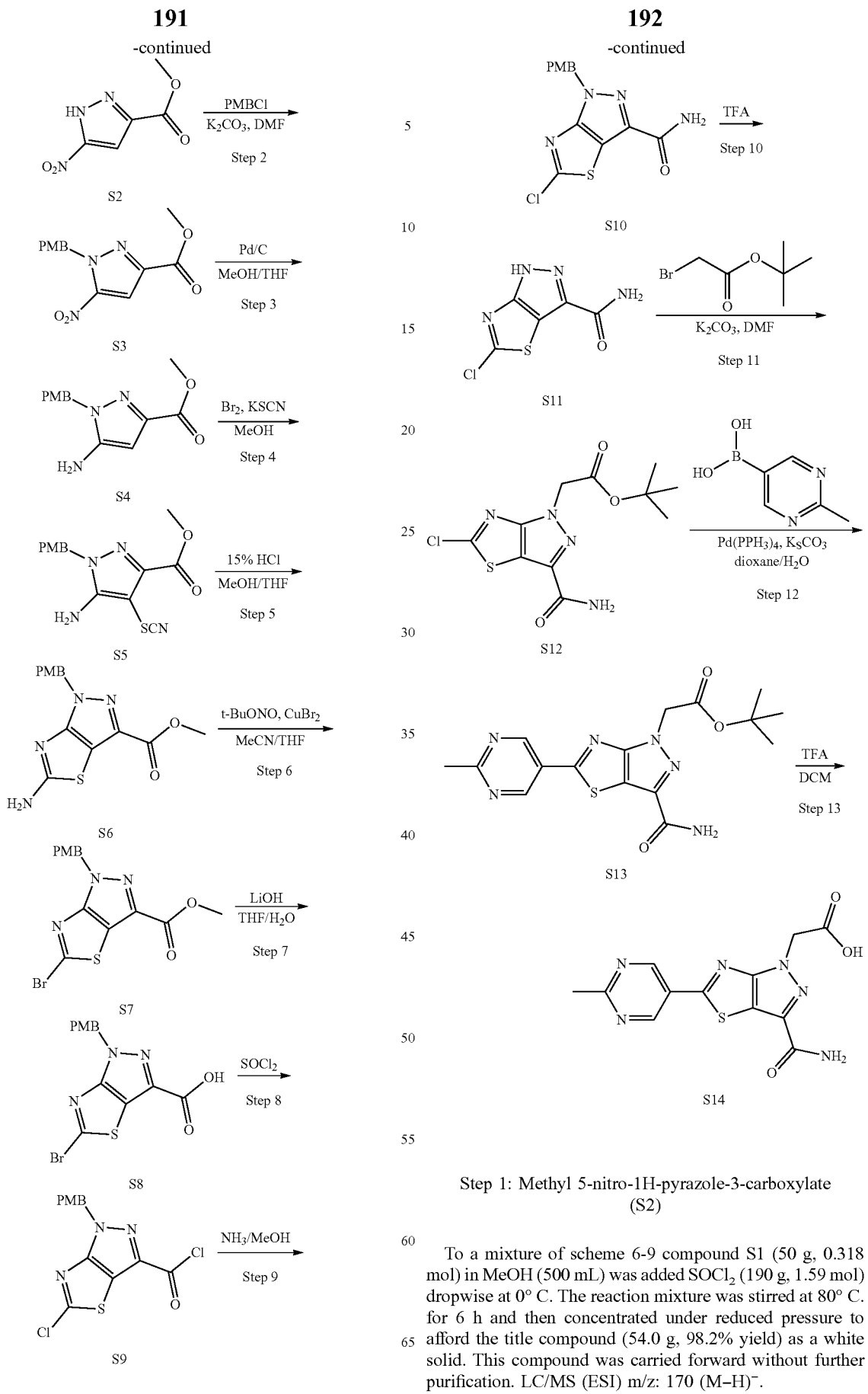
Step 1: Methyl 5-nitro-1H-pyrazole-3-carboxylate (S2)
To a mixture of scheme 6-9 compound S1 (50 g, 0.318 mol) in MeOH (500 mL) was added SOCl$_2$ (190 g, 1.59 mol) dropwise at 0° C. The reaction mixture was stirred at 80° C. for 6 h and then concentrated under reduced pressure to afford the title compound (54.0 g, 98.2% yield) as a white solid. This compound was carried forward without further purification. LC/MS (ESI) m/z: 170 (M−H)⁻.

Step 2: Methyl 1-(4-methoxybenzyl)-5-nitro-1H-pyrazole-3-carboxylate (S3)

To a mixture of scheme 6-9 compound S2 (54.0 g, 0.316 mol) and $K_2CO_3$ (87.1 g, 0.63 mol) in DMF (400 mL) was added PMBCl (59.2 g, 0.38 mol). Then the reaction mixture was stirred at 80° C. for 3 h. After cooling, the mixture was diluted with aqueous LiCl (500 mL, 10%) and extracted with EtOAc (400 mL×2). The combined organic layers were washed with brine, dried over anhydrous $Na_2SO_4$, filtered and concentrated. The residue was recrystallized with petroleum ether/EtOAc (2/1) to afford the title compound (40.4 g, 43.9% yield) as a yellow solid.

Step 3: Methyl 5-amino-1-(4-methoxybenzyl)-1H-pyrazole-3-carboxylate (S4)

To a mixture of scheme 6-9 compound S9 (40.4 g, 138.8 mmol) in MeOH/THF (400 mL, 1:1) was added 10% Pd/C (4 g). The reaction mixture was stirred at room temperature overnight under a $H_2$ balloon. After filtration, the filtrate was concentrated to dryness to afford the title compound (33.7 g, yield 93.1%) as yellow oil. The compound was carried forward without further purification. LC/MS (ESI) m/z: 262 $(M+H)^+$.

Step 4: Methyl 5-amino-1-(4-methoxybenzyl)-4-thiocyanato-1H-pyrazole-3-carboxylate (S5)

To a mixture of scheme 6-9 compound S4 (33.7 g, 128.6 mmol) and KSCN (37.4 g, 385.9 mmol) in EtOH (300 mL) was added a solution of $Br_2$ (41.1 g, 257.2 mmol) in EtOH (200 mL) dropwise to maintain the internal temperature below 0° C. under $N_2$ atmosphere. Then the reaction mixture was stirred at 0° C. for 16 h. The mixture was basified with aqueous $Na_2CO_3$ solution to pH=9 at 0° C. and extracted with EtOAc (400 ml×2). The combined organic phases were dried over anhydrous $Na_2SO_4$ and concentrated. The residue was recrystallized with THF/petroleum ether (1/1) to afford the title compound (23.0 g, 55.9% yield) as a white solid. LC/MS (ESI) m/z: 319 $(M+H)^+$.

Step 5: Methyl 5-amino-1-(4-methoxybenzyl)-1H-pyrazolo[3,4-d]thiazole-3-carboxylate (S6)

To a mixture of scheme 6-9 compound S5 (23.0 g, 72.1 mmol) in EtOH (160 mL) and $H_2O$ (108 mL) was added conc. HCl (60 mL). The reaction was stirred at 90° C. for 2 h and concentrated under reduced pressure. The residue was recrystallized with EtOAc/petroleum ether (1/2) to afford the title compound (12.2 g, yield 53.1%) as a white solid. LC/MS (ESI) m/z: 319 $(M+H)^+$.

Step 6: Methyl 5-bromo-1-(4-methoxybenzyl)-1H-pyrazolo[3,4-d]thiazole-3-carboxylate (S7)

To a mixture of scheme 6-9 compound S6 (12.2 g, 38.3 mmol) and $CuBr_2$ (17.2 g, 76.6 mmol) in dry MeCN/THF (175 mL, 1:4) was added t-BuONO (5.92 g, 57.45 mmol) at 0° C. under $N_2$ atmosphere dropwise. After stirring for 1 h at 0° C., the resulting mixture was quenched with aqueous $Na_2S_2O_3$ (150 mL, 5%) and extracted with DCM (80 mL×2). The combined organic phases were washed with brine, dried over anhydrous $Na_2SO_4$, filtered and concentrated. The residue was purified by column chromatography on silica gel (eluted with petroleum ether:ethyl acetate=30:1 to 10:1) to afford the title compound (4.59 g, 31.4% yield) as yellow oil. LC/MS (ESI) m/z: 382 $(M+H)^+$.

Step 7: 5-Bromo-1-(4-methoxybenzyl)-1H-pyrazolo[3,4-d]thiazole-3-carboxylic acid (S8)

To a mixture of scheme 6-9 compound S7 (4.59 g, 12.0 mmol) in THF/$H_2O$ (50 mL, 4:1, v/v) was added LiOH $H_2O$ (1.01 g, 24.0 mmol). The reaction mixture was stirred at room temperature for 1 h and then acidified with aqueous HCl solution (1 M) to pH=5. The mixture was extracted with DCM/MeOH (30 mL×2, 20:1, v/v). The combined organic phases were washed with brine, dried over anhydrous $Na_2SO_4$, filtered and concentrated to afford the title compound (4.04 g, 91.5% yield) as a white solid. LC/MS (ESI) m/z: 368 $(M+H)^+$.

Step 8: 5-Chloro-1-(4-methoxybenzyl)-1H-pyrazolo[3,4-d]thiazole-3-carbonyl chloride (S9)

A solution of scheme 6-9 compound S8 (4.04 g, 10.98 mmol) in $SOCl_2$ (30 mL) was stirred at 70° C. for 4 h. After cooling, the mixture was concentrated to dryness and the residue was co-evaporated with toluene twice to afford the title compound (3.75 g, 100% yield) as yellow oil. The compound was carried forward without further purification.

Step 9: 5-Chloro-1-(4-methoxybenzyl)-1H-pyrazolo[3,4-d]thiazole-3-carboxamide (S10)

To a solution of scheme 6-9 compound S9 (3.75 g, 10.97 mmol) in dry THF (25 mL) at 0° C. was added $NH_3$/MeOH solution (2 M, 15 mL) dropwise. The reaction mixture was stirred at 0° C. for 30 min and then concentrated. The residue was purified by column chromatography on silica gel (eluted with petroleum ether:ethyl acetate=15:1 to 3:1) to afford the title compound (3.25 g, 92.1% yield) as a white solid. LC/MS (ESI) m/z: 323 $(M+H)^+$.

Step 10: 5-Chloro-1H-pyrazolo[3,4-d]thiazole-3-carboxamide (11)

A solution of scheme 6-9 compound S10 (3.25 g, 10.1 mmol) in TFA (30 mL) was stirred at 70° C. for 4 h. The mixture was concentrated to dryness and the residue was co-evaporated with toluene twice, dried under vacuum to afford the title compound (3.03 g, 94.9% yield) as a brown solid. The compound was carried forward without further purification. LC/MS (ESI) m/z: 203 $(M+H)^+$.

Step 11: tert-Butyl 2-(3-carbamoyl-5-chloro-1H-pyrazolo[3,4-d]thiazol-1-yl)acetate (S12)

To a mixture of scheme 6-9 compound S11 (3.03 g, 9.59 mmol) and $K_2CO_3$ (3.97 g, 28.77 mmol) in DMF (30 mL) was added tert-butyl bromoacetate (2.62 g, 13.43 mmol.). The reaction mixture was stirred at room temperature for 16 h. The mixture was diluted with EtOAc and washed with 10% aq.LiCl solution and brine successively, dried over anhydrous $Na_2SO_4$, filtered and concentrated. The residue was purified by column chromatography on silica gel (eluted with petroleum ether:ethyl acetate=10:1 to 3:1) to afford the title compound (2.01 g, 66.2% yield) as a yellow solid. LC/MS (ESI) m/z: 317 $(M+H)^+$.

Step 12: tert-Butyl 2-(3-carbamoyl-5-(2-methylpyrimidin-5-yl)-1H-pyrazolo[3,4-d]thiazol-1-yl)acetate (S13)

To a mixture of scheme 6-9 compound S12 (300 mg, 0.84 mmol) and $K_2CO_3$ (292 mg, 2.1 mmol) in dioxane/$H_2O$ (10 mL, 9:1) was added 2-methylpyrimidin-5-ylboronic acid (138 mg, 1 mmol.) and $Pd(PPh_3)_4$ (100 mg, 0.08 mmol). The reaction was degassed under $N_2$ three times and stirred at 90° C. for 4 h under $N_2$ atmosphere. After cooling, the mixture was diluted with saturated aqueous $NaHCO_3$ (10 mL) and extracted with EtOAc (20 mL×2). The combined organic phases were washed with brine, dried over anhydrous $Na_2SO_4$, filtered and concentrated. The residue was purified by column chromatography on silica gel (eluted with DCM:MeOH=50:1 to 20:1) to afford the title compound (121 mg, 38.4% yield) as a white solid. LC/MS (ESI) m/z: 375 (M+H)$^+$.

Step 13: 2-(3-Carbamoyl-5-(2-methylpyrimidin-5-yl)-1H-pyrazolo[3,4-d]thiazol-1-yl)acetic Acid (S14)

To a mixture of scheme 6-9 compound S13 (121 mg, 0.32 mmol) in DCM (2 mL) was added TFA (1 mL) and the reaction mixture was stirred at room temperature for 2 h and then concentrated under reduced pressure to afford compound S14 (130 mg, 100% yield) as a brown solid. The compound was carried forward without further purification. LC/MS (ESI) m/z: 319 (M+H)$^+$.

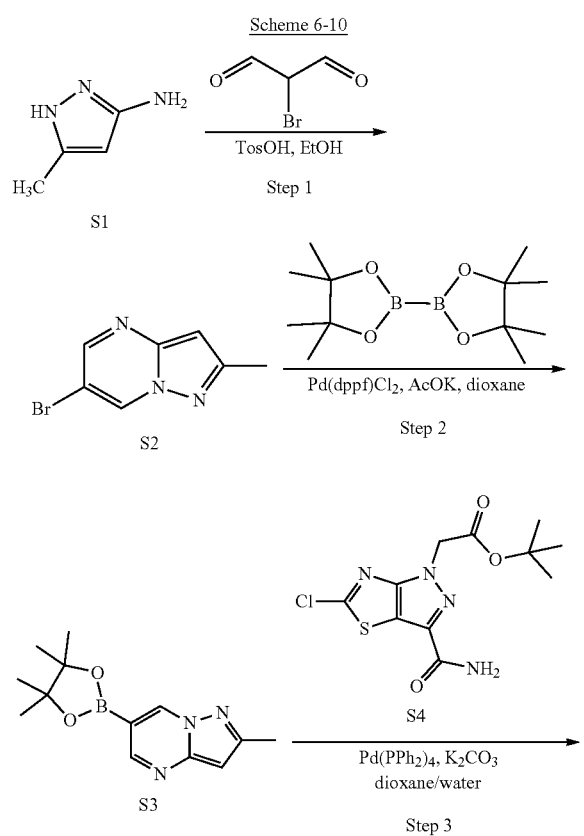

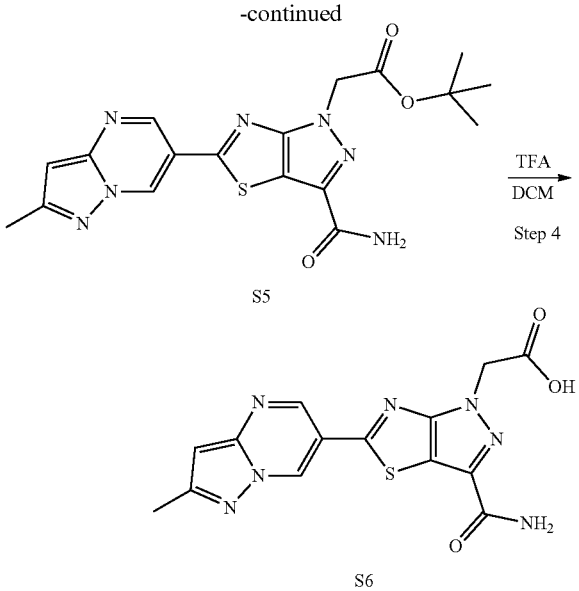

Step 1: 6-Bromo-2-methylpyrazolo[1,5-a]pyrimidine (S2)

To a mixture of 5-methyl-1H-pyrazol-3-amine (6.43 g, 0.066 mol) in EtOH (40 mL) in the presence of 4-methylbenzenesulfonic acid (0.63 g, 3.0 mmol) was added 2-bromomalonaldehyde (10.0 g, 0.066 mol). The reaction mixture was stirred at 80° C. overnight under a $N_2$ atmosphere and concentrated. The residue was purified by column chromatography on silica gel (eluted with petroleum ether/EtOAc (100:1 to 10:1) to afford the title compound (3.0 g, 21.4% yield). LC/MS (ESI) m/z: 212 (M+H)$^+$.

Step 2: 2-Methyl-6-(4,4,5,5-tetramethyl-1,3,2-dioxaborolan-2-yl)pyrazolo[1,5-a]pyrimidine (S3)

A round-bottom flask was charged with 6-bromo-2-methylpyrazolo[1,5-a]pyrimidine (2.97 g, 14.08 mmol), 4,4,4',4',5,5,5',5'-octamethyl-2,2'-bi(1,3,2-dioxaborolane) (4.29 g, 16.89 mmol), AcOK (4.14 g, 42.23 mmol), $Pd(dppf)Cl_2$ (0.52 g, 0.70 mmol) and 1,4-dioxane (40 mL). The reaction mixture was stirred at 85° C. for 2 h under $N_2$ atmosphere. After dilution with EtOAc, the resulting mixture was washed with water and brine, dried over anhydrous $Na_2SO_4$ and concentrated. The residue was purified by column chromatography on silica gel (eluted with petroleum ether/EtOAc=100:1 to 5:1) to afford the title compound (3.05 g, 83.7% yield) as a white solid. LC/MS (ESI) m/z: 260 (M+H)$^+$.

Step 3: tert-Butyl 2-(3-carbamoyl-5-(2-methylpyrazolo[1,5-a]pyrimidin-6-yl)-1H-pyrazolo[3,4-d]thiazol-1-yl)acetate (S5)

To a mixture of scheme 6-9 compound S3 (230 mg, 0.88 mmol) and $K_2CO_3$ (276 mg, 2 mmol) in dioxane/$H_2O$ (15 mL, 4:1) was added tert-butyl 2-(3-carbamoyl-5-chloro-1H-pyrazolo[3,4-d]thiazol-1-yl)acetate (253 mg, 0.8 mmol.) and $Pd(PPh_3)_4$ (93 mg, 0.08 mmol). The mixture was degassed under $N_2$ atmosphere for three times and stirred at 95° C. for 5 h under $N_2$ atmosphere. After dilution with saturated aqueous $NaHCO_3$ (10 mL), the mixture was extracted with EtOAc (20 mL×2). The combined organic phases were washed with brine, dried over anhydrous $Na_2SO_4$, filtered and concentrated. The residue was purified by column chromatography on silica gel (eluted with petroleum ether: EtOAc=20:1 to 3:1) to afford the title compound (211 mg, 63.7% yield) as a white solid. LC/MS (ESI) m/z: 414 $(M+H)^+$.

Step 4: 2-(3-Carbamoyl-5-(2-methylpyrazolo[1,5-a]pyrimidin-6-yl)-1H-pyrazolo[3,4-d]thiazol-1-yl)acetic Acid (S6)

To a mixture of scheme 6-9 compound S4 (140 mg, 0.34 mmol) in DCM (3 mL) was added TFA (1 mL). The reaction mixture was stirred at room temperature for 2 h and concentrated under reduced pressure to afford scheme 6-9 compound S6 (142 mg, 100% yield) as a brown solid. The compound was carried forward without further purification. LC/MS (ESI) m/z: 358 $(M+H)^+$.

Example 7. Synthesis of L3-A Moieties

Scheme 7-1: In Step 1 the appropriately substituted aryl compound is subjected to a bromide to afford a sulfonic acid substituted species. In Step 2 the appropriately substituted sulfonic acid species is chlorinated as known in the art.

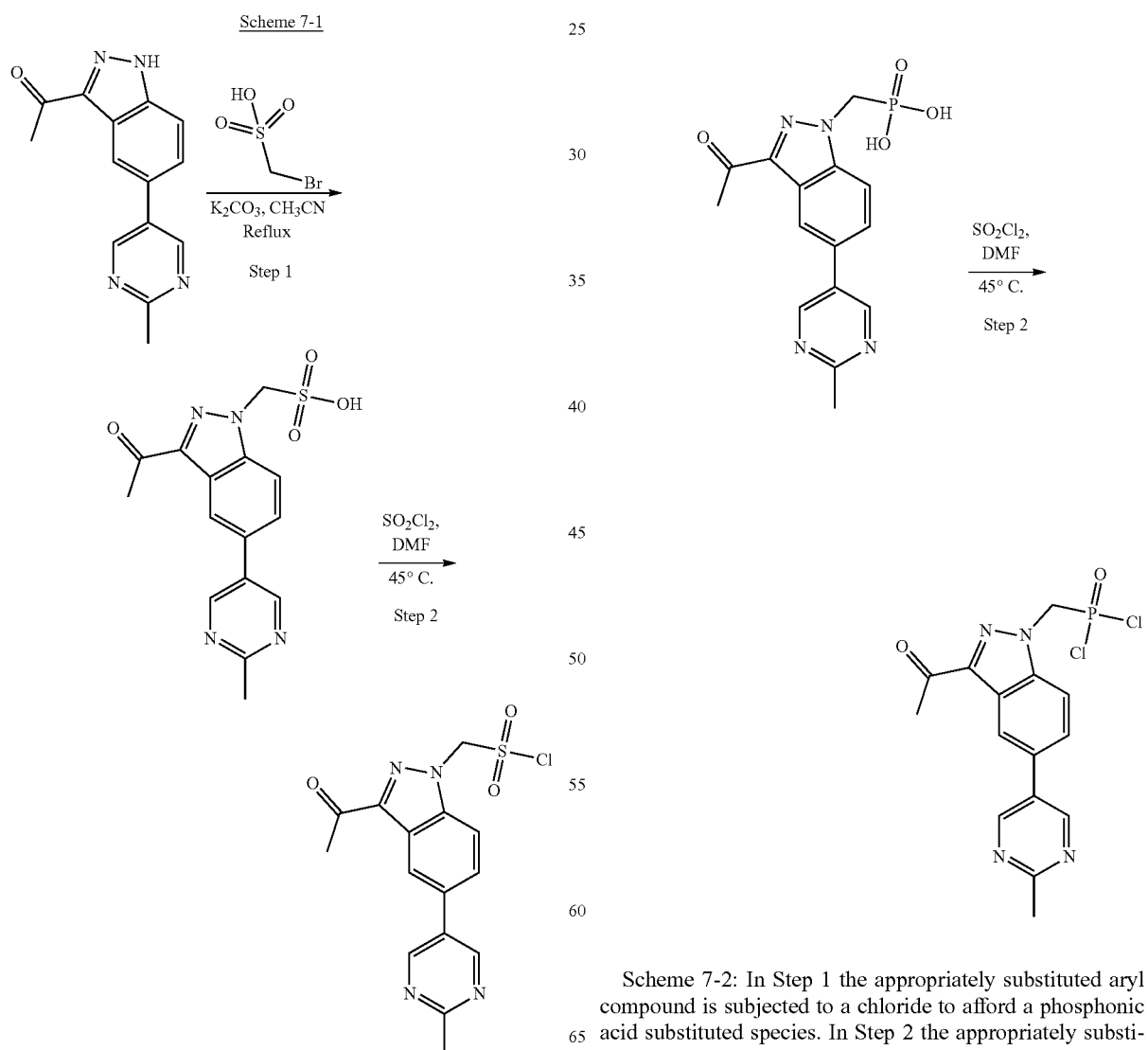

Scheme 7-2: In Step 1 the appropriately substituted aryl compound is subjected to a chloride to afford a phosphonic acid substituted species. In Step 2 the appropriately substituted phosphonic acid species is chlorinated as known in the art.

Example 8. Coupling of L3-A to C-L-B

Scheme 8-1

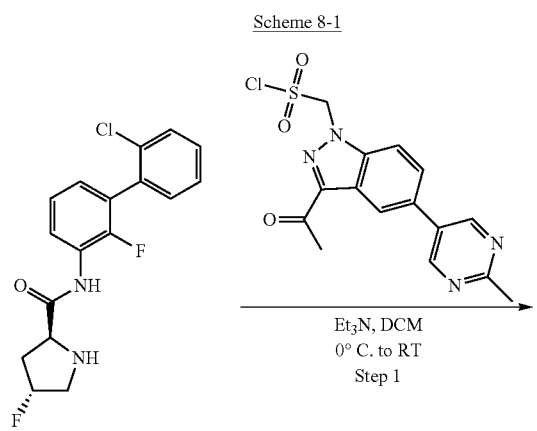

Scheme 8-1: In Step 1 the appropriately substituted amine is subjected to a sulfonyl chloride which can be prepared as described in Scheme 7-1 to afford a compound of Formula I.

Scheme 8-2

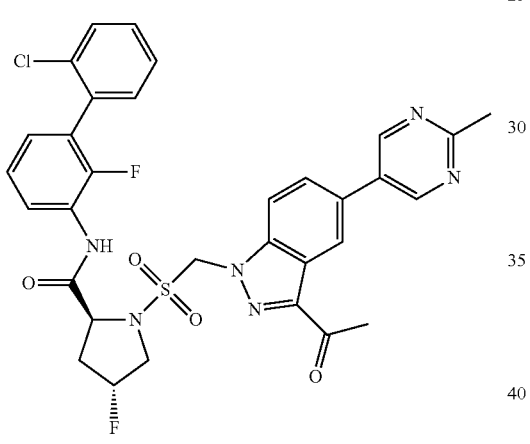

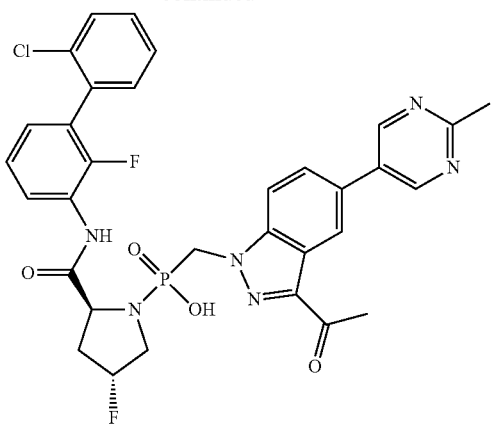

Scheme 8-2: In Step 1 the appropriately substituted amine is subjected to a phosphonic dichloride which can be prepared as described in Scheme 7-2 followed by a subsequent quench with water to afford a compound of Formula I.

Scheme 8-3

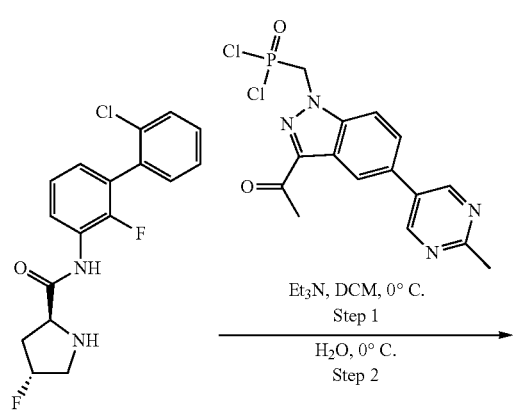

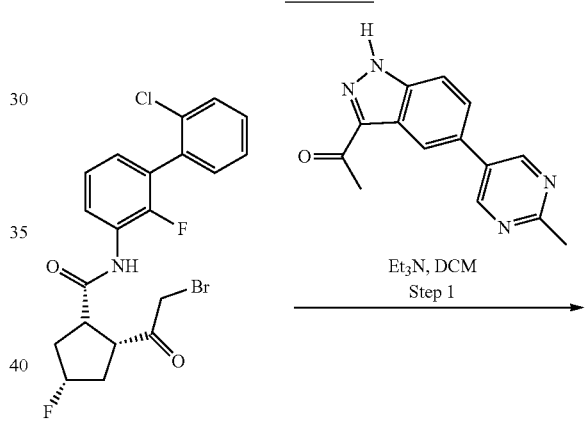

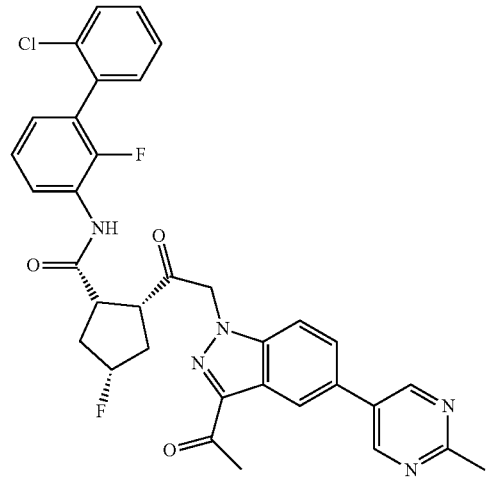

3

Scheme 8-3: In Step 1 the appropriately substituted bromide is subjected to a heteroaryl species to afford a compound of Formula I.

Scheme 8-4
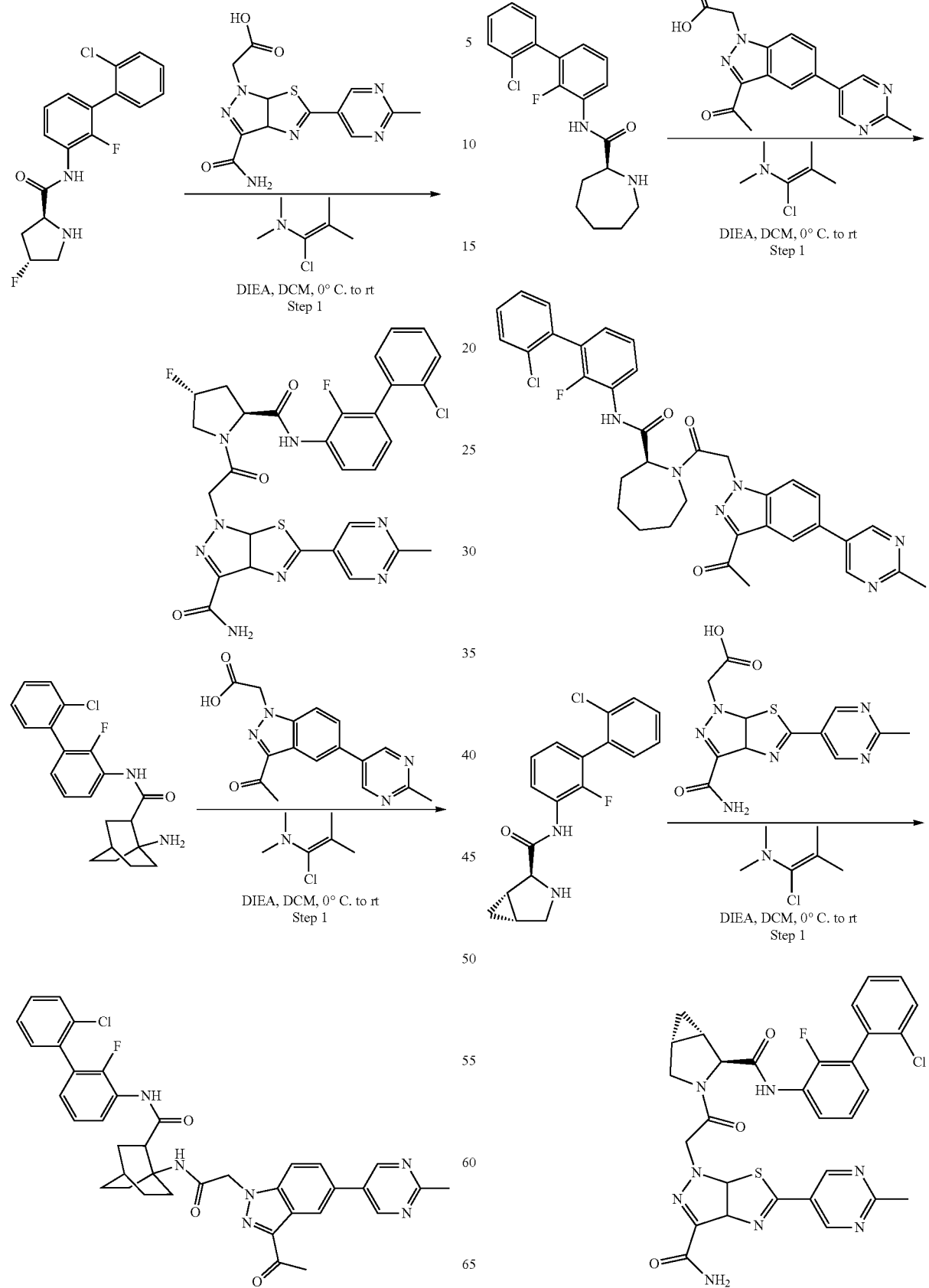

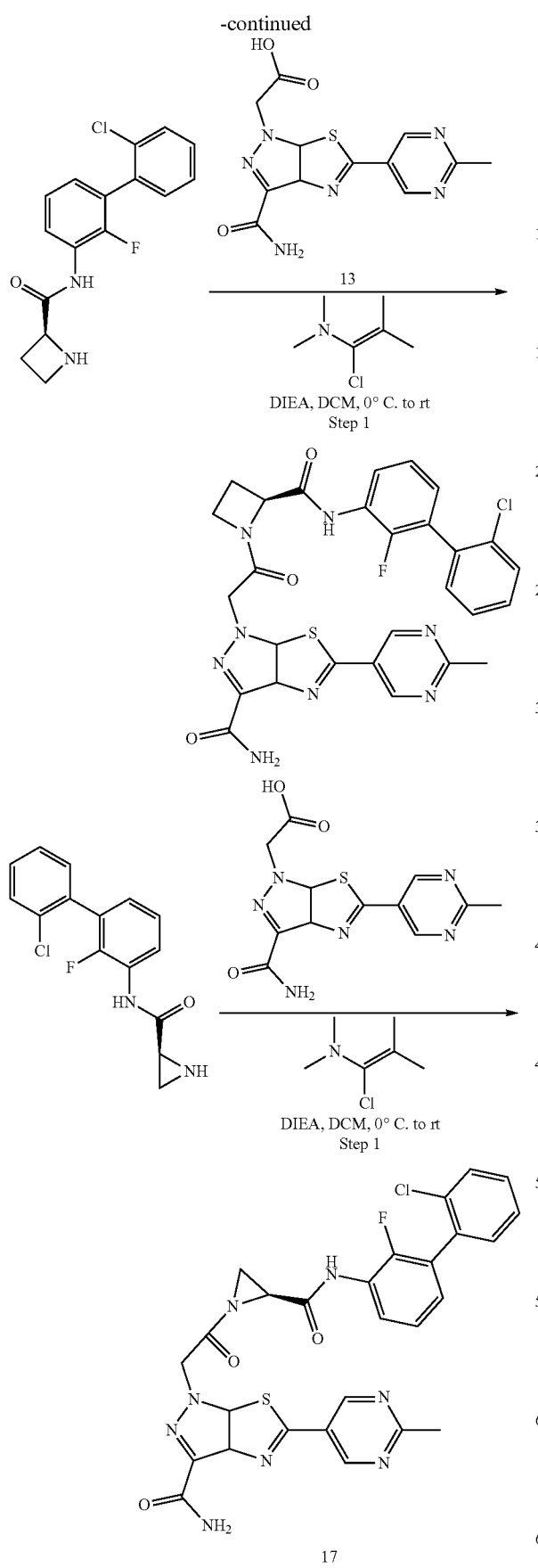
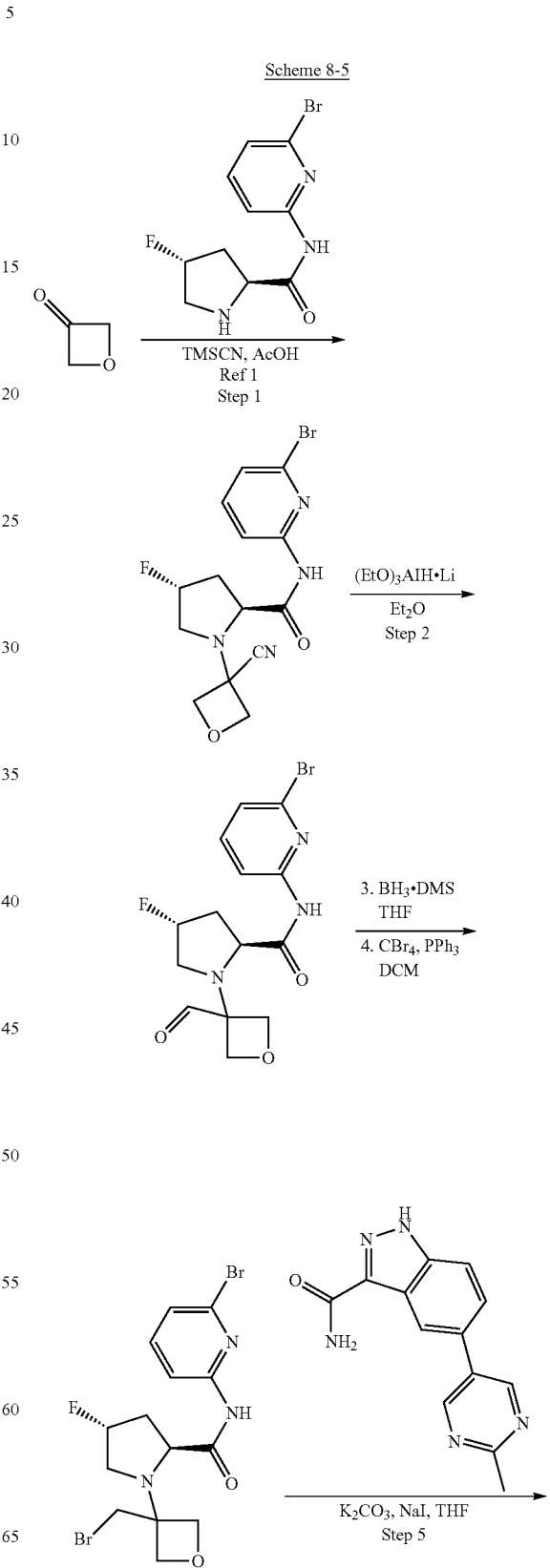
Scheme 8-4: In Step 1 the appropriately substituted carboxylic acid is coupled to the appropriately substituted amine as known in the art to form a compound of Formula I.

205
-continued

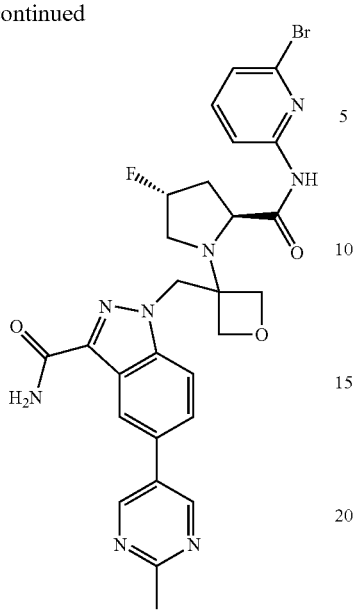

1. Wuitschik, Georg. Thesis, http://dx.doi.org/10.3929/ethz-a-005697432, ETH (2008)

Scheme 8-5: In Step 1 the appropriately substituted oxetane is subjected to conditions known in the art to form an amino/cyano substituted species. In Step 2 the appropriately substituted cyano species is reduced as known in the art to afford an aldehyde. In Step 3 the appropriately substituted aldehyde is reduced with borane to afford an alcohol. In Step 4 the appropriately substituted alcohol is converted to a bromide as known in the art. In Step 5 the appropriately substituted bromide is subjected to a heteroaryl species as known in the art to afford a compound of Formula I.

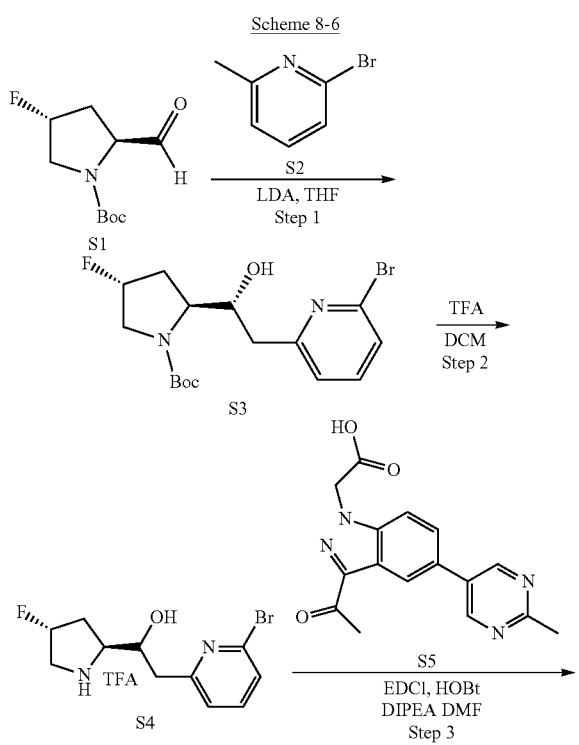

206
-continued

540

Step 1: (2S,4R)-tert-Butyl 2-((R)-2-(6-bromopyridin-2-yl)-1-hydroxyethyl)-4-fluoropyrrolidine-1-carboxylate (S3)

To a stirred solution of 2-bromo-6-methylpyridine (800 mg, 4.60 mmol) in THF (30 mL) under nitrogen was added LDA (5.1 mL, 5.1 mmol) dropwise at −70° C. The reaction was stirred at −70° C. for 30 min. A solution of scheme 8-6 compound S1 (1 g, 4.60 mmol) in THF (5 mL) was added to the mixture dropwise for 30 min and the reaction was stirred at −70° C. for another 1 h. The reaction was quenched with aq.NH$_4$Cl solution (20 mL) and the mixture was extracted with EtOAc twice. The combined organic phases were washed with brine, dried with anhydrous Na$_2$SO$_4$ and concentrated. The residue was purified by silica gel column chromatography (eluted with petroleum ether:ethyl acetate=20:1 to 10:1) to afford the title compound (300 mg, 17% yield) as a white solid.

Step 2: (R)-2-(6-Bromopyridin-2-yl)-1-((2S,4R)-4-fluoropyrrolidin-2-yl)ethanol (S4)

To a solution of scheme 8-6 compound S3 (120 mg, 0.311 mmol) in DCM (2 mL) was added TFA (1 mL). The reaction mixture was stirred at room temperature for 1 h. The mixture was concentrated to afford scheme 8-6 compound S4 (110 mg, 100% yield) as a yellow solid. The compound was carried forward without further purification.

Step 3: 2-(3-Acetyl-5-(2-methylpyrimidin-5-yl)-1H-indazol-1-yl)-1-((2S,4R)-2-((R)-2-(6-bromopyridin-2-yl)-1-hydroxyethyl)-4-fluoropyrrolidin-1-yl)ethanone (540)

To a mixture of scheme 8-6 compound S4 (90 mg, 0.23 mmol), scheme 8-6 compound S5 (80 mg, 0.25 mmol) and DIPEA (150 mg, 1.165 mmol) in DMF (2 mL) was added EDCI (98 mg, 0.51 mmol) and HOBt (70 mg, 0.513 mmol). The resulting mixture was stirred at room temperature overnight. The mixture was diluted with water and extracted with EtOAc twice. The combined organic phases were washed with 10% aqueous LiCl solution and brine successively, dried over anhydrous Na$_2$SO$_4$ and concentrated. The residue was purified with preparative HPLC to afford the title compound (20 mg, 15% yield) as a white solid. $^1$H NMR (400 MHz, DMSO-d$_6$) δ 9.06-9.03 (m, 1H), 9.00 (dd, J=9.6, 3.8 Hz, 1H), 8.44 (t, J=5.9 Hz, 1H), 7.99-7.74 (m, 2H), 7.66-7.53 (m, 1H), 7.52-7.39 (m, 1H), 7.26 (dd, J=16.0, 7.5 Hz, 1H), 5.83-5.70 (m, 1H), 5.60 (dd, J=34.2, 16.1 Hz, 1H), 5.41 (t, J=20.1 Hz, 1H), 5.06 (d, J=60.6 Hz, 1H), 4.44 (dt, J=10.7, 9.8 Hz, 1H), 4.36-4.04 (m, 2H), 3.85-3.53 (m, 1H), 2.68 (d, J=4.2 Hz, 3H), 2.65 (d, J=2.5 Hz, 3H), 2.33 (dd, J=6.4, 4.6 Hz, 1H), 2.21 (dd, J=19.0, 12.6 Hz, 1H), 2.00 (d, J=57.5 Hz, 1H), 1.26-0.96 (m, 1H). LC/MS (ESI) m/z: 581 (M+H)⁺.

Scheme 8-7

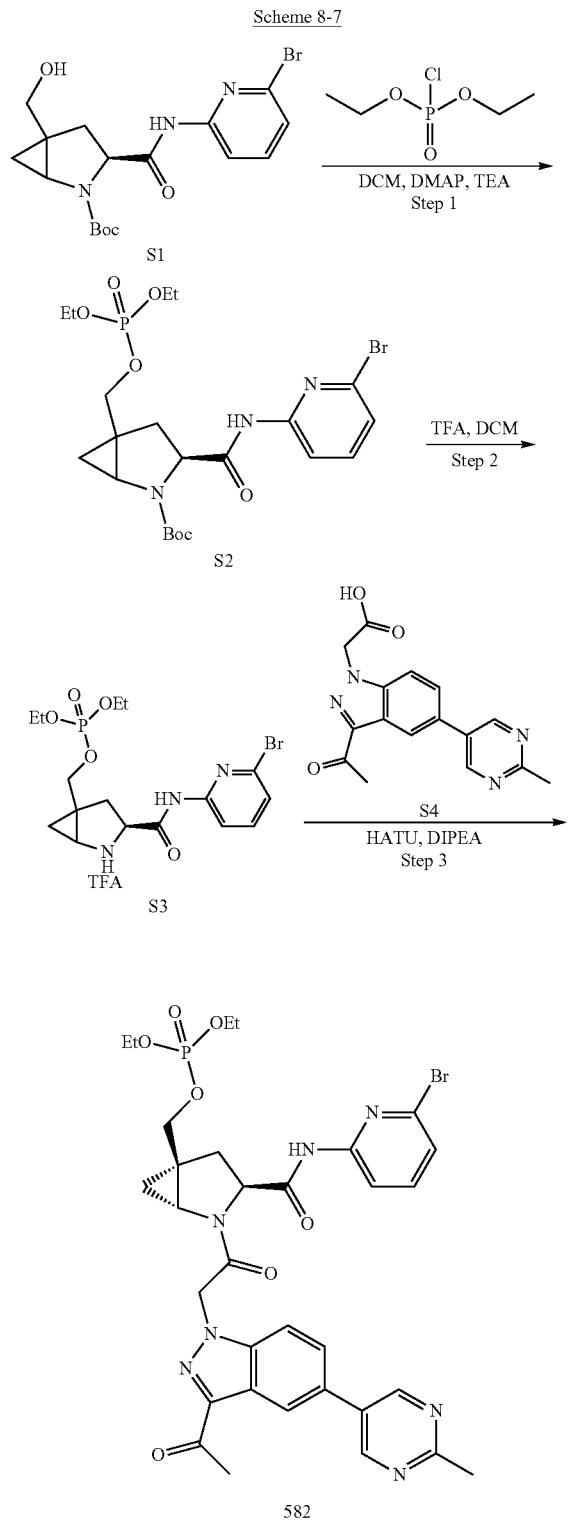

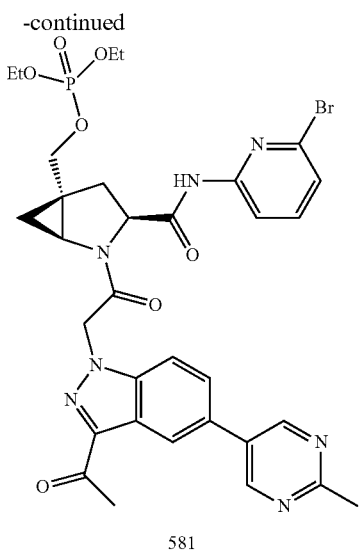

Step 1: (1R,3S,5S)-tert-Butyl 3-((6-bromopyridin-2-yl)carbamoyl)-5-(((diethoxyphosphoryl)oxy)methyl)-2-azabicyclo[3.1.0]hexane-2-carboxylate (S2)

To a solution of scheme 8-7 compound S1 (120 mg, 0.29 mmol) in THF (5 mL) was added TEA (100 mg, 1 mmol) and DMAP (12 mg, 0.1 mmol). This was followed by dropwise addition of diethyl phosphorochloridate (78 mg, 0.45 mmol) at 0° C. under N₂ atmosphere. The reaction was stirred at room temperature for 2 h. The mixture was diluted with EtOAc and washed with 10% aq.NaHCO₃ solution and brine. The organic layer was washed with brine, dried over anhydrous Na₂SO₄, and concentrated under reduced pressure. The crude product was purified by silica gel column chromatography eluted with (DCM/MeOH=100:1 to 30:1) to afford the title compound (40 mg, 25% yield) as a white solid. LC/MS (ESI) m/z: 548 (M+H)⁺.

Step 2: (3S)-tert-Butyl 3-(6-bromopyridin-2-ylcarbamoyl)-5-((diethoxyphosphoryloxy)methyl)-2-azabicyclo[3.1.0]hexane-2-carboxylate (S3)

To a solution of scheme 8-7 compound S2 (40 mg, 0.07 mmol) in DCM (1 mL) was added TFA (0.5 mL). The reaction was stirred at room temperature for 1.5 h and concentrated to afford the title compound (50 mg, 100% yield) as a grey solid. LC/MS (ESI) m/z: 448 (M+H)⁺.

Step 3: ((1R,3S,5S)-2-(2-(3-Acetyl-5-(2-methylpyrimidin-5-yl)-1H-indazol-1-yl)acetyl)-3-(6-bromopyridin-2-ylcarbamoyl)-2-azabicyclo[3.1.0]hexan-5-yl)methyl diethyl phosphate (582) & ((1S,3S,5R)-2-(2-(3-Acetyl-5-(2-methylpyrimidin-5-yl)-1H-indazol-1-yl)acetyl)-3-(6-bromopyridin-2-ylcarbamoyl)-2-azabicyclo[3.1.0]hexan-5-yl)methyl diethyl phosphate (581)

To a solution of the scheme 8-7 compound S3 (50 mg, 0.07 mmol), scheme 8-7 compound S4 (28 mg, 0.09 mmol) and HATU (50 mg, 0.13 mmol) in DMF (2 mL) was added DIPEA (30 mg, 0.23 mmol). The reaction was stirred at room temperature for 16 h. The mixture was partitioned with EtOAc and water. The organic layer was washed with brine, dried over anhydrous Na$_2$SO$_4$ and concentrated under reduced pressure. The crude product was purified by preparative HPLC to afford 582 (4.5 mg, 8.68% yield) and 581 (2 mg, 3.8% yield) as a white solid.

582: $^1$H NMR (400 MHz, CD$_3$OD) δ 9.03 (d, J=14.3 Hz, 2H), 8.56 (s, 1H), 8.09 (d, J=5.1 Hz, 1H), 7.77 (d, J=41.4 Hz, 2H), 7.63 (t, J=8.0 Hz, 1H), 7.27 (d, J=7.7 Hz, 1H), 5.85 (d, J=17.2 Hz, 1H), 5.68 (d, J=17.2 Hz, 1H), 4.63 (s, 1H), 4.24 (dd, J=11.0, 7.1 Hz, 1H), 4.18-3.98 (m, 5H), 3.84 (dd, J=5.7, 2.7 Hz, 1H), 2.80-2.62 (m, 6H), 2.62-2.46 (m, 2H), 1.42-1.20 (m, 8H). LC/MS (ESI) m/z: 740 (M+H)$^+$.

581: $^1$H NMR (400 MHz, CD$_3$OD) δ 9.06-8.97 (m, 2H), 8.53 (d, J=15.5 Hz, 1H), 8.05 (dd, J=16.9, 7.6 Hz, 1H), 7.84-7.65 (m, 2H), 7.59 (t, J=8.0 Hz, 1H), 7.23 (d, J=7.3 Hz, 1H), 5.83 (d, J=17.1 Hz, 1H), 5.72-5.59 (m, 1H), 5.03 (d, J=7.8 Hz, 1H), 4.29-4.08 (m, 6H), 3.96-3.85 (m, 1H), 2.87-2.65 (m, 6H), 2.26 (dd, J=13.6, 3.6 Hz, 1H), 1.64 (dd, J=6.0, 2.8 Hz, 1H), 1.34 (dt, J=26.0, 9.4 Hz, 7H), 1.21 (t, J=5.7 Hz, 11. LC/MS (ESI) m/z: 740 (M+H)$^+$.

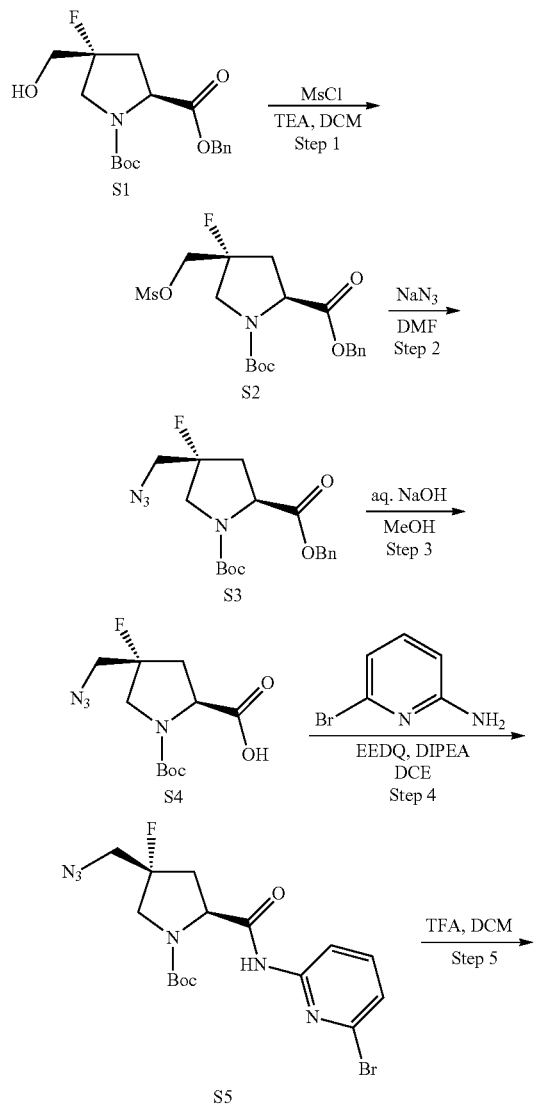

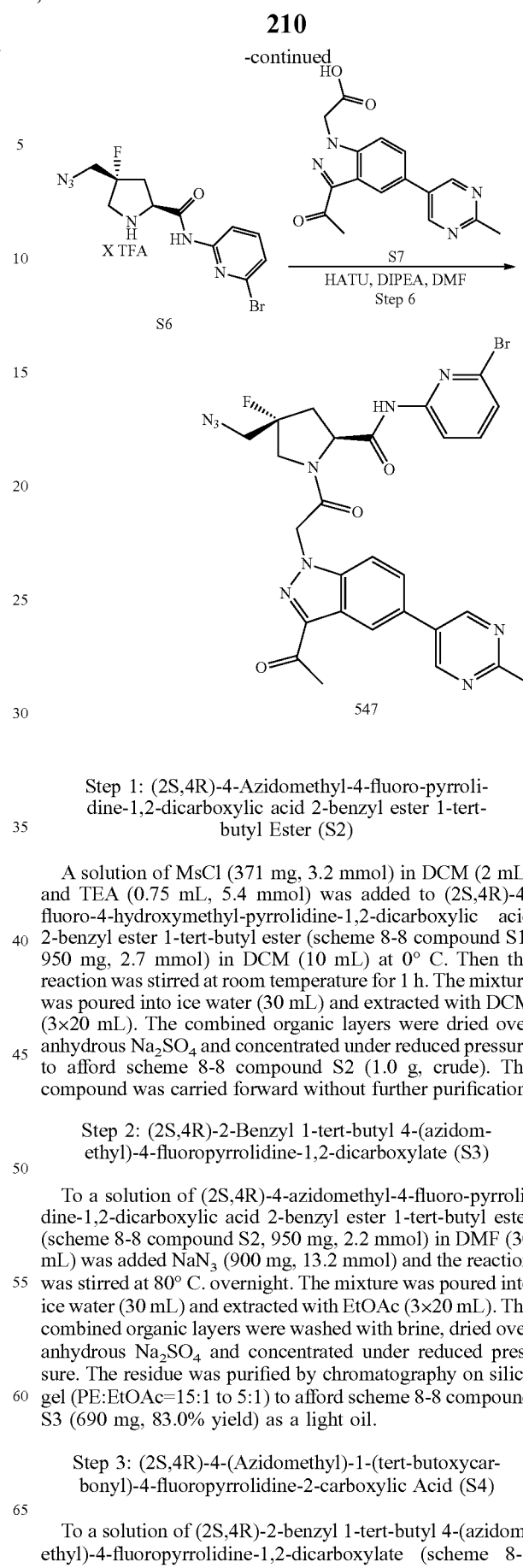

Step 1: (2S,4R)-4-Azidomethyl-4-fluoro-pyrrolidine-1,2-dicarboxylic acid 2-benzyl ester 1-tert-butyl Ester (S2)

A solution of MsCl (371 mg, 3.2 mmol) in DCM (2 mL) and TEA (0.75 mL, 5.4 mmol) was added to (2S,4R)-4-fluoro-4-hydroxymethyl-pyrrolidine-1,2-dicarboxylic acid 2-benzyl ester 1-tert-butyl ester (scheme 8-8 compound S1, 950 mg, 2.7 mmol) in DCM (10 mL) at 0° C. Then the reaction was stirred at room temperature for 1 h. The mixture was poured into ice water (30 mL) and extracted with DCM (3×20 mL). The combined organic layers were dried over anhydrous Na$_2$SO$_4$ and concentrated under reduced pressure to afford scheme 8-8 compound S2 (1.0 g, crude). The compound was carried forward without further purification.

Step 2: (2S,4R)-2-Benzyl 1-tert-butyl 4-(azidomethyl)-4-fluoropyrrolidine-1,2-dicarboxylate (S3)

To a solution of (2S,4R)-4-azidomethyl-4-fluoro-pyrrolidine-1,2-dicarboxylic acid 2-benzyl ester 1-tert-butyl ester (scheme 8-8 compound S2, 950 mg, 2.2 mmol) in DMF (30 mL) was added NaN$_3$ (900 mg, 13.2 mmol) and the reaction was stirred at 80° C. overnight. The mixture was poured into ice water (30 mL) and extracted with EtOAc (3×20 mL). The combined organic layers were washed with brine, dried over anhydrous Na$_2$SO$_4$ and concentrated under reduced pressure. The residue was purified by chromatography on silica gel (PE:EtOAc=15:1 to 5:1) to afford scheme 8-8 compound S3 (690 mg, 83.0% yield) as a light oil.

Step 3: (2S,4R)-4-(Azidomethyl)-1-(tert-butoxycarbonyl)-4-fluoropyrrolidine-2-carboxylic Acid (S4)

To a solution of (2S,4R)-2-benzyl 1-tert-butyl 4-(azidomethyl)-4-fluoropyrrolidine-1,2-dicarboxylate (scheme 8-8 compound S3, 690 mg, 1.8 mmol) in MeOH (8 mL) was added a 1 M aqueous NaOH solution (3.6 mL, 3.6 mmol) at 0° C. and the reaction mixture was stirred at room temperature for 1 h. The mixture was diluted with water (15 mL), the volatiles were removed under reduced pressure. The residue was washed with Et$_2$O (2×10 mL) and acidified with 2 N HCl to pH=–3. The resulting mixture was extracted with EtOAc (2×15 mL) and the combined organic layers were dried over anhydrous Na$_2$SO$_4$ and concentrated under reduced pressure to afford scheme 8-8 compound S4 (480 mg, 92.5% yield) as a light oil.

Step 4: (2S,4R)-tert-Butyl 4-(azidomethyl)-2-((6-bromopyridin-2-yl)carbamoyl)-4-fluoropyrrolidine-1-carboxylate (S5)

A mixture of (2S,4R)-4-(azidomethyl)-1-(tert-butoxycarbonyl)-4-fluoropyrrolidine-2-carboxylic acid (scheme 8-8 compound S4, 480 mg, 1.67 mmol), 6-bromopyridin-2-amine (316 mg, 1.84 mmol), DIPEA (539 mg, 4.18 mmol) and EEDQ (825 mg, 3.34 mmol) in DCE (10 mL) was stirred at 90° C. overnight. The mixture was evaporated under reduced pressure and the residue was purified by chromatography on silica gel (PE:EtOAC=20:1 to 4:1) to afford scheme 8-8 compound S5 (510 mg, 69.1% yield) as a light oil.

Step 5: (2S,4R)-4-(Azidomethyl)-N-(6-bromopyridin-2-yl)-4-fluoropyrrolidine-2-carboxamide (S6)

To a solution of (2S,4R)-tert-butyl 4-(azidomethyl)-2-((6-bromopyridin-2-yl) carbamoyl)-4-fluoropyrrolidine-1-carboxylate (scheme 8-8 compound S5, 200 mg) in DCM (3.0 mL) was added TFA (1 mL) at 0° C. and the reaction mixture was stirred at room temperature for 1 h. The mixture was evaporated under reduced pressure to afford scheme 8-8 compound S6 (180 mg, 100% yield). The compound was carried forward without further purification.

Step 6: (2S,4R)-1-(2-(3-Acetyl-5-(2-methylpyrimidin-5-yl)-1H-indazol-1-yl)acetyl) -4-(azidomethyl)-N-(6-bromopyridin-2-yl)-4-fluoropyrrolidine-2-carboxamide (547)

A mixture of (2S,4R)-4-(azidomethyl)-N-(6-bromopyridin-2-yl)-4-fluoropyrrolidine-2-carboxamide (scheme 8-8 compound S6, 180 mg, 0.47 mmol), 2-(3-acetyl-5-(2-methylpyrimidin-5-yl)-1H-indazol-1-yl)acetic acid (161 mg, 0.52 mmol), HATU (270 mg, 0.71 mmol) and DIPEA (0.24 mL, 1.41 mmol) in DMF (4 mL) was stirred at room temperature overnight. The mixture was partitioned between EtOAc and water. The organic layer was washed with brine, dried over anhydrous Na$_2$SO$_4$ and concentrated under reduced pressure. The residue was purified by chromatography on silica gel (DCM:MeOH=80:1 to 60:1) to afford 547 (200 mg, yield 67.1% yield) as a white solid. $^1$H NMR (400 MHz, DMSO-d$_6$) δ 11.02 (s, 1H), 9.03 (s, 2H), 8.42 (d, J=1.0 Hz, 1H), 8.02 (d, J=8.2 Hz, 1H), 7.85 (dd, J=7.3, 5.2 Hz, 2H), 7.71 (t, J=8.0 Hz, 1H), 7.33 (d, J=7.3 Hz, 1H), 5.87 (d, J=17.3 Hz, 1H), 5.64 (d, J=17.2 Hz, 1H), 4.71 (t, J=8.6 Hz, 1H), 4.32 (m, 1H), 4.07-3.92 (m, 2H), 3.90-3.79 (m, 1H), 2.66 (d, J=15.0 Hz, 6H), 2.62-2.55 (m, 1H), 2.17 (m, 1H). LC/MS (ESI) m/z: 635 (M+H)$^+$.

Scheme 8-9

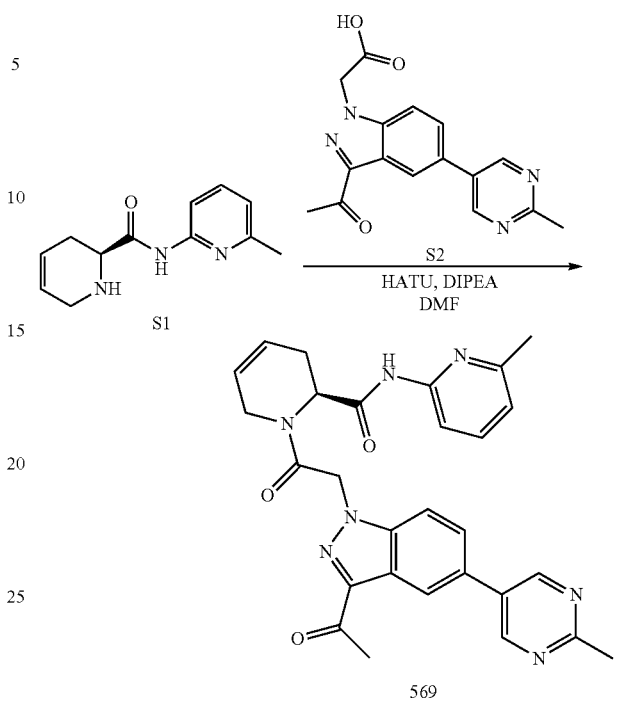

(S)-1-(2-(3-acetyl-5-(2-methylpyrimidin-5-yl)-1H-indazol-1-yl)acetyl)-N-(6-methylpyridin-2-yl)-1,2,3,6-tetrahydropyridine-2-carboxamide (569)

To a solution of scheme 8-9 compound S1 (53 mg, 0.165 mmol), scheme 8-9 compound S2 (30 mg, 0.15 mmol) and DIPEA (60 mg, 0.45 mmol) in DMF (2 mL) was added HATU (114 mg, 0.3 mmol). The reaction was stirred at room temperature overnight. The mixture was diluted with EtOAc and washed with 10% aqueous LiCl solution and brine successively, dried over anhydrous Na$_2$SO$_4$, filtered and then concentrated. The residue was purified by preparative HPLC (eluted with CH$_3$CN/water) to afford compound 569 (15 mg, 19.6% yield) as a white solid. $^1$H NMR (400 MHz, DMSO-d$_6$) δ:10.52 (s, 1H), 9.06 (s, 2H), 8.44 (d, J=4.7 Hz, 1H), 7.64-7.91 (m, 4H), 7.00 (d, J=7.5 Hz, 1H), 5.95 (d, J=17.3 Hz, 1H), 5.80 (m, 3H), 5.33 (d, J=6.2 Hz, 1H), 4.41 (m, 2H), 2.81 (m, 1H), 2.66 (d, J=8.3 Hz, 6H), 2.55 (m, 1H), 2.42 (d, J=17.3 Hz, 3H). LC/MS (ESI) m/z: 510 (M+H)$^+$.

Scheme 8-10

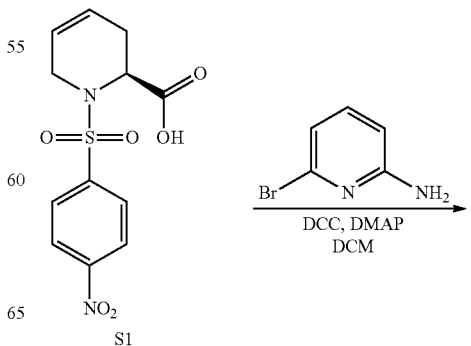

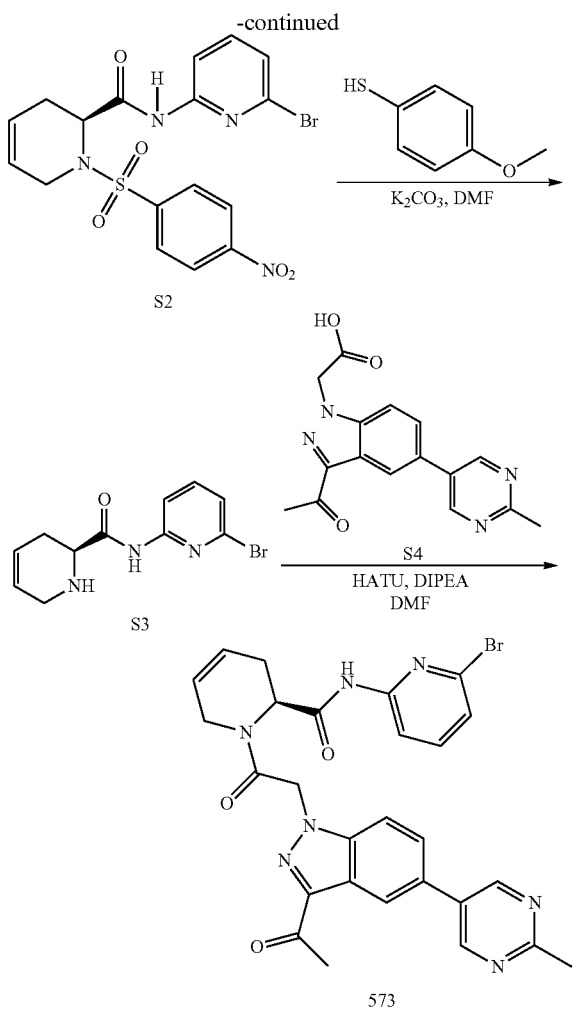

purified by column chromatography on silica gel (eluted with DCM:MeOH=100:0 to 50:1) to afford the title compound (40 mg, 83% yield) as a yellow solid. LC/MS (ESI) m/z: 282 (M+H)⁺.

Step 3: (S)-1-(2-(3-Acetyl-5-(2-methylpyrimidin-5-yl)-1H-indazol-1-yl)acetyl)-N-(6-bromopyridin-2-yl)-1,2,3,6-tetrahydropyridine-2-carboxamide (573)

To a solution of scheme 8-10 compound S3 (20 mg, 0.071 mmol), scheme 8-10 compound S4 (25 mg, 0.078 mmol) and DIPEA (28 mg, 0.213 mmol) in DMF (1 mL) was added HATU (54 mg, 0.142 mmol). The reaction was stirred overnight and diluted with EtOAc. The resulting mixture was washed with 10% aqueous LiCl solution and brine, dried over anhydrous $Na_2SO_4$, filtered and then concentrated. The residue was purified by preparative HPLC (eluted with $CH_3CN$/water) to afford compound 573 (8 mg, 19.6% yield) as a white solid. ¹H NMR (400 MHz, DMSO-d₆) δ: 10.95 (s, 1H), 9.05 (s, 2H), 8.44 (s, 1H), 7.99-8.08 (m, 1H), 7.83-7.91 (m, 2H), 7.74 (m, 1H), 7.36 (m, 1H), 5.95 (d, J=17.2 Hz, 1H), 5.87 (s, 1H), 5.75 (m, 2H), 5.31 (m, 1H), 4.25-4.45 (m, 2H), 2.82 (s, 1H), 2.54-2.73 (m, 7H). LC/MS (ESI) m/z: 574 (M+H)⁺.

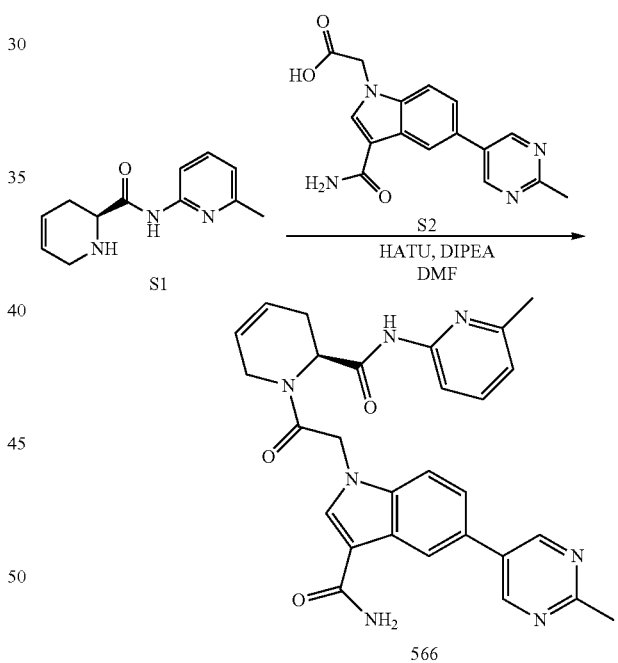

Step 1: (S)—N-(6-Bromopyridin-2-yl)-1-(4-nitrophenylsulfonyl)-1,2,3,6-tetrahydropyridine-2-carboxamide (S2)

To a solution of scheme 8-10 compound S1 (250 mg, 0.8 mmol) in DCM (20 mL) was added 6-bromopyridin-2-amine (153 mg, 0.88 mmol), DCC (332 mg, 1.6 mmol) and DMAP (99 mg, 0.8 mmol). The reaction was stirred at room temperature overnight. The mixture was washed water and brine, dried over anhydrous $Na_2SO_4$, filtered and concentrated to dryness. The residue was purified by column chromatography on silica gel (eluted with petroleum ether:ethyl acetate=8:1 to 2:1) to afford the title compound (80 mg, 22% yield) as a yellow solid. LC/MS (ESI) m/z: 489 (M+Na)⁺.

Step 2: (S)—N-(6-Bromopyridin-2-yl)-1,2,3,6-tetrahydropyridine-2-carboxamide (S3)

To a solution of scheme 8-10 compound S2 (80 mg, 0.17 mmol) in DMF (4 mL) was added $K_2CO_3$ (71 mg, 0.51 mmol) and 4-methoxybenzenethiol (31 mg, 0.22 mmol). The reaction was stirred at room temperature for 24 h. The mixture was diluted with EtOAc and washed with 10% aqueous LiCl solution and brine, dried over anhydrous $Na_2SO_4$, filtered and then concentrated. The residue was (S)-1-(2-(2-(((6-Methylpyridin-2-yl)carbamoyl)-3,6-dihydropyridin-1(2H)-yl)-2-oxoethyl)-5-(2-methylpyrimidin-5-yl)-1H-indole-3-carboxamide (566)

To a solution of scheme 8-11 compound S1 (30 mg, 0.15 mmol), scheme 8-11 compound S2 (53 mg, 0.165 mmol), and DIPEA (60 mg, 0.45 mmol) in DMF (2 mL) was added HATU (114 mg, 0.3 mmol). The reaction was stirred at room temperature overnight. The mixture was diluted with EtOAc, washed with 10% aqueous LiCl solution and brine successively, dried over anhydrous Na₂SO₄, filtered and then concentrated. The residue was purified by preparative HPLC (eluted with CH₃CN/water) to afford compound 566 (10 mg, 13% yield) as a white solid. ¹H NMR (400 MHz, CDCl₃) δ: 10.49 (s, 1H), 9.01 (s, 2H), 8.42 (s, 1H), 8.01 (s, 1H), 7.80 (d, J=8.5 Hz, 1H), 7.66 (t, J=7.8 Hz, 1H), 7.52-7.61 (m, 2H), 6.97 (d, J=7.5 Hz, 1H), 5.86 (s, 2H), 5.55 (d, J 17.5 Hz, 1H), 5.33 (d, J=17.5 Hz, 2H), 5.09-5.25 (m, 1H), 4.40 (s, 2H), 4.31 (d, J=24.9 Hz, 1H), 2.68 (s, 3H), 2.57 (m, 1H), 2.42 (s, 3H), 2.33 (m, 1H).

Scheme 8-12

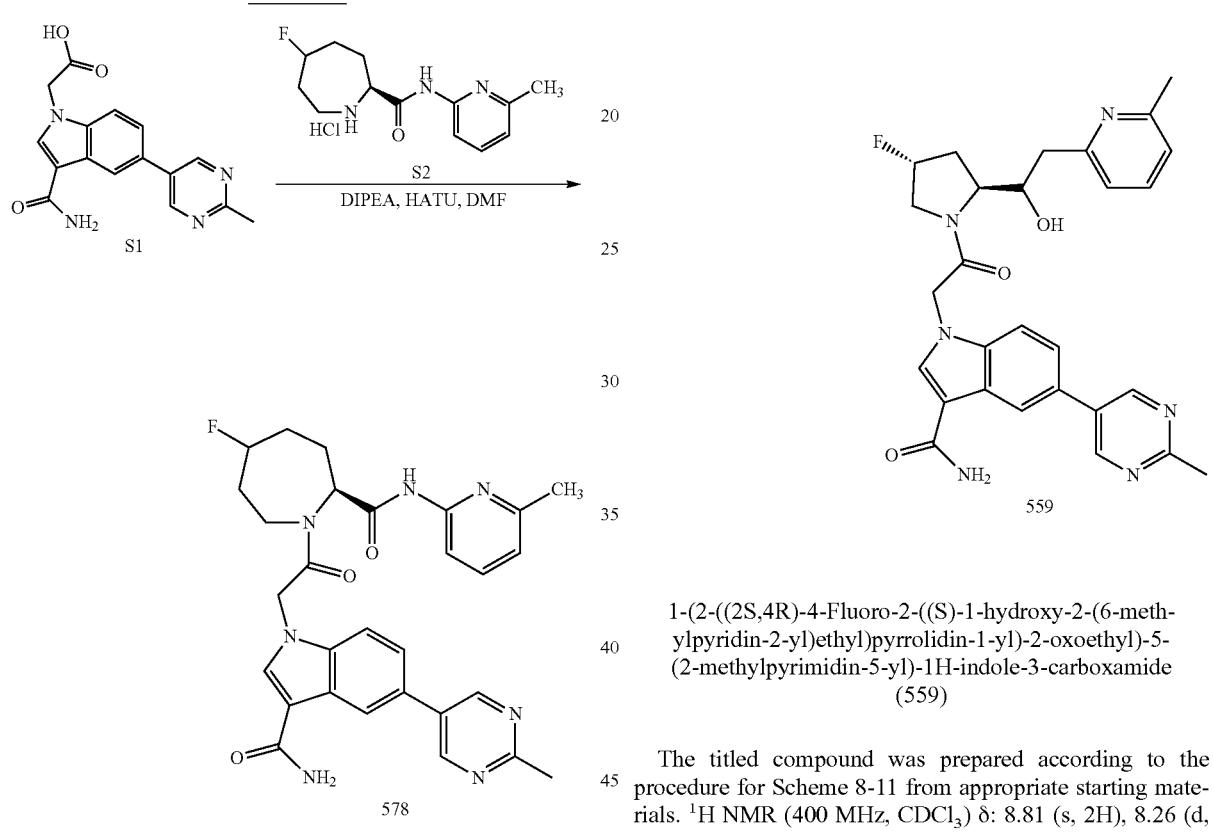

1-(2-((2S)-5-Fluoro-2-((6-methylpyridin-2-yl)carbamoyl)azepan-1-yl)-2-oxoethyl)-5-(2-methylpyrimidin-5-yl)-1H-indole-3-carboxamide (578)

The titled compound was prepared according to the procedure for Scheme 8-11 from appropriate starting materials. 1H NMR (400 MHz, CD₃OD) δ: 8.98 (d, J=8.0 Hz, 2H), 8.41 (d, J=21.6 Hz, 1H), 8.21 (s, 1H), 7.96 (d, J=9.4 Hz, 1H), 7.82 (d, J=8.2 Hz, 1H), 7.61 (t, J=7.9 Hz, 1H), 7.54 (d, J=2.6 Hz, 2H), 6.95 (d, J=7.5 Hz, 1H), 5.31 (dt, J=107.5, 17.1 Hz, 2H), 4.24-3.97 (m, 1H), 3.77-3.56 (m, 1H), 2.73 (s, 3H), 2.44 (d, J=11.0 Hz, 1H), 2.41 (d, J=4.8 Hz, 3H), 2.29 (d, J=25.2 Hz, 2H), 1.97 (dd, J=25.3, 10.9 Hz, 2H), 1.84-1.72 (m, 1H), 1.51-1.23 (m, 4H). LC/MS (ESI) m/z: 544 (M+H)⁺.

Scheme 8-13

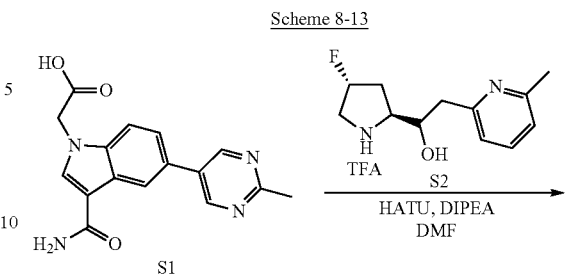

1-(2-((2S,4R)-4-Fluoro-2-((S)-1-hydroxy-2-(6-methylpyridin-2-yl)ethyl)pyrrolidin-1-yl)-2-oxoethyl)-5-(2-methylpyrimidin-5-yl)-1H-indole-3-carboxamide (559)

The titled compound was prepared according to the procedure for Scheme 8-11 from appropriate starting materials. ¹H NMR (400 MHz, CDCl₃) δ: 8.81 (s, 2H), 8.26 (d, J=7.9 Hz, 1H), 8.14 (s, 1H), 7.68 (s, 1H), 7.51 (t, J=7.4 Hz, 1H), 7.46-7.28 (m, 2H), 7.02 (t, J=8.7 Hz, 1H), 6.91 (d, J=7.6 Hz, 1H), 5.70 (d, J=23.1 Hz, 2H), 5.40 (d, J=52.6 Hz, 1H), 4.95 (d, J=13.3 Hz, 2H), 4.63 (s, 1H), 3.89 (dd, J=38.3, 17.5 Hz, 3H), 2.86 (dd, J=25.1, 12.2 Hz, 2H), 2.68 (d, J=31.3 Hz, 3H), 2.46 (d, J=14.7 Hz, 3H), 2.32 (dt, J=23.5, 11.4 Hz, 2H). LC/MS (ESI) m/z: 517 (M+H)⁺.

Scheme 8-14

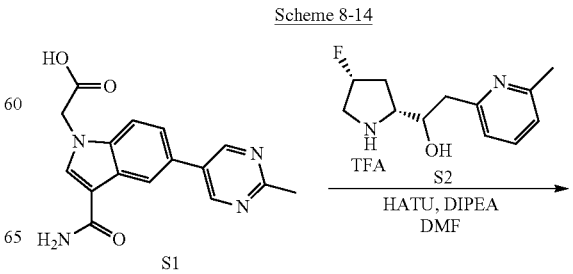

-continued
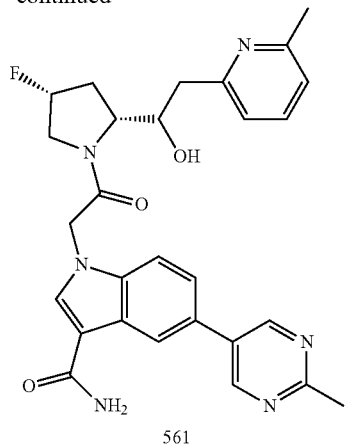
561
1-(2-((2R,4R)-4-Fluoro-2-((R)-1-hydroxy-2-(6-methylpyridin-2-yl)ethyl)pyrrolidin-1-yl)-2-oxo-ethyl)-5-(2-methylpyrimidin-5-yl)-1H-indole-3-carboxamide (561)
The titled compound was prepared according to the procedure for Scheme 8-11 from appropriate starting materials. $^1$H NMR (400 MHz, CDCl$_3$) δ: 9.02 (d, J=4.8 Hz, 2H), 8.42 (d, J=1.2 Hz, 1H), 8.32 (t, J=8.0 Hz, 1H), 7.96 (s, 1H), 7.77-7.65 (m, 2H), 7.64-7.51 (m, 2H), 7.50-7.29 (m, 1H), 7.12-6.89 (m, 1H), 5.62-5.24 (m, 3H), 5.06 (d, J=17.6 Hz, 1H), 4.66-4.38 (m, 2H) 4.22-4.17 (m, 1H), 4.16-4.09 (m, 1H), 3.04 (dd, J=14.4, 4.0 Hz, 1H), 2.83 (dd, J=14.0, 10.0 Hz, 1H), 2.70-2.66 (m, 6H), 2.37-2.18 (m, 1H). LC/MS (ESI) m/z: 517 (M+H)$^+$.
Scheme 8-15
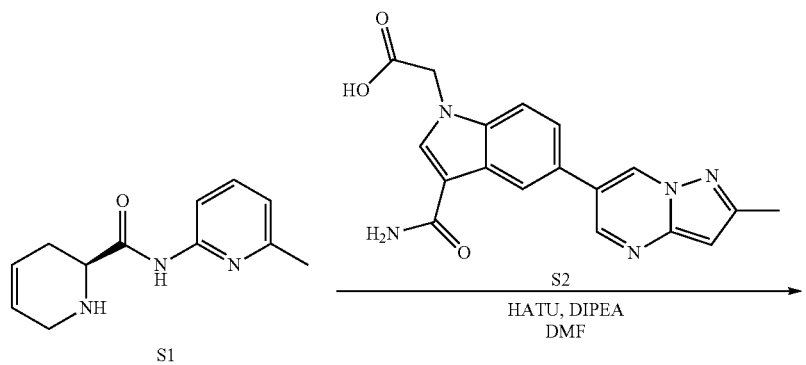
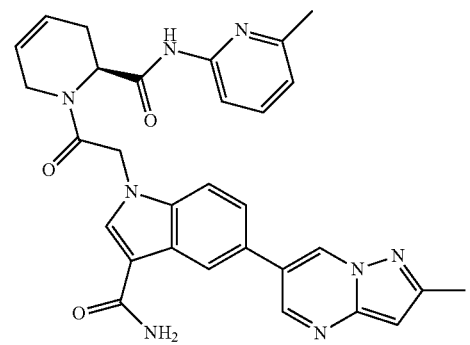
612

(S)-5-(2-Methylpyrazolo[1,5-a]pyrimidin-6-yl)-1-(2-(2-((6-methylpyridin-2-yl)carbamoyl)-3,6-dihydropyridin-1(2H)-yl)-2-oxoethyl)-1H-indole-3-carboxamide (612)

The titled compound was prepared according to the procedure for Scheme 8-11 from appropriate starting materials. $^{1}$H NMR (400 MHz, CDCl$_3$) δ: 10.48 (s, 1H), 9.27 (s, 1H), 8.86 (d, J=2.1 Hz, 1H), 8.43 (s, 1H), 8.32 (s, 1H), 8.00 (s, 1H), 7.81 (d, J=8.5 Hz, 1H), 7.53-7.75 (m, 3H), 6.96 (d, J=7.4 Hz, 1H), 6.56 (s, 1H), 5.86 (s, 2H), 5.55 (d, J=17.5 Hz, 1H), 5.34 (d, J=17.6 Hz, 2H), 5.09-5.24 (m, 1H), 4.28-4.44 (m, 2H), 3.80 (m, 1H), 2.81 (m, 1H), 2.65 (m, 1H), 2.32-2.48 (m, 6H). LC/MS (ESI) m/z: 549 (M+H)$^+$.

Scheme 8-17

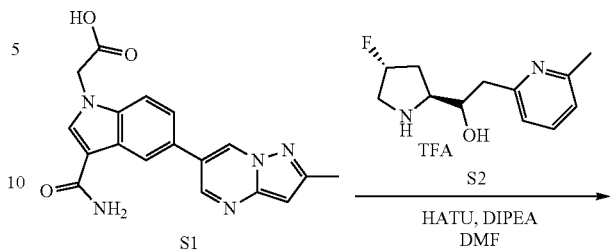

Scheme 8-16

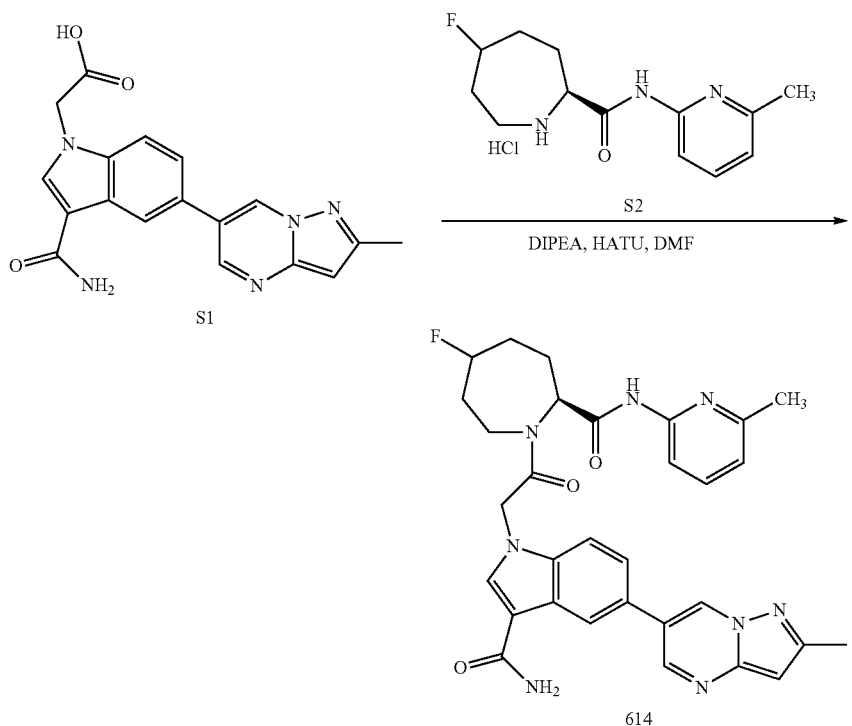

1-(2-((2S)-5-Fluoro-2-((6-methylpyridin-2-yl)carbamoyl)azepan-1-yl)-2-oxoethyl)-5-(2-methylpyrazolo[1,5-a]pyrimidin-6-yl)-1H-indole-3-carboxamide (614)

The titled compound was prepared according to the procedure for Scheme 8-11 from appropriate starting materials. $^{1}$H NMR (400 MHz, DMSO-d$_6$) δ: 10.43 (s, 1H), 9.25 (d, J=1.6 Hz, 1H), 8.85 (d, J=2.4 Hz, 1H), 8.52 (s, 1H), 8.41 (s, 1H), 8.01 (s, 1H), 7.88 (d, J=8.0 Hz, 1H), 7.76-7.35 (m, 4H), 7.02 (d, J=7.6 Hz, 1H), 6.94 (d, J=7.2 Hz, 1H), 6.55 (s, 1H), 5.52 (d, J=17.6 Hz, 1H), 5.30 (d, J=17.2 Hz, 1H), 4.94-4.65 (m, 2H), 3.98 (d, J=16.4 Hz, 1H), 3.57-3.42 (m, 1H), 2.45 (s, 3H), 2.39 (s, 3H), 2.34-2.08 (m, 3H), 2.02-1.75 (m, 2H), 1.68-1.46 (m, 1H); LCMS (ESI) m/z: 583 [M+H]$^+$.

-continued

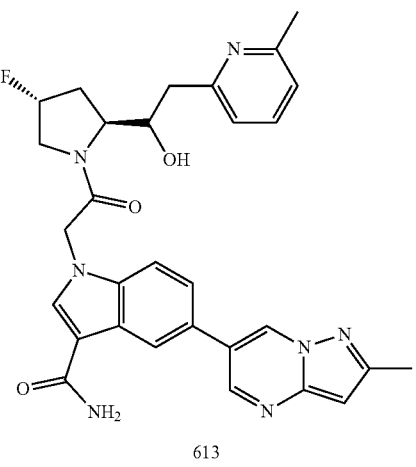

1-(2-((2S,4R)-4-fluoro-2-((S)-1-hydroxy-2-(6-methylpyridin-2-yl)ethyl)pyrrolidin-1-yl)-2-oxoethyl)-5-(2-methylpyrazolo[1,5-a]pyrimidin-6-yl)-1H-indole-3-carboxamide (613)

The title compound was prepared according to the procedure for Scheme 8-11 from appropriate starting materials. $^1$H NMR (400 MHz, DMSO-d$_6$) δ 9.34-9.25 (m, 1H), 8.90-8.86 (m, 1H), 8.44 (s, 1H), 8.31 (s, 1H), 8.05-7.93 (m, 1H), 7.83-7.53 (m, 4H), 7.48-7.32 (m, 1H), 7.28-6.92 (m, 1H), 6.56 (s, 1H), 5.74-5.28 (m, 3H), 5.27-5.07 (m, 1H), 4.52-4.38 (m, 1H), 4.26-4.12 (m, 2H), 3.13-3.06 (m, 2H), 2.93-2.80 (m, 1H), 2.66 (s, 3H), 2.47 (s, 3H), 2.40-2.21 (m, 2H); LCMS (ESI) m/z: 556 [M+H]$^+$.

Scheme 8-18

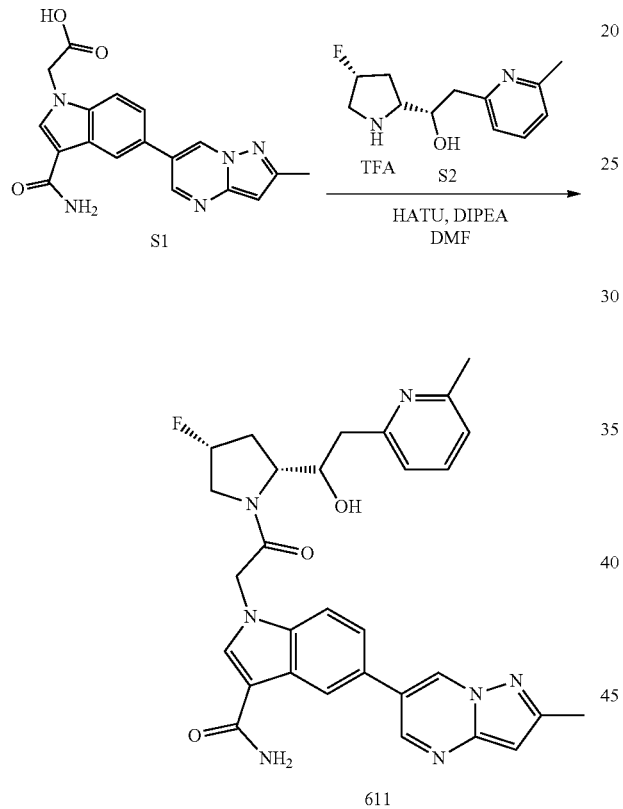

1-(2-((2R,4R)-4-Fluoro-2-((R)-1-hydroxy-2-(6-methylpyridin-2-yl)ethyl)pyrrolidin-1-yl)-2-oxoethyl)-5-(2-methylpyrazolo[1,5-a]pyrimidin-6-yl)-1H-indole-3-carboxamide (611)

The title compound was prepared according to the procedure for Scheme 8-11 from appropriate starting materials. $^1$H NMR (400 MHz, DMSO-d$_6$) δ 9.28 (d, J=2.0 Hz, 1H), 8.88 (d, J=2.4 Hz, 1H), 8.43 (s, 1H), 8.36-8.13 (m, 2H), 7.98 (s, 1H), 7.76-7.51 (m, 4H), 7.50-6.73 (m, 2H), 6.56 (s, 1H), 5.80-5.14 (m, 3H), 5.07 (d, J=17.2 Hz, 1H), 4.52-4.42 (m, 1H), 4.23-4.09 (m, 2H), 3.04 (d, J=10.8 Hz, 1H), 2.83 (dd, J=14.0, 10.4 Hz, 1H), 2.66 (s, 3H), 2.47 (s, 3H), 2.36-2.16 (m, 2H); LCMS (ESI) m/z: 556 [M+H]$^+$.

Scheme 8-19

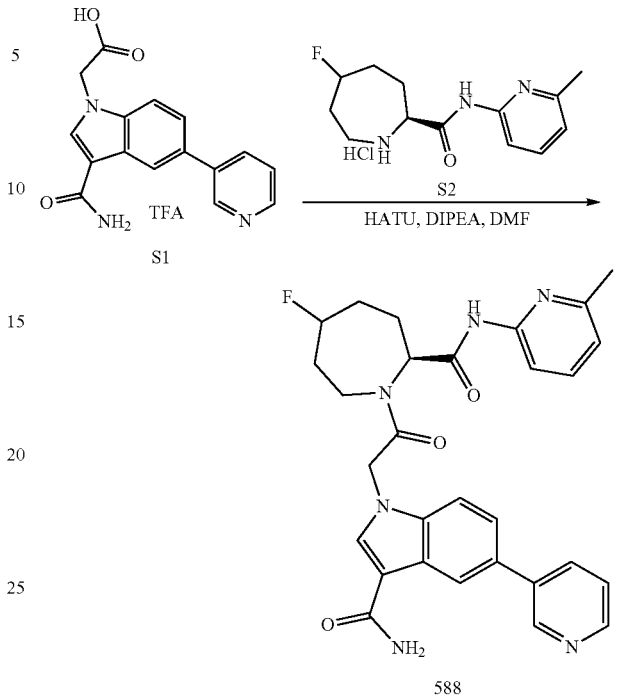

1-(2-((2S)-5-Fluoro-2-(((6-methylpyridin-2-yl)carbamoyl)azepan-1-yl)-2-oxoethyl)-5-(pyridin-3-yl)-1H-indole-3-carboxamide (588)

To a solution of scheme 8-19 compound S1, scheme 8-19 compound S2, and HATU in DMF (3 mL) was added DIPEA at 0° C. The reaction was stirred at room temperature for 16 h. The mixture was diluted with EtOAc and washed with water and brine, dried over anhydrous Na$_2$SO$_4$, filtered and concentrated to afford crude product, which was purified by preparative HPLC to afford compound 588 as a white solid.

$^1$H NMR (400 MHz, CD$_3$OD) δ 8.82 (dd, J=8.8, 1.8 Hz, 1H), 8.47 (d, J=4.8 Hz, 1H), 8.43-8.33 (m, 1H), 8.28 (s, 1H), 8.12 (ddd, J=7.0, 4.4, 1.9 Hz, 1H), 7.95-7.80 (m, 2H), 7.65 (dt, J=27.1, 7.9 Hz, 1H), 7.52-7.37 (m, 3H), 6.98 (dd, J=26.1, 7.5 Hz, 1H), 5.47 (d, J=17.2 Hz, 1H), 5.26 (dd, J=17.0, 5.0 Hz, 1H), 5.10-4.90 (m, 1H), 4.05-3.71 (m, 2H), 2.48-2.24 (m, 6H), 2.21-1.61 (m, 3H). LCMS (ESI) m/z: 529 [M+H]$^+$.

Scheme 8-20

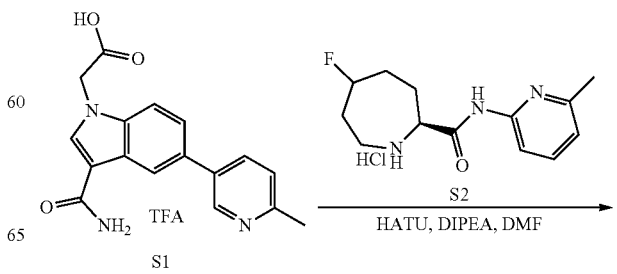

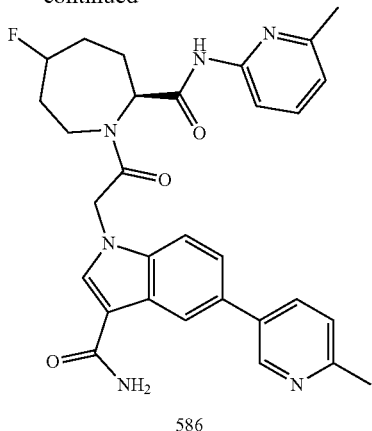

586

1-(2-((2S)-5-Fluoro-2-((6-methylpyridin-2-yl)car-bamoyl)azepan-1-yl)-2-oxoethyl)-5-(6-methylpyri-din-3-yl)-1H-indole-3-carboxamide (586)

To a solution of scheme 8-20 compound S1, scheme 8-20 compound S2, and HATU in DMF (3 mL) was added DIPEA at 0° C. The reaction was stirred at room temperature for 16 h. The mixture was diluted with EtOAc and washed with water and brine, dried over anhydrous Na₂SO₄, filtered and concentrated to afford crude product, which was purified by preparative HPLC to afford the title compound as a white solid. ¹H NMR (400 MHz, CD₃OD) δ 8.70 (s, 1H), 8.52 (s, 1H), 8.41 (s, 1H), 8.13 (m, 1H), 7.82-7.91 (m, 2H), 7.56-7.62 (m, 1H), 7.51 (s, 1H), 7.35-7.37 (m, 1H), 6.95 (d, J=7.6 Hz, 1H), 5.44-5.49 (m, 1H), 5.28-5.34 (m, 1H), 4.61-4.81 (m, 1H), 3.90-4.12 (m, 1H), 3.62-3.72 (m, 1H), 3.19-3.29 (m, 1H), 2.58 (s, 3H), 2.40 (s, 3H), 1.69-1.97 (m, 4H), 1.32-1.37 (m, 2H). LC/MS (ESI) m/z: 543 (M+H)⁺.

Scheme 8-21

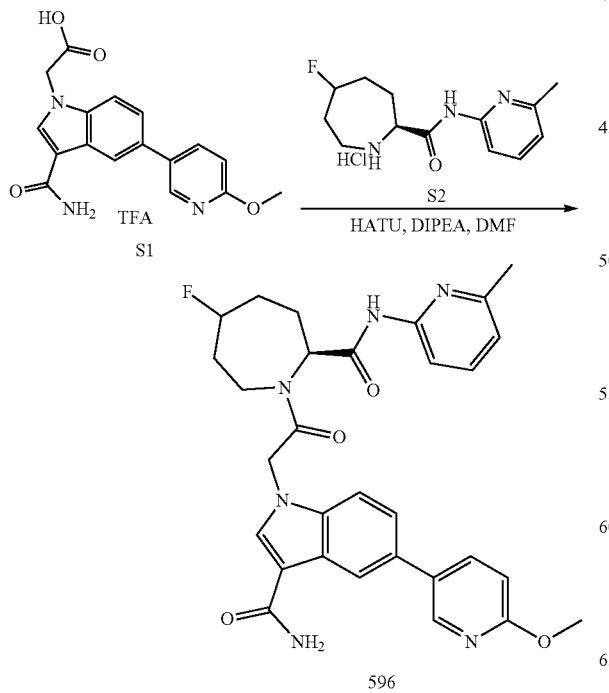

596

1-(2-((2S)-5-Fluoro-2-((6-methylpyridin-2-yl)car-bamoyl)azepan-1-yl)-2-oxoethyl)-5-(6-methoxypyri-din-3-yl)-1H-indole-3-carboxamide (596)

To a solution scheme 8-21 compound S1, scheme 8-21 compound S2, and HATU in DMF (3 mL) was added DIPEA at 0° C. The reaction was stirred at room temperature for 16 h. The mixture was diluted with EtOAc and washed with water and brine, dried over anhydrous Na₂SO₄, filtered and concentrated to afford crude product, which was purified by preparative HPLC to afford compound 596 as a white solid. ¹H NMR (400 MHz, DMSO-d₆) δ: 10.42 (s, 1H), 8.48-8.41 (m, 1H), 8.35-8.29 (m, 1H), 8.04-7.94 (m, 2H), 7.81 (d, J=8.0 Hz, 1H), 7.67 (t, J=7.6 Hz, 1H), 7.51-7.34 (m, 2H), 7.38 (d, J=8.4 Hz, 1H), 7.02 (d, J=7.6 Hz, 1H), 6.96-6.89 (m, 2H), 5.49 (d, J=17.2 Hz, 1H), 5.28 (d, J=17.2 Hz, 1H), 4.90-4.65 (m, 2H), 3.97 (d, J=16.0 Hz, 1H), 3.90 (s, 3H), 3.55-3.44 (m, 1H), 2.37 (s, 3H), 2.34-2.07 (m, 3H), 2.02-1.73 (m, 2H), 1.69-1.47 (m, 1H); LCMS (ESI) m/z: 559 [M+H]⁺.

Scheme 8-22

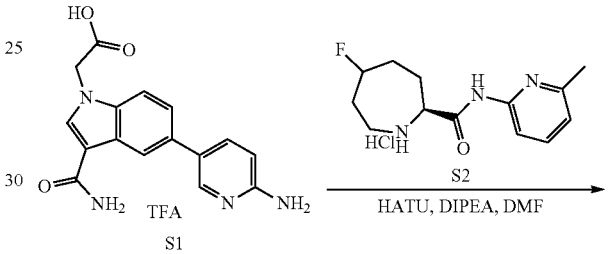

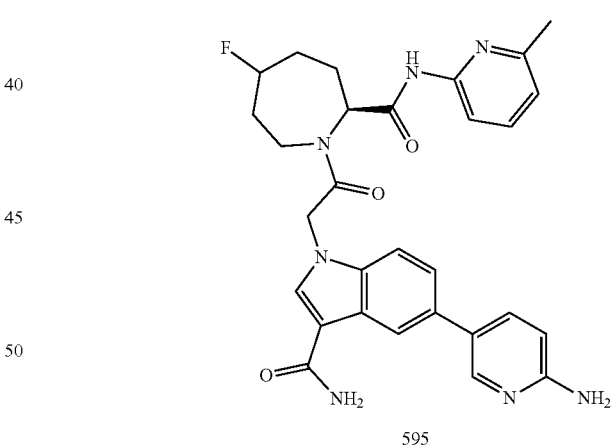

595

5-(6-Aminopyridin-3-yl)-1-(2-((2S)-5-fluoro-2-((6-methylpyridin-2-yl)carbamoyl)azepan-1-yl)-2-oxo-ethyl)-1H-indole-3-carboxamide (595)

To a solution of scheme 8-22 compound S1, scheme 8-22 compound S2, and HATU in DMF (3 mL) was added DIPEA at 0° C. The reaction was stirred at room temperature for 16 h. The mixture was diluted with EtOAc and washed with water and brine, dried over anhydrous Na₂SO₄, filtered and concentrated to afford crude product, which was purified by preparative HPLC to afford compound 595 as a white solid. ¹H NMR (400 MHz, CD₃OD) δ 8.26 (s, 1H), 8.18 (s, 1H), 7.90 (s, 1H), 7.79-7.87 (m, 2H), 7.59-7.63 (m, 1H), 7.39-7.42 (m, 2H), 6.95 (d, J=7.6 Hz, 1H), 6.68 (d, J=8.4 Hz, 1H), 5.42-5.47 (m, 1H), 5.28-5.33 (m, 1H), 4.57 (s, 2H), 3.97-4.02 (m, 1H), 3.56-3.63 (m, 1H), 2.40 (s, 3H), 1.71-2.05 (m, 4H), 1.24-1.37 (m, 2H). LCMS (ESI) m/z: 544 [M+H]$^+$.

Scheme 8-23

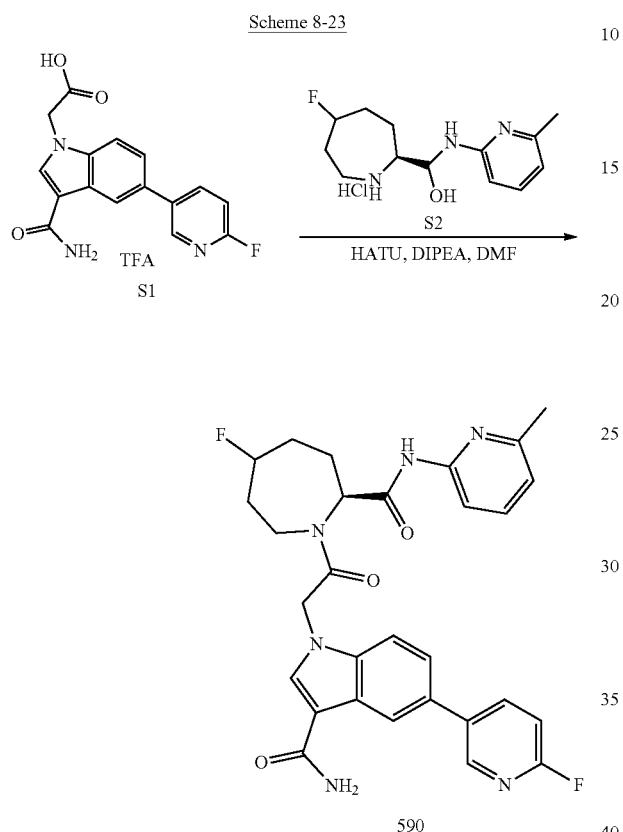

Scheme 8-24

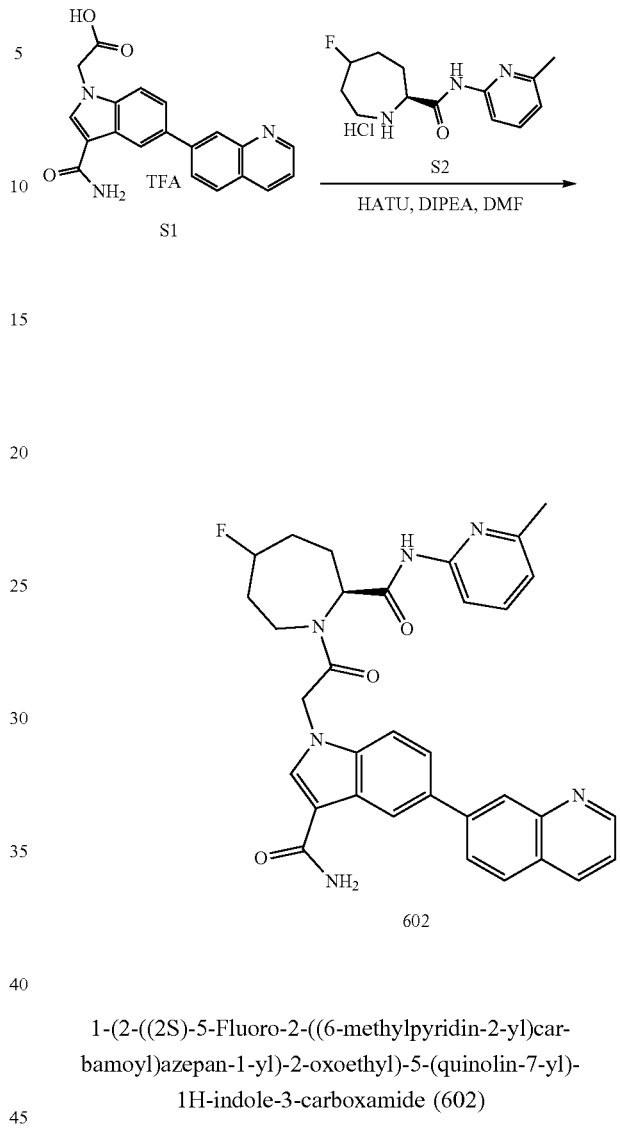

1-(2-((2S)-5-Fluoro-2-((6-methylpyridin-2-yl)carbamoyl)azepan-1-yl)-2-oxoethyl)-5-(6-fluoropyridin-3-yl)-1H-indole-3-carboxamide (590)

To a solution of scheme 8-23 compound S1, scheme 8-23 compound S2, and HATU in DMF (3 mL) was added DIPEA at 0° C. The reaction was stirred at room temperature for 16 h. The mixture was diluted with EtOAc and washed with water and brine, dried over anhydrous Na$_2$SO$_4$, filtered and concentrated to afford crude product, which was purified by preparative HPLC to afford compound 590 as a white solid. $^1$H NMR (400 MHz, CD$_3$OD) δ: 8.46 (t, J=6.1 Hz, 1H), 8.38 (s, 1H), 8.26-8.19 (m, 1H), 7.95 (s, 1H), 7.83 (d, J=7.7 Hz, 1H), 7.62 (t, J=7.9 Hz, 1H), 7.53-7.44 (m, 2H), 7.14 (dd, J=8.5, 2.6 Hz, 1H), 6.96 (d, J=7.5 Hz, 1H), 5.49 (d, 1H), 5.33 (dd, 1H), 4.90 (s, 1H), 4.57 (s, 1H), 4.02 (d, 1H), 3.71-3.54 (m, 1H), 2.40 (s, 3H), 2.27 (s, 1H), 2.06 (dd, J=95.2, 10.0 Hz, 3H), 1.80 (s, 1H), 0.90 (s, 1H). LC/MS (ESI) m/z: 547 (M+H)$^+$ 1-(2-((2S)-5-Fluoro-2-((6-methylpyridin-2-yl)carbamoyl)azepan-1-yl)-2-oxoethyl)-5-(quinolin-7-yl)-1H-indole-3-carboxamide (602)

To a solution of scheme 8-24 compound S1, scheme 8-24 compound S2, and HATU in DMF (3 mL) was added DIPEA at 0° C. The reaction was stirred at room temperature for 16 h. The mixture was diluted with EtOAc and washed with water and brine, dried over anhydrous Na$_2$SO$_4$, filtered and concentrated to afford crude product, which was purified by preparative HPLC to afford the compound 602 as a white solid. $^1$H NMR (400 MHz, CD$_3$OD) δ: 8.95-8.67 (m, 1H), 8.57 (d, J=1.4 Hz, 1H), 8.38 (d, J=8.2 Hz, 1H), 8.28 (s, 1H), 8.02 (d, J=4.2 Hz, 2H), 7.95 (s, 1H), 7.84 (d, J=8.4 Hz, 1H), 7.72-7.57 (m, 2H), 7.56-7.46 (m, 2H), 6.95 (d, J=7.5 Hz, 1H), 5.50 (d, 1H), 5.35 (d, 1H), 4.92 (dd, J=11.3, 5.2 Hz, 1H), 4.67 (s, 1H), 4.03 (d, 1H), 3.68-3.55 (m, 1H), 2.40 (s, 3H), 2.38-2.14 (m, 2H), 2.08-1.89 (m, 2H), 1.79 (dd, 1H). LC/MS (ESI) m/z: 579 (M+H)$^+$.

Scheme 8-25

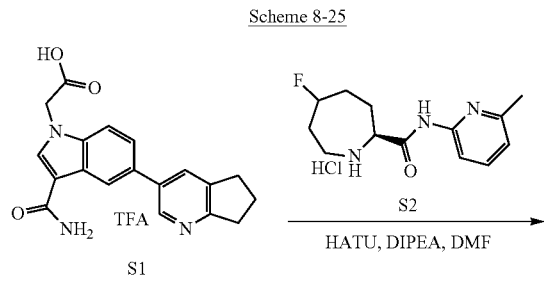

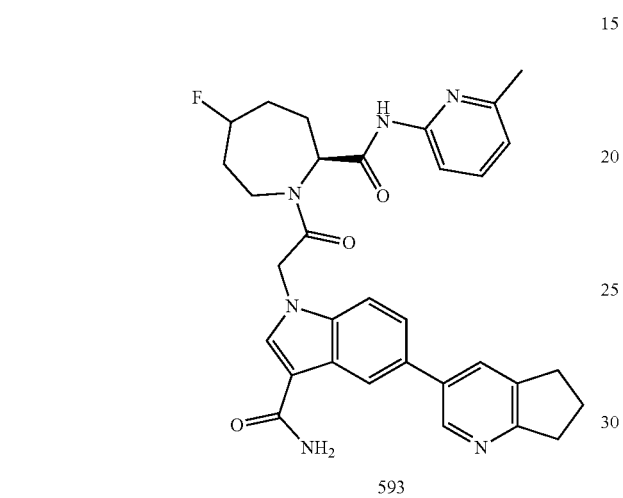

5-(6,7-Dihydro-5H-cyclopenta[b]pyridin-3-yl)-1-(2-((2S)-5-fluoro-2-((6-methylpyridin-2-yl)carbamoyl)azepan-1-yl)-2-oxoethyl)-1H-indole-3-carboxamide (593)

To a solution of scheme 8-25 compound S1, scheme 8-25 compound S2, and HATU in DMF (3 mL) was added DIPEA at 0° C. The reaction was stirred at room temperature for 16 h. The mixture was diluted with EtOAc and washed with water and brine, dried over anhydrous $Na_2SO_4$, filtered and concentrated to afford crude product, which was purified by preparative HPLC to afford compound 593 as a white solid. $^1$H NMR (400 MHz, DMSO-$d_6$) δ 10.51 (s, 1H), 8.65 (d, J=2.1 Hz, 1H), 8.45 (d, J=1.7 Hz, 1H), 8.12-8.00 (m, 1H), 7.96-7.86 (m, 2H), 7.72 (t, J=7.9 Hz, 1H), 7.62-7.46 (m, 2H), 7.03 (d, J=7.5 Hz, 2H), 5.64 (d, J=17.3 Hz, 1H), 5.37 (d, J=17.2 Hz, 1H), 5.02-4.81 (m, 2H), 4.06 (d, J=17.4 Hz, 1H), 3.65-3.51 (m, 1H), 3.05 (dt, J=18.1, 7.5 Hz, 4H), 2.48 (d, J=20.4 Hz, 3H), 2.32 (d, J=28.2 Hz, 2H), 2.20 (h, J=8.1, 7.5 Hz, 3H), 1.97 (ddd, J=59.4, 24.1, 11.6 Hz, 2H), 1.72 (d, J=13.0 Hz, 1H), 1.33 (s, 1H). LC/MS (ESI) m/z: 569 (M+H)$^+$.

Scheme 8-26

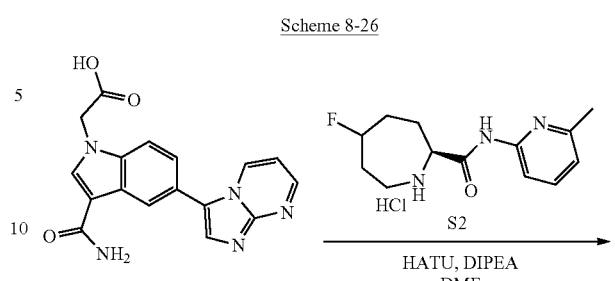

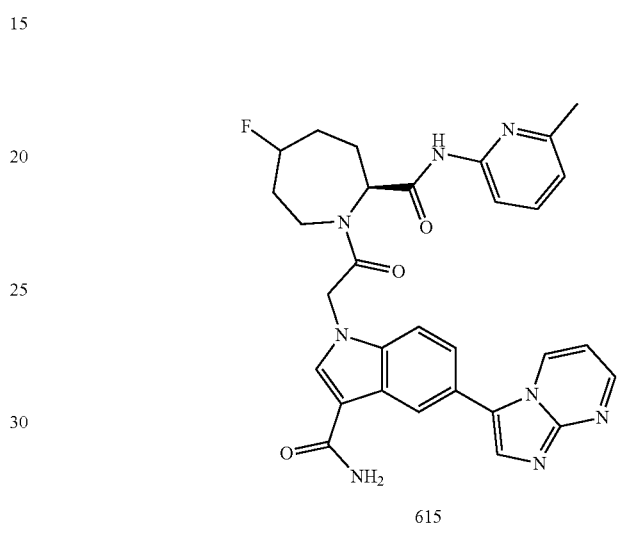

1-(2-((2S)-5-Fluoro-2-((6-methylpyridin-2-yl)carbamoyl)azepan-1-yl)-2-oxoethyl)-5-(imidazo[1,2-a]pyrimidin-3-yl)-1H-indole-3-carboxamide (615)

To a solution of scheme 8-26 compound S1, scheme 8-26 compound S2, and HATU in DMF (3 mL) was added DIPEA at 0° C. The reaction was stirred at room temperature for 16 h. The mixture was diluted with EtOAc and washed with water and brine, dried over anhydrous $Na_2SO_4$, filtered and concentrated to afford crude product, which was purified by preparative HPLC to afford compound 615 as a white solid. $^1$H NMR (400 MHz, $CD_3OD$) δ: 9.00 (d, J=6.5 Hz, 1H), 8.57 (t, J=12.5 Hz, 2H), 8.37 (d, J=17.0 Hz, 1H), 7.97 (d, J=10.6 Hz, 1H), 7.84 (t, J=11.4 Hz, 2H), 7.61 (t, J=8.8 Hz, 2H), 7.46 (d, J=8.3 Hz, 1H), 7.08 (dd, J=6.8, 4.2 Hz, 1H), 6.95 (d, J=7.4 Hz, 1H), 5.53 (d, J=17.3 Hz, 1H), 5.37 (d, J=17.3 Hz, 1H), 4.63 (d, J=40.3 Hz, 3H), 4.03 (d, J=15.8 Hz, 1H), 3.59 (dd, J=44.1, 27.4 Hz, 1H), 3.10 (dd, J=48.0, 14.5 Hz, 1H), 2.42 (d, J=13.5 Hz, 4H), 2.24 (d, J=26.8 Hz, 1H), 1.99 (d, J=11.8 Hz, 2H), 1.80 (s, 1H), 1.31 (d, J=14.1 Hz, 1H). LC/MS (ESI) m/z: 569 (M+H)$^+$.

Scheme 8-27

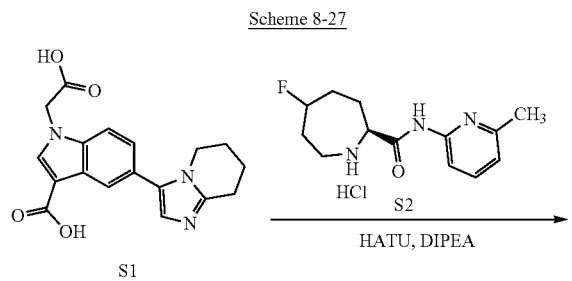

Scheme 8-28

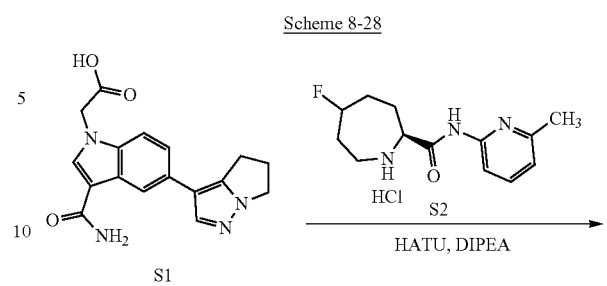

1-(2-((2S)-5-Fluoro-2-((6-methylpyridin-2-yl)carbamoyl)azepan-1-yl)-2-oxoethyl)-5-(5,6,7,8-tetrahydroimidazo[1,2-a]pyridin-3-yl)-1H-indole-3-carboxamide (616)

To a solution of scheme 8-27 compound S1, scheme 8-27 compound S2, and HATU in DMF (3 mL) was added DIPEA at 0° C. The reaction was stirred at room temperature for 16 h. The mixture was diluted with EtOAc and washed with water and brine, dried over anhydrous $Na_2SO_4$, filtered and concentrated to afford crude product, which was purified by preparative HPLC to afford compound 616 as a white solid. $^1$H NMR (400 MHz, $CD_3OD$) δ: 8.44 (s, 2H), 8.25 (t, J=4.9 Hz, 1H), 7.96 (d, J=9.6 Hz, 1H), 7.82 (d, J=8.2 Hz, 1H), 7.61 (t, J=7.9 Hz, 1H), 7.52 (d, J=8.6 Hz, 1H), 7.35-7.24 (m, 2H), 6.96 (d, J=7.5 Hz, 1H), 5.43 (dd, J=63.5, 17.3 Hz, 2H), 4.67 (s, 2H), 4.02 (d, J=18.0 Hz, 3H), 3.67-3.44 (m, 1H), 3.16-2.99 (m, 2H), 2.51 (d, J=42.9 Hz, 1H), 2.41 (s, 3H), 2.38-2.19 (m, 2H), 2.08-1.92 (m, 6H), 1.88-1.69 (m, 1H). LC-MS (ESI) found: 572 [M+1]$^+$.

5-(5,6-Dihydro-4H-pyrrolo[1,2-b]pyrazol-3-yl)-1-(2-((2S)-5-fluoro-2-((6-methylpyridin-2-yl)carbamoyl)azepan-1-yl)-2-oxoethyl)-1H-indole-3-carboxamide (617)

To a solution of scheme 8-28 compound S1, scheme 8-28 compound S2, and HATU in DMF (3 mL) was added DIPEA at 0° C. The reaction was stirred at room temperature for 16 h. The mixture was diluted with EtOAc and washed with water and brine, dried over anhydrous $Na_2SO_4$, filtered and concentrated to afford crude product, which was purified by preparative HPLC to afford compound 617 as a white solid. $^1$H NMR (400 MHz, DMSO-$d_6$) δ 10.42 (s, 1H), 8.22 (s, 1H), 7.92 (s 1H), 7.79 (s, 2H), 7.65-7.60 (m, 1H), 7.34 (m, 2H), 6.94 (d, J=7.4 Hz, 1H), 5.47 (d, J=17.3 Hz, 1H), 5.23 (d, J=17.3 Hz, 1H), 4.83 (m, 2H), 4.70 (s, 1H), 4.09 (t, J=7.3 Hz, 2H), 3.96 (d, J=15.7 Hz, 1H), 3.09-3.03 (m, 2H), 2.67-2.59 (m, 2H), 2.39 (d, J=19.4 Hz, 3H), 2.18 (m 3H), 1.93-1.78 (m, 2H), 1.62 (m 1H). LC-MS (ESI) found: 558 [M+1]$^+$.

Scheme 8-29

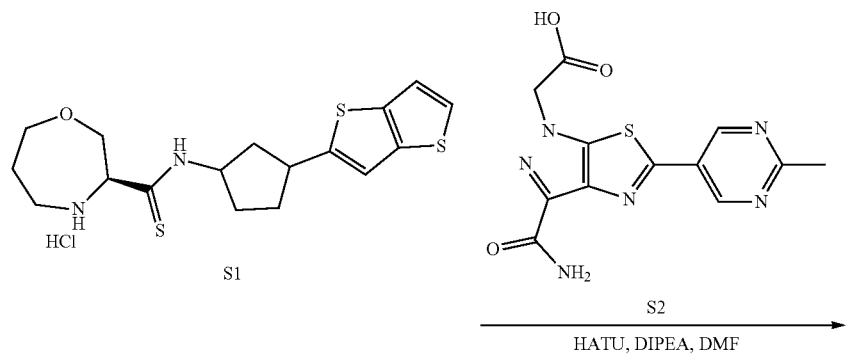

5-(2-Methylpyrimidin-5-yl)-1-(2-oxo-2-((3S)-3-((3-(thieno[3,2-b]thiophen-2-yl)cyclopentyl)carbamothioyl)-1,4-oxazepan-4-yl)ethyl)-1H-pyrazolo[3,4-d]thiazole-3-carboxamide (622)

To a solution of scheme 8-29 compound S1, scheme 8-29 compound S2, and HATU in DMF (3 mL) was added DIPEA at 0° C. The reaction was stirred at room temperature for 16 h. The mixture was diluted with EtOAc and washed with water and brine, dried over anhydrous Na$_2$SO$_4$, filtered and concentrated to afford crude product, which was purified by preparative HPLC to afford compound 622 as a white solid. $^1$H NMR (400 MHz, DMSO-d$_6$) δ 10.25 (s, 1H), 9.32-9.16 (m, 2H), 7.97 (d, J=5.7 Hz, 1H), 7.61 (s, 1H), 7.53 (dd, J 11.8, 5.2 Hz, 1H), 7.38-7.25 (m, 1H), 7.22-7.08 (m, 1H), 5.75 (dd, J=16.8, 3.8 Hz, 1H), 5.46 (d, J=17.0 Hz, 1H), 5.08-4.87 (m, 1H), 4.65 (s, 1H), 4.14 (ddd, J=44.2, 26.4, 13.3 Hz, 4H), 3.68 (ddd, J=97.6, 51.4, 7.3 Hz, 3H), 3.31 (s, 1H), 2.72 (d, J=6.3 Hz, 3H), 2.18-1.99 (m, 2H), 1.87 (s, 2H), 1.63 (d, J=6.3 Hz, 2H). LC/MS (ESI) m/z: 667 (M+H)$^+$.

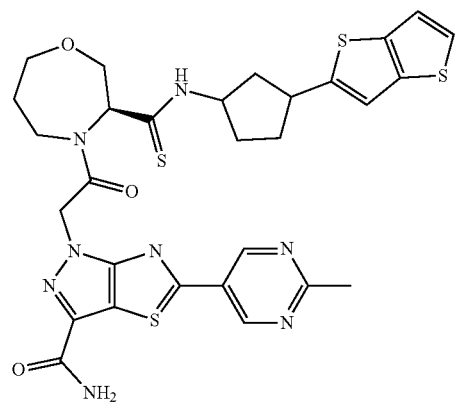

622

Scheme 8-30

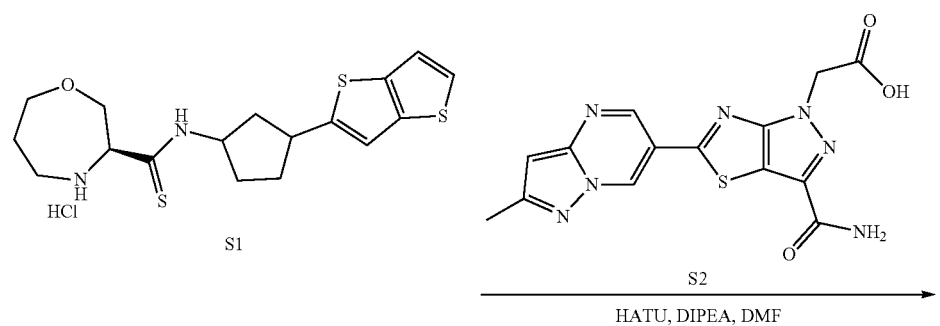

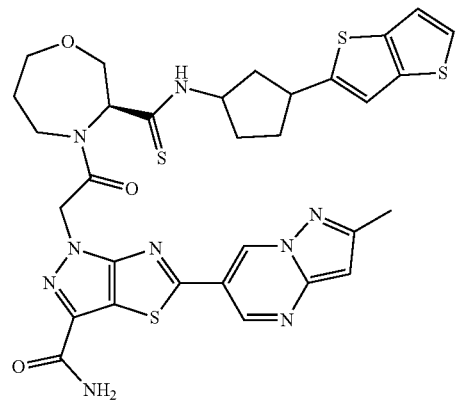
623

5-(2-Methylpyrazolo[1,5-a]pyrimidin-6-yl)-1-(2-oxo-2-((3S)-3-((3-(thieno[3,2-b]thiophen-2-yl)cyclopentyl)carbamothioyl)-1,4-oxazepan-4-yl)ethyl)-1H-pyrazolo[3,4-d]thiazole-3-carboxamide (623)

To a solution of the scheme 8-30 compound S1, scheme 8-30 compound S2, and HATU in DMF (3 mL) was added DIPEA at 0° C. The reaction was stirred at room temperature for 16 h. The mixture was diluted with EtOAc and washed with water and brine, dried over anhydrous $Na_2SO_4$, filtered and concentrated to afford crude product, which was purified by preparative HPLC to afford compound 623 as a white solid. $^1$H NMR (400 MHz, DMSO-$d_6$) δ: 10.21 (d, J=7.1 Hz, 1H), 9.56-9.67 (m, 1H), 8.96 (d, J=2.3 Hz, 1H), 7.87-7.97 (m, 1H), 7.58 (s, 1H), 7.46 (d, J=5.2 Hz, 1H), 7.07-7.31 (m, 2H), 6.68 (s, 1H), 5.72 (d, J=17.1 Hz, 1H), 5.49 (d, J=17.0 Hz, 1H), 5.01-5.12 (m, 1H), 4.63-4.79 (m, 1H), 4.23-4.41 (m, 1H), 3.97-4.16 (m, 3H), 3.70-3.86 (m, 1H), 3.45-3.65 (m, 2H), 2.48 (s, 3H), 1.52-2.28 (m, 8H). LC/MS (ESI) m/z: 706 (M+H)$^+$.

Scheme 8-31

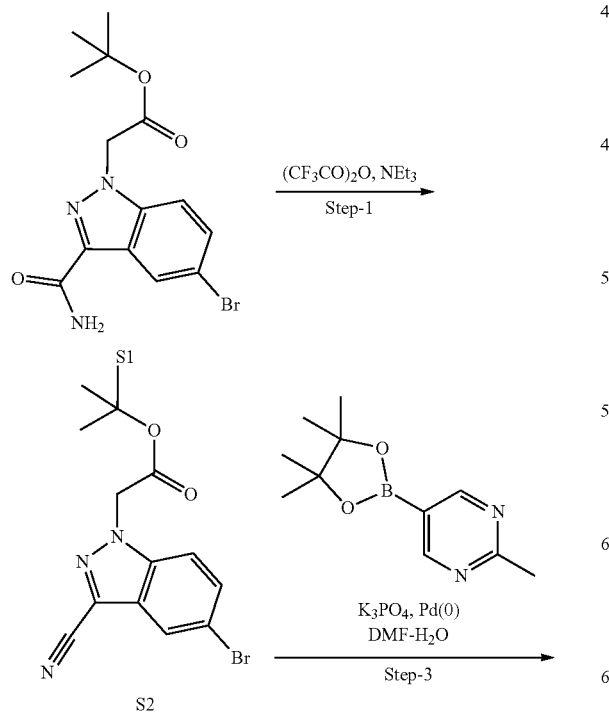

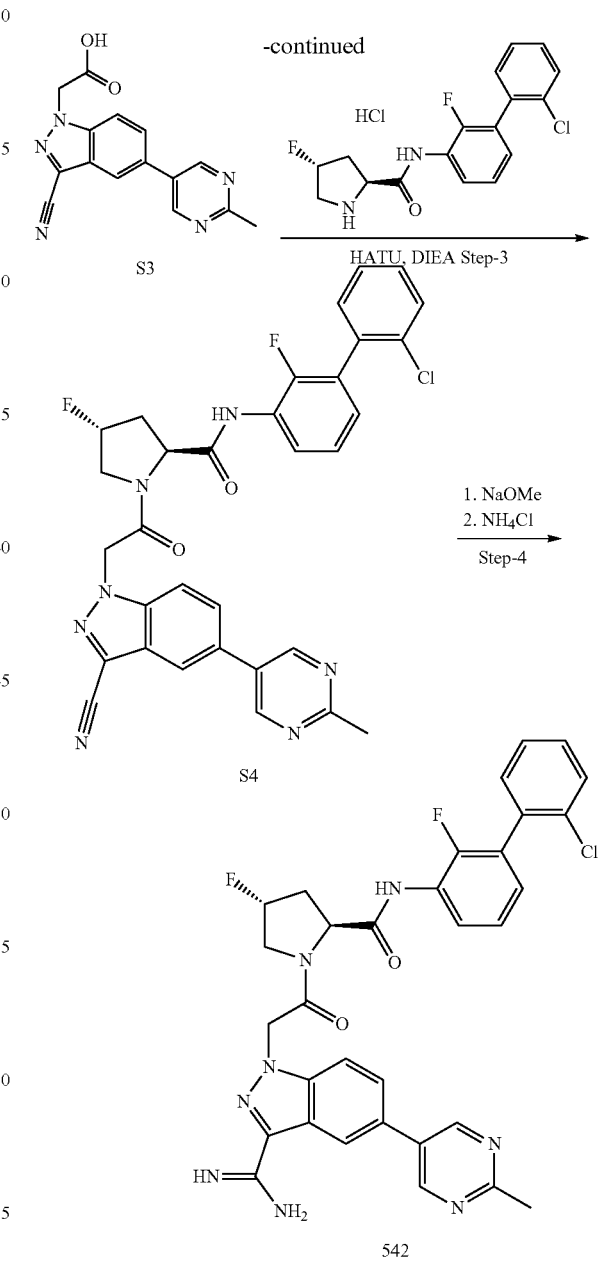

Step-1 tert-Butyl 2-(5-bromo-3-cyano-1H-indazol-1-yl)acetate (S2)

To the solution of tert-butyl 2-(5-bromo-3-carbamoyl-1H-indazol-1-yl)acetate (scheme 8-31 compound S1, 1.06 g, 3.0 mmol) in DCM (15.0 mL), trifluoroacetic anhydride (756 mg, 3.6 mmol) was added, followed by addition of triethyl amine at 0° C. The mixture was warmed up to room temperature and stirred overnight. The reaction was quenched with HCl (1N, 15 mL). The DCM layer was collected and the aqueous phase was extracted with DCM (15 mL×2). The combined DCM solution was washed with brine and dried over MgSO$_4$. The solution was filtered and the filtrate was concentrated. The remaining material was purified to afford 965 mg of title compound. $^1$H NMR (400 MHz, DMSO-d$_6$) δ: 1.41 (s, 9H), 5.51 (s, 2H), 7.76 (d, J=8.8 Hz, 1H), 7.89 (d, J=8.8 Hz, 1H), 8.20 (s, 1H). LC (method A): t$_R$=2.55 min. LC/MS (EI) m/z: [M+H]$^+$ 280.08, 282.11.

Step-2 2-(3-Cyano-5-(2-methylpyrimidin-5-yl)-1H-indazol-1-yl)acetic Acid (S3)

tert-Butyl 2-(5-bromo-3-cyano-1H-indazol-1-yl)acetate (scheme 8-31 compound S2, 965 mg, 2.86 mmol), 2-methyl-5-(4,4,5,5-tetramethyl-1,3,2-dioxaborolan-2-yl)pyrimidine (692 mg, 3.15 mmol) and K$_3$PO$_4$ (1.82 g, 8.58 mmol) are mixed in co-solvent of DMF (16 ml) and +H$_2$O (4 ml). The mixture was degassed and refilled with argon. To the mixture, Pd(PPh$_3$)$_4$ (0.1 eq) was added under Ar. The reaction was heated in an oil bath (125° C.) for 5.5 h. The reaction was cooled to rt and the volatiles were evaporated. The remaining materials are purified to afford 845 mg of title product. $^1$H NMR (400 MHz, DMSO-d$_6$) δ: 2.69 (s, 3H), 5.50 (s, 2H), 7.99-8.07 (m, 2H), 8.32 (s, 1H), 9.15 (s, 2H) ppm. LC (method A): t$_R$=0.88 min. LC/MS (EI) m/z: [M+H]$^+$ 294.23.

Step-3 (2S,4R)—N-(2'-chloro-2-fluoro-[1,1'-biphenyl]-3-yl)-1-(2-(3-cyano-5-(2-methylpyrimidin-5-yl)-1H-indazol-1-yl)acetyl)-4-fluoropyrrolidine-2-carboxamide (S4)

2-(3-cyano-5-(2-methylpyrimidin-5-yl)-1H-indazol-1-yl) acetic acid (scheme 8-31 compound S3, 293 mg, 1.0 mmol), HATU (418 mg, 1.1 mmol) and (2S,4R)—N-(2'-chloro-2-fluoro-[1,1'-biphenyl]-3-yl)-4-fluoropyrrolidine-2-carboxamide hydrochloride (336 mg, 0.90 mmol) are dissolved in DMF (2 mL). To the solution, DIEA (0.5 mL) was dropwise added at room temperature. The mixture was stirred for 1 h at rt and the volatiles were evaporated. The residue was partitioned between ethyl acetate and saturated aqueous NaHCO$_3$. The combined ethyl acetate solution was collected and washed with water, brine and dried over MgSO$_4$. The solution was concentrated and the remaining residue was purified to afford 453 mg of desire title compound. $^1$H NMR (400 MHz, DMSO-d$_6$): (major rotamer) δ: 2.12-2.29 (m, 1H), 2.51-2.63 (m, 1H), 2.69 (s, 3H), 3.95-4.07 (m, 1H), 4.18-4.27 (m, 1H), 4.77 (t, J=8.4 Hz, 1H), 5.50-5.91 (m, 3H), 7.06 (t, J=6.80 Hz, 1H), 7.22 (t, J=6.80 Hz, 1H), 7.35-7.47 (m, 3H), 7.56 (d, J=7.2 Hz, 1H), 7.95 (m, 3H), 8.32 (s, 1H), 9.13 (s, 2H), 9.99 (s, 1H) ppm. $^{19}$F NMR (376 MHz, DMSO-d$_6$): (major rotamer) δ −126.70, −176.15. LC (method A): t$_R$=2.21 min. LC/MS (EI) m/z: [M+H]$^+$ 612.38

Step-4 (2S,4R)-1-(2-(3-Carbamimidoyl-5-(2-methylpyrimidin-5-yl)-1H-indazol-1-yl)acetyl)-N-(2'-chloro-2-fluoro-[1,1'-biphenyl]-3-yl)-4-fluoropyrrolidine-2-carboxamide TFA (542)

(2S,4R)—N-(2'-chloro-2-fluoro-[1,1'-biphenyl]-3-yl)-1-(2-(3-cyano-5-(2-methylpyrimidin-5-yl)-1H-indazol-1-yl) acetyl)-4-fluoropyrrolidine-2-carboxamide (scheme 8-31 compound S4, 339 mg, 0.55 mml) was dissolved in dry methyl alcohol (3.0 mL) and treated with NaOMe in MeOH (25%)(1.5 mL). The reaction was stirred overnight at room temperature. Then NH$_4$Cl (400 mg) was added in one portion. The mixture was stirred overnight at room temperature. The mixture was purified by preparative HPLC to afford 41.6 mg of compound 542. $^1$H NMR (400 MHz, DMSO-d$_6$): (major rotamer) δ: 2.06-2.23 (m, 1H), 2.47-2.57 (m, 1H), 2.63 (s, 3H), 3.87-3.98 (m, 1H), 4.15-4.23 (m, 1H), 4.71 (t, J=8.4 Hz, 1H), 5.44-5.83 (m, 3H), 6.99 (t, J=6.80 Hz, 1H), 7.14 (t, J=6.80 Hz, 1H), 7.26-7.41 (m, 3H), 7.48-7.54 (m, 1H), 7.82-7.94 (m, 3H), 8.31 (s, 1H), 9.06-9.09 (m, 2H), 9.22 9 s, 2H), 9.30 (s, 2H), 9.93 (s, 1H) ppm. $^{19}$F NMR (376 MHz, DMSO-d$_6$): (major rotamer) δ −126.64, −175.87. LC (method A): t$_R$=1.64 min. LC/MS (EI) m/z: [M+H]$^+$ 629.46

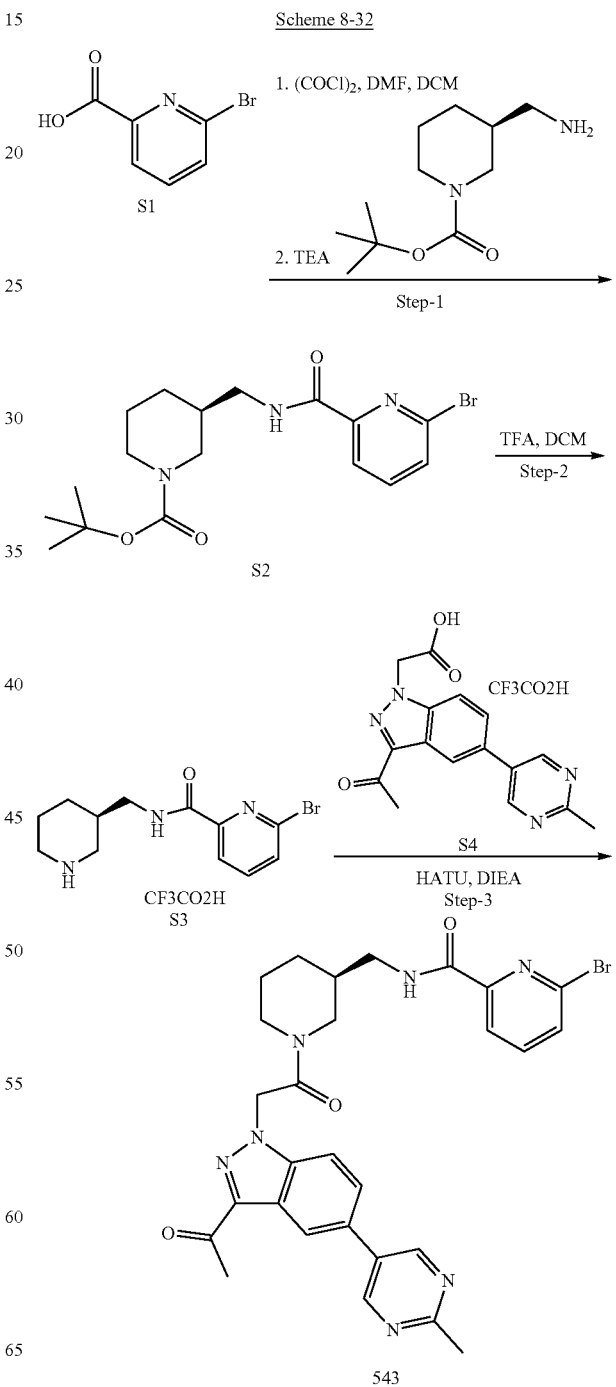

Scheme 8-32

Step-1 tert-Butyl (S)-3-((6-bromopicolinamido) methyl)piperidine-1-carboxylate (S2)

To the suspension of 6-bromopicolinic acid (scheme 8-32 compound S1, 606 mg, 3.0 mmol) in DCM (15.0 mL), a catalytic amount of DMF was added, followed by dropwise addition of oxalyl chloride (495 mg, 3.9 mmol, 0.34 mL) at 0° C. The reaction mixture was warmed up to rt and kept stirring for additional 1 h. The volatiles were evaporated and the remaining material was dissolved in DCM (15.0 mL). The solution was cooled in an ice bath. To the solution, tert-butyl (S)-3-(aminomethyl)piperidine-1-carboxylate (535 mg, 2.5 mmol) was added, followed by addition of TEA. The mixture was stirred overnight and quenched with saturated NaHCO$_3$. The two layers are separated and the organic phase was dried over MgSO$_4$, filtered and concentrated. The residue was purified to afford the title compound (900 mg). LC (method A): t$_R$=2.21 min. LC/MS (EI) m/z: [M+H]$^+$ 398.34, 400.37

Step-2 (R)-6-Bromo-N-(piperidin-3-ylmethyl)picolinamide TFA (S3)

tert-butyl (S)-3-((6-bromopicolinamido)methyl)piperidine-1-carboxylate (scheme 8-32 compound S2, 900 mg) was dissolved in DCM (8 mL) and treated with TFA (2 mL). The mixture was stirred overnight at room temperature. The volatiles were evaporated under reduced pressure. The remaining material was co-evaporated with toluene twice. The residue was used for next step without further purification.

Step-3 (S)—N-((1-(2-(3-Acetyl-5-(2-methylpyrimidin-5-yl)-1H-indazol-1-yl)acetyl)piperidin-3-yl)methyl)-6-bromopicolinamide (S4)

2-(3-acetyl-5-(2-methylpyrimidin-5-yl)-1H-indazol-1-yl) acetic acid TFA salt (288 mg, 0.68 mmol), (R)-6-bromo-N-(piperidin-3-ylmethyl)picolinamide TFA (scheme 8-32 compound S3, 280 mg, 0.68 mmol) are dissolved in DMF (10 mL) and HATU (310 mg, 0.82 equiv) was added, followed by addition of DIEA (0.59 mL, 5 equiv). The reaction mixture was stirred overnight at rt. The volatiles were evaporated under reduced pressure. The remaining material was treated with saturated NaHCO$_3$. The resulting solid was collected and dried. The solid was dissolved in minimum co-solvent MeOH-DCM (15%) and loaded on silica gel for chromatography. Purification afforded compound 543 (13.1 mg). $^1$H NMR (400 MHz, DMSO-d$_6$): (major rotamer) δ: 1.17-1.29 (m, 2H), 1.47-1.65 (m, 1H), 1.68-1.79 (m, 2H), 2.56 (s, 3H), 2.61 (s, 3H), 2.78-2.94 (m, 1H), 3.08-3.25 (m, 3H), 3.77-4.14 (m, 2H), 5.59 (s, 2H), 7.74-7.78 (m, 3H), 7.82-7.87 (m, 1H), 7.93-8.0 (m, 1H), 8.35 (s, 1H), 8.66-8.73 (m, 1H), 8.96 (s, 2H) ppm; LC (method A): t$_R$=1.72 min. LC/MS (EI) m/z: [M+H]$^+$ 590.41, 592.37

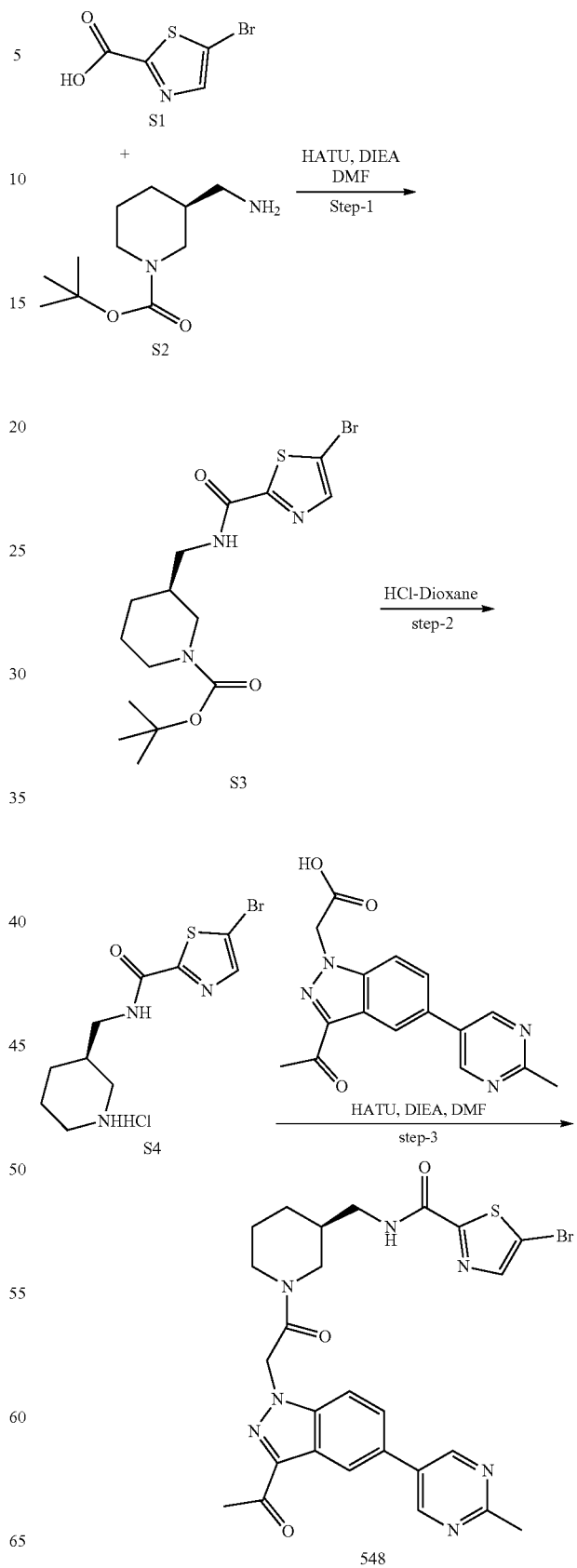

Scheme 8-33

Step-1 tert-Butyl (S)-3-((5-bromothiazole-2-carboxamido)methyl)piperidine-1-carboxylate (S3)

To the solution of 5-bromothiazole-2-carboxylic acid (scheme 8-33 compound S1, 458 mg, 2.2 mmol) and tert-butyl (S)-3-(aminomethyl)piperidine-1-carboxylate (scheme 8-33 compound S2, 429 mg, 2.0 mmol) in DCM (15.0 mL) at 0° C., HATU (912 mg, 2.4 mmol) was added, followed by addition of DIEA (3.6 mmol). The mixture was stirred for 1 h. The volatiles were evaporated under reduced pressure. The residue was diluted with ethyl acetate (60 mL) and washed with saturated NaHCO$_3$, water and brine. The organic solution was dried over MgSO$_4$. The solution was filtered and the filtrate was concentrated. The remaining material was purified to afford 513 mg of title product. LC (method A): t$_R$=2.30 min. LC/MS (EI) m/z: [M+H]$^+$ 404.06, 406.09.

Step-2 (R)-5-Bromo-N-(piperidin-3-ylmethyl)thiazole-2-carboxamide hydrochloride (S4)

tert-Butyl (S)-3-((5-bromothiazole-2-carboxamido)methyl)piperidine-1-carboxylate (scheme 8-33 compound S3, 513 mg) was taken up in 4N HCl dioxane (6 mL) and the resulting reaction mixture was stirred at rt for 2 h. After completion of the reaction monitored by HPLC, the solvent was removed under reduced pressure. The remaining residue was used directly without further purification.

Step-3 (S)—N-((1-(2-(3-Acetyl-5-(2-methylpyrimidin-5-yl)-1H-indazol-1-yl)acetyl)piperidin-3-yl)methyl)-5-bromothiazole-2-carboxamide (548)

2-(3-acetyl-5-(2-methylpyrimidin-5-yl)-1H-indazol-1-yl) acetic acid TFA salt (scheme 8-33 compound S4, 220 mg, 0.5 mmol), (R)-5-bromo-N-(piperidin-3-ylmethyl)thiazole-2-carboxamide hydrochloride (170 mg, 0.5 mmol) was dissolved in DMF (5.0 mL), and HATU (228 mg, 0.60 mmol) was added, followed by addition of DIEA (5 equiv). The reaction mixture was stirred overnight at room temperature. The volatiles were evaporated under reduced pressure. The residue was diluted with ethyl acetate (60 mL) and washed with saturated NaHCO$_3$, water and brine. The organic solution was dried over MgSO$_4$. The solution was filtered and the filtrate was concentrated. The remaining material was purified to afford 125.7 mg of compound 548. $^1$H NMR (400 MHz, DMSO-d$_6$): (major rotamer) δ 1.11-1.31 (m, 2H), 1.46-1.60 (m, 1H), 1.62-1.72 (m, 2H), 2.56 (s, 3H), 2.62 (s, 3H), 2.77-2.98 (m, 1H), 3.02-3.18 (m, 2H), 3.20-3.35 (m, 1H), 3.80-4.11 (m, 2H), 5.60 (s, 2H), 7.77 (s, 2H), 8.04 (s, 1H), 8.35 (s, 1H), 8.96 (s, 2H), 8.91 (t, J=6.0 Hz, 1H) ppm. LC (method A): t$_R$=1.78 min. LC/MS (EI) m/z: [M+H]$^+$ 598.04.

Scheme 8-34

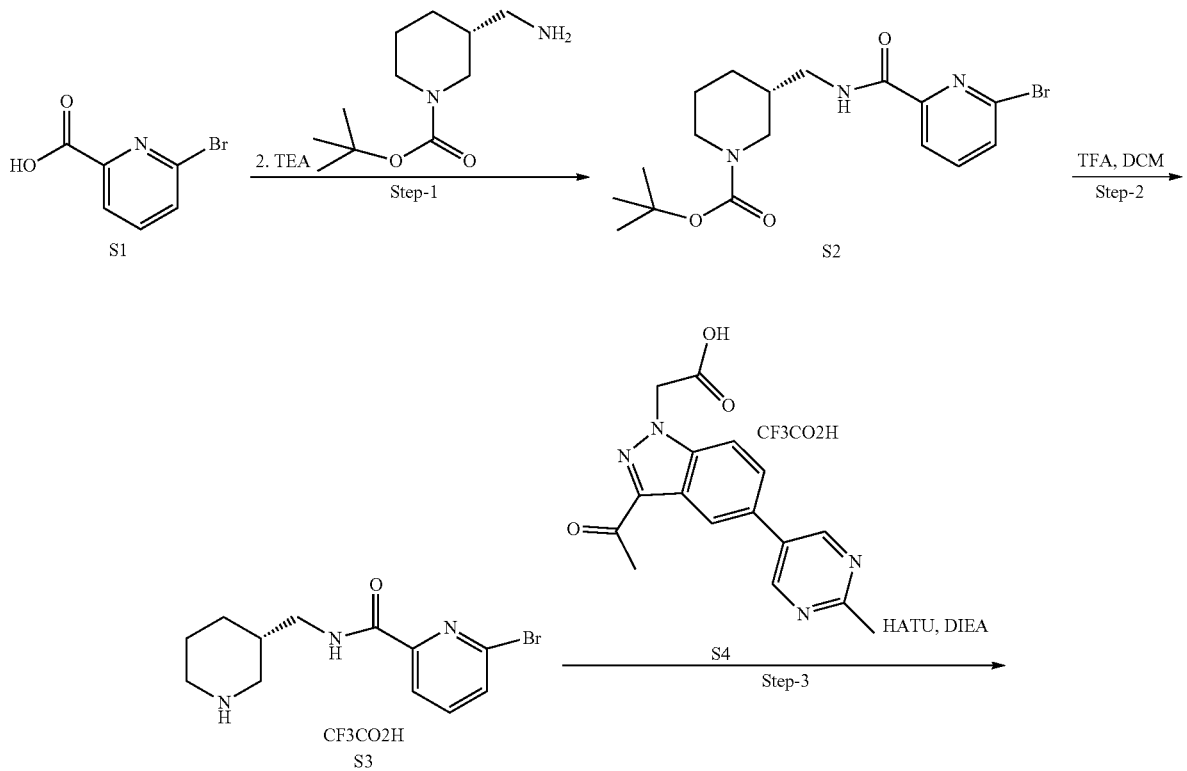

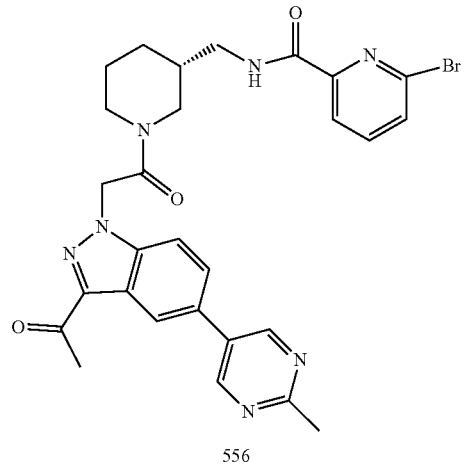

(R)—N-((1-(2-(3-Acetyl-5-(2-methylpyrimidin-5-yl)-1H-indazol-1-yl)acetyl)piperidin-3-yl)methyl)-6-bromopicolinamide (556)

Compound 556 was prepared following the procedure for the synthesis of compound 543 (Scheme 8-32). ¹H NMR (400 MHz, DMSO-d₆): (major rotamer) δ: 1.15-1.29 (m, 2H), 1.47-1.55 (m, 1H), 1.68-1.79 (m, 2H), 2.56 (s, 3H), 2.61 (s, 3H), 2.78-3.06 (m, 1H), 3.08-3.20 (m, 3H), 3.77-4.14 (m, 2H), 5.59 (s, 2H), 7.74-7.78 (m, 3H), 7.82-7.87 (m, 1H), 7.93-8.0 (m, 1H), 8.35 (s, 1H), 8.66-8.73 (m, 1H), 8.96 (s, 2H) ppm; LC (method A): $t_R$=1.72 min. LC/MS (EI) m/z: [M+H]⁺ 592.09.

Scheme 8-35

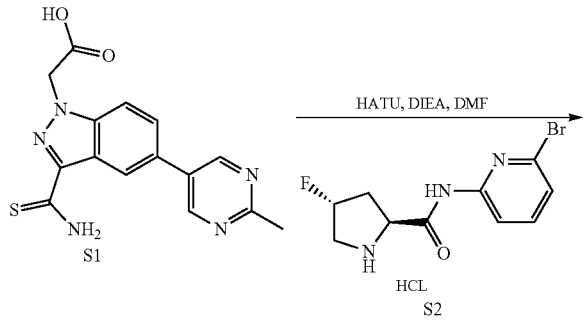

Step 1: (2S,4R)—N-(6-Bromopyridin-2-yl)-1-(2-(3-carbamothioyl-5-(2-methylpyrimidin-5-yl)-1H-indazol-1-yl)acetyl)-4-fluoropyrrolidine-2-carboxamide (527)

2-(3-carbamothioyl-5-(2-methylpyrimidin-5-yl)-1H-indazol-1-yl)acetic acid (scheme 8-35 compound S1, 327 mg) was dissolved in DMF (10 mL) and DIEA (0.3 mL) was added. This was followed by the addition of (2S,4R)—N-(6-bromopyridin-2-yl)-4-fluoropyrrolidine-2-carboxamide hydrochloride (324 mg) at 5° C. HATU (456 mg) was then added slowly at this same temperature and the reaction mixture was stirred for 3 h at room temperature. The reaction mixture was then added to water (50 mL+5 g solid NaCl) and extracted with DCM (2×20 mL). The organic layer was washed successively with an aqueous solution of NaHCO₃ (20 mL), water (20 mL), and brine (20 mL), then dried over Na₂SO₄ and concentrated under reduced pressure. The remaining residue was purified by flash column chromatography (eluted with DCM/MeOH) to afford 527. ¹H NMR (400 MHz, DMSO-d₆) δ 0.78-0.90 (m, 1H), 1.24 (s, 1H), 2.05-2.26 (m, 0.5H), 2.15-2.26 (m, 0.5H), 3.93 (d, J=12.1 Hz, 0.5H), 4.02 (d, J=12.6 Hz, 0.5H), 4.17-4.31 (m, 1H), 4.67 (t, J=8.5 Hz, 1H), 5.46-5.60 (m, 4H), 5.74 (d, J=17.3 Hz, 1H), 7.33 (d, J=7.7 Hz, 1H), 7.71 (t, J=8.0 Hz, 1H), 7.83 (s, 2H), 8.03 (d, J=8.2 Hz, 1H), 8.98 (d, J=12.7 Hz, 3H), 9.45 (s, 1H), 9.71 (s, 1H), 11.02 (s, 1H). ¹⁹F NMR (376 MHz, DMSO) δ −175.70; LC (method A): $t_R$=1.58 min. LC/MS (EI) m/z: [M+H]⁺ 597.

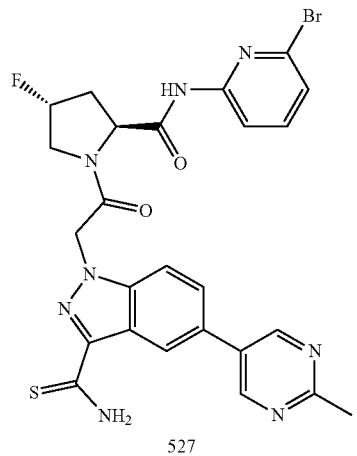

Scheme 8-36

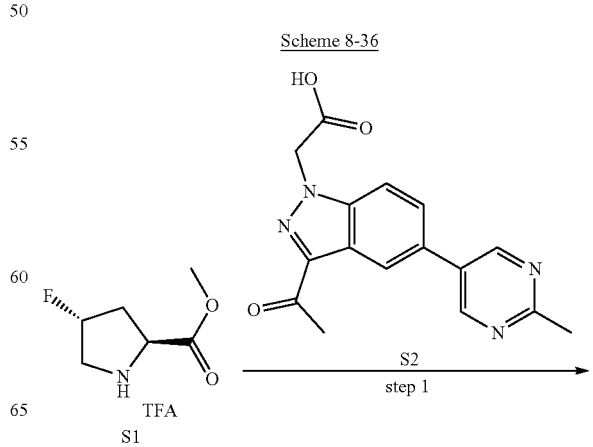

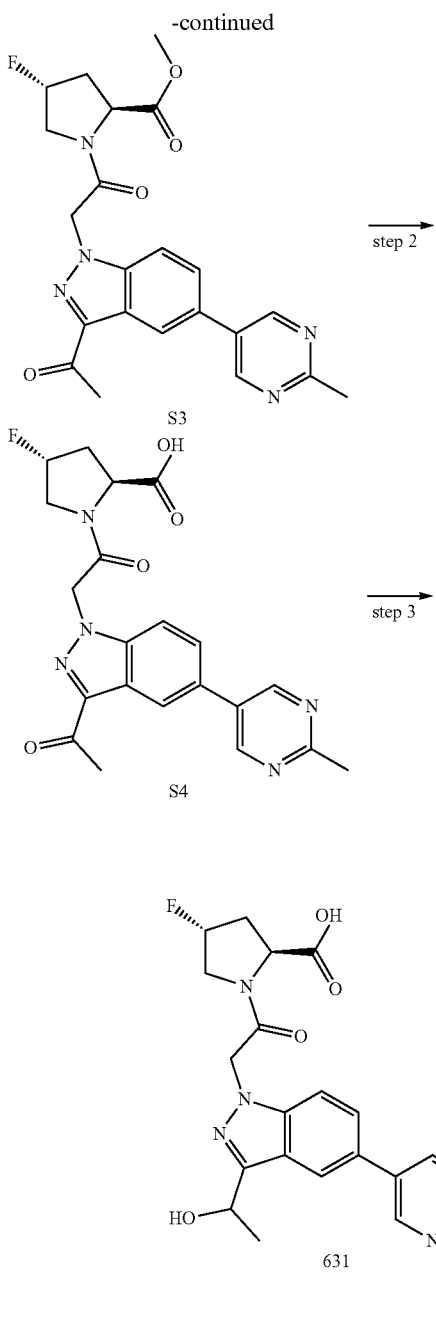

Step 2 (2S,4R)-1-(2-(3-Acetyl-5-(2-methylpyrimidin-5-yl)-1H-indazol-1-yl)acetyl)-4-fluoropyrrolidine-2-carboxylic Acid (S4)

To a solution of methyl (2S,4R)-1-(2-(3-acetyl-5-(2-methylpyrimidin-5-yl)-1H-indazol-1-yl)acetyl)-4-fluoropyrrolidine-2-carboxylate (scheme 8-36 compound S3, 439 mg) in MeOH (5 mL) was added LiOH (48 mg) in 2 mL water solution. The reaction was then stirred for 3 h at room temperature. The reaction mixture was then added HCl/water (pH ~3) and removed all solvent. The remaining residue was purified by HPLC to afford the title compound.

Step 3 (2S,4R)-4-Fluoro-1-(2-(3-(1-hydroxyethyl)-5-(2-methylpyrimidin-5-yl)-1H-indazol-1-yl)acetyl)pyrrolidine-2-carboxylic Acid (631)

To a solution of methyl (2S,4R)-1-(2-(3-acetyl-5-(2-methylpyrimidin-5-yl)-1H-indazol-1-yl)acetyl)-4-fluoropyrrolidine-2-carboxylic acid (scheme 8-36 compound S4, 425 mg) in MeOH (5 mL) was added NaBH$_4$ (40 mg) then stirred for 3 h at room temperature. AcOH was added to the reaction mixture and solvent was removed in vacuo. The residue was purified by HPLC to afford compound 631. $^1$H NMR (400 MHz, DMSO) δ 1.59 (dd, J=1.8, 6.6 Hz, 3H), 2.08 (s, 1H), 2.01-2.23 (m, 1H), 2.57 (td, J=7.1, 12.2, 13.4 Hz, 1H), 2.69 (s, 3H), 3.87-4.07 (m, 1H), 4.17 (dd, J=12.5, 21.7 Hz, 1H), 4.32 (t, J=8.5 Hz, 1H), 5.16 (m, 1H), 5.33 (dd, J=2.6, 17.3 Hz, 1H), 5.43 (d, J=4.0 Hz, 1H), 5.48-5.60 (m, 1H), 6.35 (s, 1H), 7.60 (dd, J=2.3, 8.8 Hz, 1H), 7.71-7.80 (m, 1H), 8.28 (s, 1H), 9.05 (s, 2H); $^{19}$F NMR (376 MHz, DMSO-d$_6$): (major rotamer) δ −176.06. LC (method A): t$_R$=0.72 min. LC/MS (EI) m/z: [M+H]$^+$ 428.

Scheme 8-37

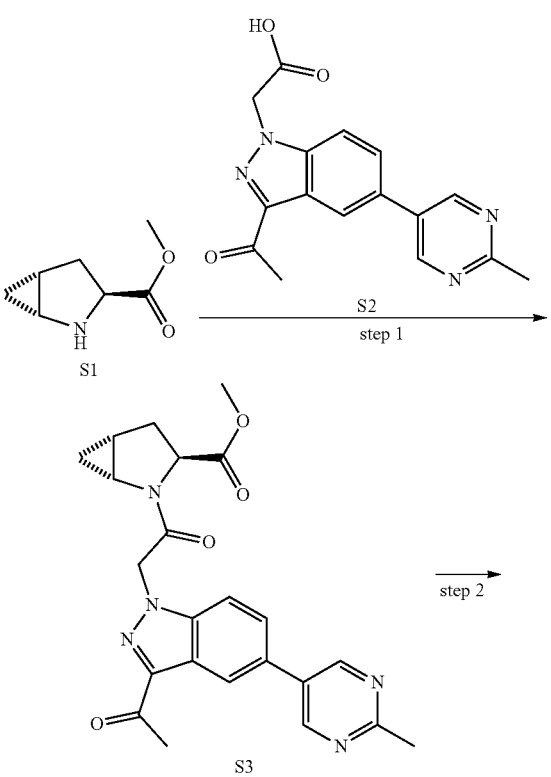

Step 1 Methyl (2S,4R)-1-(2-(3-acetyl-5-(2-methylpyrimidin-5-yl)-1H-indazol-1-yl)acetyl)-4-fluoropyrrolidine-2-carboxylate (S3)

To a solution of 2-(3-acetyl-5-(2-methylpyrimidin-5-yl)-1H-indazol-1-yl)acetic acid (scheme 8-36 compound S2, 310 mg) in DMF (5 mL) was added DIEA (0.5 mL) followed by methyl (2S,4R)-4-fluoropyrrolidine-2-carboxylate (scheme 8-36 compound S1, 150 mg). HATU (456 mg) was then added slowly and the reaction mixture was stirred for 18 h at room temperature. The reaction mixture was then added to water (10 mL) and extracted with EtOAc (2×15 mL). The organic layer was washed successively with an aqueous solution of NaHCO$_3$ (10 mL), water (10 mL), and brine (10 mL), dried over Na$_2$SO$_4$, and concentrated under reduced pressure. The remaining residue was purified by HPLC to afford the title compound.

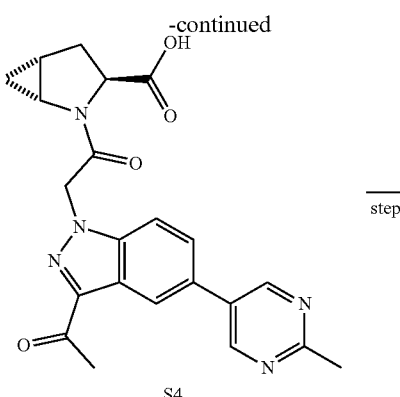

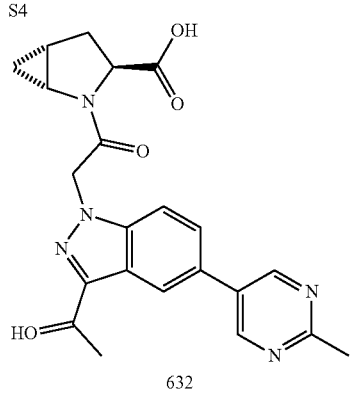

Step 1 Methyl (1R,3S,5R)-2-(2-(3-acetyl-5-(2-methylpyrimidin-5-yl)-1H-indazol-1-yl)acetyl)-2-azabicyclo[3.1.0]hexane-3-carboxylate (S3)

To a solution of 2-(3-acetyl-5-(2-methylpyrimidin-5-yl)-1H-indazol-1-yl)acetic acid (scheme 8-37 compound S2, 310 mg) in DMF (5 mL) was added DIEA (0.5 mL) followed by methyl (2S,4R)-4-fluoropyrrolidine-2-carboxylate (scheme 8-37 compound S1, 141 mg). HATU (456 mg) was then added slowly and the reaction mixture was stirred for 18 h at rt. The reaction mixture was then added to water (10 mL) and extracted with EtOAc (2×15 mL). The organic layer was washed successively with an aqueous solution of NaHCO$_3$ (10 mL), water (10 mL), and brine (10 mL), dried over Na$_2$SO$_4$ and concentrated under reduced pressure. The remaining residue was purified by HPLC to afford the title compound.

Step 2 (1R,3S,5R)-2-(2-(3-Acetyl-5-(2-methylpyrimidin-5-yl)-1H-indazol-1-yl)acetyl)-2-azabicyclo[3.1.0]hexane-3-carboxylic Acid (S4)

To a solution of methyl methyl (1R,3S,5R)-2-(2-(3-acetyl-5-(2-methylpyrimidin-5-yl)-1H-indazol-1-yl)acetyl)-2-azabicyclo[3.1.0]hexane-3-carboxylate (scheme 8-37 compound S3, 433 mg) in MeOH (5 mL) was added LiOH (48 mg) in 2 mL water solution then stirred for 3 h at room temperature. The reaction mixture was then added HCl/water (pH ~3) and removed all solvent. The remaining residue was purified by HPLC to afford the title compound.

Step 3 (1R,3S,5R)-2-(2-(3-(1-Hydroxyethyl)-5-(2-methylpyrimidin-5-yl)-1H-indazol-1-yl)acetyl)-2-azabicyclo[3.1.0]hexane-3-carboxylic Acid (632)

To a solution of (1R,3S,5R)-2-(2-(3-acetyl-5-(2-methylpyrimidin-5-yl)-1H-indazol-1-yl)acetyl)-2-azabicyclo[3.1.0]hexane-3-carboxylic acid (scheme 8-37 compound S4, 419 mg) in MeOH (5 mL) was added NaBH$_4$ (40 mg). The reaction was then stirred for 3 h at room temperature. AcOH was added to the reaction mixture and solvent was removed in vacuo. The remaining residue was purified by HPLC to afford compound 632. $^1$H NMR (400 MHz, DMSO) δ 0.83 (m, 1H), 1.01 (m, 1H), 1.89 (m, 1H), 2.09-2.48 (m, 3H), 2.68 (m, 5H), 3.80 (m, 1H), 4.18-4.31 (m, 1H), 5.60 (d, J=17.2 Hz, 1H), 5.98 (d, J=17.3 Hz, 1H), 7.81-7.93 (m, 2H), 8.45 (s, 1H), 9.06 (s, 2H), 12.56 (s, 1H). LC (method A): t$_R$=1.11 min. LC/MS (EI) m/z: [M+H]$^+$ 420.

Scheme 8-38

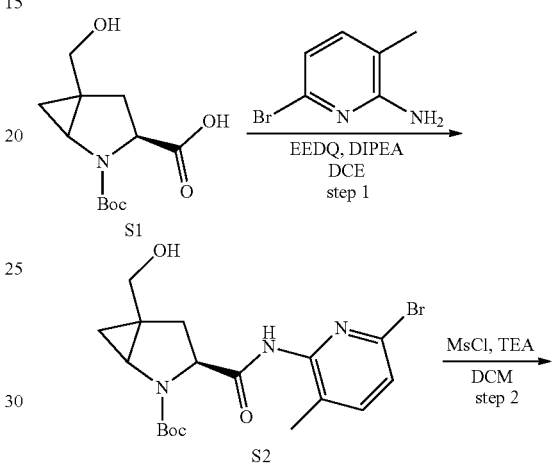

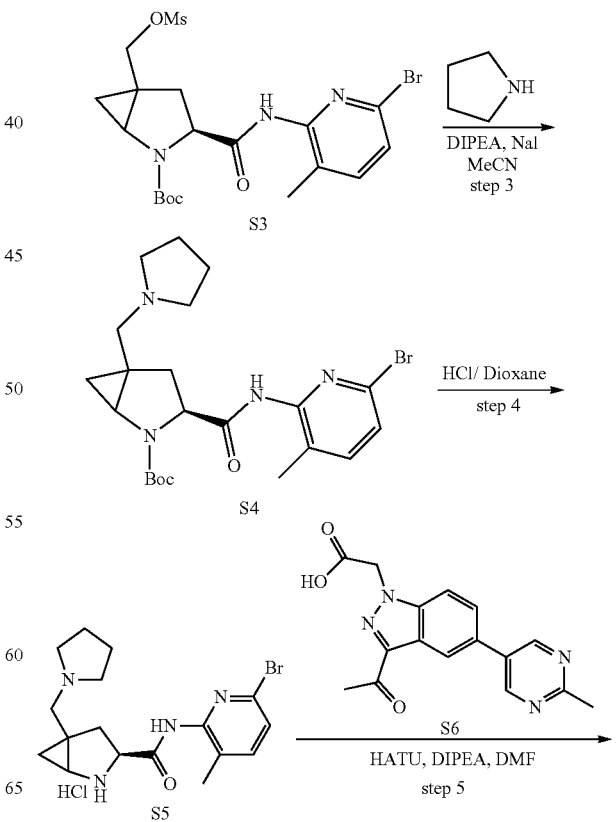

-continued

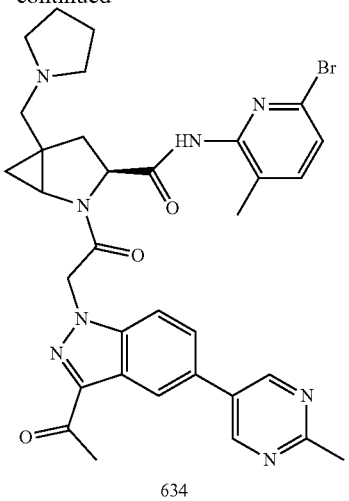

634

Step 1: (3S)-tert-Butyl 3-(6-bromo-3-methylpyridin-2-ylcarbamoyl)-5-(hydroxymethyl)-2-azabicyclo[3.1.0]hexane-2-carboxylate (S2)

To a solution of scheme 8-38 compound S1 (1 g, 3.89 mmol) and 6-bromo-3-methylpyridin-2-amine (870 mg, 4.67 mmol) in DCE (10 ml) was added DIPEA (2.56 mL, 15.56 mmol) and EEDQ (1.92 g, 7.78 mmol). The reaction was stirred at 90° C. overnight. The solvent was removed under vacuum. The residue was purified by column chromatography on silica gel (petroleum ether:ethyl acetate=2:1) to afford scheme 8-38 compound S2 (710 mg, 43.0% yield) as a white solid. LC/MS (ESI) m/z: 426 (M+H)$^+$.

Step 2: (3S)-tert-Butyl 3-(6-bromo-3-methylpyridin-2-ylcarbamoyl)-5-((methylsulfonyloxy)methyl)-2-azabicyclo[3.1.0]hexane-2-carboxylate (S3)

Methanesulfonyl chloride (0.08 mL, 1.05 mmol) was added to a solution of scheme 8-38 compound S2 (300 mg, 0.70 mmol) and triethylamine (0.19 mL, 1.41 mmol) in DCM (6 mL) dropwise at 0° C. After the addition was complete, the reaction was stirred at 0° C. for 2 h. The mixture was poured into ice-water. The organic layer was separated, washed with brine, dried over anhydrous Na$_2$SO$_4$ and filtered. The filtrate was concentrated to afford the crude scheme 8-38 compound S3 (320 mg, 90.2% yield) as a yellow solid. The compound was carried forward without any further purification.

Step 3: (3S)-tert-Butyl 3-((6-bromo-3-methylpyridin-2-yl)carbamoyl)-5-(pyrrolidin-1-ylmethyl)-2-azabicyclo[3.1.0]hexane-2-carboxylate (S4)

To a mixture of (1R,3S,5S)-tert-butyl 3-((6-bromo-3-methylpyridin-2-yl)carbamoyl)-5-(((methylsulfonyl)oxy)methyl)-2-azabicyclo[3.1.0]hexane-2-carboxylate (scheme 8-38 compound S3, 25 mg, 0.05 mmol) in CH$_3$CN (2 mL) was added DIPEA (0.035 mL, 0.2 mmol) and pyrrolidine (4 mg, 0.055 mmol). The reaction mixture was stirred at room temperature for 3 h. The mixture was diluted with DCM and washed with water and brine. The organic layer was dried over anhydrous Na$_2$SO$_4$, filtered and concentrated to afford scheme 8-38 compound S4 (15 mg, 62.6% yield) as a brown solid. LC/MS (ESI) m/z: 479 (M+H)$^+$.

Step 4: (3S)—N-(6-Bromo-3-methylpyridin-2-yl)-5-(pyrrolidin-1-ylmethyl)-2-azabicyclo[3.1.0]hexane-3-carboxamide (S5)

To a solution of (3S)-tert-butyl 3-((6-bromo-3-methylpyridin-2-yl)carbamoyl)-5-(pyrrolidin-1-ylmethyl)-2-azabicyclo[3.1.0]hexane-2-carboxylate (scheme 8-38 compound S4, 15 mg, 0.03 mmol) in dioxane (1 mL) was added HCl/dioxane (1 mL) at 0° C. The reaction was stirred at room temperature for 1 h. The mixture was concentrated to afford scheme 8-38 compound S5 (17 mg, yield 100%) as a brown solid, which was directly used in the next reaction without further purification. LC/MS (ESI) m/z: 379 (M+H)$^+$.

Step 5: (3S)-2-(2-(3-Acetyl-5-(2-methylpyrimidin-5-yl)-1H-indazol-1-yl)acetyl)-N-(6-bromo-3-methylpyridin-2-yl)-5-(pyrrolidin-1-ylmethyl)-2-azabicyclo[3.1.0]hexane-3-carboxamide (634)

To a mixture of 2-(3-acetyl-5-(1H-benzo[d]imidazol-2-yl)-1H-indazol-1-yl)acetic acid (scheme 8-38 compound S6, 17 mg, 0.03 mmol), 2-(3-acetyl-5-(2-methylpyrimidin-5-yl)-1H-indazol-1-yl)acetic acid (scheme 8-38 compound S5, 9.3 mg, 0.03 mmol) and HATU (22.8 mg, 0.06 mmol) in DMF (1 mL) was added DIPEA (0.09 mL, 0.02 mmol) at 0° C. The reaction mixture was stirred at room temperature overnight. The mixture was diluted with EtOAc and washed with 10% aqueous LiCl solution and brine. The organic layer was dried over anhydrous Na$_2$SO$_4$, filtered and concentrated. The residue was purified by preparative HPLC to afford compound 634 (2.2 mg, 10.9% yield) as a white solid. $^1$H-NMR (400 MHz, CD$_3$OD) δ 9.02 (s, 2H), 8.56 (s, 1H), 7.83 (d, J=3.7 Hz, 2H), 7.58 (d, J=7.8 Hz, 1H), 7.41 (d, J=8.0 Hz, 1H), 7.23 (s, 1H), 5.86 (d, J=17.3 Hz, 1H), 5.70 (s, 1H), 5.34 (t, J=4.7 Hz, 3H), 2.76 (s, 3H), 2.70 (d, J=3.3 Hz, 3H), 2.23-2.17 (m, 3H), 2.13 (s, 5H), 2.03 (s, 4H), 1.60 (s, 4H), 0.91 (s, 2H). LC/MS (ESI) m/z: 671 (M+H)$^+$.

Scheme 8-39

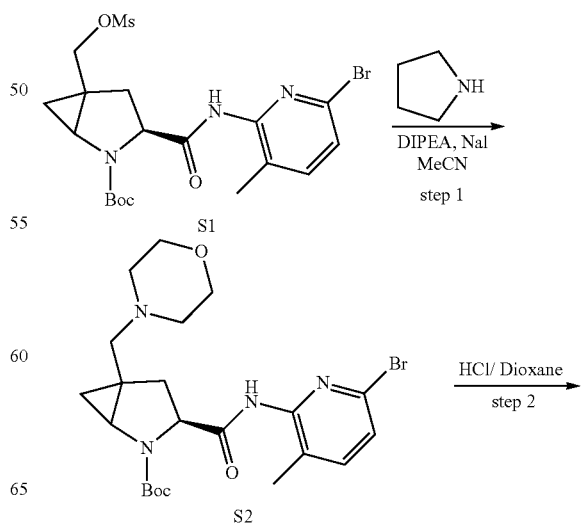

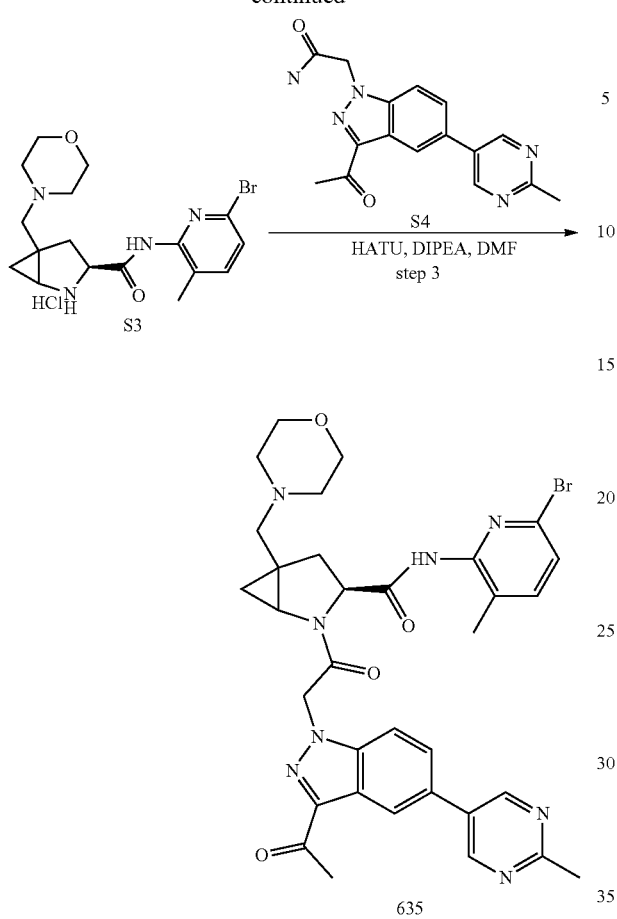

(3S)-2-(2-(3-Acetyl-5-(2-methylpyrimidin-5-yl)-1H-indazol-1-yl)acetyl)-N-(6-bromo-3-methylpyridin-2-yl)-5-(morpholinomethyl)-2-azabicyclo[3.1.0]hexane-3-carboxamide (635)

Compound 635 was prepared according to the procedure for example 8-38 from appropriate starting materials. $^1$H NMR (400 MHz, MeOD) δ 9.00 (s, 2H), 8.54 (s, 1H), 7.83 (t, J=8.0, 2H), 7.53 (d, J=8.0 Hz, 1H), 7.36 (d, J=8.0 Hz, 1H), 5.83 (d, J=17.2 Hz, 1H), 5.63 (d, J=17.2 Hz, 1H), 3.74 (t, J=4.8 Hz, 4H), 3.65 (dd, J=2.4, 2.4 Hz, 1H), 3.35 (s, 1H), 2.87 (s, J=8.8 Hz, 1H), 2.75 (s, 3H), 2.70 (s, 3H), 2.55 (d, J=17.6 Hz, 4H), 2.44 (d, J=12.8 Hz, 1H), 2.35-2.27 (m, 1H), 2.20 (t, J=3.6 Hz, 1H), 2.06 (d, J=17.6 Hz, 3H), 1.62-1.60 (m, 1H), 1.03 (t, J=5.6 Hz, 1H), 0.89 (d, J=6.0 Hz, 1H). LC/MS (ESI) m/z: 687 (M+H)$^+$.

Scheme 8-40

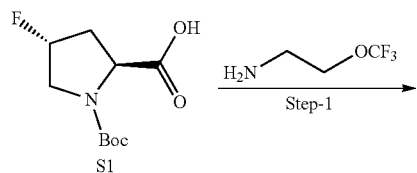

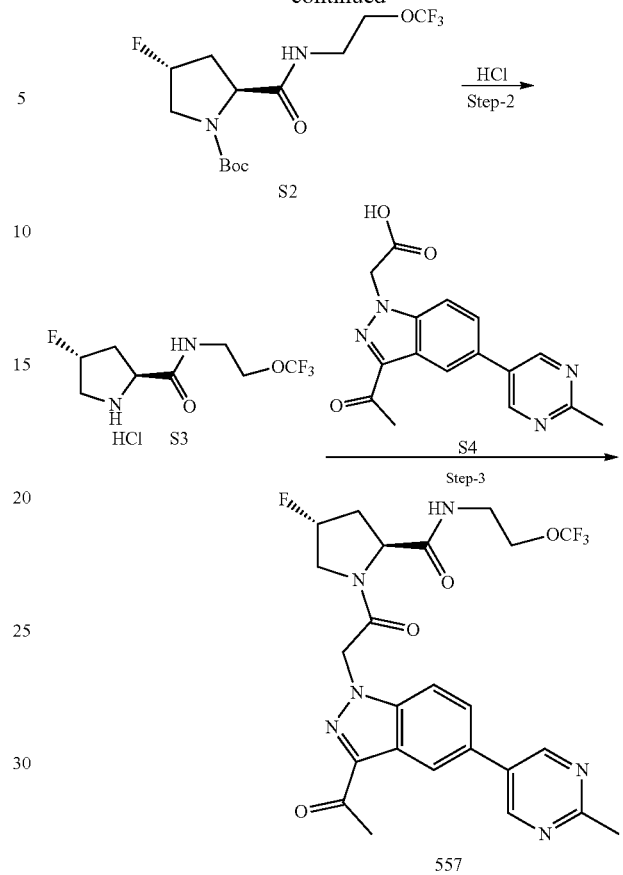

Step 1: tert-Butyl (2S,4R)-4-fluoro-2-((2-(trifluoromethoxy)ethyl)carbamoyl)pyrrolidine-1-carboxylate (S2)

To a stirred solution of (2S,4R)-1-(tert-butoxycarbonyl)-4-fluoropyrrolidine-2-carboxylic acid (scheme 8-40 compound S1, 160 mg, 0.7 mmole) in 10 mL of DMF was added 2-(trifluoromethoxy)ethan-1-amine (116 mg, 1 equiv), DIEA (0.4 mL, 3 equiv). This was followed by addition of HATU (319 mg, 1.2 equiv) under nitrogen atmosphere. The reaction mixture was stirred at room temperature. Water (10 mL) and ethyl acetate (15 mL) were added to the reaction mixture, layers were separated and the aqueous layer was extracted with EtOAc (1×10 mL). The combined organic layer was washed with 1N HCl (10 mL), saturated NaHCO$_3$ (10 mL), and brine (10 mL). Combined organic layers were dried over Na$_2$SO$_4$, concentrated and 250 mg (quantitative yield) of 557 was obtained.

Step-2: (2S,4R)-4-Fluoro-N-(2-(trifluoromethoxy)ethyl)pyrrolidine-2-carboxamide (S3)

To tert-butyl (2S,4R)-4-fluoro-2-((2-(trifluoromethoxy)ethyl)carbamoyl)pyrrolidine-1-carboxylate (scheme 8-40 compound S2) was added 10 ml of 4N HCl in dioxane. The resulting solution was stirred at room temperature for 6 h. The reaction mixture was then concentrated in vacuo and carried forward without further purification.

Step-3: (2S,4R)-1-(2-(3-Acetyl-5-(2-methylpyrimidin-5-yl)-1H-indazol-1-yl)acetyl)-4-fluoro-N-(2-(trifluoromethoxy)ethyl)pyrrolidine-2-carboxamide (557)

To a stirred solution of (2S,4R)-4-fluoro-N-(2-(trifluoromethoxy)ethyl)pyrrolidine-2-carboxamide (hydrochloride salt, scheme 8-40 compound S3, 118 mg) in DMF (10 mL) was added 2-(3-acetyl-5-(2-methylpyrimidin-5-yl)-1H-indazol-1-yl)acetic acid (scheme 8-40 compound S4, 119 mg, 1.0 equiv.), HATU (173 mg, 1.2 equiv), and DIEA (0.4 mL, 5.0 equiv). The reaction was stirred at room temperature and then diluted with EtOAC (15 mL), and water (10 mL). The organic layer was washed with brine (3×15 mL), dried over $Na_2SO_4$ and concentrated in vacuo. The resulting oil was purified by silica gel column chromatography (silica gel, eluted with 10% MeOH in DCM gradient) to yield 109 mg (54%) of compound 557. 1H NMR (400 MHz, DMSO-$d_6$): (major rotamer) δ 1.96-2.14 (m, 1H), 2.53-2.61 (m, 1H), 2.65 (s, 3H), 2.69 (s, 3H), 3.23-3.32 (m, 2H), 3.95-4.05 (m, 3H), 4.15-4.26 (m, 1H), 4.40 (t, 1H, J=8.2 Hz), 5.43-5.83 (m, 3H), 7.76-7.90 (m, 2H), 8.45 (s, 1H), 9.06 (s, 2H); 19F NMR (376 MHz, DMSO-$d_6$): (major rotamer) δ −58.86 (3F), −176.24 (1F). LC (method A): $t_R$=1.42 min. LC/MS (EI) m/z: [M+H]$^+$ 537.

Step 1: tert-Butyl (2S,4R)-2-((3,3-dimethylbutyl)carbamoyl)-4-fluoropyrrolidine-1-carboxylate (S2)

To a stirred solution of (2S,4R)-1-(tert-butoxycarbonyl)-4-fluoropyrrolidine-2-carboxylic acid (scheme 8-41 compound S1, 157 mg, 0.7 mmole) in 10 mL of DMF was added 3,3-dimethylbutan-1-amine (0.1 mL, 1 equiv) and DIEA (0.4 mL, 3 equiv). This was followed by addition of HATU (319 mg, 1.2 equiv) under nitrogen atmosphere. The reaction mixture was stirred at room temperature. Water (10 mL) and ethyl acetate (15 mL) were added to the reaction mixture, layers were separated and the aqueous layer was extracted with EtOAc (1×10 mL). The combined organic layer was washed with 1N HCl (10 mL), saturated $NaHCO_3$ (10 mL) and brine (10 mL). Combined organic layers were dried over $Na_2SO_4$ and concentrated to yield 225 mg (quantitative yield) of the title compound.

Step-2: (2S,4R)—N-(3,3-Dimethylbutyl)-4-fluoropyrrolidine-2-carboxamide (S3)

To tert-butyl (2S,4R)-2-((3,3-dimethylbutyl)carbamoyl)-4-fluoropyrrolidine-1-carboxylate (scheme 8-41 compound S2) was added 10 ml of 4N HCl in Dioxane. The resulting solution was stirred at room temperature for 6 h. Then, the reaction mixture was concentrated in vacuo and used for the following step.

Step-3: (2S,4R)-1-(2-(3-Acetyl-5-(2-methylpyrimidin-5-yl)-1H-indazol-1-yl)acetyl)-N-(3,3-dimethylbutyl)-4-fluoropyrrolidine-2-carboxamide (558)

To a stirred solution of (2S,4R)—N-(3,3-dimethylbutyl)-4-fluoropyrrolidine-2-carboxamide (scheme 8-41 compound S3, hydrochloride salt, 125 mg) in DMF (10 mL) was added 2-(3-acetyl-5-(2-methylpyrimidin-5-yl)-1H-indazol-1-yl)acetic acid (scheme 8-41 compound S4, 155 mg, 1.0 equiv.), HATU (228 mg, 1.2 equiv), and DIEA (0.5 mL, 5.0 equiv). The reaction was stirred at room temperature for 2 h then diluted with EtOAC (15 mL) and water (10 mL). The organic layer was washed with brine (3×15 mL), dried over $Na_2SO_4$ and concentrated in vacuo. The resulting oil was purified by silica gel column chromatography (silica gel, eluted with 10% MeOH in DCM gradient) to yield 125 mg (49%) of compound 558. 1H NMR (400 MHz, DMSO-$d_6$): (major rotamer) δ 0.93 (s, 9H), 1.31-1.38 (m, 2H), 2.03-2.22 (m, 1H), 2.41-2.55 (m, 1H), 2.74 (s, 3H), 2.78 (s, 3H), 2.97-3.21 (m, 2H), 3.95-4.09 (m, 1H), 4.21-4.32 (m, 1H), 4.41 (t, 1H, J=8.2 Hz), 5.51-5.92 (m, 3H), 7.89-8.04 (m, 2H), 8.53 (s, 1H), 9.15 (s, 2H); 19F NMR (376 MHz, DMSO-$d_6$): (major rotamer) −176.13 (1F). LC (method A): tR=1.69 min. LC/MS (EI) m/z: [M+H]+ 509.

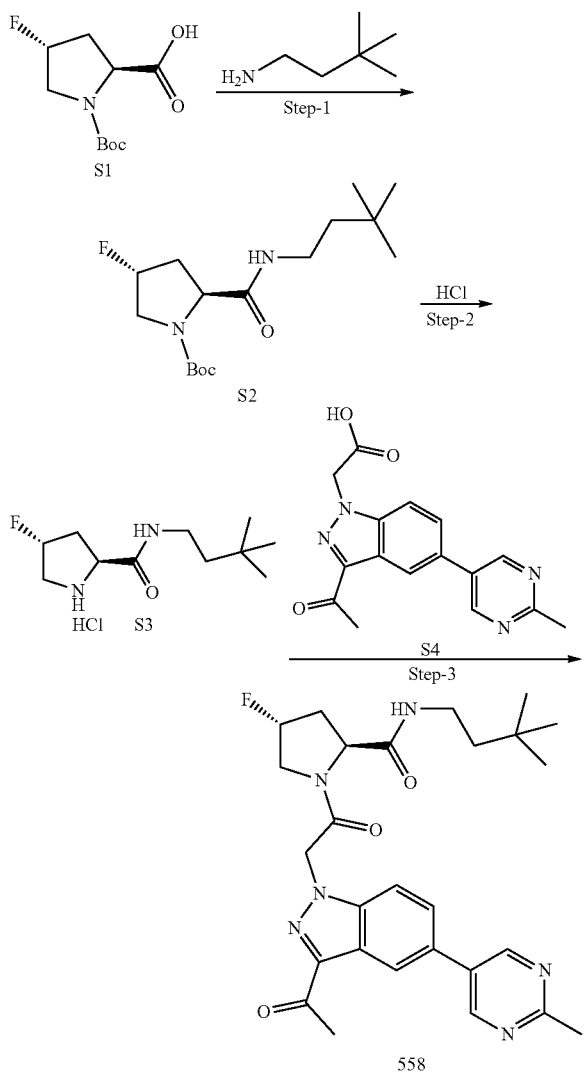

Scheme 8-41

Scheme 8-42

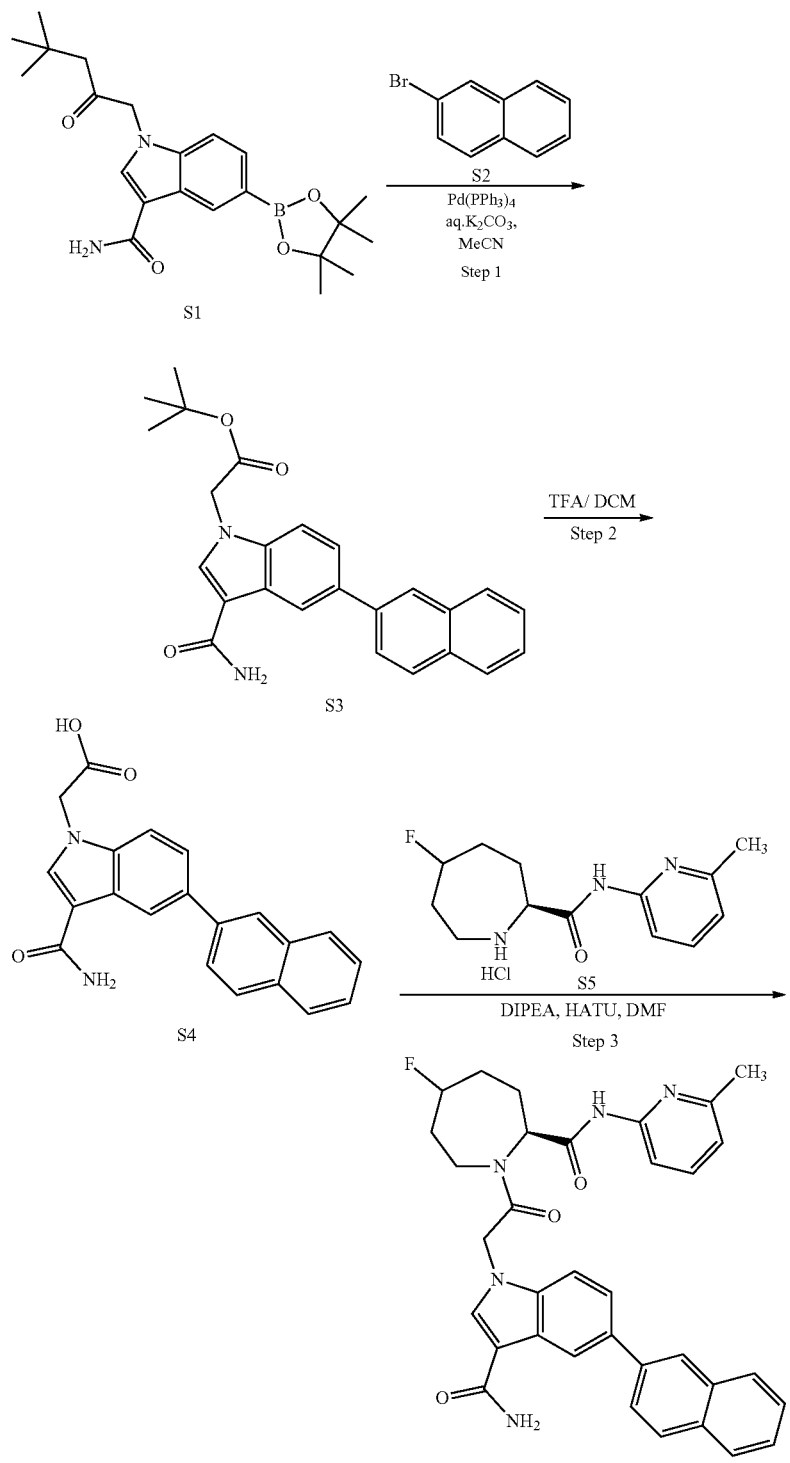

Step 1: tert-Butyl 2-(3-carbamoyl-5-(naphthalen-2-yl)-1H-indol-1-yl)acetate (S3)

To a mixture of scheme 8-42 compound S1 (200 mg, 0.5 mmol) and scheme 8-42 compound S2 (123 mg, 0.6 mmol) in CH$_3$CN (5 mL) and water (2 mL) was added K$_2$CO$_3$ (206 mg, 1.5 mmol) and Pd(PPh$_3$)$_4$ (20 mg) at 0° C. The reaction was degassed under N$_2$ atmosphere three times and stirred at 80° C. under N$_2$ atmosphere for 8 h. The mixture was diluted with EtOAc and washed with water and brine. The organic layer was dried over anhydrous Na$_2$SO$_4$, filtered and concentrated. The residue was purified by silica gel column chromatography (dichloromethane:methanol=100:1) to afford scheme 8-42 compound S3 (104 mg, 52.0% yield) as a white solid. LC/MS (ESI) m/z: 401 (M+1)+.

Step 2: 2-(3-Carbamoyl-5-(naphthalen-2-yl)-1H-indol-1-yl)acetic acid (S4)

TFA (0.5 mL) was added dropwise to a solution of scheme 8-42 compound S3 (52 mg, 0.13 mmol) in DCM (1 mL) at 0° C. The reaction was stirred at room temperature for 3 h. The resulting mixture was concentrated under vacuum to afford compound S4 (60 mg, 100% yield) as a brown solid. LC/MS (ESI) m/z: 345 (M+1)+.

Step 3: 1-(2-((2S)-5-Fluoro-2-((6-methylpyridin-2-yl)carbamoyl)azepan-1-yl)-2-oxoethyl)-5-(naphthalen-2-yl)-1H-indole-3-carboxamide (S6)

To a mixture of scheme 8-42 compound S4 (60 mg, 0.13 mmol) and scheme 8-42 compound S5 (33 mg, 0.13 mmol) in DMF (1 mL) was added DIPEA (67 mg, 0.52 mmol) and HATU (99 mg, 0.26 mmol) at 0° C. The reaction was stirred at room temperature for 16 h. The mixture was diluted with EtOAc and washed with 10% aqueous LiCl solution and brine successively. The organic layer was dried over anhydrous Na$_2$SO$_4$, filtered and concentrated to dryness. The residue was purified by prep-TLC (DCM/MeOH=20:1) to afford 594 (6 mg, 8.0% yield) as a white solid. $^1$H NMR (400 MHz, MeOD) δ: 8.53 (d, J=1.3 Hz, 1H), 8.12 (s, 1H), 7.96-7.89 (m, 3H), 7.85 (dd, J=8.5, 1.9 Hz, 3H), 7.72-7.58 (m, 2H), 7.48 (dd, J=11.1, 5.1 Hz, 3H), 6.96 (d, J=7.5 Hz, 1H), 5.41 (dd, J=55.4, 17.2 Hz, 2H), 4.92 (d, J=6.6 Hz, 1H), 4.03 (d, J=16.4 Hz, 1H), 3.81-3.62 (m, 2H), 3.25-3.20 (m, 1H), 2.41 (d, J=5.2 Hz, 3H), 2.37-2.13 (m, 2H), 1.97 (t, J=11.1 Hz, 2H), 1.79 (d, J=9.8 Hz, 1H). LC/MS (ESI) m/z: 578 (M+1)+.

Scheme 8-43

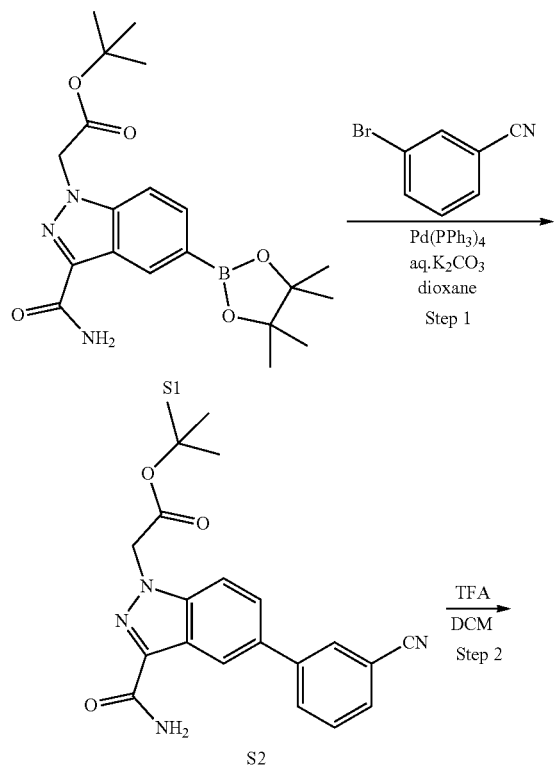

Step 1: tert-Butyl 2-(3-carbamoyl-5-(4,4,5,5-tetramethyl-1,3,2-dioxaborolan-2-yl)-1H-indazol-1-yl)acetate (S2)

To a mixture of scheme 8-43 compound S1 (200 mg, 0.498 mmol), 3-bromobenzonitrile (100 mg, 0.548 mmol) and potassium carbonate (147 mg, 1.06 mmol) in dioxane (9 mL) and water (2 mL) was added tetrakis(triphenylphosphine)palladium (58 mg, 0.05 mmol). The reaction was degassed under N$_2$ atmosphere three times and stirred at 100° C. for 2 h under N$_2$ atmosphere. The mixture was diluted with EtOAc and washed with water and brine. The organic layer was dried over Na$_2$SO$_4$, filtered and concentrated to dryness. The residue was purified by silica gel column chromatography (eluted with Petroleum ether:Ethyl acetate=5:1 to 3:1) to afford scheme 8-43 compound S2 (140 mg, 74.8% yield) as a white solid. LC/MS (ESI) m/z: 377 (M+H)+.

Step 2: 2-(3-Carbamoyl-5-(3-cyanophenyl)-1H-indazol-1-yl)acetic Acid (S3)

To a solution of scheme 8-42 compound S2 (140 mg, 0.372 mmol) in DCM (2 mL) was added TFA (1 mL). The reaction was stirred at room temperature for 2 h. The mixture was concentrated to dryness to afford scheme 8-43 compound S3 (110 mg, 92.4% yield) as a white solid. LC/MS (ESI) m/z: 321 (M+H)+.

Step 3: 5-(3-Cyanophenyl)-1-(2-((2S)-5-fluoro-2-(6-methylpyridin-2-ylcarbamoyl)azepan-1-yl)-2-oxoethyl)-1H-indole-3-carboxamide (591)

1-(2-((2S)-5-fluoro-2-((6-methylpyridin-2-yl)carbamoyl)azepan-1-yl)-2-oxoethyl)-5-(5,6,7,8-tetrahydronaphthalen-2-yl)-1H-indole-3-carboxamide (591)

Compound 591 was prepared according to the procedure for the synthesis from example 8-46 from appropriate starting materials. $^1$H NMR (400 MHz, DMSO-$d_6$) δ: 10.44 (d, J=11.9 Hz, 1H), 8.41 (s, 1H), 8.12 (s, 1H), 8.06-7.94 (m, 2H), 7.77 (ddd, J=25.4, 18.1, 7.9 Hz, 2H), 7.62 (ddd, J=45.1, 25.2, 5.0 Hz, 3H), 6.94 (d, J=7.5 Hz, 1H), 5.57 (d, J=17.2 Hz, 1H), 5.13 (dd, J=71.9, 31.9 Hz, 2H), 4.79 (d, J=9.6 Hz, 1H), 3.96 (d, J=14.6 Hz, 1H), 3.69-3.58 (m, 1H), 2.51 (s, 3H), 2.39 (d, J=20.7 Hz, 2H), 2.17 (dd, J=44.9, 27.6 Hz, 4H), 1.65 (d, J=42.0 Hz, 2H). LC/MS (ESI) m/z: 553 (M+H)$^+$.

Scheme 8-45

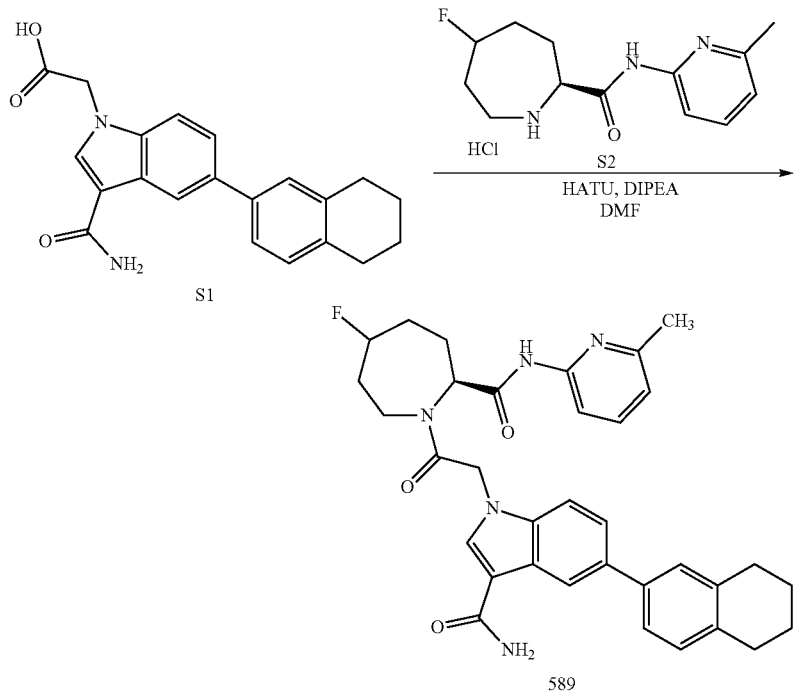

1-(2-((2S)-5-fluoro-2-((6-methylpyridin-2-yl)carbamoyl)azepan-1-yl)-2-oxoethyl)-5-(5,6,7,8-tetrahydronaphthalen-2-yl)-1H-indole-3-carboxamide (589)

Compound 589 was prepared according to the procedure for the synthesis from Example 8-46 from appropriate starting materials. $^1$H NMR (400 MHz, MeOD) δ: 8.32 (dd, J=1.8, 0.7 Hz, 1H), 7.91-7.78 (m, 2H), 7.64 (dt, J=25.8, 7.9 Hz, 1H), 7.46-7.25 (m, 4H), 7.07 (d, J=7.8 Hz, 1H), 6.98 (dd, J=25.4, 7.5 Hz, 1H), 5.38 (d, J=17.2 Hz, 1H), 5.19 (d, J=17.2 Hz, 1H), 5.08-4.89 (m, 1H), 3.96-3.74 (m, 2H), 2.80 (d, J=15.6 Hz, 4H), 2.46-2.19 (m, 6H), 2.11 (td, J=16.1, 15.0, 7.6 Hz, 1H), 1.90-1.60 (m, 6H). LC/MS (ESI) m/z: 582 (M+H)$^+$.

Scheme 8-46

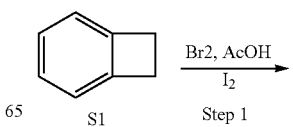

S1　　Step 1

-continued

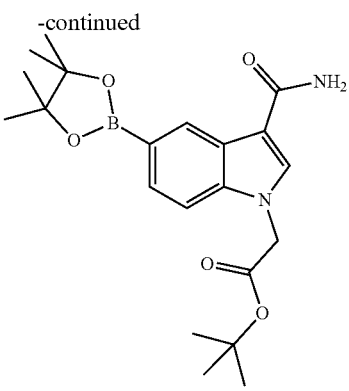

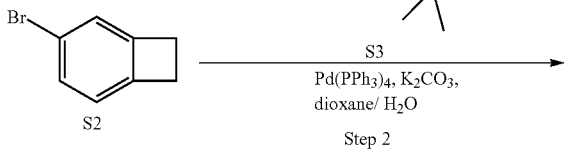

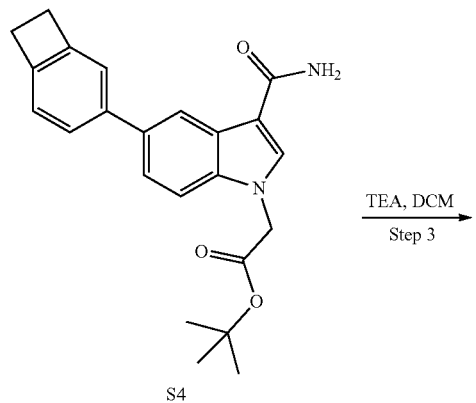

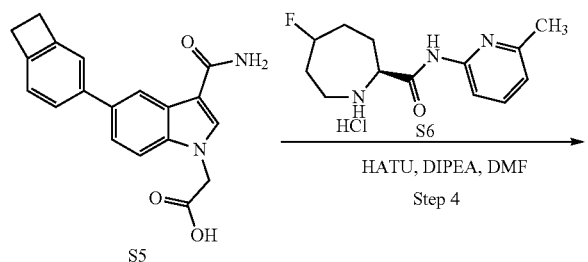

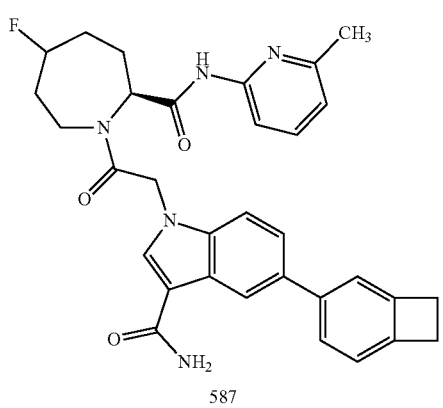 [SMILES: Cc1cccc(NC(=O)[C@@H]2CCC(F)CCN2C(=O)Cn2cc(C(N)=O)c3cc(-c4ccc5c(c4)CC5)ccc32)n1]

Step 1: 4-Bromo-1,2-dihydrocyclobutabenzene (S2)

Br$_2$ (1.10 g, 6.88 mmol) dropwise to a mixture of 1,2-dihydrocyclobutabenzene (scheme 8-46 compound S1, 650 mg, 6.25 mmol) and I$_2$ (14 mg, 0.056 mmol) in AcOH/H$_2$O (8 mL/0.4 mL) at 0° C. for 20 min. The reaction was stirred at room temperature overnight. The mixture was poured into water and extracted with petroleum ether (50 mL). The organic layer was washed with aqueous Na$_2$CO$_3$ solution and water, dried over anhydrous Na$_2$SO$_4$, and concentrated. The residue was purified by column chromatography on silica gel eluted with petroleum ether to afford scheme 8-46 compound S2 (490 mg, 51.1%) as a light yellow oil.

Step 2: tert-Butyl 2-(3-carbamoyl-5-(1,2-dihydrocyclobutabenzen-4-yl)-1H-indol-1-yl) acetate (S4)

To a solution of 4-bromo-1,2-dihydrocyclobutabenzene (scheme 8-46 compound S2, 490 mg, 2.68 mmol) in dioxane/H$_2$O (10 mL, v/v=9:1) was added scheme 8-43 compound S3 (1.07 g, 2.68 mmol), K$_2$CO$_3$ (924 mg, 6.69 mmol), and tetrakis(triphenylphosphine) palladium (154 mg, 0.13 mmol) under N$_2$ atmosphere. The reaction was stirred at 80° C. overnight. The mixture was diluted with EtOAc and washed with water and brine. The organic layer was dried over anhydrous Na$_2$SO$_4$ and concentrated. The residue was purified by column chromatography on silica gel eluted with DCM/MeOH (100:1 to 50:1) to afford scheme 8-43 compound S4 (700 mg, 69.5% yield) as a light yellow solid. LC/MS (ESI) m/z: 377 (M+H)$^+$.

Step 3: 2-(3-Carbamoyl-5-(1,2-dihydrocyclobutabenzen-4-yl)-1H-indol-1-yl) acetic acid (S5)

To a solution of tert-butyl 2-(3-carbamoyl-5-(1,2-dihydrocyclobutabenzen-4-yl)-1H-indol-1-yl) acetate (scheme 8-46 compound S4, 340 mg, 0.91 mmol) in DCM (2 mL) was added TFA (2 mL). The reaction was stirred at room temperature for 2 h. The mixture was concentrated to afford scheme 8-46 compound S5 (170 mg, 58.8% yield) as a yellow solid, which was used directly in the next step. LC/MS (ESI) m/z: 321 (M+H)$^+$.

Step 4: 5-(1,2-Dihydrocyclobutabenzen-4-yl)-1-(2-((2S)-5-fluoro-2-(6-methylpyridin-2-ylcarbamoyl) azepan-1-yl)-2-oxoethyl)-1H-indole-3-carboxamide (587)

Compound 587 was prepared according the procedure for according to the procedure from Example 8-46 from appropriate starting materials. $^1$H NMR (400 MHz, DMSO-d$_6$) δ:10.42 (s, 1H), 8.30 (d, J=1.2 Hz, 1H), 8.00-7.92 (m, 1H), 7.81 (d, J=8.4 Hz, 1H), 7.62 (t, J=8.0, Hz, 1H), 7.56-7.22 (m, 5H), 7.15 (d, J=7.6 Hz, 1H), 6.98 (d, J=7.6 Hz, 2H), 5.47 (d, J=17.2 Hz, 1H), 5.26 (d, J=17.2 Hz, 1H), 4.88-4.62 (m, 2H), 3.97 (d, J=16.2 Hz, 1H), 3.68-3.43 (m, 1H), 3.18 (d, J=2.8 Hz, 4H), 2.39 (s, 3H), 2.33-2.08 (m, 3H), 2.03-1.75 (m, 2H), 1.68-1.50 (m, 1H); LC/MS (ESI) m/z: 554 (M+H)$^+$.

Scheme 8-47

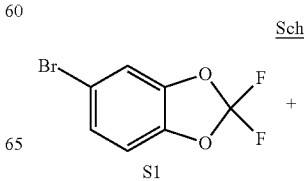

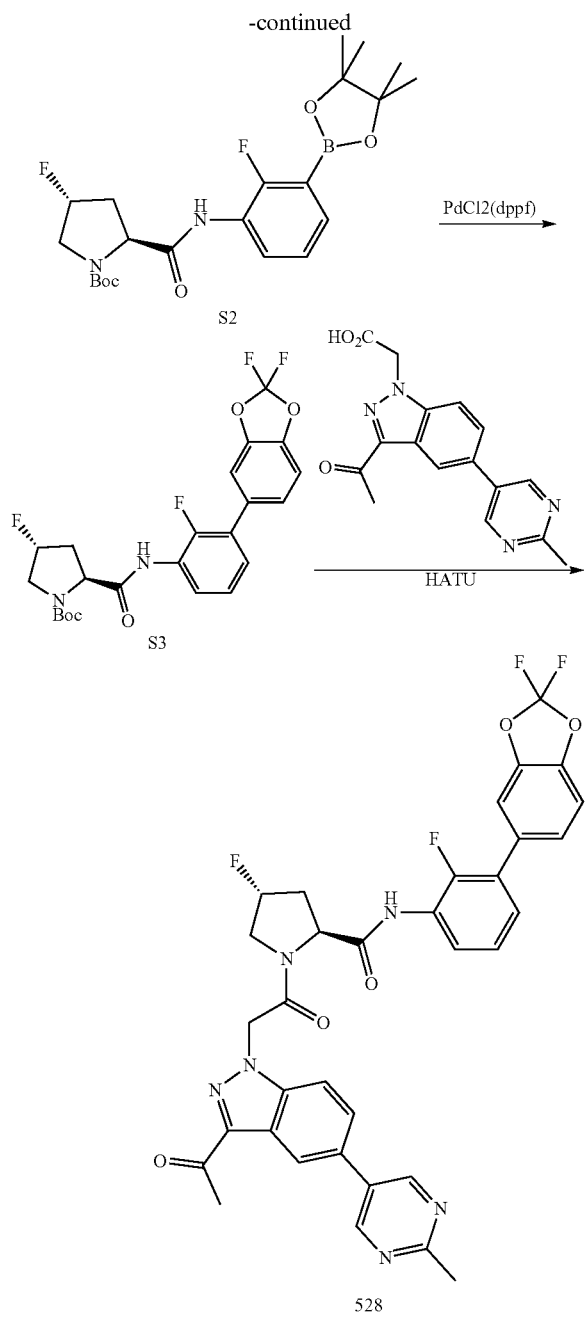

residue was purified by silica gel column chromatography (0-1.5% MeOH in CH$_2$Cl$_2$) to afford the desired product.

(2S,4R)-1-(2-(3-Acetyl-5-(2-methylpyrimidin-5-yl)-1H-indazol-1-yl)acetyl)-N-(3-(2,2-difluorobenzo[d][1,3]dioxol-5-yl)-2-fluorophenyl)-4-fluoropyrrolidine-2-carboxamide (528)

tert-Butyl (2S,4R)-2-((3-(2,2-difluorobenzo[d][1,3]dioxol-5-yl)-2-fluorophenyl)carbamoyl)-4-fluoropyrrolidine-1-carboxylate (scheme 8-46 compound S3, 60 mg) was dissolved in CH$_2$Cl$_2$ (1 mL) and an equal volume of TFA was added. The mixture was stirred for 30 min at room temperature. Then the volatiles were removed under reduced pressure. The residue was dissolved in DMF (1.0 mL) and $^i$Pr$_2$NEt (160 μL) was added, followed by the sequential addition of 2-(3-acetyl-5-(2-methylpyrimidin-5-yl)-1H-indazol-1-yl)acetic acid (38 mg) and HATU (57 mg) slowly at 5° C. The reaction mixture was then stirred for 30 min at room temperature and poured into water (10 mL). The solid was isolated by filtration, washed with water and dried in vacuo. The solid was then purified by silica gel column chromatography (eluent: 0-2.5% MeOH in CH$_2$Cl$_2$) to afford compound 528. $^1$H NMR (400 MHz, CD$_3$OD) (major rotamer): δ 2.29-2.46 (m, 1H), 2.67 (s, 3H), 2.71-2.26 (m, 1H), 2.74 (s, 3), 3.99-4.12 (m, 1H), 4.27 (dd, J=20.4, 12 Hz, 1H), 4.87 (t, J=8.4 Hz, 1H), 5.53 (d, J=52 Hz, 1H), 5.53 (d, J=16.8 Hz, 1H), 5.64 (d, J=16.8 Hz, 1H), 7.09-7.37 (m, 5H), 7.62 (d, J=8.8 Hz, 1H), 7.70 (d, J=8.8 Hz, 1H), 7.81 (t, J=7.6 Hz, 1H), 8.44 (s, 1H), 8.89 (s, 2H). $^{19}$F NMR (376 MHz, CD$_3$OD) (major rotamer): δ −52.3, −132.1, −178.5.

Scheme 8-48

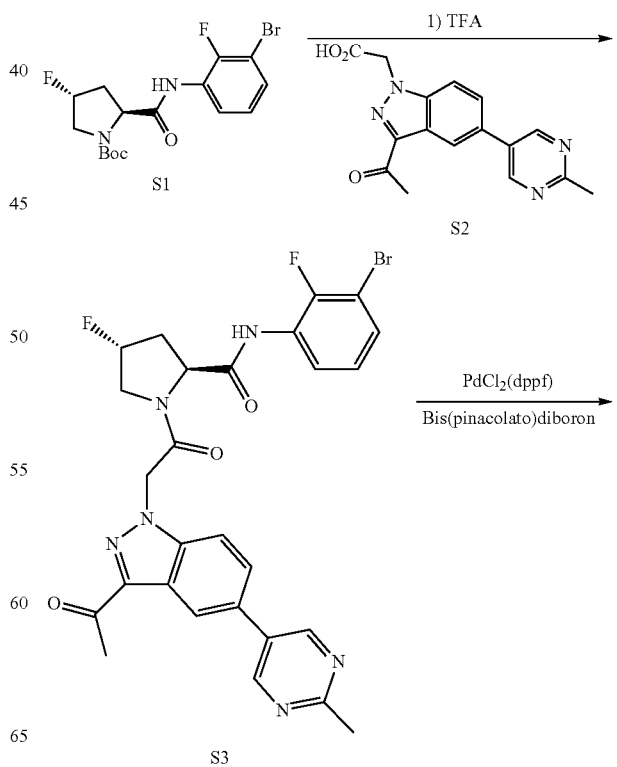

tert-Butyl(2S,4R)-2-((3-(2,2-difluorobenzo[d][1,3]dioxol-5-yl)-2-fluorophenyl)carbamoyl)-4-fluoropyrrolidine-1-carboxylate (S3)

tert-Butyl (2S,4R)-4-fluoro-2-((2-fluoro-3-(4,4,5,5-tetramethyl-1,3,2-dioxaborolan-2-yl)phenyl)carbamoyl)pyrrolidine-1-carboxylate (scheme 8-47 compound S2, 0.100 g), 5-bromo-2,2-difluorobenzo[d][1,3]dioxole (scheme 8-46 compound S1, 0.05 g), Pd(PPh$_3$)$_4$ and sodium carbonate were mixed in a pressure tube under argon. To this mixture, 4 mL of dioxane and 1 mL of water were added. The mixture was bubbled with argon for 5 min and the vial stoppered and subjected to microwave irradiation at 100° C. for 45 min. The volatiles were removed under reduced pressure and the

263

-continued

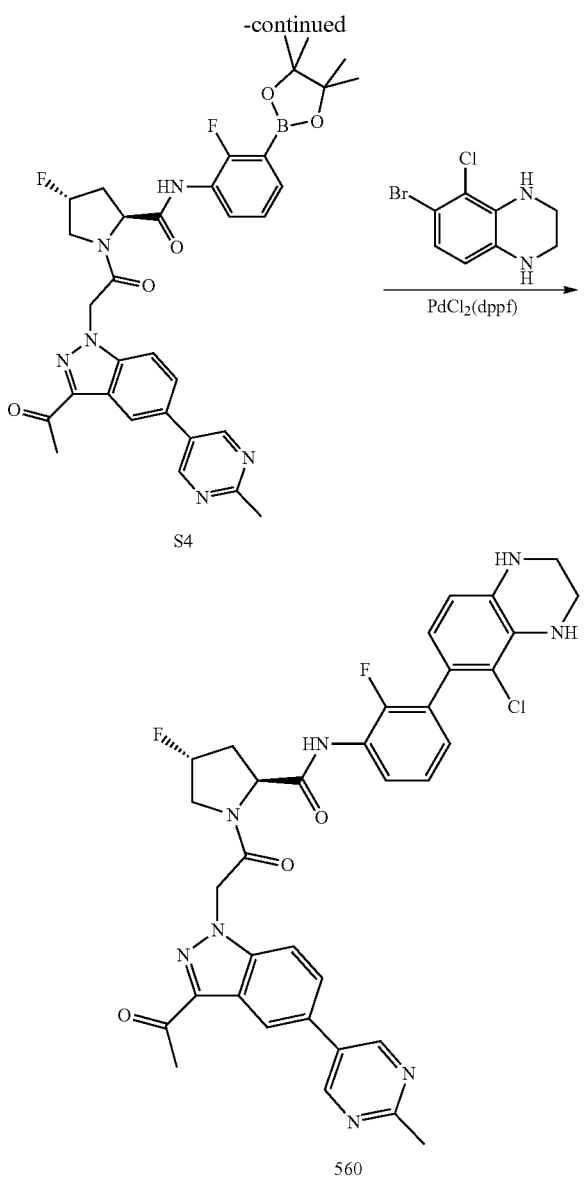

(2S,4R)-1-(2-(3-Acetyl-5-(2-methylpyrimidin-5-yl)-1H-indazol-1-yl)acetyl)-N-(3-bromo-2-fluorophenyl)-4-fluoropyrrolidine-2-carboxamide (S3)

tert-Butyl (2S,4R)-2-((3-bromo-2-fluorophenyl)carbamoyl)-4-fluoropyrrolidine-1-carboxylate (scheme 8-48 compound S1, 0.653 g) was dissolved in CH₂Cl₂ (6 mL) and an equal volume of TFA was added. The mixture was stirred for 30 min at room temperature. Then the volatiles were removed under reduced pressure. The residue was dissolved in DMF (5 mL) and $^i$Pr₂NEt (1.4 mL) was added, followed by the sequential addition 2-(3-acetyl-5-(2-methylpyrimidin-5-yl)-1H-indazol-1-yl)acetic acid (scheme 8-48 compound S2, 0.450 g) and HATU (0.735 g, 1.2 equiv) slowly at 5° C. The reaction mixture was then stirred for 30 min at room temperature, poured into water (10 mL) and the solid was isolated by filtration, washed with water and dried in vacuo. The solid was then purified by silica gel column chromatography (eluent: 0-2.5% MeOH in CH₂Cl₂) to get a white solid, scheme 8-48 compound S3.

264

(2S,4R)-1-(2-(3-Acetyl-5-(2-methylpyrimidin-5-yl)-1H-indazol-1-yl)acetyl)-4-fluoro-N-(2-fluoro-3-(4,4,5,5-tetramethyl-1,3,2-dioxaborolan-2-yl)phenyl)pyrrolidine-2-carboxamide (S4)

(2S,4R)-1-(2-(3-Acetyl-5-(2-methylpyrimidin-5-yl)-1H-indazol-1-yl)acetyl)-N-(3-bromo-2-fluorophenyl)-4-fluoro-pyrrolidine-2-carboxamide (scheme 8-48 compound S3, 0.82 g), bis(pinacolato)diboron (0.875 g), Pd(dppf)Cl₂ (0.225 g) and potassium acetate (0.406 g) were taken up in a pressure tube under argon. To this mixture, 20 mL of dioxane was added. The mixture was bubbled with argon for 5 min and the vial stoppered and heated at 90° C. overnight. The reaction mixture was filtered through Celite and the filtrate was concentrated under reduced pressure. The residue was purified by silica gel column chromatography (0-5% MeOH in CH₂Cl₂) to afford the desired product.

(2S,4R)-1-(2-(3-Acetyl-5-(2-methylpyrimidin-5-yl)-1H-indazol-1-yl)acetyl)-N-(3-(5-chloro-1,2,3,4-tetrahydroquinoxalin-6-yl)-2-fluorophenyl)-4-fluoropyrrolidine-2-carboxamide (560)

(2S,4R)-1-(2-(3-Acetyl-5-(2-methylpyrimidin-5-yl)-1H-indazol-1-yl)acetyl)-4-fluoro-N-(2-fluoro-3-(4,4,5,5-tetramethyl-1,3,2-dioxaborolan-2-yl)phenyl)pyrrolidine-2-carboxamide (scheme 8-48 compound S4, 0.196 g), 6-bromo-5-chloro-1,2,3,4-tetrahydroquinoxaline (0.05 g), Pd(dppf)Cl₂ (33 mg) and potassium carbonate (0.140 g) were taken in a pressure tube under argon. To this mixture, 4 mL of dioxane and 1 mL of water were added. The mixture was bubbled with argon for 5 min and the vial stoppered subjected to microwave irradiation at 100° C. for 45 min. The volatiles were removed under reduced pressure and the residue was purified by silica gel column chromatography (0-3% MeOH in CH₂Cl₂) to afford the desired product. $^1$H NMR (400 MHz, DMSO) (major rotamer) δ 2.04-2.28 (m, 1H), 2.50-2.57 (m, 1H), 2.57 (s, 3H), 2.61 (s, 3H), 3.12-3.18 (m, 2H), 3.29-3.32 (m, 2H), 3.88-3.99 (m, 1H), 4.11-4.22 (m, 1H), 4.71 (t, J=8.4 Hz, 1H), 5.21 (s, 1H), 5.42-5.79 (m, 3H), 6.22 (d, J=8.0 Hz, 1H), 6.32 (d, J=7.8 Hz, 1H), 6.86 (t, J=7.1 Hz, 1H), 7.01 (t, J=6.4 Hz, 1H), 7.67-7.78 (m, 3H), 8.36 (s, 1H), 8.96 (s, 2H), 9.80 (s, 1H). $^{19}$F NMR (376 MHz, DMSO) (major rotamer): δ −126.5, −175.9.

Example 9. Synthesis of Aryl, Heteroaryl, and Heterocyclic Compounds of Formula I, Formula I' and Formula I''

Scheme 9-1

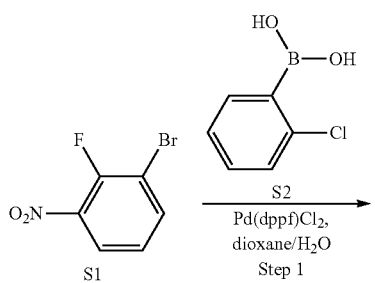

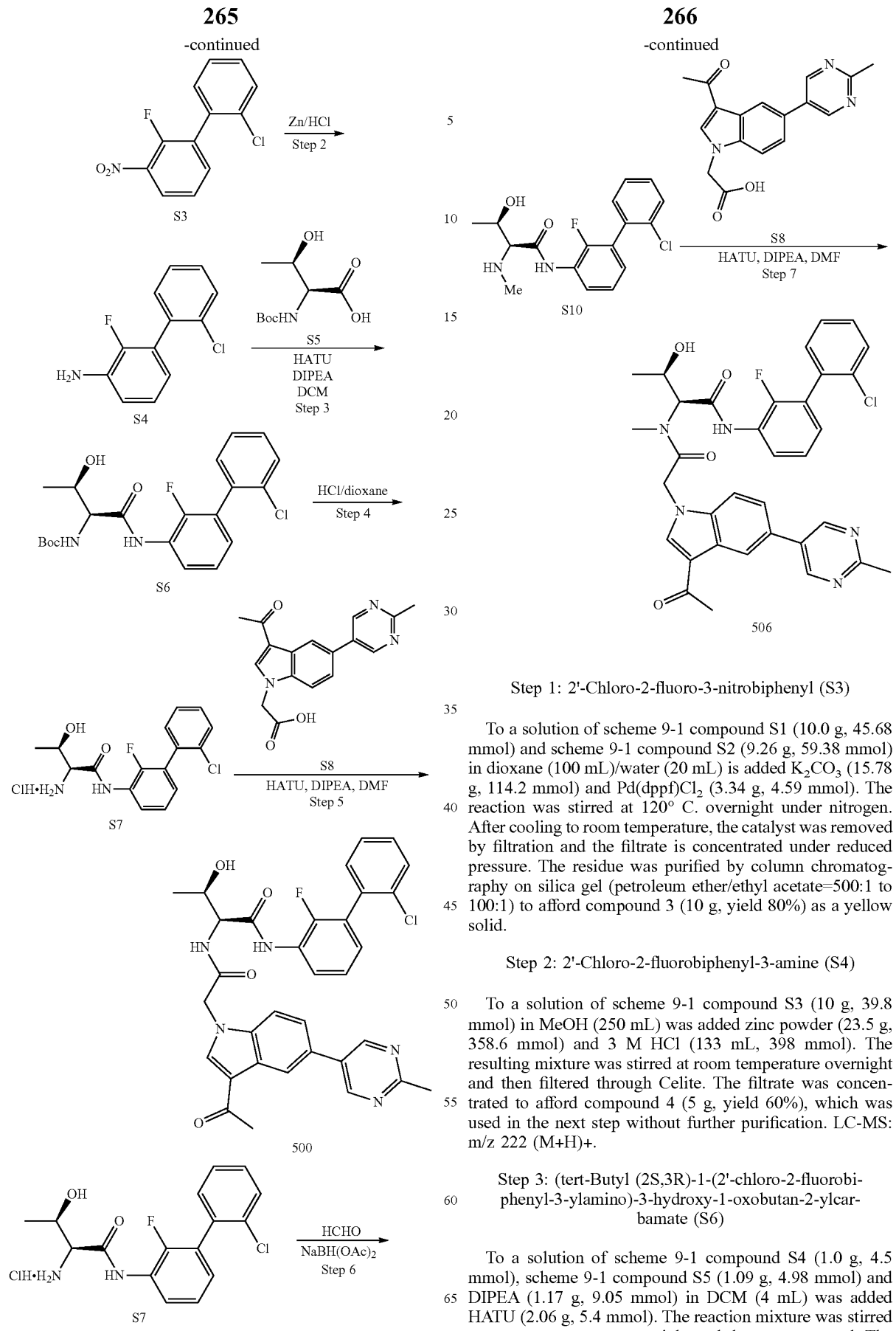

Step 1: 2'-Chloro-2-fluoro-3-nitrobiphenyl (S3)

To a solution of scheme 9-1 compound S1 (10.0 g, 45.68 mmol) and scheme 9-1 compound S2 (9.26 g, 59.38 mmol) in dioxane (100 mL)/water (20 mL) is added $K_2CO_3$ (15.78 g, 114.2 mmol) and Pd(dppf)Cl$_2$ (3.34 g, 4.59 mmol). The reaction was stirred at 120° C. overnight under nitrogen. After cooling to room temperature, the catalyst was removed by filtration and the filtrate is concentrated under reduced pressure. The residue was purified by column chromatography on silica gel (petroleum ether/ethyl acetate=500:1 to 100:1) to afford compound 3 (10 g, yield 80%) as a yellow solid.

Step 2: 2'-Chloro-2-fluorobiphenyl-3-amine (S4)

To a solution of scheme 9-1 compound S3 (10 g, 39.8 mmol) in MeOH (250 mL) was added zinc powder (23.5 g, 358.6 mmol) and 3 M HCl (133 mL, 398 mmol). The resulting mixture was stirred at room temperature overnight and then filtered through Celite. The filtrate was concentrated to afford compound 4 (5 g, yield 60%), which was used in the next step without further purification. LC-MS: m/z 222 (M+H)+.

Step 3: (tert-Butyl (2S,3R)-1-(2'-chloro-2-fluorobiphenyl-3-ylamino)-3-hydroxy-1-oxobutan-2-ylcarbamate (S6)

To a solution of scheme 9-1 compound S4 (1.0 g, 4.5 mmol), scheme 9-1 compound S5 (1.09 g, 4.98 mmol) and DIPEA (1.17 g, 9.05 mmol) in DCM (4 mL) was added HATU (2.06 g, 5.4 mmol). The reaction mixture was stirred at room temperature overnight and then concentrated. The residue is purified by preparative HPLC (acidic condition, using $CH_3CN/H_2O$ as eluent) to afford compound 6 (0.5 g, yield 30%) as a white solid.

Step 4: (2S,3R)-2-Amino-N-(2'-chloro-2-fluorobiphenyl-3-yl)-3-hydroxybutanamide (S7)

A mixture of scheme 9-1 compound S6 (840 mg, 1.99 mmol) and HCl/dioxane (40 mL) was stirred at room temperature overnight, and then concentrated to afford the crude compound 7 (700 mg), which was used in the next step without further purification. LC-MS: m/z 323 (M+H)+.

Step 5: (2S,3R)-2-(2-(3-Acetyl-1H-indol-1-yl)acetamido)-N-(2'-chloro-2-fluorobiphenyl-3-yl)-3-hydroxybutanamide (500)

To a solution of scheme 9-1 compound S7 (80 mg, 0.25 mmol), scheme 9-1 compound S8 (92 mg, 0.29 mmol) and DIPEA (160 mg, 1.24 mmol) in DMF (3 mL) was added HATU (208 mg, 0.55 mmol). The reaction mixture was stirred at room temperature overnight and then concentrated. The residue was purified by preparative HPLC (acidic condition, using CH3CN/H2O as eluent) to afford scheme 9-1 compound 500 as a white solid (37 mg, yield 24%). LC-MS: m/z 614 (M+H)+. 1H-NMR: δ 9.83 (s, 1H), 8.97 (s, 2H), 8.62 (d, J=8.0 Hz, 1H), 8.44 (d, 2H), 8.01 (t, J=7.6 Hz, 1H), 7.65 (d, J=8.0 Hz, 1H), 7.59 (m, 2H), 7.54-7.36 (m, 3H), 7.27 (t, J=8.0 Hz, 1H), 7.11 (t, J=8.0 Hz, 1H), 5.14-5.25 (m, 3H), 4.57 (dd, J=31.2, 4.3 Hz, 1H), 4.16 (s, 1H), 2.68 (s, 3H), 2.47 (s, 3H), 1.15 (d, J=11.2 Hz, 3H).

Step 6: (2S,3R)—N-(2'-Chloro-2-fluorobiphenyl-3-yl)-3-hydroxy-2-(methylamino)butanamide (S10)

To a solution of scheme 9-1 compound S7 (0.35 g, 1.08 mmol) in $ClCH_2CH_2Cl$ (10 mL) was added $(CH_2O)_n$ (16.3 mg, 0.54 mmol). The resulting mixture was stirred at 80° C. overnight and concentrated under high vacuum. The residue was dissolved in methanol (5 mL) followed by the addition of $NaBH(OAc)_3$. The resulting mixture was stirred at room temperature overnight and then concentrated to afford the crude scheme 9-1 compound S10 (0.35 g), which was used in the next step without further purification.

Step 7: (2S,3R)-2-(2-(3-Acetyl-5-(2-methylpyrimidin-5-yl)-1H-indol-1-yl)-N-methylacetamido)-N-(2'-chloro-2-fluorobiphenyl-3-yl)-3-hydroxybutanamide (S11)

To a solution of scheme 9-1 compound S10 (170 mg, 0.50 mmol), scheme 9-1 compound S8 (187 mg, 0.61 mmol), and DIPEA (423 mg, 1.11 mmol) in DMF (3 mL) was added HATU (326 mg, 2.5 mmol). The reaction mixture is stirred at room temperature overnight and concentrated. The residue was purified by preparative HPLC (acidic condition, using CH3CN/H2O as eluent) to afford scheme 9-1 compound 506 as a white solid (5 mg, yield 2%). LC-MS: m/z 628 (M+H)+. 1H-NMR: δ 8.83 (s, 2H), 8.49 (s, 2H), 8.09 (t, J=6.4 Hz, 1H), 7.78 (s, 1H), 7.41 (d, J=7.6 Hz, 1H), 7.29-7.21 (m, 5H), 7.15 (m, 2H), 7.03 (t, J=6.4 Hz, 1H), 5.08 (s, 2H), 4.98 (d, J=3.6 Hz, 1H), 4.49 (s, 1H), 3.32 (s, 3H), 2.78 (s, 3H), 2.39 (s, 3H), 1.29 (d, J=6.0 Hz, 3H).

Scheme 9-2

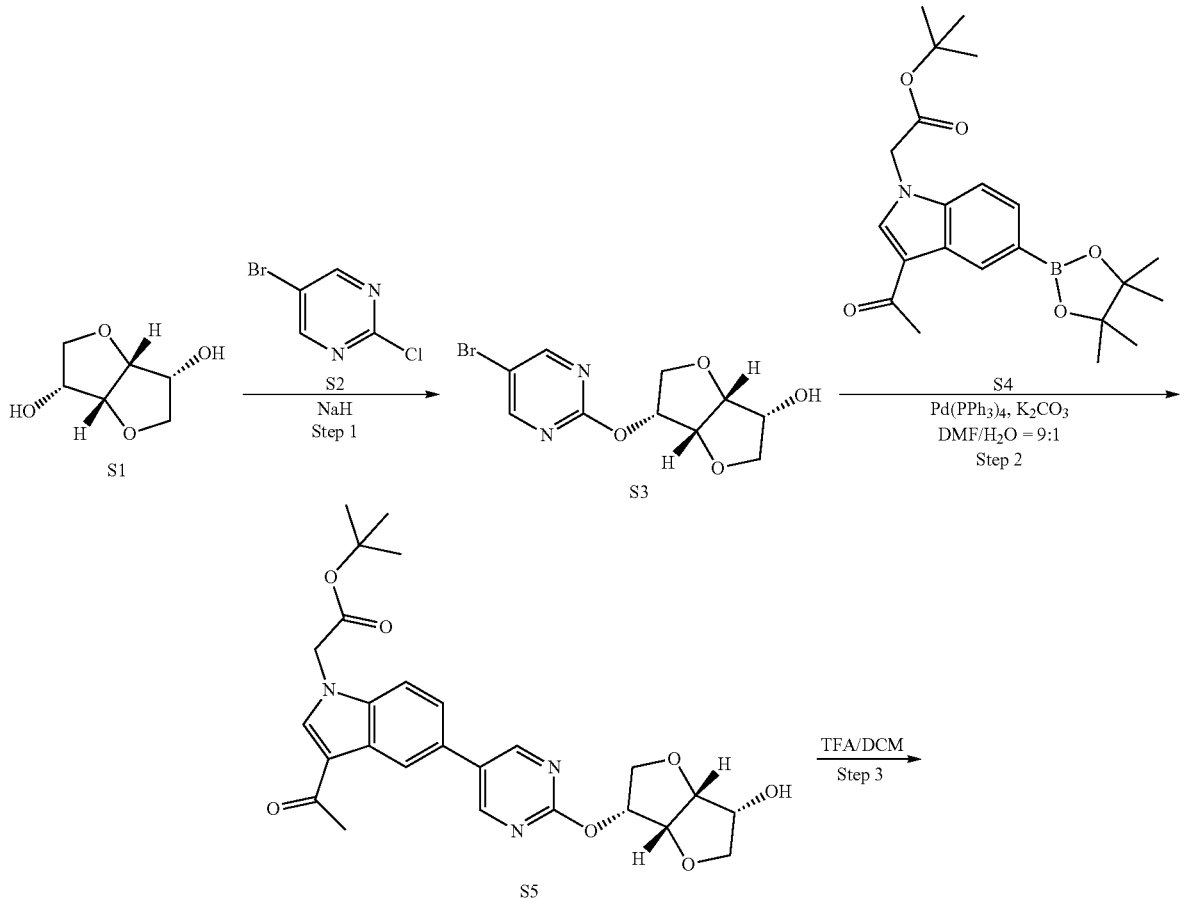

269
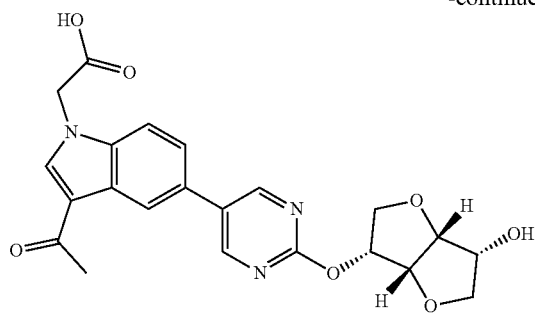
S6
270
-continued
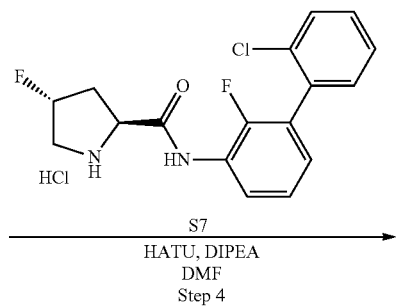
$\xrightarrow[\text{DMF}]{\text{S7}}$
HATU, DIPEA
Step 4
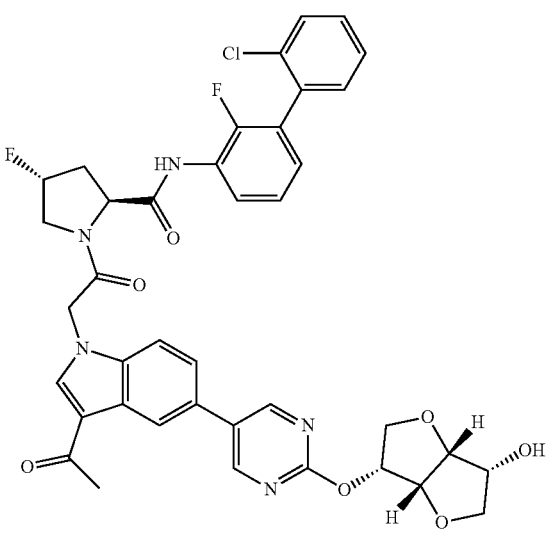
501
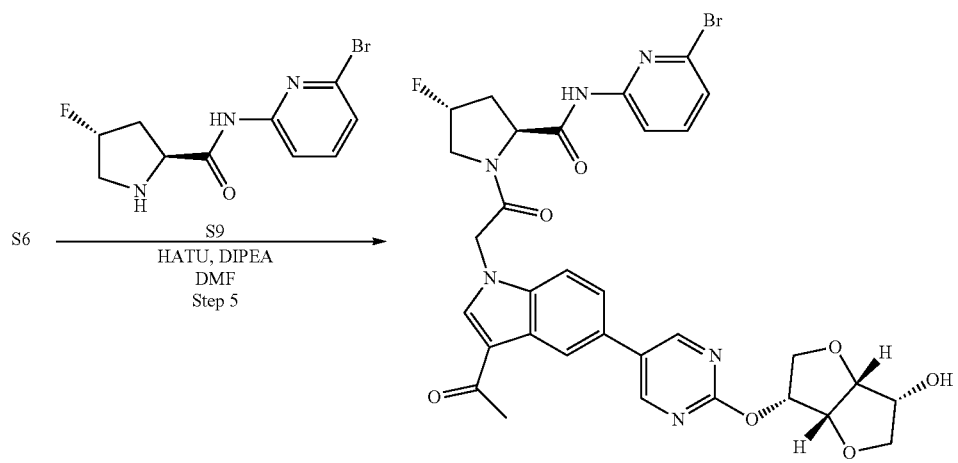
S6 $\xrightarrow[\text{DMF}]{\text{S9}}$ HATU, DIPEA
Step 5
502

Step 1: (3R,3aR,6R,6aR)-6-(5-Bromopyrimidin-2-yloxy)hexahydrofuro[3,2-b]furan-3-ol (S3)

To an ice-water cooled solution of scheme 9-2 compound S1 (5.0 g, 13.69 mmol) in DMF (20 mL) was added NaH (1.09 g, 27.37 mmol) under nitrogen protection. The reaction mixture was stirred at this temperature for 30 min and compound 2 (2.65 g, 13.69 mmol) was added. The reaction mixture was stirred at 60° C. for 2 h and then the reaction was poured carefully into saturated NH$_4$Cl solution. The resulting mixture was extracted with ethyl acetate (200 mL). The organic layer was dried over anhydrous Na$_2$SO$_4$ and concentrated. The residue was purified by preparative HPLC (acidic condition, using CH3CN/H2O as eluent) to afford scheme 9-2 compound S3 (0.75 g, yield 20%) as a white solid.

Step 2: tert-Butyl 2-(3-acetyl-5-(2-((3R,3aR,6R,6aR)-6-hydroxyhexahydrofuro[3,2-b]furan-3-yloxy) pyrimidin-5-yl)-1H-indol-1-yl)acetate (S5)

To a solution of scheme 9-2 compound S3 (0.75 g, 2.47 mmol) and scheme 9-2 compound S4 (1.09 g, 2.72 mmol) in DMF (18 mL)/water (2 mL) was added K$_2$CO$_3$ (0.68 g, 4.95 mmol) and Pd(PPh$_3$)$_4$ (0.29 g, 0.25 mmol). The reaction mixture was stirred at 120° C. under N$_2$ protection for 2 h and then quenched with water (50 mL). The resulting mixture was extracted with ethyl acetate (50 mL). The organic phase was washed with brine, dried over anhydrous Na$_2$SO$_4$, filtered, and concentrated. The residue was purified by column chromatography on silica gel (eluted with petroleum ether/ethyl acetate=100:1 to 5:1) to afford scheme 9-2 compound S5 (0.4 g, yield 35%) as a yellow solid. LC-MS: m/z 496 (M+H)+.

Step 3: 2-(3-Acetyl-5-(2-((3R,3aR,6R,6aR)-6-hydroxyhexahydrofuro[3,2-b]furan-3-yloxy) pyrimidin-5-yl)-1H-indol-1-yl)acetic Acid (S6)

To a solution of scheme 9-2 compound S5 (400 mg, 0.81 mmol) in DCM (5 mL), TFA (5 mL) was added. The resulting mixture was stirred at room temperature for 4 h and then concentrated to afford crude product 6 (300 mg). The compound was carried forward without further purification. LC-MS: m/z 440 (M+H)+.

Step 4: (2S,4R)-1-(2-(3-Acetyl-5-(2-((3R,3aR,6R,6aR)-6-hydroxyhexahydrofuro[3,2-b]furan-3-yloxy) pyrimidin-5-yl)-1H-indol-1-yl)acetyl)-N-(2'-chloro-2-fluorobiphenyl-3-yl)-4-fluoropyrrolidine-2-carboxamide (501)

To a solution of scheme 9-2 compound S6 (100 mg, 0.23 mmol), scheme 9-2 compound S7 (76 mg, 0.23 mmol), and DIPEA (60 mg, 0.46 mmol) in DMF (2 mL) was added HATU (175 mg, 0.46 mmol). The resulting mixture was stirred at room temperature overnight and then concentrated under high vacuum. The residue was purified by preparative HPLC (acidic condition, using CH$_3$CN/H2O as eluent) to afford the desired product 501 as a white solid (50 mg, yield 29%). LC-MS: m/z 758 (M+H)+. 1H-NMR: δ 10.00 (s, 1H), 8.86 (s, 2H), 8.40 (s, 1H), 8.32 (s, 1H), 7.96 (t, 1H), 7.30-7.64 (m, 7H), 7.22 (t, 1H), 7.01-7.13 (m, 1H), 5.01-5.81 (m, 5H), 4.96 (d, 1H), 4.83 (t, 1H), 4.77 (t, 1H), 4.37 (t, 1H), 3.84-4.28 (m, 5H), 3.74 (t, 1H), 2.56-2.66 (m, 1H), 2.45 (s, 3H), 2.11-2.31 (m, 1H).

Step 5: (2S,4R)-1-(2-(3-Acetyl-5-(2-((3R,3aR,6R,6aR)-6-hydroxyhexahydrofuro[3,2-b]furan-3-yloxy) pyrimidin-5-yl)-1H-indol-1-yl)acetyl)-N-(6-bromopyridin-2-yl)-4-fluoropyrrolidine-2-carboxamide (502)

To a solution of scheme 9-2 compound S6 (100 mg, 0.23 mmol), scheme 9-2 compound S8 (66 mg, 0.23 mmol), and DIPEA (60 mg, 0.46 mmol) in DMF (2 mL) was added HATU (175 mg, 0.46 mmol). The resulting mixture was stirred at room temperature overnight and then concentrated under high vacuum. The residue was purified by preparative HPLC (acidic condition, using CH$_3$CN/H$_2$O as eluent) to afford the desired product 502 as a white solid (65 mg, yield 40%). LC-MS: m/z 709 (M+H)+. 1H-NMR: δ 8.80 (s, 2H), 8.47 (d, 1H), 8.20 (d, 1H), 7.89-8.00 (m, 1H), 7.57 (d, 1H), 7.43-7.52 (m, 2H), 7.25-7.41 (m, 3H), 7.17 (t, 1H), 7.00-7.09 (m, 1H), 5.34-5.58 (m, 3H), 5.24 (d, 1H), 4.95-4.99 (m, 1H), 4.84 (d, 1H), 4.64 (t, 1H), 4.20-4.29 (m, 1H), 3.88-4.19 (m, 5H), 3.60-3.66 (m, 1H), 3.47 (s, 3H), 2.84-3.00 (m, 1H), 2.66-2.78 (m, 1H), 2.51 (s, 3H), 2.24-2.43 (m, 1H).

Scheme 9-3

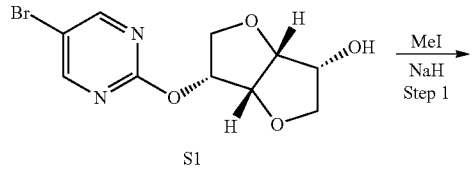

S1

-continued
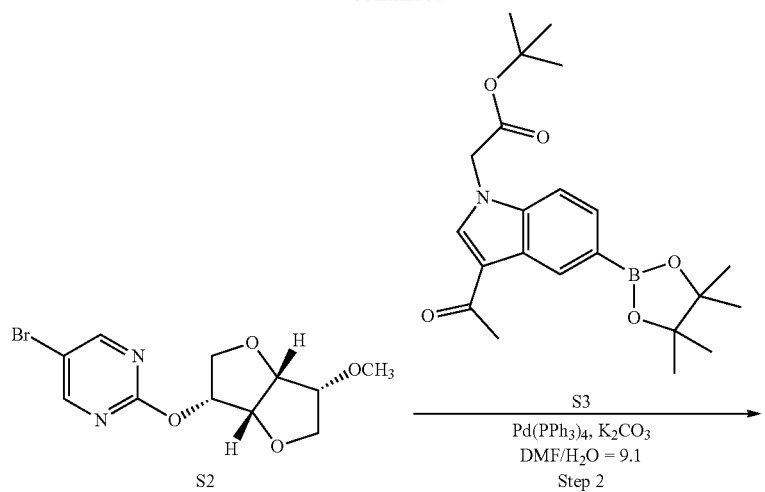
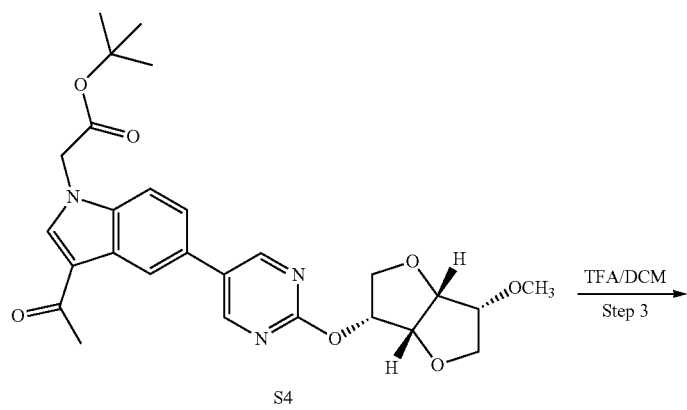
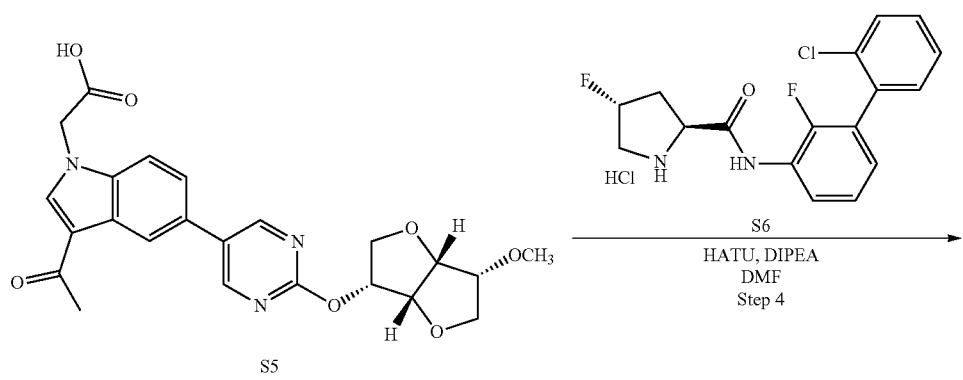

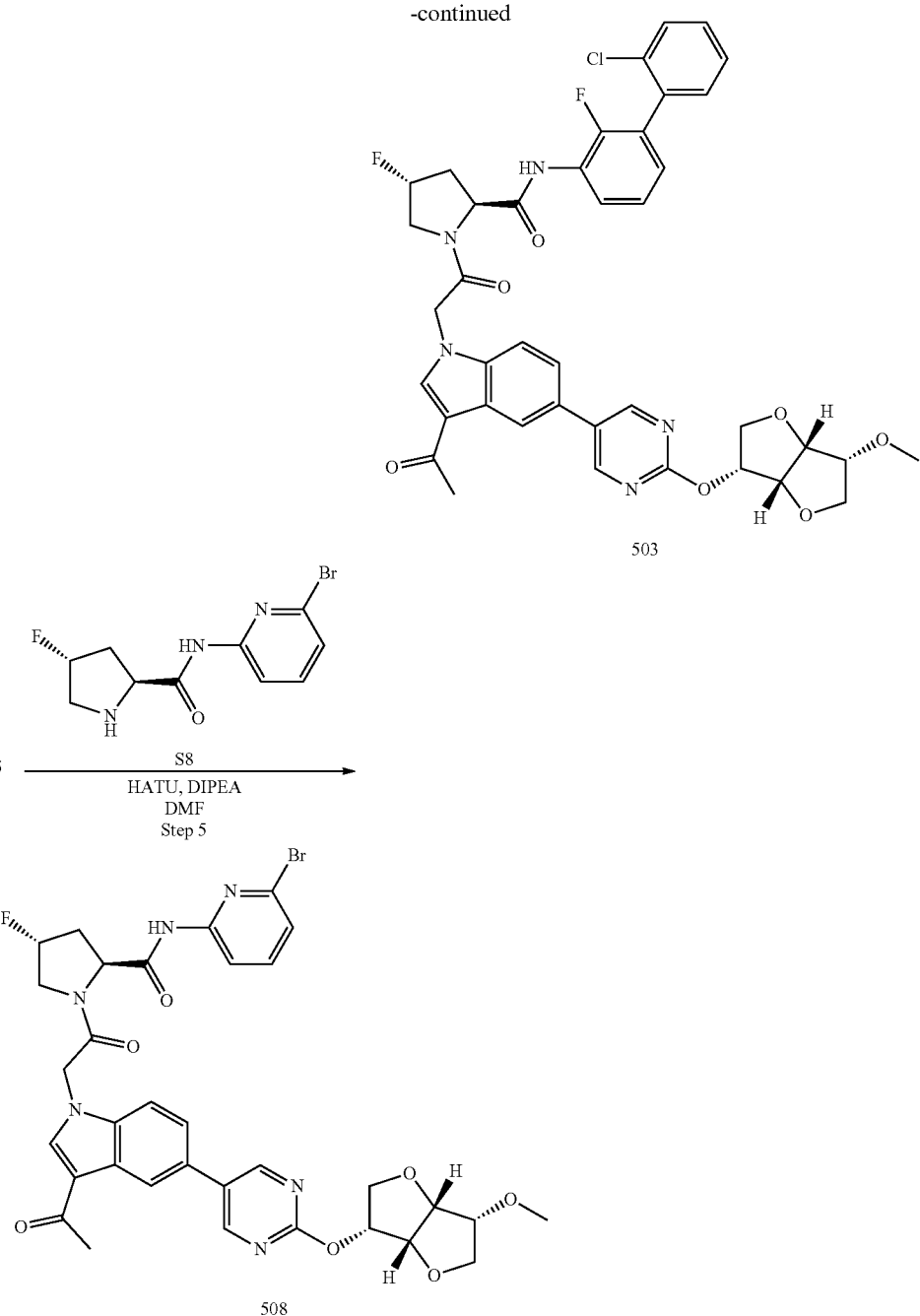

Step 1: 5-Bromo-2-((3R,3aR,6R,6aR)-6-methoxy-hexahydrofuro[3,2-b]furan-3-yloxy)pyrimidine (S2)

To an ice-water cooled solution of scheme 9-3 compound 1 (0.15 g, 0.2 mmol) in DMF (5 mL) was added NaH (16 mg, 0.4 mmol, 60% wt) under nitrogen protection. The reaction was stirred at this temperature for 30 min followed by the addition of MeI (60 mg, 0.4 mmol). The reaction mixture was stirred at 0° C. for 2 h and then poured carefully into a saturated $NH_4Cl$ solution. The resulting mixture was extracted with ethyl acetate (50 mL). The organic layer was dried over anhydrous $Na_2SO_4$, filtered, and concentrated. The residue was purified by preparative HPLC (acidic condition, using $CH_3CN/H_2O$ as eluent) to afford scheme 9-3 compound S2 (80 mg, yield 53%) as a white solid.

Step 2: tert-Butyl 2-(3-acetyl-5-(2-((3R,3aR,6R,6aR)-6-methoxyhexahydrofuro[3,2-b]furan-3-yloxy)pyrimidin-5-yl)-1H-indol-1-yl)acetate (S4)

To a solution of scheme 9-3 compound S2 (0.08 g, 0.25 mmol) and scheme 9-3 compound S3 (0.2 g, 0.5 mmol) in DMF (5 mL)/water (1 mL) was added $K_2CO_3$ (0.07 g, 0.5 mmol) and $Pd(PPh_3)_4$ (0.03 g, 0.025 mmol). The mixture was stirred at 120° C. under N2 protection for 2 h. After cooling to room temperature, the reaction mixture was filtered and the filtrate was concentrated under high vacuum.

The residue was purified by preparative HPLC (acidic condition, using CH$_3$CN/H$_2$O as eluent) to afford scheme 9-3 compound S4 (0.06 g, yield 50%) as a yellow solid. LC-MS: m/z 510 (M+H)+.

Step 3: 2-(3-Acetyl-5-(2-((3R,3aR,6R,6aR)-6-methoxyhexahydrofuro[3,2-b]furan-3-yloxy)pyrimidin-5-yl)-1H-indol-1-yl)acetic Acid (S5)

To a solution of scheme 9-3 compound S4 (60 mg, 0.12 mmol) in DCM (1 mL), TFA (1 mL) was added dropwise. The resulting solution was stirred at room temperature for 4 h and then concentrated to afford crude product 6 (60 mg), which was used in the next step without further purification. LC-MS: m/z 454 (M+H)+.

Step 4: (2S,4R)-1-(2-(3-Acetyl-5-(2-((3R,3aR,6R,6aR)-6-methoxyhexahydrofuro[3,2-b]furan-3-yloxy)pyrimidin-5-yl)-1H-indol-1-yl)acetyl)-N-(2'-chloro-2-fluorobiphenyl-3-yl)-4-fluoropyrrolidine-2-carboxamide (503)

To a solution of scheme 9-3 compound S5 (30 mg, 0.06 mmol), scheme 9-3 compound S6 (23 mg, 0.06 mmol), and DIPEA (15 mg, 0.12 mmol) in DMF (2 mL) was added HATU (45 mg, 0.12 mmol). The resulting mixture was stirred at room temperature overnight and then concentrated under vacuum. The residue was purified by preparative HPLC (acidic condition, using CH$_3$CN/H$_2$O as eluent) to afford the desired product 503 as a white solid (10 mg, yield 22%). LC-MS: m/z 772 (M+H)+. 1H-NMR: δ 11.05 (s, 1H), 8.87 (s, 2H), 8.38 (s, 1H), 8.34 (d, 1H), 8.04 (d, 1H), 7.71 (t, 1H), 7.59 (q, 2H), 7.33 (d, 1H), 5.08-5.67 (m, 5H), 4.96 (s, 1H), 4.83 (t, 1H), 4.68 (t, 1H), 4.37 (t, 1H), 4.06-4.22 (m, 4H), 3.91 (dd, 1H), 3.74 (t, 1H), 2.57 (m, 1H), 2.47 (s, 3H), 2.05-2.25 (m, 1H).

Step 5: (2S,4R)-1-(2-(3-Acetyl-5-(2-((3R,3aR,6R,6aR)-6-methoxyhexahydrofuro[3,2-b]furan-3-yloxy)pyrimidin-5-yl)-1H-indol-1-yl)acetyl)-N-(6-bromopyridin-2-yl)-4-fluoropyrrolidine-2-carboxamide (508)

To a solution of scheme 9-3 compound S5 (30 mg, 0.06 mmol), scheme 9-3 compound S8 (17 mg, 0.06 mmol), and DIPEA (15 mg, 0.12 mmol) in DMF (2 mL) was added HATU (45 mg, 0.12 mmol). The resulting solution was stirred at room temperature overnight and concentrated under high vacuum. The residue was purified by preparative HPLC (acidic condition, using CH$_3$CN/H$_2$O as eluent) to afford the desired product 508 as a white solid (5 mg, yield 12%). LC-MS: m/z 723 (M+H)+. 1H-NMR: δ 8.79 (s, 2H), 8.39 (s, 1H), 8.07 (s, 1H), 7.95 (d, 1H), 7.39-7.47 (m, 3H), 7.14 (d, 1H), 4.85-5.46 (m, 5H), 4.75 (t, 1H), 4.64 (t, 1H), 4.54 (t, 1H), 3.77-4.12 (m, 7H), 3.56 (t, 1H), 3.39 (s, 3H), 2.52-2.53 (m, 1H), 2.42 (s, 3H), 2.09-2.15 (m, 1H).

Scheme 9-4

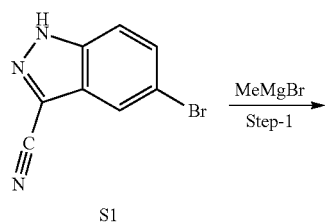

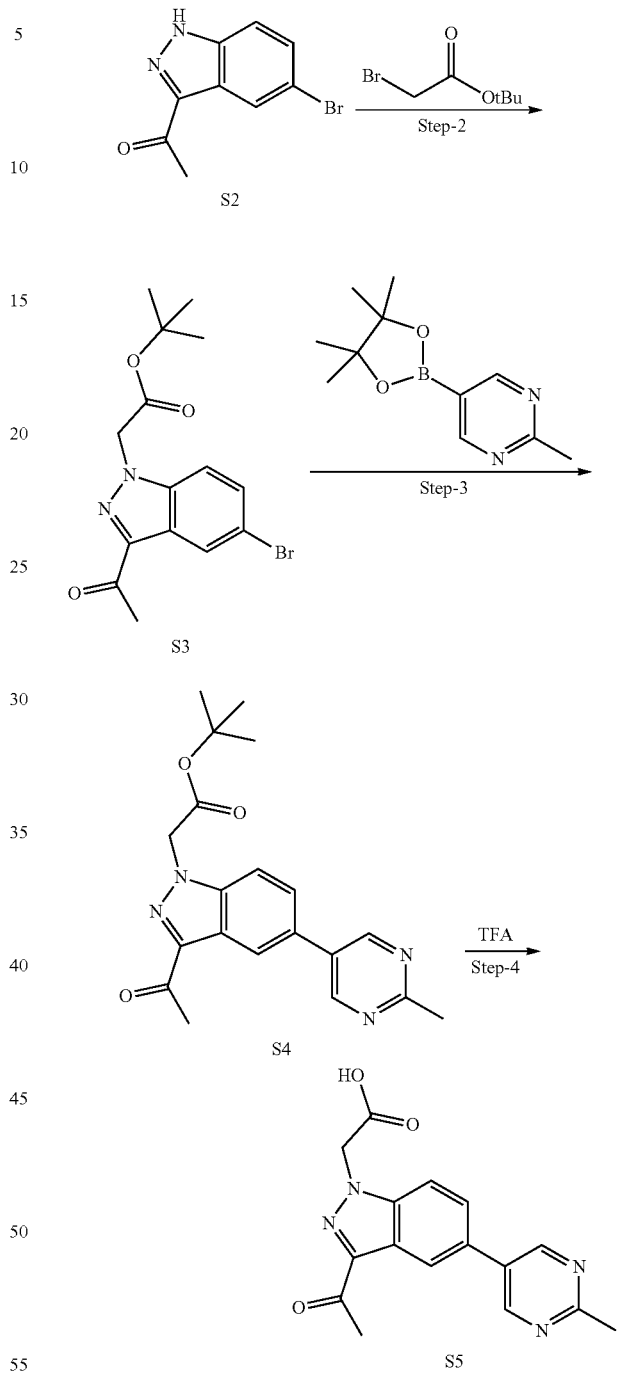

Step-1: 1-(5-Bromo-1H-indazol-3-yl)ethan-1-one (S2)

To an ice-cold solution of 5-bromo-1H-indazole-3-carbonitrile (scheme 9-4 compound S1, 110 g) in a mixture of 1.1 L THF and 3.3 L diethyl ether, methyl magnesium bromide (1 M in THF, 1.48 L, 3 equiv) was added dropwise. After completion of addition, the reaction mixture was brought to room temperature and stirred for 3 h (monitored by HPLC). Then the reaction was cooled to 0° C. and the pH was adjusted to 5 using 1.5N HCl (pH≈5, not <5). The reaction was stirred at room temperature for another 30 min. The reaction mixture was diluted with EtOAc and the layers were separated. The aqueous layer was again extracted with EtOAc. The combined organic layer was washed with water, washed with brine, dried over Na₂SO₄, and concentrated. The crude residue was recrystallized with a mixture of DCM:hexane (1:2, total 10 volume based on crude weight) to afford brown solid (100 g).

Step-2: tert-Butyl 2-(3-acetyl-5-bromo-1H-indazol-1-yl)acetate (S3)

Br₂ (1.10 g, 6.88 mmol) dropwise to 1-(5-bromo-1H-indazol-3-yl)ethan-1-one (scheme 9-4 compound S2, 155 g, 1 equiv) and potassium carbonate (225.6 g, 2.5 equiv) in DMF (1.6 L) at room temperature. The resulting mixture was stirred at 50° C. for 3 h. Then the reaction mixture was poured into water (16 L) and the precipitated solid was collected by filtration and dried to afford 186 g of the title product. The obtained material was used in the next step without further purification.

Step-3: tert-Butyl 2-(3-acetyl-5-(2-methylpyrimidin-5-yl)-1H-indazol-1-yl)acetate (S4)

A mixture of tert-butyl 2-(3-acetyl-5-bromo-1H-indazol-1-yl)acetate (scheme 9-4 compound S3, 150 g, 1 equiv), 2-methyl-5-(4,4,5,5-tetramethyl-1,3,2-dioxaborolan-2-yl) pyrimidine (112.2 g, 1.2 equiv), cesium carbonate (166.1 g, 1.2 equiv) in DMF (1.5 L) and water (150 mL) was purged with nitrogen gas for 30 min. Tetrakis(triphenylphosphine) palladium(0) (24.5 g, 0.05 equiv) was then added under an atmosphere of nitrogen and the reaction mixture was heated at 95° C. for 2 h. The reaction mixture was cooled to room temperature and added slowly to water (15 L). The solid was collected by filtration and dried. The crude residue was purified by column chromatography (silica gel, ethyl acetate/methanol) to afford the title compound as an off-white solid (135 g).

Step-4: 2-(3-Acetyl-5-(2-methylpyrimidin-5-yl)-1H-indazol-1-yl)acetic Acid (S5)

tert-Butyl 2-(3-acetyl-5-(2-methylpyrimidin-5-yl)-1H-indazol-1-yl)acetate (scheme 9-4 compound S4, 134 g, 1 equiv) was taken in a mixture of 1340 mL DCM and 670 mL TFA and heated at 50° C. for 2 h. After completion of the reaction (monitored by TLC), the solvent was removed under reduced pressure. The remaining crude material was stirred over MTBE for 30 min, collected by filtration and dried. The obtained solid was used in the next step without further purification.

Scheme 9-5

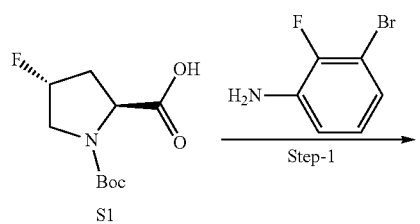

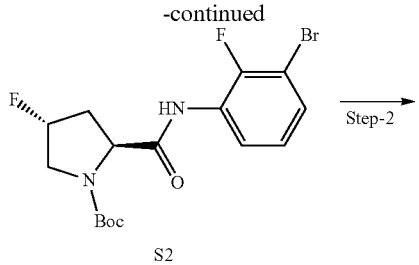

S2

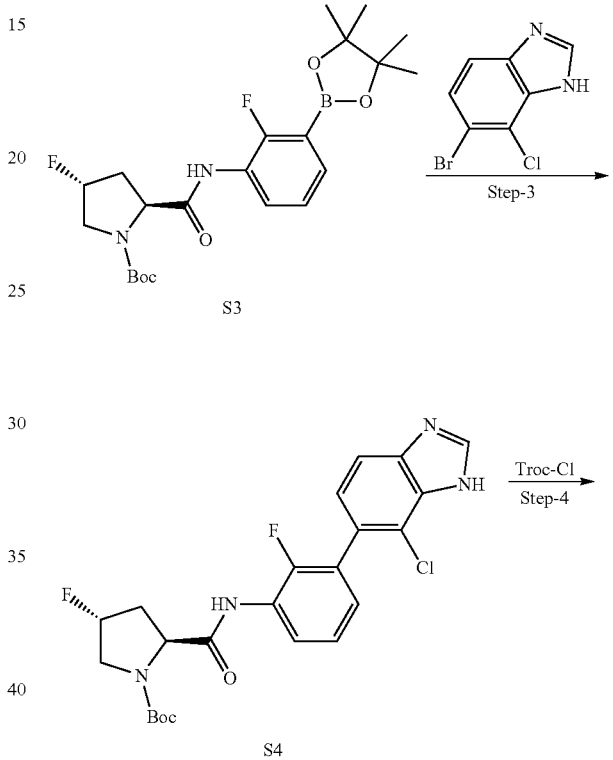

S3

S4

S5

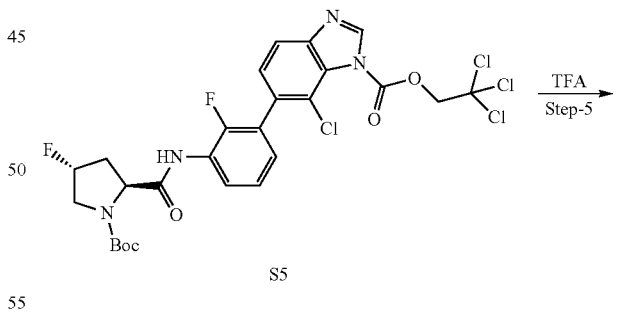

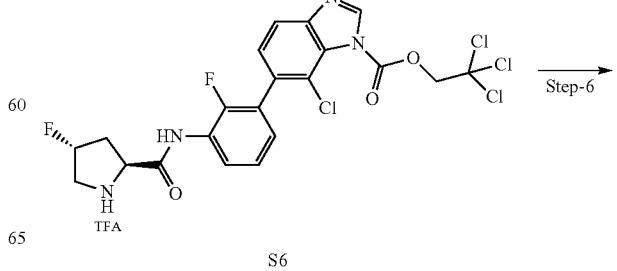

S6

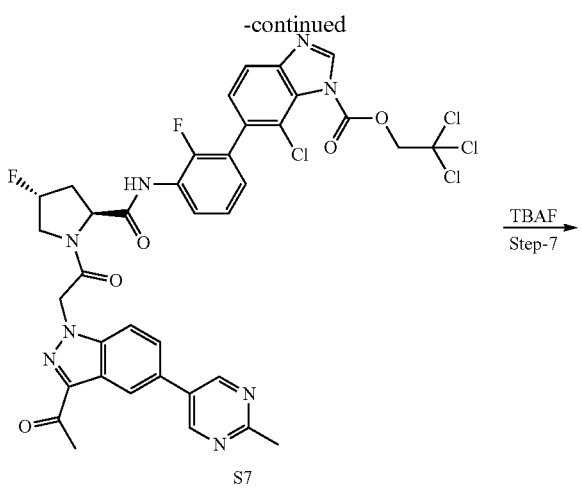

S7

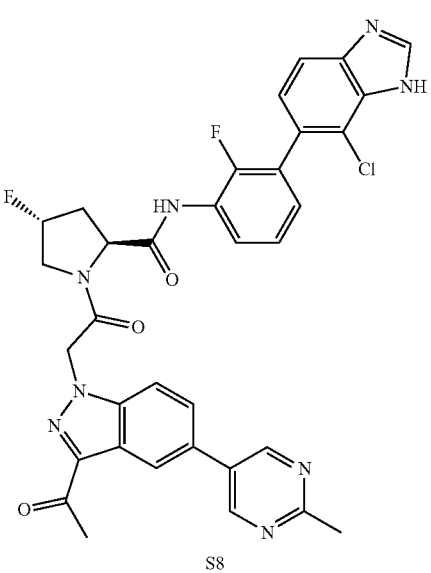

S8

Step-1: tert-Butyl (2S,4R)-2-((3-bromo-2-fluorophenyl)carbamoyl)-4-fluoropyrrolidine-1-carboxylate (S2)

To a stirred solution of N-Boc-trans-4-fluoro-proline (scheme 9-5 compound S1, 25 g, 1 equiv), 3-bromo-2-fluoroaniline (14.5 mL, 1.2 equiv) and HATU (53 g, 1.3 equiv) in DMF (250 mL) was added DIPEA (37 mL, 2 equiv). The resulting solution was stirred at room temperature under an atmosphere of nitrogen. The reaction mixture was poured into water and filtered. The collected solid was washed with excess water and the solid was dissolved in DCM and washed with 10% NaHCO$_3$, 1.5 N HCl, and brine. The solvent was removed under vacuum, hexane was added, and the precipitated solid was collected by filtration to afford the title product (27 g).

Step-2: tert-Butyl (2S,4R)-4-fluoro-2-((2-fluoro-3-(4,4,5,5-tetramethyl-1,3,2-dioxaborolan-2-yl)phenyl)carbamoyl)pyrrolidine-1-carboxylate (S3)

A stirred solution of tert-butyl (2S,4R)-2-((3-bromo-2-fluorophenyl)carbamoyl)-4-fluoropyrrolidine-1-carboxylate (scheme 9-5 compound S2, 30 g, 1 equiv), bis(pinacolato) diboron (47 g, 2.5 equiv), PdCl2 (dppf) (12 g, 0.22 equiv) and KOAc (21.8 g, 3 equiv) in 570 mL dioxane was purged with nitrogen gas for 10 min and then heated at 90° C. for 12 h. Then the reaction mixture was filtered through Celite and the filtrate was concentrated under reduced pressure. The crude residue obtained was purified by column chromatography to afford the title product as a viscous liquid (31.5 g).

Step-3: tert-Butyl (2S,4R)-2-((3-(7-chloro-1H-benzo[d]imidazol-6-yl)-2-fluorophenyl)carbamoyl)-4-fluoropyrrolidine-1-carboxylate (S4)

A solution of 6-bromo-7-chlorobenzimidazole (scheme 9-5 compound S3, 6.5 g, 1 equiv), tert-butyl (2S,4R)-4-fluoro-2-((2-fluoro-3-(4,4,5,5-tetramethyl-1,3,2-dioxaborolan-2-yl)phenyl)carbamoyl)pyrrolidine-1-carboxylate (25.4 g, 2 equiv), tetrakis(triphenylphosphine)palladium(0) (4.5 g, 0.14 equiv), and K$_2$CO$_3$ (19.4 g, 5 equiv) in 358 mL dioxane and 88 mL water was purged with nitrogen gas for 10 min. The reaction mixture was heated at 100° C. for 12 h. Then the reaction mixture was filtered through Celite and the filtrate was concentrated under reduced pressure. The crude residue was purified by column chromatography to afford the title product as an off-white solid (7.8 g).

Step-4: 2,2,2-Trichloroethyl 6-(3-((2S,4R)-1-(tert-butoxycarbonyl)-4-fluoropyrrolidine-2-carboxamido)-2-fluorophenyl)-7-chloro-1H-benzo[d]imidazole-1-carboxylate (S5)

Troc-Cl (2.65 mL, 1.2 equiv) was added dropwise to a mixture of tert-butyl (2S,4R)-2-((3-(7-chloro-1H-benzo[d]imidazol-6-yl)-2-fluorophenyl)carbamoyl)-4-fluoropyrrolidine-1-carboxylate (scheme 9-5 compound S4, 7.8 g, 1 equiv) and K$_2$CO$_3$ (3.4 g, 1.5 equiv) in DCM (98 mL) cooled to 0° C. This mixture was stirred for 1 h at the same temperature. Then the cooling bath was removed and the reaction mixture was stirred at room temperature for 12 h. The reaction mixture was filtered and the filtrate was concentrated under reduced pressure. The crude residue was purified by column chromatography to afford the title product as an off-white solid (8.4 g).

Step-5: 2,2,2-Trichloroethyl 7-chloro-6-(2-fluoro-3-((2S,4R)-4-fluoropyrrolidine-2-carboxamido)phenyl)-1H-benzo[d]imidazole-1-carboxylate (S6)

2,2,2-Trichloroethyl 6-(3-((2S,4R)-1-(tert-butoxycarbonyl)-4-fluoropyrrolidine-2-carboxamido)-2-fluorophenyl)-7-chloro-1H-benzo[d]imidazole-1-carboxylate (scheme 9-5 compound S5, 1 g) was stirred in a mixture of DCM (10 mL) and TFA (5 mL) for 30 min. Then the volatiles were removed under reduced pressure. The residue was triturated with MTBE and decanted. The solid obtained was dried to afford the title product and this material was used in the next step without further purification.

Step-6: 2,2,2-Trichloroethyl 6-(3-((2S,4R)-1-(2-(3-acetyl-5-(2-methylpyrimidin-5-yl)-1H-indazol-1-yl)acetyl)-4-fluoropyrrolidine-2-carboxamido)-2-fluorophenyl)-7-chloro-1H-benzo[d]imidazole-1-carboxylate (S7)

2-(3-Acetyl-5-(2-methylpyrimidin-5-yl)-1H-indazol-1-yl)acetic acid (Scheme 9-4, compound S6, 310 mg) was dissolved in DMF (10 mL) and DIPEA (0.412 mL) was added. This was followed by the addition of (2S,4R)-2-((3-(7-chloro-1-((2,2,2-trichloroethoxy)carbonyl)-1H-benzo[d]imidazol-6-yl)-2-fluorophenyl)carbamoyl)-4-fluoropyrrolidin-1-ium 2,2,2-trifluoroacetate (TFA salt, 315 mg) at 5° C. HATU (380 mg) was then added slowly at this same temperature and the reaction mixture was stirred for 3 h at room temperature. The reaction mixture was then added to water (25 mL+5 g solid NaCl) and extracted with DCM (2×15 mL). The organic layer was washed successively with an aqueous solution of NaHCO$_3$ (10 mL), water (10 mL), and brine (10 mL), dried over Na$_2$SO$_4$ and concentrated under reduced pressure. The remaining residue was purified by column chromatography (silica gel, DCM/MeOH) to afford the title compound.

Step-7: (2S,4R)-1-(2-(3-Acetyl-5-(2-methylpyrimidin-5-yl)-1H-indazol-1-yl)acetyl)-N-(3-(7-chloro-1H-benzo[d]imidazol-6-yl)-2-fluorophenyl)-4-fluoropyrrolidine-2-carboxamide (S8)

2,2,2-Trichloroethyl 6-(3-((2S,4R)-1-(2-(3-acetyl-5-(2-methylpyrimidin-5-yl)-1H-indazol-1-yl)acetyl)-4-fluoropyrrolidine-2-carboxamido)-2-fluorophenyl)-7-chloro-1H-benzo[d]imidazole-1-carboxylate (scheme 9-5 compound S7, 160 mg) was dissolved in THF (5 mL) and treated with TBAF (1 M in THF, 0.285 mL). The resulting solution was stirred at room temperature for 1 h. Then the reaction mixture was concentrated under reduced pressure, the remaining residue was purified by column chromatography (silica gel, DCM/MeOH) to afford the title compound. 1H NMR (400 MHz, DMSO-d$_6$): (major rotamer) δ 2.14-2.31 (m, 1H), 2.54-2.2.59 (m, 1H), 2.64 (s, 3H), 2.69 (s, 3H), 3.97-4.08 (m, 1H), 4.21-4.30 (m, 1H), 4.79 (t, J=8.4 Hz, 1H), 5.51-5.67 (m, 2H), 5.85 (d, J=17.2 Hz, 1H), 7.07-7.11 (m, 1H), 7.16 (d, J=8 Hz, 1H), 7.22 (t, J=8 Hz, 1H), 7.55-7.57 (m, 1H), 7.85 (s, 2H), 7.97 (t, J=7.2 Hz, 1H), 8.35 (s, 1H)), 8.43 (s, 1H), 9.02 (s, 2H), 9.97 (s, 1H), 12.83. (s, 1H). 19F NMR (376 MHz, CDCl3): δ −126.72, −176.18. LC (method A): tR=1.51 min. LC/MS (EI) m/z: [M+H]+ 669.

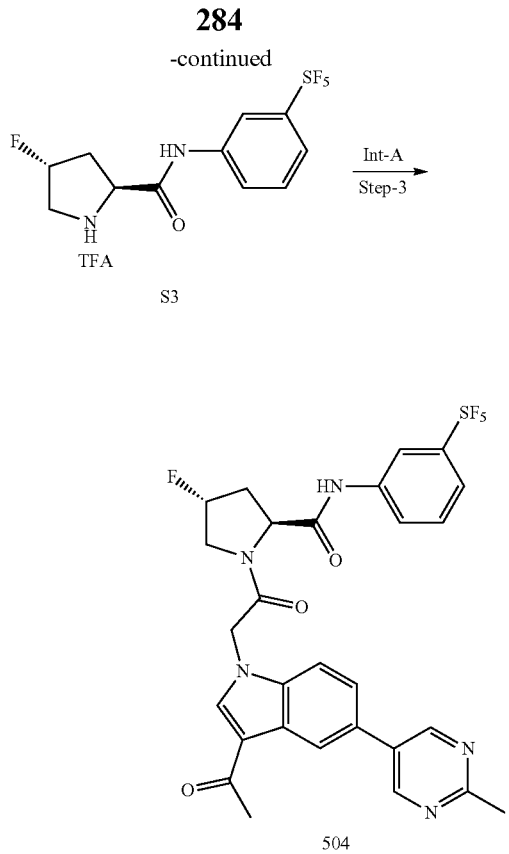

Step-1: tert-Butyl (2S,4R)-4-fluoro-2-((3-(pentafluoro-λ$^6$-sulfanyl)phenyl)carbamoyl)pyrrolidine-1-carboxylate (S2)

To an ice-cold solution of (2S,4R)-1-(tert-butoxycarbonyl)-4-fluoropyrrolidine-2-carboxylic acid (scheme 9-6 compound S1, 329 mg, 1.4 mmol) in DCM, (6 mL), 1-chloro-N,N,2-trimethylprop-1-en-1-amine (0.19 mL, 1.1 equiv) was added dropwise with stirring. The stirring was continued for 3 h at the same temperature. Then 3-(pentafluoro-λ6-sulfanyl)aniline (338 mg, 1.1 equiv) was added, followed by DIPEA (0.73 mL, 3 equiv). The cooling bath was removed and the reaction mixture was stirred at rt overnight. The solvent was co-evaporated with 5 mL of methanol, and the residue was purified by column chromatography (silica gel, ethyl acetate in hexane, gradient) to obtain the title compound as a white solid (592 mg).

Step-2: (2S,4R)-4-Fluoro-N-(3-(pentafluoro-λ$^6$-sulfanyl)phenyl)pyrrolidine-2-carboxamide (S3)

tert-Butyl (2S,4R)-4-fluoro-2-((3-(pentafluoro-λ6 sulfanyl)phenyl)carbamoyl)pyrrolidine-1-carboxylate (scheme 9-6 compound S2, 592 mg) was dissolved in DCM (8 mL) and treated with TFA (8 mL). The resulting solution was stirred at room temperature for 2 h. Then the reaction mixture was concentrated under reduced pressure and a portion of the remaining residue was used directly in the next synthetic step.

Step-3: (2S,4R)-1-(2-(3-Acetyl-5-(2-methylpyrimidin-5-yl)-1H-indazol-1-yl)acetyl)-4-fluoro-N-(3-(pentafluoro-λ⁶-sulfanyl)phenyl)pyrrolidine-2-carboxamide (504)

To a stirred solution of (2S,4R)-4-fluoro-N-(3-(pentafluoro-λ6-sulfanyl)phenyl)pyrrolidine-2-carboxamide (scheme 9-6 compound S3, TFA salt, 121 mg) in DMF (5 mL) was added Int-A (from Scheme 4) (92 mg), HATU (154 mg, 1.1 equiv), and DIPEA (0.14 mL, 3 equiv). The reaction mixture was stirred at room temperature for 2 h and then diluted with EtOAc (15 mL) and water (10 mL). The organic layer was washed with brine (3×15 mL), dried over Na$_2$SO$_4$, and concentrated under reduced pressure. The resulting oil was purified by column chromatography (silica gel, 10% MeOH in DCM, gradient) to yield 92 mg (54%) of compound 504. 1H NMR (400 MHz, DMSO-d$_6$): (major rotamer) δ 2.12-2.39 (m, 2H), 2.52-2.2.64 (m, 1H), 2.65 (s, 3H), 2.69 (s, 3H), 3.96-4.11 (m, 1H), 4.21-4.31 (m, 1H), 4.55 (t, 1H), 5.52-5.89 (m, 3H), 7.51-7.58 (m, 2H), 7.70 (d, 1H), 7.83-7.89 (m, 2H), 8.27 (s, 1H), 8.43 (s, 1H), 9.04 (s, 2H), 10.55 (s, 1H); 19F NMR (376 MHz, DMSO-d$_6$): (major rotamer) δ −175.9. LC (method A): tR=2.13 min. LC/MS (EI) m/z: [M+H]+ 627.

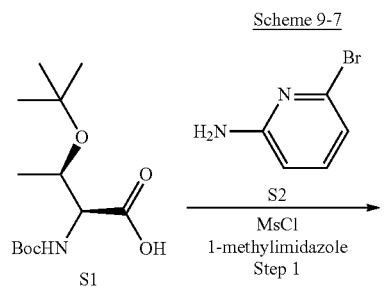

Scheme 9-7

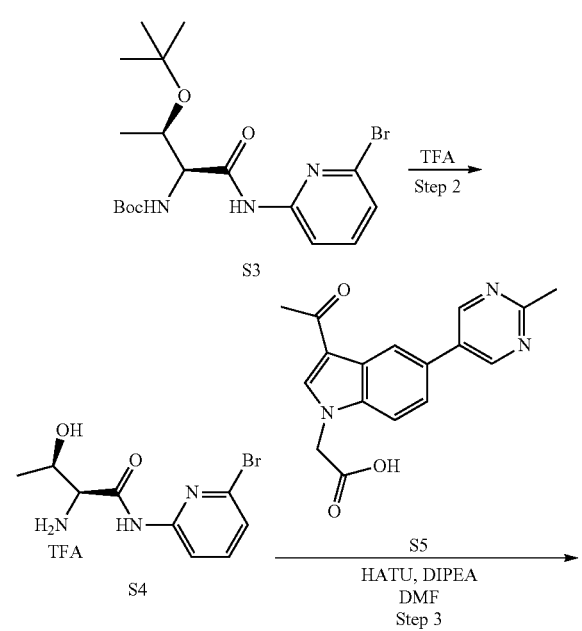

Step 1: tert-Butyl (2S,3R)-1-(6-bromopyridin-2-ylamino)-3-tert-butoxy-1-oxobutan-2-yl carbamate (S3)

To an ice-water cooled solution of scheme 9-7 compound S1 (0.5 g, 1.82 mmol) in DCM (10 mL) was added 1-methylimidazole (0.23 g, 2.0 mmol) under nitrogen protection. The reaction was stirred at this temperature for 30 min followed by the addition of MeSO$_2$Cl (0.15 mL, 2.0 mmol). After stirring at 0° C. for 15 min, compound 2 (0.35 g, 2.0 mmol) was added. The mixture was stirred at room temperature overnight and then quenched with aqueous NaHCO$_3$. The resulting mixture was extracted with ethyl acetate (100 mL). The organic layer was dried over anhydrous Na$_2$SO$_4$, filtered, and concentrated. The residue was purified by column chromatography on silica gel (petroleum ether/ethyl acetate=100:1 to 2:1) to afford scheme 9-7 compound S3 (0.25 g, yield 32%) as a yellow solid.

Step 2: (2S,3R)-2-Amino-N-(6-bromopyridin-2-yl)-3-hydroxybutanamide (S4)

To a solution of scheme 9-7 compound S3 (50 mg, 0.12 mmol) in DCM (2 mL) was dropwise added TFA (0.05 mL, 0.58 mmol). The resulting solution was stirred at room temperature for 4 h and then concentrated to afford crude scheme 9-7 compound S4 (35 mg), which was used in the next step without further purification. LC-MS: m/z 274 (M+H)+.

Step 3: (2S,3R)-2-(2-(3-Acetyl-5-(2-methylpyrimidin-5-yl)-1H-indol-1-yl)acetamido)-N-(6-bromopyridin-2-yl)-3-hydroxybutanamide (505)

To a solution of scheme 9-7 compound S5 (43.6 mg, 0.1 mmol), scheme 9-7 compound S4 (31 mg, 0.1 mmol), and DIPEA (25.8 mg, 0.2 mmol) in DMF (2 mL) was added HATU (57 mg, 0.15 mmol). The resulting solution was stirred at room temperature overnight and concentrated under high vacuum. The residue was purified by preparative HPLC (acidic condition, using CH$_3$CN/H$_2$O as eluent) to afford the desired product 505 as a white solid (39 mg, yield 22%). LC-MS: m/z 565 (M+H)⁺. 1H-NMR: δ 10.8 (s, 1H), 8.98 (s, 2H), 8.57 (d, 1H), 8.42-8.45 (m, 2H), 8.08 (d, 1H), 7.73 (t, 1H), 7.62-7.65 (m, 2H), 7.35 (d, 1H), 5.18-5.22 (m, 3H), 4.47 (d, 1H), 4.16 (m, 1H), 2.68 (s, 3H), 2.45 (s, 3H), 1.12 (d, 3H).

Scheme 9-8

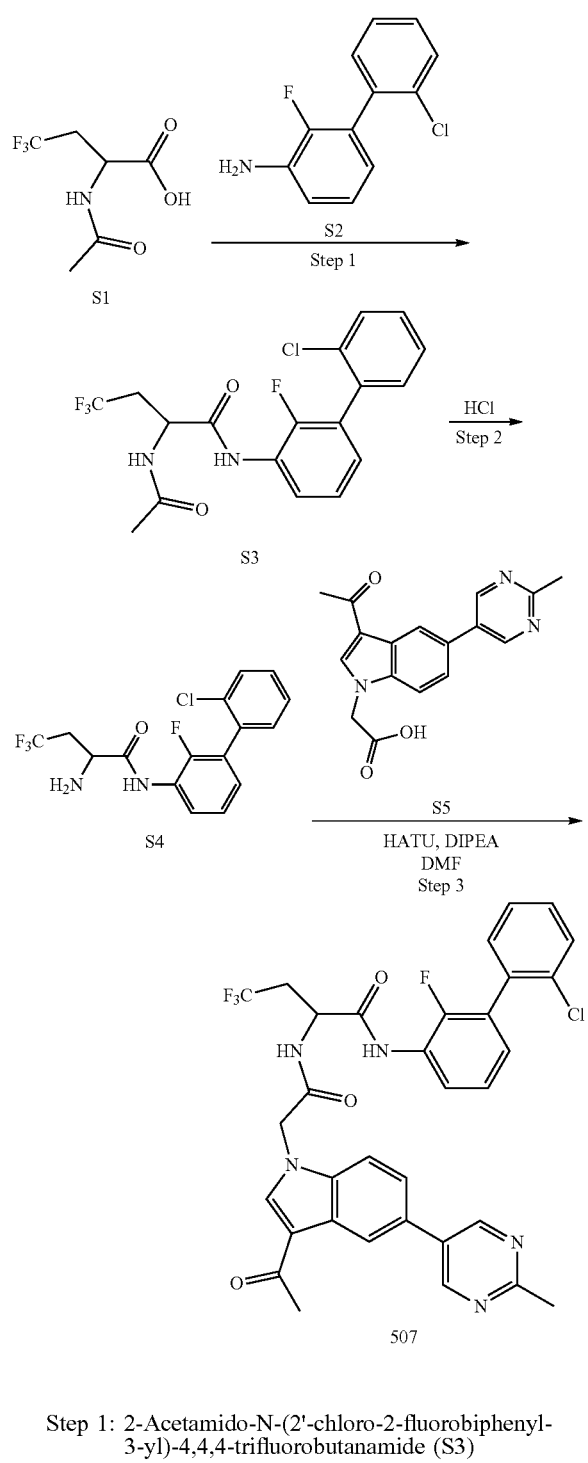

organic layer was dried over Na₂SO₄, filtered, and concentrated. The residue was purified by column chromatography on silica gel (petroleum ether/ethyl acetate=100:1 to 2:1) to afford scheme 9-8 compound S3 (0.15 g, yield 50%) as a yellow solid.

Step 2: 2-Amino-N-(2'-chloro-2-fluorobiphenyl-3-yl)-4,4,4-trifluorobutanamide (S4)

To a mixture of scheme 9-8 compound S3 (0.15 g, 0.38 mmol) in MeOH (5 mL) was added concentrated HCl (1 mL). The resulting solution is stirred at 80° C. overnight and then concentrated to afford crude scheme 9-8 compound S4 (0.1 g), which is used in the next step without further purification. LC-MS: m/z 274 (M+H)+.

Step 3: 2-(2-(3-Acetyl-5-(2-methylpyrimidin-5-yl)-1H-indol-1-yl)acetamido)-N-(2'-chloro-2-fluoro biphenyl-3-yl)-4,4,4-trifluorobutanamide (507)

To a solution of scheme 9-8 compound S4 (36 mg, 0.1 mmol), scheme 9-8 compound S5 (31 mg, 0.1 mmol), and DIPEA (25.8 mg, 0.2 mmol) in DMF (2 mL) is added HATU (57 mg, 0.15 mmol). The resulting mixture is stirred at room temperature overnight and concentrated under high vacuum. The residue was purified by preparative HPLC (acidic condition, using CH₃CN/H2O as eluent) to afford the desired product 507 as a white solid (30 mg, yield 54%). LC-MS: m/z 652 (M+H)⁺. 1H-NMR: δ 8.84 (s, 2H), 8.45 (s, 1H), 8.17 (s, 1H), 7.81 (t, 1H), 7.43-7.40 (m, 3H), 7.29-7.21 (m, 3H), 7.22 (t, 1H), 7.03-7.01 (m, 1H), 5.01 (s, 2H), 4.97-4.94 (m, 1H), 2.89-2.82 (m, 2H), 2.68 (s, 3H), 2.44 (s, 3H).

Scheme 9-9

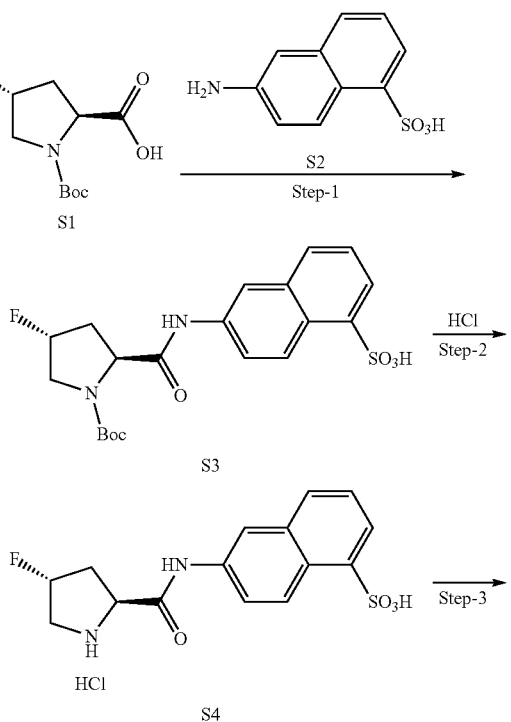

Step 1: 2-Acetamido-N-(2'-chloro-2-fluorobiphenyl-3-yl)-4,4,4-trifluorobutanamide (S3)

To the solution of scheme 9-8 compound S1 (0.15 g, 0.75 mmol) in DCM (10 mL) was added oxalyl dichloride (1 mL) under nitrogen protection. After being stirred at room temperature for 2 h, the reaction mixture was concentrated under high vacuum. The residue was dissolved with DCM (10 mL) and scheme 9-8 compound S2 (0.22 g, 1 mmol) was added, followed by the addition of TEA (0.15 g, 1.5 mmol). The reaction mixture was stirred at room temperature overnight and then quenched with aqueous NaHCO₃. The resulting mixture was extracted with ethyl acetate (50 mL). The

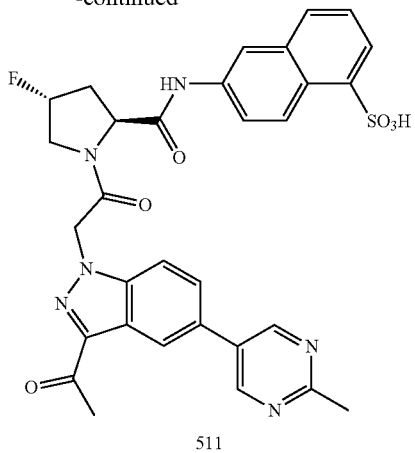

511

Step-1: 6-((2S,4R)-1-(tert-Butoxycarbonyl)-4-fluoropyrrolidine-2-carboxamido)naphthalene-1-sulfonic Acid (S3)

To an ice-cold solution of (2S,4R)-1-(tert-butoxycarbonyl)-4-fluoropyrrolidine-2-carboxylic acid (scheme 9-9 compound S1, 233 mg) in DCM (20 mL) was added 1-chloro-N,N,2-trimethyl-1-propenylamine (146 mg, 1.1 equiv) dropwise with stirring. Stirring was continued for 3 h at this temperature, and then solid 6-aminonaphthalene-1-sulfonic acid (256 mg, 1.1 equiv) was added, followed by DIPEA (0.49 mL, 3 equiv). The cooling bath was removed and the reaction mixture was stirred overnight at room temperature. The reaction mixture was then added to water (10 mL) and extracted with DCM (2×10 mL). The organic layer was washed successively with an aqueous solution of $NaHCO_3$ (10 mL), water (10 mL), and brine (10 mL), dried over $Na_2SO_4$ and concentrated under reduced pressure. The remaining material was used directly in the next synthetic step.

Step-2: 6-((2S,4R)-4-Fluoropyrrolidine-2-carboxamido)naphthalene-1-sulfonic acid hydrochloride (S4)

6-((2S,4R)-1-(tert-Butoxycarbonyl)-4-fluoropyrrolidine-2-carboxamido)naphthalene-1-sulfonic acid (scheme 9-9 compound S3, 438 mg) was stirred in 4 N HCl in dioxane (4 mL) for 5 h at room temperature. The volatiles were then removed under reduced pressure and the remaining material was used directly in the next synthetic step.

Step-3: 6-((2S,4R)-1-(2-(3-Acetyl-5-(2-methylpyrimidin-5-yl)-1H-indazol-1-yl)acetyl)-4-fluoropyrrolidine-2-carboxamido)naphthalene-1-sulfonic Acid (511)

2-(3-Acetyl-5-(2-methylpyrimidin-5-yl)-1H-indazol-1-yl)acetic acid (310 mg) was dissolved in DMF (30 mL) and DIPEA (0.6 mL) was added. This was followed by the addition of 6-((2S,4R)-4-fluoropyrrolidine-2-carboxamido)naphthalene-1-sulfonic acid hydrochloride (scheme 9-9 compound S4, 375 mg) at 5° C. HATU (400 mg) was added slowly at this same temperature and the reaction mixture was stirred for 3 h at rt. The reaction mixture was then added to water (50 mL+10 g solid NaCl) and extracted with DCM (2×20 mL). The organic layer was washed successively with an aqueous solution of $NaHCO_3$ (20 mL), water (20 mL), and brine (20 mL), dried over $Na_2SO_4$ and concentrated under reduced pressure. The remaining residue was purified by column chromatography (silica gel, DCM/MeOH) to afford the title compound 511. 1H NMR (400 MHz, DMSO-$d_6$): (major rotamer) δ 2.07-2.37 (m, 2H), 2.54-2.75 (m, 7H), 3.95-4.36 (m, 2H), 4.57-4.68 (m, 1H), 5.41-5.90 (m, 3H), 7.32-7.56 (m, 2H), 7.61-7.97 (m, 5H), 8.24 (s, 1H), 8.45 (s, 1H), 8.70 (m, 1H), 9.10 (s, 1H), 10.30 (s, 1H);). 19F NMR (376 MHz, DMSO-$d_6$): (major rotamer) δ −175.9. LC (method A): tR=0.98 min. LC/MS (EI) m/z: [M+H]+ 631.

Scheme 9-10

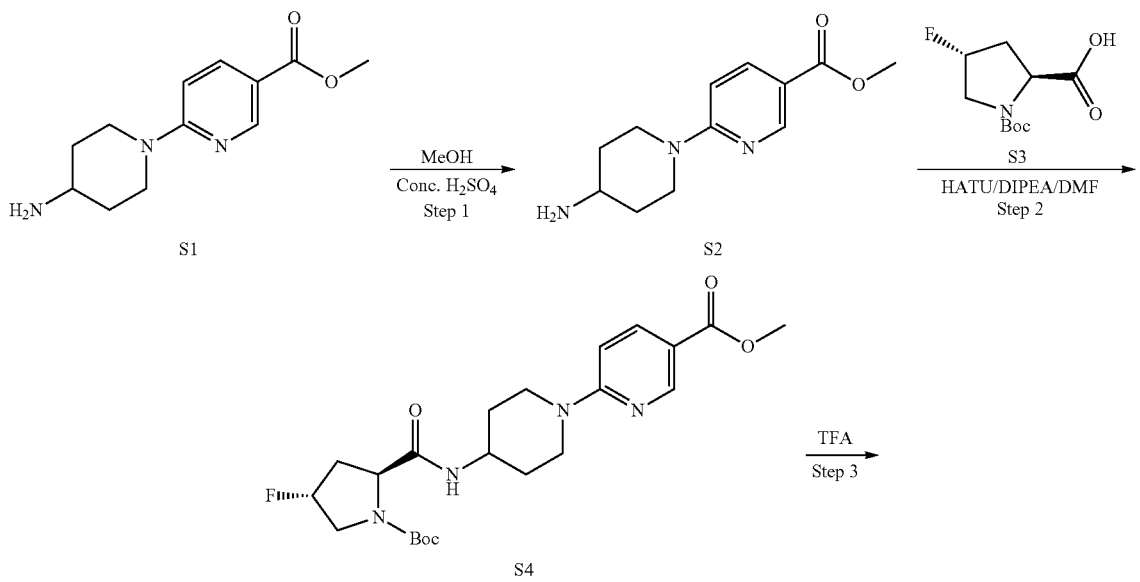

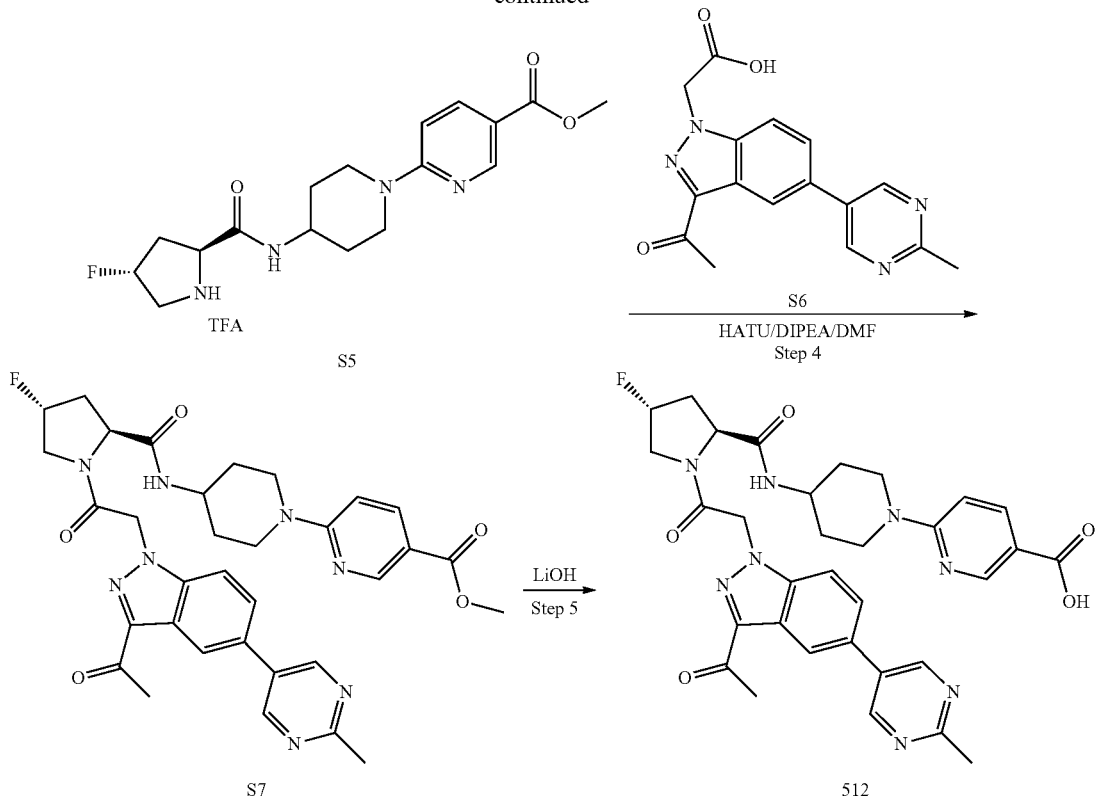

Step 1: Methyl 6-(4-aminopiperidin-1-yl)nicotinate (S2)

To an ice-water cooled solution of scheme 9-10 compound S1 (0.25 g, 1.1 mmol) in MeOH (10 mL) was added conc. $H_2SO_4$ (0.5 mL). The reaction mixture was stirred at 80° C. overnight and then quenched with aqueous $NaHCO_3$. The resulting mixture was extracted with ethyl acetate (50 mL). The organic layer was dried over anhydrous $Na_2SO_4$ and then concentrated to afford scheme 9-10 compound S2 (0.2 g, yield 32%) as a black solid. The compound was carried forward without further purification.

Step 2: Methyl 6-(4-((2S,4R)-1-(tert-butoxycarbonyl)-4-fluoropyrrolidine-2-carboxamido) piperidin-1-yl)nicotinate (S4)

To a solution of scheme 9-10 compound S2 (150 mg, 0.64 mmol), scheme 9-10 compound S3 (298 mg, 1.28 mmol), and DIPEA (165 mg, 1.28 mmol) in DMF (10 mL) was added HATU (300 mg, 1.28 mmol). The resulting solution was stirred at room temperature overnight and then concentrated under high vacuum. The residue was purified by preparative HPLC (acidic condition, using $CH_3CN/H_2O$ as eluent) to afford scheme 9-10 compound S4 (200 mg, yield 70%) as a white solid.

Step 3: Methyl 6-(4-((2S,4R)-4-fluoropyrrolidine-2-carboxamido)piperidin-1-yl)nicotinate (S5)

To a solution of scheme 9-10 compound S4 (200 mg, 0.44 mmol) in DCM (5 mL), TFA (1 mL mmol) was added dropwise over 10 min. The resulting mixture was stirred at room temperature for 2 h and then concentrated to afford crude scheme 9-10 compound S5 (200 mg), which was used in the next step without further purification. LC-MS: m/z 351 $(M+H)^+$.

Step 4: Methyl 6-(4-((2S,4R)-1-(2-(3-acetyl-5-(2-methylpyrimidin-5-yl)-1H-indazol-1-yl)acetyl)-4-fluoropyrrolidine-2-carboxamido)piperidin-1-yl) nicotinate (S7)

To a solution of scheme 9-10 compound S5 (200 mg, 0.45 mmol), scheme 9-10 compound S6 (280 mg, 0.9 mmol), and DIPEA (116 mg, 0.9 mmol) in DMF (5 mL) was added HATU (340 mg, 0.9 mmol). The resulting solution was stirred at room temperature overnight and then concentrated under high vacuum. The residue was purified by preparative HPLC (acidic condition, using $CH_3CN/H_2O$ as eluent) to afford the desired product scheme 9-10 compound S7 as a white solid (90 mg, yield 32%).

Step 5: 6-(4-((2S,4R)-1-(2-(3-Acetyl-5-(2-methylpyrimidin-5-yl)-1H-indazol-1-yl)acetyl)-4-fluoropyrrolidine-2-carboxamido)piperidin-1-yl)nicotinic Acid (512)

To a solution of scheme 9-10 compound S7 (40 mg, 0.06 mmol) in THF (2 mL)/water (1 mL) is added LiOH $H_2O$ (25 mg, 0.6 mmol). The resulting mixture was stirred at room temperature overnight and then concentrated under high vacuum. The residue was purified by preparative HPLC (acidic condition, using $CH_3CN/H_2O$ as eluent) to afford the desired product 512 as a white solid (10 mg, yield 25%).

293
LC-MS: m/z 629 (M+H)+. 1H-NMR: δ 12.46 (s, 1H), 9.05 (d, 2H), 8.60 (dd, 1H), 8.44 (s, 1H), 7.73-7.99 (m, 4H), 6.85 (d, 1H), 5.79 (d, 1H), 5.58 (d, 1H), 5.43 (s, 1H), 4.10-4.43
294
(m, 4H), 3.86-4.03 (m, 1H), 3.81 (d, 1H), 3.07 (t, 2H), 2.59-2.76 (m, 6H), 2.37 (dd, 1H), 1.97-2.13 (m, 1H), 1.72 (d, 2H), 1.29 (d, 2H).
Scheme 9-11
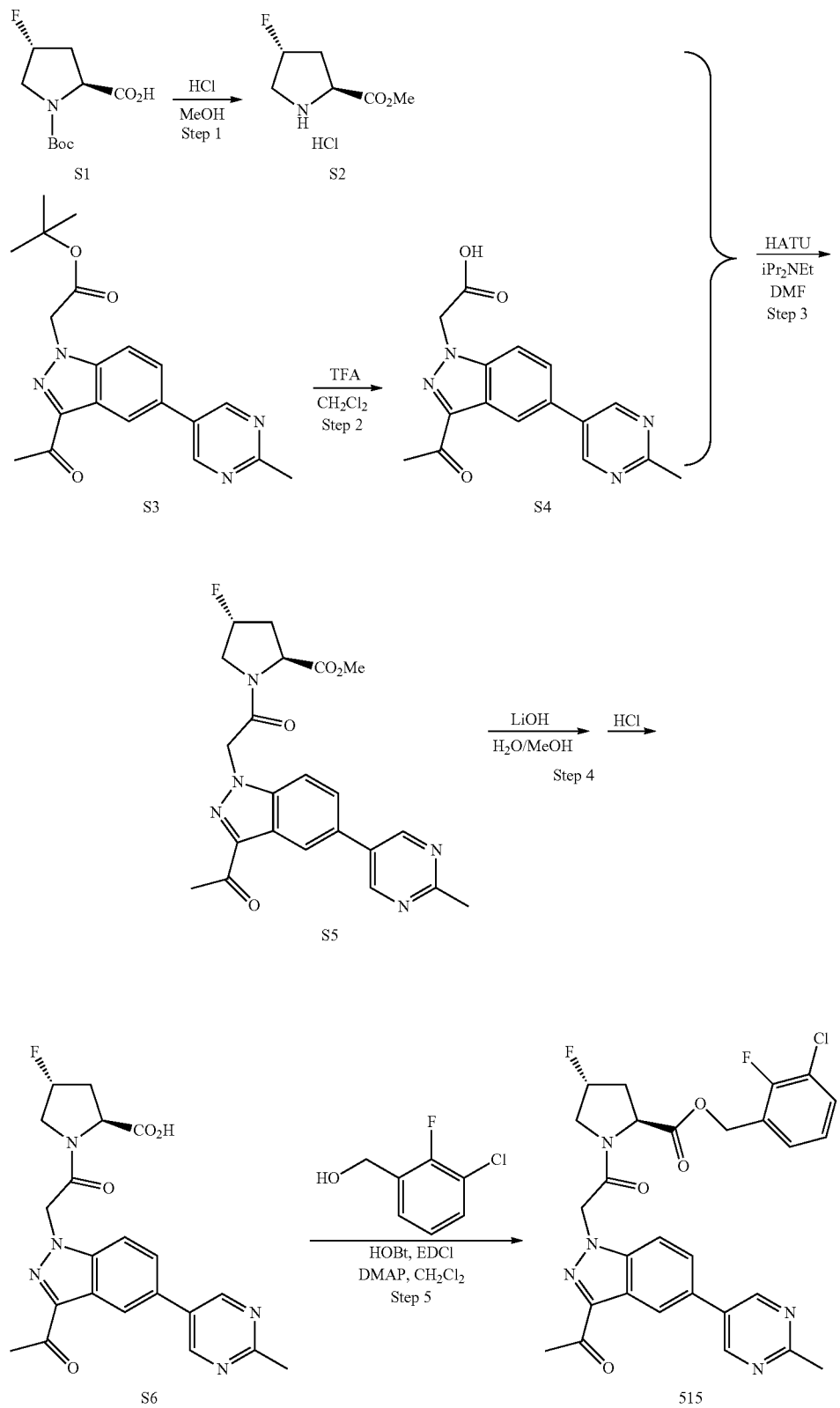

Step 1: Methyl (2S,4R)-4-fluoropyrrolidine-2-carboxylate hydrochloride (S2)

(2S,4R)-1-(tert-Butoxycarbonyl)-4-fluoropyrrolidine-2-carboxylic acid (scheme 9-11 compound S1, 233 mg) was treated with saturated HCl in MeOH (20 mL) and stirred for 18 h at room temperature. The solvent was removed under reduced pressure and the remaining crude title product was used directly in the next synthetic step.

Step 2: 2-(3-Acetyl-5-(2-methylpyrimidin-5-yl)-1H-indazol-1-yl)acetic Acid (S4)

tert-Butyl 2-(3-acetyl-5-(2-methylpyrimidin-5-yl)-1H-indazol-1-yl)acetate (scheme 9-11 compound S3, 366 mg) was treated with TFA (2 mL) in $CH_2Cl_2$ (2 mL) and stirred for 5 h at room temperature. The solvent was removed under reduced pressure and the remaining crude title product was used directly in the next synthetic step.

Step 3: Methyl (2S,4R)-1-(2-(3-acetyl-5-(2-methylpyrimidin-5-yl)-1H-indazol-1-yl)acetyl)-4-fluoropyrrolidine-2-carboxylate (S5)

To a mixture of methyl (2S,4R)-4-fluoropyrrolidine-2-carboxylate hydrochloride scheme 9-11 compound S2), 2-(3-acetyl-5-(2-methylpyrimidin-5-yl)-1H-indazol-1-yl)acetic acid (scheme 9-11 compound S4, 310 mg, 1 equiv), DMF (9 mL), and N-ethyl-N-isopropylpropan-2-amine (3 mL) was added HATU (380 mg). The reaction mixture was stirred for 10 min and concentrated under reduced pressure. The remaining residue was purified by column chromatography (silica gel, DCM/MeOH) to afford the title compound (400 mg).

Step 4: (2S,4R)-1-(2-(3-Acetyl-5-(2-methylpyrimidin-5-yl)-1H-indazol-1-yl)acetyl)-4-fluoropyrrolidine-2-carboxylic Acid (S6)

Methyl (2S,4R)-1-(2-(3-acetyl-5-(2-methylpyrimidin-5-yl)-1H-indazol-1-yl)acetyl)-4-fluoropyrrolidine-2-carboxylate (scheme 9-11 compound S5, 439 mg) was treated with 2 N aqueous LiOH (10 mL) and stirred for 5 h at rt. The reaction mixture was treated with HCl (pH adjusted to ~1) and was then concentrated under reduced pressure. The remaining crude title product was used directly in the next synthetic step.

Step 5: 3-Chloro-2-fluorobenzyl (2S,4R)-1-(2-(3-acetyl-5-(2-methylpyrimidin-5-yl)-1H-indazol-1-yl)acetyl)-4-fluoropyrrolidine-2-carboxylate (515)

(2S,4R)-1-(2-(3-Acetyl-5-(2-methylpyrimidin-5-yl)-1H-indazol-1-yl)acetyl)-4-fluoropyrrolidine-2-carboxylic acid (scheme 9-11 compound S6, 425 mg) from the previous step was dissolved in $CH_2Cl_2$ (20 mL) and HOBt (145 mg) was added. This was followed by the addition of EDCI (192 mg), DMAP (10 mg) and (3-chloro-2-fluorophenyl)methanol (g) (161 mg) at 5° C. HATU (400 mg) was then added slowly at this same temperature and the reaction mixture was stirred for 18 h at rt. The reaction mixture was concentrated under reduced pressure. The remaining residue was purified by column chromatography (silica gel, DCM/MeOH) to afford the title product 515. 1H NMR (400 MHz, DMSO-$d_6$): (major rotamer) δ 2.07-2.67 (m, 1H), 2.65 (s, 3H), 2.70 (s, 3H), 3.91-3.96 (m, 1H), 3.99-4.08 (m, 1H), 4.18-4.30 (m, 1H), 4.46-4.53 (m, 1H), 5.11-5.25 (m, 1H), 5.27-5.87 (m, 2H), 7.13-7.19 (m, 1H), 7.36-7.42 (m, 1H), 7.53-7.58 (m, 1H), 7.77-7.88 (m, 2H), 8.45 (s, 1H), 9.06 (s, 2H);). 19F NMR (376 MHz, DMSO-$d_6$): (major rotamer) δ −120.5, −176.1 LC (method A): tR=2.09 min. LC/MS (EI) m/z: [M+H]+ 568.

Scheme 9-12

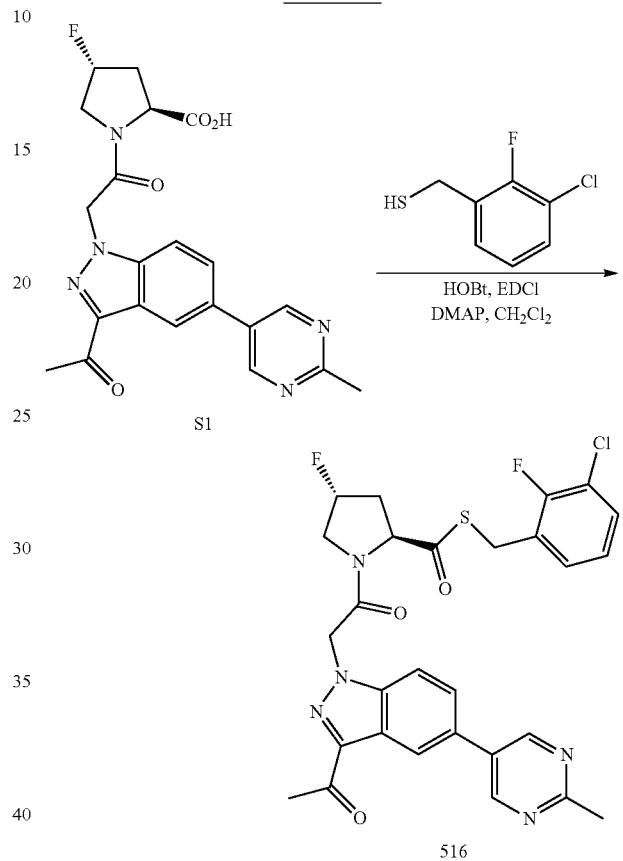

S-(3-Chloro-2-fluorobenzyl) (2S,4R)-1-(2-(3-acetyl-5-(2-methylpyrimidin-5-yl)-1H-indazol-1-yl)acetyl)-4-fluoropyrrolidine-2-carbothioate (516)

(2S,4R)-1-(2-(3-Acetyl-5-(2-methylpyrimidin-5-yl)-1H-indazol-1-yl)acetyl)-4-fluoropyrrolidine-2-carboxylic acid (scheme 9-12 compound S1, 425 mg) was dissolved in $CH_2Cl_2$ (20 mL) and HOBt (145 mg) was added, which was followed by the addition of EDCI (192 mg), DMAP (10 mg) and (3-chloro-2-fluorophenyl)methanethiol (177 mg) at 5° C. The reaction mixture was stirred for 18 h at room temperature and then concentrated under reduced pressure. The remaining residue was purified by column chromatography (silica gel, DCM/MeOH) to afford the title compound 516. 1H NMR (400 MHz, DMSO-$d_6$): (major rotamer) δ 1.99-2.20 (m, 1H), 2.64 (s, 3H), 2.71 (s, 3H), 3.87-4.36 (m, 4H), 4.69 (m, 1H), 5.44 (m, 1H), 5.58 (m, 1H), 5.67-5.76 (m, 1H), 5.83-5.89 (m, 1H), 7.07-7.13 (m, 1H), 7.30-7.352 (m, 1H), 7.43-7.49 (m, 1H), 7.79-7.83 (m, 2H), 8.45 (s, 1H), 9.06 (s, 2H);). 19F NMR (376 MHz, DMSO-$d_6$): (major rotamer) δ −119.3, −176.0 LC (method A): tR=2.23 min. LC/MS (EI) m/z: [M+H]+ 584.

Scheme 9-13

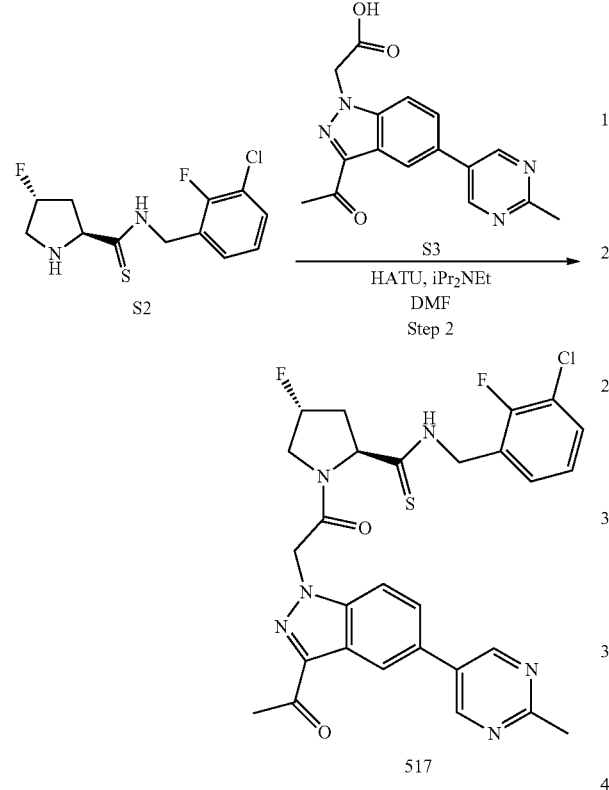

Step 1: (2S,4R)—N-(3-Chloro-2-fluorobenzyl)-4-fluoropyrrolidine-2-carbothioamide (S2)

A mixture of (2S,4R)—N-(3-chloro-2-fluorobenzyl)-4-fluoropyrrolidine-2-carboxamide (scheme 9-13 compound S1, 275 mg), Lawesson's Reagent (607 mg), and pyridine (20 mL) was refluxed for 18 h. The reaction mixture was then concentrated under reduced pressure and the remaining residue was purified by column chromatography (silica gel, DCM/MeOH) to afford the title compound.

Step 2: (2S,4R)-1-(2-(3-Acetyl-5-(2-methylpyrimidin-5-yl)-1H-indazol-1-yl)acetyl)-N-(3-chloro-2-fluorobenzyl)-4-fluoropyrrolidine-2-carbothioamide (517)

(2S,4R)—N-(3-Chloro-2-fluorobenzyl)-4-fluoropyrrolidine-2-carbothioamide (scheme 9-13 compound S2, 291 mg) from the previous step was dissolved in DMF (30 mL) and DIEA (0.6 mL) was added, which was followed by the addition of 2-(3-acetyl-5-(2-methylpyrimidin-5-yl)-1H-indazol-1-yl)acetic acid (scheme 9-13 compound S3, 310 mg) at 5° C. HATU (400 mg) was then added slowly at this same temperature and the reaction mixture was stirred for 3 h at room temperature. The reaction mixture was then added to water (50 mL+10 g solid NaCl) and extracted with DCM (2×20 mL). The organic layer was washed successively with an aqueous solution of NaHCO$_3$ (20 mL), water (20 mL), and brine (20 mL), dried over Na$_2$SO$_4$ and concentrated under reduced pressure. The remaining residue was purified by column chromatography (silica gel, DCM/MeOH) to afford the title compound. 1H NMR (400 MHz, DMSO-d$_6$): (major rotamer) δ 2.12-2.32 (m, 1H), 2.65 (s, 3H), 2.70 (s, 3H), 3.95-4.42 (m, 2H), 4.69-5.04 (m, 3H), 5.21-5.89 (m, 4H), 6.89-6.99 (m, 1H), 7.11-7.23 (m, 1H), 7.39-7.54 (m, 1H), 7.72-7.94 (m, 2H), 8.44 (s, 1H), 9.05 (s, 2H), 10.28-10.23 (m, 1H);). 19F NMR (376 MHz, DMSO-d$_6$): (major rotamer) δ −121.0, −175.5 LC (method A): tR=2.12 min. LC/MS (EI) m/z: [M+H]+ 583.

Scheme 9-14

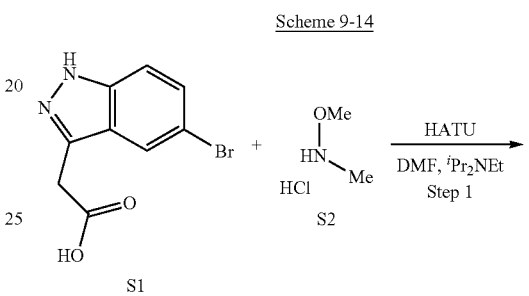

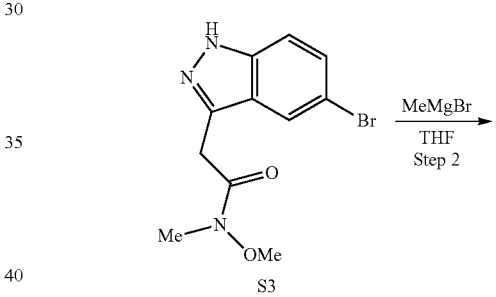

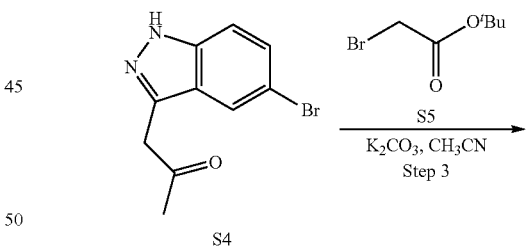

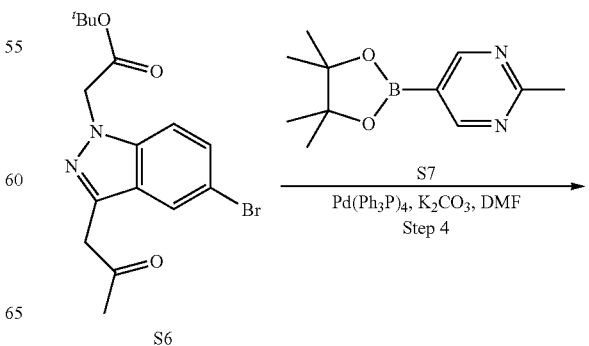

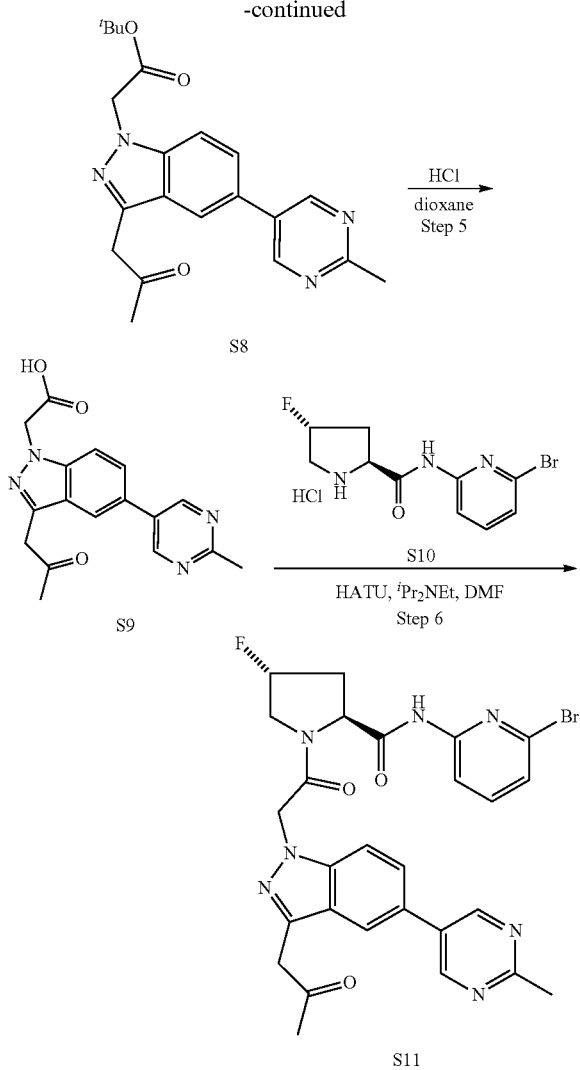

Step 1: 2-(5-Bromo-1H-indazol-3-yl)-N-methoxy-N-methylacetamide (S3)

To a solution of scheme 9-14 compound S1 (255 mg, 1 mmol), scheme 9-14 compound S2 (293 mg, 3 mmol), and DIPEA (646 mg, 5 mmol) in DMF (10 mL) at room temperature was added HATU (418 mg, 1.05 mmol). The resulting mixture was stirred at room temperature overnight and then concentrated. The residue was purified by column chromatography on silica gel (eluted with CH2Cl2/MeOH) to afford compound 3 (260 mg, yield 87%) as a white solid. LC-MS: m/z 298 (M+H)$^+$.

Step 2: 1-(5-Bromo-1H-indazol-3-yl)propan-2-one (S4)

To a solution of scheme 9-14 compound S3 (298 mg, 1 mmol) in THF (10 mL) at room temperature was added 3 N methylmagnesiumbromide in Et2O (2 mL, 6 mmol) at 5° C. The reaction mixture was stirred at room temperature for 1 h and then quenched with 2 N HCl solution (20 mL). The resulting mixture was extracted with DCM (20 mL). The organic layer was separated, dried over anhydrous Na2SO4, filtered, and then concentrated. The residue was purified by column chromatography on silica gel to afford scheme 9-14 compound S4 (220 mg, 87% yield). LC-MS: m/z 253 (M+H)$^+$.

Step 3: tert-Butyl 2-(5-bromo-3-(2-oxopropyl)-1H-indazol-1-yl)acetate (S6)

To a mixture of scheme 9-14 compound S4 (253 mg, 1 mmol) and K2CO3 (415 mg, 3 mmol) in MeCN (5 mL) was added scheme 9-14 compound S5 (215 mg, 1.1 mmol). The resulting mixture was stirred at 60° C. for 4 h. After filtration, the filtrate was concentrated and the residue was purified by column chromatography on silica gel (eluted with hexanes/ethyl acetate=1:1) to afford scheme 9-14 compound S6 (355 mg, yield 97%). LC-MS: m/z 367 (M+H)+.

Step 4: tert-Butyl 2-(5-(2-methylpyrimidin-5-yl)-3-(2-oxopropyl)-1H-indazol-1-yl)acetate (S8)

A solution of scheme 9-14 compound S6 (367 mg, 1 mmol), Pd(Ph3P)4 (231 mg, 0.2 mmol), K2CO3 (415 mg, 3 mmol), and scheme 9-14 compound S7 (220 mg, 1 mmol) in DMF (20 mL) under nitrogen was stirred at 90° C. for 3 h and then concentrated. The residue was purified by column chromatography on silica gel to afford scheme 9-14 compound S8 (360 mg, 95% yield). LC-MS: m/z 381 (M+H)+.

Step 5: 2-(5-(2-Methylpyrimidin-5-yl)-3-(2-oxopropyl)-1H-indazol-1-yl)acetic Acid (S9)

Scheme 9-14 compound S8 (380 mg, 1 mmol) was treated with 4 N HCl in dioxane (3 mL) at room temperature and stirred for 6 h. The reaction mixture was concentrated and the remaining material (scheme 9-14 compound S9) was used directly in the next synthetic step. LC-MS: m/z 325 (M+H)+.

Step 6: (2S,4R)—N-(6-Bromopyridin-2-yl)-4-fluoro-1-(2-(5-(2-methylpyrimidin-5-yl)-3-(2-oxopropyl)-1H-indazol-1-yl)acetyl)pyrrolidine-2-carboxamide (S11)

To a solution of scheme 9-14 compound S9 (324 mg, 1 mmol), scheme 9-14 compound S10 (325 mg, 1 mmol), and DIPEA (646 mg, 5 mmol) in DMF (10 mL) at room temperature was added HATU (418 mg, 1.05 mmol). The resulting mixture was stirred at room temperature overnight and then concentrated. The residue was purified by column chromatography on silica gel (eluted with CH2Cl2/MeOH) to afford scheme 9-14 compound S11 (550 mg, yield 93%) as a white solid. 1H-NMR: 10.95 (s, 1H), 9.04 (s, 2H), 8.00-8.13 (m, 2H), 7.64-7.83 (m, 3H), 7.29-7.42 (m, 1H), 5.34-5.61 (m, 3H), 4.65 (m, 1H), 3.87-4.24 (m, 3H), 3.38 (m, 1H), 3.30 (s, 3H), 2.67 (s, 3H), 1.10 (m, 1H), 0.96 (m, 1H). LC-MS: m/z 594 (M+H)+.

Scheme 9-15

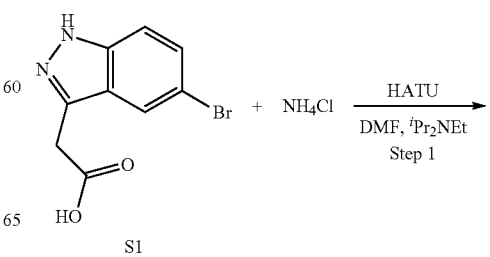

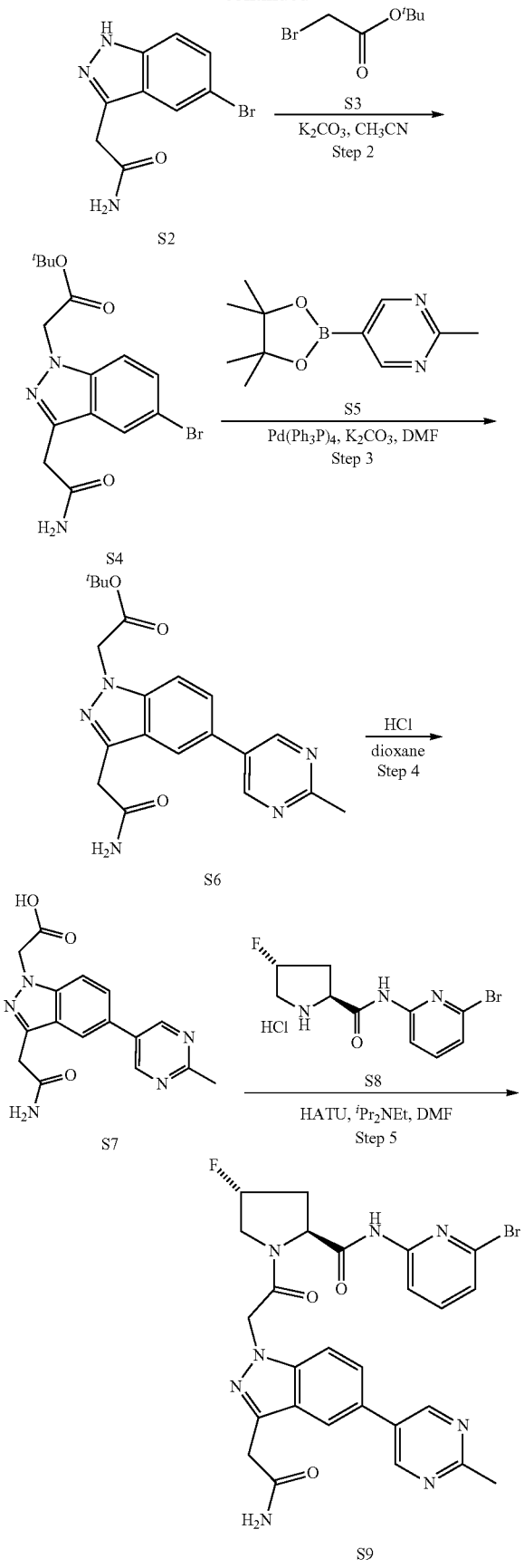

Step 1: 2-(5-Bromo-1H-indazol-3-yl)acetamide (S2)

To a solution of scheme 9-15 compound S1 (255 mg, 1 mmol), ammonium chloride (160 mg, 3 mmol), and DIPEA (646 mg, 5 mmol) in DMF (10 mL) at room temperature was added HATU (418 mg, 1.05 mmol). The resulting mixture was stirred at room temperature overnight and then concentrated. The residue was purified by column chromatography on silica gel (eluted with CH2Cl2/MeOH) to afford scheme 9-15 compound S2 (229 mg, yield 90%) as a white solid. LC-MS: m/z 254 (M+H)+.

Step 2: tert-Butyl 2-(3-(2-amino-2-oxoethyl)-5-bromo-1H-indazol-1-yl)acetate (S4)

To a mixture of scheme 9-15 compound S2 (254 mg, 1 mmol) and $K_2CO_3$ (415 mg, 3 mmol) in MeCN (5 mL) was added scheme 9-15 compound S3 (215 mg, 1.1 mmol). The resulting mixture was stirred at 60° C. for 4 h. After filtration, the filtrate was concentrated and the residue was purified by column chromatography on silica gel (eluted with hexanes/ethyl acetate=1:1) to afford scheme 9-15 compound S4 (355 mg, yield 96%). LC-MS: m/z 368 (M+H)+.

Step 3: tert-Butyl 2-(3-(2-amino-2-oxoethyl)-5-(2-methylpyrimidin-5-yl)-1H-indazol-1-yl)acetate (S6)

A solution of scheme 9-15 compound S4 (368 mg, 1 mmol), $Pd(Ph_3P)_4$, (231 mg, 0.2 mmol), $K_2CO_3$ (415 mg, 3 mmol), and scheme 9-15 compound S5 (220 mg, 1 mmol) in DMF (20 mL) under nitrogen was stirred at 90° C. for 3 h and then concentrated. The residue was purified by column chromatography on silica gel to afford scheme 9-15 compound S6 (350 mg, 92% yield). LC-MS: m/z 382 (M+H)+.

Step 4: 2-(3-(2-Amino-2-oxoethyl)-5-(2-methylpyrimidin-5-yl)-1H-indazol-1-yl)acetic Acid (S7)

Scheme 9-15 compound S6 (381 mg, 1 mmol) was treated with 4 N HCl in dioxane (3 mL) at room temperature and stirred for 6 h. The reaction mixture was concentrated and the remaining material (scheme 9-15 compound S7) was used directly in the next synthetic step. LC-MS: m/z 326 (M+H)+.

Step 5: (2S,4R)-1-(2-(3-(2-Amino-2-oxoethyl)-5-(2-methylpyrimidin-5-yl)-1H-indazol-1-yl)acetyl)-N-(6-bromopyridin-2-yl)-4-fluoropyrrolidine-2-carboxamide (S9)

To a solution of scheme 9-15 compound S7 (325 mg, 1 mmol), scheme 9-15 compound S8 (325 mg, 1 mmol), and DIPEA (646 mg, 5 mmol) in DMF (10 mL) at room temperature was added HATU (418 mg, 1.05 mmol). The resulting mixture was stirred at room temperature overnight and then concentrated. The residue was purified by column chromatography on silica gel (eluted with $CH_2Cl_2$/MeOH) to afford scheme 9-15 compound S9 (550 mg, yield 93%) as a white solid. 1H-NMR: 10.96 (s, 1H), 9.03 (s, 2H), 8.18 (s, 1H), 8.04 (d, J=8.0 Hz, 1H), 7.79-7.63 (m, 3H), 7.54 (m, 1H), 7.33 (d, J=7.8 Hz, 1H), 7.00 (m, 1H), 5.32-5.61 (m, 3H), 4.65 (m, 1H), 4.18 (m, 1H), 3.88-4.04 (m, 1H), 3.80 (m, 2H), 3.31 (s, 3H), 1.25 (m, 1H), 0.86 (m, 1H). LC-MS: m/z 595 (M+H)+.

Scheme 9-16

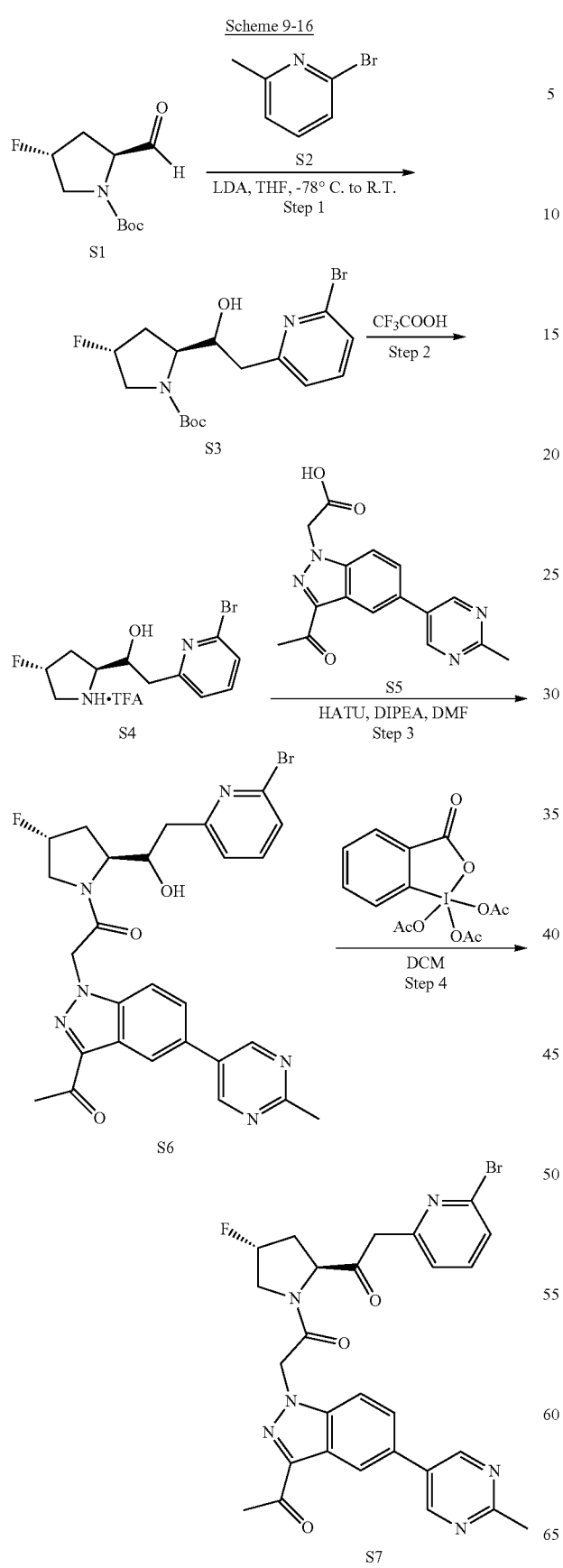

Step 1: (2S,4R)-tert-Butyl 2-((R)-2-(6-bromopyridin-2-yl)-1-hydroxyethyl)-4-fluoropyrrolidine-1-carboxylate (S3)

To a dry-ice/ethanol cooled solution of scheme 9-16 compound S2 (80 mg, 0.46 mmol) in THF (2 mL) was added LDA (0.5 mL, 0.5 mmol). After addition, the reaction mixture was stirred at room temperature for 30 min and cooled to −70° C. followed by the addition of scheme 9-16 compound S1 (100 mg, 0.46 mmol). After stirring at this temperature for 30 min, the reaction mixture was quenched with aqueous $NaHCO_3$ (10 mL). The reaction mixture was extracted with ethyl acetate (20 mL). The organic phase was washed with brine, dried over anhydrous $Na_2SO_4$, filtered, and then concentrated. The residue was purified by column chromatography on silica gel (eluted with petroleum ether/ethyl acetate=100:1 to 4:1) to afford scheme 9-16 compound S3 (60 mg, yield 35%) as a yellow oil.

Step 2: (R)-2-(6-Bromopyridin-2-yl)-1-((2S,4R)-4-fluoropyrrolidin-2-yl)ethanol (S4)

To a solution of scheme 9-16 compound S3 (60 mg, 0.15 mmol) in dry DCM (1 mL) was added TFA (1 mL) in portions. After stirring at room temperature for 1 h, the reaction mixture was concentrated to afford crude scheme 9-16 compound S4 (50 mg, yield 95%) as a yellow oil. This material was used in the next synthetic step without purification.

Scheme 9-17

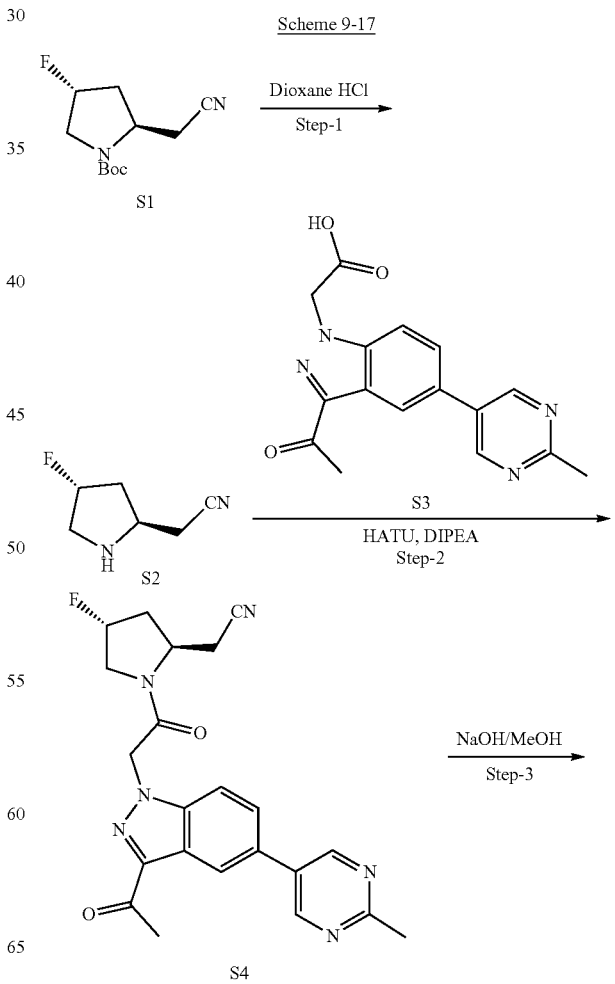

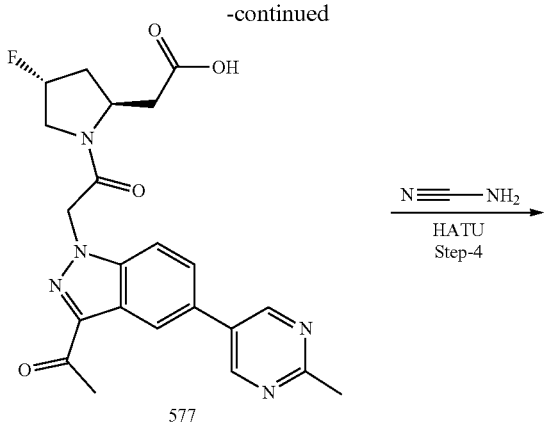

577

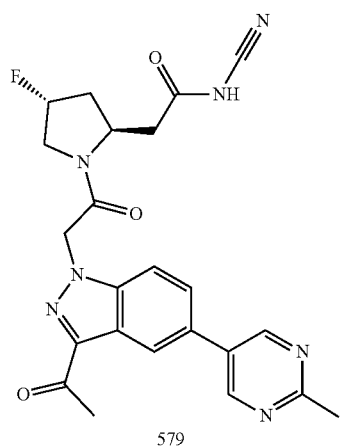

579

Step 1: 2-((2R,4R)-4-Fluoropyrrolidin-2-yl)acetonitrile (S2)

To a solution of tert-butyl (2R,4R)-2-(cyanomethyl)-4-fluoropyrrolidine-1-carboxylate (9-17 compound S1, 1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to afford scheme 9-17 compound S2.

Step 2: 2-((2R,4R)-1-(2-(3-Acetyl-5-(2-methylpyrimidin-5-yl)-1H-indazol-1-yl)acetyl)-4-fluoropyrrolidin-2-yl)acetonitrile (S4)

To a solution of scheme 9-17 compound S2 (1 equiv) in DMF (10 vol) at 0° C. under nitrogen atmosphere was added scheme 9-17 compound S3 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to afford scheme 9-17 compound S4.

Step 3: 2-((2R,4R)-1-(2-(3-Acetyl-5-(2-methylpyrimidin-5-yl)-1H-indazol-1-yl)acetyl)-4-fluoropyrrolidin-2-yl)acetic Acid (577)

To a solution of scheme 9-17 compound S4 (1 equiv) in MeOH (30 vol) at 0° C. was added 30% aqueous NaOH solution (4 vol). The reaction mixture was stirred at 100° C. for 16 h and then concentrated. The resulting mixture was acidified with 1.5 N HCl and extracted with ethyl acetate. The organic layer was separated, dried over anhydrous Na$_2$SO$_4$, filtered and then concentrated. The residue was purified by column chromatography on silica gel using DCM/MeOH to afford compound 577. $^1$H NMR (400 MHz, CD$_3$OD) δ 9.02 (s, 2H), 8.55 (s, 1H), 7.82-7.73 (m, 2H), 5.62-5.58 (m, 1H), 5.48-5.30 (m, 2H), 4.45-4.42 (m, 1H), 4.21-4.13 (m, 1H), 3.92-3.79 (m, 1H), 3.03-2.99 (m, 1H), 2.68 (s, 3H), 2.66 (s, 3H), 2.55-2.53 (m, 2H), 2.12-2.10 (m, 1H).

Step 4: 2-((2R,4R)-1-(2-(3-Acetyl-5-(2-methylpyrimidin-5-yl)-1H-indazol-1-yl)acetyl)-4-fluoropyrrolidin-2-yl)-N-cyanoacetamide (579)

To a solution of scheme 9-17 compound 577 (1 equiv) in DMF (10 vol) at 0° C. under nitrogen atmosphere was added cyanamide (1.2 equiv), HATU (1.5 equiv) and TEA (3 equiv). The reaction mixture was stirred at room temperature for 12 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to afford compound 579. $^1$H NMR (400 MHz, CD$_3$OD) δ 9.05 (s, 2H), 8.54 (s, 1H), 7.81-7.71 (m, 2H), 5.61-5.49 (m, 1H), 5.45-5.31 (m, 2H), 4.44-4.42 (m, 1H), 4.20-4.12 (m, 1H), 3.94-3.81 (m, 1H), 3.01-2.86 (m, 2H), 2.77 (s, 3H), 2.70 (s, 3H), 2.59-2.50 (m, 1H), 2.28-2.00 (m, 1H).

Scheme 9-18

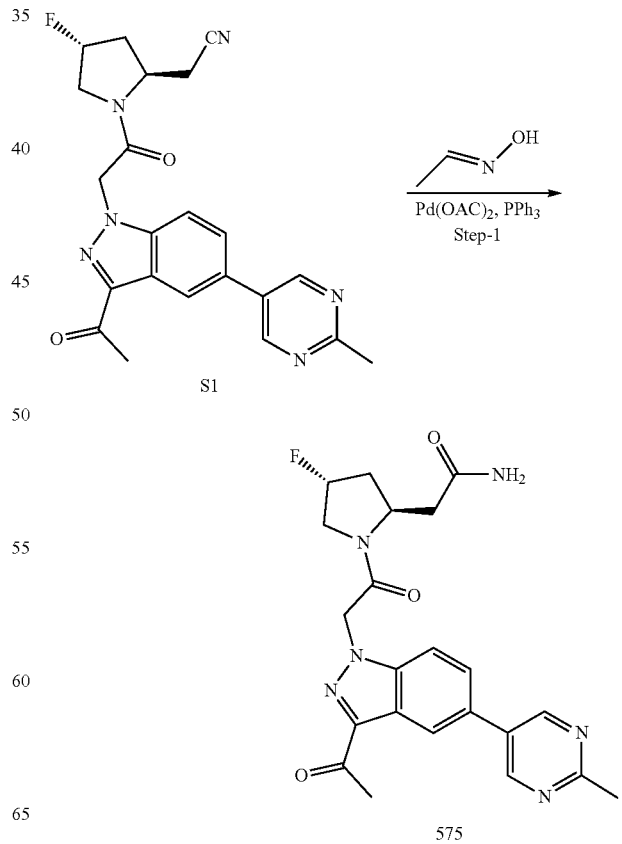

Step-1: 2-((2R,4R)-1-(2-(3-Acetyl-5-(2-methylpyrimidin-5-yl)-1H-indazol-1-yl)acetyl)-4-fluoropyrrolidin-2-yl)acetamide (575)

To a solution of 2-((2R,4R)-1-(2-(3-acetyl-5-(2-methylpyrimidin-5-yl)-1H-indazol-1-yl)acetyl)-4-fluoropyrrolidin-2-yl)acetonitrile (scheme 9-18 compound S1, 1 equiv) in H$_2$O/EtOH (1:4, 10 vol) at 0° C. under nitrogen atmosphere was added acetaldoxime (2 equiv), Pd(OAc)$_2$ (0.05 equiv) and PPh$_3$ (0.1 equiv). The reaction mixture was stirred at 90° C. for 3 h. After completion of the reaction, the reaction mixture was filtered through celite and then concentrated. The residue was purified by column chromatography on silica gel using DCM/MeOH to afford compound 575. $^1$H NMR (400 MHz, DMSO-d$_6$) δ 9.07 (s, 2H), 8.45 (s, 1H), 7.87-7.84 (m, 2H), 7.32 (s, 1H), 6.83 (s, 1H), 5.77-5.72 (m, 1H), 5.54-5.36 (m, 2H), 4.24-4.22 (m, 1H), 4.14-4.06 (m, 1H), 3.87-3.75 (m, 1H), 2.89-2.86 (s, 1H), 2.69 (s, 3H), 2.65 (s, 3H), 2.36-2.33 (m, 1H), 2.25-1.98 (m, 2H).

Scheme 9-19

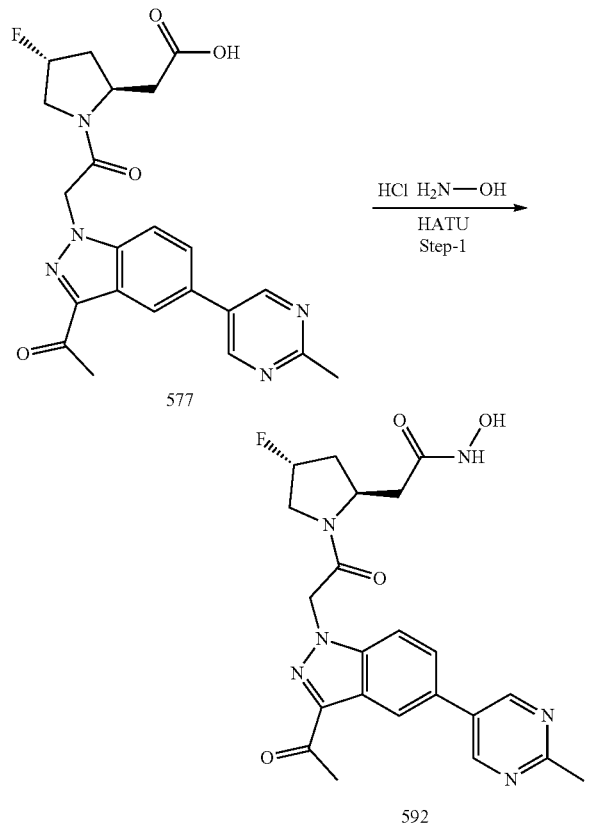

Step-1: 2-((2R,4R)-1-(2-(3-Acetyl-5-(2-methylpyrimidin-5-yl)-1H-indazol-1-yl)acetyl)-4-fluoropyrrolidin-2-yl)-N-hydroxyacetamide (592)

To a solution of compound 577 (1 equiv) in DMF (10 vol) at 0° C. under nitrogen atmosphere was added hydroxylamine hydrochloride (1.5 equiv), HATU (1.5 equiv) and DIPEA (5 equiv). The reaction mixture was stirred at room temperature for 12 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to afford compound 592. $^1$H NMR (400 MHz, DMSO-d$_6$) δ 10.42 (s, 1H), 9.06 (s, 2H), 8.44 (s, 1H), 7.86 (d, J=8.9 Hz, 2H), 5.77-5.73 (m, 1H), 5.56-5.49 (m, 1H), 5.38-5.34 (m, 1H), 4.25-4.12 (m, 2H), 4.10-4.07 (m, 1H), 2.68 (s, 3H), 2.65 (s, 3H), 2.36-2.30 (m, 2H), 2.14-2.08 (m, 2H).

Scheme 9-20

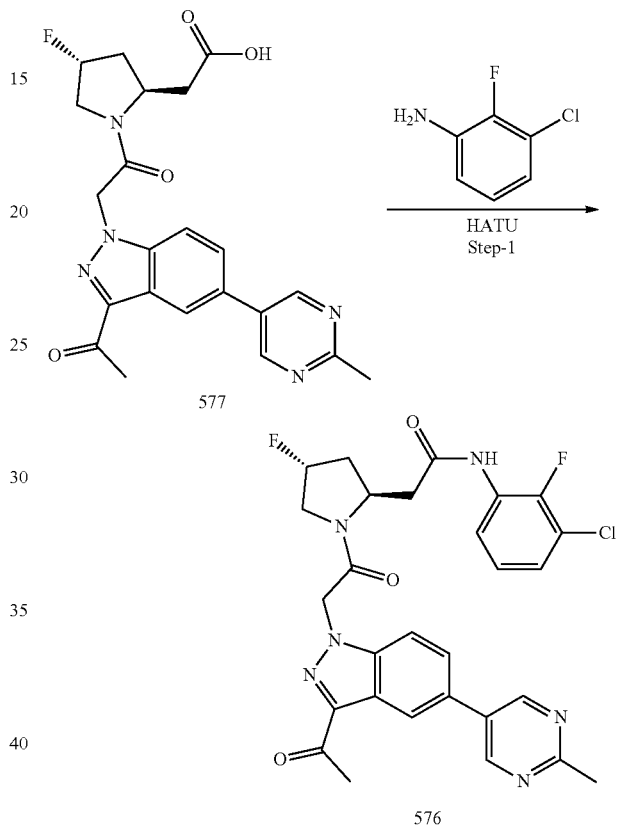

Step-1: 2-((2R,4R)-1-(2-(3-Acetyl-5-(2-methylpyrimidin-5-yl)-1H-indazol-1-yl)acetyl)-4-fluoropyrrolidin-2-yl)-N-(3-chloro-2-fluorophenyl)acetamide (576)

To a solution of compound 577 (1 equiv) in DMF (10 vol) at 0° C. under nitrogen atmosphere was added 3-chloro-2-fluoroaniline (1.5 equiv), HATU (1.5 equiv) and DIPEA (5 equiv). The reaction mixture was stirred at room temperature for 12 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to afford compound 576. $^1$H NMR (400 MHz, DMSO-d$_6$) δ 9.91 (s, 1H), 9.05 (s, 2H), 8.43 (m, 1H), 7.85-7.72 (m, 3H), 7.33-7.13 (m, 2H), 5.79-5.75 (m, 1H), 5.57-5.40 (m, 2H), 4.35-4.32 (m, 1H), 4.18-4.10 (m, 1H), 3.91-3.79 (m, 1H), 3.10 (dd, J=18.4 Hz, 3.4 Hz, 1H), 2.69 (s, 3H), 2.64 (s, 3H), 2.25-2.00 (m, 1H), 1.27-1.24 (m, 2H).

Scheme 9-21

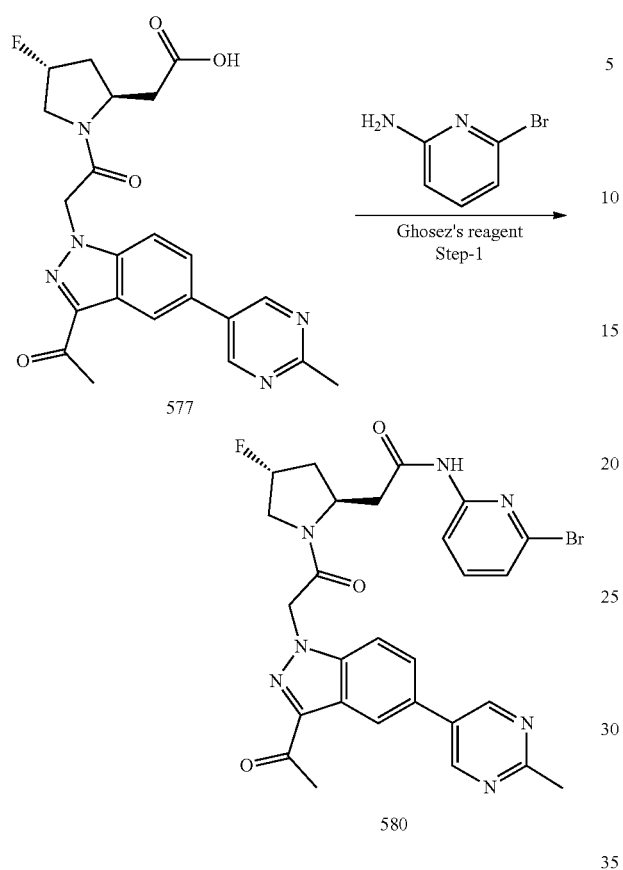

577

580

Step-1: 2-((2R,4R)-1-(2-(3-Acetyl-5-(2-methylpyrimidin-5-yl)-1H-indazol-1-yl)acetyl)-4-fluoropyrrolidin-2-yl)-N-(6-bromopyridin-2-yl)acetamide (580)

To a solution of compound 577 (1 equiv) in DCM (10 vol) at 0° C. under nitrogen atmosphere was added Ghosez's reagent. The reaction mixture was stirred at same temperature for 3 h and then 6-bromopyridin-2-amine (1 equiv), DIPEA (3 equiv) was added to the reaction mixture and the reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to afford compound 580. $^1$H NMR (400 MHz, DMSO-$d_6$) δ 10.80 (s, 1H), 9.04 (s, 2H), 8.43 (s, 1H), 8.04 (d, J=8.0 Hz, 1H), 7.88-7.67 (m, 3H), 7.29 (d, J=7.6 Hz, 1H), 5.76-5.71 (m, 1H), 5.52-5.38 (m, 2H), 4.34-4.32 (m, 1H), 4.13-4.07 (m, 1H), 3.80-3.78 (m, 1H), 3.08-3.03 (m, 1H), 2.70 (s, 3H), 2.08-2.66 (m, 1H), 2.63 (s, 3H), 2.61-2.59 (m, 1H), 2.18-2.00 (m, 1H).

Scheme 9-22

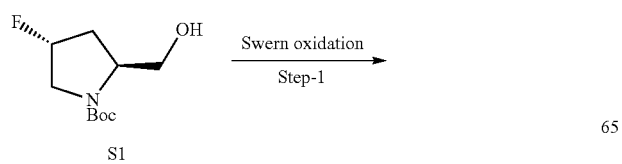

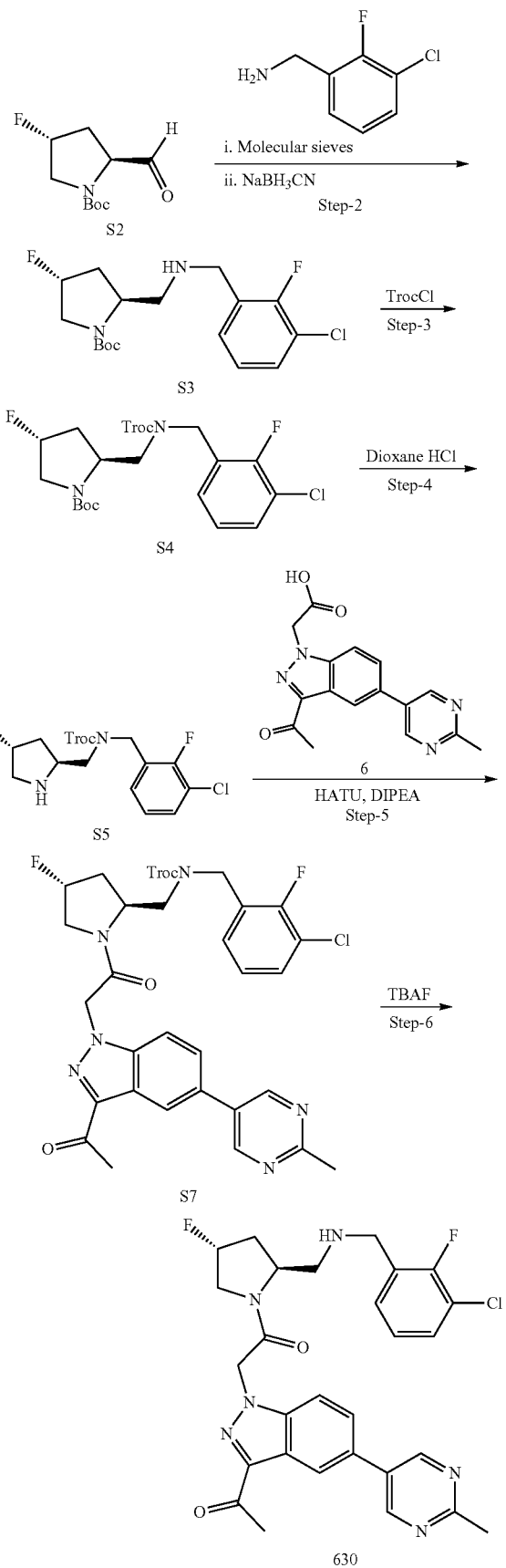

Step-1: tert-Butyl (2S,4R)-4-fluoro-2-formylpyrrolidine-1-carboxylate (S2)

To a solution of oxalyl chloride (1.3 equiv) in DCM (20 vol) at −78° C. under nitrogen atmosphere was added DMSO (1.4 equiv). The reaction mixture was stirred at the same temperature for 30 min and then (2S,4R)-4-fluoro-2-(hydroxymethyl)pyrrolidine-1-carboxylate (scheme 9-22 compound S1, 1 equiv) was added to the reaction mixture and stirred at −78° C. for 2 h. The reaction mixture was cooled to 0° C. TEA (4 equiv) was added to the reaction mixture and stirred at 0° C. for 1 h. After completion of the reaction, the reaction mixture was quenched with water. The resulting mixture was extracted with DCM. The organic layer was washed with 1.5 N HCl, 10% NaHCO$_3$ and brine, dried over anhydrous Na$_2$SO$_4$, filtered and then concentrated to afford scheme 9-22 compound S2.

Step-2: tert-Butyl (2S,4R)-2-(((3-chloro-2-fluorobenzyl)amino)methyl)-4-fluoropyrrolidine-1-carboxylate (S3)

(3-chloro-2-fluorophenyl)methanamine (1.2 equiv), molecular sieves (5%, w/w) and acetic acid (catalytic amount) were added to a solution of scheme 9-22 compound S2 (1 equiv) in MeOH (10 vol) at 0° C. under nitrogen atmosphere. The reaction mixture was stirred at room temperature for 3 h. Sodium cyanoborohydride (1.5 equiv) was added to the reaction mixture and stirred at room temperature for 12 h. After completion of the reaction, the reaction mixture was filtered through celite and then concentrated. The residue was purified by column chromatography on silica gel using Hexane/EtOAc to afford scheme 9-22 compound S3.

Step-3: tert-Butyl (2S,4R)-2-(((3-chloro-2-fluorobenzyl)((2,2,2-trichloroethoxy)carbonyl)amino)methyl)-4-fluoropyrrolidine-1-carboxylate (S4)

To a solution of scheme 9-22 compound S3 (1 equiv) in DCM (20 vol) was added 2,2,2-trichlorethoxycarbonyl chloride (1.5 equiv) and potassium carbonate (1.5 equiv). The reaction mixture was stirred at room temperature for 12 h. After completion of the reaction, the reaction mixture was filtered through celite and then concentrated. The residue was purified by column chromatography on silica gel using hexane/EtOAc to afford scheme 9-22 compound S4.

Step 4: 2,2,2-Trichloroethyl (3-chloro-2-fluorobenzyl)(((2S,4R)-4-fluoropyrrolidin-2-yl)methyl)carbamate (S5)

To a solution of scheme 9-22 compound S4 (1 equiv) in 1,4-dioxane (3 vol) at 0° C. under nitrogen atmosphere was added 4 N HCl in 1,4-dioxane (10 vol). The reaction was stirred at room temperature for 3 h and then concentrated. The residue was taken in MTBE and stirred for 30 min. The resultant solid was filtered and dried to afford scheme 9-22 compound S5.

Step-5: 2,2,2-Trichloroethyl (((2S,4R)-1-(2-(3-acetyl-5-(2-methylpyrimidin-5-yl)-1H-indazol-1-yl)acetyl)-4-fluoropyrrolidin-2-yl)methyl)(3-chloro-2-fluorobenzyl)carbamate (S7)

To a solution of scheme 9-22 compound S5 (1 equiv) in DMF (10 vol) at 0° C. under nitrogen atmosphere was added scheme 9-22 compound S6 (1.5 equiv), HATU (1.5 equiv) and DIPEA (5 equiv). The reaction mixture was stirred at room temperature for 12 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to afford scheme 9-22 compound S7.

Step-6: 2-(3-Acetyl-5-(2-methylpyrimidin-5-yl)-1H-indazol-1-yl)-1-((2S,4R)-2-(((3-chloro-2-fluorobenzyl)amino)methyl)-4-fluoropyrrolidin-1-yl)ethan-1-one (630)

To a solution of scheme 9-22 compound S7 (1 equiv) in THF (10 vol) at 0° C. was added TBAF (1.5 equiv). The reaction mixture was stirred at room temperature for 12 h and then concentrated. The residue was purified by column chromatography on silica gel using DCM/MeOH to afford compound 630. $^1$H NMR (400 MHz, CD$_3$OD) δ 9.03 (s, 2H), 8.57-8.55 (m, 1H), 7.84-7.78 (m, 2H), 7.53-7.50 (m, 1H), 7.34-7.30 (m, 1H), 7.14-7.10 (m, 1H), 5.77-5.73 (m, 1H), 5.55-5.35 (m, 2H), 4.49-4.47 (m, 1H), 4.35-4.25 (m, 3H), 4.03-3.91 (m, 1H), 3.42-3.36 (m, 2H), 2.78 (s, 3H), 2.70 (s, 3H), 2.64-2.62 (m, 1H), 2.18-2.03 (m, 1H).

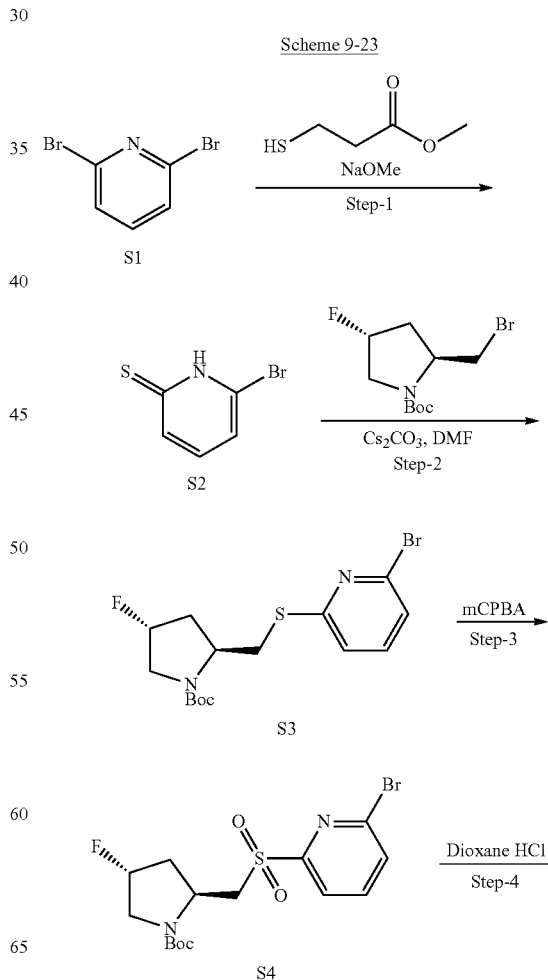

Scheme 9-23

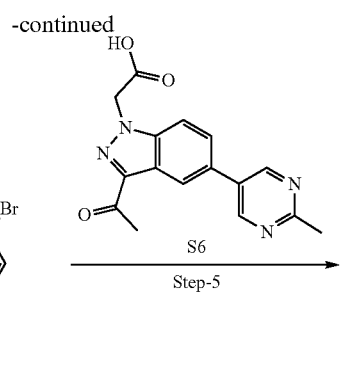

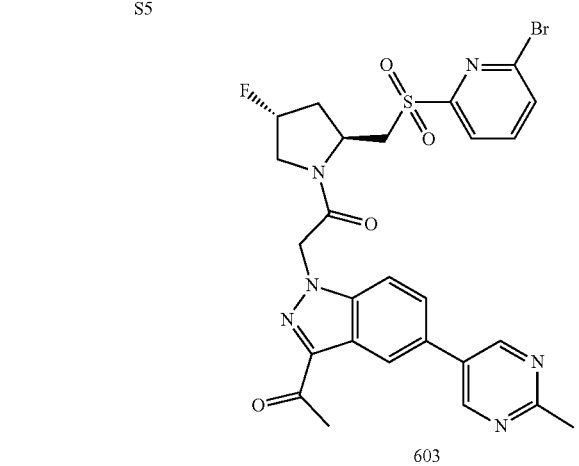

Step-1: 6-Bromopyridine-2(1H)-thione (S2)

To a solution of 2,6-dibromopyridine (scheme 9-23 compound S1, 1 equiv) in DMF (10 vol) at 0° C. under nitrogen atmosphere was added sodium methoxide (2 equiv) and methyl 3-mercaptopropanoate (2 equiv). The reaction mixture was stirred at 70° C. for 2 h and then concentrated. The resulting mixture was dissolved in MeOH (10 vol) and then sodium methoxide (2 equiv) was added to the reaction mixture. The resulting mixture was stirred at 65° C. for 1 h. After completion of the reaction, the reaction mixture was concentrated and extracted with ether. The aqueous layer was acidified with acetic acid and filtered the solid and dried to afford scheme 9-23 compound S2.

Step-2: tert-Butyl (2S,4R)-2-(((6-bromopyridin-2-yl)thio)methyl)-4-fluoropyrrolidine-1-carboxylate (S3)

To a solution of scheme 9-23 compound S2 (1 equiv) in DMF (10 vol) was added cesium carbonate (2 equiv) and tert-butyl (2S,4R)-2-(bromomethyl)-4-fluoropyrrolidine-1-carboxylate (1 equiv). The reaction mixture was stirred at room temperature for 12 h. After completion of the reaction, the reaction mixture was filtered through celite and then concentrated. The residue was purified by column chromatography on silica gel using hexane/EtOAc to afford scheme 9-23 compound S3.

Step-3: tert-Butyl (2S,4R)-2-(((6-bromopyridin-2-yl)sulfonyl)methyl)-4-fluoropyrrolidine-1-carboxylate (S4)

To a solution of scheme 9-23 compound S3 (1 equiv) in DCM (20 vol) was added mCPBA (0.7 equiv). The reaction mixture was stirred at room temperature for 12 h. After completion of the reaction, the reaction mixture was concentrated. The residue was purified by column chromatography on silica gel using hexane/EtOAc to afford scheme 9-23 compound S4.

Step 4: 2-Bromo-6-((((2S,4R)-4-fluoropyrrolidin-2-yl)methyl)sulfonyl)pyridine (S5)

To a solution of scheme 9-23 compound S4 (1 equiv) in 1,4-dioxane (3 vol) at 0° C. under nitrogen atmosphere was added 4 N HCl in 1,4-dioxane (10 vol) and stirred at room temperature for 3 h and then concentrated. The residue was taken up in MTBE and stirred for 30 min. The resultant solid was filtered and dried to afford 9-23 compound S5.

Step-5: 2-(3-Acetyl-5-(2-methylpyrimidin-5-yl)-1H-indazol-1-yl)-1-((2S,4R)-2-(((6-bromopyridin-2-yl)sulfonyl)methyl)-4-fluoropyrrolidin-1-yl)ethan-1-one (603)

To a solution of scheme 9-23 compound S5 (1 equiv) in DMF (10 vol) at 0° C. under nitrogen atmosphere was added scheme 9-23 compound S6 (1.5 equiv), HATU (1.5 equiv) and DIPEA (5 equiv). The reaction mixture was stirred at room temperature for 12 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to afford compound 603. $^1$H NMR (400 MHz, DMSO-$d_6$) δ 9.05 (s, 2H), 8.41 (s, 1H), 8.10-8.01 (m, 3H), 7.89-7.83 (m, 2H), 5.79-5.74 (m, 1H), 5.54-5.41 (m, 2H), 4.39-4.37 (m, 1H), 4.19-4.07 (m, 2H), 3.86-3.69 (m, 2H), 2.69 (s, 3H), 2.64 (s, 3H), 2.48-2.47 (m, 2H).

Scheme 9-24

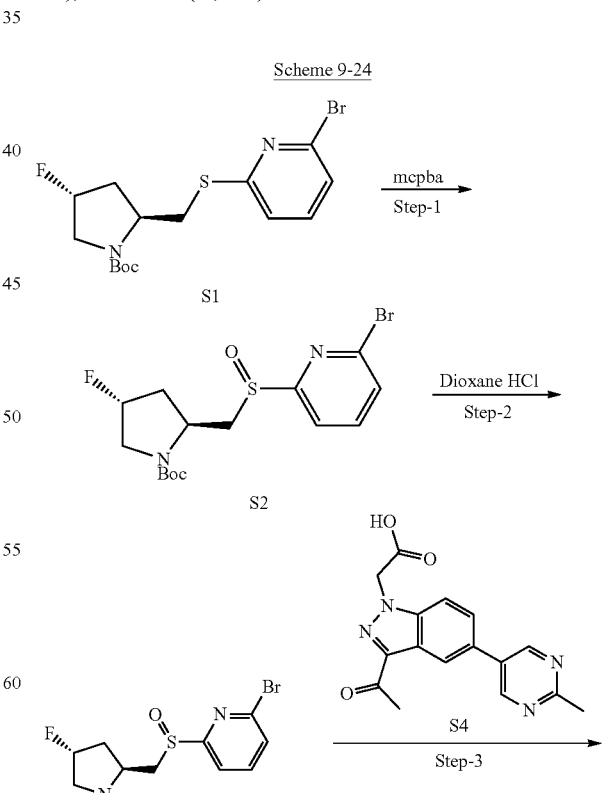

315

-continued

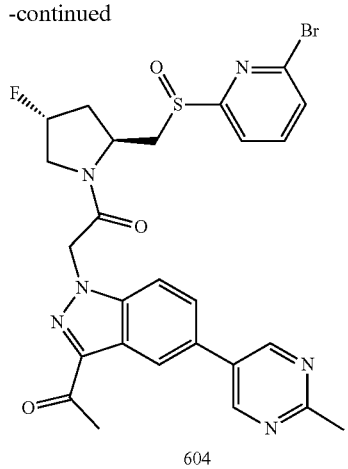

604

Step-1: tert-Butyl (2S,4R)-2-(((6-bromopyridin-2-yl)sulfinyl)methyl)-4-fluoropyrrolidine-1-carboxylate (S2)

To a solution of tert-butyl (2S,4R)-2-(((6-bromopyridin-2-yl)thio)methyl)-4-fluoropyrrolidine-1-carboxylate (9-24 compound S1, 1 equiv) in DCM (20 vol) was added mCPBA (0.7 equiv). The reaction mixture was stirred at room temperature for 1 h. After completion of the reaction, the reaction mixture was concentrated. The residue was purified by column chromatography on silica gel using hexane/EtOAc to afford scheme 9-24 compound S2.

Step 2: 2-Bromo-6-((((2S,4R)-4-fluoropyrrolidin-2-yl)methyl)sulfinyl)pyridine (S3)

To a solution of scheme 9-24 compound S2 (1 equiv) in 1,4-dioxane (3 vol) at 0° C. under nitrogen atmosphere was added 4 N HCl in 1,4-dioxane (10 vol) and stirred at room temperature for 3 h and then concentrated. The residue was taken in MTBE and stirred for 30 min. The resultant solid was filtered and dried to afford scheme 9-24 compound S3.

Step-3: 2-(3-Acetyl-5-(2-methylpyrimidin-5-yl)-1H-indazol-1-yl)-1-((2S,4R)-2-(((6-bromopyridin-2-yl)sulfinyl)methyl)-4-fluoropyrrolidin-1-yl)ethan-1-one (604)

To a solution of scheme 9-24 compound S4 (1 equiv) in DMF (10 vol) at 0° C. under nitrogen atmosphere was added scheme 9-24 compound S3 (1.5 equiv), HATU (1.5 equiv) and DIPEA (5 equiv). The reaction mixture was stirred at room temperature for 12 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to afford compound 604. $^1$H NMR (400 MHz, $CD_3OD$) δ 9.04-9.02 (m, 2H), 8.55 (s, 1H), 7.94-7.92 (m, 2H), 7.79-7.78 (m, 2H), 7.73-7.68 (m, 1H), 5.61-5.37 (m, 3H), 4.30-4.22 (m, 1H), 3.98-3.86 (m, 1H), 3.66-3.63 (m, 1H), 3.51-3.49 (m, 2H), 2.77 (s, 3H), 2.71 (s, 3H), 2.69-2.58 (m, 1H), 2.41-2.38 (m, 1H).

316

Scheme 9-25

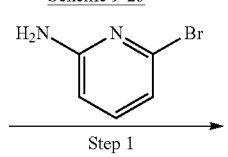

S1

Step 1

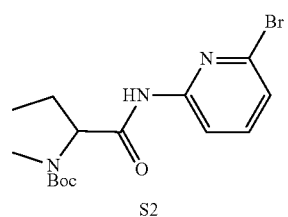

S2

Dioxane-HCl
Step 2

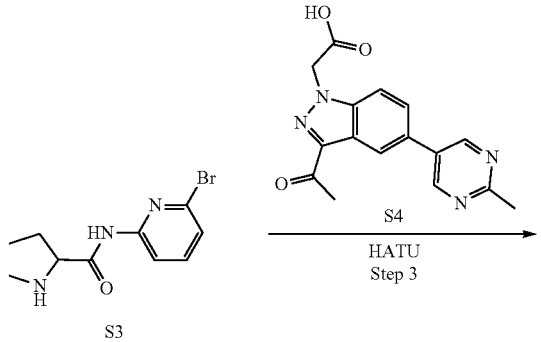

S3

S4

HATU
Step 3

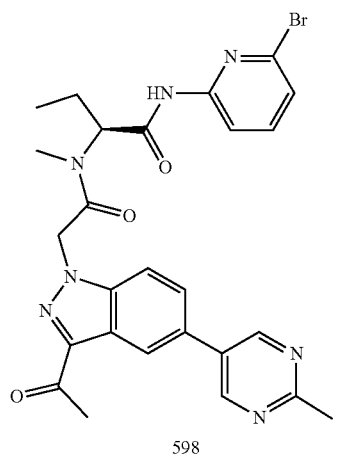

598

+

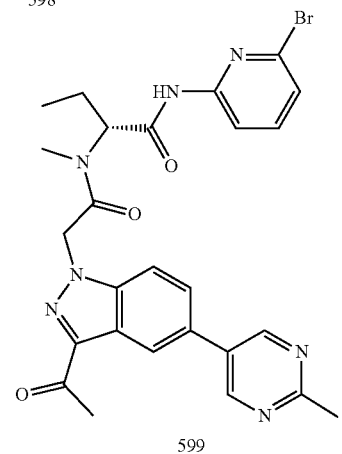

599

Step-1: tert-Butyl (1-((6-bromopyridin-2-yl)amino)-1-oxobutan-2-yl)(methyl)carbamate (S2)

To a solution of (S)-2-((tert-butoxycarbonyl)(methyl)amino)butanoic acid (scheme 9-25 compound S1, 1 equiv) in 1,2-dichloroethane (10 vol) at 0° C. under nitrogen atmosphere was added 6-bromopyridin-2-amine (1.2 equiv), EEDQ (1.5 equiv) and DIPEA (3 equiv). The reaction mixture was stirred at 80° C. for 16 h. After completion of the reaction, the reaction mixture was concentrated and the residue was extracted with ethyl acetate. The organic layer was separated, dried over anhydrous $Na_2SO_4$, filtered and then concentrated. The residue was purified by column chromatography on silica gel using Hexane/EtOAc to afford scheme 9-25 compound S2.

Step 2: N-(6-Bromopyridin-2-yl)-2-(methylamino)butanamide hydrochloride (S3)

To a solution of scheme 9-25 compound S2 (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to afford scheme 9-25 compound S3.

Step-3: (S)-2-(2-(3-Acetyl-5-(2-methylpyrimidin-5-yl)-1H-indazol-1-yl)-N-methylacetamido)-N-(6-bromopyridin-2-yl)butanamide (598) & (R)-2-(2-(3-Acetyl-5-(2-methylpyrimidin-5-yl)-1H-indazol-1-yl)-N-methylacetamido)-N-(6-bromopyridin-2-yl)butanamide (599)

To a solution of scheme 9-25 compound S3 (1 equiv) in DMF (10 vol) at 0° C. under nitrogen atmosphere was added scheme 9-25 compound S4 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to afford racemic product. This racemic product was purified by SFC to afford compound 598 as one isomer and compound 599 was another isomer. 598: $^1$H NMR (400 MHz, DMSO-$d_6$) δ 10.82 (s, 1H), 9.05 (s, 2H), 8.44 (s, 1H), 8.05 (d, J=7.4 Hz, 1H), 7.91-7.72 (m, 3H), 7.35 (d, J=7.6 Hz, 1H), 5.82-5.81 (m, 2H), 4.98-4.89 (m, 1H), 3.21 (s, 3H), 2.69 (s, 3H), 2.65 (s, 3H), 1.91-1.72 (m, 2H), 0.92 (t, J=7.3 Hz, 3H). 599: $^1$H NMR (400 MHz, DMSO-$d_6$) δ 10.79 (s, 1H), 9.04 (s, 2H), 8.43 (s, 1H), 8.04 (d, J=7.4 Hz, 1H), 7.87-7.71 (m, 3H), 7.34 (d, J=7.6 Hz, 1H), 5.79-5.78 (m, 2H), 4.97-4.93 (m, 1H), 3.20 (s, 3H), 2.68 (s, 3H), 2.64 (s, 3H), 1.97-1.77 (m, 2H), 0.92 (t, J=7.3 Hz, 3H).

Scheme 9-26

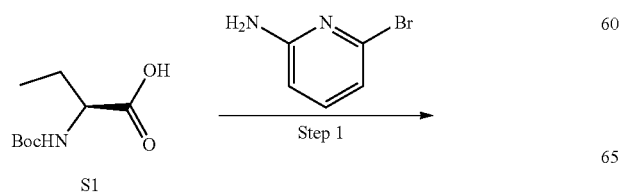

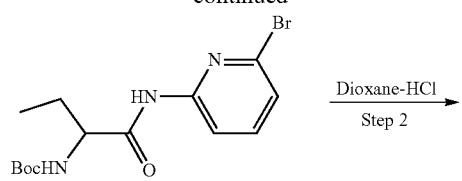

S2

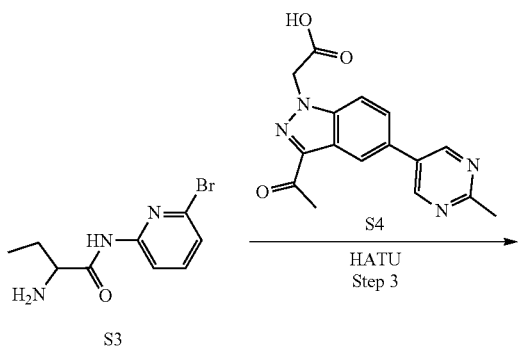

S3

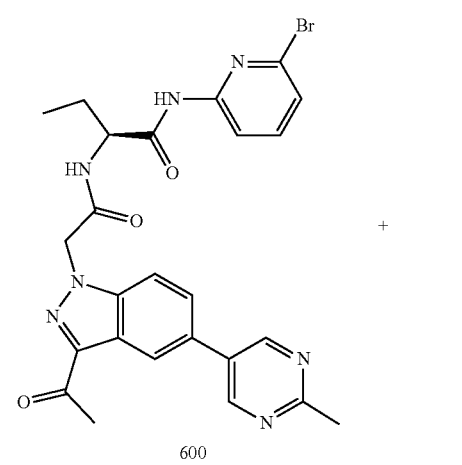

600

+

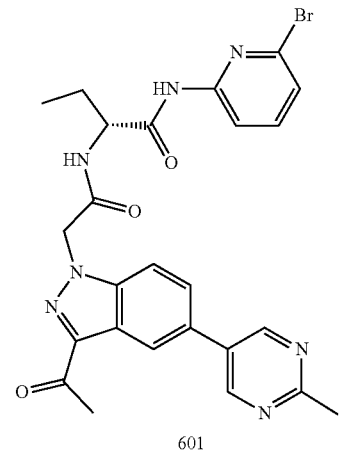

601

Step-1: tert-Butyl (1-((6-bromopyridin-2-yl)amino)-1-oxobutan-2-yl)carbamate (S2)

To a solution of (S)-2-((tert-butoxycarbonyl)amino)butanoic acid (scheme 9-26 compound S1, 1 equiv) in DMF (10 vol) at 0° C. under nitrogen atmosphere was added 6-bromopyridin-2-amine (1.2 equiv), EEDQ (1.5 equiv) and DIPEA (3 equiv). The reaction mixture was stirred at 80° C. for 16 h. After completion of the reaction, the reaction mixture was concentrated and the residue was extracted with ethyl acetate. The organic layer was separated, dried over anhydrous $Na_2SO_4$, filtered and then concentrated. The residue was purified by column chromatography on silica gel using hexane/EtOAc to afford scheme 9-26 compound S2.

Step 2:
2-amino-N-(6-bromopyridin-2-yl)butanamide hydrochloride (S3)

To a solution of scheme 9-26 compound S2 (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to afford scheme 9-26 compound S3.

Step-3: (S)-2-(2-(3-Acetyl-5-(2-methylpyrimidin-5-yl)-1H-indazol-1-yl)acetamido)-N-(6-bromopyridin-2-yl)butanamide (600) & (R)-2-(2-(3-Acetyl-5-(2-methylpyrimidin-5-yl)-1H-indazol-1-yl)acetamido)-N-(6-bromopyridin-2-yl)butanamide (601)

To a solution of scheme 9-26 compound S3 (1 equiv) in DMF (10 vol) at 0° C. under nitrogen atmosphere was added scheme 9-26 compound S4 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to afford racemic product. This racemic product was purified by SFC to afford compound 600 as one isomer and compound 601 was another isomer. 600: $^1$H NMR (400 MHz, DMSO-$d_6$) δ 10.98 (s, 1H), 9.05 (s, 2H), 8.77 (d, J=7.4 Hz, 1H), 8.43 (s, 1H), 8.09 (d, J=8.1 Hz, 1H), 7.92-7.86 (m, 2H), 7.17-7.73 (m, 1H), 7.35 (d, J=7.6 Hz, 1H), 5.48-5.38 (m, 2H), 4.52-4.47 (m, 1H), 2.69 (s, 3H), 2.65 (s, 3H), 1.81-1.72 (m, 2H), 0.96 (t, J=7.3 Hz, 3H). 601: $^1$H NMR (400 MHz, DMSO-$d_6$) δ 10.96 (s, 1H), 9.04 (s, 2H), 8.72 (S, 1H), 8.43 (d, J=2.4 Hz, 1H), 8.09-8.07 (m, 1H), 7.88-7.87 (m, 2H), 7.76-7.71 (m, 1H), 7.35-7.33 (m, 1H), 5.46-5.40 (m, 2H), 4.48-4.47 (m, 1H), 2.68 (s, 3H), 2.63 (s, 3H), 1.17-1.69 (m, 2H), 0.94 (t, J=7.3 Hz, 3H).

Scheme 9-27

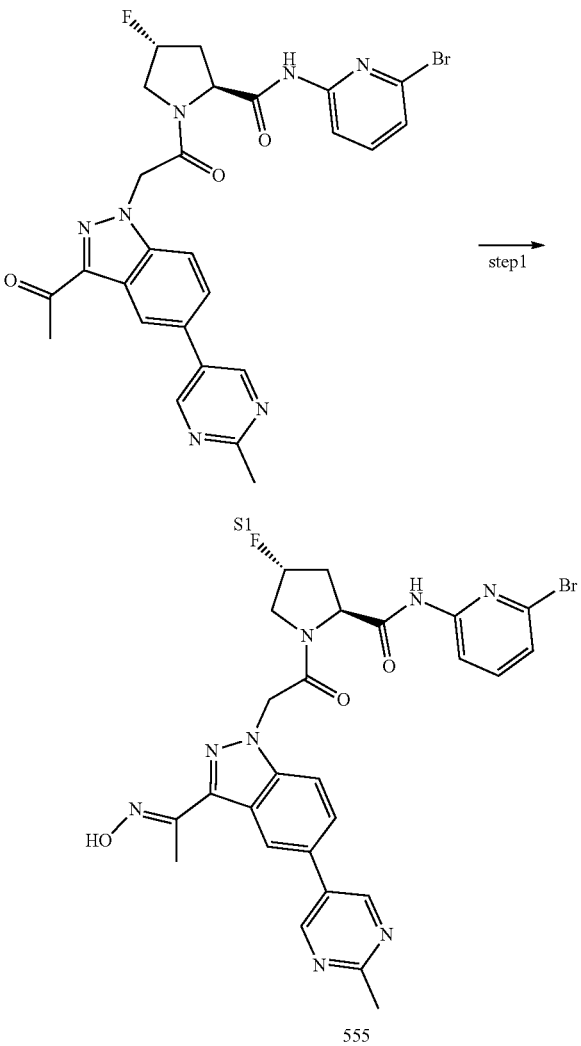

Step 1: (2S,4R)—N-(6-Bromopyridin-2-yl)-4-fluoro-1-(2-(3-((E)-1-(hydroxyimino)ethyl)-5-(2-methylpyrimidin-5-yl)-1H-indazol-1-yl)acetyl)pyrrolidine-2-carboxamide (555)

The solution of (2S,4R)-1-(2-(3-acetyl-5-(2-methylpyrimidin-5-yl)-1H-indazol-1-yl)acetyl)-N-(6-bromopyridin-2-yl)-4-fluoropyrrolidine-2-carboxamide (scheme 9-27 compound S1, 50 mg, 0.086 mmol) and hydroxylamine hydrochloride (90 mg, 1.3 mmol) in the co-solvent of ethanol-$H_2O$ (2.0 mL-0.5 mL) was heated at 90° C. for 30 min with microwave reactor. The mixture was purified by preparative HPLC to afford 29.2 mg of title product 555. $^1$H NMR (400 MHz, DMSO-$d_6$): (major rotamer) δ: 2.02-2.17 (m, 1H), 2.19 (s, 3H), 2.47-2.54 (m, 1H), 2.60 (s, 3H), 3.86-3.90 (m, 1H), 3.97-4.19 (m, 1H), 4.59 (t, J=8.4 Hz, 1H), 5.39-5.53 (m, 3H), 7.24 (d, J=7.6 Hz, 1H), 7.63-7.73 (m, 3H), 7.95 (d, J=8.0 Hz, 1H), 8.32 (s, 1H), 8.90 (s, 2H), 10.90 (s, 1H), 11.32 (s, 1H) ppm; 19F NMR (376 MHz, DMSO-$d_6$): (major rotamer) δ −175.66; LC (method A): $t_R$=1.62 min. LC/MS (EI) m/z: [M+H]$^+$ 597.06.

Scheme 9-28

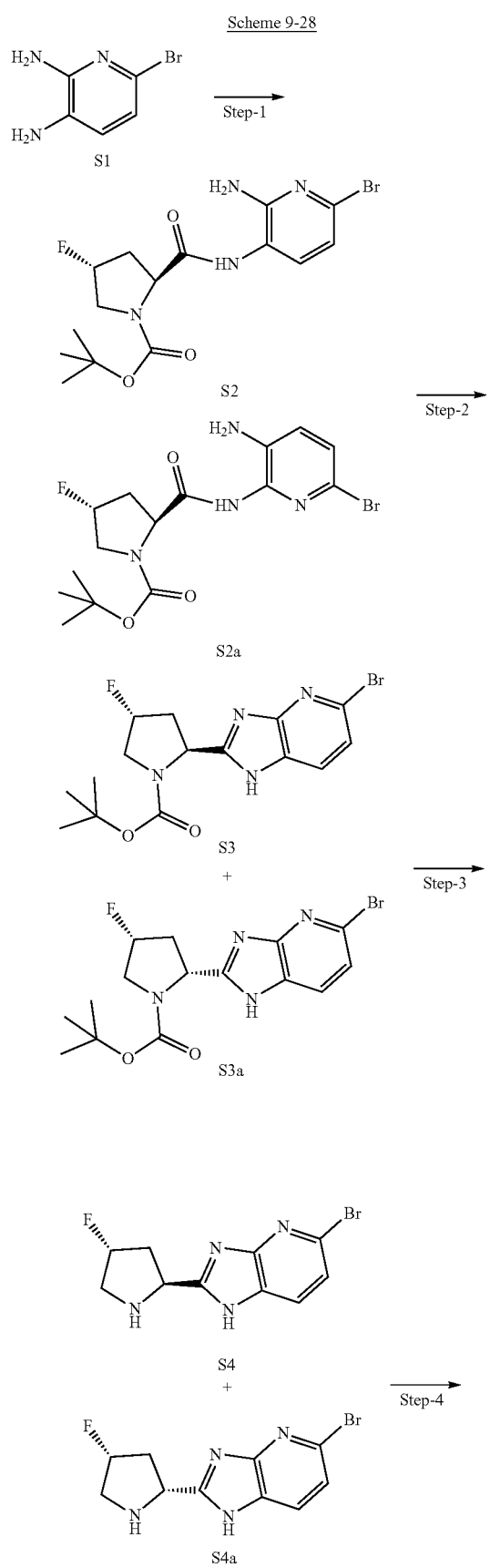

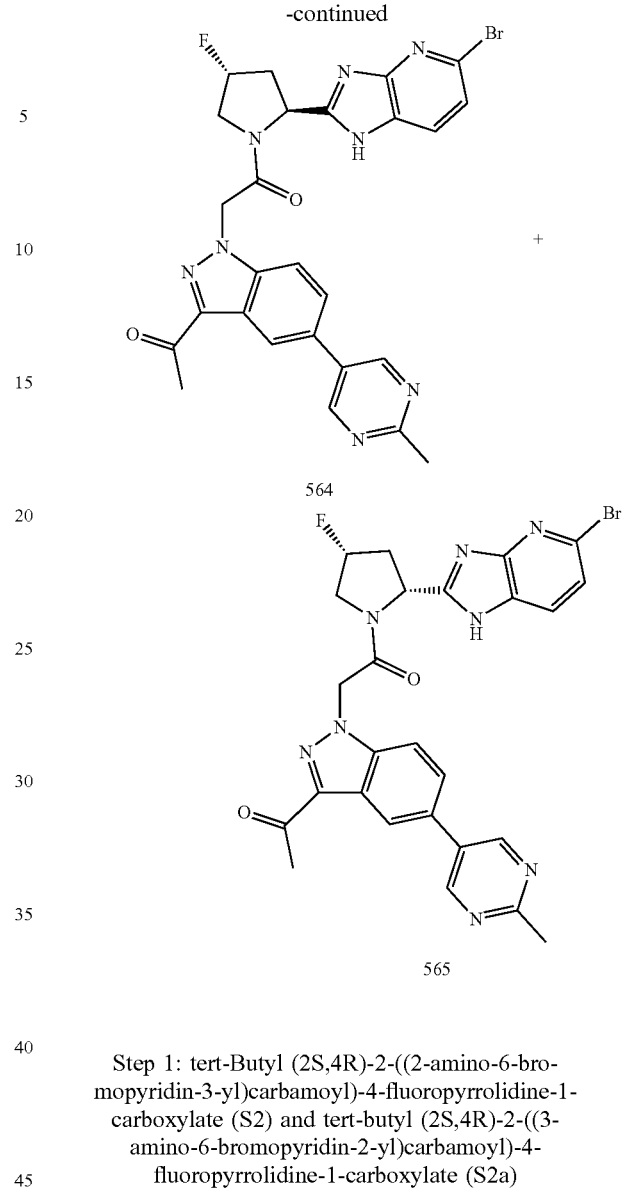

564

565

Step 1: tert-Butyl (2S,4R)-2-((2-amino-6-bromopyridin-3-yl)carbamoyl)-4-fluoropyrrolidine-1-carboxylate (S2) and tert-butyl (2S,4R)-2-((3-amino-6-bromopyridin-2-yl)carbamoyl)-4-fluoropyrrolidine-1-carboxylate (S2a)

To the solution of (2S,4R)-1-(tert-butoxycarbonyl)-4-fluoropyrrolidine-2-carboxylic acid (456 mg, 1.95 mmol), 6-bromopyridine-2,3-diamine (scheme 9-28 compound S1, 405 mg, 2.15 mmol) and EDCI (412 mg, 2.15 mmol) in CH$_3$CN (15 mL), DIEA (775 mg, 6.0 mmol) was added dropwise at 0° C. After completion of addition, the mixture was warmed to room temperature and stirred for additional 2 h. The volatiles were evaporated and the residue was mixed with water (25 mL), the resulting solid was collected, washed with water and dried. The compounds scheme 9-28 S2a and S2 were carried forward without further purification.

Step 2: tert-Butyl (2S,4R)-2-(5-bromo-1H-imidazo[4,5-b]pyridin-2-yl)-4-fluoropyrrolidine-1-carboxylate (S3) and tert-butyl (2R,4R)-2-(5-bromo-1H-imidazo[4,5-b]pyridin-2-yl)-4-fluoropyrrolidine-1-carboxylate (S3a)

Scheme 9-28 compounds S2a and S2 were suspended in toluene (20 ml) followed by addition of acetic acid (4 mL).

The mixture was heated at 130° C. overnight. The reaction was cooled to room temperature and the volatiles were evaporated. The resulting residue was neutralized with ammonium hydroxide. The precipitation was dissolved in ethyl acetate, washed with water and dried over MgSO$_4$. The solution was filtered and concentrated. The resulting title compounds were used in the next step without further purification.

Step 3: 5-Bromo-2-((2S,4R)-4-fluoropyrrolidin-2-yl)-1H-imidazo[4,5-b]pyridine hydrochloride (S4) and 5-bromo-2-((2R,4R)-4-fluoropyrrolidin-2-yl)-1H-imidazo[4,5-b]pyridine (S4a)

Scheme 9-28 compounds S3a and S3 were taken in 4N HCl dioxane (3.0 mL) and the resulting reaction mixture was stirred at room temperature for 2 h. After completion of the reaction, which was monitored by HPLC, the solvent was removed under reduced pressure and the compound mixture was carried forward without further purification.

Step 4: 2-(3-Acetyl-5-(2-methylpyrimidin-5-yl)-1H-indazol-1-yl)-1-((2S,4R)-2-(5-bromo-1H-imidazo[4,5-b]pyridin-2-yl)-4-fluoropyrrolidin-1-yl)ethan-1-one (564) and 2-(3-Acetyl-5-(2-methylpyrimidin-5-yl)-1H-indazol-1-yl)-1-((2R,4R)-2-(5-bromo-1H-imidazo[4,5-b]pyridin-2-yl)-4-fluoropyrrolidin-1-yl)ethan-1-one (565)

To the solution of 2-(3-acetyl-5-(2-methylpyrimidin-5-yl)-1H-indazol-1-yl)acetic acid (106 mg, 0.34 mmol), scheme 9-28 compounds S4a and S4 (101 mg, 0.31 mmol) in DMF (3.0 mL), HATU (178 mg, 0.47 mmol) was added, followed by dropwise addition of DIEA (0.55 mL) at room temperature. The mixture was stirred for 1 h at room temperature and the solution was purified by preparative HPLC. The fractions were combined and lyophilized to afford 16.9 mg of compound 564 and 14.4 mg of 565.

564: $^1$H NMR (400 MHz, DMSO-d$_6$): (major rotamer) a 2.42-2.55 (m, 1H), 2.66 (s, 3H), 2.69 (s, 3H), 2.74-2.82 (m, 1H), 4.20-4.29 (m, 2H), 5.38-5.92 (m, 4H), 7.38 (d, J=8.0 Hz, 1H), 7.89-8.01 (m, 3H), 8.43 (s, 1H), 9.09 (s, 2H) ppm. $^{19}$F NMR (376 MHz, DMSO-d$_6$): (major) δ −172.56 ppm. LC (method A): t$_R$=1.29 min. LC/MS (EI) m/z: [M+H]$^+$ 577.11.

565: $^1$H NMR (400 MHz, DMSO-d$_6$): (major rotamer) a 2.37-2.45 (m, 1H), 2.62 (s, 3H), 2.68 (s, 3H), 2.75-2.82 (m, 1H), 4.10-4.40 (m, 2H), 5.23 (t, J=8.40 Hz, 1H), 5.58-5.89 (m, 3H), 7.38 (d, J=8.0 Hz, 1H), 7.89-8.01 (m, 3H), 8.43 (s, 1H), 9.09 (s, 2H) ppm. $^{19}$F NMR (376 MHz, DMSO-d$_6$): (major) a −176.95 ppm. LC (method A): t$_R$=1.32 min. LC/MS (EI) m/z: [M+H]$^+$ 577.09.

Scheme 9-29

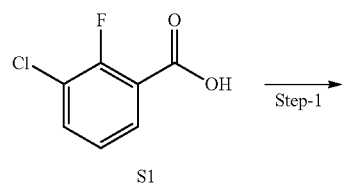

S1

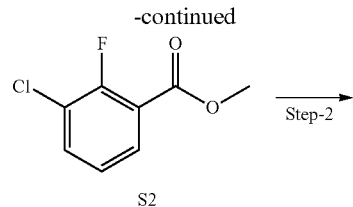

S2

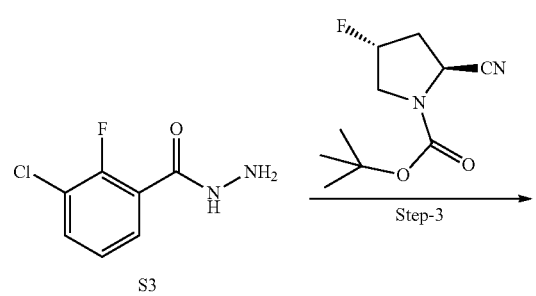

S3

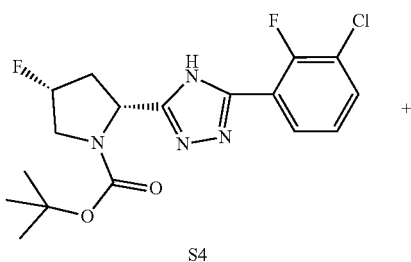

S4

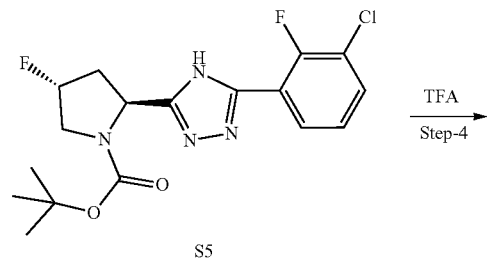

S5

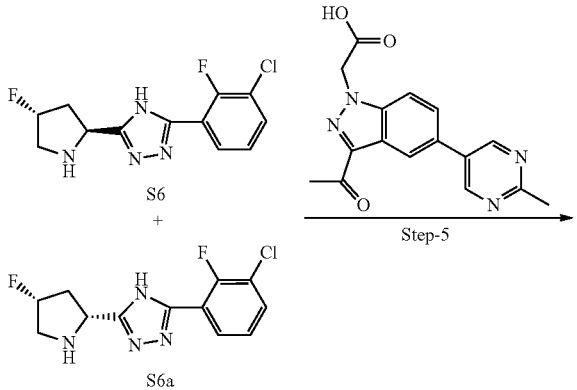

S6

+

S6a

-continued

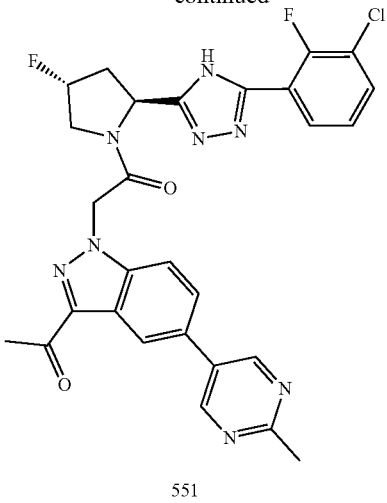
551

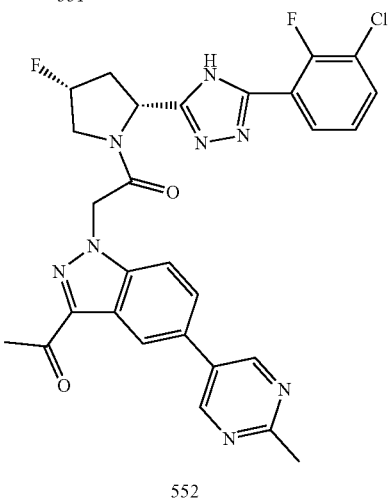
552

Step-1: Methyl 3-chloro-2-fluorobenzoate (S2)

To the solution of 3-chloro-2-fluorobenzoic acid (Scheme 9-29 compound S1 9.56 g, 54.8 mmol) in 100 mL of anhydrous methanol, concentrated $H_2SO_4$ (0.8 mL) was added carefully. The mixture was refluxed for 24 h and then cooled to room temperature. The volatiles were evaporated. The residue was dissolved in ethyl acetate (80 mL) and quenched carefully with saturated aqueous $NaHCO_3$ to PH=7. The organic layer was washed with water, brine, and then dried over $MgSO_4$. The solid was filtered off and the filtrate was concentrated. The resulting oil (10.7 g) was carried forward without further purification.

Step-2: 3-Chloro-2-fluorobenzohydrazide (S3)

To the solution of methyl 3-chloro-2-fluorobenzoate (Scheme 9-29 compound S2, 4.74 g, 25 mmol) in methanol (60 mL), hydrazine monohydrate (3.77 g, 3.65 mL, 75 mmol) was added dropwise at room temperature. Following overnight stirring, the volatiles were evaporated. The residue was suspended in hexane (100 mL), filtered and washed with hexanes. The solid was carried forward without further purification to afford the title compound. $^1$H NMR (400 MHz, $CDCl_3$): δ 4.17 (s, br, 2H), 7.21-7.27 (m, 1H), 7.56 (t, J=7.6 Hz, 1H), 7.87 (s, br, 1H), 7.98 (t, J=7.6 Hz, 1H) ppm; LC (method A): $t_R$=0.53 min. LC/MS (EI) m/z: [M+H]$^+$ 189.08, 191.04.

Step-3: tert-Butyl (2S,4R)-2-(5-(3-chloro-2-fluorophenyl)-4H-1,2,4-triazol-3-yl)-4-fluoropyrrolidine-1-carboxylate (S5) and tert-butyl (2R,4R)-2-(5-(3-chloro-2-fluorophenyl)-4H-1,2,4-triazol-3-yl)-4-fluoropyrrolidine-1-carboxylate (S4)

To the solution of 3-chloro-2-fluorobenzohydrazide (Scheme 9-29 compound S3, 377 mg, 2.0 mmol) and tert-butyl (2S,4R)-2-cyano-4-fluoropyrrolidine-1-carboxylate (428 mg, 2.0 mmol) in butanol (10 mL), solid potassium carbonate (65 mg) was added. The mixture was heated in an oil bath at 110° C. for 6 h. The reaction mixture was cooled to rt, and the volatiles were evaporated. The residue was purified to afford 508 mg of desired product Scheme 9-28 compound S5, and racemized product Scheme 9-29 compound S4 (ratio 70:30).

Step-4: 3-(3-Chloro-2-fluorophenyl)-5-((2S,4R)-4-fluoropyrrolidin-2-yl)-4H-1,2,4-triazole (S6) and 3-(3-Chloro-2-fluorophenyl)-5-((2R,4R)-4-fluoropyrrolidin-2-yl)-4H-1,2,4-triazole (S6a)

Scheme 9-29 compounds S5 and S4 were dissolved in DCM (4 mL) and treated with TFA (2 mL) at room temperature. The mixture was stirred overnight. The volatiles were evaporated and the resulting residue was co-evaporated with toluene (10 mL) twice. The residue was further dried via vacuum and carried forward without further purification.

Step-5: 2-(3-Acetyl-5-(2-methylpyrimidin-5-yl)-1H-indazol-1-yl)-1-((2S,4R)-2-(5-(3-chloro-2-fluorophenyl)-4H-1,2,4-triazol-3-yl)-4-fluoropyrrolidin-1-yl)ethan-1-one (551) and 2-(3-Acetyl-5-(2-methylpyrimidin-5-yl)-1H-indazol-1-yl)-1-((2R,4R)-2-(5-(3-chloro-2-fluorophenyl)-4H-1,2,4-triazol-3-yl)-4-fluoropyrrolidin-1-yl)ethan-1-one (552)

To the solution of 2-(3-acetyl-5-(2-methylpyrimidin-5-yl)-1H-indazol-1-yl)acetic acid (170 mg, 0.55 mmol), Scheme 9-29 compounds S4 and S5 (250 mg, 0.65 mmol) in DMF (3.0 mL), HATU (272 mg, 0.72 mmol) and DIEA (0.55 mL) were added successively at room temperature. The mixture was stirred for 1 h at room temperature and the solution was purified by preparative HPLC. The fractions were combined and lyophilized to afford 119.8 mg of compound 551 and 62.2 mg of compound 552.

551: $^1$H NMR (400 MHz, DMSO-$d_6$): (major rotamer) δ 2.25-2.41 (m, 1H), 2.55 (s, 3H), 2.61 (s, 3H), 2.62-2.71 (m, 1H), 4.22-4.30 (m, 2H), 5.18 (t, J=8.0 Hz, 1H), 5.49-5.84 (m, 3H), 7.26 (t, J=8.0 Hz, 1H), 7.58 (t, J=6.8 Hz, 1H), 7.66-7.64 (m, 2H), 7.84 (t, J=6.8 Hz, 1H), 8.34 (s, 1H), 8.94 (s, 2H) ppm. $^{19}$F NMR (376 MHz, DMSO-$d_6$): (major) δ-115.28, -177.12 ppm. LC (method A): $t_R$=1.63 min. LC/MS (EI) m/z: [M+H]$^+$ 577.11.

552: $^1$H NMR (400 MHz, DMSO-$d_6$): (major rotamer) δ 2.30-2.51 (m, 1H), 2.57 (s, 3H), 2.61 (s, 3H), 2.62-2.78 (m, 1H), 4.08-4.25 (m, 2H), 5.30-5.36 (m, 1H), 5.44-5.84 (m, 3H), 7.24 (t, J=8.0 Hz, 1H), 7.56 (t, J=6.8 Hz, 1H), 7.80-7.92 (m, 2H), 7.94-7.98 (m, 1H), 8.36 (s, 1H), 8.97 (s, 2H) ppm. $^{19}$F NMR (376 MHz, DMSO-$d_6$): (major) δ-115.24, -172.60 ppm. LC (method A): $t_R$=1.60 min. LC/MS (EI) m/z: [M+H]$^+$ 577.11.

Scheme 9-30

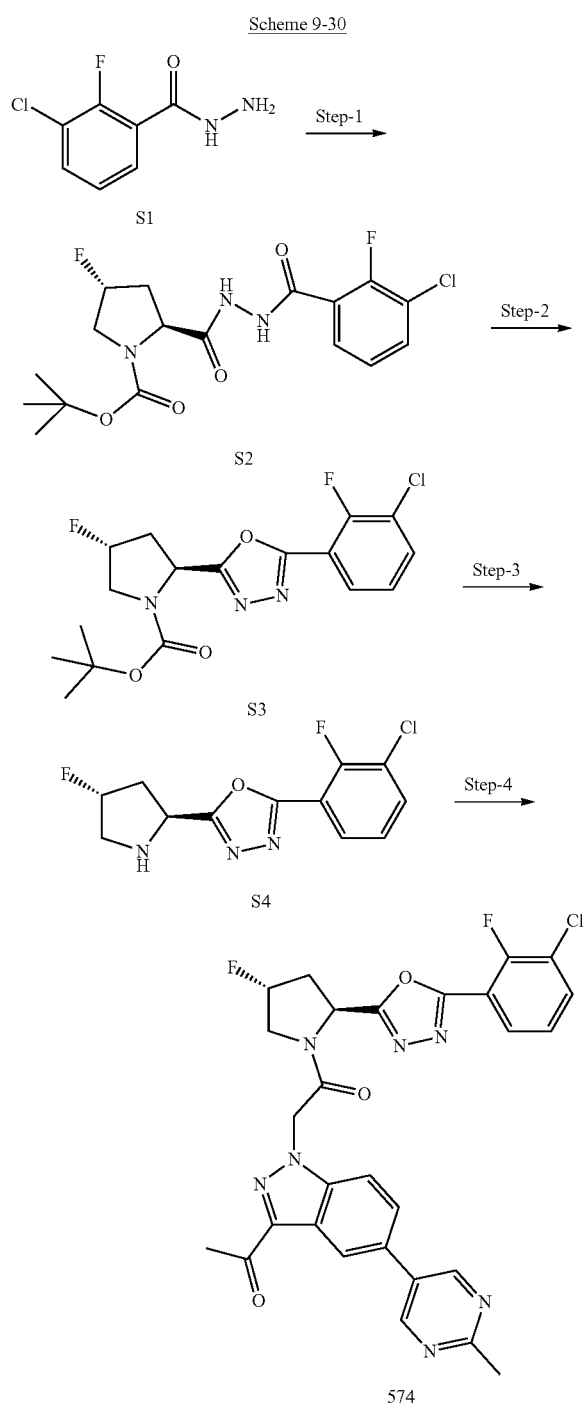

Step 1: tert-Butyl (2S,4R)-2-(2-(3-chloro-2-fluorobenzoyl)hydrazine-1-carbonyl)-4-fluoropyrrolidine-1-carboxylate (S2)

To the solution of (2S,4R)-1-(tert-butoxycarbonyl)-4-fluoropyrrolidine-2-carboxylic acid (466 mg, 2.0 mmol), 3-chloro-2-fluorobenzohydrazide (Scheme 9-30 compound S1, 380 mg, 2.0 mmol), EDCI (1.2 eq) in CH$_3$CN (10 mL), DIEA (3.0 eq) was added dropwise, and the mixture was stirred for 2 h at room temperature. The volatiles were evaporated and the resulting residue was dissolved in 30 mL of ethyl acetate. The solution was quenched with saturated aqueous NaHCO$_3$ (10 mL), extracted with ethyl acetate (30 mL), washed with water and brine and dried. The solution was filtered and concentrated to afford 702 mg of desired product. The compound was carried forward without further purification.

Step 2: tert-Butyl (2S,4R)-2-(5-(3-chloro-2-fluorophenyl)-1,3,4-oxadiazol-2-yl)-4-fluoropyrrolidine-1-carboxylate (S3)

The solution of tert-butyl (2S,4R)-2-(2-(3-chloro-2-fluorobenzoyl)hydrazine-1-carbonyl)-4-fluoropyrrolidine-1-carboxylate (Scheme 9-30 compound S2, 702 mg, 1.74 mmol) and Burgess' reagent (1.2 eq) in THF (15 mL) was refluxed for 2 h under Ar. The solution was cooled to room temperature and further concentrated. The resulting residue was purified to afford 615 mg of desire product. $^1$H NMR (400 MHz, CCl$_3$D): (major rotamer) δ1.30 (s, 9H), 2.43-2.53 (m, 1H), 2.73-2.83 (m, 1H), 3.69-3.82 (m, 1H), 3.97-4.13 (m, 1H), 5.27-5.40 (m, 2H), 7.22-7.30 (m, 1H), 7.58-7.61 (m, 1H), 7.96 (t, J=7.2 Hz, 1H) ppm

Step 3: 2-(3-Chloro-2-fluorophenyl)-5-((2S,4R)-4-fluoropyrrolidin-2-yl)-1,3,4-oxadiazole hydrochloride (S4)

tert-Butyl (2S,4R)-2-(5-(3-chloro-2-fluorophenyl)-1,3,4-oxadiazol-2-yl)-4-fluoropyrrolidine-1-carboxylate (Scheme 9-30 compound S3, 615 mg) was taken in 4N HCl dioxane (3.0 mL) and the resulting reaction mixture was stirred at rt for 2 h. After completion of the reaction, which was monitored by HPLC, the solvent was removed under reduced pressure. The residue was used carried forward without further purification.

Step 4: 2-(3-Acetyl-5-(2-methylpyrimidin-5-yl)-1H-indazol-1-yl)-1-((2S,4R)-2-(5-(3-chloro-2-fluorophenyl)-1,3,4-oxadiazol-2-yl)-4-fluoropyrrolidin-1-yl) ethan-1-one (574)

To the solution of 2-(3-chloro-2-fluorophenyl)-5-((2S,4R)-4-fluoropyrrolidin-2-yl)-1,3,4-oxadiazole hydrochloride (Scheme 9-30 compound S4, 180 mg, 0.56 mmol), 2-(3-acetyl-5-(2-methylpyrimidin-5-yl)-1H-indazol-1-yl) acetic acid (173 mg, 0.56 mmol) in DMF (2.5 mL), HATU (277 mg, 0.73 mmol) was added followed by dropwise addition of DIEA (4.0 eq) at room temperature. The mixture was stirred for 1 h at room temperature and the volatiles were evaporated. The residue was diluted with 50 mL of 10% sodium carbonate and extracted with ethyl acetate. The combined organic solution was successively washed with water, brine and dried over MgSO$_4$. The solution was filtered and the solvent was removed. The residue was purified to afford 152.4 mg of the title compound. $^1$H NMR (400 MHz, DMSO-d$_6$): (major rotamer) δ 2.37-2.47 (m, 1H), 2.53 (s, 3H), 2.60 (s, 3H), 2.67-2.78 (m, 1H), 4.05-4.31 (m, 2H), 5.33 (t, J=8.0 Hz, 1H), 5.47-5.80 (m, 3H), 7.37 (t, J=8.0 Hz, 1H), 7.65 (d, J=8.8 Hz, 1H), 7.73 (d, J=8.8 Hz, 1H), 7.80 (t, J=8.0 Hz, 1H), 7.87 (t, J=8.0 Hz, 1H), 8.31 (s, 1H), 8.90 (s, 2H) ppm. $^{19}$F NMR (376 MHz, DMSO-d$_6$): (major) δ -112.74, -176.79 ppm. LC (method A): t$_R$=1.77 min. LC/MS (EI) m/z: [M+H]$^+$ 578.16.

Scheme 9-31

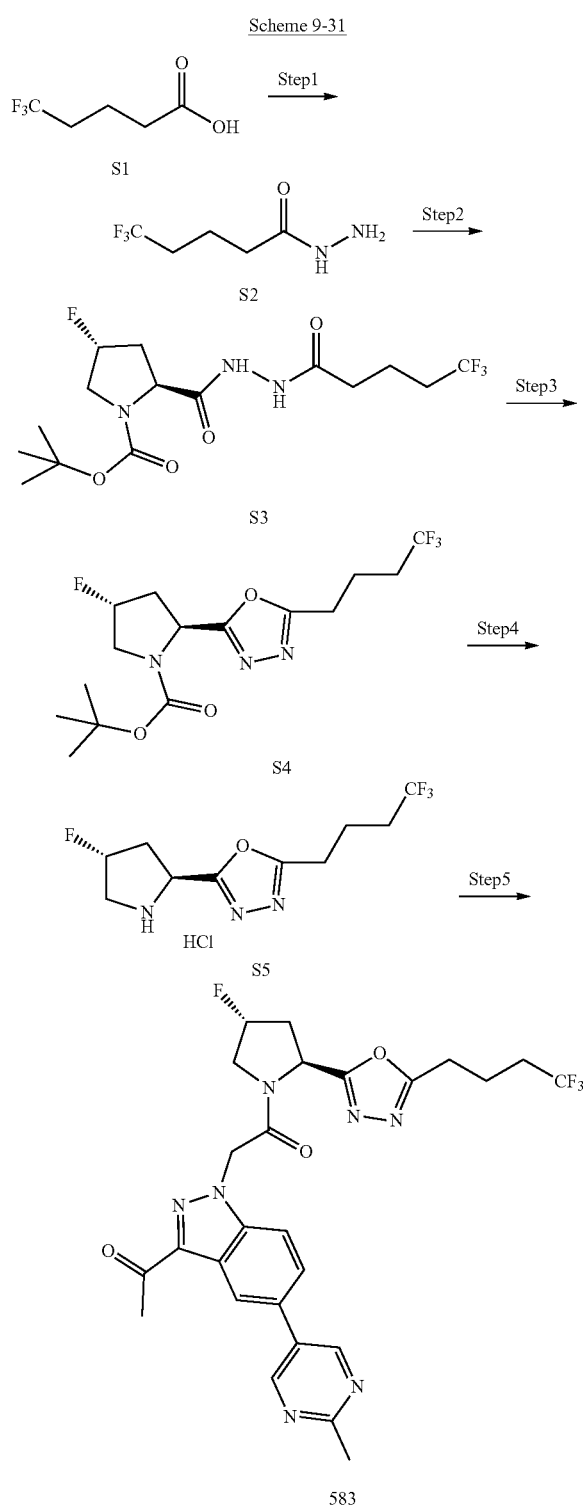

Step 1: 5,5,5-Trifluoropentanehydrazide (S2)

To the solution of 5,5,5-trifluoropentanoic acid (Scheme 9-31 compound S1, 1.05 g, 6.72 mmol) in methanol (30 mL), concentrated $H_2SO_4$ (0.2 mL) was added. The mixture was refluxed for 6 h and then cooled to room temperature. Hydrazine monohydrate (1.69 g, 1.64 mL, 33.6 mmol) was added dropwise at room temperature and the mixture was allowed to stir for 72 h. Following evaporation of the volatiles, the white solid residue was mixed with a minimal volume of water and filtered. The title compound (925 mg) was carried forward without further purification.

Step 2: tert-Butyl (2S,4R)-4-fluoro-2-(2-(5,5,5-trifluoropentanoyl)hydrazine-1-carbonyl)pyrrolidine-1-carboxylate (S3)

To the solution of (2S,4R)-1-(tert-butoxycarbonyl)-4-fluoropyrrolidine-2-carboxylic acid (Scheme 9-31 compound S2, 1.15 g, 4.93 mmol), 5,5,5-trifluoropentanehydrazide (840 mg, 4.93 mmol), EDCI (1.2 eq) in $CH_3CN$ (15 mL), DIEA (3.0 eq) was added dropwise and the mixture was stirred for 2 h at room temperature. The volatiles were evaporated and the resulting residue was dissolved in 50 mL of ethyl acetate. The solution was quenched with saturated aqueous $NaHCO_3$ (15 mL) and the upper layer of the solution was collected. The aqueous phase was extracted with ethyl acetate (50 mL). The combined organic phase was washed with water and brine and dried. The solution was filtered and concentrated to afford 1.65 g of desired product. The compound was carried forward without further purification.

Step 3: tert-Butyl (2S,4R)-4-fluoro-2-(5-(4,4,4-trifluorobutyl)-1,3,4-oxadiazol-2-yl)pyrrolidine-1-carboxylate (S4)

The solution of tert-butyl (2S,4R)-4-fluoro-2-(2-(5,5,5-trifluoropentanoyl)hydrazine-1-carbonyl)pyrrolidine-1-carboxylate (Scheme 9-31 compound S3, 1.1 g, 2.88 mmol) and Burgess' reagent (2.4 eq, 1.64 g) in THF (15 mL) was refluxed for 24 h under Ar. The solution was cooled to room temperature and further concentrated. The resulting residue was purified to afford 873 mg of the title compound.

Step 4: 2-((2S,4R)-4-Fluoropyrrolidin-2-yl)-5-(4,4,4-trifluorobutyl)-1,3,4-oxadiazole hydrochloride (S5)

tert-Butyl (2S,4R)-4-fluoro-2-(5-(4,4,4-trifluorobutyl)-1,3,4-oxadiazol-2-yl)pyrrolidine-1-carboxylate (Scheme 9-31 compound S4, 315 mg, 0.85 mmol) was taken up in 4N HCl dioxane (3.0 mL) and the resulting reaction mixture was stirred at rt for 2 h. After completion of the reaction, which was monitored by HPLC, the solvent was removed under reduced pressure. The remaining residue was used directly without further purification.

Step 5: 2-(3-Acetyl-5-(2-methylpyrimidin-5-yl)-1H-indazol-1-yl)-1-((2S,4R)-4-fluoro-2-(5-(4,4,4-trifluorobutyl)-1,3,4-oxadiazol-2-yl)pyrrolidin-1-yl)ethan-1-one (583)

To the solution of 2-((2S,4R)-4-fluoropyrrolidin-2-yl)-5-(4,4,4-trifluorobutyl)-1,3,4-oxadiazole hydrochloride (Scheme 9-31 compound S5, 0.85 mmol), 2-(3-acetyl-5-(2-methylpyrimidin-5-yl)-1H-indazol-1-yl)acetic acid (267 mg, 0.85 mmol) in DMF (3.0 mL), HATU (485 mg, 1.23 mmol) was added followed by dropwise addition of DIEA (4.0 eq) at room temperature. The mixture was stirred for 1 h at rt and the volatiles were evaporated. The residue was diluted with 50 mL of 10% sodium carbonate and extracted with ethyl acetate. The combined organic solution was successively washed with water, brine and dried over MgSO$_4$. The solution was filtered and the solvent was removed. The residue was purified to afford 83.6 mg of the title compound 583. $^1$H NMR (400 MHz, DMSO-d$_6$): (major rotamer) δ1.76-1.84 (m, 2H), 2.20-2.28 (m, 2H), 2.37-2.42 (m, 1H), 2.56 (s, 3H), 2.62 (s, 3H), 2.60-2.63 (m, 1H), 2.84 (t, J=7.6 Hz, 1H), 3.97-4.10 (m, 1H), 4.18-4.27 (m, 1H), 5.19 (t, J=8.4 Hz, 1H), 5.47-5.94 (m, 3H), 7.72 (t, J=8.8 Hz, 2H), 8.36 (s, 1H), 8.97 (s, 2H) ppm. $^{19}$F NMR (376 MHz, DMSO-d$_6$): (major) δ -64.93, -176.91 ppm. LC (method A): t$_R$=1.63 min. LC/MS (EI) m/z: [M+H]$^+$ 560.10.

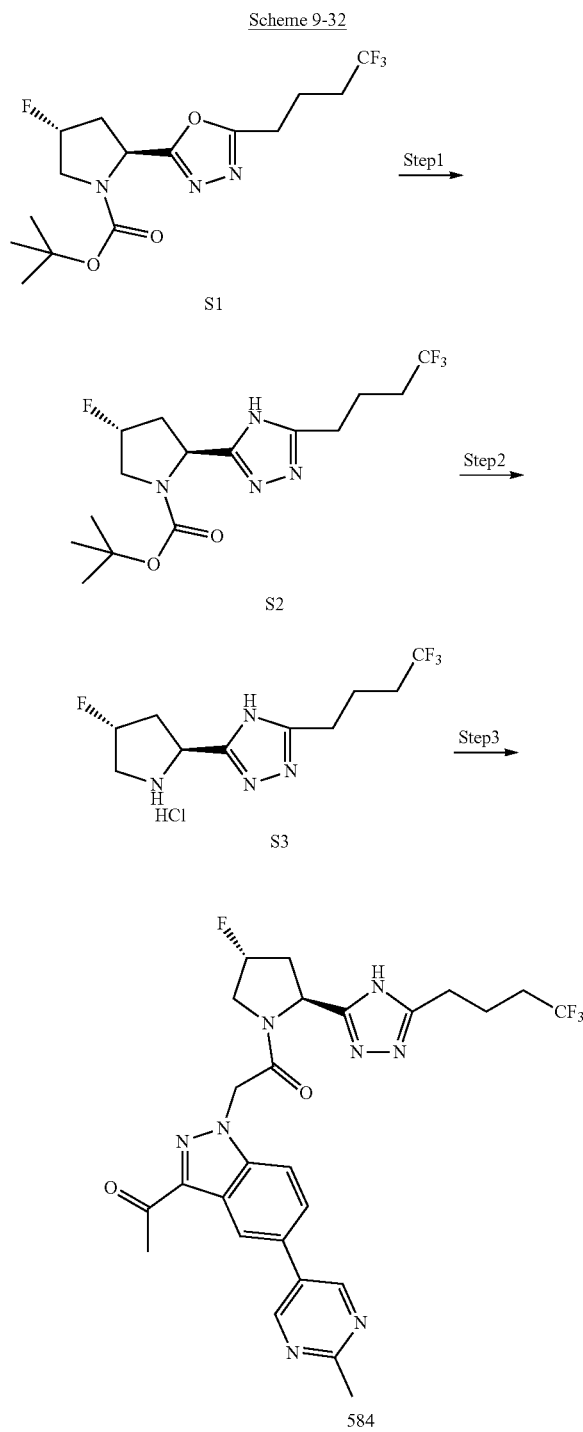

Step 1: tert-Butyl (2S,4R)-4-fluoro-2-(5-(4,4,4-trifluorobutyl)-4H-1,2,4-triazol-3-yl)pyrrolidine-1-carboxylate (S2)

To the solution of tert-Butyl (2S,4R)-4-fluoro-2-(5-(4,4,4-trifluorobutyl)-1,3,4-oxadiazol-2-yl)pyrrolidine-1-carboxylate (Scheme 9-32 compound S1, 70 mg) in o-xylene, ammonium acetate (150 mg) was added. The mixture was refluxed for 72 h while three additional batches of ammonium acetate (150 mg) were added periodically. Following consumption of the starting material, the remaining residue was dissolved in 50 mL of ethyl acetate. The solution was quenched carefully with saturated aqueous NaHCO$_3$ (15 mL), extracted into EtOAc, washed with water and brine, dried, and filtered. The title compound was carried forward without additional purification.

Step 2: 3-((2S,4R)-4-Fluoropyrrolidin-2-yl)-5-(4,4,4-trifluorobutyl)-4H-1,2,4-triazole hydrochloride (S3)

tert-Butyl (2S,4R)-4-fluoro-2-(5-(4,4,4-trifluorobutyl)-4H-1,2,4-triazol-3-yl)pyrrolidine-1-carboxylate (Scheme 9-32 compound S2) was taken up in 4N HCl dioxane (3.0 mL) and the resulting reaction mixture was stirred at rt for 2 h. After completion of the reaction, which was monitored by HPLC, the solvent was removed under reduced pressure. The remaining residue was used directly without further purification.

Step: 3 2-(3-Acetyl-5-(2-methylpyrimidin-5-yl)-1H-indazol-1-yl)-1-((2S,4R)-4-fluoro-2-(5-(4,4,4-trifluorobutyl)-4H-1,2,4-triazol-3-yl)pyrrolidin-1-yl)ethan-1-one (584)

To the solution of 3-((2S,4R)-4-fluoropyrrolidin-2-yl)-5-(4,4,4-trifluorobutyl)-4H-1,2,4-triazole hydrochloride (Scheme 9-32 compound S3, 0.13 mmol), 2-(3-acetyl-5-(2-methylpyrimidin-5-yl)-1H-indazol-1-yl)acetic acid (0.13 mmol) in DMF (3.0 mL), HATU (1.3 eq) was added followed by dropwise addition of DIEA (4.0 eq) at room temperature. The mixture was stirred for 1 h at rt and the volatiles were evaporated. The residue was diluted with 50 mL of 10% sodium carbonate and extracted with ethyl acetate. The combined organic solution was successively washed with water and brine and dried over MgSO$_4$. The solution was filtered and the solvent was removed. The residue was purified to afford 41.1 mg of the title compound. $^1$H NMR (400 MHz, DMSO-d$_6$): (major rotamer) δ1.84-1.98 (m, 2H), 2.24-2.40 (m, 3H), 2.58-2.66 (m, 1H), 2.63 (s, 3H), 2.69 (s, 3H), 2.75 (t, J=7.6 Hz, 1H), 2.86-2.90 (m, 1H), 4.01-4.12 (m, 1H), 4.24-4.33 (m, 1H), 5.15 (t, J=8.4 Hz, 1H), 5.27-5.65 (m, 2H), 5.84 (t, J=16.8 Hz, 1H), 7.82 (t, J=8.8 Hz, 2H), 8.43 (s, 1H), 9.04 (s, 2H) ppm. $^{19}$F NMR (376 MHz, DMSO-d$_6$): (major) δ -64.76, -177.07 ppm. LC (method A): t$_R$=1.43 min. LC/MS (EI) m/z: [M+H]$^+$ 559.26.

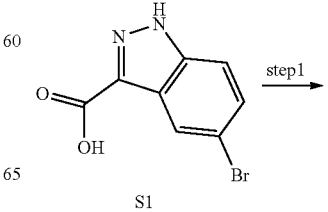

Scheme 9-33

333
-continued

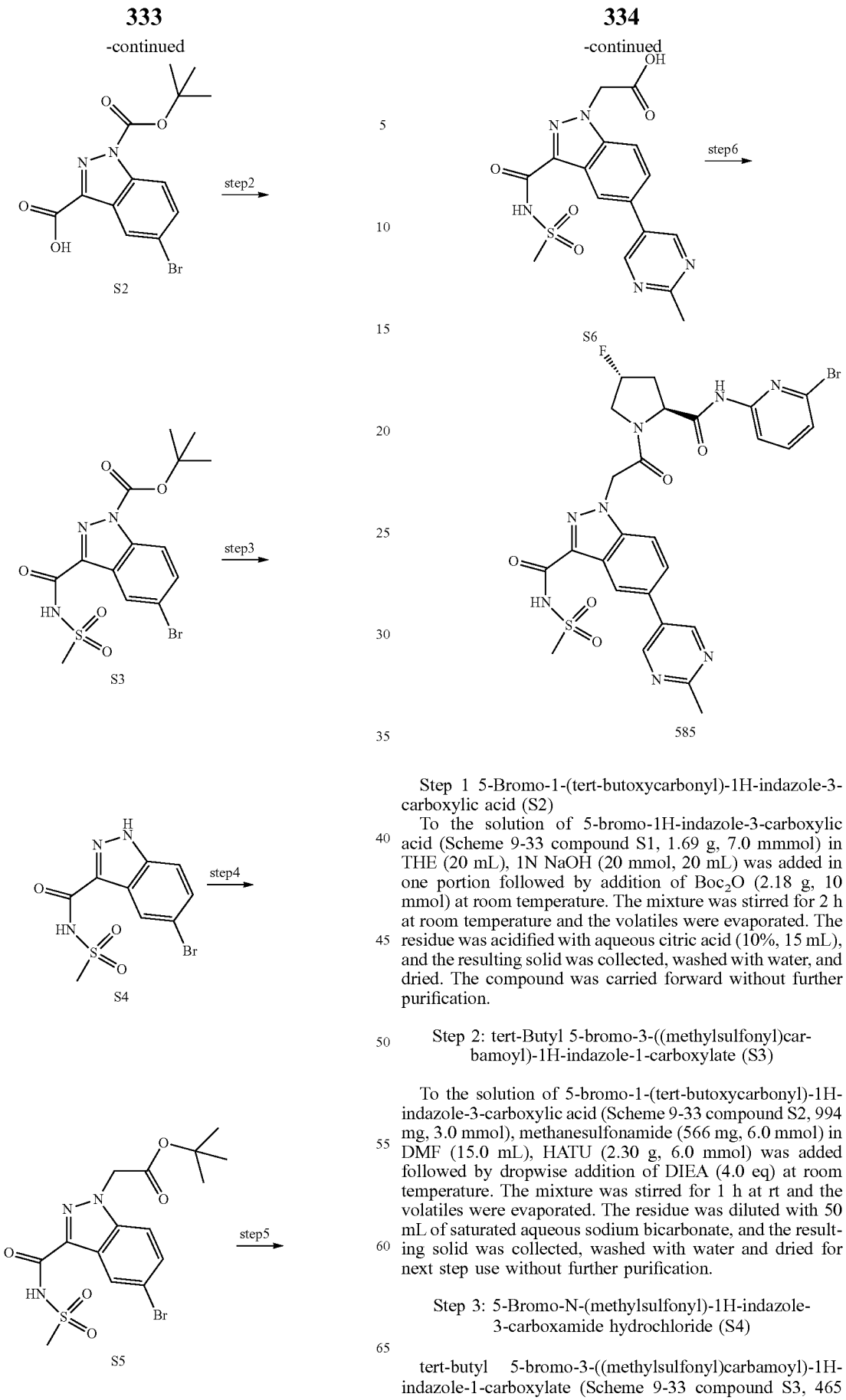

Step 1 5-Bromo-1-(tert-butoxycarbonyl)-1H-indazole-3-carboxylic acid (S2)

To the solution of 5-bromo-1H-indazole-3-carboxylic acid (Scheme 9-33 compound S1, 1.69 g, 7.0 mmmol) in THF (20 mL), 1N NaOH (20 mmol, 20 mL) was added in one portion followed by addition of Boc₂O (2.18 g, 10 mmol) at room temperature. The mixture was stirred for 2 h at room temperature and the volatiles were evaporated. The residue was acidified with aqueous citric acid (10%, 15 mL), and the resulting solid was collected, washed with water, and dried. The compound was carried forward without further purification.

Step 2: tert-Butyl 5-bromo-3-((methylsulfonyl)carbamoyl)-1H-indazole-1-carboxylate (S3)

To the solution of 5-bromo-1-(tert-butoxycarbonyl)-1H-indazole-3-carboxylic acid (Scheme 9-33 compound S2, 994 mg, 3.0 mmol), methanesulfonamide (566 mg, 6.0 mmol) in DMF (15.0 mL), HATU (2.30 g, 6.0 mmol) was added followed by dropwise addition of DIEA (4.0 eq) at room temperature. The mixture was stirred for 1 h at rt and the volatiles were evaporated. The residue was diluted with 50 mL of saturated aqueous sodium bicarbonate, and the resulting solid was collected, washed with water and dried for next step use without further purification.

Step 3: 5-Bromo-N-(methylsulfonyl)-1H-indazole-3-carboxamide hydrochloride (S4)

tert-butyl 5-bromo-3-((methylsulfonyl)carbamoyl)-1H-indazole-1-carboxylate (Scheme 9-33 compound S3, 465 mg, 1.11 mmol) was taken up in 4N HCl dioxane (3.0 mL) and stirred overnight at rt. After completion of the reaction, which was monitored by HPLC, the solvent was removed under reduced pressure. The remaining residue was used directly without further purification.

Step 4 tert-Butyl 2-(5-bromo-3-((methylsulfonyl) carbamoyl)-1H-indazol-1-yl)acetate (S5)

5-bromo-N-(methylsulfonyl)-1H-indazole-3-carboxamide hydrochloride (Scheme 9-33 compound S4) was mixed with tert-butyl 2-bromoacetate (1.5 eq) and solid potassium carbonate (3.0 eq) in $CH_3CN$ (15 mL) and the mixture was refluxed overnight. The reaction was cooled to rt and filtered. The solid residue was acidified with citric acid (10%, 50 mL) and the resulting aqueous phase was extracted with ethyl acetate three times (3×50 mL). The combined organic phases were washed with water and brine and dried. The solution was filtered, concentrated, and purified to afford 400 mg of title product. LC (method A): $t_R$=2.16 min. LC/MS (EI) m/z: [M+H]$^+$ 431.99, 434.09.

Step 5: 2-(5-(2-Methylpyrimidin-5-yl)-3-((methylsulfonyl)carbamoyl)-1H-indazol-1-yl)acetic Acid (S6)

A mixture of tert-butyl 2-(5-bromo-3-((methylsulfonyl) carbamoyl)-1H-indazol-1-yl)acetate (Scheme 9-33 compound S5, 400 mg), 2-methyl-5-(4,4,5,5-tetramethyl-1,3,2-dioxaborolan-2-yl)pyrimidine (220 mg), $K_3PO_4$ (675 mg) and Pd(dppf)$_2$Cl2 (124 mg) in solvent (dioxane 12 mL, H2O 3.0 mL) was purged with argon in a pressure vessel for 5 min and stirred for 15 h at 95° C. The volatiles were removed under reduced pressure and the residue was washed with ethyl acetate twice. The remaining solid was then quenched with citric acid (10%) and the resulting precipitate was collected and dried for next step use without further purification. LC (method A): $t_R$=0.65 min. LC/MS (EI) m/z: [M+H]$^+$ 390.13.

Step 6: 1-(2-((2S,4R)-2-((6-bromopyridin-2-yl)carbamoyl)-4-fluoropyrrolidin-1-yl)-2-oxoethyl)-5-(2-methylpyrimidin-5-yl)-N-(methylsulfonyl)-1H-indazole-3-carboxamide (585)

To the solution of (2S,4R)—N-(6-bromopyridin-2-yl)-4-fluoropyrrolidine-2-carboxamide hydrochloride (0.24 mmol), 2-(5-(2-methylpyrimidin-5-yl)-3-((methylsulfonyl) carbamoyl)-1H-indazol-1-yl)acetic acid (Scheme 9-33 compound S6, 94 mg, 0.24 mmol) in DMF (3.0 mL), HATU (1.3 eq) was added followed by dropwise addition of DIEA (4.0 eq) at room temperature. The mixture was stirred for 1 h at rt and the solution was purified by preparative HPLC to afford 87.9 mg of the title compound. $^1$H NMR (400 MHz, DMSO-d$_6$): (major rotamer) δ 2.01-2.24 (m, 1H), 2.51-2.61 (m, 1H), 2.69 (s, 3H), 3.39 (s, 3H), 3.86-4.09 (m, 1H), 4.20-4.29 (m, 1H), 4.67 (t, J=8.4 Hz, 1H), 5.45-5.82 (m, 3H), 7.32 (d, J=7.6 Hz, 1H), 7.71 (t, J=7.6 Hz, 1H), 7.90 (s, 2H), 8.01 (d, J=8.4 Hz, 1H), 8.39 (s, 1H), 9.06 (s, 2H), 11.01 (s, 1H), 12.00 (br, s, 1H) ppm. $^{19}$F NMR (376 MHz, DMSO-d$_6$): (major) δ −175.68 ppm. LC (method A): $t_R$=1.51 min. LC/MS (EI) m/z: [M+H]$^+$ 658.88, 661.05.

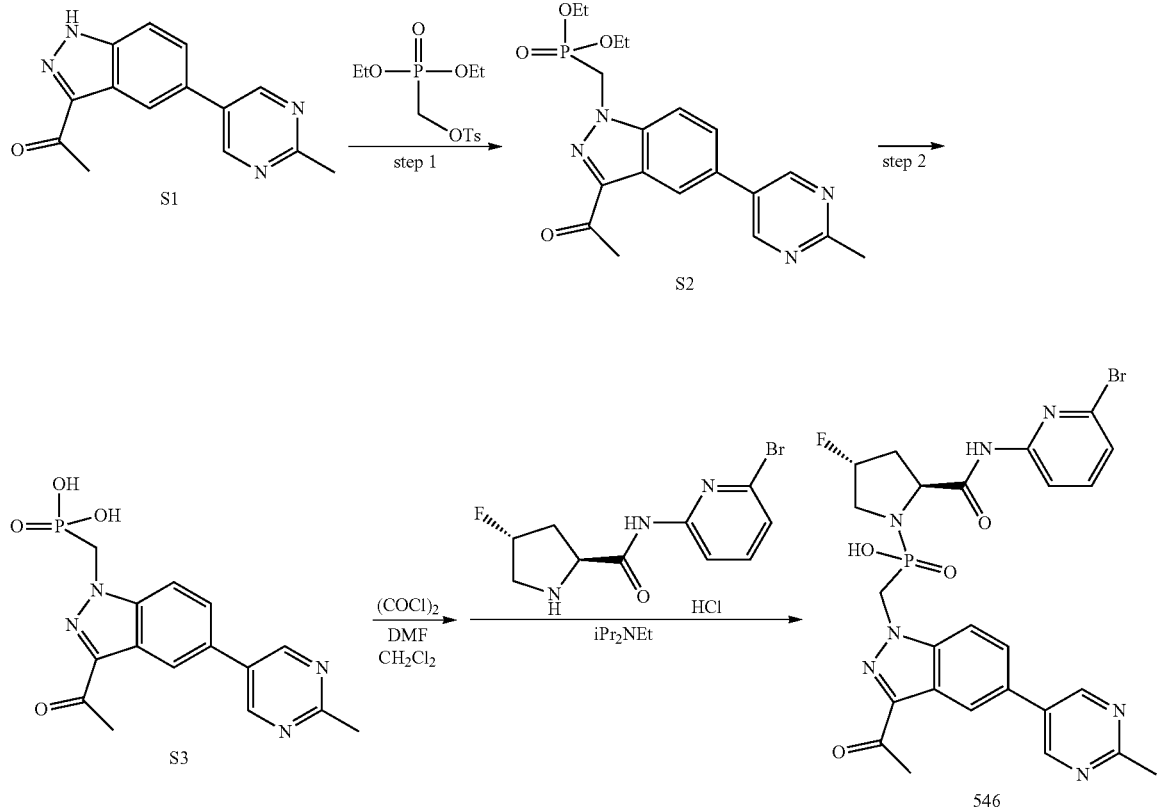

Step 1: Diethyl ((3-acetyl-5-(2-methylpyrimidin-5-yl)-1H-indazol-1-yl)methyl)phosphonate (S2)

A mixture of 1-(5-(2-methylpyrimidin-5-yl)-1H-indazol-3-yl)ethan-1-one (scheme 9-34 compound S1, 500 mg), (diethoxyphosphoryl)methyl 4-methylbenzenesulfonate (770 mg) and potassium carbonate (820 mg) in CH₃CN (20 mL) was stirred for 16 h at 90° C. Volatiles were removed in vacuo and the residue was purified by silicagel chromatography to afford 790 mg of the title compound.

Step 2: ((3-Acetyl-5-(2-methylpyrimidin-5-yl)-1H-indazol-1-yl)methyl)phosphonic Acid (S3)

diethyl ((3-acetyl-5-(2-methylpyrimidin-5-yl)-1H-indazol-1-yl)methyl)phosphonate (scheme 9-34 compound S2, 402 mg) was dissolved in DCM (5 mL) and TMS-Br (1 mL) was added. The reaction mixture was stirred overnight at rt and then the solvent was removed under reduced pressure. The remaining material was used directly in the next step.

Step 3 (2S,4R)-1-(2-(3-Acetyl-5-(2-methylpyrimidin-5-yl)-1H-indazol-1-yl)acetyl)-N-(6-bromopyridin-2-yl)-4-fluoropyrrolidine-2-carboxamide (546)

To a solution of ((3-acetyl-5-(2-methylpyrimidin-5-yl)-1H-indazol-1-yl)methyl)phosphonic acid (scheme 9-34 compound S3) in DCM (5 mL) was added oxalyl chloride (1 mL) followed by DMF. The reaction was refluxed. Following removal of solvent, the residue was added to DCM (10 mL). (2S,4R)—N-(6-bromopyridin-2-yl)-4-fluoropyrrolidine-2-carboxamide hydrochloride and DIEA (0.5 mL) were added successively and the reaction was stirred for 16 h at room temperature. Excess solvent was removed in vacuo and the residue was purified by HPLC to afford the title compound.

$^1$H NMR (400 MHz, DMSO) δ 1.91-2.04 (m, 1H), 2.01-2.21 (m, 1H), 2.52 (d, J=5.4 Hz, 1H), 2.53-2.64 (m, 2H), 2.97-3.12 (m, 2H), 3.15 (s, 1H), 3.25 (m, 1H), 3.46-3.54 (m, 1H), 4.17 (t, J=8.7 Hz, 1H), 4.55 (t, J=10.2 Hz, 1H), 4.62-4.74 (m, 1H), 5.17-5.27 (m, 0.5H), 5.31-5.42 (m, 0.5H), 7.22-7.36 (m, 1H), 7.62-7.76 (m, 2H), 7.87 (d, J=11.2 Hz, 1H), 7.88-8.04 (m, 2H), 8.29 (d, J=7.8 Hz, 1H), 8.82 (d, J=11.4 Hz, 1H), 8.93 (d, J=14.4 Hz, 1H), 10.77 (s, 1H); $^{19}$F NMR (376 MHz, DMSO) (major rotamer) δ −174.64. $^{31}$P NMR (162 MHz, DMSO) δ 9.50. LC (method A): $t_R$=1.10 min. LC/MS (EI) m/z: [M+H]⁺ 616.

Scheme 9-35

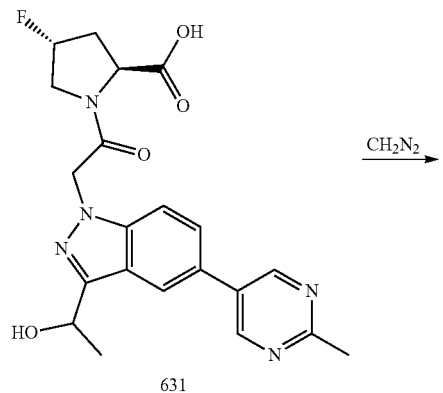

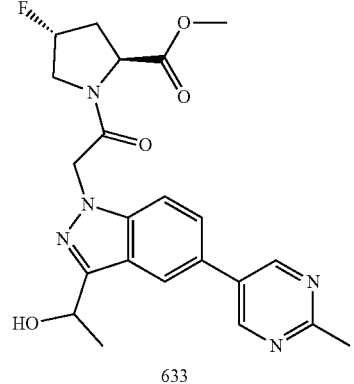

Methyl (2S,4R)-4-fluoro-1-(2-(3-(1-hydroxyethyl)-5-(2-methylpyrimidin-5-yl)-1H-indazol-1-yl)acetyl)pyrrolidine-2-carboxylate (633)

To a solution of (2S,4R)-4-fluoro-1-(2-(3-(1-hydroxyethyl)-5-(2-methylpyrimidin-5-yl)-1H-indazol-1-yl)acetyl)pyrrolidine-2-carboxylic acid (scheme 9-35 compound 631, 427 mg) in Et₂O (5 mL) was added diazomethane Et₂O solution dropwise. The reaction was stirred for 3 h. The reaction mixture was then added AcOH and removed all solvent. The remaining residue was purified by HPLC to afford the title compound 633. $^1$H NMR (400 MHz, DMSO) δ 1.59 (m, 2H), 2.01-2.23 (m, 1H), 2.68 (s, 3H), 3.01 (s, 0.5H), 3.61 (s, 3H), 3.77-3.89 (m, 1H), 3.95 (d, J=12.5 Hz, 0.5H), 4.18 (dd, J=12.6, 21.9 Hz, 1H), 4.39 (m, 1H), 5.12-5.20 (m, 1H), 5.26-5.58 (m, 3H), 5.57 (d, J=8.2 Hz, 1H), 7.42 (s, 0.5H), 7.46-7.68 (m, 1H), 7.77 (d, J=8.7 Hz, 1H), 8.04 (s, 0.5H), 8.28 (s, 1H), 9.05 (s, 2H); $^{19}$F NMR (376 MHz, DMSO-d₆): (major rotamer) δ −176.06. LC (method A): $t_R$=0.95 min. LC/MS (EI) m/z: [M+H]⁺ 442.

Scheme 9-36

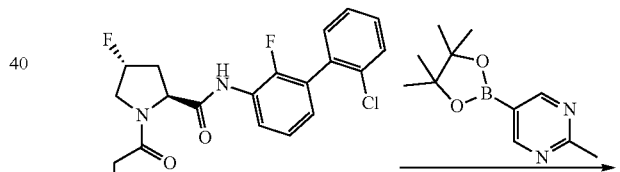

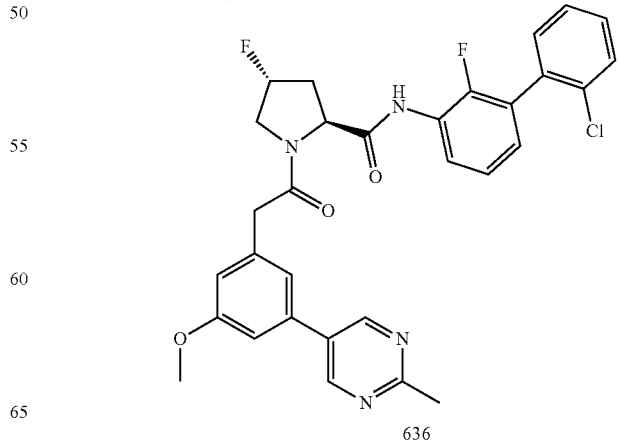

339

(2S,4R)—N-(2'-chloro-2-fluoro-[1,1'-biphenyl]-3-yl)-4-fluoro-1-(2-(3-methoxy-5-(2-methylpyrimidin-5-yl)phenyl)acetyl)pyrrolidine-2-carboxamide (636)

Pd(PPh$_3$)$_4$ (3.7 mg, 0.0032 mmol) was added into a mixture of (2S,4R)-1-(2-(3-bromo-5-methoxyphenyl)acetyl)-N-(2'-chloro-2-fluoro-[1,1'-biphenyl]-3-yl)-4-fluoropyrrolidine-2-carboxamide (scheme 9-36 compound S1, 36 mg, 0.064 mmol), 2-methyl-5-(4,4,5,5-tetramethyl-1,3,2-dioxaborolan-2-yl)pyrimidine (17 mg, 0.077 mmol), and Cs$_2$CO$_3$ (42 mg, 0.128 mmol) in DMF-water (1-0.1 mL) The mixture was heated at 80° C. under Ar for 6 h and then cooled to rt. Water was added and the mixture was extracted with AcOEt. After washing with brine and drying over anhydrous Na$_2$SO$_4$, solvent was removed by evaporation. The residue was purified on silica gel column chromatography with EtOAc in hexane (50-100%) as the eluent to afford (2S,4R)—N-(2'-chloro-2-fluoro-[1,1'-biphenyl]-3-yl)-4-fluoro-1-(2-(3-methoxy-5-(2-methylpyrimidin-5-yl)phenyl)acetyl)pyrrolidine-2-carboxamide (scheme 9-36 compound 636, 24.3 mg).

$^1$H NMR (400 MHz, CDCl$_3$) δ 9.34 (d, J=2.9 Hz, 1H), 8.78 (s, 2H), 8.26 (ddd, J=1.7, 7.3, 8.7 Hz, 1H), 7.46 (ddt, J=1.6, 3.2, 6.4 Hz, 1H), 7.36-7.25 (m, 3H), 7.16 (td, J=1.1, 8.0 Hz, 1H), 7.06-6.97 (m, 2H), 6.94 (dd, J=1.6, 2.4 Hz, 1H), 6.85 (dd, J=1.5, 2.4 Hz, 1H), 5.43-5.22 (m, 1H), 5.00 (dd, J=7.0, 8.4 Hz, 1H), 3.99 (ddt, J=1.7, 12.5, 19.7 Hz, 1H), 3.87-3.75 (m, 2H), 3.73 (s, 3H), 3.64 (ddd, J=3.5, 12.4, 32.8 Hz, 1H), 2.96-2.80 (m, 1H), 2.54-2.37 (m, 1H). LC (method A): t$_R$=2.18 min. LC/MS (EI) m/z: [M+H]$^+$ 577.

Scheme 9-37

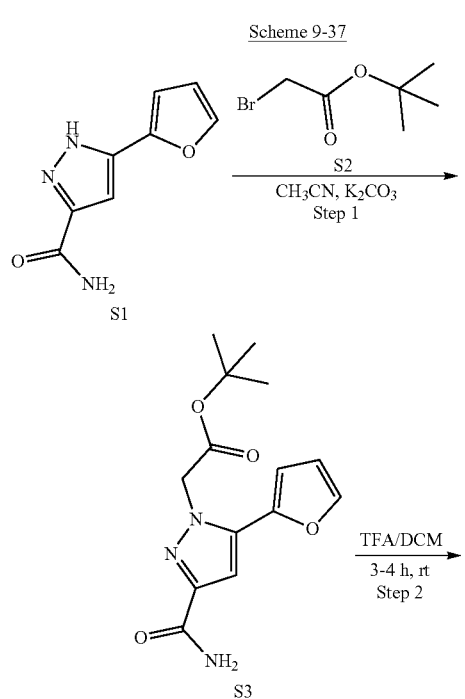

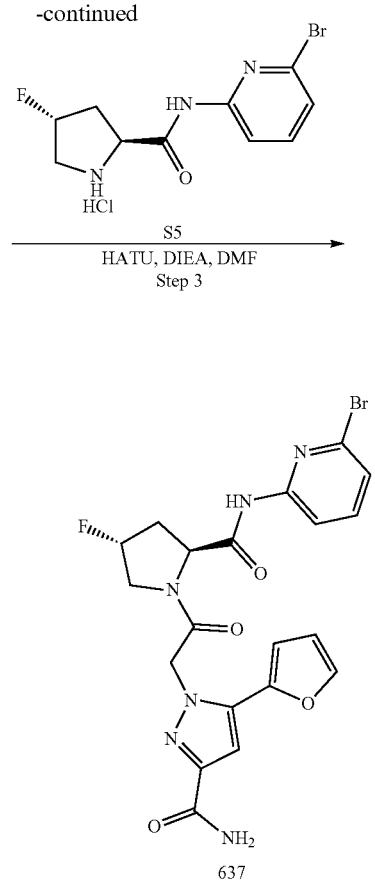

340

Step 1: tert-Butyl 2-(3-carbamoyl-5-(furan-2-yl)-1H-pyrazol-1-yl)acetate (S3)

To a solution of 5-(furan-2-yl)-1H-pyrazole-3-carboxamide (scheme 9-37 compound S1, 1 equiv) in CH$_3$CN (10 vol) was added tert-butyl 2-bromoacetate (scheme 9-37 compound S2, 1.1 equiv) and potassium carbonate (1.1 equiv). The mixture was refluxed overnight under an atmosphere of argon. After cooling the reaction mixture to room temperature, the mixture was filtered through Celite and washed with CH$_3$CN. The filtrate was concentrated under high vacuum and the residue was purified by column chromatography on silica gel (EtOAc/DCM) to afford scheme 9-37 compound S3.

Step 2: 2-(3-Carbamoyl-5-(furan-2-yl)-1H-pyrazol-1-yl)acetic acid (S4)

To a solution of scheme 9-37 compound S3 (1 equiv) in DCM (10 vol) at 0° C. under an atmosphere of nitrogen was added TFA (5 vol). The reaction mixture was stirred at room temperature for 3 h and then concentrated. The remaining material was carried forward without further purification.

Step 3: 1-(2-((2S,4R)-2-((6-Bromopyridin-2-yl)carbamoyl)-4-fluoropyrrolidin-1-yl)-2-oxoethyl)-5-(furan-2-yl)-1H-pyrazole-3-carboxamide (637)

To a solution of scheme 9-37 compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to afford compound 637. $^1$H NMR (400 MHz, DMSO-d$_6$) δ 2.04-2.27 (m, 1H), 2.53-2.63 (m, 1H), 3.82-4.01 (m, 1H), 4.12-4.29 (m, 1H), 4.68 (t, J=8.5 Hz, 1H), 5.22 (d, J=17.4 Hz, 1H), 5.43-5.61 (m, 2H), 6.64 (dd, J=1.8, 3.5 Hz, 1H), 6.77 (d, J=3.5 Hz, 1H), 6.94 (s, 1H), 7.25-7.39 (m, 2H), 7.53 (s, 1H), 7.72 (t, J=8.0 Hz, 1H), 7.78 (s, 1H), 8.03 (d, J=8.2 Hz, 1H), 11.02 (s, 1H). $^{19}$F NMR (376 MHz, DMSO-d$_6$): δ −175.15. LC (method A): t$_R$=1.39 min. LC/MS (EI) m/z: [M+H]$^+$ 505.

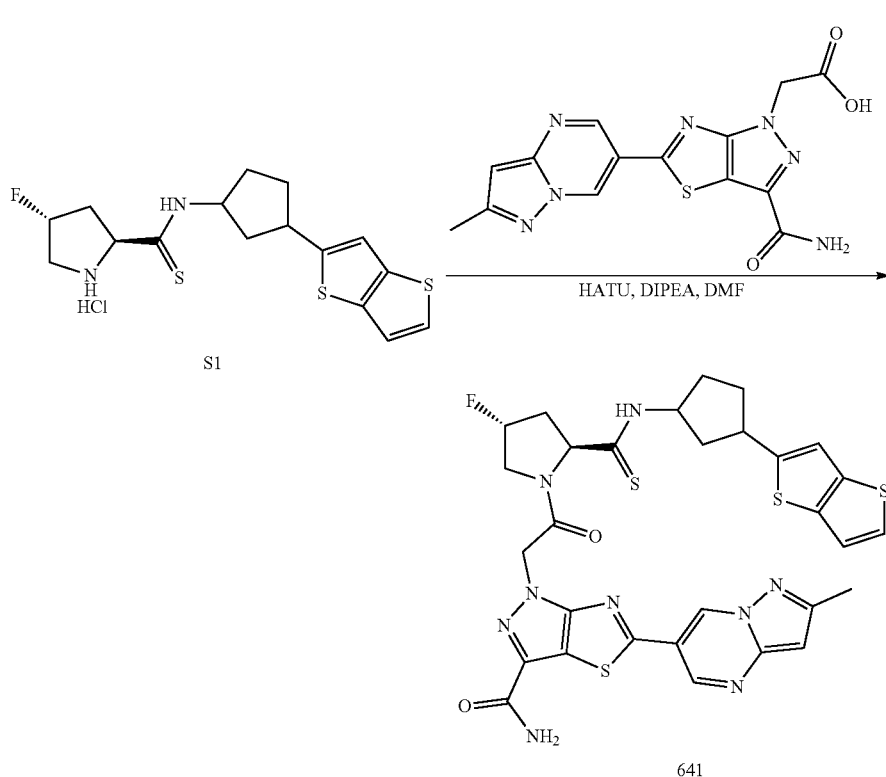

Example 9-39

1-(2-((2S,4R)-4-fluoro-2-((3-(thieno[3,2-b]thiophen-2-yl)cyclopentyl)carbamothioyl)pyrrolidin-1-yl)-2-oxoethyl)-5-(2-methylpyrazolo[1,5-a]pyrimidin-6-yl)-1H-pyrazolo[3,4-d]thiazole-3-carboxamide (641)

The titled compound was prepared according to the procedure from Scheme 38 from appropriate starting materials. 1H NMR (400 MHz, DMSO-d$_6$) δ: 10.03 (d, J=6 Hz, 1H), 9.67 (s, 1H), 9.01 (s, 1H), 8.45 (s, 1H), 7.87-7.90 (m, 1H), 7.53-7.63 (m, 2H), 7.09-7.34 (m, 2H), 6.69 (s, 1H), 5.30-5.68 (m, 3H), 4.53-4.89 (m, 2H), 4.01-4.24 (m, 2H), 2.46 (s, 3H), 1.99-2.07 (m, 2H), 1.74-1.79 (m, 2H), 1.63-1.69 (m, 2H). LC/MS (ESI) m/z: 694 (M+H).

(2S,4R)-1-(2-(1-Acetyl-7-(2-methylpyrimidin-5-yl) indolizin-3-yl) acetyl)-N-(6-bromopyridin-2-yl)-4-fluoropyrrolidine-2-carboxamide (642)

Scheme 9-40

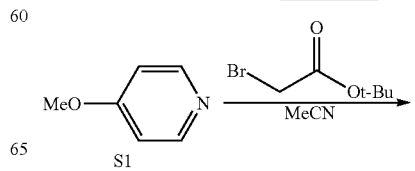

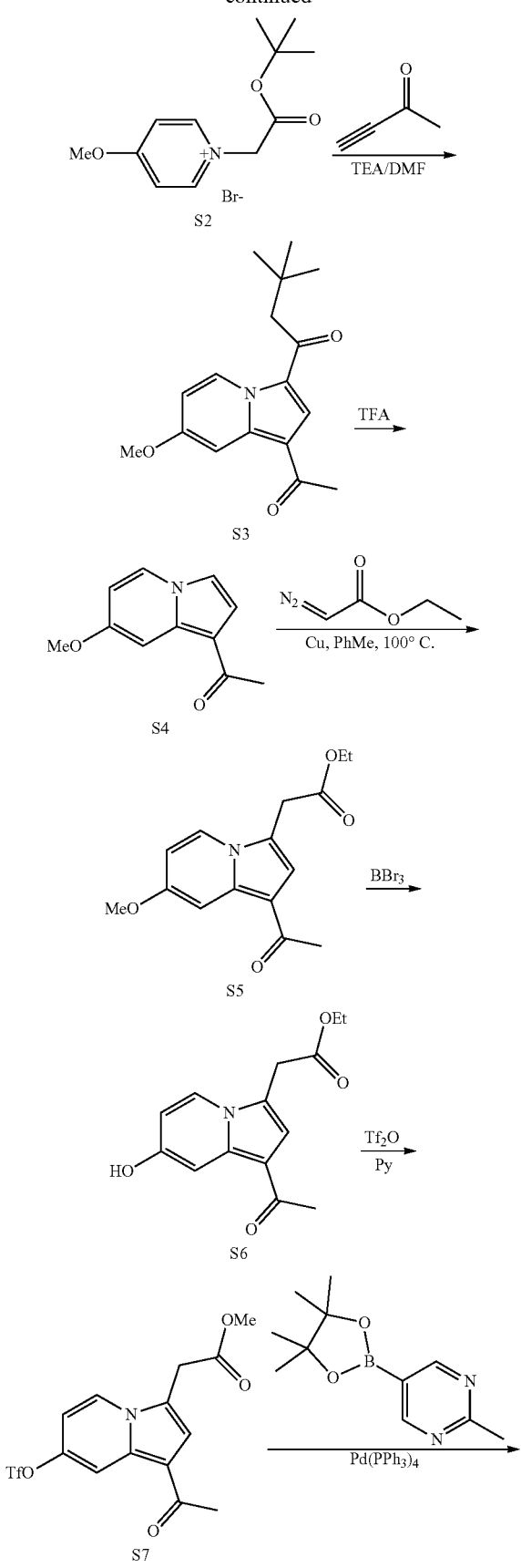

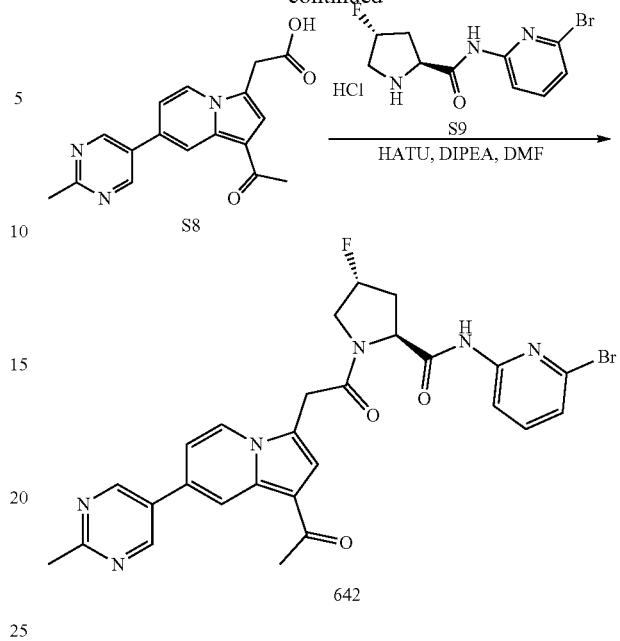

Step 1: 1-(2-(tert-Butoxy)-2-oxoethyl)-4-methoxy-pyridin-1-ium bromide (S2)

To a solution of 4-methoxypyridine (5.0 g, 45.9 mmol) in MeCN (100 mL) was added tert-butyl 2-bromoacetate (8.9 g, 45.9 mmol) and the reaction mixture was stirred at 50° C. for 2 hrs. The mixture was evaporated under reduced pressure and the residue was re-crystallized from $Et_2O$ to give the title compound (12.6 g, 90.6% yield) as white solid.

Step 2: tert-Butyl 1-acetyl-7-methoxyindolizine-3-carboxylate (S3)

To a solution of 1-(2-(tert-butoxy)-2-oxoethyl)-4-methoxypyridin-1-ium bromide (8.0 g, 26.4 mmol) in DMF (120 mL) was added but-3-yn-2-one (1.8 g, 26.4 mmol) and TEA (11 mL, 79.2 mmol) and the reaction mixture was stirred at 60° C. for 3 hrs. The mixture was poured into ice water (250 mL) and extracted with EtOAc 9(2×50 mL). The combined organic layers are washed with brine, dried over anhydrous sodium sulfate and evaporated under reduced pressure. The residue was purified by chromatography on silica gel (PE:EtOAc=20:1 to 10:1) to give the title compound (6.6 g, 86.8% yield) as yellow solid.

Step 3: 1-(7-Methoxyindolizin-1-yl)ethanone (S4)

To a solution of tert-butyl 1-acetyl-7-methoxyindolizine-3-carboxylate (2.0 g, 6.9 mmol) in DCM (150 mL) was added TFA (5.1 mL, 69.2 mmol) at 0° C. and the reaction was stirred at room temperature overnight. The mixture was poured into ice-cooled aq.$NaHCO_3$ solution (250 mL) and extracted with DCM (2×50 mL). The combined organic layers are washed with brine, dried over anhydrous sodium sulfate and evaporated under reduced pressure. The residue was purified by chromatography on silica gel (PE:EtOAc=6:1 to 4:1) to give the title compound (530 mg, 40.8% yield) as yellow solid.

Step 4: Ethyl 2-(1-acetyl-7-methoxyindolizin-3-yl)acetate (S5)

To a mixture of 1-(7-methoxyindolizin-1-yl)ethanone (1.0 g, 5.3 mmol) and Cu powder (371 mg, 5.8 mmol) in toluene (25 mL) at 100° C. was added a solution of ethyl 2-diazoacetate (661.2 mg, 5.8 mmol) in toluene (4 mL) dropwise. The reaction was stirred at this temperature for 4 hrs. The mixture was cooled to room temperature and filtered. The filtrate was evaporated under reduced pressure. The residue was purified by chromatography on silica gel (PE:EtOAc=6:1 to 4:1) to give the title compound (500 mg, 34.4% yield) as a brown solid.

Step 5: Ethyl 2-(1-acetyl-7-hydroxyindolizin-3-yl)acetate (S6)

To a solution of ethyl 2-(1-acetyl-7-methoxyindolizin-3-yl)acetate (430 mg, 1.6 mmol) in DCM (20 mL) was added dropwise a solution of $BBr_3$ (3.9 g, 16.0 mmol) in DCM (5 mL) at −78° C. and the reaction mixture was stirred at room temperature overnight. The mixture was quenched by addition MeOH (10 mL) at −78° C. then allowed to stir at room temperature for 1 hr. The mixture was evaporated under reduced pressure and the residue was purified by chromatography on silica gel (DCM:MeOH=40:1 to 20:1) to give the title compound (230 mg, crude) as a green solid.

Step 6: Methyl 2-(1-acetyl-7-(((trifluoromethyl)sulfonyl)oxy)indolizin-3-yl)acetate (S7)

To a solution of ethyl 2-(1-acetyl-7-hydroxyindolizin-3-yl)acetate (230 mg, 0.93 mmol) in pyridine (3 mL) was added dropwise $Tf_2O$ (288 mg, 1.02 mol) at 0° C. for 30 min. The reaction was stirred at room temperature for 1 hr. The mixture was diluted with DCM and washed with brine, dried over anhydrous sodium sulfate and evaporated under reduced pressure. The residue was purified by chromatography on silica gel (PE:EtOAc=4:1 to 2:1) to give the title compound (30 mg, 8.5% yield) as green oil.

Step 7 and Step 8: 2-(1-Acetyl-7-(2-methylpyrimidin-5-yl)indolizin-3-yl)acetic acid (S8)

A mixture of methyl 2-(1-acetyl-7-(((trifluoromethyl)sulfonyl)oxy)indolizin-3-yl) acetate (20 mg, 0.058 mmol), (2-methylpyrimidin-5-yl)boronic acid (11 mg, 0.08 mmol), $Na_2CO_3$ (22 mg, 0.15 mmol) and $Pd(PPh_3)_4$ (12 mg, 0.01 mmol) in 1,4-dioxane (2 mL) and water (0.5 mL) was degassed and stirred at 90° C. under $N_2$ atmosphere overnight. The mixture was diluted with EtOAc and washed with brine, dried over anhydrous sodium sulfate, filtered and concentrated to dryness. The residue was purified by prep-TLC (PE:EtOAc=1:2) to afford the desired product (12 mg, 68.9% yield) as yellow solid.

To a solution of 2-(1-acetyl-7-(2-methylpyrimidin-5-yl)indolizin-3-yl)acetic acid (12 mg, 0.04 mmol) in THF (1 mL) was added a solution of LiOH (3 mg, 0.11 mmol) in water (0.5 mL) at 0° C. Then the reaction mixture was stirred at room temperature for 1 hr. The mixture was washed with diethyl ether and acidified by adding 1 N aq. HCl. The mixture was extracted with DCM and the organic layer dried over anhydrous sodium sulfate, and concentrated to give the title compound (11 mg, 100% yield) as yellow solid.

Step 9: (2S,4R)-1-(2-(1-Acetyl-7-(2-methylpyrimidin-5-yl)indolizin-3-yl)acetyl)-N-(6-bromopyridin-2-yl)-4-fluoropyrrolidine-2-carboxamide (642)

A mixture of 2-(1-acetyl-7-(2-methylpyrimidin-5-yl)indolizin-3-yl)acetic acid (10 mg, 0.03 mmol), S9 (13 mg, 0.04 mmol), HATU (17 mg, 0.05 mmol) and DIPEA (12 mg, 0.09 mmol) in DMF (2 mL) was stirred at room temperature overnight. The mixture was partitioned with EtOAc and water. The organic layer was washed with brine, dried over anhydrous sodium sulfate and concentrated under reduced pressure. The residue was purified by prep-HPLC to afford the desired product (1.2 mg, 6.9% yield) as white solid. $^1$H NMR (400 MHz, CDCl$_3$) δ: 9.04 (s, 1H), 8.94 (s, 2H), 8.74 (d, J=1.1 Hz, 1H), 8.21 (d, J=7.3 Hz, 1H), 8.03 (d, J=8.1 Hz, 1H), 7.51 (t, J=5.0 Hz, 1H), 7.21 (d, J=7.7 Hz, 1H), 7.14 (s, 1H), 7.07 (dd, J=7.3, 2.0 Hz, 1H), 5.44 (s, 1H), 5.31 (s, 1H), 4.87 (t, 1H), 4.07 (s, 3H), 3.76 (dd, J=12.3, 3.2 Hz, 1H), 3.68 (dd, J=12.4, 3.4 Hz, 1H), 2.81 (s, 3H), 2.54 (s, 3H). LC/MS (ESI) m/z: 579 (M+H)$^+$ (R)-1-(2-(3-Acetyl-5-(2-methylpyrimidin-5-yl)-1H-indazol-1-yl)acetyl)-N-((6-bromopyridin-2-yl)methyl)piperidine-3-carboxamide (643)

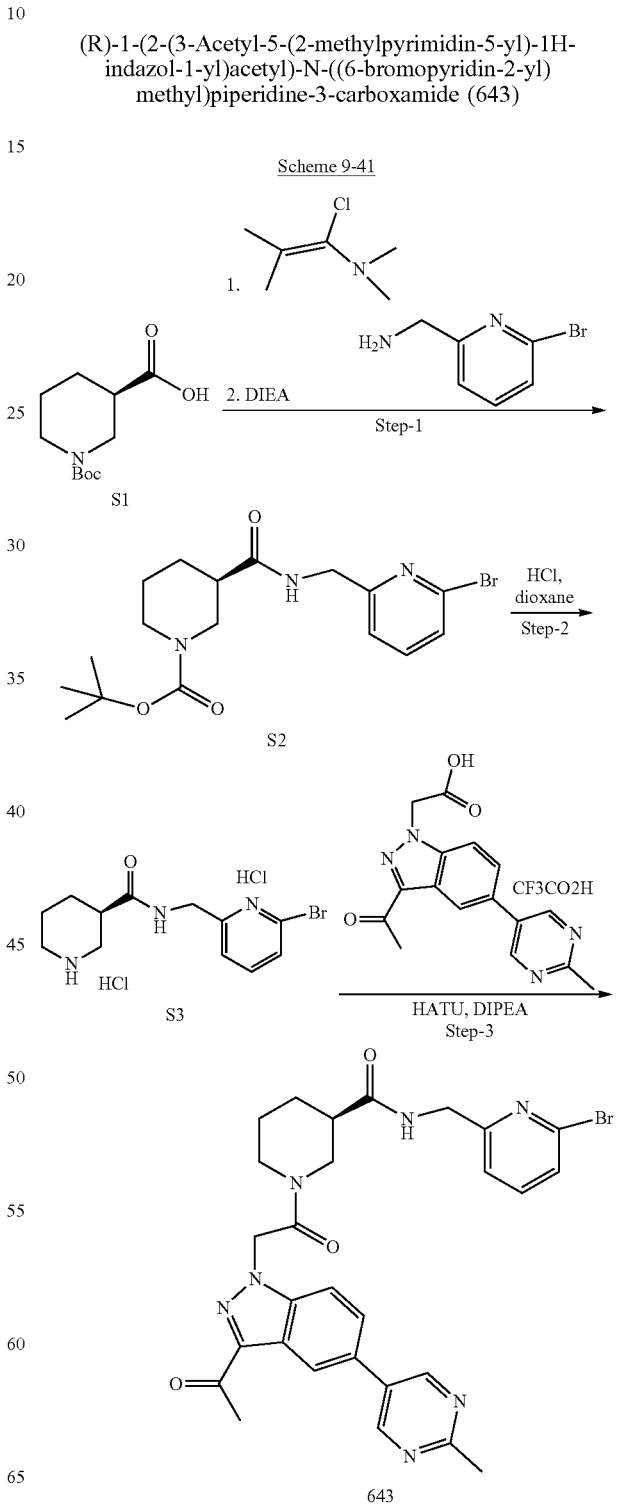

643

Step-1: tert-Butyl (R)-3-(((6-bromopyridin-2-yl)methyl)carbamoyl)piperidine-1-carboxylate (S2)

To an ice-cold solution of (R)-1-(tert-butoxycarbonyl)piperidine-3-carboxylic acid (1.09 g, 4.75 mmol) in 50 mL of CH$_2$Cl$_2$, 1-chloro-N,N,2-trimethyl-1-propenylamine (0.69 mL, 5.3 mmol) was added dropwise with stirring. The stirring was continued for 2 h at this temperature, then (6-bromopyridin-2-yl)methanamine (750 mg, 4.0 mmol) was added, followed by 1.6 mL of iPr$_2$NEt. The cooling bath was removed and the reaction mixture was stirred overnight at rt. After completion of the reaction monitored by HPLC, the reaction mixture was added to water (120 mL) and extracted with DCM (2×120 mL). The organic layer was washed successively with an aqueous solution of NaHCO$_3$ (20 mL), water (20 mL), and brine (20 mL), then dried over Na$_2$SO$_4$ and concentrated under reduced pressure. The remaining residue was purified by flash column chromatography (ISCO eluted with Hexanes/EtOAC) to give 1.10 g of desire title compound.

Step-2: (R)—N-((6-Bromopyridin-2-yl)methyl)piperidine-3-carboxamide dihydrochloride (S3)

Tert-butyl (R)-3-(((6-bromopyridin-2-yl)methyl)carbamoyl)piperidine-1-carboxylate (1.10 g) was taken in 4N HCl dioxane (10 mL) and the resulting reaction mixture was stirred at room temperature for 2 h. After completion of the reaction monitored by HPLC, the solvent was removed under reduced pressure. The remaining residue was used directly without further purification.

Step-3: (R)-1-(2-(3-Acetyl-5-(2-methylpyrimidin-5-yl)-1H-indazol-1-yl)acetyl)-N-((6-bromopyridin-2-yl)methyl)piperidine-3-carboxamide (643)

2-(3-acetyl-5-(2-methylpyrimidin-5-yl)-1H-indazol-1-yl) acetic acid TFA salt (502 mg, 1.14 mmol), (R)—N-((6-bromopyridin-2-yl)methyl)piperidine-3-carboxamide dihydrochloride (400 mg, 1.31 mmol) are dissolved in DMF (10 mL) and HATU (548 mg, 1.44 mmol) was added, followed by addition of DIEA (5 equiv). The reaction mixture was stirred overnight at rt. The volatiles are evaporated under reduced pressure. The remaining material was treated with saturated NaHCO$_3$. The resulting solid was collected and dried. The solid was dissolved in minimum co-solvent MeOH-DCM (15%) and loaded on silica gel for chromatography. The purification affords title compound (14.4 mg). $^1$H NMR (400 MHz, DMSO-d$_6$): (major rotamer) δ: 1.32-1.37 (m, 1H), 1.54-1.77 (m, 2H), 1.79-1.92 (m, 1H), 2.23-2.35 (m, 1H), 2.57 (s, 3H), 2.62 (s, 3H), 2.78-2.84 (m, 1H), 3.27-3.38 (m, 1H), 3.86-3.9 (m, 2H), 4.24-4.40 (m, 2H), 5.58-5.75 (m, 2H), 7.18-7.31 (m, 1H), 7.41-7.46 (m, 1H), 7.59-7.78 (m, 3H), 8.37 (s, 1H), 8.51-8.59 (m, 1H), 8.97 (s, 2H) ppm; LC (method A): t$_R$=1.48 min. LC/MS (EI) m/z: [M+H]$^+$ 590.34, 592.30

Example 10. Synthesis of Aryl, Heteroaryl, and Heterocyclic Compounds of Formula I'

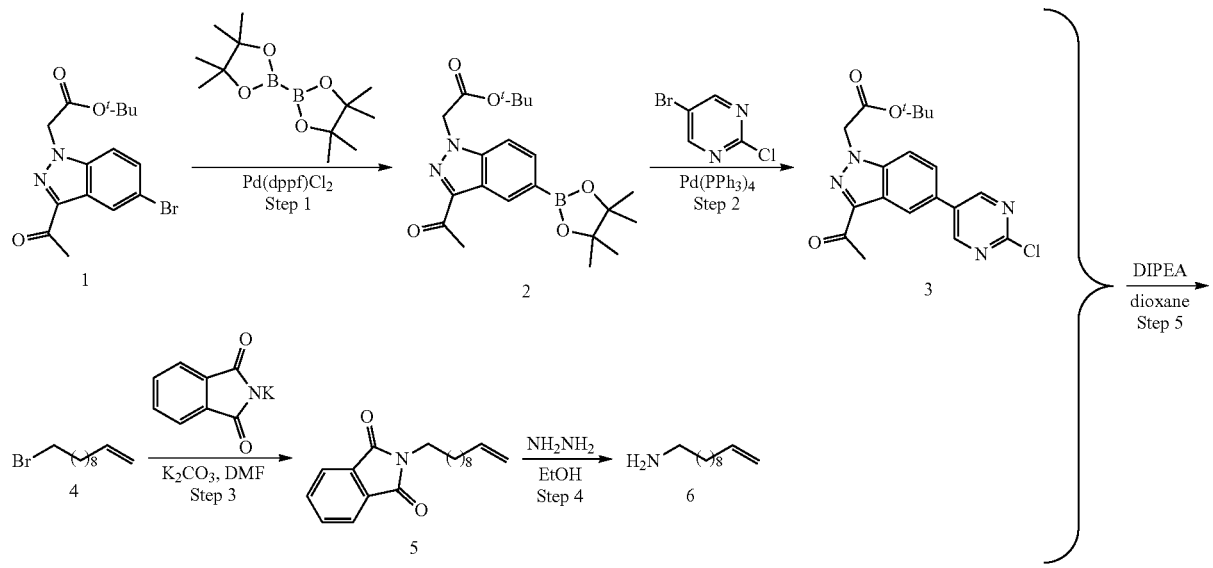

Scheme 10-1

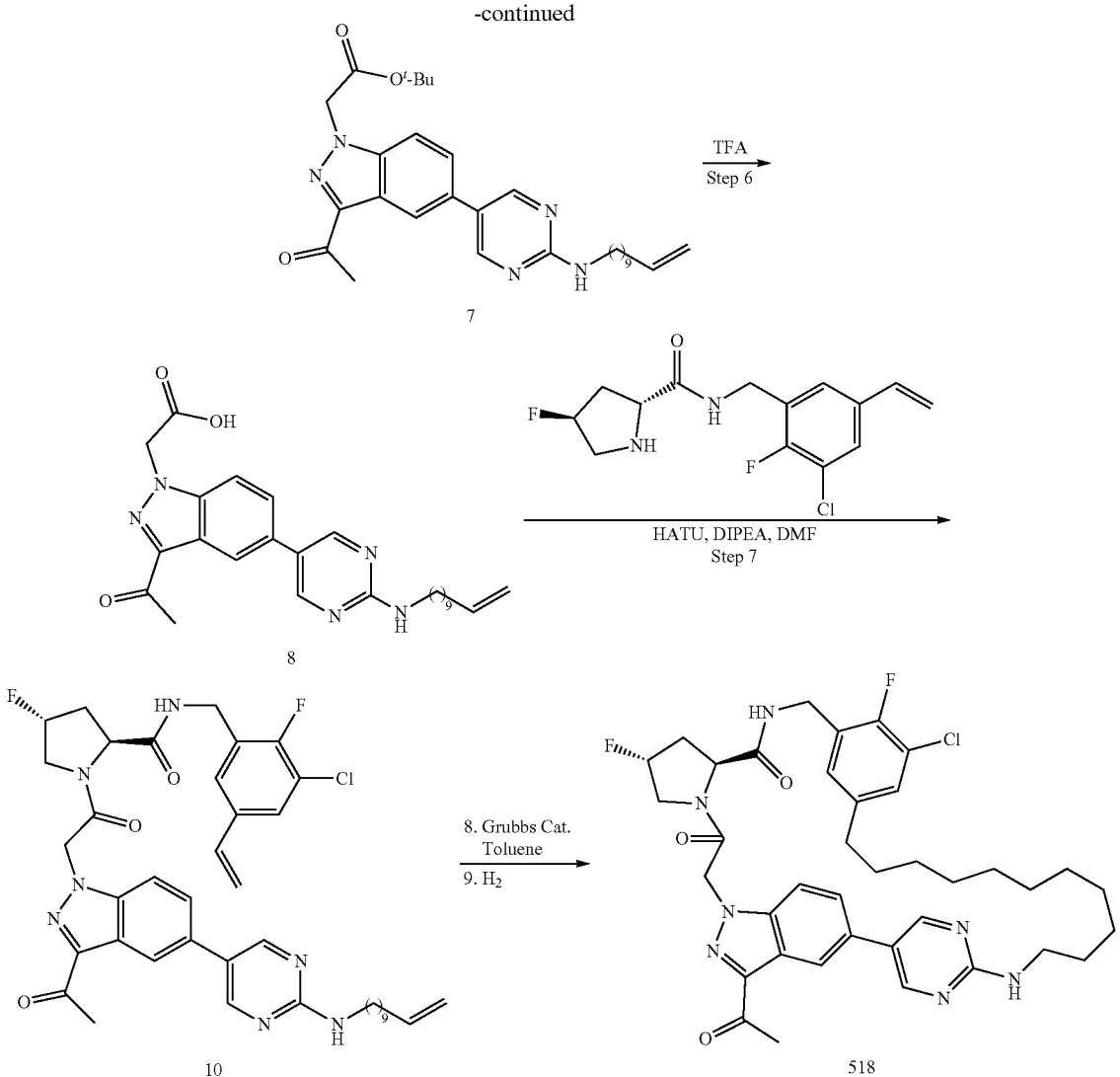

Scheme 10-1: In Step 1 the appropriately substituted aryl bromide is converted to a boronic acid as known in the art. In Step 2 the appropriately substituted boronic acid is subjected to an aryl bromide as known in the art to afford a biaryl species. In Step 3 the appropriately substituted bromide is subjected to a phthalimide to afford a protected alkene species. In Step 4 the appropriately substituted phthalimide-protected amine is subjected to hydrazine as known in the art to afford a free amine. In Step 5 the two appropriately substituted species previously prepared react as known in the art to afford an alkene species. In Step 6 the appropriately substituted ester is treated with TFA to afford a carboxylic acid. In Step 7 the appropriately substituted carboxylic acid is converted to an amide as known in the art. In Step 8 the di-alkene species is cyclized as known in the art to form a macrocyclic species. In Step 9 the appropriately substituted macrocyclic-alkene species is reduced with hydrogen to afford a macrocyclic-alkyl species.

Example 11. Non-Limiting Examples of Aryl, Heteroaryl, and Heterocyclic Compounds of Formula I In the illustrative compounds of FIG. 17, and elsewhere herein, $R^{32}$ is depicted as $Z_{32}$, which are intended to be the same moieties.

Example 12. Non-Limiting Examples of Compounds of Formula I, Formula I' and Formula I"

Table 3 shows illustrative Factor D inhibitors with characterizing data. The assay of Example 13 was used to determine the $IC_{50}$'s of the compounds. Other standard factor D inhibition assays are also available. Three *s are used to denote compounds with an $IC_{50}$ less than 1 micromolar; two s indicate compound with an $IC_{50}$ between 1 micromolar and 10 micromolar, and one * denotes compounds with an $IC_{50}$ greater than 10 micromolar.

TABLE 3

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 500 | 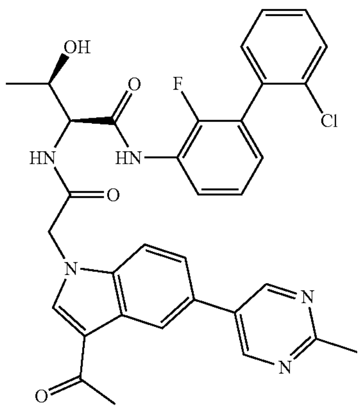 [SMILES: CC(=O)c1cn(CC(=O)N[C@H](C(=O)Nc2cccc(-c3ccccc3Cl)c2F)[C@@H](C)O)c2ccc(-c3cnc(C)nc3)cc12] | (2S,3R)-2-(2-(3-acetyl-5-(2-methylpyrimidin-5-yl)-1H-indol-1-yl)acetamido)-N-(2'-chloro-2-fluorobiphenyl-3-yl)-3-hydroxybutanamide | *** | 3.58 (B) | 614 |
| 501 | 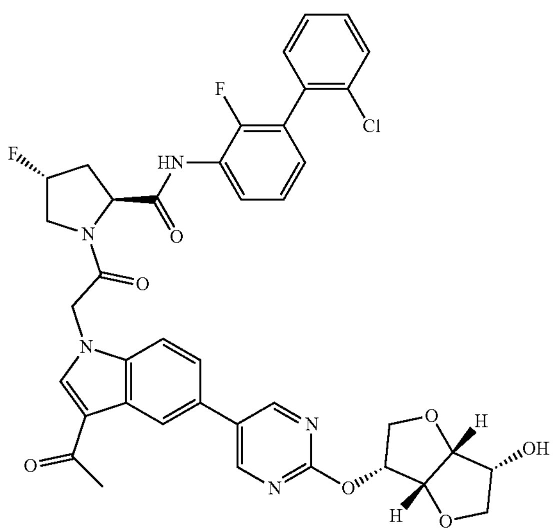 [SMILES: CC(=O)c1cn(CC(=O)N2C[C@H](F)C[C@H]2C(=O)Nc2cccc(-c3ccccc3Cl)c2F)c2ccc(-c3cnc(O[C@@H]4CO[C@H]5[C@@H]4OC[C@H]5O)nc3)cc12] | (2S,4R)-1-(2-(3-acetyl-5-(2-((3R,3aR,6R,6aR)-6-hydroxyhexahydrofuro[3,2-b]furan-3-yloxy)pyrimidin-5-yl)-1H-indol-1-yl)acetyl)-N-(2'-chloro-2-fluorobiphenyl-3-yl)-4-fluoropyrrolidine-2-carboxamide | *** | 3.42 (B) | 758 |
| 502 | 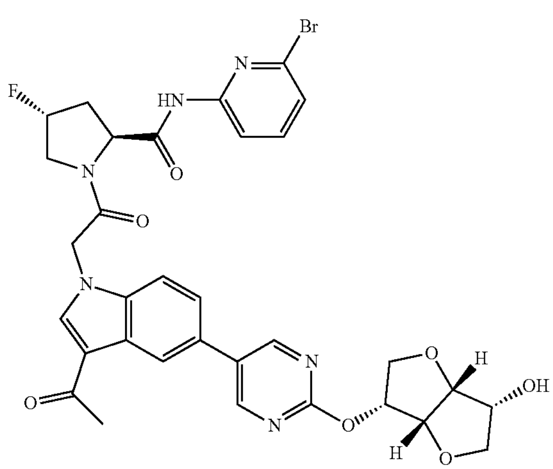 [SMILES: CC(=O)c1cn(CC(=O)N2C[C@H](F)C[C@H]2C(=O)Nc2cccc(Br)n2)c2ccc(-c3cnc(O[C@@H]4CO[C@H]5[C@@H]4OC[C@H]5O)nc3)cc12] | (2S,4R)-1-(2-(3-acetyl-5-(2-((3R,3aR,6R,6aR)-6-hydroxyhexahydrofuro[3,2-b]furan-3-yloxy)pyrimidin-5-yl)-1H-indol-1-yl)acetyl)-N-(6-bromopyridin-2-yl)-4-fluoropyrrolidine-2-carboxamide | *** | 2.94 (B) | 709 |

TABLE 3-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 503 | 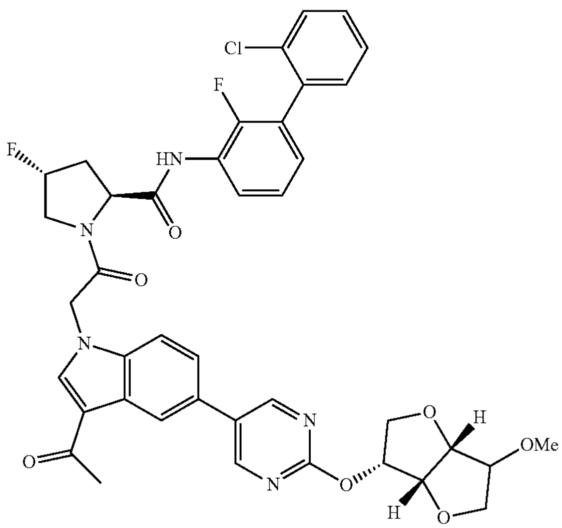 [SMILES: COC1CO[C@H]2[C@@H]1OC[C@H]2Oc1ncc(-c2ccc3c(c2)c(C(C)=O)cn3CC(=O)N2C[C@H](F)C[C@H]2C(=O)Nc2cccc(-c3ccccc3Cl)c2F)cn1] | (2S,4R)-1-(2-(3-acetyl-5-(2-((3R,3aR,6R,6aR)-6-methoxyhexahydrofuro[3,2-b]furan-3-yloxy)pyrimidin-5-yl)-1H-indol-1-yl)acetyl)-N-(2'-chloro-2-fluorobiphenyl-3-yl)-4-fluoropyrrolidine-2-carboxamide | *** | 3.63 (B) | 772 |
| 504 | 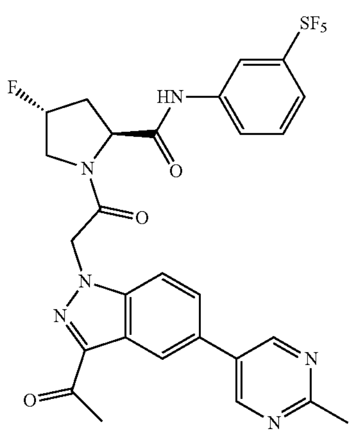 | (2S,4R)-1-(2-(3-acetyl-5-(2-methylpyrimidin-5-yl)-1H-indazol-1-yl)acetyl)-4-fluoro-N-(3-(pentafluoro-□⁶-sulfanyl)phenyl)pyrrolidine-2-carboxamide | *** | 2.13 (A) | 627 |
| 505 | 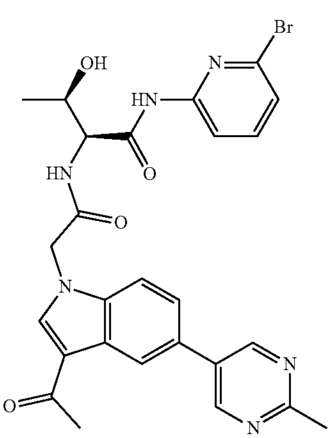 [SMILES: CC(=O)c1cn(CC(=O)N[C@H](C(=O)Nc2cccc(Br)n2)[C@@H](C)O)c2ccc(-c3cnc(C)nc3)cc12] | (2S,3R)-2-(2-(3-acetyl-5-(2-methylpyrimidin-5-yl)-1H-indol-1-yl)acetamido)-N-(6-bromopyridin-2-yl)-3-hydroxybutanamide | *** | 2.85 (B) | 565 |

TABLE 3-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 506 | 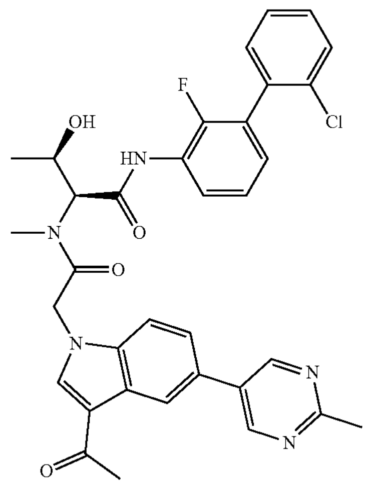 [SMILES: CC(=O)c1cn(CC(=O)N(C)[C@H](C(=O)Nc2cccc(-c3ccccc3Cl)c2F)[C@@H](C)O)c2ccc(-c3cnc(C)nc3)cc12] | (2S,3R)-2-(2-(3-acetyl-5-(2-methylpyrimidin-5-yl)-1H-indol-1-yl)-N-methylacetamido)-N-(2'-chloro-2-fluorobiphenyl-3-yl)-3-hydroxybutanamide | ** | 4.07 (B) | 628 |
| 507 | 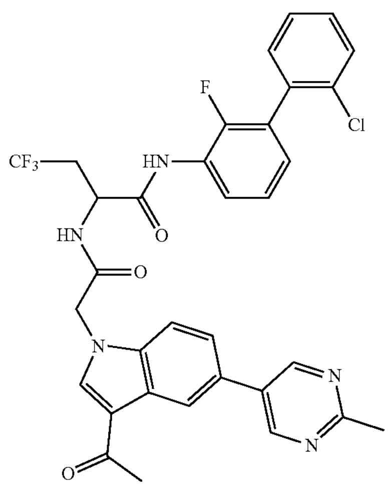 [SMILES: CC(=O)c1cn(CC(=O)NC(CC(F)(F)F)C(=O)Nc2cccc(-c3ccccc3Cl)c2F)c2ccc(-c3cnc(C)nc3)cc12] | 2-(2-(3-acetyl-5-(2-methylpyrimidin-5-yl)-1H-indol-1-yl)acetamido)-N-(2'-chloro-2-fluorobiphenyl-3-yl)-4,4,4-trifluorobutanamide | * | 4.02 (B) | 652 |
| 508 | 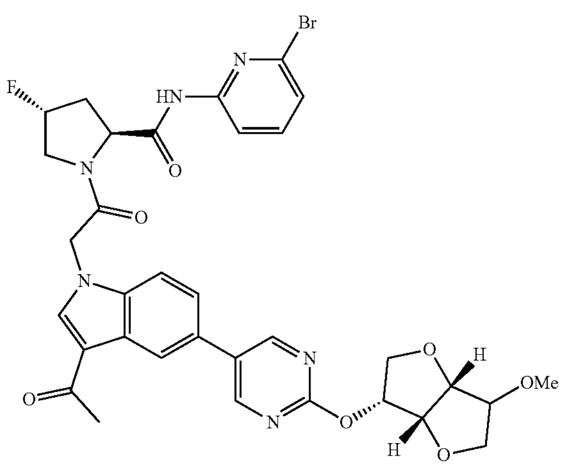 [SMILES: COC1CO[C@H]2[C@@H]1OC[C@H]2Oc1ncc(-c2ccc3c(c2)c(C(C)=O)cn3CC(=O)N2C[C@H](F)C[C@H]2C(=O)Nc2cccc(Br)n2)cn1] | (2S,4R)-1-(2-(3-acetyl-5-(2-((3R,3aR,6R,6aR)-6-methoxyhexahydrofuro[3,2-b]furan-3-yloxy)pyrimidin-5-yl)-1H-indol-1-yl)acetyl)-N-(6-bromopyridin-2-yl)-4-fluoropyrrolidine-2-carboxamide | *** | 3.14 (B) | 723 |

TABLE 3-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 509 | 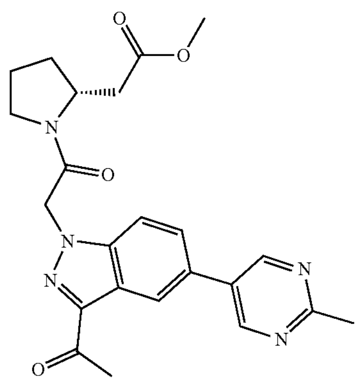 [SMILES: COC(=O)C[C@H]1CCCN1C(=O)Cn1nc(C(C)=O)c2cc(-c3cnc(C)nc3)ccc21] | (R)-methyl 2-(1-(2-(3-acetyl-5-(2-methylpyrimidin-5-yl)-1H-indazol-1-yl)acetyl)pyrrolidin-2-yl)acetate | * | 2.35 (A) | 436 |
| 510 | 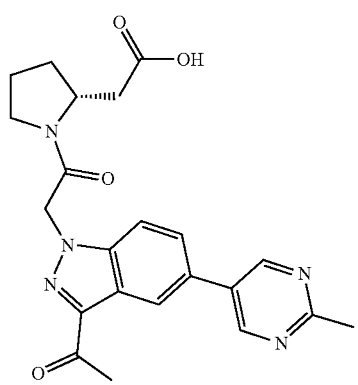 [SMILES: CC(=O)c1nn(CC(=O)N2CCC[C@@H]2CC(=O)O)c2ccc(-c3cnc(C)nc3)cc12] | (R)-2-(1-(2-(3-acetyl-5-(2-methylpyrimidin-5-yl)-1H-indazol-1-yl)acetyl)pyrrolidin-2-yl)acetic acid | * | 2.33 (A) | 422 |
| 511 | 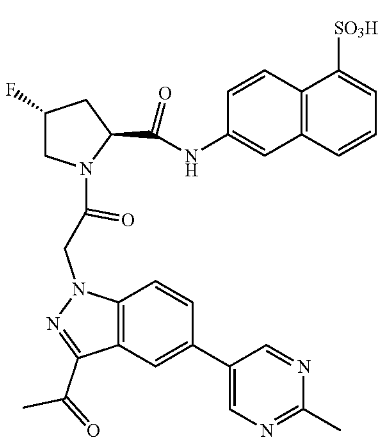 [SMILES: CC(=O)c1nn(CC(=O)N2C[C@H](F)C[C@H]2C(=O)Nc2ccc3c(S(=O)(=O)O)cccc3c2)c2ccc(-c3cnc(C)nc3)cc12] | 6-((2S,4R)-1-(2-(3-acetyl-5-(2-methylpyrimidin-5-yl)-1H-indazol-1-yl)acetyl)-4-fluoropyrrolidine-2-carboxamido)naphthalene-1-sulfonic acid | ** | 0.98 (A) | 631 |

TABLE 3-continued

Non-limiting Examples of Compounds of Formula I, Formula I' and Formula I''

| Cmp No. | Structure | Name | IC$_{50}$ | RT min (Method A or B) | MS (M + 1) |
|---|---|---|---|---|---|
| 512 | 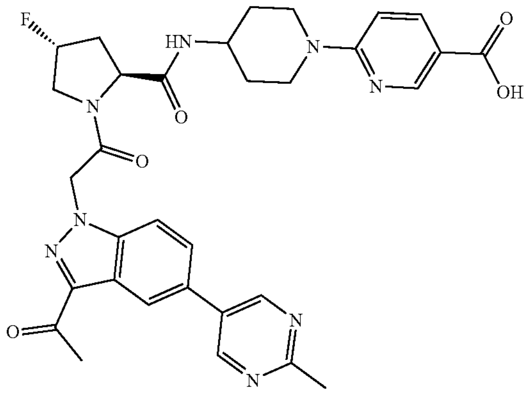 [SMILES: CC(=O)c1nn(CC(=O)N2C[C@H](F)C[C@H]2C(=O)NC2CCN(c3ccc(C(=O)O)cn3)CC2)c2ccc(-c3cnc(C)nc3)cc12] | 6-(4-((2S,4R)-1-(2-(3-acetyl-5-(2-methylpyrimidin-5-yl)-1H-indazol-1-yl)acetyl)-4-fluoropyrrolidine-2-carboxamido) piperidin-1-yl) nicotinic acid | ** | 2.17 (B) | 629 |
| 513 | 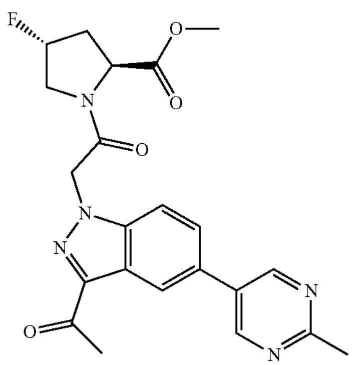 [SMILES: COC(=O)[C@@H]1C[C@@H](F)CN1C(=O)Cn1nc(C(C)=O)c2cc(-c3cnc(C)nc3)ccc21] | (2S,4R)-methyl 1-(2-(3-acetyl-5-(2-methylpyrimidin-5-yl)-1H-indazol-1-yl)acetyl)-4-fluoropyrrolidine-2-carboxylate | * | 1.21 (A) | 440 |
| 514 | 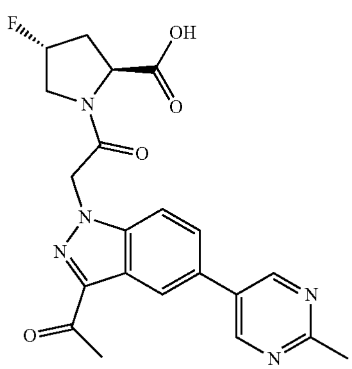 [SMILES: CC(=O)c1nn(CC(=O)N2C[C@H](F)C[C@H]2C(=O)O)c2ccc(-c3cnc(C)nc3)cc12] | (2S,4R)-1-(2-(3-acetyl-5-(2-methylpyrimidin-5-yl)-1H-indazol-1-yl)acetyl)-4-fluoropyrrolidine-2-carboxylic acid | * | 0.88 (A) | 311 |

TABLE 3-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 515 | 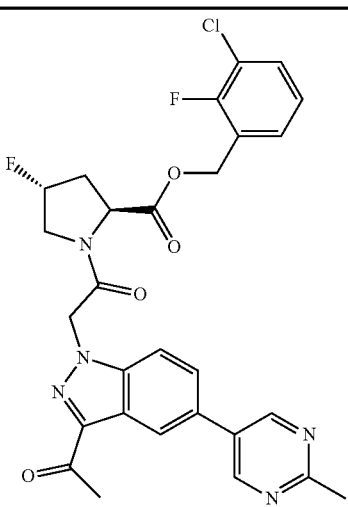 | (2S,4R)-3-chloro-2-fluorobenzyl 1-(2-(3-acetyl-5-(2-methylpyrimidin-5-yl)-1H-indazol-1-yl)acetyl)-4-fluoropyrrolidine-2-carboxylate | ** | 2.09 (A) | 568 |
| 516 | 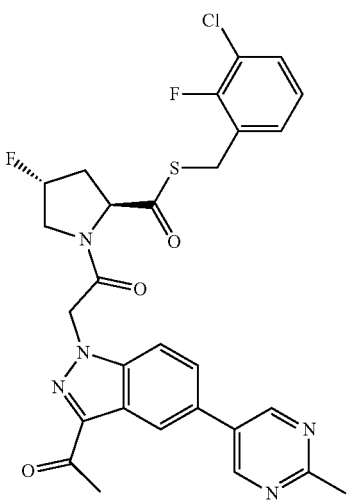 [SMILES: CC(=O)c1nn(CC(=O)N2C[C@H](F)C[C@H]2C(=O)SCc2cccc(Cl)c2F)c2ccc(-c3cnc(C)nc3)cc12] | (2S,4R)-S-3-chloro-2-fluorobenzyl 1-(2-(3-acetyl-5-(2-methylpyrimidin-5-yl)-1H-indazol-1-yl)acetyl)-4-fluoropyrrolidine-2-carbothioate | ** | 2.23 (A) | 584 |
| 517 | 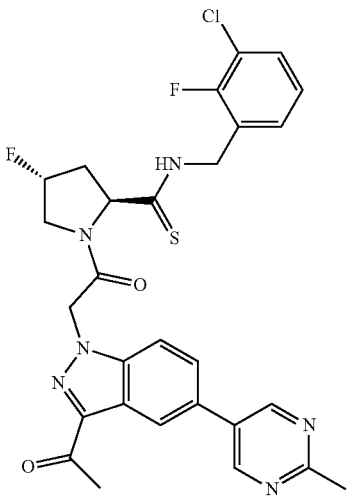 [SMILES: CC(=O)c1nn(CC(=O)N2C[C@H](F)C[C@H]2C(=S)NCc2cccc(Cl)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(3-chloro-2-fluorobenzyl)-4-fluoropyrrolidine-2-carbothioamide | *** | 2.12 (A) | 583 |

TABLE 3-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 518 | 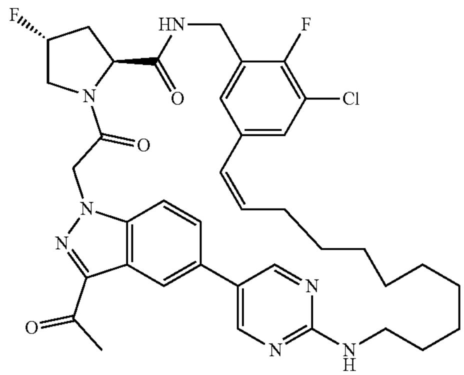 [SMILES: CC(=O)c1nn2c3ccc(cc13)-c1cnc(nc1)NCCCCCCCCC/C=C\c1cc(Cl)c(F)c(c1)CNC(=O)[C@@H]1C[C@@H](F)CN1C(=O)C2] | (5$^2$S,5$^4$R,Z)-2$^3$-acetyl-9$^5$-chloro-5$^4$,9$^6$-difluoro-2$^1$H-7,21-diaza-2(5,1)-indazola-1(5,2)-pyrimidina-5(1,2)-pyrrolidina-9(1,3)-benzenacyclo-henicosaphan-10-ene-4,6-dione | *** | 4.60 (B) | 718 |
| 519 | 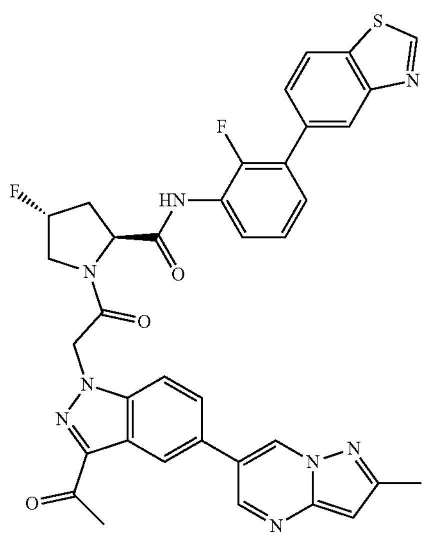 [SMILES: CC(=O)c1nn(CC(=O)N2C[C@H](F)C[C@H]2C(=O)Nc2cccc(-c3ccc4scnc4c3)c2F)c2ccc(-c3cnc4cc(C)nn4c3)cc12] | (2S,4R)-1-(2-(3-acetyl-5-(2-methylpyrazolo[1,5-a]pyrimidin-6-yl)-1H-indazol-1-yl)acetyl)-N-(3-(benzo[d]thiazol-5-yl)-2-fluorophenyl)-4-fluoropyrrolidine-2-carboxamide | *** | 2.10 (A) | 691 |
| 520 | 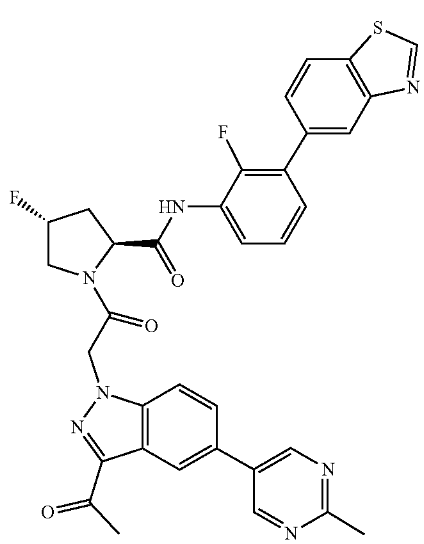 [SMILES: CC(=O)c1nn(CC(=O)N2C[C@H](F)C[C@H]2C(=O)Nc2cccc(-c3ccc4scnc4c3)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(3-(benzo[d]thiazol-5-yl)-2-fluorophenyl)-4-fluoropyrrolidine-2-carboxamide | *** | 1.87 (A) | 652 |

TABLE 3-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 521 | 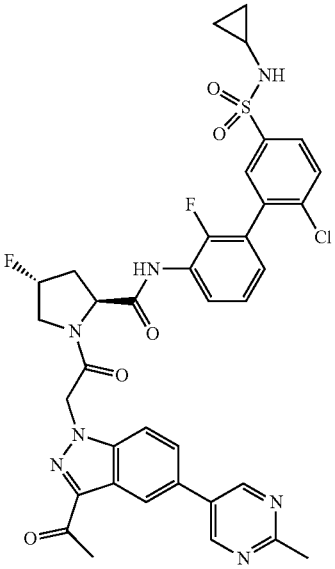 [SMILES: CC(=O)c1nn(CC(=O)N2C[C@H](F)C[C@H]2C(=O)Nc2cccc(-c3cc(S(=O)(=O)NC4CC4)ccc3Cl)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(2'-chloro-5'-(N-cyclopropylsulfamoyl)-2-fluorobiphenyl-3-yl)-4-fluoropyrrolidine-2-carboxamide | *** | | |
| 522 | 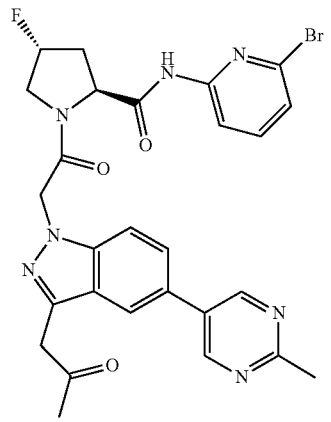 [SMILES: CC(=O)Cc1nn(CC(=O)N2C[C@H](F)C[C@H]2C(=O)Nc2cccc(Br)n2)c2ccc(-c3cnc(C)nc3)cc12] | (2S,4R)-N-(6-bromopyridin-2-yl)-4-fluoro-1-(2-(5-(2-methylpyrimidin-5-yl)-3-(2-oxopropyl)-1H-indazol-1-yl)acetyl)pyrrolidine-2-carboxamide | *** | 1.53 (A) | 594 |
| 523 | 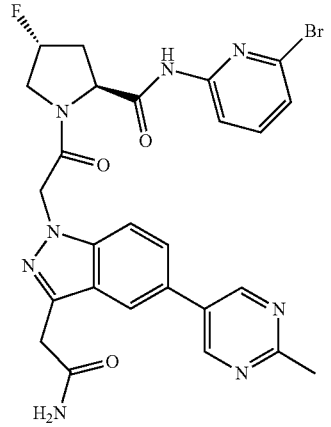 [SMILES: Cc1ncc(-c2ccc3c(c2)c(CC(N)=O)nn3CC(=O)N2C[C@H](F)C[C@H]2C(=O)Nc2cccc(Br)n2)cn1] | (2S,4R)-1-(2-(3-(2-amino-2-oxoethyl)-5-(2-methylpyrimidin-5-yl)-1H-indazol-1-yl)acetyl)-N-(6-bromopyridin-2-yl)-4-fluoropyrrolidine-2-carboxamide | ** | 1.25 (A) | 595 |

TABLE 3-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 524 | 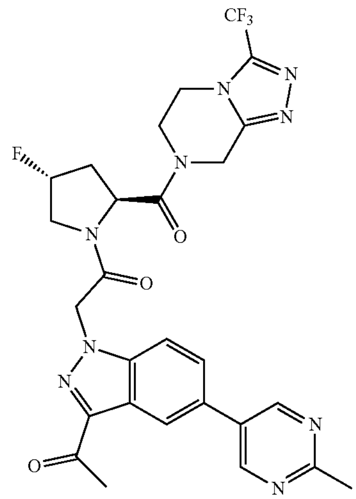 [SMILES: CC(=O)c1nn(CC(=O)N2C[C@H](F)C[C@H]2C(=O)N2CCn3c(nnc3C(F)(F)F)C2)c2ccc(-c3cnc(C)nc3)cc12] | 2-(3-acetyl-5-(2-methylpyrimidin-5-yl)-1H-indazol-1-yl)-1-((2S,4R)-4-fluoro-2-(3-(trifluoromethyl)-5,6,7,8-tetrahydro-[1,2,4]triazolo[4,3-a]pyrazine-7-carbonyl)pyrrolidin-1-yl)ethanone | * | 1.23 (A) | 600 |
| 525 | 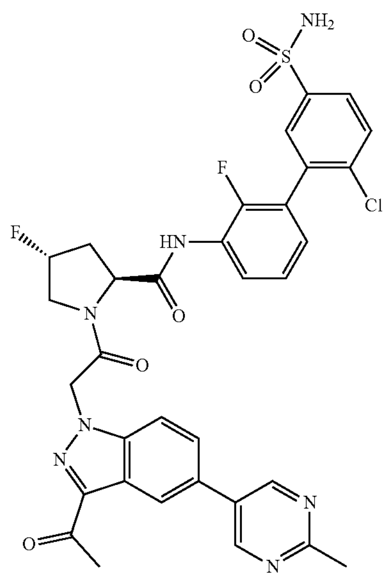 [SMILES: CC(=O)c1nn(CC(=O)N2C[C@H](F)C[C@H]2C(=O)Nc2cccc(-c3cc(S(N)(=O)=O)ccc3Cl)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(2'-chloro-2-fluoro-5'-sulfamoylbiphenyl-3-yl)-4-fluoropyrrolidine-2-carboxamide | *** | 1.68 (A) | 708 |
| 526 | 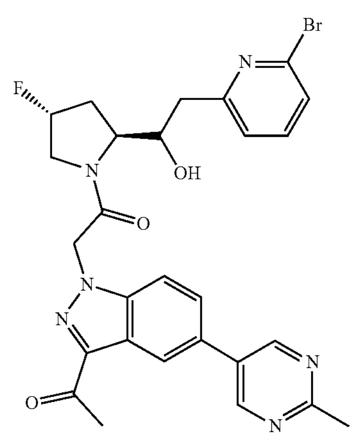 [SMILES: CC(=O)c1nn(CC(=O)N2C[C@H](F)C[C@H]2C(O)Cc2cccc(Br)n2)c2ccc(-c3cnc(C)nc3)cc12] | 2-(3-acetyl-5-(2-methylpyrimidin-5-yl)-1H-indazol-1-yl)-1-((2S,4R)-2-((S)-2-(6-bromopyridin-2-yl)-1-hydroxyethyl)-4-fluoropyrrolidin-1-yl)ethanone | ** | | |

TABLE 3-continued

Non-limiting Examples of Compounds of Formula I, Formula I' and Formula I''

| Cmp No. | Structure | Name | IC$_{50}$ | RT min (Method A or B) | MS (M + 1) |
|---|---|---|---|---|---|
| 527 | 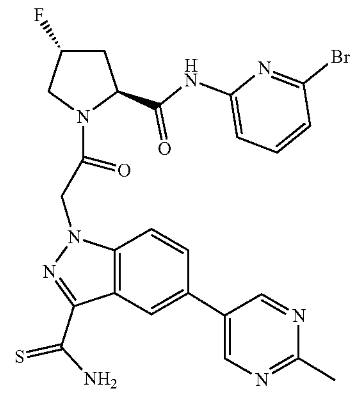 [SMILES: Cc1ncc(-c2ccc3c(c2)c(C(N)=S)nn3CC(=O)N2C[C@H](F)C[C@H]2C(=O)Nc2cccc(Br)n2)cn1] | (2S,4R)-N-(6-bromopyridin-2-yl)-1-(2-(3-carbamothioyl-5-(2-methylpyrimidin-5-yl)-1H-indazol-1-yl)acetyl)-4-fluoropyrrolidine-2-carboxamide | *** | 1.58 (A) | 597 |
| 528 | 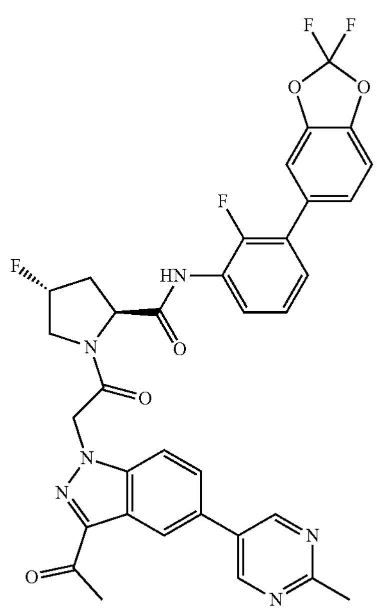 [SMILES: CC(=O)c1nn(CC(=O)N2C[C@H](F)C[C@H]2C(=O)Nc2cccc(-c3ccc4c(c3)OC(F)(F)O4)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(3-(2,2-difluorobenzo[d][1,3]dioxol-5-yl)-2-fluorophenyl)-4-fluoropyrrolidine-2-carboxamide | *** | 2.36 (A) | 675 |

TABLE 3-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 529 | 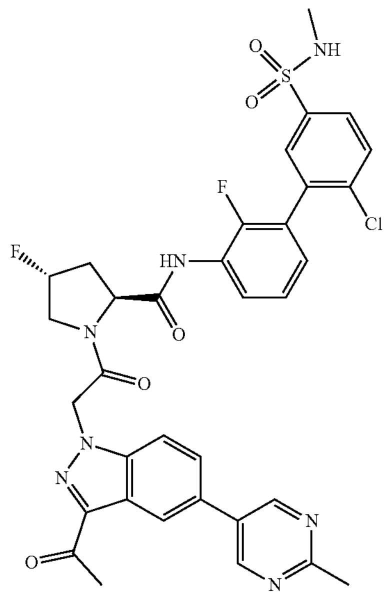 [SMILES: CNS(=O)(=O)c1ccc(Cl)c(-c2cccc(NC(=O)[C@@H]3C[C@@H](F)CN3C(=O)Cn3nc(C(C)=O)c4cc(-c5cnc(C)nc5)ccc43)c2F)c1] | (2S,4R)-1-(2-(3-acetyl-5-(2-methylpyrimidin-5-yl)-1H-indazol-1-yl)acetyl)-N-(2'-chloro-2-fluoro-5'-(N-methylsulfamoyl)biphenyl-3-yl)-4-fluoropyrrolidine-2-carboxamide | *** | 1.86 (A) | 722 |
| 530 | 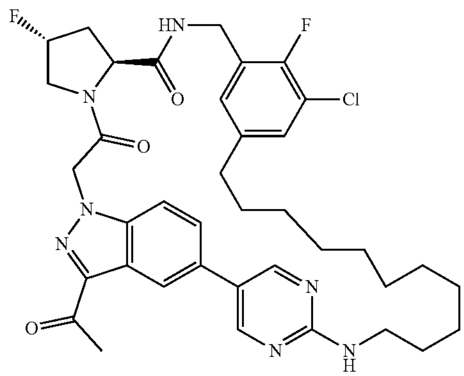 [SMILES: CC(=O)c1nn2c3ccc(cc13)-c1cnc(nc1)NCCCCCCCCCCCc1cc(Cl)c(F)c(c1)CNC(=O)[C@@H]1C[C@@H](F)CN1C(=O)C2] | ($5^2$S,$5^4$R)-$2^3$-acetyl-$9^5$-chloro-$5^4$,$9^6$-difluoro-$2^1$H-7,21-diaza-2(5,1)-indazola-1(5,2)-pyrimidina-5(1,2)-pyrrolidina-9(1,3)-benzenacyclohenicosaphane-4,6-dione | | | |
| 531 | 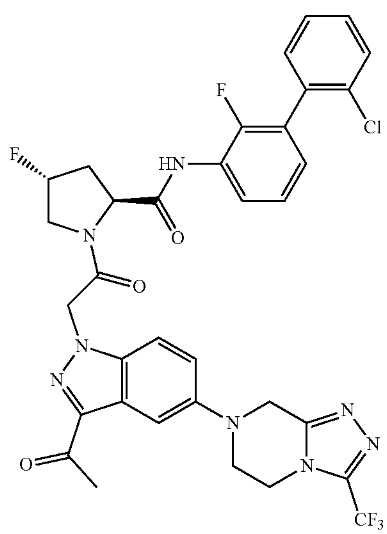 [SMILES: CC(=O)c1nn(CC(=O)N2C[C@H](F)C[C@H]2C(=O)Nc2cccc(-c3ccccc3Cl)c2F)c2ccc(N3CCn4c(nnc4C(F)(F)F)C3)cc12] | (2S,4R)-1-(2-(3-acetyl-5-(3-(trifluoromethyl)-5,6-dihydro-[1,2,4]triazolo[4,3-a]pyrazin-7(8H)-yl)-1H-indazol-1-yl)acetyl)-N-(2'-chloro-2-fluorobiphenyl-3-yl)-4-fluoropyrrolidine-2-carboxamide | *** | | |

Example 13. Non-Limiting Synthetic Examples of Aryl, Heteroaryl, and Heterocyclic Compounds of Formula I
Synthesis of 1-(1-((3-(((2S,4R)-4-fluoro-2-(((2-fluoro-3-methoxyphenyl)amino)methyl)pyrrolidin-1-yl)oxetan-3-yl)methyl)-5-(pyridazin-4-yl)-1H-indol-3-yl)ethan-1-one
Scheme 1
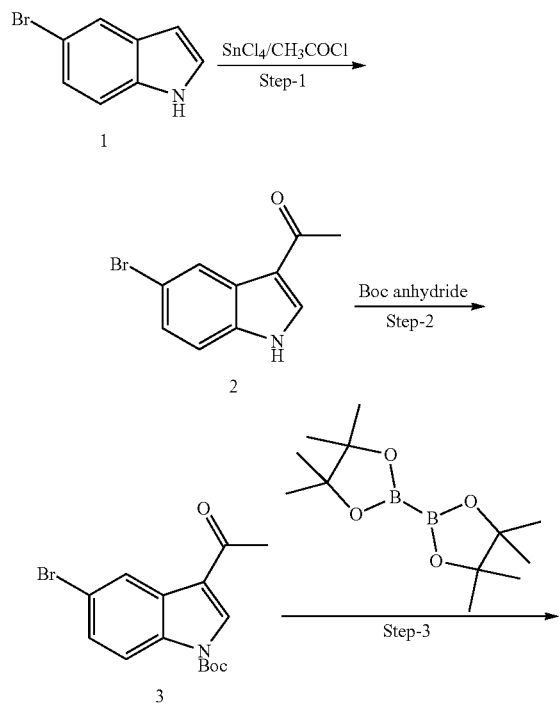
Scheme 2
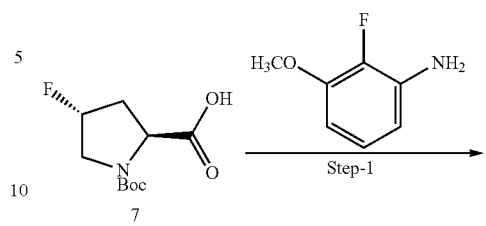
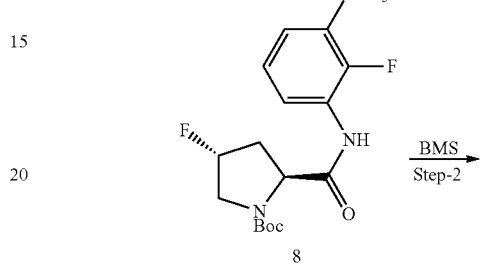
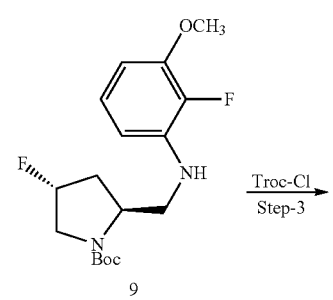
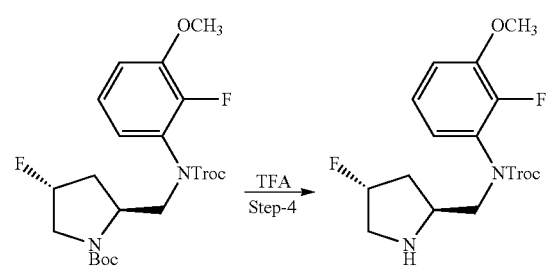
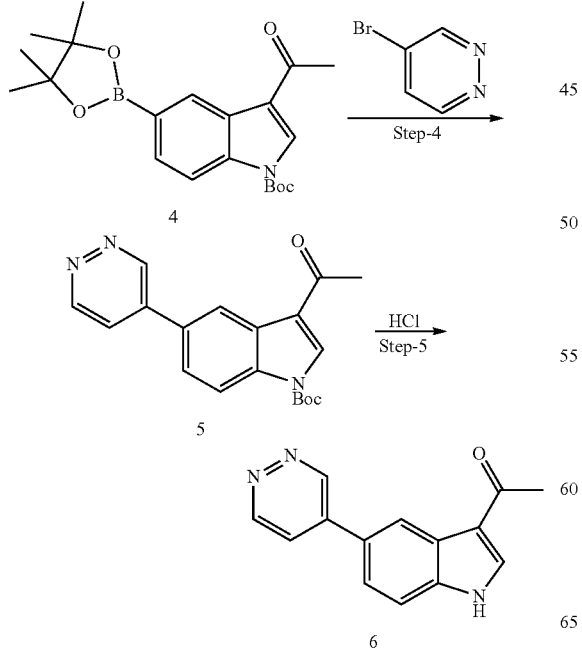
Scheme 3
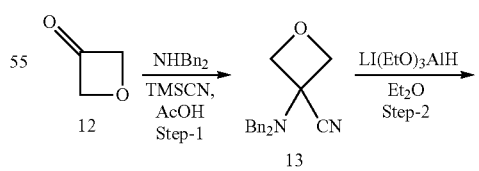
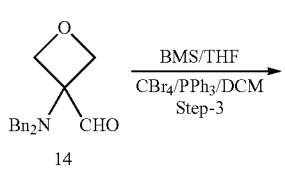

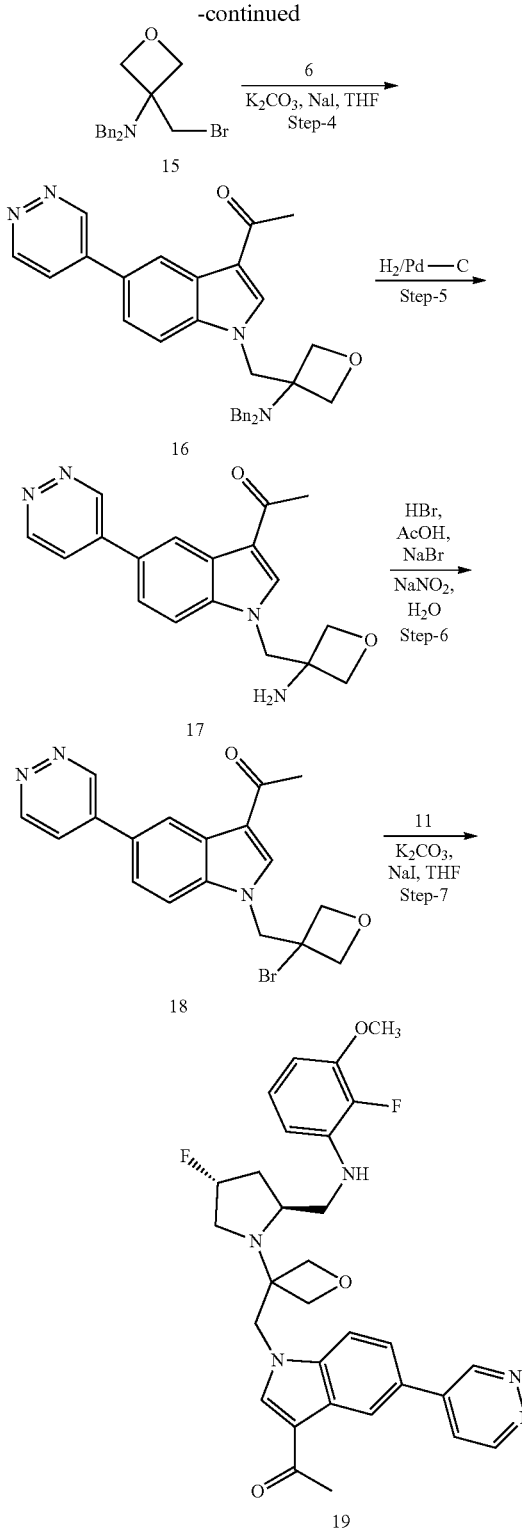

NaHCO3. The resulting mixture is extracted with ethyl acetate, washed with water. The organic layer is separated, dried over anhydrous Na2SO4, filtered and then concentrated to afford compound 2.

Step 2: tert-butyl 3-acetyl-5-bromo-1H-indole-1-carboxylate (3)

To a solution of compound 2 (1 equiv) in DCM (10 vol) is added Boc anhydride (1.2 equiv) and DMAP (0.1 equiv). The reaction mixture is stirred at room temperature for 12 h and then quenched with water. The resulting mixture is extracted with DCM. The organic layer is separated, dried over anhydrous Na2SO4, filtered and then concentrated to afford compound 3.

Step 3: tert-butyl 3-acetyl-5-(4,4,5,5-tetramethyl-1,3,2-dioxaborolan-2-yl)-1H-indole-1-carboxylate (4)

To a mixture of compound 3 (1 equiv) and Bis(pinacolato)diboron (1.1 equiv) in DMF (10 vol) is added Pd(PPh3)2Cl2 (0.1 equiv) and potassium acetate (2 equiv). After degassing with nitrogen, the resulting mixture is stirred at 100° C. for 24 h and then cooled to room temperature. Water is added to the reaction mixture and the resulting mixture is extracted with ethyl acetate. The organic layer is separated, dried over anhydrous Na2SO4, filtered and then concentrated. The residue is purified by column chromatography on silica gel to afford compound 4.

Step 4: tert-butyl 3-acetyl-5-(pyridazin-4-yl)-1H-indole-1-carboxylate (5)

To a mixture of compound 4 (1.5 equiv) and 4-bromopyridazine (1 equiv) in DMF/water (10:1) is added cesium carbonate (1.4 equiv) and Pd(PPh3)4 (0.1 equiv). After degassing with nitrogen, the resulting mixture is stirred at 100° C. for 12 h and then cooled to room temperature. Water is added to the reaction mixture and the resulting mixture is extracted with ethyl acetate. The organic layer is separated, dried over anhydrous Na2SO4, filtered and then concentrated. The residue is purified by column chromatography on silica gel to afford compound 5.

Step 5: 1-(5-(pyridazin-4-yl)-1H-indol-3-yl)ethan-1-one (6)

To a solution of compound 5 (1 equiv) in 1,4-dioxane (2 vol) at 0° C. is added 4 N HCl in dioxane (10 vol). The reaction mixture is stirred at room temperature for 6 h and then concentrated. The residue is taken in MTBE and stirred for 30 min. The resultant solid is filtered and dried to afford compound 6.

Scheme 2

Step 1: tert-butyl (2S,4R)-4-fluoro-2-((2-fluoro-3-methoxyphenyl)carbamoyl)pyrrolidine-1-carboxylate (8)

To a solution of 2-fluoro-3-methoxyaniline (1.2 equiv) and compound 7 (1 equiv) in DMF (10 vol) is added DIPEA (2 equiv) and HATU (1.2 equiv). The reaction mixture is stirred at room temperature for 12 h then quenched with water. The resulting mixture is extracted with EtOAc. The organic layer is separated, dried over anhydrous Na2SO4, Step 1: 1-(5-bromo-1H-indol-3-yl)ethan-1-one (2)

To a solution of compound 1 (1 equiv) in toluene (10 vol) at 0° C. is added acetyl chloride (2 equiv) and SnCl4 in toluene (2 equiv) drop wise. The reaction mixture is stirred at room temperature for 3 h and then quenched with 10% filtered and then concentrated. The residue is purified by column chromatography on silica gel to afford compound 8.

Step 2: tert-butyl (2S,4R)-4-fluoro-2-(((2-fluoro-3-methoxyphenyl)amino)methyl)pyrrolidine-1-carboxylate (9)

To a solution of compound 8 (1 equiv) in THF (2 vol) at 0° C. is added Borane dimethyl sulphide complex (5 equiv). The reaction mixture is stirred at 50° C. for 12 h then quenched with methanol. The resulting mixture is extracted with ethyl acetate. The organic layer is separated, dried over anhydrous Na2SO4, filtered and then concentrated. The residue is purified by column chromatography on silica gel to afford compound 9.

Step 3: tert-butyl (2S,4R)-4-fluoro-2-(((2-fluoro-3-methoxyphenyl)((2,2,2-trichloroethoxy)carbonyl)amino)methyl)pyrrolidine-1-carboxylate (10)

To a solution of compound 9 (1 equiv) and potassium carbonate (2 equiv) in DCM (10 vol) at 0° C. is added Troc-Cl (1.1 equiv). The reaction mixture is stirred at room temperature for 12 h and then quenched with water. The resulting mixture is extracted with ethyl acetate. The organic layer is separated, dried over anhydrous Na2SO4, filtered and then concentrated. The residue is purified by column chromatography on silica gel to afford compound 10.

Step 4: (2,2,2-trichloroethyl (2-fluoro-3-methoxyphenyl)(((2S,4R)-4-fluoropyrrolidin-2-yl)methyl)carbamate (11)

To a solution of compound 10 (1 equiv) in DCM (10 vol) at 0° C. is added TFA (5 vol). The reaction mixture is stirred at 50° C. for 3 h and then concentrated. The residue is re-crystallized from MTBE to afford compound 11.
Scheme 3

Step 1: 3-(dibenzylamino)oxetane-3-carbonitrile (13)

To a solution of dibenzylamine (2 equiv) in acetic acid (10 vol) is added compound 12 (2 equiv) and trimethylsilyl cyanide (2 equiv). The reaction mixture is stirred at room temperature for 16 h and then concentrated. The resulting mixture is extracted with ethyl acetate. The organic layer is separated, dried over anhydrous Na2SO4, filtered and then concentrated. The residue is purified by column chromatography on silica gel to afford compound 13.

Step 2: 3-(dibenzylamino)oxetane-3-carbaldehyde (14)

To a solution of compound 13 (1 equiv) in toluene (10 vol) at −78° C. under nitrogen atmosphere is added DIBAL-H (1.2 equiv). The resulting mixture is stirred at −78° C. for 1 h and then quenched with 10% sodium bicarbonate and stirred at room temperature for 1 h. The resulting mixture is extracted with ethyl acetate. The organic layer is separated, dried over anhydrous Na2SO4, filtered and then concentrated. The residue is purified by column chromatography on silica gel to afford compound 14.

Step 3: N,N-dibenzyl-3-(bromomethyl)oxetan-3-amine (15)

To a solution of compound 14 (1 equiv) in THF (2 vol) at 0° C. is added Boranedimethyl sulphide complex (5 equiv). The reaction mixture is stirred at 50° C. for 12 h then quenched with methanol. The resulting mixture is extracted with ethyl acetate. The organic layer is separated, dried over anhydrous Na2SO4, filtered and then concentrated. The residue is purified by column chromatography on silica gel to afford hydroxy compound.

To a solution of hydroxy compound (1 equiv) and triphenylphosphine (1.2 equiv) in DCM (10 vol) at 0° C. under nitrogen atmosphere, is added carbon tetrabromide (1.5 equiv). The reaction mixture is stirred at 0° C. for 1 h then quenched with water. The resulting mixture is extracted with ethyl acetate. The organic layer is separated, dried over anhydrous Na2SO4, filtered and then concentrated. The residue is purified by column chromatography on silica gel to afford compound 15.

Step 4: 1-(1-((3-(dibenzylamino)oxetan-3-yl)methyl)-5-(pyridazin-4-yl)-1H-indol-3-yl)ethan-1-one (16)

To a solution of compound 6 (1 equiv) in THF (10 vol) is added compound 6 (1.2 equiv), K2CO3 (2 equiv) and NaI (cat). The reaction mixture is stirred at room temperature for 16 h and then quenched with water. The resulting mixture is extracted with ethyl acetate. The organic layer is separated, dried over anhydrous Na2SO4, filtered and then concentrated. The residue is purified by column chromatography on silica gel to afford compound 16.

Step 5: 1-(1-((3-aminooxetan-3-yl)methyl)-5-(pyridazin-4-yl)-1H-indol-3-yl)ethan-1-one (17)

To a solution of compound 16 (1 equiv) in methanol (10 vol) is added Pd/C (10% w/w). The reaction mixture is degassed and stirred at room temperature for 9 h under an atmosphere of hydrogen gas (50 psi). After completion of the reaction, the catalyst is removed by filtration through Celite. The filtrate is concentrated to afford compound 17.

Step 6: 1-(1-((3-bromooxetan-3-yl)methyl)-5-(pyridazin-4-yl)-1H-indol-3-yl)ethan-1-one (18)

To a solution of compound 17 (1 equiv) in acetic acid at 0° C. is added potassium bromide (1 equiv) and hydrogen bromide in acetic acid (3 equiv) under nitrogen atmosphere. The resulting mixture is cooled to 0° C. and sodium nitrite (1.5 equiv) is added and stirred for 1 h and then quenched with water. The resulting mixture is extracted with DCM. The organic layer is separated, dried over anhydrous Na2SO4, filtered and then concentrated to afford compound 18.

Step 7: 1-(1-((3-((2S,4R)-4-fluoro-2-(((2-fluoro-3-methoxyphenyl)amino)methyl)pyrrolidin-1-yl)oxetan-3-yl)methyl)-5-(pyridazin-4-yl)-1H-indol-3-yl)ethan-1-one (19)

To a solution of compound 18 (1 equiv) in THF (10 vol) is added compound 11 (1.2 equiv), K2CO3 (2 equiv) and NaI (cat). The reaction mixture is stirred at room temperature for 16 h. The resulting mixture is concentrated and quenched with water, extracted with ethyl acetate, washed with 10% sodium bicarbonate. The organic layer is separated, dried over anhydrous Na2SO4, filtered and then concentrated. The residue is purified by column chromatography on silica gel to afford compound 19.

Synthesis of (S)-3-(((2-((3-(benzo[b]thiophen-3-yl)-2-fluorophenyl)carbamoyl)azepan-1-yl)sulfonyl)methyl)-6-(2-methylpyrimidin-5-yl)-2-oxo-2,3-dihydro-1H-benzo[d]imidazole-1-carboxamide
Scheme-4
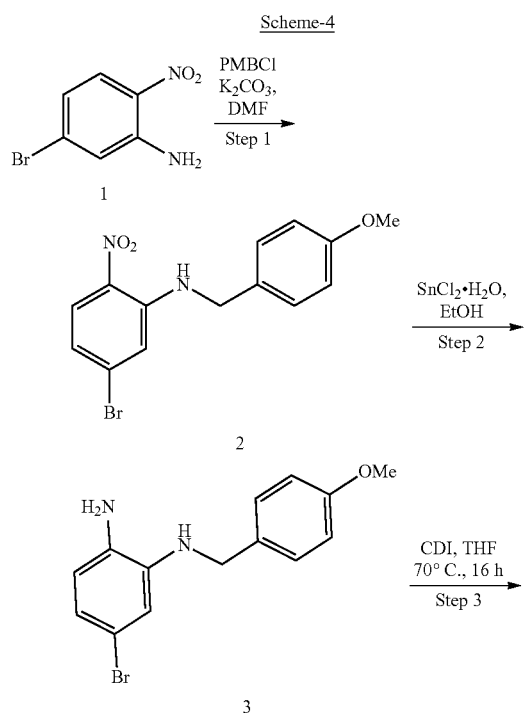
Scheme-5
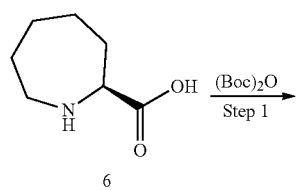
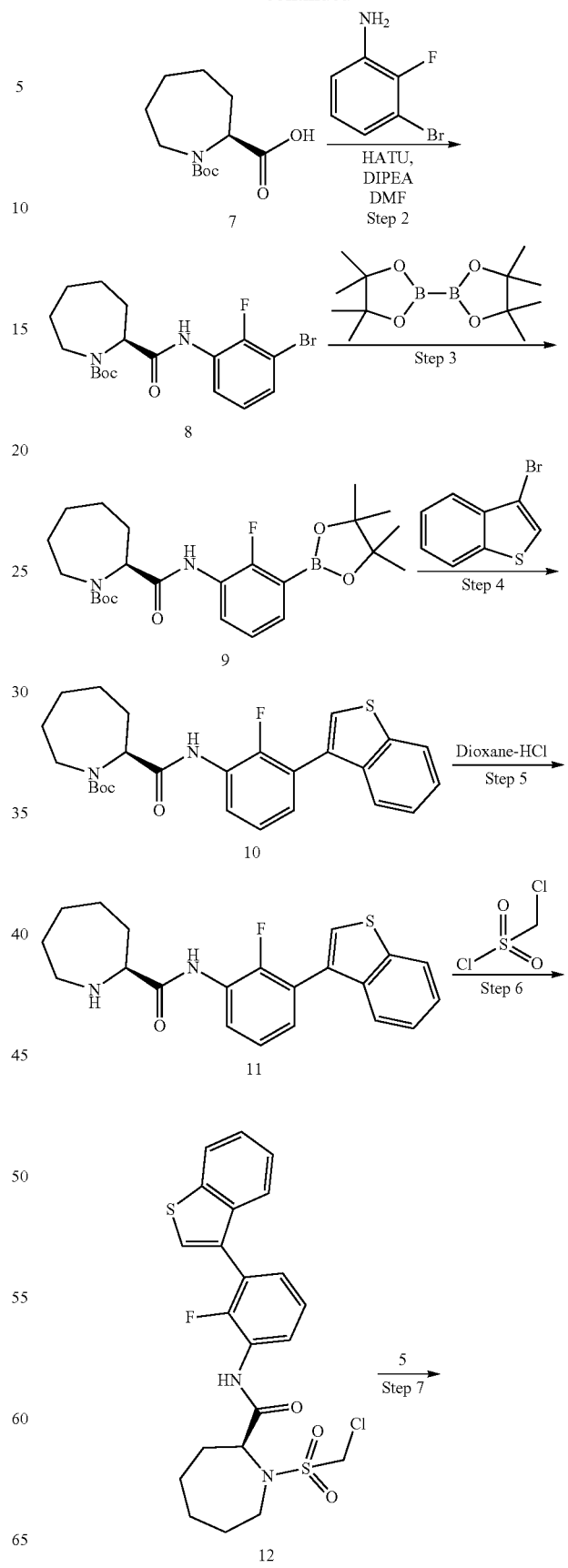

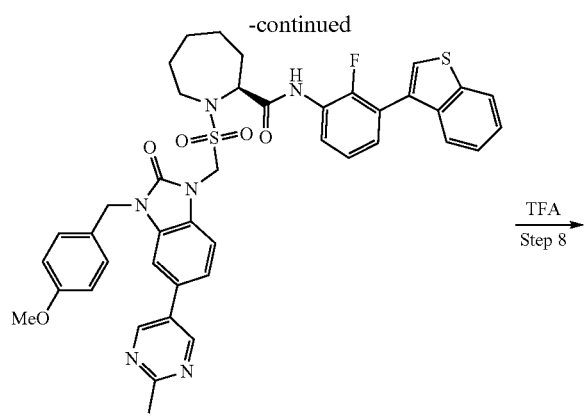

13

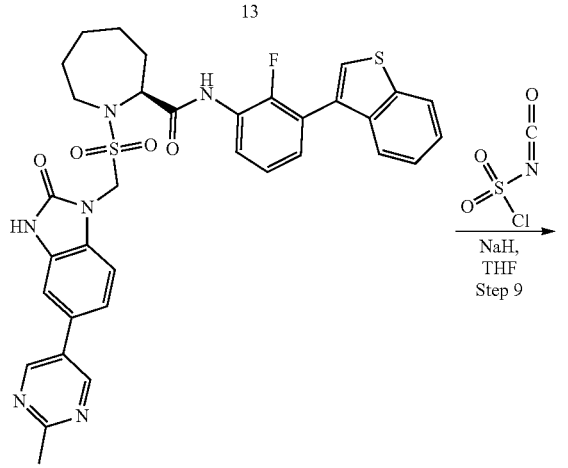

14

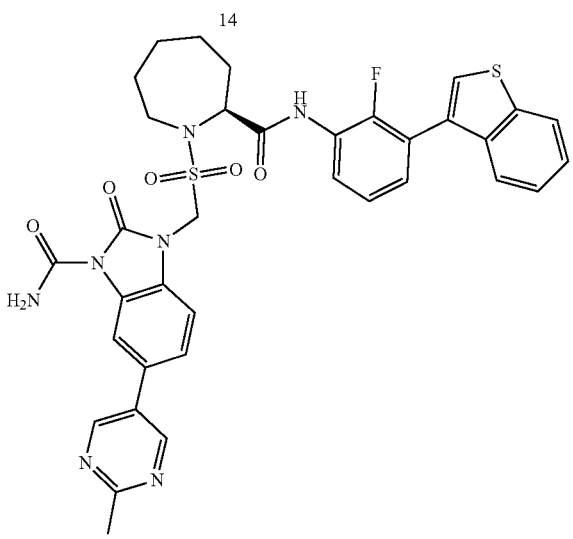

15

Scheme 4

Step 1:
5-bromo-N-(4-methoxybenzyl)-2-nitroaniline (2)

To a solution of compound 1 (1 equiv) and potassium carbonate (2 equiv) in DMF (20 vol) is added 4-methoxybenzylchloride (1.5 equiv). The reaction mixture is stirred at room temperature for 12 h and then quenched with water. The resulting mixture is extracted with ethyl acetate. The organic layer is separated, dried over anhydrous Na2SO4, filtered and then concentrated. The residue is purified by column chromatography on silica gel to afford compound 2.

Step 2: 5-bromo-$N^1$-(4-methoxybenzyl)benzene-1,2-diamine (3)

To a solution of compound 2 (1 equiv) in EtOH/water (10:2) at 0° C. is added stannous chloride (1.5 equiv). The reaction mixture is stirred at 50° C. for 4 h and then quenched with saturated NaHCO3 solution. The resulting mixture is extracted with ethyl acetate. The organic layer is separated, dried over anhydrous Na2SO4, filtered and then concentrated. The residue is purified by column chromatography on silica gel to afford compound 3.

Step 3: 6-bromo-1-(4-methoxybenzyl)-1,3-dihydro-2H-benzo[d]imidazol-2-one (4)

To a solution of compound 3 (1 equiv) in THF (10 vol) is added CDI (5 equiv). The reaction mixture is stirred at 65° C. for 16 h and then concentrated. The residue is taken in ethyl acetate and washed with water, dried over Na2SO4, filtered and then concentrated. The residue is purified by column chromatography on silica gel to afford compound 4.

Step 4: 1-(4-methoxybenzyl)-6-(2-methylpyrimidin-5-yl)-1,3-dihydro-2H-benzo[d]imidazol-2-one (5)

To a mixture of 2-methyl-5-(4,4,5,5-tetramethyl-1,3,2-dioxaborolan-2-yl)pyrimidine (1.5 equiv) and compound 4 (1 equiv) in DMF/water (10:1) is added cesium carbonate (1.4 equiv) and Pd(PPh3)4. After degassing with nitrogen, the resulting mixture is stirred at 100° C. for 12 h and then cooled to room temperature. Water is added to the reaction mixture and the resulting mixture is extracted with ethyl acetate. The organic layer is separated, dried over anhydrous Na2SO4, filtered and then concentrated. The residue is purified by column chromatography on silica gel to afford compound 5.

Scheme 5

Step 1: (S)-1-(tert-butoxycarbonyl)azepane-2-carboxylic Acid (7)

To a solution of compound 6 (1 equiv) and 2 M NaOH (2 equiv) in THF (10 vol) at 0° C. is added Boc anhydride (1.2 equiv). The reaction mixture is stirred at room temperature for 16 h and then quenched 1 M HCl. The resulting mixture is extracted with ethyl acetate. The organic layer is separated, dried over anhydrous Na2SO4, filtered and then concentrated. The residue is re-crystallized from MTBE to afford compound 7.

Step 2: tert-butyl (S)-2-((3-bromo-2-fluorophenyl)carbamoyl)azepane-1-carboxylate (8)

To a solution of compound 7 (1 equiv) and 3-bromo-2-fluoroaniline (1.2 equiv) in DMF (10 vol) is added DIPEA (3 equiv) and HATU (1.2 equiv). The reaction mixture is stirred at room temperature for 16 h and then quenched with water. The resulting mixture is extracted with ethyl acetate. The organic layer is separated, dried over anhydrous Na2SO4, filtered and then concentrated. The residue is purified by column chromatography on silica gel to afford compound 8.

Step 3: tert-butyl (S)-2-((2-fluoro-3-(4,4,5,5-tetramethyl-1,3,2-dioxaborolan-2-yl)phenyl)carbamoyl)azepane-1-carboxylate (9)

To a mixture of compound 8 (1 equiv) and Bis(pinacolato) diboron (1.1 equiv) in DMF (10 vol) is added PdCl$_2$(PPh$_3$)$_2$ (0.1 equiv) and potassium acetate (2 equiv). After degassing with nitrogen, the resulting mixture is stirred at 100° C. for 24 h and then cooled to room temperature. Water is added to the reaction mixture and the resulting mixture is extracted with ethyl acetate. The organic layer is separated, dried over anhydrous Na2SO4, filtered and then concentrated. The residue is purified by column chromatography on silica gel to afford compound 9.

Step 4: tert-butyl (S)-2-((3-(benzo[b]thiophen-3-yl)-2-fluorophenyl)carbamoyl)azepane-1-carboxylate (10)

To a mixture of 3-bromobenzo[b]thiophene (1.5 equiv) and compound 9 (1 equiv) in DMF/water (10:1) is added cesium carbonate (1.4 equiv) and Pd(PPh$_3$)$_4$. After degassing with nitrogen, the resulting mixture is stirred at 100° C. for 12 h and then cooled to room temperature. Water is added to the reaction mixture and the resulting mixture is extracted with ethyl acetate. The organic layer is separated, dried over anhydrous Na$_2$SO$_4$, filtered and then concentrated. The residue is purified by column chromatography on silica gel to afford compound 10.

Step 5: (S)—N-(3-(benzo[b]thiophen-3-yl)-2-fluorophenyl)azepane-2-carboxamide (11)

To a solution of compound 10 (1 equiv) in 1,4-dioxane (2 vol) at 0° C. is added 4 N HCl in dioxane (10 vol). The reaction mixture is stirred at room temperature for 6 h and then concentrated. The residue is taken in MTBE and stirred for 30 min. The resultant solid is filtered and dried to afford compound 11.

Step 6: (S)—N-(3-(benzo[b]thiophen-3-yl)-2-fluorophenyl)-1-((chloromethyl)sulfonyl)azepane-2-carboxamide (12)

To a solution of compound 11 (1 equiv) in DCM (2 vol) at 0° C. is added chloromethanesulfonylchloride (1.2 equiv). The reaction mixture is stirred at room temperature for 3 h and then quenched with water. The resulting mixture is extracted with DCM. The organic layer is separated, dried over anhydrous Na$_2$SO$_4$, filtered and then concentrated to afford compound 12.

Step 7: (S)—N-(3-(benzo[b]thiophen-3-yl)-2-fluorophenyl)-1-(((3-(4-methoxybenzyl)-5-(2-methylpyrimidin-5-yl)-2-oxo-2,3-dihydro-1H-benzo[d]imidazol-1-yl)methyl)sulfonyl)azepane-2-carboxamide (13)

To a solution of compound 12 (1 equiv) and compound 5 (1.2 equiv) in DMF (10 vol) is added potassium carbonate (3 equiv). The reaction mixture is stirred at 80° C. for 2 h and then quenched with water. The resulting mixture is extracted with ethyl acetate. The organic layer is separated, dried over anhydrous Na$_2$SO$_4$, filtered and then concentrated. The residue is purified by column chromatography on silica gel to afford compound 13.

Step 8: (S)—N-(3-(benzo[b]thiophen-3-yl)-2-fluorophenyl)-1-(((5-(2-methylpyrimidin-5-yl)-2-oxo-2,3-dihydro-1H-benzo[d]imidazol-1-yl)methyl)sulfonyl)azepane-2-carboxamide (14)

To a solution of compound 13 (1 equiv) in DCM (10 vol) at 0° C. is added TFA (5 vol). The reaction mixture is stirred at 50° C. for 3 h and then concentrated. The residue is re-crystallized from MTBE to afford compound 14.

Step 9: (S)-3-(((2-((3-(benzo[b]thiophen-3-yl)-2-fluorophenyl)carbamoyl)azepan-1-yl)sulfonyl)methyl)-6-(2-methylpyrimidin-5-yl)-2-oxo-2,3-dihydro-1H-benzo[d]imidazole-1-carboxamide (15)

To a solution of NaH (1.5 equiv) in THF (20 vol) at 0° C. is added compound 14 (1 equiv). The reaction mixture is stirred at 0° C. for 30 min then chlorosulfonyl isocyanate (2 equiv) is added. The reaction mixture is stirred at room temperature for 4 h, acetic acid (10 vol) is added and stirred for 1 h. The resulting mixture is quenched with ice-water, extracted with ethyl acetate. The organic layer is separated, dried over anhydrous Na$_2$SO$_4$, filtered and then concentrated. The residue is purified by column chromatography on silica gel to afford compound 15.

Example 14. Human Factor D Assay

Human Factor D (purified from human serum, Complement Technology, Inc.) at 80 nM final concentration is incubated with test compound at various concentrations for 5 min at room temperature in 50 mM Tris, 1M NaCl, pH 7.5. A synthetic substrate Z-L-Lys-SBzl and DTNB (Ellman's reagent) are added to final concentrations of 100 μM each. Absorbance at 405 nm ($A_{405}$) is recorded at 30 second intervals for 30 min using a microplate spectrophotometer. IC$_{50}$ values are calculated by nonlinear regression of complement Factor D reaction rates as a function of test compound concentration.

Example 15. Hemolysis Assay

The hemolysis assay was previously described by G. Ruiz-Gomez, et al., J. Med. Chem. (2009) 52: 6042-6052. Prior to the assay, the optimum concentration of Normal Human Serum (NHS) needed to achieve 100% lysis of rabbit erythrocytes (RE) is determined by titration. In the assay, NHS (Complement Technology) is diluted in GVB$^0$ Buffer (0.1% gelatin, 5 mM Veronal, 145 mM NaCl, 0.025% NaN$_3$, pH 7.3, Complement Technology) plus 10 mM Mg-EGTA and incubated with test compound at various concentrations for 15 min at 37° C. RE (Complement Technology) freshly suspended in GVB$^0$ plus 10 mM Mg-EGTA are added to a final concentration of 1×10$^8$ cells/mL and reactions are incubated for 30 min at 37° C. Positive control reactions (100% lysis) consist of GVB$^0$ plus 10 mM Mg-EGTA with NHS and RE but without test compound; negative control reactions (0% lysis) consist of GVB$^0$ plus 10 mM Mg-EGTA with RE only. Samples are centrifuged at 2000 g for 3 min and supernatants collected. Absorbance at 405 nm ($A_{405}$) is recorded using a microplate spectrophotometer. IC$_{50}$ values are calculated by nonlinear regression from the percentage of hemolysis as a function of test compound concentration.

Example 16. Additional Non-Limiting Examples of Compounds of Formula I, Formula I' and Formula I"

Table 4 shows illustrative Factor D inhibitors with characterizing data. The assay of Example 14 was used to

TABLE 4

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 532 | 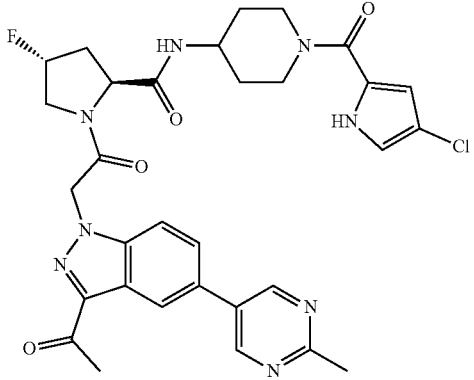 [SMILES: CC(=O)c1nn(CC(=O)N2C[C@H](F)C[C@H]2C(=O)NC2CCN(C(=O)c3cc(Cl)c[nH]3)CC2)c2ccc(-c3cnc(C)nc3)cc12] | (2S,4R)-1-(2-(3-acetyl-5-(2-methylpyrimidin-5-yl)-1H-indazol-1-yl)acetyl)-N-(1-(4-chloro-1H-pyrrole-2-carbonyl)piperidin-4-yl)-4-fluoropyrrolidine-2-carboxamide | *** | 3.16 (B) | 635 |
| 533 | 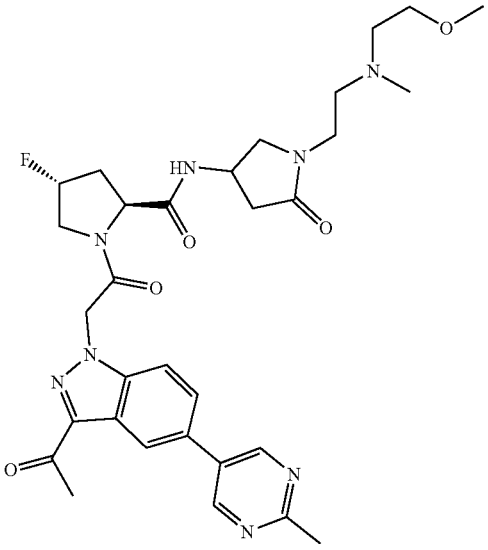 [SMILES: COCCN(C)CCN1CC(NC(=O)[C@@H]2C[C@@H](F)CN2C(=O)Cn2nc(C(C)=O)c3cc(-c4cnc(C)nc4)ccc32)CC1=O] | (2S,4R)-1-(2-(3-acetyl-5-(2-methylpyrimidin-5-yl)-1H-indazol-1-yl)acetyl)-4-fluoro-N-(1-(2-((2-methoxyethyl)(methyl)amino)ethyl)-5-oxopyrrolidin-3-yl)pyrrolidine-2-carboxamide | * | 2.63 (B) | 623 |
| 534 | 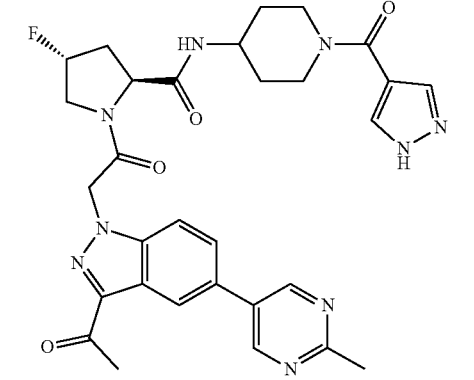 [SMILES: CC(=O)c1nn(CC(=O)N2C[C@H](F)C[C@H]2C(=O)NC2CCN(C(=O)c3cn[nH]c3)CC2)c2ccc(-c3cnc(C)nc3)cc12] | 6-(4-((2S,4R)-1-(2-(3-acetyl-5-(2-methylpyrimidin-5-yl)-1H-indazol-1-yl)acetyl)-4-fluoropyrrolidine-2-carboxamido)piperidin-1-yl)nicotinic acid | ** | 2.54 (B) | 602 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 535 | 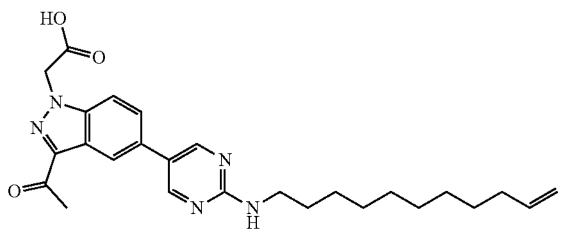 [SMILES: C=CCCCCCCCCCNc1ncc(-c2ccc3c(c2)c(C(C)=O)nn3CC(=O)O)cn1] | 2-(3-acetyl-5-(2-(undec-10-en-1-ylamino)pyrimidin-5-yl)-1H-indazol-1-yl)acetic acid | * | 4.77 (B) | 464 |
| 536 | 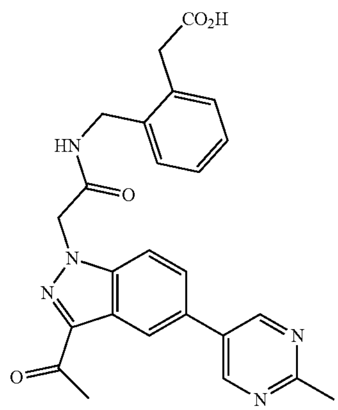 [SMILES: CC(=O)c1nn(CC(=O)NCc2ccccc2CC(=O)O)c2ccc(-c3cnc(C)nc3)cc12] | 2-(2-((2-(3-acetyl-5-(2-methylpyrimidin-5-yl)-1H-indazol-1-yl)acetamido)methyl)phenyl)acetic acid | * | 1.29 (A) | 458 |
| 537 | 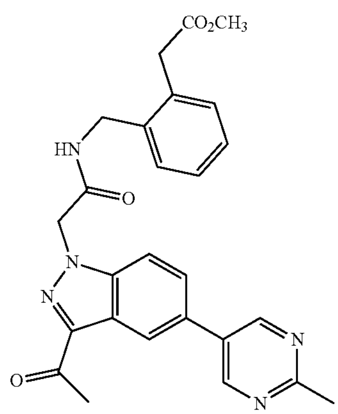 [SMILES: COC(=O)Cc1ccccc1CNC(=O)Cn1nc(C(C)=O)c2cc(-c3cnc(C)nc3)ccc21] | methyl 2-(2-((2-(3-acetyl-5-(2-methylpyrimidin-5-yl)-1H-indazol-1-yl)acetamido)methyl)phenyl)acetate | * | 1.56 (A) | 472 |
| 538 | 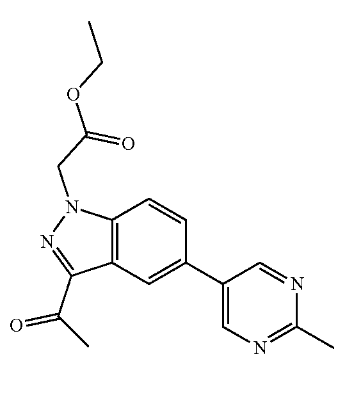 [SMILES: CCOC(=O)Cn1nc(C(C)=O)c2cc(-c3cnc(C)nc3)ccc21] | ethyl 2-(3-acetyl-5-(2-methylpyrimidin-5-yl)-1H-indazol-1-yl)acetate | | | |

TABLE 4-continued

Non-limiting Examples of Compounds of Formula I, Formula I' and Formula I''

| Cmp No. | Structure | Name | IC$_{50}$ | RT min (Method A or B) | MS (M + 1) |
|---|---|---|---|---|---|
| 539 | 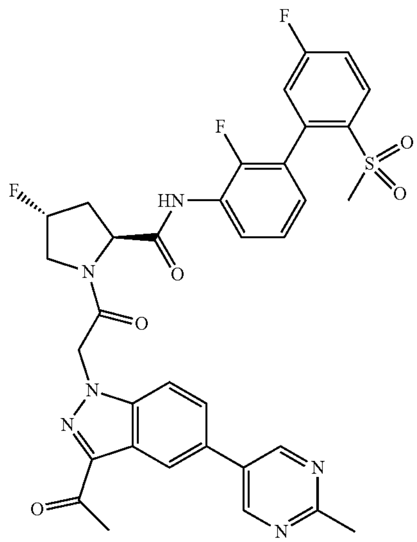 [SMILES: CC(=O)c1nn(CC(=O)N2C[C@H](F)C[C@H]2C(=O)Nc2cccc(-c3cc(F)ccc3S(C)(=O)=O)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(2,5'-difluoro-2'-(methylsulfonyl)-[1,1'-biphenyl]-3-yl)-4-fluoropyrrolidine-2-carboxamide | *** | 1.74 (A) | 691 |
| 540 | 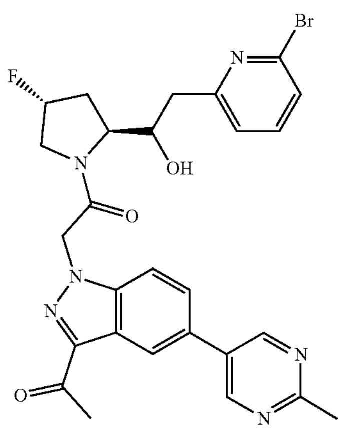 [SMILES: CC(=O)c1nn(CC(=O)N2C[C@H](F)C[C@H]2C(O)Cc2cccc(Br)n2)c2ccc(-c3cnc(C)nc3)cc12] | 2-(3-acetyl-5-(2-methylpyrimidin-5-yl)-1H-indazol-1-yl)-1-((2S,4R)-2-((S)-2-(6-bromopyridin-2-yl)-1-hydroxyethyl)-4-fluoropyrrolidin-1-yl)ethan-1-one | ** | 3.60 (B) | 581 |
| 541 | 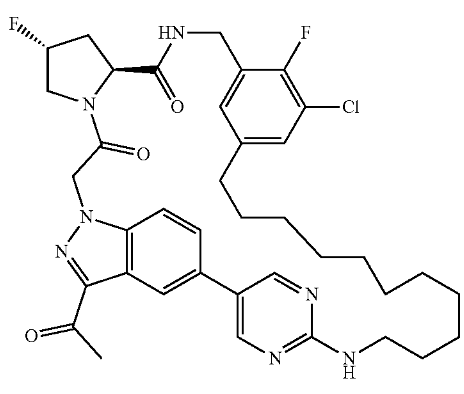 [SMILES: CC(=O)c1nn2c3ccc(cc13)-c1cnc(nc1)NCCCCCCCCCCCc1cc(Cl)c(F)c(c1)CNC(=O)[C@@H]1C[C@@H](F)CN1C(=O)C2] | | * | 2.30 (B) | 720 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 542 | 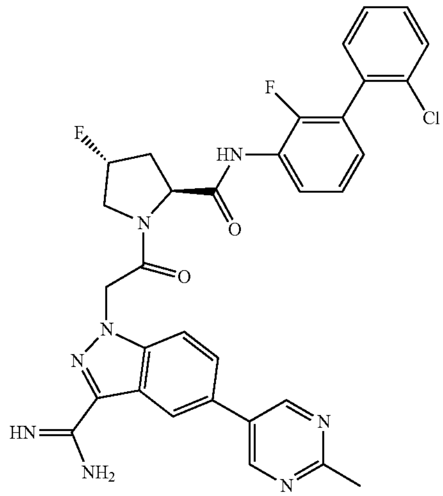 [SMILES: Cc1ncc(-c2ccc3c(c2)c(C(=N)N)nn3CC(=O)N2C[C@H](F)C[C@H]2C(=O)Nc2cccc(-c3ccccc3Cl)c2F)cn1] | (2S,4R)-1-(2-(3-carbamimidoyl-5-(2-methylpyrimidin-5-yl)-1H-indazol-1-yl)acetyl)-N-(2'-chloro-2-fluoro-[1,1'-biphenyl]-3-yl)-4-fluoropyrrolidine-2-carboxamide | *** | 1.64 (A) | 629 |
| 543 | 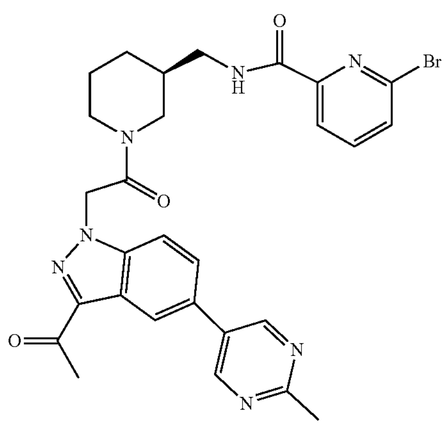 [SMILES: CC(=O)c1nn(CC(=O)N2CCC[C@@H](CNC(=O)c3cccc(Br)n3)C2)c2ccc(-c3cnc(C)nc3)cc12] | (S)-N-((1-(2-(3-acetyl-5-(2-methylpyrimidin-5-yl)-1H-indazol-1-yl)acetyl)piperidin-3-yl)methyl)-6-bromopicolinamide | * | 1.72 (A) | 592 |
| 544 | 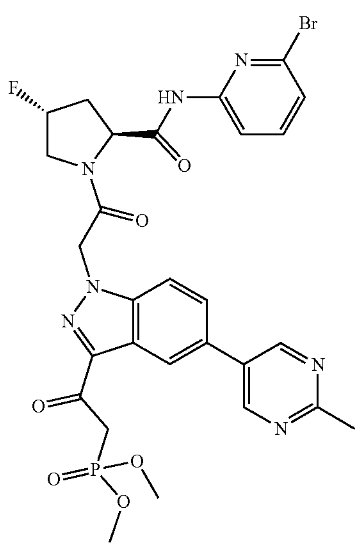 [SMILES: COP(=O)(CC(=O)c1nn(CC(=O)N2C[C@H](F)C[C@H]2C(=O)Nc2cccc(Br)n2)c2ccc(-c3cnc(C)nc3)cc12)OC] | dimethyl (2-(1-(2-((2S,4R)-2-((6-bromopyridin-2-yl)carbamoyl)-4-fluoropyrrolidin-1-yl)-2-oxoethyl)-5-(2-methylpyrimidin-5-yl)-1H-indazol-3-yl)-2-oxoethyl)phosphonate | * | 1.49 (A) | 690 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 545 | 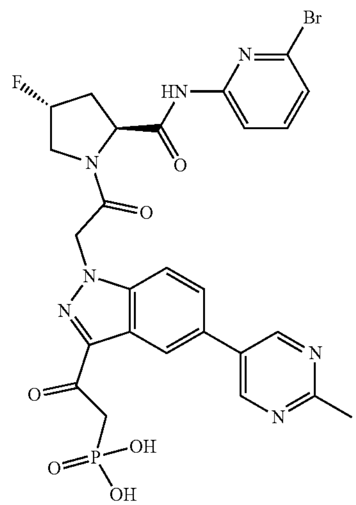 [SMILES: Cc1ncc(-c2ccc3c(c2)c(C(=O)CP(=O)(O)O)nn3CC(=O)N2C[C@H](F)C[C@H]2C(=O)Nc2cccc(Br)n2)cn1] | (2-(1-(2-((2S,4R)-2-((6-bromopyridin-2-yl)carbamoyl)-4-fluoropyrrolidin-1-yl)-2-oxoethyl)-5-(2-methylpyrimidin-5-yl)-1H-indazol-3-yl)-2-oxoethyl)phosphonic acid | * | 1.02 (A) | 662 |
| 546 | 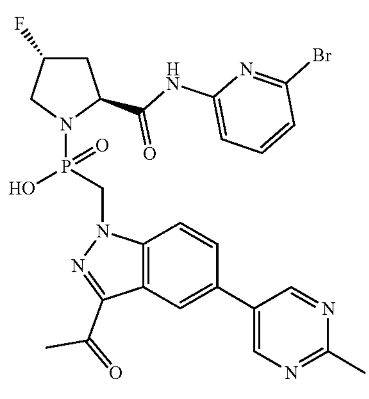 [SMILES: CC(=O)c1nn(CP(=O)(O)N2C[C@H](F)C[C@H]2C(=O)Nc2cccc(Br)n2)c2ccc(-c3cnc(C)nc3)cc12] | ((3-acetyl-5-(2-methylpyrimidin-5-yl)-1H-indazol-1-yl)methyl)((2S,4R)-2-((6-bromopyridin-2-yl)carbamoyl)-4-fluoropyrrolidin-1-yl)phosphinic acid | * | 1.10 (A) | 616 |
| 547 | 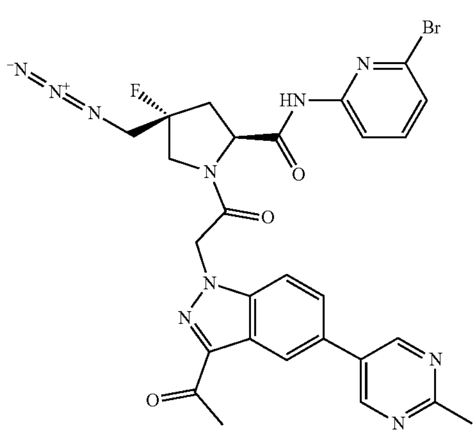 | (2S,4R)-1-(2-(3-acetyl-5-(2-methylpyrimidin-5-yl)-1H-indazol-1-yl)acetyl)-4-(azidomethyl)-N-(6-bromopyridin-2-yl)-4-fluoropyrrolidine-2-carboxamide | *** | 3.66 (B) | 635 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 548 | 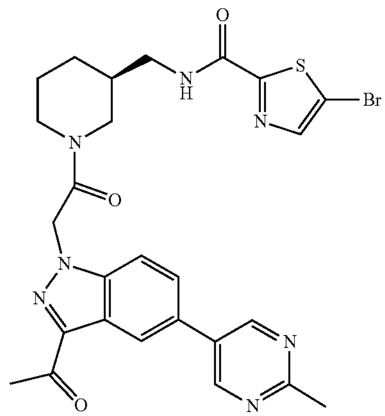 [SMILES: CC(=O)c1nn(CC(=O)N2CCC[C@@H](CNC(=O)c3ncc(Br)s3)C2)c2ccc(-c3cnc(C)nc3)cc12] | (S)-N-((1-(2-(3-acetyl-5-(2-methylpyrimidin-5-yl)-1H-indazol-1-yl)acetyl)piperidin-3-yl)methyl)-5-bromothiazole-2-carboxamide | * | 1.78 (A) | 598 |
| 549 | 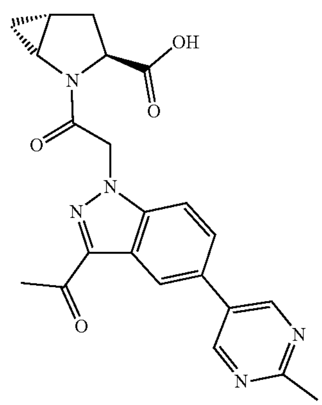 | (1R,3S,5R)-2-(2-(3-acetyl-5-(2-methylpyrimidin-5-yl)-1H-indazol-1-yl)acetyl)-2-azabicyclo[3.1.0]hexane-3-carboxylic acid | * | 1.11 (A) | 420 |
| 550 | 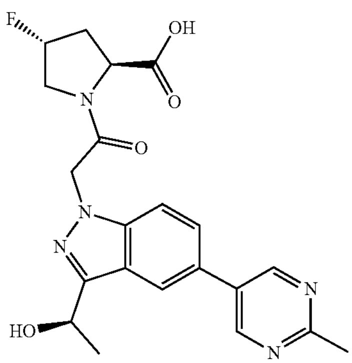 [SMILES: Cc1ncc(-c2ccc3c(c2)c([C@@H](C)O)nn3CC(=O)N2C[C@H](F)C[C@H]2C(=O)O)cn1] | (2S,4R)-4-fluoro-1-(2-(3-((R)-1-hydroxyethyl)-5-(2-methylpyrimidin-5-yl)-1H-indazol-1-yl)acetyl)pyrrolidine-2-carboxylic acid | * | | |
| 551 | 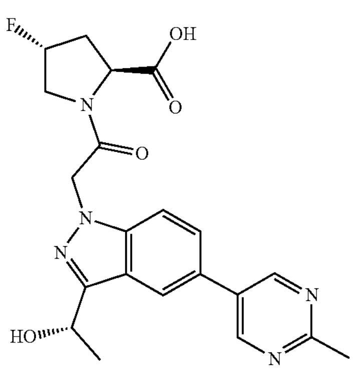 [SMILES: Cc1ncc(-c2ccc3c(c2)c([C@H](C)O)nn3CC(=O)N2C[C@H](F)C[C@H]2C(=O)O)cn1] | (2S,4R)-4-fluoro-1-(2-(3-((S)-1-hydroxyethyl)-5-(2-methylpyrimidin-5-yl)-1H-indazol-1-yl)acetyl)pyrrolidine-2-carboxylic acid | * | | |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 552 | 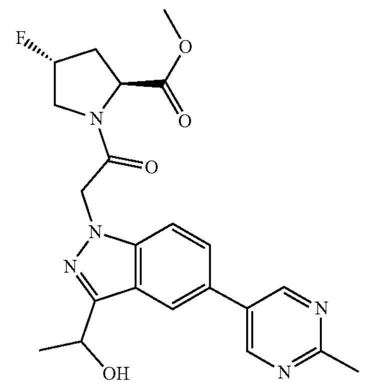 [SMILES: COC(=O)[C@@H]1C[C@@H](F)CN1C(=O)Cn1nc(C(C)O)c2cc(-c3cnc(C)nc3)ccc21] | (2S,4R)-methyl 4-fluoro-1-(2-(3-(1-hydroxyethyl)-5-(2-methylpyrimidin-5-yl)-1H-indazol-1-yl)acetyl)pyrrolidine-2-carboxylate | * | 0.95 (A) | 442 |
| 553 | 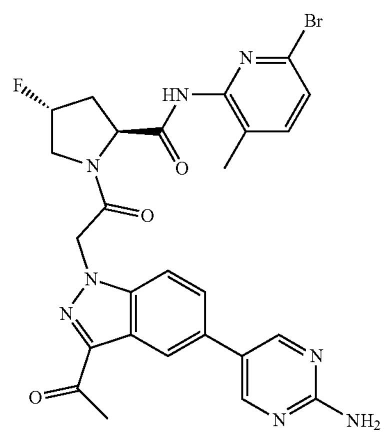 [SMILES: CC(=O)c1nn(CC(=O)N2C[C@H](F)C[C@H]2C(=O)Nc2nc(Br)ccc2C)c2ccc(-c3cnc(N)nc3)cc12] | (2S,4R)-1-(2-(3-acetyl-5-(2-aminopyrimidin-5-yl)-1H-indazol-1-yl)acetyl)-N-(6-bromo-3-methylpyridin-2-yl)-4-fluoropyrrolidine-2-carboxamide | *** | 1.28 (A) | 595 |
| 554 | 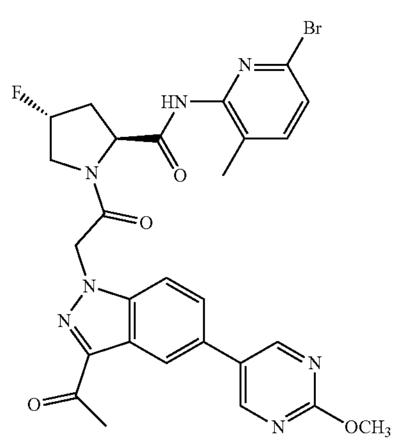 [SMILES: COc1ncc(-c2ccc3c(c2)c(C(C)=O)nn3CC(=O)N2C[C@H](F)C[C@H]2C(=O)Nc2nc(Br)ccc2C)cn1] | (2S,4R)-1-(2-(3-acetyl-5-(2-methoxypyrimidin-5-yl)-1H-indazol-1-yl)acetyl)-N-(6-bromo-3-methylpyridin-2-yl)-4-fluoropyrrolidine-2-carboxamide | *** | 1.67 (A) | 610 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 555 | 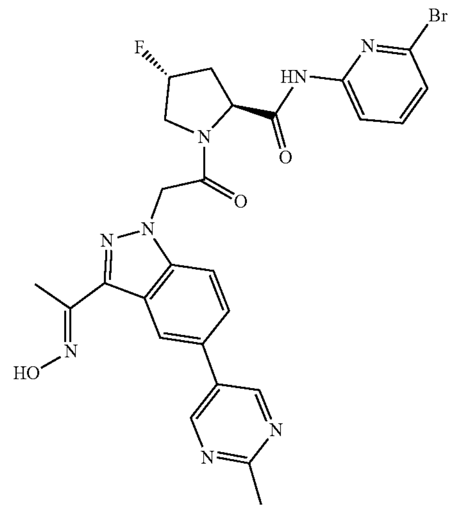 [SMILES: C/C(=N\O)c1nn(CC(=O)N2C[C@H](F)C[C@H]2C(=O)Nc2cccc(Br)n2)c2ccc(-c3cnc(C)nc3)cc12] | (2S,4R)-N-(6-bromopyridin-2-yl)-4-fluoro-1-(2-(3-((E)-1-(hydroxyimino)ethyl)-5-(2-methylpyrimidin-5-yl)-1H-indazol-1-yl)acetyl)pyrrolidine-2-carboxamide | *** | 1.62 (A) | 597 |
| 556 | 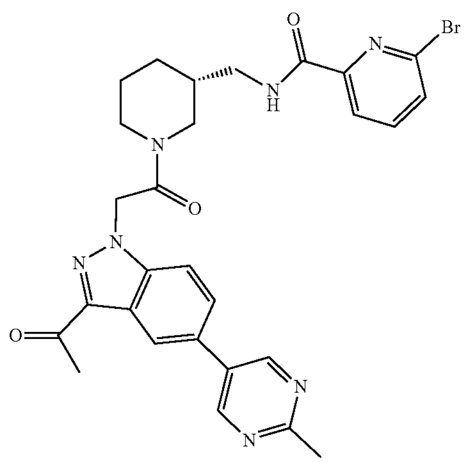 [SMILES: CC(=O)c1nn(CC(=O)N2CCC[C@H](CNC(=O)c3cccc(Br)n3)C2)c2ccc(-c3cnc(C)nc3)cc12] | (R)-N-((1-(2-(3-acetyl-5-(2-methylpyrimidin-5-yl)-1H-indazol-1-yl)acetyl)piperidin-3-yl)methyl)-6-bromopicolinamide | * | 1.72 (A) | 592 |
| 557 | 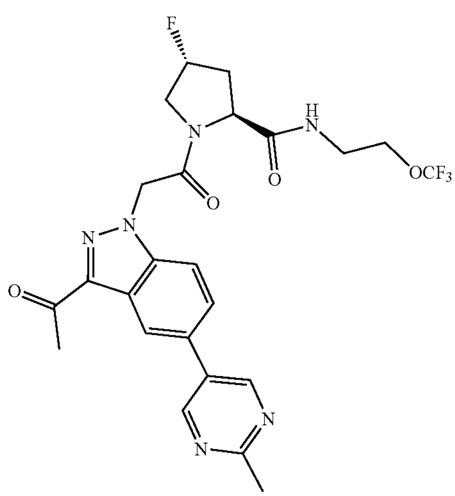 [SMILES: CC(=O)c1nn(CC(=O)N2C[C@H](F)C[C@H]2C(=O)NCCOC(F)(F)F)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(2-(trifluoromethoxy)ethyl)pyrrolidine-2-carboxamide | *** | 1.42 (A) | 536 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 558 | 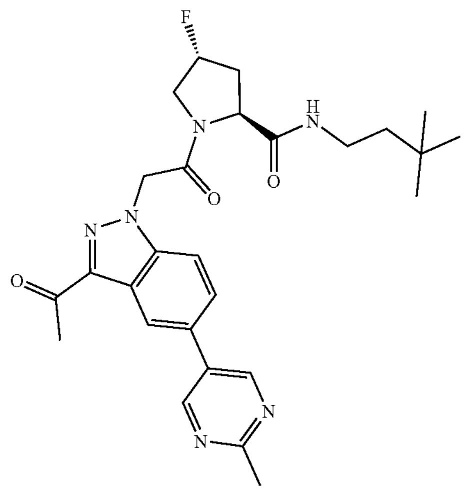 [SMILES: CC(=O)c1nn(CC(=O)N2C[C@H](F)C[C@H]2C(=O)NCCC(C)(C)C)c2ccc(-c3cnc(C)nc3)cc12] | (2S,4R)-1-(2-(3-acetyl-5-(2-methylpyrimidin-5-yl)-1H-indazol-1-yl)acetyl)-N-(3,3-dimethylbutyl)-4-fluoropyrrolidine-2-carboxamide | *** | 1.69 (A) | 508 |
| 559 | 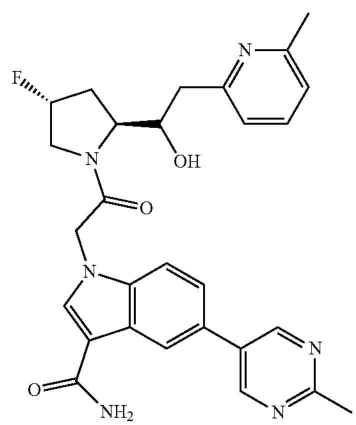 [SMILES: Cc1cccc(CC(O)[C@@H]2C[C@@H](F)CN2C(=O)Cn2cc(C(N)=O)c3cc(-c4cnc(C)nc4)ccc32)n1] | 1-(2-((2S,4R)-4-fluoro-2-((S)-1-hydroxy-2-(6-methylpyridin-2-yl)ethyl)pyrrolidin-1-yl)-2-oxoethyl)-5-(2-methylpyrimidin-5-yl)-1H-indole-3-carboxamide | * | 1.33 (B) | 517 |
| 560 | 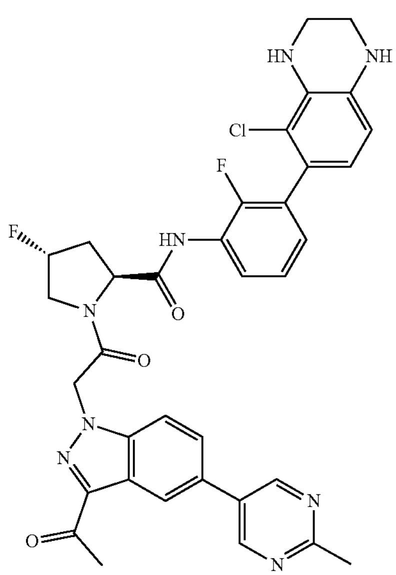 [SMILES: CC(=O)c1nn(CC(=O)N2C[C@H](F)C[C@H]2C(=O)Nc2cccc(-c3ccc4c(c3Cl)NCCN4)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(3-(5-chloro-1,2,3,4-tetrahydroquinoxalin-6-yl)-2-fluorophenyl)-4-fluoropyrrolidine-2-carboxamide | *** | 1.77 (A) | 685 |

TABLE 4-continued

Non-limiting Examples of Compounds of Formula I, Formula I' and Formula I''

| Cmp No. | Structure | Name | IC$_{50}$ | RT min (Method A or B) | MS (M + 1) |
|---|---|---|---|---|---|
| 561 | 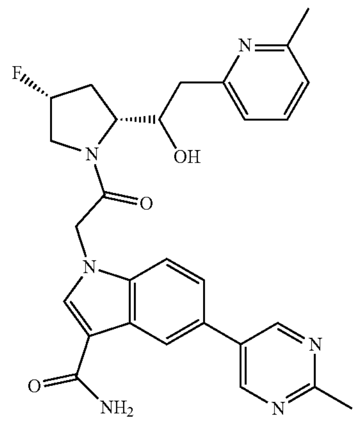 [SMILES: Cc1cccc(CC(O)[C@H]2C[C@@H](F)CN2C(=O)Cn2cc(C(N)=O)c3cc(-c4cnc(C)nc4)ccc32)n1] | 1-(2-((2R,4R)-4-fluoro-2-((R)-1-hydroxy-2-(6-methylpyridin-2-yl)ethyl)pyrrolidin-1-yl)-2-oxoethyl)-5-(2-methylpyrimidin-5-yl)-1H-indole-3-carboxamide | * | | |
| 562 | 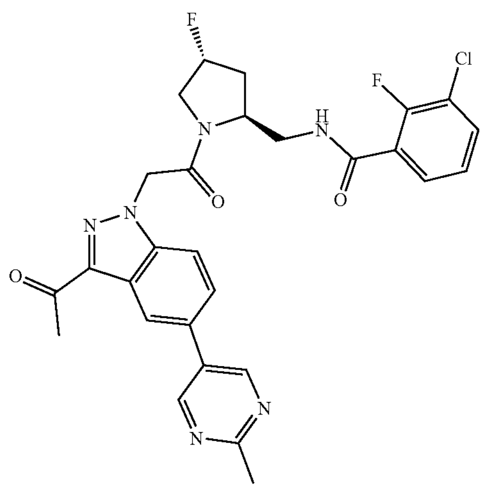 [SMILES: CC(=O)c1nn(CC(=O)N2C[C@H](F)C[C@H]2CNC(=O)c2cccc(Cl)c2F)c2ccc(-c3cnc(C)nc3)cc12] | N-(((2S,4R)-1-(2-(3-acetyl-5-(2-methylpyrimidin-5-yl)-1H-indazol-1-yl)acetyl)-4-fluoropyrrolidin-2-yl)methyl)-3-chloro-2-fluorobenzamide | * | 1.68 (A) | 567 |
| 563 | 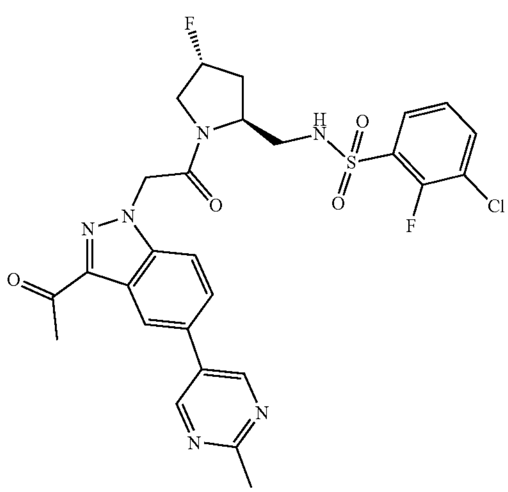 [SMILES: CC(=O)c1nn(CC(=O)N2C[C@H](F)C[C@H]2CNS(=O)(=O)c2cccc(Cl)c2F)c2ccc(-c3cnc(C)nc3)cc12] | N-(((2S,4R)-1-(2-(3-acetyl-5-(2-methylpyrimidin-5-yl)-1H-indazol-1-yl)acetyl)-4-fluoropyrrolidin-2-yl)methyl)-3-chloro-2-fluorobenzenesulfonamide | *** | 1.82 (A) | 603 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 564 | 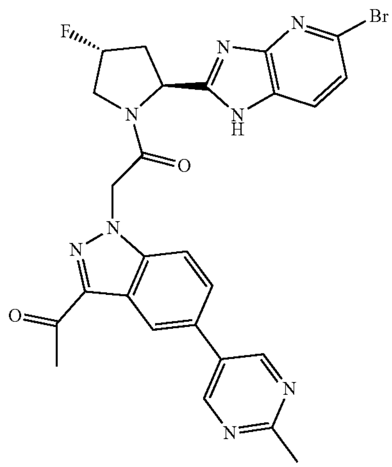 [SMILES: CC(=O)c1nn(CC(=O)N2C[C@H](F)C[C@H]2c2nc3nc(Br)ccc3[nH]2)c2ccc(-c3cnc(C)nc3)cc12] | 2-(3-acetyl-5-(2-methylpyrimidin-5-yl)-1H-indazol-1-yl)-1-((2S,4R)-2-(5-bromo-1H-imidazo[4,5-b]pyridin-2-yl)-4-fluoropyrrolidin-1-yl)ethan-1-one | * | 1.29 (A) | 577 |
| 565 | 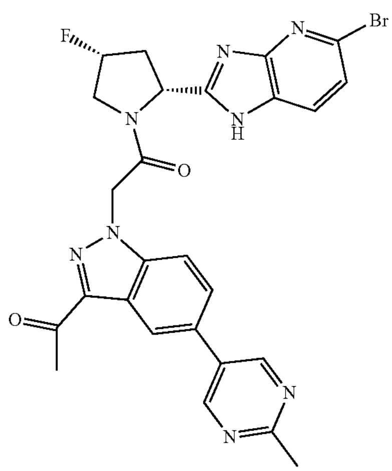 [SMILES: CC(=O)c1nn(CC(=O)N2C[C@H](F)C[C@@H]2c2nc3nc(Br)ccc3[nH]2)c2ccc(-c3cnc(C)nc3)cc12] | 2-(3-acetyl-5-(2-methylpyrimidin-5-yl)-1H-indazol-1-yl)-1-((2R,4R)-2-(5-bromo-1H-imidazo[4,5-b]pyridin-2-yl)-4-fluoropyrrolidin-1-yl)ethan-1-one | * | 1.32 (A) | 579 |
| 566 | 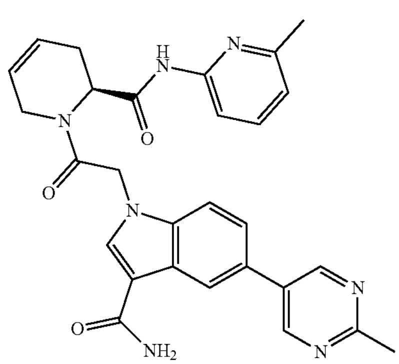 [SMILES: Cc1cccc(NC(=O)[C@@H]2CC=CCN2C(=O)Cn2cc(C(N)=O)c3cc(-c4cnc(C)nc4)ccc32)n1] | (S)-1-(2-(6-((6-methylpyridin-2-yl)carbamoyl)-5,6-dihydropyridin-1(2H)-yl)-2-oxoethyl)-5-(2-methylpyrimidin-5-yl)-1H-indole-3-carboxamide | * | 1.75 (B) | 510 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 569 | 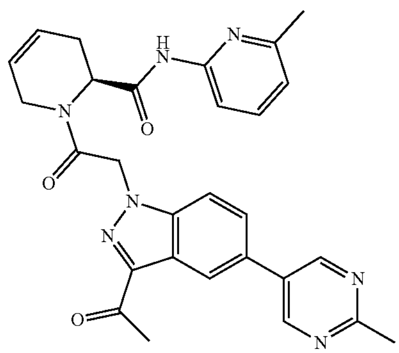 [SMILES: CC(=O)c1nn(CC(=O)N2CC=CC[C@H]2C(=O)Nc2cccc(C)n2)c2ccc(-c3cnc(C)nc3)cc12] | (S)-1-(2-(3-acetyl-5-(2-methylpyrimidin-5-yl)-1H-indazol-1-yl)acetyl)-N-(6-methylpyridin-2-yl)-1,2,3,6-tetrahydropyridine-2-carboxamide | * | 2.79 (B) | 510 |
| 570 | 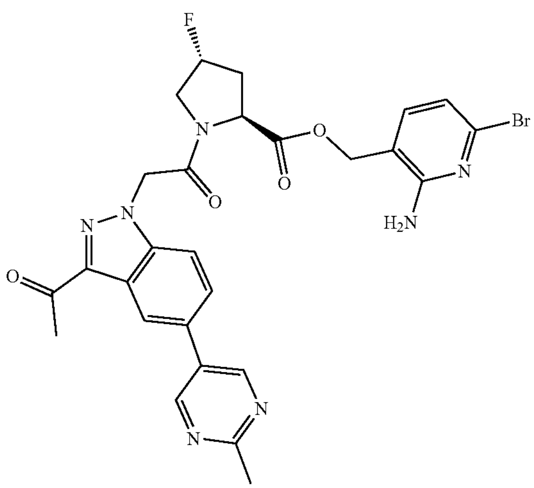 [SMILES: CC(=O)c1nn(CC(=O)N2C[C@H](F)C[C@H]2C(=O)OCc2ccc(Br)nc2N)c2ccc(-c3cnc(C)nc3)cc12] | (2S,4R)-(2-amino-6-bromopyridin-3-yl)methyl 1-(2-(3-acetyl-5-(2-methylpyrimidin-5-yl)-1H-indazol-1-yl)acetyl)-4-fluoropyrrolidine-2-carboxylate | * | 1.65 (A) | 610 |
| 571 | 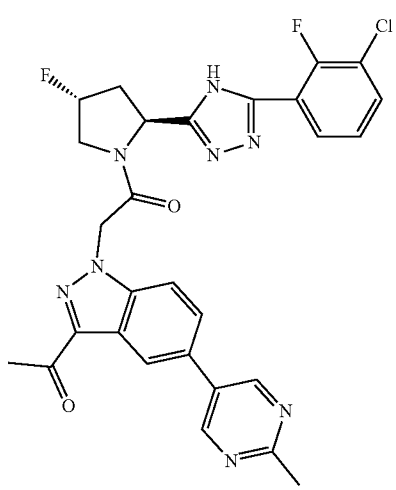 [SMILES: CC(=O)c1nn(CC(=O)N2C[C@H](F)C[C@H]2c2nnc(-c3cccc(Cl)c3F)[nH]2)c2ccc(-c3cnc(C)nc3)cc12] | 2-(3-acetyl-5-(2-methylpyrimidin-5-yl)-1H-indazol-1-yl)-1-((2S,4R)-2-(5-(3-chloro-2-fluorophenyl)-4H-1,2,4-triazol-3-yl)-4-fluoropyrrolidin-1-yl)ethan-1-one | * | 1.63 (A) | 577 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 572 | 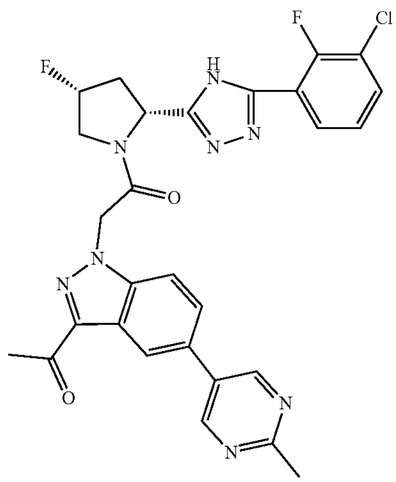 [SMILES: CC(=O)c1nn(CC(=O)N2C[C@H](F)C[C@@H]2c2nnc(-c3cccc(Cl)c3F)[nH]2)c2ccc(-c3cnc(C)nc3)cc12] | 2-(3-acetyl-5-(2-methylpyrimidin-5-yl)-1H-indazol-1-yl)-1-((2R,4R)-2-(5-(3-chloro-2-fluorophenyl)-4H-1,2,4-triazol-3-yl)-4-fluoropyrrolidin-1-yl)ethan-1-one | * | 1.60 (A) | 577 |
| 573 | 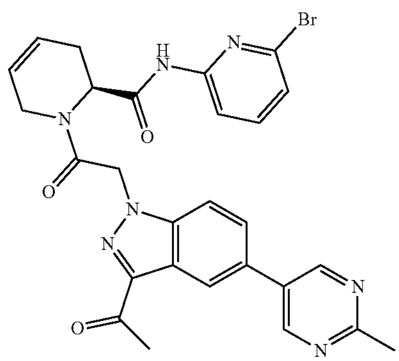 [SMILES: CC(=O)c1nn(CC(=O)N2CC=CC[C@H]2C(=O)Nc2cccc(Br)n2)c2ccc(-c3cnc(C)nc3)cc12] | (S)-1-(2-(3-acetyl-5-(2-methylpyrimidin-5-yl)-1H-indazol-1-yl)acetyl)-N-(6-bromopyridin-2-yl)-1,2,3,6-tetrahydropyridine-2-carboxamide | *** | 3.41 (B) | 574 |
| 574 | 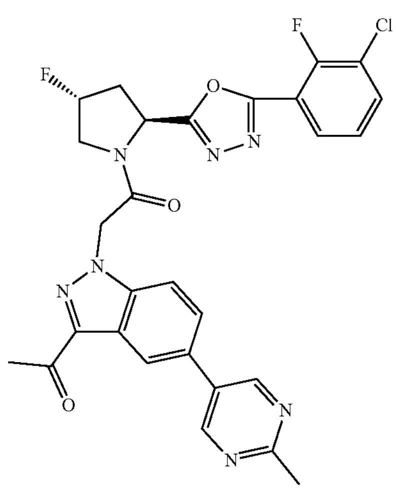 [SMILES: CC(=O)c1nn(CC(=O)N2C[C@H](F)C[C@H]2c2nnc(-c3cccc(Cl)c3F)o2)c2ccc(-c3cnc(C)nc3)cc12] | 2-(3-acetyl-5-(2-methylpyrimidin-5-yl)-1H-indazol-1-yl)-1-((2S,4R)-2-(5-(3-chloro-2-fluorophenyl)-1,3,4-oxadiazol-2-yl)-4-fluoropyrrolidin-1-yl)ethan-1-one | ** | 1.77 (A) | 578 |

TABLE 4-continued

Non-limiting Examples of Compounds of Formula I, Formula I' and Formula I''

| Cmp No. | Structure | Name | IC$_{50}$ | RT min (Method A or B) | MS (M + 1) |
|---|---|---|---|---|---|
| 575 | 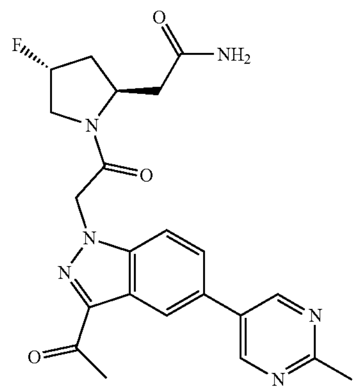 [SMILES: CC(=O)c1nn(CC(=O)N2C[C@H](F)C[C@H]2CC(N)=O)c2ccc(-c3cnc(C)nc3)cc12] | 2-((2R,4R)-1-(2-(3-acetyl-5-(2-methylpyrimidin-5-yl)-1H-indazol-1-yl)acetyl)-4-fluoropyrrolidin-2-yl)acetamide | * | 7.39 (D) | 439 |
| 576 | 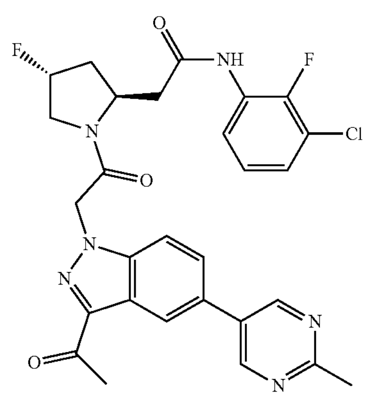 [SMILES: CC(=O)c1nn(CC(=O)N2C[C@H](F)C[C@H]2CC(=O)Nc2cccc(Cl)c2F)c2ccc(-c3cnc(C)nc3)cc12] | 2-((2R,4R)-1-(2-(3-acetyl-5-(2-methylpyrimidin-5-yl)-1H-indazol-1-yl)acetyl)-4-fluoropyrrolidin-2-yl)-N-(3-chloro-2-fluorophenyl)acetamide | * | 11.03 (D) | 567 |
| 577 | 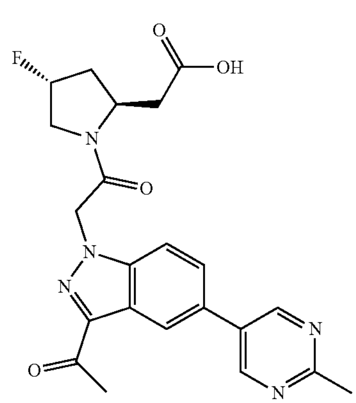 | 2-((2R,4R)-1-(2-(3-acetyl-5-(2-methylpyrimidin-5-yl)-1H-indazol-1-yl)acetyl)-4-fluoropyrrolidin-2-yl)acetic acid | * | 6.46 (D) | 440 |

TABLE 4-continued

Non-limiting Examples of Compounds of Formula I, Formula I' and Formula I''

| Cmp No. | Structure | Name | IC$_{50}$ | RT min (Method A or B) | MS (M + 1) |
|---|---|---|---|---|---|
| 578 | 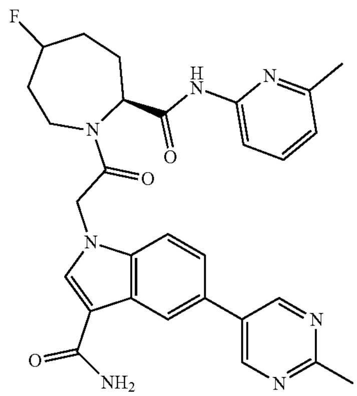 [SMILES: Cc1cccc(NC(=O)[C@@H]2CCC(F)CCN2C(=O)Cn2cc(C(N)=O)c3cc(-c4cnc(C)nc4)ccc32)n1] | 1-(2-((2S)-5-fluoro-2-((6-methylpyridin-2-yl)carbamoyl)azepan-1-yl)-2-oxoethyl)-5-(2-methylpyrimidin-5-yl)-1H-indole-3-carboxamide | * | 3.39 (B) | 544 |
| 579 | 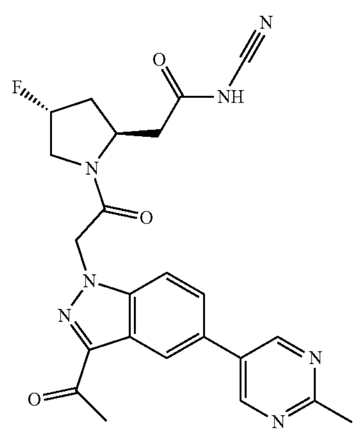 [SMILES: CC(=O)c1nn(CC(=O)N2C[C@H](F)C[C@H]2CC(=O)NC#N)c2ccc(-c3cnc(C)nc3)cc12] | 2-((2R,4R)-1-(2-(3-acetyl-5-(2-methylpyrimidin-5-yl)-1H-indazol-1-yl)acetyl)-4-fluoropyrrolidin-2-yl)-N-cyanoacetamide | * | 6.79 (D) | 464 |
| 580 | 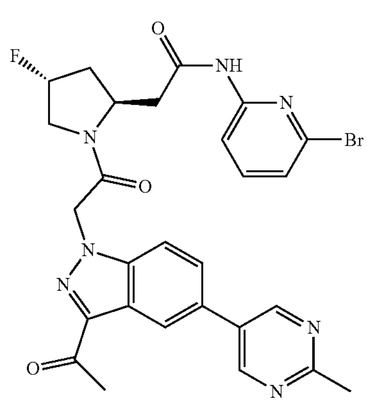 [SMILES: CC(=O)c1nn(CC(=O)N2C[C@H](F)C[C@H]2CC(=O)Nc2cccc(Br)n2)c2ccc(-c3cnc(C)nc3)cc12] | 2-((2R,4R)-1-(2-(3-acetyl-5-(2-methylpyrimidin-5-yl)-1H-indazol-1-yl)acetyl)-4-fluoropyrrolidin-2-yl)-N-(6-bromopyridin-2-yl)acetamide | * | 10.68 (D) | 596 (M + 2) |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 581 | 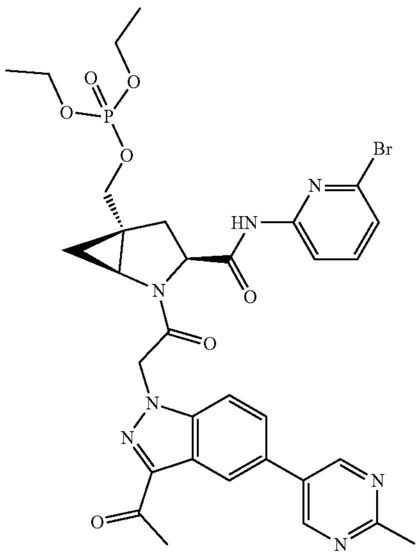 [SMILES: CCOP(=O)(OCC)OC[C@@]12C[C@@H]1N(C(=O)Cn1nc(C(C)=O)c3cc(-c4cnc(C)nc4)ccc31)[C@H](C(=O)Nc1cccc(Br)n1)C2] | ((1S,3S,5R)-2-(2-(3-acetyl-5-(2-methylpyrimidin-5-yl)-1H-indazol-1-yl)acetyl)-3-((6-bromopyridin-2-yl)carbamoyl)-2-azabicyclo[3.1.0]hexan-5-yl)methyl diethyl phosphate | ** | 3.66 (B) | 740 |
| 582 | 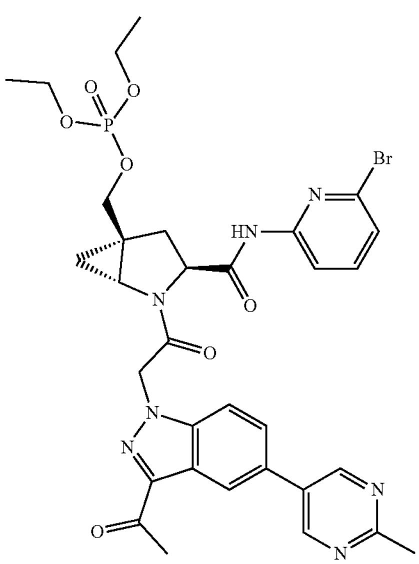 [SMILES: CCOP(=O)(OCC)OC[C@@]12C[C@@H](C(=O)Nc3cccc(Br)n3)N(C(=O)Cn3nc(C(C)=O)c4cc(-c5cnc(C)nc5)ccc43)[C@@H]1C2] | ((1R,3S,5S)-2-(2-(3-acetyl-5-(2-methylpyrimidin-5-yl)-1H-indazol-1-yl)acetyl)-3-((6-bromopyridin-2-yl)carbamoyl)-2-azabicyclo[3.1.0]hexan-5-yl)methyl diethyl phosphate | *** | 3.50 (B) | 740 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 583 | 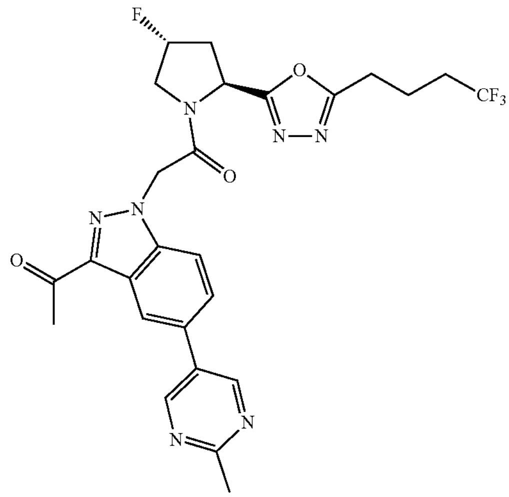 [SMILES: CC(=O)c1nn(CC(=O)N2C[C@H](F)C[C@H]2c2nnc(CCCC(F)(F)F)o2)c2ccc(-c3cnc(C)nc3)cc12] | 2-(3-acetyl-5-(2-methylpyrimidin-5-yl)-1H-indazol-1-yl)-1-((2S,4R)-4-fluoro-2-(5-(4,4,4-trifluorobutyl)-1,3,4-oxadiazol-2-yl)pyrrolidin-1-yl)ethan-1-one | ** | 1.63 (A) | 560 |
| 584 | 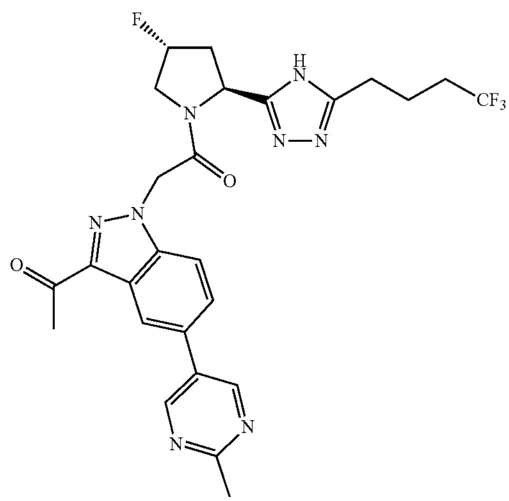 [SMILES: CC(=O)c1nn(CC(=O)N2C[C@H](F)C[C@H]2c2nnc(CCCC(F)(F)F)[nH]2)c2ccc(-c3cnc(C)nc3)cc12] | 2-(3-acetyl-5-(2-methylpyrimidin-5-yl)-1H-indazol-1-yl)-1-((2S,4R)-4-fluoro-2-(5-(4,4,4-trifluorobutyl)-4H-1,2,4-triazol-3-yl)pyrrolidin-1-yl)ethan-1-one | ** | 1.43 (A) | 559 |
| 585 | 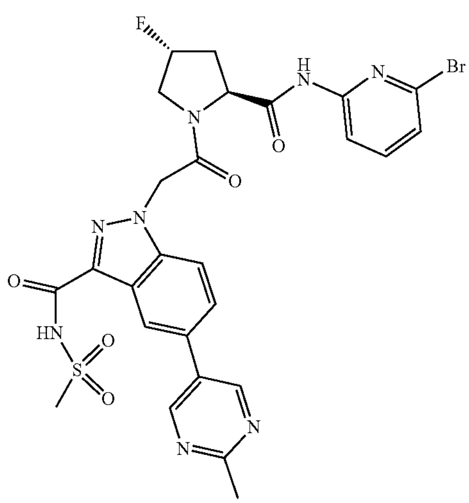 [SMILES: Cc1ncc(-c2ccc3c(c2)c(C(=O)NS(C)(=O)=O)nn3CC(=O)N2C[C@H](F)C[C@H]2C(=O)Nc2cccc(Br)n2)cn1] | 1-(2-((2S,4R)-2-((6-bromopyridin-2-yl)carbamoyl)-4-fluoropyrrolidin-1-yl)-2-oxoethyl)-5-(2-methylpyrimidin-5-yl)-N-(methylsulfonyl)-1H-indazole-3-carboxamide | * | 1.51 (A) | 659 |

TABLE 4-continued

Non-limiting Examples of Compounds of Formula I, Formula I' and Formula I''

| Cmp No. | Structure | Name | IC$_{50}$ | RT min (Method A or B) | MS (M + 1) |
|---|---|---|---|---|---|
| 586 | 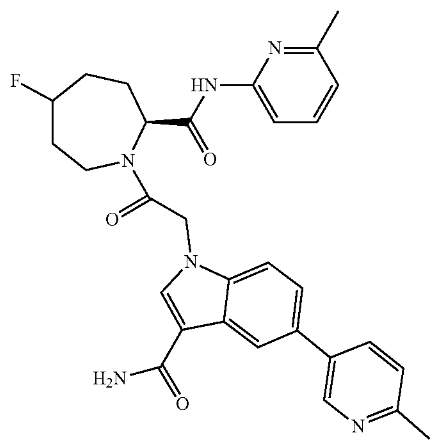 [SMILES: Cc1ccc(-c2ccc3c(c2)c(C(N)=O)cn3CC(=O)N2CCC(F)CC[C@H]2C(=O)Nc2cccc(C)n2)cn1] | 1-(2-((2S)-5-fluoro-2-((6-methylpyridin-2-yl)carbamoyl)azepan-1-yl)-2-oxoethyl)-5-(6-methylpyridin-3-yl)-1H-indole-3-carboxamide | * | 3.30 (B) | 543 |
| 587 | 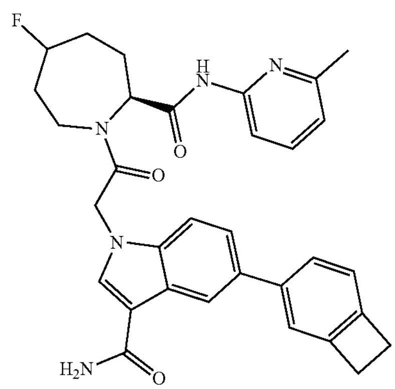 [SMILES: Cc1cccc(NC(=O)[C@@H]2CCC(F)CCN2C(=O)Cn2cc(C(N)=O)c3cc(-c4ccc5c(c4)CC5)ccc32)n1] | 5-(bicyclo[4.2.0]octa-1(6),2,4-trien-3-yl)-1-(2-((2S)-5-fluoro-2-((6-methylpyridin-2-yl)carbamoyl)azepan-1-yl)-2-oxoethyl)-1H-indole-3-carboxamide | * | 3.38 (B) | 554 |
| 588 | 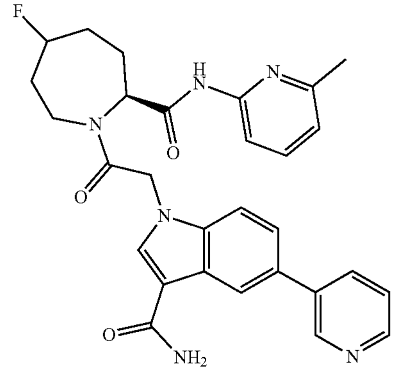 [SMILES: Cc1cccc(NC(=O)[C@@H]2CCC(F)CCN2C(=O)Cn2cc(C(N)=O)c3cc(-c4cccnc4)ccc32)n1] | 1-(2-((2S)-5-fluoro-2-((6-methylpyridin-2-yl)carbamoyl)azepan-1-yl)-2-oxoethyl)-5-(pyridin-3-yl)-1H-indole-3-carboxamide | * | 3.27 (B) | 529 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 589 | 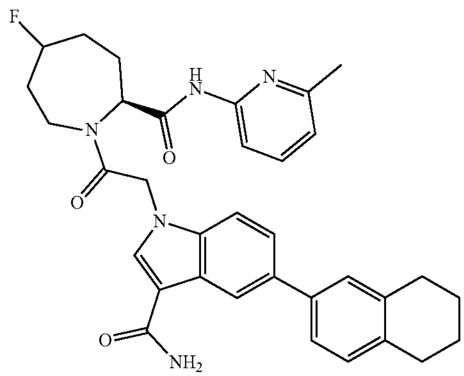 [SMILES: Cc1cccc(NC(=O)[C@@H]2CCC(F)CCN2C(=O)Cn2cc(C(N)=O)c3cc(-c4ccc5c(c4)CCCC5)ccc32)n1] | 1-(2-((2S)-5-fluoro-2-((6-methylpyridin-2-yl)carbamoyl)azepan-1-yl)-2-oxoethyl)-5-(5,6,7,8-tetrahydronaphthalen-2-yl)-1H-indole-3-carboxamide | * | 3.98 (B) | 582 |
| 590 | 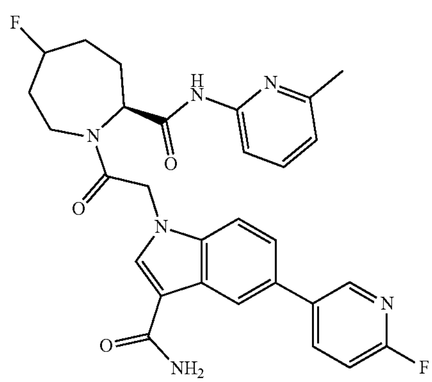 [SMILES: Cc1cccc(NC(=O)[C@@H]2CCC(F)CCN2C(=O)Cn2cc(C(N)=O)c3cc(-c4ccc(F)nc4)ccc32)n1] | 1-(2-((2S)-5-fluoro-2-((6-methylpyridin-2-yl)carbamoyl)azepan-1-yl)-2-oxoethyl)-5-(6-fluoropyridin-3-yl)-1H-indole-3-carboxamide | * | 2.33 (B) | 547 |
| 591 | 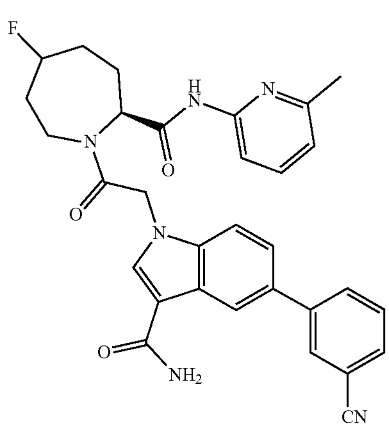 [SMILES: Cc1cccc(NC(=O)[C@@H]2CCC(F)CCN2C(=O)Cn2cc(C(N)=O)c3cc(-c4cccc(C#N)c4)ccc32)n1] | 5-(3-cyanophenyl)-1-(2-((2S)-5-fluoro-2-((6-methylpyridin-2-yl)carbamoyl)azepan-1-yl)-2-oxoethyl)-1H-indole-3-carboxamide | * | 2.82 (B) | 553 |

TABLE 4-continued

Non-limiting Examples of Compounds of Formula I, Formula I' and Formula I''

| Cmp No. | Structure | Name | IC$_{50}$ | RT min (Method A or B) | MS (M + 1) |
|---|---|---|---|---|---|
| 592 | 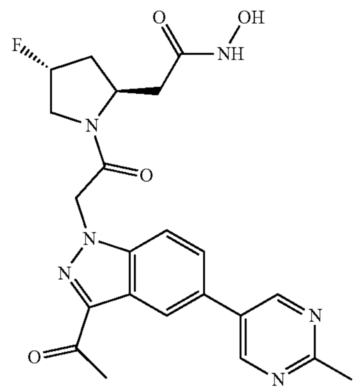 [SMILES: CC(=O)c1nn(CC(=O)N2C[C@H](F)C[C@H]2CC(=O)NO)c2ccc(-c3cnc(C)nc3)cc12] | 2-((2R,4R)-1-(2-(3-acetyl-5-(2-methylpyrimidin-5-yl)-1H-indazol-1-yl)acetyl)-4-fluoropyrrolidin-2-yl)-N-hydroxyacetamide | * | 5.53 (C) | 455 |
| 593 | 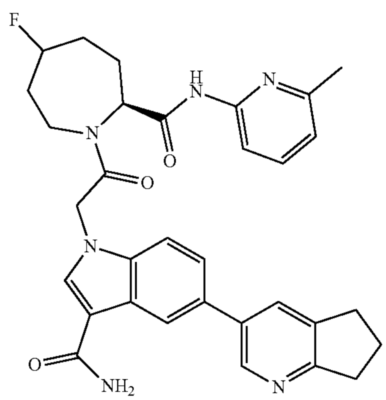 [SMILES: Cc1cccc(NC(=O)[C@@H]2CCC(F)CCN2C(=O)Cn2cc(C(N)=O)c3cc(-c4cnc5c(c4)CCC5)ccc32)n1] | 5-(6,7-dihydro-5H-cyclopenta[b]pyridin-3-yl)-1-(2-((2S)-5-fluoro-2-((6-methylpyridin-2-yl)carbamoyl)azepan-1-yl)-2-oxoethyl)-1H-indole-3-carboxamide | * | 3.86 (B) | 569 |
| 594 | 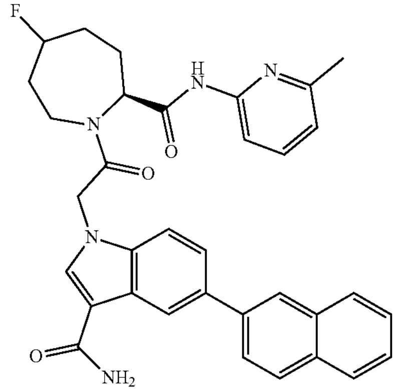 [SMILES: Cc1cccc(NC(=O)[C@@H]2CCC(F)CCN2C(=O)Cn2cc(C(N)=O)c3cc(-c4ccc5ccccc5c4)ccc32)n1] | 1-(2-((2S)-5-fluoro-2-((6-methylpyridin-2-yl)carbamoyl)azepan-1-yl)-2-oxoethyl)-5-(naphthalen-2-yl)-1H-indole-3-carboxamide | * | 4.02 (B) | 578 |

US 11,926,617 B2

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 595 | 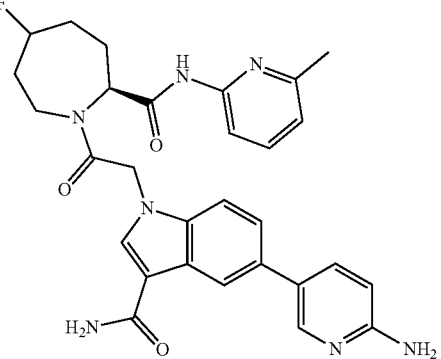 | 5-(6-aminopyridin-3-yl)-1-(2-((2S)-5-fluoro-2-((6-methylpyridin-2-yl)carbamoyl)azepan-1-yl)-2-oxoethyl)-1H-indole-3-carboxamide | * | 3.25 (B) | 544 |
| 596 | 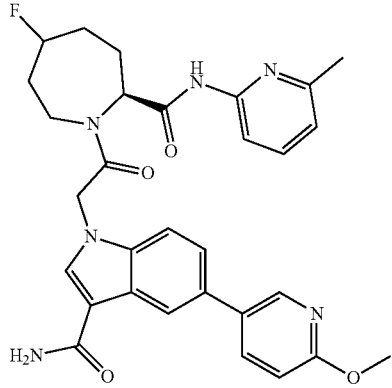 [SMILES: COc1ccc(-c2ccc3c(c2)c(C(N)=O)cn3CC(=O)N2CCC(F)CC[C@H]2C(=O)Nc2cccc(C)n2)cn1] | 1-(2-((2S)-5-fluoro-2-((6-methylpyridin-2-yl)carbamoyl)azepan-1-yl)-2-oxoethyl)-5-(6-methoxypyridin-3-yl)-1H-indole-3-carboxamide | * | 2.48 (B) | 559 |
| 597 | 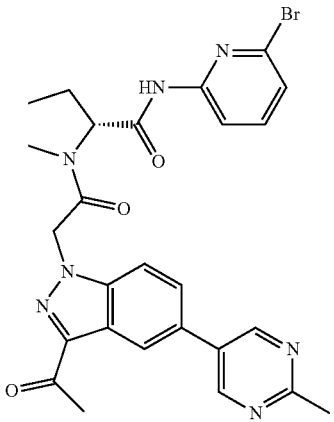 [SMILES: CC[C@H](C(=O)Nc1cccc(Br)n1)N(C)C(=O)Cn1nc(C(C)=O)c2cc(-c3cnc(C)nc3)ccc21] | (R)-2-(2-(3-acetyl-5-(2-methylpyrimidin-5-yl)-1H-indazol-1-yl)-N-methylacetamido)-N-(6-bromopyridin-2-yl)butanamide | * | 11.72 (D) | 564 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 598 | 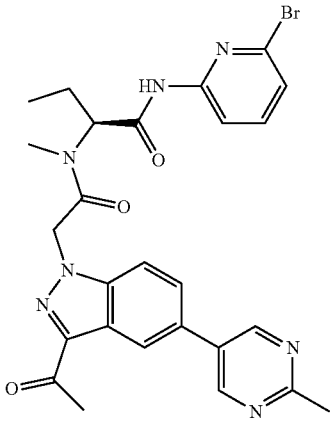 [SMILES: CC[C@@H](C(=O)Nc1cccc(Br)n1)N(C)C(=O)Cn1nc(C(C)=O)c2cc(-c3cnc(C)nc3)ccc21] | (S)-2-(2-(3-acetyl-5-(2-methylpyrimidin-5-yl)-1H-indazol-1-yl)-N-methylacetamido)-N-(6-bromopyridin-2-yl)butanamide | ** | 11.72 (D) | 564 |
| 599 | 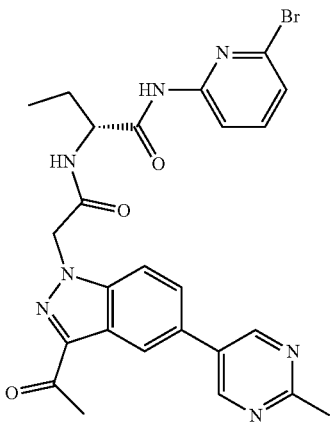 [SMILES: CC[C@@H](NC(=O)Cn1nc(C(C)=O)c2cc(-c3cnc(C)nc3)ccc21)C(=O)Nc1cccc(Br)n1] | (R)-2-(2-(3-acetyl-5-(2-methylpyrimidin-5-yl)-1H-indazol-1-yl)acetamido)-N-(6-bromopyridin-2-yl)butanamide | * | 10.69 (D) | 550 |
| 600 | 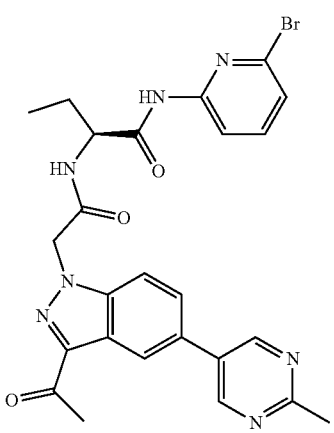 [SMILES: CC[C@H](NC(=O)Cn1nc(C(C)=O)c2cc(-c3cnc(C)nc3)ccc21)C(=O)Nc1cccc(Br)n1] | (S)-2-(2-(3-acetyl-5-(2-methylpyrimidin-5-yl)-1H-indazol-1-yl)acetamido)-N-(6-bromopyridin-2-yl)butanamide | *** | 10.67 (D) | 552 (M + 2) |

TABLE 4-continued

Non-limiting Examples of Compounds of Formula I, Formula I' and Formula I''

| Cmp No. | Structure | Name | IC$_{50}$ | RT min (Method A or B) | MS (M + 1) |
|---|---|---|---|---|---|
| 601 | 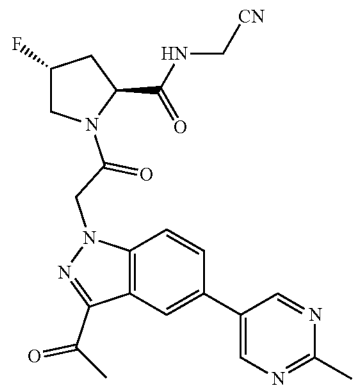 [SMILES: CC(=O)c1nn(CC(=O)N2C[C@H](F)C[C@H]2C(=O)NCC#N)c2ccc(-c3cnc(C)nc3)cc12] | (2S,4R)-1-(2-(3-acetyl-5-(2-methylpyrimidin-5-yl)-1H-indazol-1-yl)acetyl)-N-(cyanomethyl)-4-fluoropyrrolidine-2-carboxamide | *** | 1.91 (B) | 464 |
| 602 | 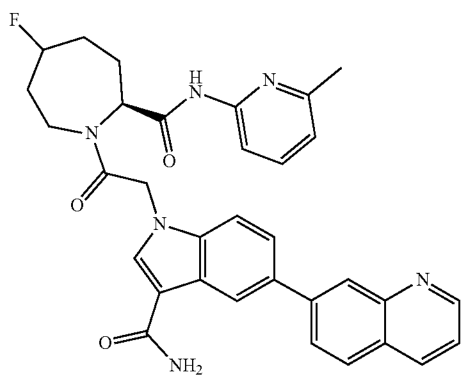 [SMILES: Cc1cccc(NC(=O)[C@@H]2CCC(F)CCN2C(=O)Cn2cc(C(N)=O)c3cc(-c4ccc5cccnc5c4)ccc32)n1] | 1-(2-((2S)-5-fluoro-2-((6-methylpyridin-2-yl)carbamoyl)azepan-1-yl)-2-oxoethyl)-5-(quinolin-7-yl)-1H-indole-3-carboxamide | * | 2.99 (B) | 579 |
| 603 | 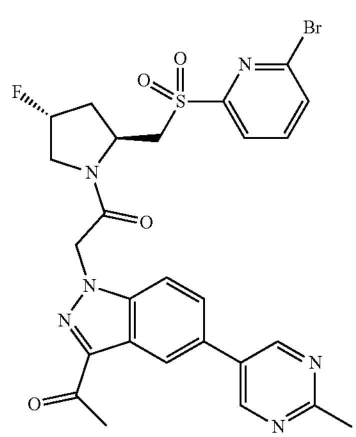 [SMILES: CC(=O)c1nn(CC(=O)N2C[C@H](F)C[C@H]2CS(=O)(=O)c2cccc(Br)n2)c2ccc(-c3cnc(C)nc3)cc12] | 2-(3-acetyl-5-(2-methylpyrimidin-5-yl)-1H-indazol-1-yl)-1-((2S,4R)-2-(((6-bromopyridin-2-yl)sulfonyl)methyl)-4-fluoropyrrolidin-1-yl)ethan-1-one | * | 10.54 (D) | 615 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 604 | 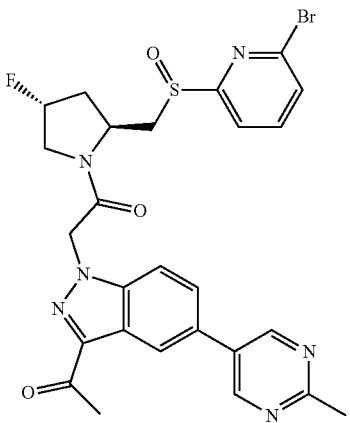 [SMILES: CC(=O)c1nn(CC(=O)N2C[C@H](F)C[C@H]2CS(=O)c2cccc(Br)n2)c2ccc(-c3cnc(C)nc3)cc12] | 2-(3-acetyl-5-(2-methylpyrimidin-5-yl)-1H-indazol-1-yl)-1-((2S,4R)-2-(((6-bromopyridin-2-yl)sulfinyl)methyl)-4-fluoropyrrolidin-1-yl)ethan-1-one | ** | 9.74 (D) | 599 |
| 606 | 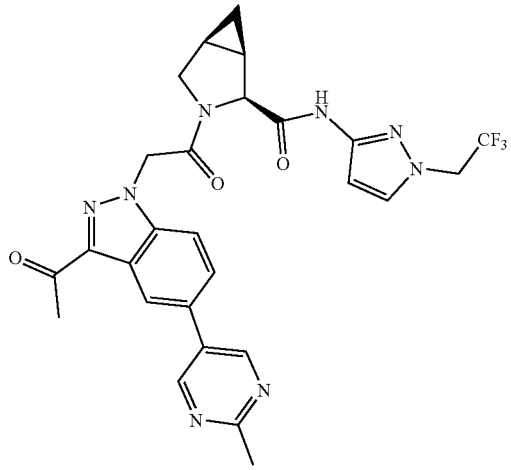 [SMILES: CC(=O)c1nn(CC(=O)N2C[C@H]3C[C@H]3[C@H]2C(=O)Nc2ccn(CC(F)(F)F)n2)c2ccc(-c3cnc(C)nc3)cc12] | (1R,2S,5S)-3-(2-(3-acetyl-5-(2-methylpyrimidin-5-yl)-1H-indazol-1-yl)acetyl)-N-(1-(2,2,2-trifluoroethyl)-1H-pyrazol-3-yl)-3-azabicyclo[3.1.0]hexane-2-carboxamide | *** | 1.49 (A) | 567 |
| 611 | 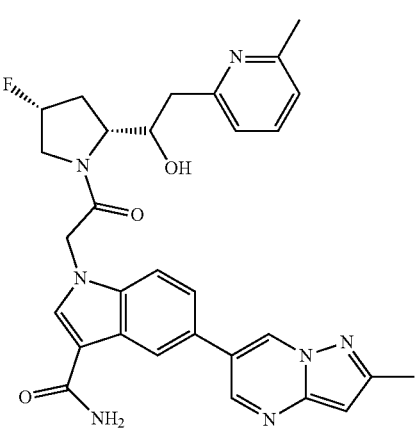 | 1-(2-((2R,4R)-4-fluoro-2-((R)-1-hydroxy-2-(6-methylpyridin-2-yl)ethyl)pyrrolidin-1-yl)-2-oxoethyl)-5-(2-methylpyrazolo[1,5-a]pyrimidin-6-yl)-1H-indole-3-carboxamide | * | 3.80 (B) | 556 |

TABLE 4-continued

Non-limiting Examples of Compounds of Formula I, Formula I' and Formula I''

| Cmp No. | Structure | Name | IC$_{50}$ | RT min (Method A or B) | MS (M + 1) |
|---|---|---|---|---|---|
| 612 | 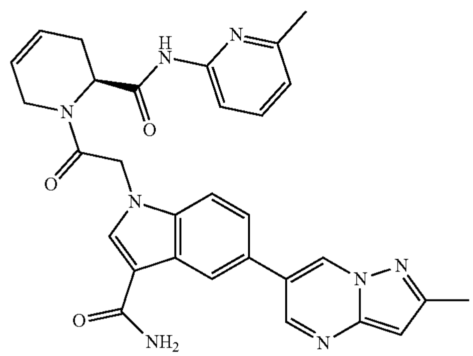 [SMILES: Cc1cccc(NC(=O)[C@@H]2CC=CCN2C(=O)Cn2cc(C(N)=O)c3cc(-c4cnc5cc(C)nn5c4)ccc32)n1] | (S)-5-(2-methylpyrazolo[1,5-a]pyrimidin-6-yl)-1-(2-(6-((6-methylpyridin-2-yl)carbamoyl)-5,6-dihydropyridin-1(2H)-yl)-2-oxoethyl)-1H-indole-3-carboxamide | * | 2.45 (B) | 549 |
| 613 | 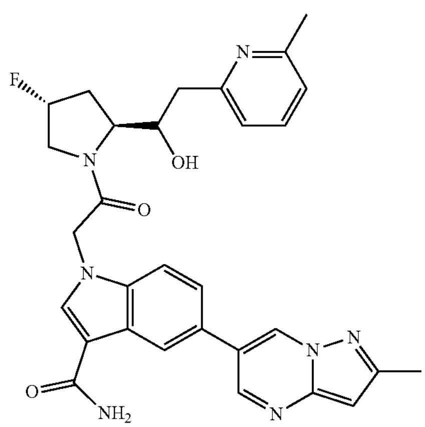 [SMILES: Cc1cccc(CC(O)[C@@H]2C[C@@H](F)CN2C(=O)Cn2cc(C(N)=O)c3cc(-c4cnc5cc(C)nn5c4)ccc32)n1] | 1-(2-((2S,4R)-4-fluoro-2-((S)-1-hydroxy-2-(6-methylpyridin-2-yl)ethyl)pyrrolidin-1-yl)-2-oxoethyl)-5-(2-methylpyrazolo[1,5-a]pyrimidin-6-yl)-1H-indole-3-carboxamide | * | 3.63 (B) | 557 |
| 614 | 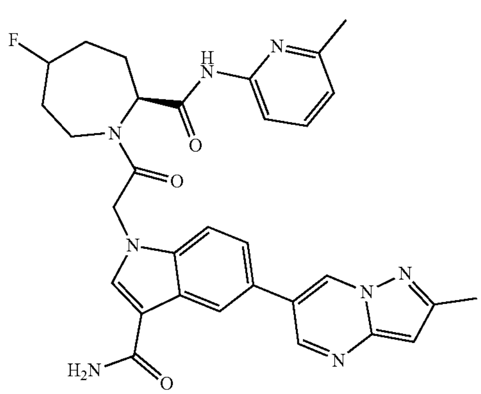 [SMILES: Cc1cccc(NC(=O)[C@@H]2CCC(F)CCN2C(=O)Cn2cc(C(N)=O)c3cc(-c4cnc5cc(C)nn5c4)ccc32)n1] | 1-(2-((2S)-5-fluoro-2-((6-methylpyridin-2-yl)carbamoyl)azepan-1-yl)-2-oxoethyl)-5-(2-methylpyrazolo[1,5-a]pyrimidin-6-yl)-1H-indole-3-carboxamide | * | 2.42 (B) | 583 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 615 | 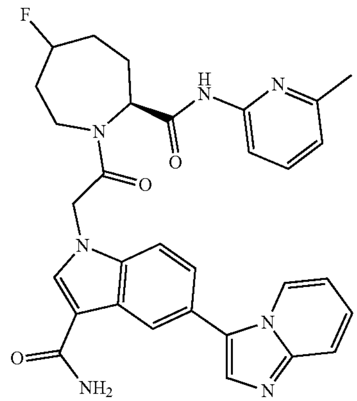 [SMILES: Cc1cccc(NC(=O)[C@@H]2CCC(F)CCN2C(=O)Cn2cc(C(N)=O)c3cc(-c4cnc5ccccn45)ccc32)n1] | 1-(2-((2S)-5-fluoro-2-((6-methylpyridin-2-yl)carbamoyl)azepan-1-yl)-2-oxoethyl)-5-(imidazo[1,2-a]pyridin-3-yl)-1H-indole-3-carboxamide | * | 2.52 (B) | 569 |
| 616 | 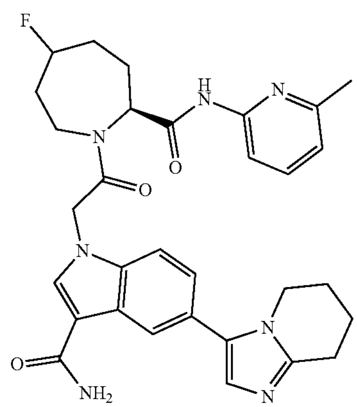 [SMILES: Cc1cccc(NC(=O)[C@@H]2CCC(F)CCN2C(=O)Cn2cc(C(N)=O)c3cc(-c4cnc5n4CCCC5)ccc32)n1] | 1-(2-((2S)-5-fluoro-2-((6-methylpyridin-2-yl)carbamoyl)azepan-1-yl)-2-oxoethyl)-5-(5,6,7,8-tetrahydroimidazo[1,2-a]pyridin-3-yl)-1H-indole-3-carboxamide | * | 2.86 (B) | 572 |
| 617 | 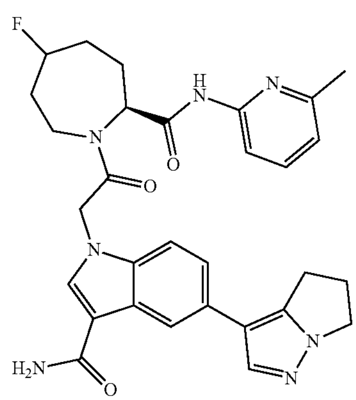 [SMILES: Cc1cccc(NC(=O)[C@@H]2CCC(F)CCN2C(=O)Cn2cc(C(N)=O)c3cc(-c4cnn5c4CCC5)ccc32)n1] | 5-(5,6-dihydro-4H-pyrrolo[1,2-b]pyrazol-3-yl)-1-(2-((2S)-5-fluoro-2-((6-methylpyridin-2-yl)carbamoyl)azepan-1-yl)-2-oxoethyl)-1H-indole-3-carboxamide | * | 1.92 (B) | 558 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 618 | 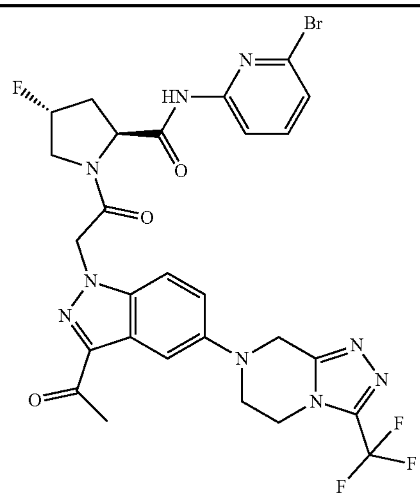 | (2S,4R)-1-(2-(3-acetyl-5-(3-(trifluoromethyl)-5,6-dihydro-[1,2,4]triazolo[4,3-a]pyrazin-7(8H)-yl)-1H-indazol-1-yl)acetyl)-N-(6-bromopyridin-2-yl)-4-fluoropyrrolidine-2-carboxamide | *** | 2.35 (A) | 678 |
| 619 | 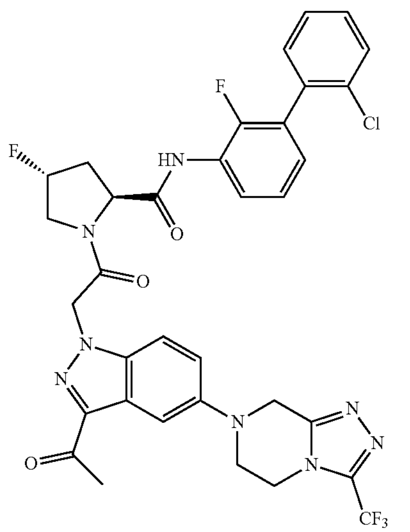 [SMILES: CC(=O)c1nn(CC(=O)N2C[C@H](F)C[C@H]2C(=O)Nc2cccc(-c3ccccc3Cl)c2F)c2ccc(N3CCn4c(nnc4C(F)(F)F)C3)cc12] | (2S,4R)-1-(2-(3-acetyl-5-(3-(trifluoromethyl)-5,6-dihydro-[1,2,4]triazolo[4,3-a]pyrazin-7(8H)-yl)-1H-indazol-1-yl)acetyl)-N-(2'-chloro-2-fluoro-[1,1'-biphenyl]-3-yl)-4-fluoropyrrolidine-2-carboxamide | *** | | |
| 620 | 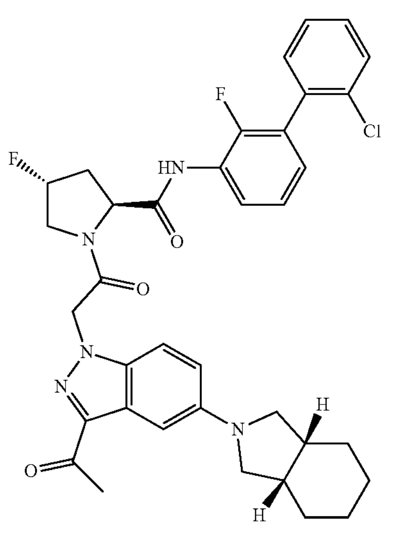 [SMILES: CC(=O)c1nn(CC(=O)N2C[C@H](F)C[C@H]2C(=O)Nc2cccc(-c3ccccc3Cl)c2F)c2ccc(N3C[C@H]4CCCC[C@H]4C3)cc12] | (2S,4R)-1-(2-(3-acetyl-5-((3aR,7aS)-hexahydro-1H-isoindol-2(3H)-yl)-1H-indazol-1-yl)acetyl)-N-(2'-chloro-2-fluoro-[1,1'-biphenyl]-3-yl)-4-fluoropyrrolidine-2-carboxamide | *** | 3.12 (A) | 661 |

| Cmp No. | Structure | Name | IC$_{50}$ | RT min (Method A or B) | MS (M + 1) |
|---|---|---|---|---|---|
| 621 | 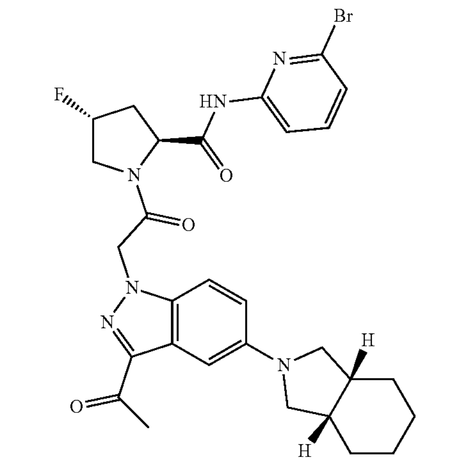 [SMILES: CC(=O)c1nn(CC(=O)N2C[C@H](F)C[C@H]2C(=O)Nc2cccc(Br)n2)c2ccc(N3C[C@H]4CCCC[C@H]4C3)cc12] | (2S,4R)-1-(2-(3-acetyl-5-((3aR,7aS)-hexahydro-1H-isoindol-2(3H)-yl)-1H-indazol-1-yl)acetyl)-N-(6-bromopyridin-2-yl)-4-fluoropyrrolidine-2-carboxamide | *** | 2.79 (A) | 611 |
| 622 | 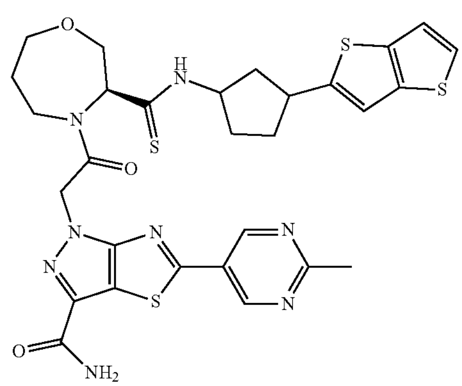 [SMILES: Cc1ncc(-c2nc3c(s2)c(C(N)=O)nn3CC(=O)N2CCCOC[C@H]2C(=S)NC2CCC(c3cc4sccc4s3)C2)cn1] | 5-(2-methylpyrimidin-5-yl)-1-(2-oxo-2-((3S)-3-((3-(thieno[3,2-b]thiophen-2-yl)cyclopentyl)carbamothioyl)-1,4-oxazepan-4-yl)ethyl)-1H-pyrazolo[3,4-d]thiazole-3-carboxamide | | 2.98 (B) | 667 |
| 623 | 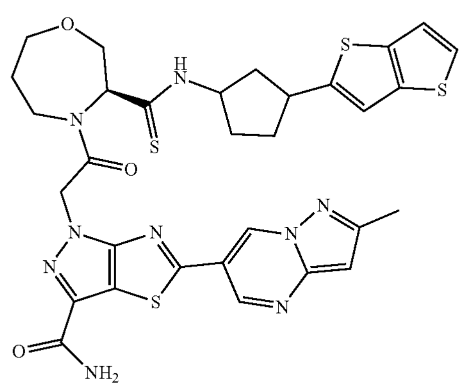 [SMILES: Cc1cc2ncc(-c3nc4c(s3)c(C(N)=O)nn4CC(=O)N3CCCOC[C@H]3C(=S)NC3CCC(c4cc5sccc5s4)C3)cn2n1] | 5-(2-methylpyrazolo[1,5-a]pyrimidin-6-yl)-1-(2-oxo-2-((3S)-3-((3-(thieno[3,2-b]thiophen-2-yl)cyclopentyl)carbamothioyl)-1,4-oxazepan-4-yl)ethyl)-1H-pyrazolo[3,4-d]thiazole-3-carboxamide | | 4.00 (B) | 706 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 624 | 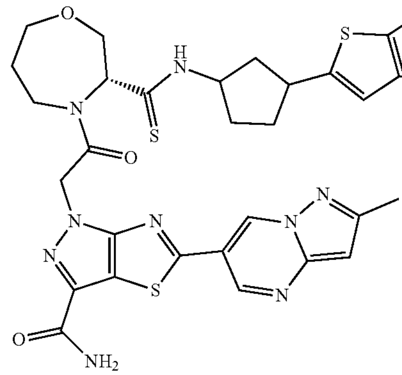 | 5-(2-methylpyrazolo[1,5-a]pyrimidin-6-yl)-1-(2-oxo-2-((3R)-3-((3-(thieno[3,2-b]thiophen-2-yl)cyclopentyl)carbamothioyl)-1,4-oxazepan-4-yl)ethyl)-1H-pyrazolo[3,4-d]thiazole-3-carboxamide | | 4.16 (B) | 706 |
| 625 | 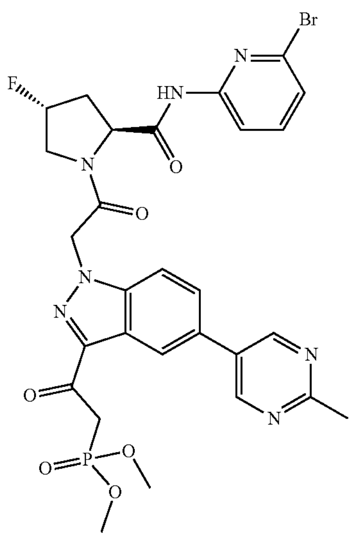 [SMILES: COP(=O)(CC(=O)c1nn(CC(=O)N2C[C@H](F)C[C@H]2C(=O)Nc2cccc(Br)n2)c2ccc(-c3cnc(C)nc3)cc12)OC] | dimethyl (2-(1-(2-((2S,4R)-2-((6-bromopyridin-2-yl)carbamoyl)-4-fluoropyrrolidin-1-yl)-2-oxoethyl)-5-(2-methylpyrimidin-5-yl)-1H-indazol-3-yl)-2-oxoethyl) phosphonate | * | 1.49 (A) | 690 |
| 626 | 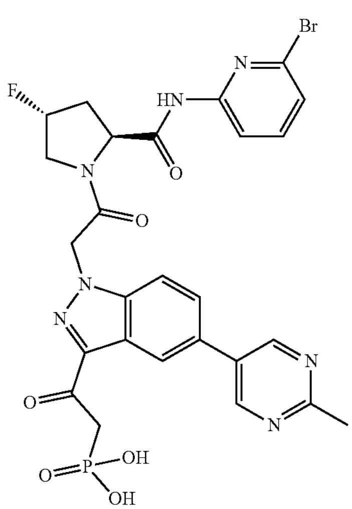 [SMILES: Cc1ncc(-c2ccc3c(c2)c(C(=O)CP(=O)(O)O)nn3CC(=O)N2C[C@H](F)C[C@H]2C(=O)Nc2cccc(Br)n2)cn1] | (2-(1-(2-((2S,4R)-2-((6-bromopyridin-2-yl)carbamoyl)-4-fluoropyrrolidin-1-yl)-2-oxoethyl)-5-(2-methylpyrimidin-5-yl)-1H-indazol-3-yl)-2-oxoethyl)phosphonic acid | * | 1.02 (A) | 662 |

TABLE 4-continued

Non-limiting Examples of Compounds of Formula I, Formula I' and Formula I''

| Cmp No. | Structure | Name | IC$_{50}$ | RT min (Method A or B) | MS (M + 1) |
|---|---|---|---|---|---|
| 627 | 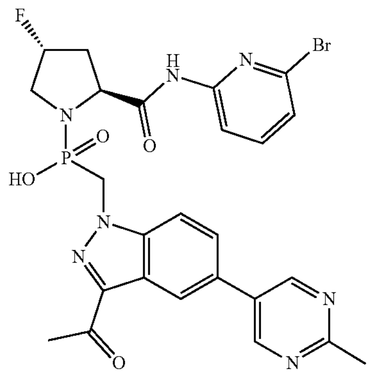 [SMILES: CC(=O)c1nn(CP(=O)(O)N2C[C@H](F)C[C@H]2C(=O)Nc2cccc(Br)n2)c2ccc(-c3cnc(C)nc3)cc12] | ((3-acetyl-5-(2-methylpyrimidin-5-yl)-1H-indazol-1-yl)methyl)((2S,4R)-2-((6-bromopyridin-2-yl)carbamoyl)-4-fluoropyrrolidin-1-yl)phosphinic acid | * | 1.10 (A) | 616 |
| 628 | 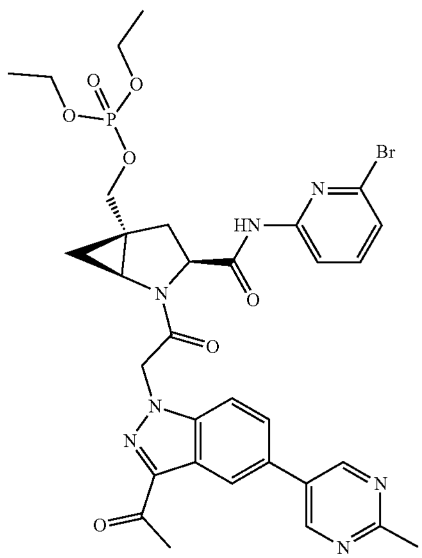 [SMILES: CCOP(=O)(OCC)OC[C@@]12C[C@@H]1N(C(=O)Cn1nc(C(C)=O)c3cc(-c4cnc(C)nc4)ccc31)[C@H](C(=O)Nc1cccc(Br)n1)C2] | ((1S,3S,5R)-2-(2-(3-acetyl-5-(2-methylpyrimidin-5-yl)-1H-indazol-1-yl)acetyl)-3-((6-bromopyridin-2-yl)carbamoyl)-2-azabicyclo[3.1.0]hexan-5-yl)methyl diethyl phosphate | ** | 3.66 (B) | 740 |
| 629 | 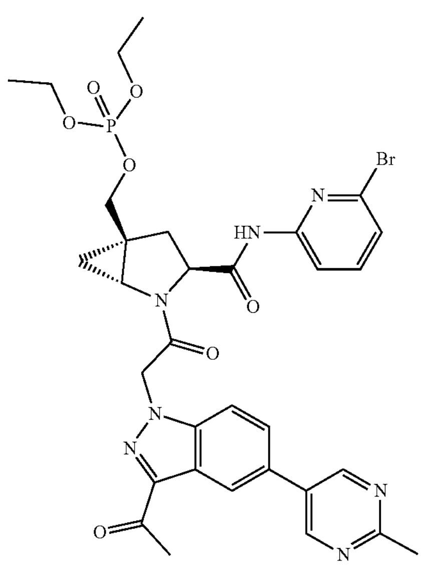 [SMILES: CCOP(=O)(OCC)OC[C@@]12C[C@@H](C(=O)Nc3cccc(Br)n3)N(C(=O)Cn3nc(C(C)=O)c4cc(-c5cnc(C)nc5)ccc43)[C@@H]1C2] | ((1R,3S,5S)-2-(2-(3-acetyl-5-(2-methylpyrimidin-5-yl)-1H-indazol-1-yl)acetyl)-3-((6-bromopyridin-2-yl)carbamoyl)-2-azabicyclo[3.1.0]hexan-5-yl)methyl diethyl phosphate | *** | 3.50 (B) | 740 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 630 | 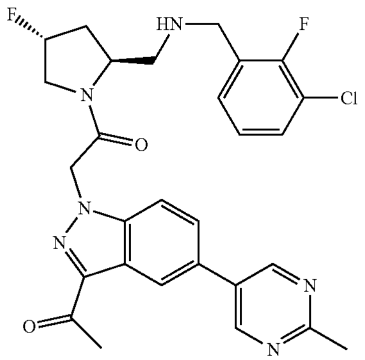 [SMILES: CC(=O)c1nn(CC(=O)N2C[C@H](F)C[C@H]2CNCc2cccc(Cl)c2F)c2ccc(-c3cnc(C)nc3)cc12] | 2-(3-acetyl-5-(2-methylpyrimidin-5-yl)-1H-indazol-1-yl)-1-((2S,4R)-2-(((3-chloro-2-fluorobenzyl)amino)methyl)-4-fluoropyrrolidin-1-yl)ethan-1-one | ** | 11.14 (D) | 553 |
| 631 | 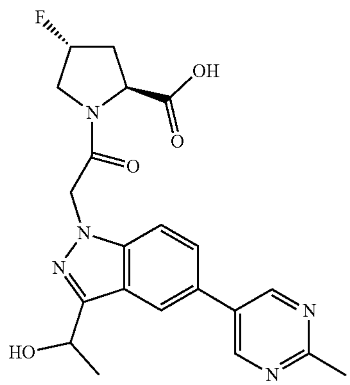 [SMILES: Cc1ncc(-c2ccc3c(c2)c(C(C)O)nn3CC(=O)N2C[C@H](F)C[C@H]2C(=O)O)cn1] | (2S,4R)-4-fluoro-1-(2-(3-(1-hydroxyethyl)-5-(2-methylpyrimidin-5-yl)-1H-indazol-1-yl)acetyl)pyrrolidine-2-carboxylic acid | * | 0.72 (A) | 428 |
| 632 | 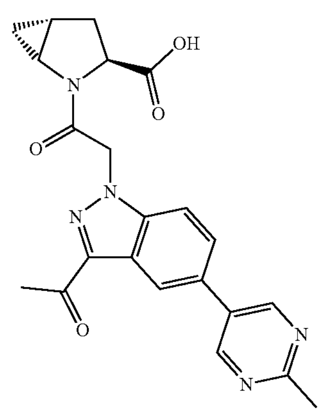 | (1R,3S,5R)-2-(2-(3-acetyl-5-(2-methylpyrimidin-5-yl)-1H-indazol-1-yl)acetyl)-2-azabicyclo[3.1.0]hexane-3-carboxylic acid | * | 1.11 (A) | 420 |
| 633 | 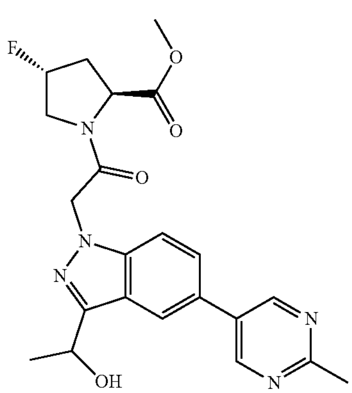 [SMILES: COC(=O)[C@@H]1C[C@@H](F)CN1C(=O)Cn1nc(C(C)O)c2cc(-c3cnc(C)nc3)ccc21] | (2S,4R)-methyl 4-fluoro-1-(2-(3-(1-hydroxyethyl)-5-(2-methylpyrimidin-5-yl)-1H-indazol-1-yl)acetyl)pyrrolidine-2-carboxylate | * | 0.95 (A) | 442 |

TABLE 4-continued

Non-limiting Examples of Compounds of Formula I, Formula I' and Formula I"

| Cmp No. | Structure | Name | IC$_{50}$ | RT min (Method A or B) | MS (M + 1) |
|---|---|---|---|---|---|
| 636 | 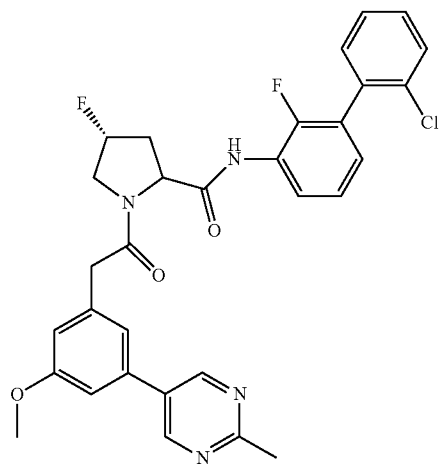 [SMILES: COc1cc(CC(=O)N2C[C@H](F)CC2C(=O)Nc2cccc(-c3ccccc3Cl)c2F)cc(-c2cnc(C)nc2)c1] | (4R)-N-(2'-chloro-2-fluoro-[1,1'-biphenyl]-3-yl)-4-fluoro-1-(2-(3-methoxy-5-(2-methylpyrimidin-5-yl)phenyl)acetyl)pyrrolidine-2-carboxamide | *** | 2.18 (A) | 577 |
| 637 | 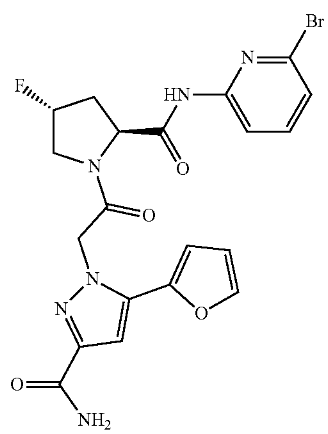 [SMILES: NC(=O)c1cc(-c2ccco2)n(CC(=O)N2C[C@H](F)C[C@H]2C(=O)Nc2cccc(Br)n2)n1] | 1-(2-((2S,4R)-2-((6-bromopyridin-2-yl)carbamoyl)-4-fluoropyrrolidin-1-yl)-2-oxoethyl)-5-(furan-2-yl)-1H-pyrazole-3-carboxamide | *** | 1.39 (A) | 504 |
| 638 | 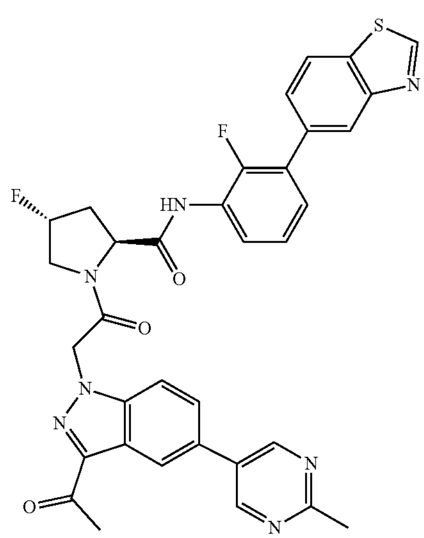 [SMILES: CC(=O)c1nn(CC(=O)N2C[C@H](F)C[C@H]2C(=O)Nc2cccc(-c3ccc4scnc4c3)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(3-(benzo[d]thiazol-5-yl)-2-fluorophenyl)-4-fluoropyrrolidine-2-carboxamide | *** | 1.87 (A) | 652 |

TABLE 4-continued

Non-limiting Examples of Compounds of Formula I, Formula I' and Formula I''

| Cmp No. | Structure | Name | IC$_{50}$ | RT min (Method A or B) | MS (M + 1) |
|---|---|---|---|---|---|
| 639 | 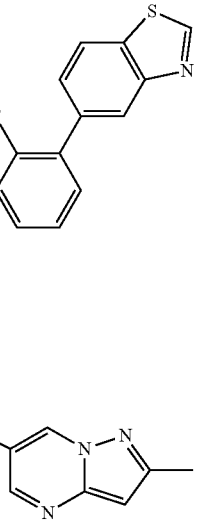 | (2S,4R)-1-(2-(3-acetyl-5-(2-methylpyrazolo[1,5-a]pyrimidin-6-yl)-1H-indazol-1-yl)acetyl)-N-(3-(benzo[d]thiazol-5-yl)-2-fluorophenyl)-4-fluoropyrrolidine-2-carboxamide | *** | 2.10 (A) | 691 |
| 640 | 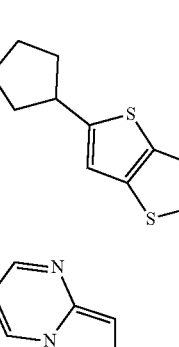 | 1-(2-((2S,4R)-4-fluoro-2-((3-(thieno[3,2-b]thiophen-2-yl)cyclopentyl)carbamothioyl)pyrrolidin-1-yl)-2-oxoethyl)-5-(2-methylpyrazolo[1,5-a]pyrimidin-6-yl)-1H-pyrazolo[3,4-d]thiazole-3-carboxamide | * | 4.07 (B) | 694 |
| 641 | 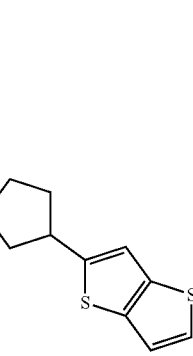 | 1-(2-((2S,4R)-4-fluoro-2-((3-(thieno[3,2-b]thiophen-2-yl)cyclopentyl)carbamothioyl)pyrrolidin-1-yl)-2-oxoethyl)-5-(2-methylpyrimidin-5-yl)-1H-pyrazolo[4,3-d]thiazole-3-carboxamide | * | 3.65 (B) | 655 |

TABLE 4-continued

Non-limiting Examples of Compounds of Formula I, Formula I' and Formula I''

| Cmp No. | Structure | Name | IC$_{50}$ | RT min (Method A or B) | MS (M + 1) |
|---|---|---|---|---|---|
| 642 | 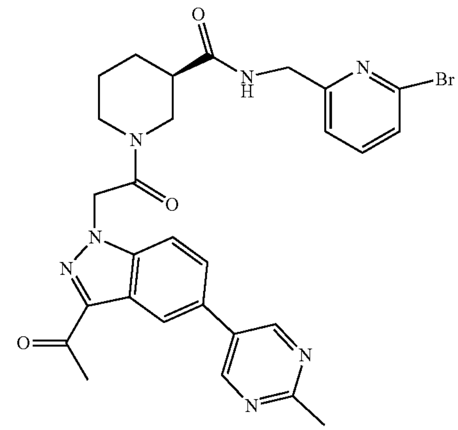 [SMILES: CC(=O)c1nn(CC(=O)N2CCC[C@@H](C(=O)NCc3cccc(Br)n3)C2)c2ccc(-c3cnc(C)nc3)cc12] | (R)-1-(2-(3-acetyl-5-(2-methylpyrimidin-5-yl)-1H-indazol-1-yl)acetyl)-N-((6-bromopyridin-2-yl)methyl)piperidine-3-carboxamide | * | 1.48 (A) | 592 |
| 643 | 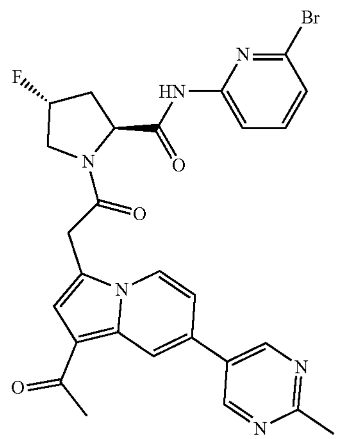 [SMILES: CC(=O)c1cc(CC(=O)N2C[C@H](F)C[C@H]2C(=O)Nc2cccc(Br)n2)n2ccc(-c3cnc(C)nc3)cc12] | (2S,4R)-1-(2-(1-acetyl-7-(2-methylpyrimidin-5-yl)indolizin-3-yl)acetyl)-N-(6-bromopyridin-2-yl)-4-fluoropyrrolidine-2-carboxamide | *** | 2.61 (B) | 579 |

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. A method for the treatment of a disorder mediated by complement factor D, comprising administering to a host in need thereof an effective amount of a compound of Formula:

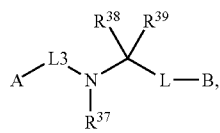

or a pharmaceutically acceptable salt thereof, wherein
A is selected from A1 and A2;
B is selected from B1, B1', B2, and B3;
L is selected from L1 and L2;
L3 is selected from L4 and L5;

A1 is selected from:

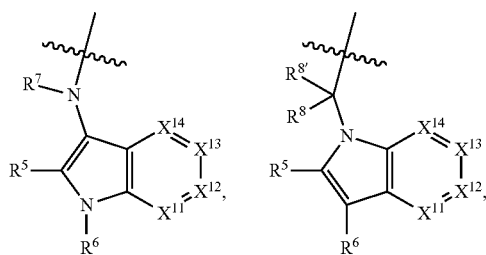

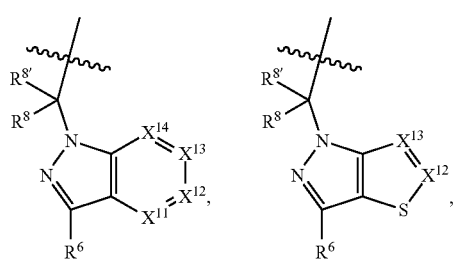

-continued

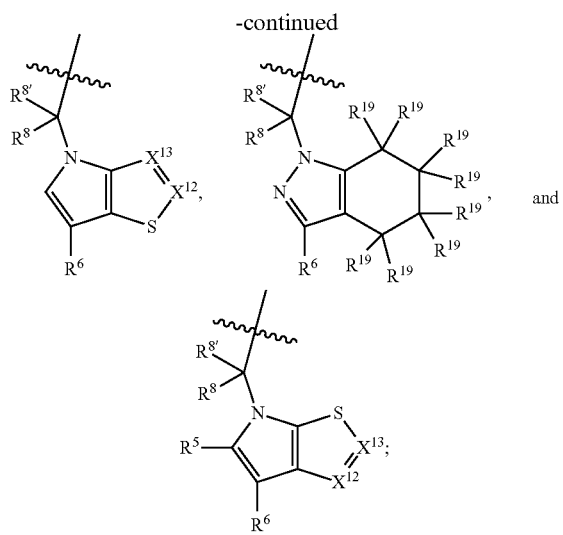

A2 is selected from:

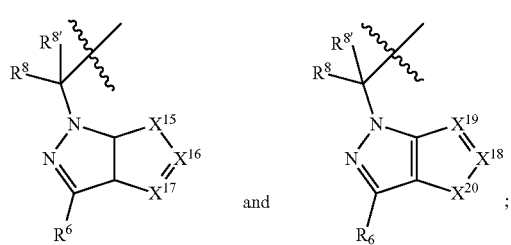

B1 is selected from a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl), each of which B1 is unsubstituted or substituted with one or more substituents independently chosen from $R^{33}$ and $R^{34}$, and 0 or 1 substituents chosen from $R^{35}$ and $R^{36}$;

B1' is selected from:

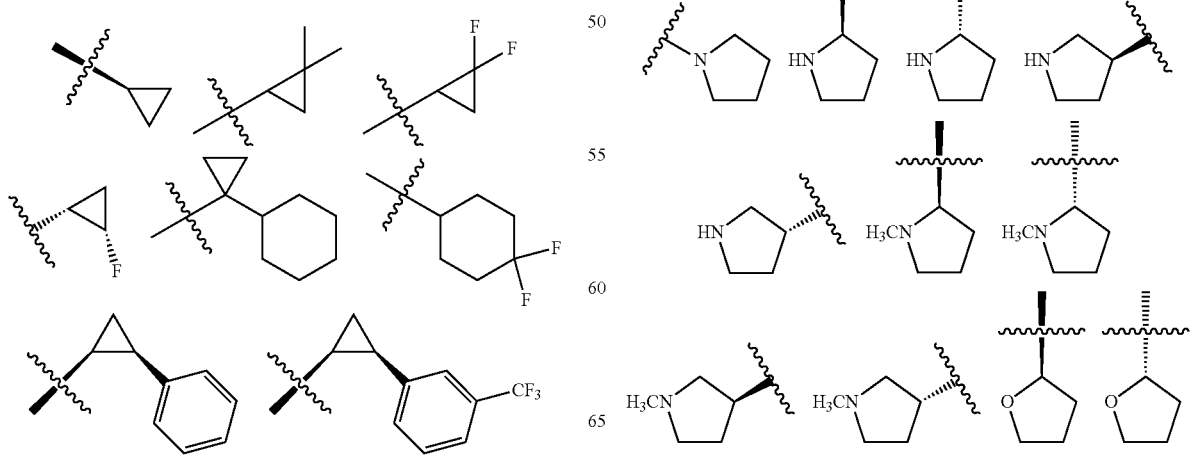

-continued

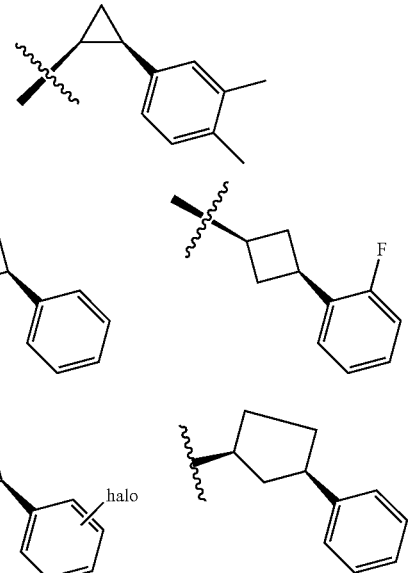

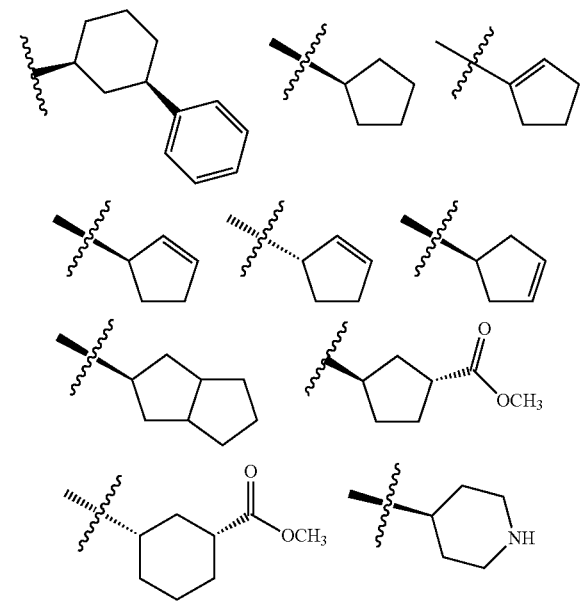

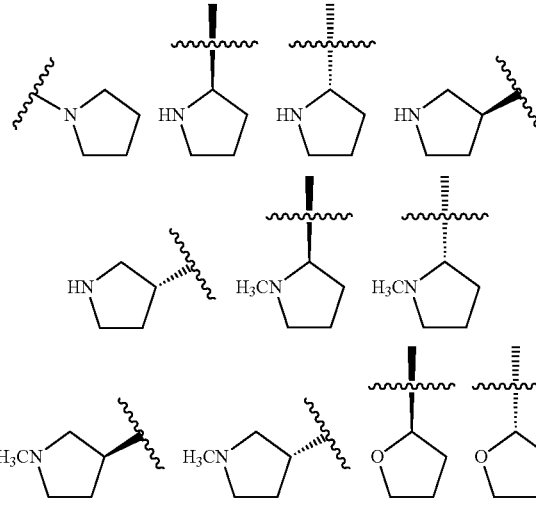

-continued
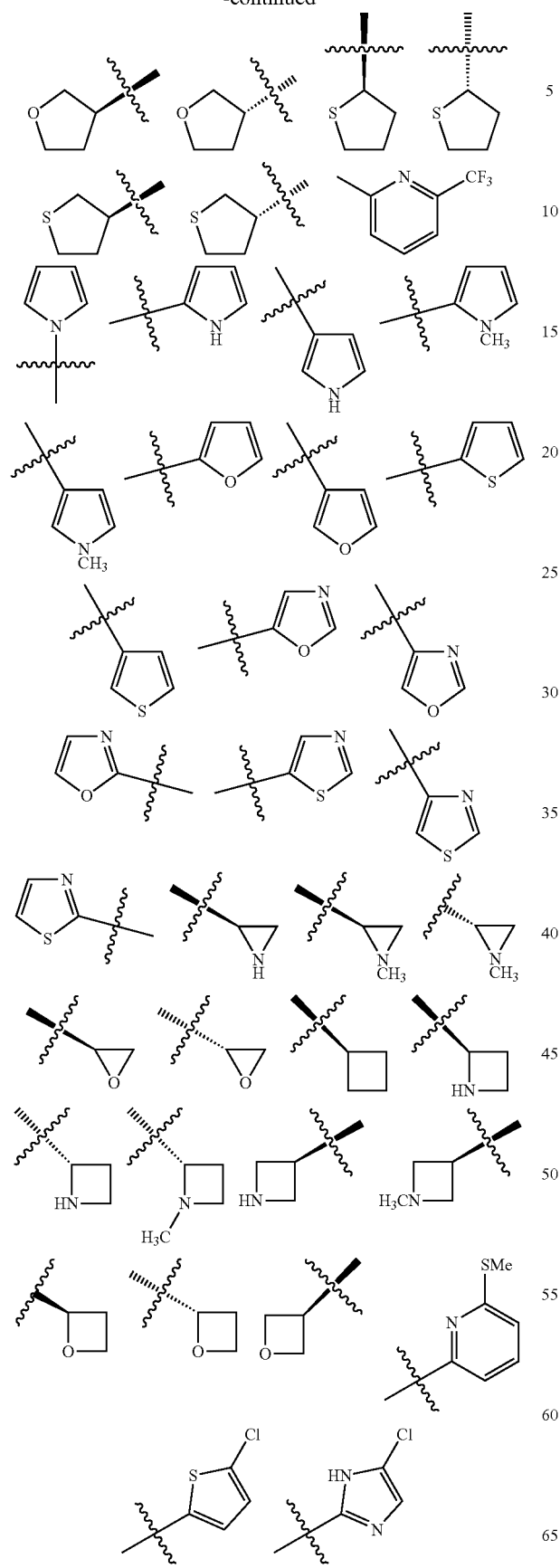
-continued
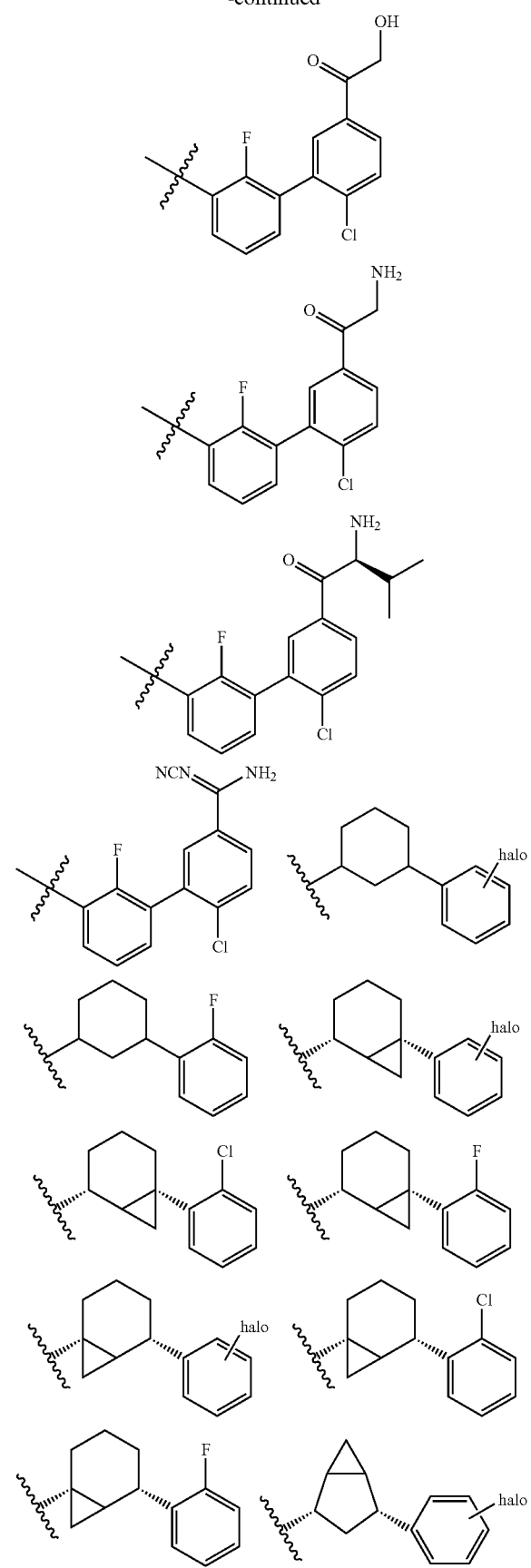

457
-continued
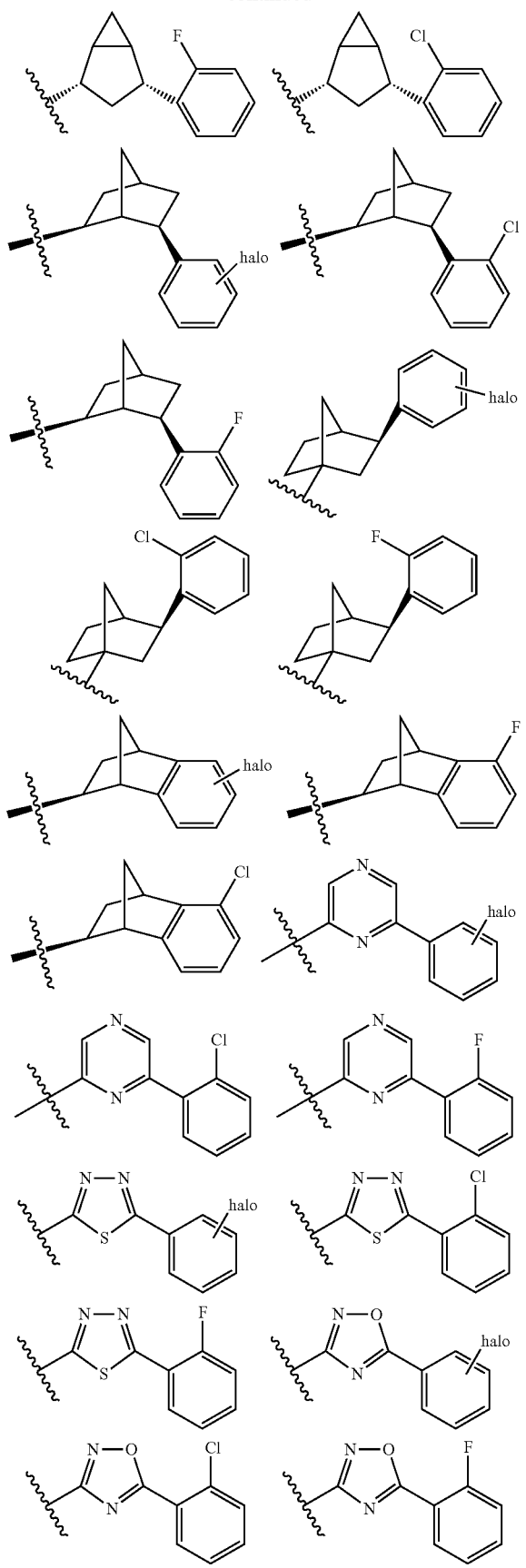
458
-continued
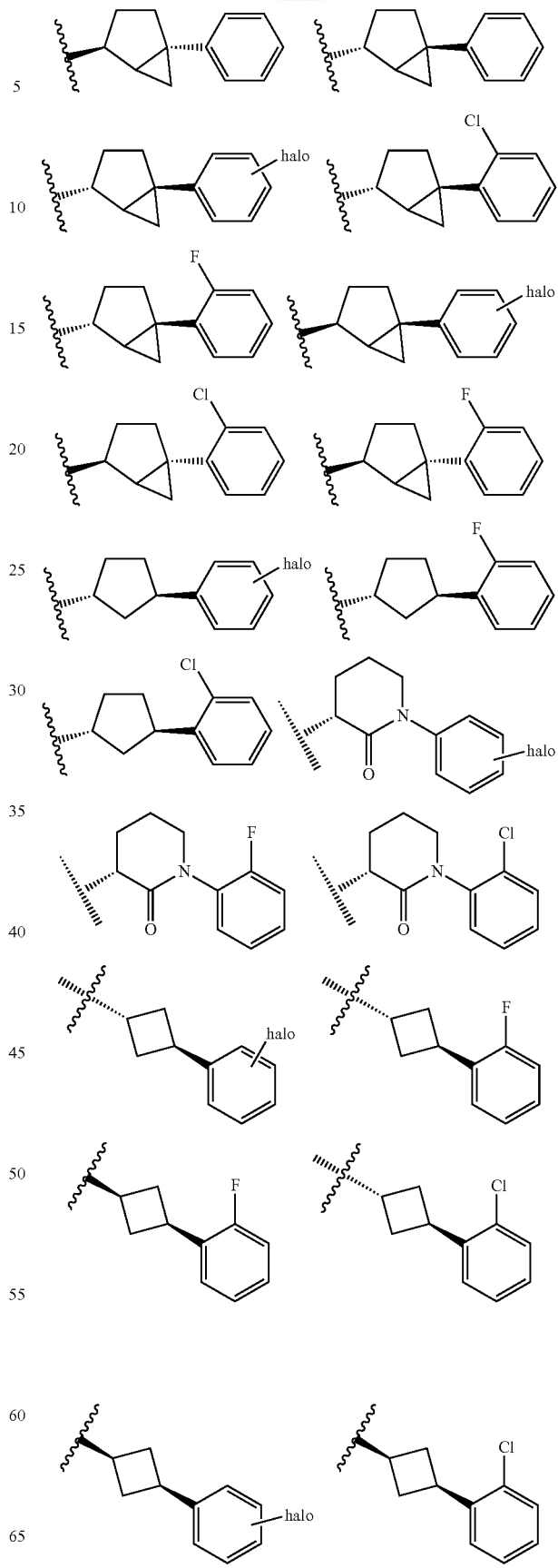

-continued
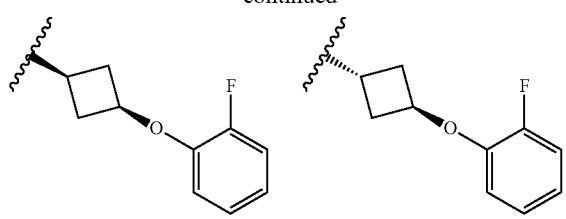
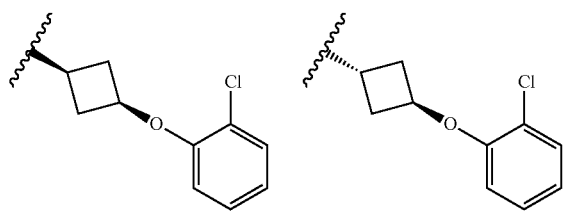
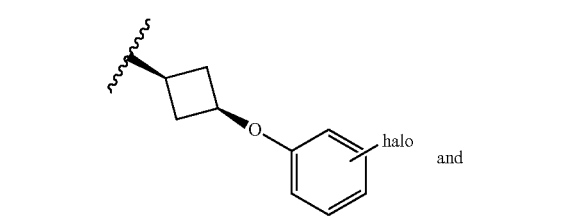
and
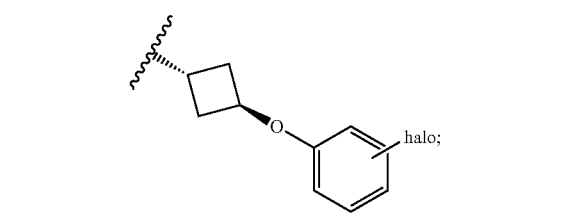
halo;
B2 is selected from:
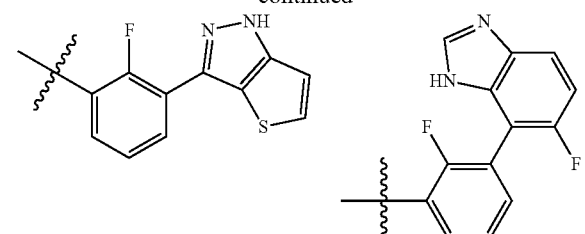
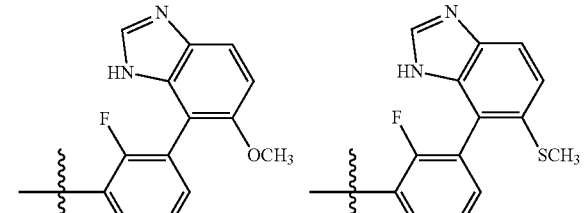
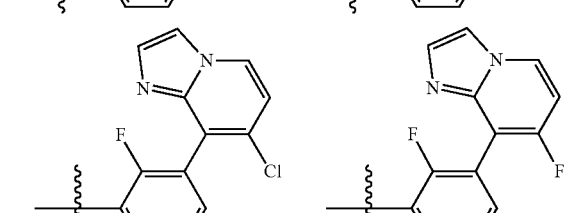
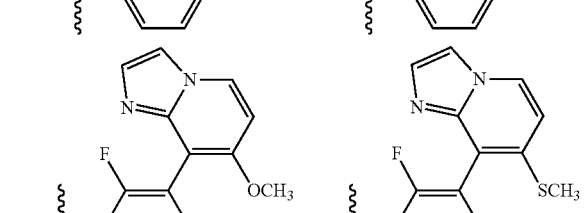
-continued
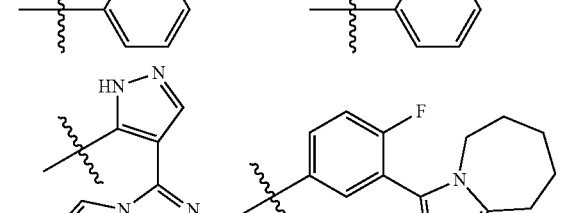
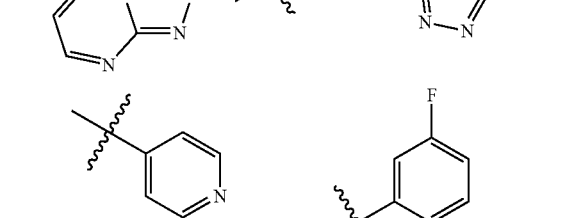
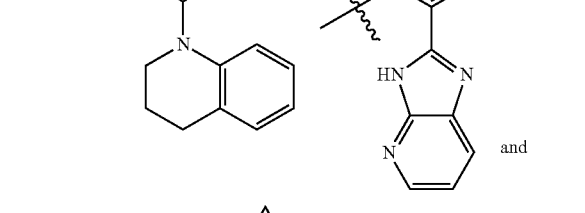
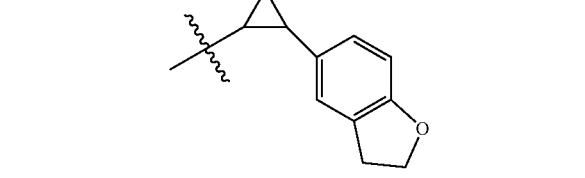
and
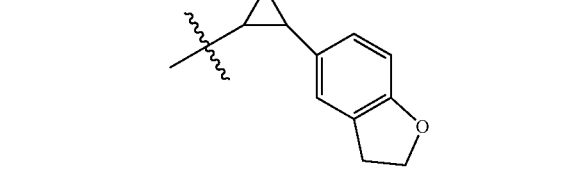

461
-continued

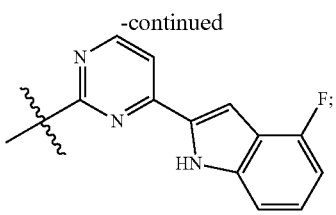

B3 is selected from:
(i) a monocyclic or bicyclic carbocyclic group; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl); each of which B3 is substituted with one or more of the following: $S(O)=NHR^{21}$, $SF_5$, and $JC(R^9)=N^{21}$;
(ii) a monocyclic, bicyclic, or tricyclic heterocyclic group that has at least one boron or silicon atom in the ring or a monocyclic, bicyclic, or tricyclic heteroaryl group that has at least one boron in the ring;
(iii) a 6-membered aryl group fused to a 5-membered saturated cyclic group that optionally contains 1 or 2 heteroatoms independently chosen from N and S wherein one of the $CH_2$ groups of the 5-membered cyclic group is substituted by oxo, excluding dihydrobenzofuran; and
(iv) (alkyl)-(cycloalkyl), (alkenyl)-(cycloalkyl), or (alkynyl)-(cycloalkyl);
wherein B3 can be further substituted one or more times with the substituents independently selected from $R^{35}$, $R^{36}$, and $R^{48}$;
L1 is a bond or is chosen from the formulas

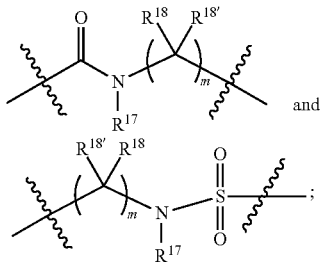
and

L2 is selected from:

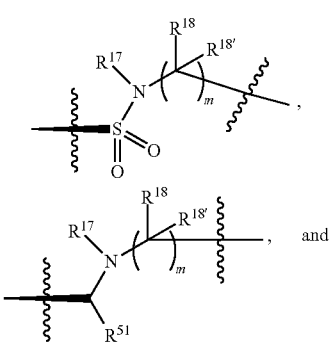

462
-continued

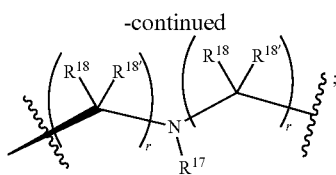

L3 is selected from L4 or L5;
L4 is —C(O)—;
L5 is —C(S)—, —P(O)OH—, —S(O)—, —$S(O)_2$— or —$C(R^{52})_2$—;
$X^{11}$ is N or $CR^{11}$;
$X^{12}$ is N or $CR^{12}$;
$X^{13}$ is N or $CR^{13}$;
$X^{14}$ is N or $CR^{14}$, and wherein no more than 2 of $X^{11}$, $X^{12}$, $X^{13}$, and $X^{14}$ are N;
$X^{15}$ is NH, O, or S;
$X^{16}$ is $CR^{12}$;
$X^{17}$ is N or $CR^{13}$;
$X^{18}$ is $CR^{12}$;
$X^{19}$ is N or $CR^{13}$;
$X^{20}$ is NH or O;
$R^4$, $R^5$, and $R^6$ are selected from hydrogen, -JCHO, -$JC(O)NH_2$, -$JC_2$-$C_6$alkanoyl, -$JC(O)NH(CH_3)$, -J-COOH, -$JP(O)(OR^9)_2$, -$JOC(O)R^9$, -$JC(O)OR^9$, -$JC(O)N(CH_2CH_2R^9)(R^{10})$, -$JNR^9C(O)R^{10}$, -$JSO_2NH_2$, -$JS(O)NH_2$, -$JC(CH_2)_2F$, -$JCH(CF_3)NH_2$, -$JC(O)C_0$-$C_2$alkyl($C_3$-$C_7$cycloalkyl), -$JNR^9(C_2$-$C_6$alkanoyl), -$JNR^9C(O)NR^9R^{10}$, -$JSO_2(C_1$-$C_6$alkyl), -$JSO_2(C_1$-$C_6$haloalkyl), -$JSO_2NR^7R^7$, -$JSO=NH(C_1$-$C_6$alkyl), -J-nitro, -J-halogen, -J-hydroxyl, -J-phenyl, a 5- to 6-membered heteroaryl, -J-cyano, -J-cyanoimino, -J-amino, -J-imino, —$C_1$-$C_6$alkyl, -$C_0$-$C_4$alkyl($C_3$-$C_7$heterocycloalkyl), —$C_0$-$C_4$alkyl($C_3$-$C_7$cycloalkyl),

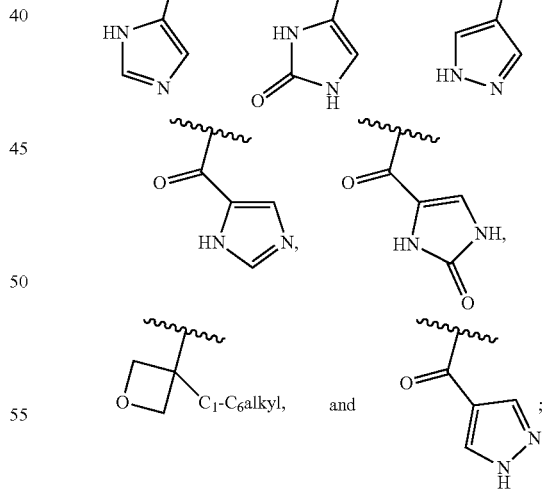

each of which $R^4$, $R^5$, and $R^6$ other than hydrogen, nitro, halogen, cyano, cyanoimino, or —CHO, is unsubstituted or substituted with one or more of amino, imino, halogen, hydroxyl, cyano, cyanoimino, $C_1$-$C_2$alkyl, $C_1$-$C_2$alkoxy, —$C_0$-$C_2$alkyl(mono- and di-$C_1$-$C_4$alkylamino), $C_1$-$C_2$haloalkyl, and $C_1$-$C_2$haloalkoxy;
$R^7$ is hydrogen, $C_1$-$C_6$alkyl, or —$C_0$-$C_4$alkyl($C_3$-$C_7$cycloalkyl);

$R^8$ and $R^{8'}$ are independently chosen from hydrogen, halogen, hydroxyl, $C_1$-$C_6$alkyl, —$C_0$-$C_4$alkyl($C_3$-$C_7$cycloalkyl), $C_1$-$C_6$alkoxy, and ($C_1$-$C_4$alkylamino)$C_0$-$C_2$alkyl; or $R^8$ and $R^{8'}$ are taken together to form an oxo group; or $R^8$ and $R^{8'}$ can be taken together with the carbon that they are bonded to form a 3-membered carbocyclic ring;

$R^9$ and $R^{10}$ are independently chosen at each occurrence from hydrogen, $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl);

$R^{11}$ and $R^{14}$ are independently chosen at each occurrence from hydrogen, halogen, hydroxyl, nitro, cyano, —O(PO)(OR$^9$)$_2$, —(PO)(OR$^9$)$_2$, $C_1$-$C_6$alkyl, $C_2$-$C_6$alkenyl, $C_2$-$C_6$alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), $C_2$-$C_6$alkynyl, $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, and $C_1$-$C_2$haloalkoxy;

one of $R^{12}$ and $R^{13}$ is chosen from $R^{31}$ and the other of $R^{12}$ and $R^{13}$ is chosen from $R^{32}$ or both $R^{12}$ and $R^{13}$ are each independently selected from a $R^{32}$;

$R^{17}$ is hydrogen, $C_1$-$C_6$alkyl, or —$C_0$-$C_4$alkyl($C_3$-$C_7$cycloalkyl);

$R^{18}$ and $R^{18'}$ are independently selected from hydrogen, halogen, hydroxymethyl, and methyl;

m is 0, 1, 2, or 3;

r is 1, 2, or 3;

$R^{19}$ is hydrogen, $C_1$-$C_6$alkyl, $C_2$-$C_6$alkenyl, $C_2$-$C_6$alkanoyl, —SO$_2$$C_1$-$C_6$alkyl, (mono- and di-$C_1$-$C_6$alkylamino)$C_1$-$C_4$alkyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), $C_0$-$C_4$alkyl(heteroaryl), and wherein $R^{19}$ other than hydrogen is unsubstituted or substituted with one or more substituents independently chosen from halogen, hydroxyl, amino, —COOH, and —C(O)O$C_1$-$C_4$alkyl;

$R^{21}$ and $R^{22}$ are independently chosen at each occurrence from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)$C_1$-$C_6$alkyl, —$C_1$-$C_4$alkylOC(O)O$C_1$-$C_6$alkyl, —$C_1$-$C_4$alkylOC(O)$C_1$-$C_6$alkyl, —$C_1$-$C_4$alkylC(O)O$C_1$-$C_6$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S;

$R^{23}$ is independently chosen at each occurrence from $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S;

$R^{31}$ is chosen from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)OR$^9$, $C_1$-$C_6$thioalkyl, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)

NR$^9$R$^{10}$, each of which $R^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —CONH$_2$$C_1$-$C_2$haloalkyl, and $C_1$-$C_2$haloalkoxy, and each of which $R^{31}$ is also optionally substituted with one substituent chosen from phenyl and 4- to 7-membered heterocycle containing 1, 2, or 3 heteroatoms independently chosen from N, O, and S; which phenyl or 4- to 7-membered heterocycle is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), $C_1$-$C_2$haloalkyl, and $C_1$-$C_2$haloalkoxy;

$R^{32}$ is selected from aryl; 5- or 6-membered heteroaryl having 1, 2, or 3 heteroatoms independently chosen from N, O, and S; or a 4- to 7-membered heterocycle having 1, 2, or 3 heteroatoms independently chosen from N, O, and S; and wherein the aryl, heteroaryl, and heterocycle can be optionally substituted with one or more groups independently selected from halogen, hydroxyl, amino, cyano, —CHO, —COOH, —CONH$_2$, $C_1$-$C_6$alkyl, $C_2$-$C_6$alkenyl, $C_2$-$C_6$alkynyl, —$C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, hydoxy$C_1$-$C_6$alkyl, ester, carbamate, urea, sulfonamide, —$C_1$-$C_6$alkyl(heterocyclo), $C_1$-$C_6$alkyl(heteroaryl), —$C_1$-$C_6$alkyl($C_3$-$C_7$cycloalkyl), O—$C_1$-$C_6$alkyl($C_3$-$C_7$cycloalkyl), B(OH)$_2$, phosphate, phosphonate, and $C_1$-$C_2$haloalkoxy;

$R^{33}$ is independently chosen from halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, and $C_1$-$C_2$haloalkoxy;

$R^{34}$ is independently chosen from nitro, $C_2$-$C_6$alkenyl, $C_2$-$C_6$alkynyl, $C_1$-$C_6$thioalkyl, -J$C_3$-$C_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$) -JNR$^9$P(O)(OR$^{21}$)(NHR$^{22}$) -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)═NR$^{22}$, -JCH(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JNR$^9$C(O)R$^{21}$, -JC(O)R$^{21}$, -JNR$^9$C(O)NR$^{10}$R$^{22}$, —CCR$^{21}$, —(CH$_2$)$_{1-4}$OC(O)R$^{21}$, and -JC(O)OR$^{23}$; each of which $R^{34}$ may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, —$C_0$-$C_4$alkyl($C_3$-$C_7$cycloalkyl), $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy;

$R^{35}$ is independently chosen from naphthyl, naphthyloxy, indanyl, (4- to 7-membered heterocycloalkyl)$C_0$-$C_4$alkyl containing 1 or 2 heteroatoms chosen from N, O, and S, and bicyclic heterocycle containing 1, 2, or 3 heteroatoms independently chosen from N, O, and S, and containing 4- to 7-ring atoms in each ring; each of which $R^{35}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, $C_1$-$C_2$haloalkyl, and $C_1$-$C_2$haloalkoxy;

$R^{36}$ is independently chosen from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently chosen from N, O, B, and S, each of which $R^{36}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, —$OSi(CH_3)_2C(CH_3)_3$, —$Si(CH_3)_2C(CH_3)_3$, $C_1$-$C_2$haloalkyl, and $C_1$-$C_2$haloalkoxy;

$R^{48}$ is independently chosen from hydrogen, halogen, hydroxyl, nitro, cyano, amino, $C_1$-$C_6$alkyl, $C_1$-$C_6$haloalkyl, $C_2$-$C_6$alkenyl, $C_2$-$C_6$alkynyl, $C_1$-$C_6$thioalkyl, $C_1$-$C_6$alkoxy, -J$C_3$-$C_7$cycloalkyl, —$B(OH)_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$) -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)=NR$^{22}$, -JCH(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JNR$^9$C(O)R$^{21}$, -JC(O)R$^{21}$, -JNR$^9$C(O)NR$^{10}$R$^{22}$, —CCR$^{21}$, —(CH$_2$)$_{1-4}$OC(O)R$^{21}$, -JC(O)OR$^{23}$, and SC$_1$-C$_6$alkyl(O)=NH; each of which $R^{48}$ may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, C$_1$-C$_6$alkyl, —C$_0$-C$_4$alkyl(C$_3$-C$_7$cycloalkyl), C$_1$-C$_6$alkoxy, —C$_0$-C$_4$alkyl(mono- and di-C$_1$-C$_4$alkylNR$^9$R$^{10}$), C$_1$-C$_6$alkylester, C$_1$-C$_4$alkylamino, C$_1$-C$_4$hydroxylalkyl, C$_1$-C$_2$haloalkyl, C$_1$-C$_2$haloalkoxy, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, C$_1$-C$_2$haloalkyl, and C$_1$-C$_2$haloalkoxy;

$R^{51}$ is $CH_3$, $CH_2F$, $CHF_2$, or $CF_3$;

$R^{52}$ is independently selected from halo, hydrogen, and $C_1$-$C_6$alkyl;

J is independently chosen at each occurrence from a covalent bond, $C_1$-$C_4$alkylene, —O$C_1$-$C_4$alkylene, $C_2$-$C_4$alkenylene, and $C_2$-$C_4$alkynylene;

$R^{37}$ is hydrogen, $C_1$-$C_6$alkyl, or —($C_0$-$C_2$alkyl)($C_3$-$C_6$cycloalkyl); and $R^{38}$ and $R^{39}$ are independently hydrogen, $C_1$-$C_6$alkyl, $C_1$-$C_6$haloalkyl, $C_1$-$C_6$hydroxyalkyl, $C_2$-$C_6$alkenyl, $C_2$-$C_6$alkynyl, $C_1$-$C_6$alkoxy, ($C_3$-$C_6$cycloalkyl)$C_0$-$C_4$alkyl-, (aryl)$C_0$-$C_2$alkyl-, or (heteroaryl)$C_0$-$C_2$alkyl-;

and wherein the disorder is selected from acute respiratory distress syndrome, arthritis, asthma, Alzheimer's dementia, antibody-mediated transplant rejection, anti-neutrophil cytoplasm antibody-associated vasculitis, antiphospholipid syndrome, atypical or typical hemolytic uremic syndrome, cold agglutinin disease, chronic obstructive pulmonary disease, Crohn's disease, diabetic retinopathy, dense deposit disease, dermatitis, epidermolysis bullosa acquisita, focal segmental glomerulosclerosis, geographic atrophy, glomerulonephritis, graft versus host disease, Guillain Barre syndrome, hemolytic anemia, hidradenitis suppurativa, IgA nephropathy, ischemia/reperfusion injury, lupus nephritis, membrane proliferative glomerulonephritis, multifocal motor neuropathy, myasthenia gravis, neuromyelitis optica, pancreatitis, pemphigoid, pemphigus vulgaris, pre-eclampsia, reduced glomerular filtration rate, a renovascular disorder, retinal detachment, scleroderma, sepsis, shiga toxin *E. coli*-related hemolytic uremic syndrome, spinal cord injury, sickle cell disease, traumatic brain injury, and ulcerative colitis.

2. The method of claim 1, wherein the compound is a compound of formula:

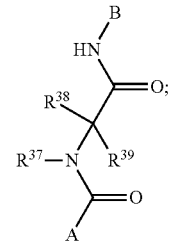

or a pharmaceutically acceptable salt thereof.

3. The method of claim 1, wherein the compound is a compound of formula:

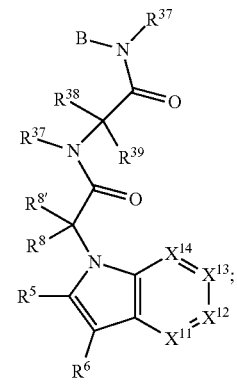

or a pharmaceutically acceptable salt thereof.

4. The method of claim 3, wherein B is B1.

5. The method of claim 1, wherein the compound is a compound of formula:

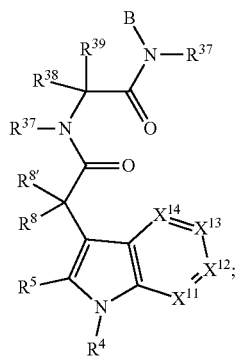

or a pharmaceutically acceptable salt thereof.

6. The method of claim 5, wherein B is B1.

7. The method of claim 1, wherein the compound is a compound of formula:

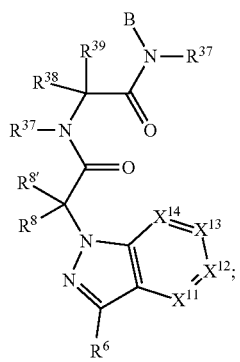

or a pharmaceutically acceptable salt thereof.

8. The method of claim 7, wherein B is B1.

9. The method of claim 1, wherein the compound is selected from:

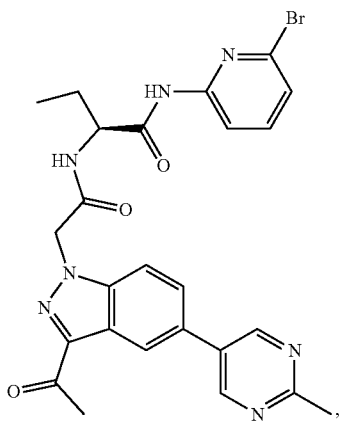

-continued

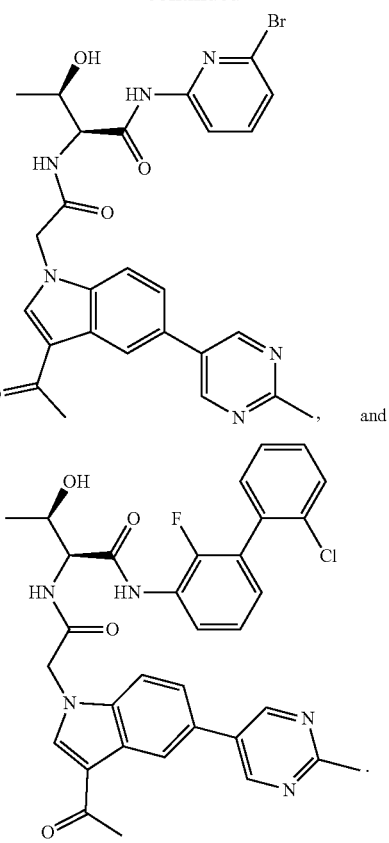

10. The method of claim 1, wherein the host is a human.

11. The method of claim 1, wherein the disorder is atypical hemolytic uremic syndrome.

12. The method of claim 1, wherein the disorder is dense deposit disease.

13. The method of claim 1, wherein the disorder is geographic atrophy.

14. The method of claim 1, wherein the disorder is IgA nephropathy.

15. The method of claim 1, wherein the disorder is lupus nephritis.

16. The method of claim 1, wherein the disorder is myasthenia gravis.

17. The method of claim 1, wherein the disorder is neuromyelitis optica.

18. The method of claim 1, wherein the disorder is reduced glomerular filtration rate.

19. The method of claim 1, wherein the disorder is a renovascular disorder.

20. The method of claim 1, wherein the disorder is sickle cell disease.

* * * * *